US011939596B2

(12) United States Patent
Wardell et al.

(10) Patent No.: US 11,939,596 B2
(45) Date of Patent: *Mar. 26, 2024

(54) PROCESSES FOR PRODUCTION OF TUMOR INFILTRATING LYMPHOCYTES AND USES OF SAME IN IMMUNOTHERAPY

(71) Applicant: Iovance Biotherapeutics, Inc., San Carlos, CA (US)

(72) Inventors: Seth Wardell, Tampa, FL (US); James Bender, Rancho Santa Margarita, CA (US)

(73) Assignee: Iovance Biotherapeutics, Inc., San Carlos, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/823,445

(22) Filed: Aug. 30, 2022

(65) Prior Publication Data

US 2023/0013765 A1 Jan. 19, 2023

Related U.S. Application Data

(63) Continuation of application No. 17/147,412, filed on Jan. 12, 2021, and a continuation of application No. 17/041,305, filed as application No. PCT/US2018/040474 on Jun. 29, 2018, which is a continuation of application No. 15/940,901, filed on Mar. 29, 2018, now Pat. No. 10,918,666, said application No. 17/147,412 is a continuation of application No. 17/110,179, filed on Dec. 2, 2020, which is a continuation-in-part of application No. 15/940,901, filed on Mar. 29, 2018, now Pat. No. 10,918,666, which is a continuation-in-part of application No. 15/863,634, filed on Jan. 5, 2018, now Pat. No. 10,894,063.

(60) Provisional application No. 62/596,374, filed on Dec. 8, 2017, provisional application No. 62/582,874, filed on Nov. 7, 2017, provisional application No. 62/577,655, filed on Oct. 26, 2017, provisional application No. 62/567,121, filed on Oct. 2, 2017, provisional application No. 62/559,374, filed on Sep. 15, 2017, provisional application No. 62/554,538, filed on Sep. 5, 2017, provisional application No. 62/548,306, filed on Aug. 21, 2017, provisional application No. 62/539,410, filed on Jul. 31, 2017, provisional application No. 62/478,506, filed on Mar. 29, 2017.

(51) Int. Cl.
C12N 5/0783 (2010.01)
A01N 1/02 (2006.01)
A61K 9/00 (2006.01)
A61K 31/675 (2006.01)
A61K 31/7076 (2006.01)
A61K 35/17 (2015.01)
A61K 38/20 (2006.01)
A61P 35/00 (2006.01)
C12N 5/078 (2010.01)
A61K 38/21 (2006.01)
A61K 39/00 (2006.01)

(52) U.S. Cl.
CPC ......... *C12N 5/0636* (2013.01); *A01N 1/0284* (2013.01); *A61K 9/0019* (2013.01); *A61K 31/675* (2013.01); *A61K 31/7076* (2013.01); *A61K 35/17* (2013.01); *A61K 38/2013* (2013.01); *A61P 35/00* (2018.01); *C12N 5/0634* (2013.01); *C12N 5/0638* (2013.01); *A61K 38/217* (2013.01); *A61K 39/0011* (2013.01); *A61K 2039/5154* (2013.01); *A61K 2039/5156* (2013.01); *A61K 2039/5158* (2013.01); *A61K 2039/55533* (2013.01); *C12N 2501/04* (2013.01); *C12N 2501/2302* (2013.01); *C12N 2501/2315* (2013.01); *C12N 2501/2321* (2013.01); *C12N 2501/24* (2013.01); *C12N 2501/603* (2013.01); *C12N 2502/11* (2013.01); *C12N 2506/30* (2013.01)

(58) Field of Classification Search
None
See application file for complete search history.

(56) References Cited

U.S. PATENT DOCUMENTS

| | | |
|---|---|---|
| 4,766,106 A | 8/1988 | Katre et al. |
| 4,902,502 A | 2/1990 | Nitecki et al. |
| 5,089,261 A | 2/1992 | Nitecki et al. |
| 5,126,132 A | 6/1992 | Rosenberg |
| 5,206,344 A | 4/1993 | Katre et al. |
| 5,443,983 A | 8/1995 | Ochoa et al. |

(Continued)

FOREIGN PATENT DOCUMENTS

| | | |
|---|---|---|
| CN | 102816734 A | 12/2012 |
| CN | 106244538 A | 12/2016 |

(Continued)

OTHER PUBLICATIONS

U.S. Appl. No. 17/856,806, filed Jul. 1, 2022.

(Continued)

*Primary Examiner* — Michail A Belyavskyi
(74) *Attorney, Agent, or Firm* — Morgan, Lewis & Bockius LLP

(57) ABSTRACT

The present invention provides improved and/or shortened methods for expanding TILs and producing therapeutic populations of TILs, including novel methods for expanding TIL populations in a closed system that lead to improved efficacy, improved phenotype, and increased metabolic health of the TILs in a shorter time period, while allowing for reduced microbial contamination as well as decreased costs. Such TILs find use in therapeutic treatment regimens.

30 Claims, 151 Drawing Sheets

Specification includes a Sequence Listing.

(56) References Cited

U.S. PATENT DOCUMENTS

| | | |
|---|---|---|
| 6,352,694 B1 | 3/2002 | June et al. |
| 6,534,055 B1 | 3/2003 | June et al. |
| 6,706,289 B2 | 3/2004 | Lewis et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 7,144,575 B2 | 12/2006 | June et al. |
| 7,175,843 B2 | 2/2007 | June et al. |
| 7,232,566 B2 | 6/2007 | June et al. |
| 7,479,269 B2 | 1/2009 | June et al. |
| 7,572,631 B2 | 8/2009 | Berenson et al. |
| 7,943,743 B2 | 5/2011 | Korman et al. |
| 7,951,365 B2 | 5/2011 | Winqvist et al. |
| 8,007,785 B2 | 8/2011 | Winqvist et al. |
| 8,008,449 B2 | 8/2011 | Korman et al. |
| 8,034,334 B2 | 10/2011 | Dudley et al. |
| 8,206,702 B2 | 6/2012 | Winqvist et al. |
| 8,211,424 B2 | 7/2012 | Winqvist et al. |
| 8,211,425 B2 | 7/2012 | Winqvist et al. |
| 8,287,857 B2 | 11/2012 | Dudley et al. |
| 8,383,099 B2 | 2/2013 | Dudley et al. |
| 8,617,884 B2 | 12/2013 | Berenson et al. |
| 8,809,050 B2 | 8/2014 | Vera et al. |
| 8,956,860 B2 | 2/2015 | Vera et al. |
| 9,074,185 B2 | 7/2015 | Dudley et al. |
| 9,476,028 B2 | 10/2016 | Karlsson-Parra et al. |
| 9,528,088 B2 | 12/2016 | Berenson et al. |
| 9,687,510 B2 | 6/2017 | Borrello et al. |
| 9,844,569 B2 | 12/2017 | Gros et al. |
| 9,914,783 B1 | 3/2018 | Afar et al. |
| 10,130,659 B2 | 11/2018 | Wardell |
| 10,363,273 B2 | 7/2019 | Wardell |
| 10,517,894 B2 | 12/2019 | Frank |
| 10,537,595 B2 | 1/2020 | Wardell |
| 10,653,723 B1 | 5/2020 | Wardell |
| 10,905,718 B2 | 2/2021 | Wardell |
| 10,918,666 B2 | 2/2021 | Wardell |
| 10,933,094 B2 | 3/2021 | Wardell |
| 10,946,044 B2 | 3/2021 | Wardell |
| 10,946,045 B2 | 3/2021 | Wardell |
| 10,953,046 B2 | 3/2021 | Wardell |
| 10,953,047 B2 | 3/2021 | Wardell |
| 11,013,770 B1 | 5/2021 | Wardell |
| 11,026,974 B2 | 6/2021 | Frank |
| 11,168,303 B2 | 11/2021 | Wardell |
| 11,168,304 B2 | 11/2021 | Wardell |
| 11,220,670 B2 | 1/2022 | Simpson-Abelson |
| 11,254,913 B1 | 2/2022 | Wardell |
| 11,293,009 B2 | 4/2022 | Simpson-Abelson |
| 11,351,198 B2 | 6/2022 | Frank |
| 11,357,841 B2 | 6/2022 | Ritthipichai |
| 11,401,507 B2 | 8/2022 | Simpson-Abelson |
| 11,433,097 B2 | 9/2022 | Fardis |
| 11,517,592 B1 | 12/2022 | Wardell |
| 11,529,372 B1 | 12/2022 | Wardell |
| 11,541,077 B2 | 1/2023 | Wardell |
| 11,631,483 B2 | 4/2023 | Brooks |
| 11,713,446 B2 | 8/2023 | Chartier-Courtaud |
| 11,819,517 B2 | 11/2023 | Wardell |
| 2005/0106717 A1 | 5/2005 | Wilson et al. |
| 2011/0052530 A1 | 3/2011 | Dudley et al. |
| 2011/0136228 A1 | 6/2011 | Vera et al. |
| 2012/0244133 A1 | 9/2012 | Rosenberg et al. |
| 2013/0102075 A1 | 4/2013 | Vera et al. |
| 2013/0115617 A1 | 5/2013 | Wilson |
| 2014/0328791 A1 | 11/2014 | Bossard et al. |
| 2014/0377739 A1 | 12/2014 | Welch et al. |
| 2015/0175966 A1 | 6/2015 | Vera et al. |
| 2015/0320798 A1 | 11/2015 | Borrello et al. |
| 2016/0010058 A1 | 1/2016 | Gros et al. |
| 2016/0208216 A1 | 7/2016 | Vera et al. |
| 2016/0215262 A1 | 7/2016 | Powell |
| 2017/0044496 A1 | 2/2017 | Sarnaik et al. |
| 2017/0081635 A1 | 3/2017 | Sarnaik et al. |
| 2017/0107490 A1 | 4/2017 | Maeurer |
| 2017/0114321 A1 | 4/2017 | Berenson et al. |
| 2017/0152478 A1 | 6/2017 | Rosenberg et al. |
| 2017/0258838 A1 | 9/2017 | Borrello et al. |
| 2018/0127715 A1 | 5/2018 | Veerapathran et al. |
| 2018/0148690 A1 | 5/2018 | Gros et al. |
| 2018/0187150 A1 | 7/2018 | De Larichaudy |
| 2018/0207201 A1 | 7/2018 | Wardell et al. |
| 2018/0228841 A1 | 8/2018 | Frank et al. |
| 2019/0000070 A1 | 1/2019 | De Larichaudy et al. |
| 2019/0062706 A1 | 2/2019 | Almaasbak et al. |
| 2019/0136186 A1 | 5/2019 | Germeroth et al. |

FOREIGN PATENT DOCUMENTS

| | | |
|---|---|---|
| CN | 106591232 A | 4/2017 |
| CN | 107384867 A | 11/2017 |
| EP | 1539929 B1 | 4/2013 |
| EP | 2925329 A1 | 10/2015 |
| EP | 3188740 A1 | 7/2017 |
| EP | 3365434 A1 | 8/2018 |
| EP | 3368659 A1 | 9/2018 |
| EP | 3487990 A1 | 5/2019 |
| WO | WO 2004031370 A1 | 4/2004 |
| WO | WO 2009040789 A2 | 4/2009 |
| WO | WO 2011072088 A2 | 6/2011 |
| WO | WO 2012065086 A1 | 5/2012 |
| WO | WO 2012129201 A1 | 9/2012 |
| WO | WO 2013057500 A1 | 4/2013 |
| WO | WO 2013088147 A1 | 6/2013 |
| WO | WO 2013173835 A1 | 11/2013 |
| WO | WO 2013188427 A1 | 12/2013 |
| WO | WO 2014210036 A1 | 12/2014 |
| WO | WO 2015009604 A1 | 1/2015 |
| WO | WO 2015157636 A1 | 10/2015 |
| WO | WO 2015188839 A1 | 12/2015 |
| WO | WO 2015189356 A1 | 12/2015 |
| WO | WO 2015189357 A1 | 12/2015 |
| WO | WO 2016053338 A1 | 4/2016 |
| WO | WO 2016096903 A1 | 6/2016 |
| WO | WO 2017048614 A1 | 3/2017 |
| WO | WO 2018005712 A1 | 1/2018 |
| WO | WO 2018081473 A1 | 5/2018 |
| WO | WO 2018102761 A1 | 6/2018 |
| WO | WO 2018129332 A1 | 7/2018 |
| WO | WO 2018170188 A2 | 9/2018 |
| WO | WO 2018182817 A1 | 10/2018 |
| WO | WO 2018209115 A1 | 11/2018 |
| WO | WO 2018226714 A1 | 12/2018 |

OTHER PUBLICATIONS

U.S. Appl. No. 17/817,217, filed Aug. 3, 2022.
U.S. Appl. No. 17/817,232, filed Aug. 3, 2022, now allowed.
U.S. Appl. No. 17/817,239, filed Aug. 3, 2022.
U.S. Appl. No. 17/819,209, filed Aug. 11, 2022.
U.S. Appl. No. 17/819,909, filed Aug. 11, 2022.
U.S. Appl. No. 17/819,910, filed Aug. 11, 2022.
U.S. Appl. No. 16/618,039, filed Nov. 27, 2019.
U.S. Appl. No. 16/211,159, filed Dec. 5, 2018.
Peng, Weiyi et al. "PD-1 blockade enhances T-cell migration to tumors by elevating IFN-γ inducible chemokines." Cancer research vol. 72,20 (2012): 5209-18. doi:10.1158/0008-5472.CAN-12-1187.
U.S. Appl. No. 17/856,800, filed Jul. 1, 2022.
U.S. Appl. No. 17/817,207, filed Aug. 3, 2022.
U.S. Appl. No. 17/817,276, filed Aug. 3, 2022.
U.S. Appl. No. 17/817,279, filed Aug. 3, 2022.
U.S. Appl. No. 17/817,226, filed Aug. 3, 2022.
U.S. Appl. No. 17/817,281, filed Aug. 3, 2022.
Akkök, C. A et al. "Use of different DMSO concentrations for cryopreservation of autologous peripheral blood stem cell grafts does not have any major impact on levels of leukocyte- and platelet-derived soluble mediators." Cytotherapy vol. 11,6 (2009): 749-60. doi:10.3109/14653240902980443.
Andersen, Rikke et al. "Long-Lasting Complete Responses in Patients with Metastatic Melanoma after Adoptive Cell Therapy

(56) References Cited

OTHER PUBLICATIONS with Tumor-Infiltrating Lymphocytes and an Attenuated IL2 Regimen." Clinical cancer research : an official journal of the American Association for Cancer Research vol. 22,15 (2016): 3734-45. doi:10.1158/1078-0432.CCR-15-1879.

Axelsson et al., "Cryopreserved peripheral blood mononuclear cells are suitable for the assessment of immunological markers in type 1 diabetic children", Cryobiology, Aug. 2008, 57, 201-208.

Bajgain, P. et al., "Optimizing the production of suspension cells using the G-Rex "M" series", Molecular Therapy—Methods and Clinical Development, vol. 1, Jan. 1, 2014.

Baruch et al., "Adoptive T cell therapy: An overview of obstacles and opportunities : ACT Obstacles and Opportunities", Cancer, vol. 123, No. S11, May 19, 2017, pp. 2154-2162.

Besser et al., "Minimally Cultured or Selected Autologous Tumor-infiltrating Lymphocytes After a Lympho-depleting Chemotherapy Regimen in Metastatic Melanoma Patients"; J Immunother 32, 415-423 (2009).

Besser, et al., "Adoptive Transfer of Tumor-Infiltrating Lymphocytes in Patients with Metastatic Melanoma: Intent-to-Treat Analysis and Efficacy after Failure to Prior Immunotherapies"; Clin Cancer Res, 19(17):0F1-0F9 (2013).

Besser, Michal J et al. "Clinical responses in a phase II study using adoptive transfer of short-term cultured tumor infiltration lymphocytes in metastatic melanoma patients." Clinical cancer research : an official journal of the American Association for Cancer Research vol. 16,9 (2010): 2646-55. doi:10.1158/1078-0432.CCR-10-0041.

Chacon et al., "Co-stimulation through 4-1BB/CD137 Improves the Expansion and Fundtion of CD8+ Melanoma Tumor-Infiltrating Lymphocytes for Adoptive T-Cell Therapy", PLOS One, vol. 8, No. 4, Apr. 1, 2013, 25 pages.

Chang C.-H. et al., "Metabolic competition in the tumor microenvironment is a driver of cancer progression", Cell., Sep. 10, 2015, vol. 162, No. 6, pp. 1229-1241.

Chang et al., "Emerging concepts in immunotherapy T-cell metabolism as a therapeutic target", Nat. Immunol., Apr. 2016, 17(4), 364-368.

Donia, M et al., "Characterization and comparison of 'standard' and 'young' tumour-infiltrating lymphocytes for adoptive cell therapy at a Danish translational research institution." Scandinavian journal of immunology vol. 75,2 (2012): 157-67.

Donia, M, et al.. "Simplified protocol for clinical-grade tumor-infiltrating lymphocyte manufacturing with use of the Wave bioreactor", Cytotherapy. Aug. 2014;16(8):1117-20. doi: 10.1016/j.jcyt.2014.02.004; PubMed PMID: 24831841.

Dudley et al., "CD8+ Enriched "Young" Tumor Infiltrating Lymphocytes Can Mediate Regression of Metastatic Melanoma" Clin Cancer Res, 16:6122-6131 (2010).

Dudley et al., "Generation of Tumor-Infiltrating Lymphocyte Cultures for Use in Adoptive Transfer Therapy for Melanoma Patients," J Immunother., 2003: 26(4): 332-342.

Dudley, et al., "Adoptive Cell Therapy for Patients with Metastatic Melanoma: Evaluation of Intensive Myeloablative Chemoradiation Preparative Regimens", J. Clin. Oncol., Nov. 2008, 26(32), 5233-39.

Dudley, et al., "Cancer Regression and Autoimmunity in Patients After Clonal Repopulation with Antitumor Lymphocytes", Science, Oct. 2002, 298, 850-54.

Dudley, et at., "Adoptive Cell Transfer Following Non-Myeloablative but Lymphodepleting Chemotherapy for the Treatment of Patients with Refractory Metastatic Melanoma", J. Clin. Oncol. Apr. 2005, 23(10), 2346-57.

Forget et al., "Activation and propagation of tumor infiltrating lymphocytes on clinical-grade designer artificial antigen presenting cells for adoptive immunotherapy of melanoma", Journal of Immunotherapy, vol. 37 No. 9, Nov. 1, 2014, pp. 448-460.

Forget, Marie-Andree et al. "The beneficial effects of a gas-permeable flask for expansion of Tumor-Infiltrating lymphocytes as reflected in their mitochondrial function and respiration Capacity." Oncoimmunology vol. 5,2 e1057386. Jun. 5, 2015, doi:10.1080/2162402X.2015.1057386.

Frank et al., "Remarkably Stable Tumor-Infiltrating Lymphocytes (TIL) for Infusion Phenotype Following Cryopreservation", Nov. 6, 2016, Retrieved from the Internet: http://www.iovance.com/wp-content/uploads/2017/05/LION16701_Frank_POSTER3_final-0005.

Garaud, Soizic et al. "A simple and rapid protocol to non-enzymatically dissociate fresh human tissues for the analysis of infiltrating lymphocytes." Journal of visualized experiments : JoVE , 94 52392. Dec. 6, 2014, doi:10.3791/52392.

Gassner, et al., "Fludarabine modulates composition and function of the T Cell pool in patients with chronic lymphocytic leukaemia", Cancer. Immunol. Immunother., 2011, 60, 75-85.

Gattinoni, et al., "Adoptive immunotherapy for cancer: building on success", Nat. Rev. Immunol. May 2006, 6(5), 383-393.

Gladstone, D E et al. "Infusion of cryopreserved autologous lymphocytes using a standard peripheral i.v. catheter." Bone marrow transplantation vol. 49,8 (2014): 1119-20. doi:10.1038/bmt.2014.98.

Glassman, A B, and C E Bennett. "Cryopreservation of human lymphocytes: a brief review and evaluation of an automated liquid nitrogen freezer." Transfusion vol. 19,2 (1979): 178-81. doi: 10.1046/j.1537-2995.1979.19279160289.x.

Goff et al., "Tumor Infiltrating Lymphocyte Therapy for Metastatic Melanoma: Analysis of Tumors Resected for Til", J. Immunother, Oct. 2010, 33(8), 840-847.

Goff SL, et al., "Randomized, Prospective Evaluation Comparing Intensity of Lymphodepletion Before Adoptive Transfer of Tumor-Infiltrating Lymphocytes for Patients With Metastatic Melanoma", J Clin Oncol. Jul. 10, 2016;34(20):2389-79.

Hall et al., "Expansion of tumor-infiltrating lymphocytes (TIL) from human pancreatic tumors", Journal for Immuno Therapy of Cancer, vol. 4, No. 1, pp. 1-12.

Hasan et al., "Artificial Antigen Presenting Cells: An Off the Shelf Approach for Generation of Desirable T-Cell Populations for Broad Application of Adoptive Immunotherapy", Adv Genet Eng, 2015, 4:3.

Henning AL, et al.. Measurement of T-Cell Telomere Length Using Amplified-Signal FISH Staining and Flow Cytometry. Curr Protoc Cytom. Jan. 5, 2017;79:7.47.1-7.47.10. doi: 10.1002/cpcy.11. PubMed PMID 28055115.

Hernandez-Chacon et al., "Costimulation through the CD137/4-1BB Pathway Protects Human Melanoma Tumor-infiltrating Lymphocytes from Activation-induced Cell Death and Enhances Antitumor Effector Function", Journal of Immuno Therapy, vol. 34, No. 3, Apr. 1, 2011, pp. 236-250.

Hinrichs CS, Rosenberg SA. Exploiting the curative potential of adoptive T-cell therapy for cancer. Immunol Rev. Jan. 2014;257(1):56-71. doi:10.1111/imr.12132. Review. PubMed PMID: 24329789; PubMed Central PMCID: PMC3920180.

Huang et al., "Survival, Persistence, and Progressive Differentiation of Adoptively Transferred Tumor-Reactive T Cells Associated with Tumor Regression"; J. Immunother, 28(3), 258-267 (2005).

Ikarashi, H et al., "Solid-phase anti-CD3 antibody activation and cryopreservation of human tumor-infiltrating lymphocytes derived from epithelial ovarian cancer", Japanese Journal of Cancer Research, vol. 83, No. 12, Dec. 1, 1992.

International Search Report and Written Opinion for International Patent Application No. PCT/US2017/058610 dated Mar. 8, 2018, 13 pages.

International Search Report and Written Opinion for International Patent Application No. PCT/US2018/012633 dated May 25, 2018, 14 pages.

International Search Report and Written Opinion for International Patent Application No. PCT/US2018/040474 dated Nov. 14, 2018, 17 pages.

Itzhaki, Orit et al. "Establishment and large-scale expansion of minimally cultured "young" tumor infiltrating lymphocytes for adoptive transfer therapy." Journal of immunotherapy (Hagerstown, Md. : 1997) vol. 34,2 (2011): 212-20. doi:10.1097/CJI.0b013e318209c94c.

(56) References Cited

OTHER PUBLICATIONS

Iyer, R.K. et al., "Industrializing Autologous Adoptive Immunotherapies: Manufacturing Advances and Challenges", Frontiers in Medicine, vol. 5, May 23, 2018.
Jia He et al., "Ex vivo expansion of tumor-infiltrating lymphocytes from nasopharyngeal carcinoma patients for adoptive immunotherapy," Chinese Journal of Cancer, vol. 31, No. 6, Jun. 5, 2012.
Jin et al., "Enhanced clinical-scale manufacturing of TCR transduced T-cells using closed culture system modules", Journal of Transactional Medicine, col. 16. No. 1, Jan. 24, 2018.
Jin et al., "Simplified method of the growth of human tumor infiltrating lymphocytes in gas- permiable flasks to numbers needed for patient treatment", J. Immunotherapy, 2012, 35:283-292.
Junker, Niels et al. "Bimodal ex vivo expansion of T cells from patients with head and neck squamous cell carcinoma: a prerequisite for adoptive cell transfer." Cytotherapy vol. 13,7 (2011): 822-34. doi:10.3109/14653249.2011.563291.
Klapper, J.A. et al., "Single-pass, closed-system rapid expansion of lymphocyte cultures for adoptive cell therapy", Journal of Immunological Methods, vol. 345, No. 1-2, Jun. 30, 2009.
Lee et al., "Tumor-Infiltrating Lymphocytes in Melanoma", Curr Oncol Rep. Aug. 2012, 14, 468-474.
Li et al. MART-1-specific melanoma tumor-infiltrating lymphocytes maintaining CD28 expression have improved survival and expansion capability following antigenic restimulation in vitro. J Immunol. Jan. 1, 2010;184(1):452-65. doi: 10.4049/jimmunol.0901101. Epub Nov. 30, 2009. PubMed PMID: 19949105.
Merhavi-Shoham et al., "Adoptive Cell Therapy for Metastatic Melanoma", Cancer Journal, vol. 23, No. 1, Jan. 1, 2017.
Mullinax et al., "Combination of Ipilimumab and Adoptive Cell Therapy with Tumor-Infiltrating Lymphocytes for Patients with Metastatic Melanoma", Frontiers in Oncology, vol. 8, Mar. 2, 2018.
Muranski, et al., "Increased intensity lymphodepletion and adoptive immunotherapy—how far can we go?", Nat. Clin. Pract. Oncol., Dec. 2006, 3, 668-681.
Nguyen, Linh T et al. "Expansion and characterization of human melanoma tumor-infiltrating lymphocytes (TILs)." PloS one vol. 5,11 e13940. Nov. 10, 2010, doi:10.1371/journal.pone.0013940.
Riddell, et al., "Restoration of Viral Immunity in Immunodeficient Humans by the Adoptive Transfer of T Cell Clones", Science, Jul. 1992, 257, 238-41.
Robbins, et al., "Cutting Edge: Persistence of Transferred Lymphocyte Clonotypes Correlates with Cancer Regression in Patients Receiving Cell Transfer Therapy"; J. Immunol 2004; 173, 7125-7130.
Rohaan et al., "Adoptive transfer of tumor-infiltrating lymphocytes in melanoma: a viable treatment option", Journal for Immunotherapy of Cancer, vol. 6, No. 1, Oct. 3, 2018, pp. 1-16.
Rosenberg SA, Dudley ME. Adoptive cell therapy for the treatment of patients with metastatic melanoma. Curr Opin Immunol. Apr. 2009;21(2):233-40.
Rosenberg SA, et al. "Durable Complete Responses in Heavily Pretreated Patients with Metastatic Melanoma Using T Cell Transfer Immunotherapy", Clinical Cancer research, vol. 17, No. 13, Jul. 1, 2011 pp. 4550-4557.
Rosenberg, "IL-2: The First Effective Immunotherapy for Human Cancer," The Journal of Immunology, col. 192, No. 12, Jun. 6, 2014.
Rosenberg, S A et al. "A new approach to the adoptive immunotherapy of cancer with tumor-infiltrating lymphocytes." Science (New York, N.Y.) vol. 233,4770 (1986): 1318-21. doi:10.1126/science.3489291.
Rosenberg, S A et al. "Treatment of patients with metastatic melanoma with autologous tumor-infiltrating lymphocytes and interleukin 2." Journal of the National Cancer Institute vol. 86,15 (1994): 1159-66. doi:10.1093/jnci/86.15.1159.
Rosenberg, S A et al. "Use of tumor-infiltrating lymphocytes and interleukin-2 in the immunotherapy of patients with metastatic melanoma. A preliminary report." The New England journal of medicine vol. 319,25 (1988): 1676-80. doi:10.1056/NEJM198812223192527.

Rufer N, et al., "Telomere length dynamics in human lymphocyte subpopulations measured by flow cytometry", Nat Biotechnol. Aug. 1998; 16(8): 743-7. PubMed PMID: 9702772.
Sadeghi, et al., "Rapid expansion of T cells: Effects of culture and cryopreservation and improtance of short-term cell recovery", Acta Oncologica 2013, 52, 978-986.
Schiltz, P M et al. "Characterization of tumor-infiltrating lymphocytes derived from human tumors for use as adoptive immunotherapy of cancer." Journal of immunotherapy (Hagerstown, Md. : 1997) vol. 20,5 (1997): 377-86. doi:10.1097/00002371-199709000-00007.
Shen X,et al.. Persistence of tumor infiltrating lymphocytes in adoptive immunotherapy correlates with telomere length. J Immunother. Jan. 2007;30(1):123-9. PubMed PMID: 17198091; PubMed Central PMCID: PMC2151201.
Somerville RP, et al.. Clinical scale rapid expansion of lymphocytes for adoptive cell transfer therapy in the WAVE® bioreactor. J Transl Med. Apr. 4, 2012;10:69.
Spiess, P J et al. "In vivo antitumor activity of tumor-infiltrating lymphocytes expanded in recombinant interleukin-2." Journal of the National Cancer Institute vol. 79,5 (1987): 1067-75.
Tran et al., "Minimally Cultured tumor-infiltrating lymphocytes display optimal characteristics for adoptive cell therapy", 2008, J. Immunother., Oct. 2008 31(8), 742-751.
Tsoukas et al., "Activation of resting T lymphocytes by anti-CD3 (T3) antibodies in the absence of monocytes", J. Immunol. 1985, 135, 1719.
Van den Bossche, J. et al. "Metabolic Characterization of Polarized M1 and M2 Bone Marrow-derived Macrophages Using Real-time Extracellular Flux Analysis." Journal of visualized experiments : JoVE , 105 53424. Nov. 28, 2015, doi:10.3791/53424.
Wang & Riviere, "Manufacture of tumor- and virus-specific T lymphocytes for adoptive cell therapies", Cancer Gene Therapy, 2015, 22: 85-94.
Wardell et al., "A cryopreserved tumor infiltrating lymphocyte (TIL) product for LN-44", Nov. 8, 2017, retrieved from the Internet: URL: http://www.iovance.com/wp-content/uploads/2017/11/SITC2017_Seth_poster_FINAL_SWDE_PRINT_7Nov2017.pdf.
Wilson Wolf—Superior Cell Culture Devices, G-Rex, Oct. 31, 2016.
Ye, et al., "Engineered Artificial antigen presenting cells facilitate direct and efficient expansion of tumor infiltrating lymphocytes", J. Translat. Med. 2011, 9(131), 13 pages.
Zhou J, et al.. Telomere length of transferred lymphocytes correlates with in vivo persistence and tumor regression in melanoma patients receiving cell transfer therapy. J Immunol. Nov. 15, 2005;175(10):7046-52. PubMed PMID: 16272366; PubMed Central PMCID: PMC135131.
Zhou, et al., "Persistence of Multiple Tumor-Specific T-Cell Clones Is Associated with Complete Tumor Regression in a Melanoma Patient Receiving Adoptive Cell Transfer Therapy"; J. Immunother, 28, 53-62 (2005).
Zuliani, T. et al., "Value of large scale expansion of tumor infiltrating lymphocytes in a compartmentalised gas-permiable bag: interests for adoptive immunotherapy", Journal of Translational Medicine, vol. 9, No. 1, May 16, 2011.
U.S. Appl. No. 17/856,800, filed Jul. 1, 2022, now allowed.
U.S. Appl. No. 17/817,279, filed Aug. 3, 2022, now allowed.
U.S. Appl. No. 17/817,281, filed Aug. 3, 2022, now allowed.
Wu, Richard et al. "Adoptive T-cell therapy using autologous tumor-infiltrating lymphocytes for metastatic melanoma: current status and future outlook." Cancer journal (Sudbury, Mass.) vol. 18,2 (2012): 160-75. doi:10.1097/PPO.0b013e31824d4465.
Meng, Qingda et al. "Expansion of Tumor-reactive T Cells From Patients With Pancreatic Cancer." Journal of immunotherapy (Hagerstown, Md. : 1997) vol. 39,2 (2016): 81-9. doi:10.1097/CJI.0000000000000111.
U.S. Appl. No. 15/863,634, filed Jan. 5, 2018, now U.S. Pat. No. 10,894,063.
U.S. Appl. No. 15/874,718, filed Jan. 18, 2018, now U.S. Pat. No. 10,166,257.
U.S. Appl. No. 15/892,311, filed Feb. 8, 2018, now U.S. Pat. No. 10,130,659.

(56) References Cited

OTHER PUBLICATIONS

U.S. Appl. No. 16/136,147, filed Sep. 19, 2018, now U.S. Pat. No. 10,272,113.
U.S. Appl. No. 16/136,157, filed Sep. 19, 2018, now U.S. Pat. No. 10,420,799.
U.S. Appl. No. 16/201,957, filed Nov. 27, 2018, now U.S. Pat. No. 10,398,734.
U.S. Appl. No. 16/192,707, filed Nov. 15, 2018, now U.S. Pat. No. 10,537,595.
U.S. Appl. No. 16/425,746, filed May 29, 2019, now U.S. Pat. No. 10,639,330.
U.S. Appl. No. 16/203,467, filed Nov. 28, 2018, now U.S. Pat. No. 10,463,697.
U.S. Appl. No. 16/203,478, filed Nov. 28, 2018, now U.S. Pat. No. 10,363,273.
U.S. Appl. No. 16/425,767, filed May 29, 2019, now U.S. Pat. No. 10,695,372.
U.S. Appl. No. 16/425,778, filed May 29, 2019, now U.S. Pat. No. 10,646,517.
U.S. Appl. No. 16/746,416, filed Jan. 17, 2020, now U.S. Pat. No. 10,653,723.
U.S. Appl. No. 16/848,361, filed Apr. 14, 2020, now U.S. Pat. No. 10,905,718.
U.S. Appl. No. 16/848,386, filed Apr. 14, 2020, now U.S. Pat. No. 10,953,046.
U.S. Appl. No. 16/848,454, filed Apr. 14, 2020, now U.S. Pat. No. 10,946,044.
U.S. Appl. No. 16/848,426, filed Apr. 14, 2020, now U.S. Pat. No. 10,953,047.
U.S. Appl. No. 16/848,442, filed Apr. 14, 2020, now U.S. Pat. No. 10,933,094.
U.S. Appl. No. 16/848,474, filed Apr. 14, 2020, now U.S. Pat. No. 10,946,045.
U.S. Appl. No. 16/879,711, filed May 20, 2020, now U.S. Pat. No. 10,925,900.
U.S. Appl. No. 17/110,207, filed Dec. 2, 2020, now U.S. Pat. No. 11,083,752.
U.S. Appl. No. 17/127,768, filed Dec. 18, 2020, now U.S. Pat. No. 11,007,225.
U.S. Appl. No. 17/127,840, filed Dec. 18, 2020, now U.S. Pat. No. 11,052,116.
U.S. Appl. No. 17/127,790, filed Dec. 18, 2020, now U.S. Pat. No. 11,007,226.
U.S. Appl. No. 17/127,795, filed Dec. 18, 2020, now U.S. Pat. No. 11,052,115.
U.S. Appl. No. 17/147,073, filed Jan. 12, 2021, now U.S. Pat. No. 11,013,770.
U.S. Appl. No. 17/147,080, filed Jan. 12, 2021.
U.S. Appl. No. 17/147,090, filed Jan. 12, 2021, now U.S. Pat. No. 11,040,070.
U.S. Appl. No. 17/147,096, filed Jan. 12, 2021.
U.S. Appl. No. 17/326,088, filed May 20, 2021, now U.S. Pat. No. 11,202,803.
U.S. Appl. No. 17/382,831, filed Jul. 22, 2021, now U.S. Pat. No. 11,241,456.
U.S. Appl. No. 17/383,272, filed Jul. 22, 2021, now U.S. Pat. No. 11,202,804.
U.S. Appl. No. 17/383,276, filed Jul. 22, 2021, now U.S. Pat. No. 11,273,180.
U.S. Appl. No. 17/383,280, filed Jul. 22, 2021, now U.S. Pat. No. 11,304,979.
U.S. Appl. No. 17/856,793, filed Jul. 1, 2022.
U.S. Appl. No. 17/817,247, filed Aug. 3, 2022.
U.S. Appl. No. 17/819,214, filed Aug. 11, 2022.
U.S. Appl. No. 17/819,219, filed Aug. 11, 2022.
U.S. Appl. No. 17/823,445, filed Aug. 30, 2022.
NCT03374839, ClinicalTrials.gov.
U.S. Appl. No. 17/480,525, filed Sep. 21, 2021, now U.S. Pat. No. 11,273,181.
U.S. Appl. No. 17/480,534, filed Sep. 21, 2021, now U.S. Pat. No. 11,291,687.
U.S. Appl. No. 17/480,587, filed Sep. 21, 2021, now U.S. Pat. No. 11,344,579.
U.S. Appl. No. 17/480,596, filed Sep. 21, 2021, now U.S. Pat. No. 11,337,998.
U.S. Appl. No. 17/856,793, filed Jul. 1, 2022, now allowed.
U.S. Appl. No. 17/856,800, filed Jul. 1, 2022, now U.S. Pat. No. 11,517,592.
U.S. Appl. No. 17/856,806, filed Jul. 1, 2022, now allowed.
U.S. Appl. No. 17/817,207, filed Aug. 3, 2022, now allowed.
U.S. Appl. No. 17/817,273, filed Aug. 3, 2022.
U.S. Appl. No. 17/817,276, filed Aug. 3, 2022, now allowed.
U.S. Appl. No. 17/817,217, filed Aug. 3, 2022, now allowed.
U.S. Appl. No. 17/817,279, filed Aug. 3, 2022, now U.S. Pat. No. 11,541,077.
U.S. Appl. No. 17/817,226, filed Aug. 3, 2022, now allowed.
U.S. Appl. No. 17/817,232, filed Aug. 3, 2022.
U.S. Appl. No. 17/817,239, filed Aug. 3, 2022, now allowed.
U.S. Appl. No. 17/817,281, filed Aug. 3, 2022, now U.S. Pat. No. 11,529,372.
U.S. Appl. No. 17/817,247, filed Aug. 3, 2022, now allowed.
U.S. Appl. No. 15/751,440, filed Feb. 8, 2018, now U.S. Pat. No. 11,026,974.
U.S. Appl. No. 15/892,331, filed Feb. 8, 2018, now U.S. Pat. No. 10,517,894.
U.S. Appl. No. 17/225,993, filed Apr. 8, 2021, now U.S. Pat. No. 11,058,728.
U.S. Appl. No. 17/233,290, filed Apr. 16, 2021, now U.S. Pat. No. 11,179,419.
U.S. Appl. No. 17/233,295, filed Apr. 16, 2021, now U.S. Pat. No. 11,123,371.
U.S. Appl. No. 17/233,299, filed Apr. 16, 2021, now U.S. Pat. No. 11,141,438.
U.S. Appl. No. 17/459,988, filed Aug. 27, 2021, now U.S. Pat. No. 11,304,980.
U.S. Appl. No. 17/480,900, filed Sep. 21, 2021, now U.S. Pat. No. 11,311,578.
U.S. Appl. No. 17/480,916, filed Sep. 21, 2021, now U.S. Pat. No. 11,351,197.
U.S. Appl. No. 17/480,919, filed Sep. 21, 2021, now U.S. Pat. No. 11,351,198.
U.S. Appl. No. 17/480,935, filed Sep. 21, 2021, now U.S. Pat. No. 11,344,580.
U.S. Appl. No. 17/480,941, filed Sep. 21, 2021, now U.S. Pat. No. 11,266,694.
U.S. Appl. No. 17/548,502, filed Dec. 11, 2021, now U.S. Pat. No. 11,364,266.
U.S. Appl. No. 17/548,504, filed Dec. 11, 2021, now U.S. Pat. No. 11,369,637.
U.S. Appl. No. 17/547,190, filed Dec. 9, 2021, now U.S. Pat. No. 11,344,581.
U.S. Appl. No. 17/547,192, filed Dec. 9, 2021, now U.S. Pat. No. 11,351,199.
U.S. Appl. No. 17/829,087, filed May 31, 2022.
U.S. Appl. No. 17/819,209, filed Aug. 11, 2022, now U.S. Pat. No. 11,857,573.
U.S. Appl. No. 17/819,214, filed Aug. 11, 2022, now allowed.
U.S. Appl. No. 17/819,219, filed Aug. 11, 2022, now allowed.
U.S. Appl. No. 17/819,909, filed Aug. 11, 2022, now allowed.
U.S. Appl. No. 17/819,910, filed Aug. 11, 2022, now U.S. Pat. No. 11,865,140.
U.S. Appl. No. 15/940,901, filed Mar. 29, 2018, now U.S. Pat. No. 10,918,666.
U.S. Appl. No. 17/041,305, filed Sep. 24, 2020.
U.S. Appl. No. 17/110,179, filed Dec. 2, 2020.
U.S. Appl. No. 17/147,412, filed Jan. 12, 2021.
U.S. Appl. No. 17/148,475, filed Jan. 13, 2021, now U.S. Pat. No. 11,168,303.
U.S. Appl. No. 17/148,508, filed Jan. 13, 2021, now U.S. Pat. No. 11,168,304.
U.S. Appl. No. 17/353,430, filed Jun. 21, 2021, now U.S. Pat. No. 11,254,913.

(56) References Cited

OTHER PUBLICATIONS

U.S. Appl. No. 17/823,445, filed Aug. 30, 2022, now allowed.
U.S. Appl. No. 17/823,448, filed Aug. 30, 2022.
U.S. Appl. No. 17/823,454, filed Aug. 30, 2022.
U.S. Appl. No. 17/823,419, filed Aug. 30, 2022.
U.S. Appl. No. 16/618,039, filed Nov. 27, 2019, now U.S. Pat. No. 11,819,517.
U.S. Appl. No. 18/464,469, filed Sep. 11, 2023.
U.S. Appl. No. 16/211,159, filed Dec. 5, 2018, now U.S. Pat. No. 11,433,097.
U.S. Appl. No. 17/311,591, filed Jun. 7, 2021.
Katz, Steven C et al. "Phase I Hepatic Immunotherapy for Metastases Study of Intra-Arterial Chimeric Antigen Receptor-Modified T-cell Therapy for CEA+ Liver Metastases." Clinical cancer research: an official journal of the American Association for Cancer Research vol. 21,14 (2015): 3149-59. doi:10.1158/1078-0432.CCR-14-1421.

Process Development

| Step | Current Process-1C | New Process-2A | Impact |
|---|---|---|---|
| 1 | 4 Fragments/10 G-Rex 10-21 Days | 40 Fragments/1-G-Rex 100 CS- (x2?) 11 Days | Increases Tumor Sample/Container, Shortens Culture, Reduces Steps, Amenable To Closed System |
| 2 | PreREP Freeze-> Testing -> Thaw- ~Day 27- >40e6TIL | Direct To REP- Day 11- <200e6 | Shorten Process, Reduces Steps, Eliminates Testing |
| 3 | 36 G-Rex 100-~Day 30 >5e6TIL - Split ~Day 36 | 4-5 G-Rex 500CS- TIL- Split Day 16 | Reduces Steps, Closed System, Shorter REP |
| 4 | Harvest Day ~43+ Harvesting By Centrifugation | Harvest Day 22 LOVO-Automated Cell Washer | Reduces Steps, Automated, Closed System |
| 5 | Fresh Product- Hypothermosol-Single Infusion Bag | Cryopreserved Product-CS10 In $LN_2$, Multiple Aliquots | Shipping Flexibility, Patient Scheduling, Easier Release Testing, Global Trials |
| 6 | 43+ Day Process Time | 22 Day Process Time | Turnaround To Patient, Clean Room Throughput, COGs |

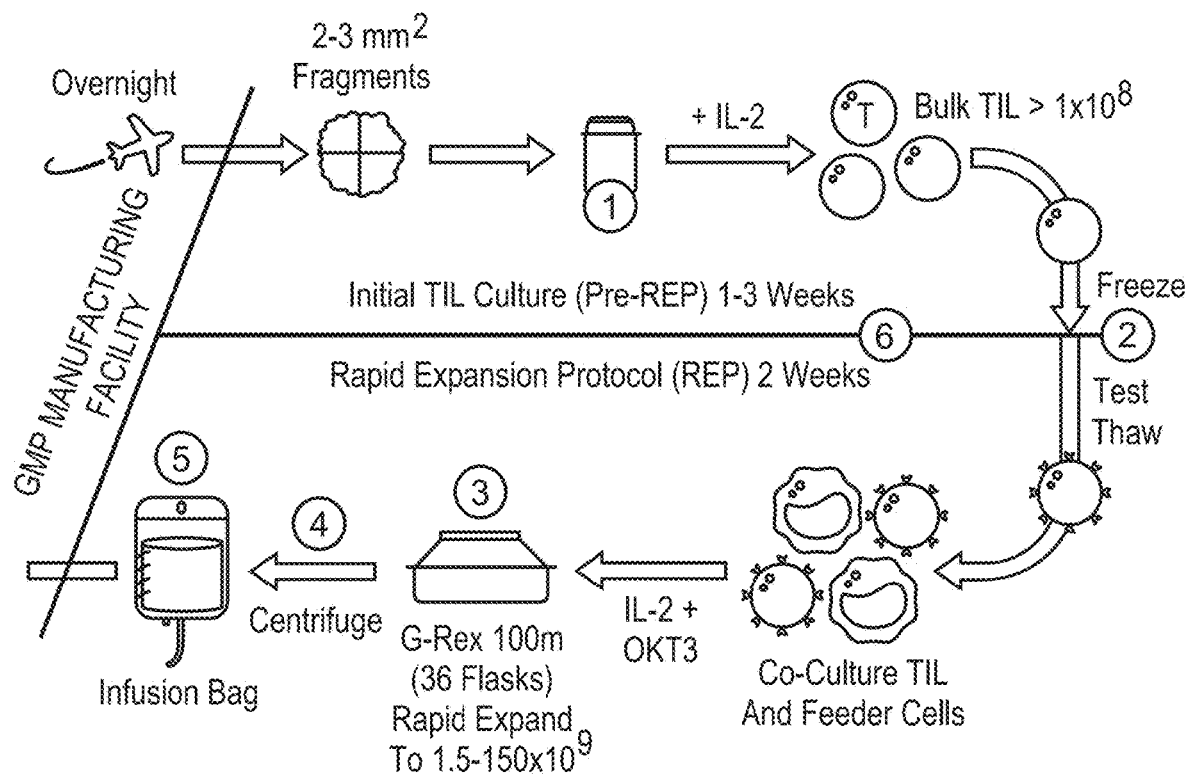

Figure 2

| | |
|---|---|
| P value | 0.9797 |
| P value summary | ns |
| Significantly different? (P < 0.05) | No |
| One- or two-tailed P value? | Two-tailed |
| t, df | t=0.02626 df=8 |
| Number of pairs | 9 |

How effective was the pairing?

Correlation coefficient (r)

P value (one tailed)

P value summary

Was the pairing significantly effective?

| | |
|---|---|
| P value summary | ns |
| Significantly different? (P < 0.05) | No |
| One- or two-tailed P value? | Two-tailed |
| t, df | t=0.8479 df=7 |
| Number of pairs | 8 |

| | |
|---|---|
| How effective was the pairing? | |
| Correlation coefficient (r) | 0.9711 |
| P value (one tailed) | < 0.0001 |
| P value summary | **** |
| Was the pairing significantly effective? | Yes |

| | |
|---|---|
| P value summary | ns |
| Significantly different? (P < 0.05) | No |
| One- or two-tailed P value? | Two-tailed |
| t, df | t=1.568 df=7 |
| Number of pairs | 8 |

| | |
|---|---|
| How effective was the pairing? | |
| Correlation coefficient (r) | 0.7448 |
| P value (one tailed) | 0.017 |
| P value summary | * |
| Was the pairing significantly effective? | Yes |

| | |
|---|---|
| P value summary | ns |
| Significantly different? (P < 0.05) | No |
| One- or two-tailed P value? | Two-tailed |
| t, df | t=1.596 df=7 |
| Number of pairs | 8 |

| | |
|---|---|
| How effective was the pairing? | |
| Correlation coefficient (r) | 0.6932 |
| P value (one tailed) | 0.0283 |
| P value summary | * |
| Was the pairing significantly effective? | Yes |

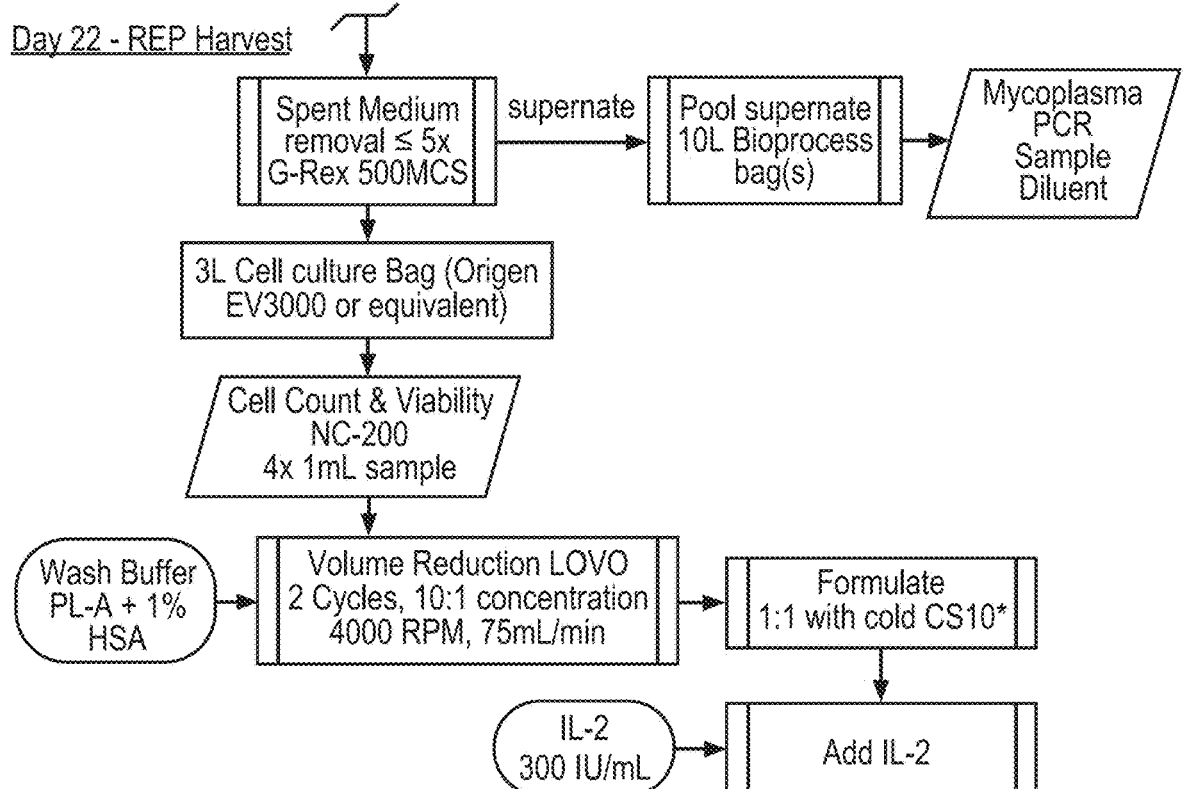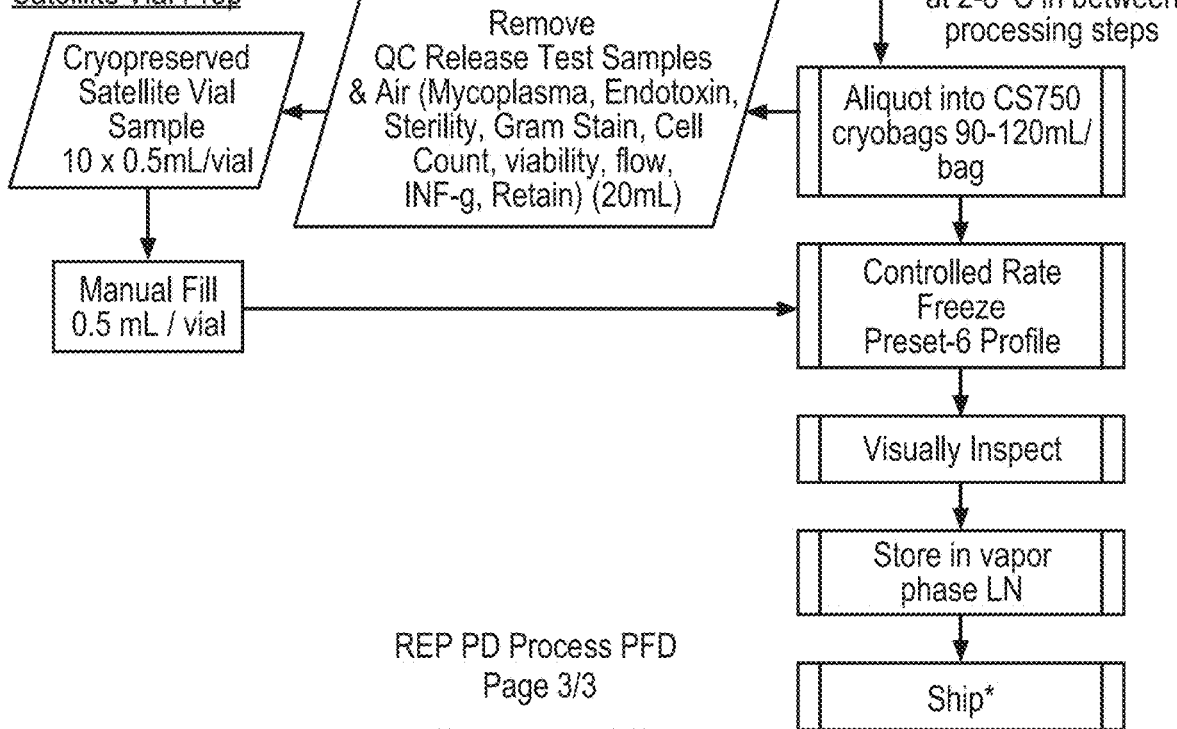
Figure 11C

*Figure 27*

Process 2A: about 22 days from Steps A - E

1. STEP A

Obtain Patient Tumor Sample

2. STEP B

Fragmentation and First Expansion 3 days to 14 days

3. STEP C

First Expansion to Second Expansion Transition

No Storage and Closed System

4. STEP D

Second Expansion

IL-2, OKT-3, and antigen-presenting feeder cells

Closed System

5. STEP E

Harvest TILS from Step D

Closed System

6. STEP F

Final Formulation and/or Transfer to Infusion Bag (optionally cryopreserve)

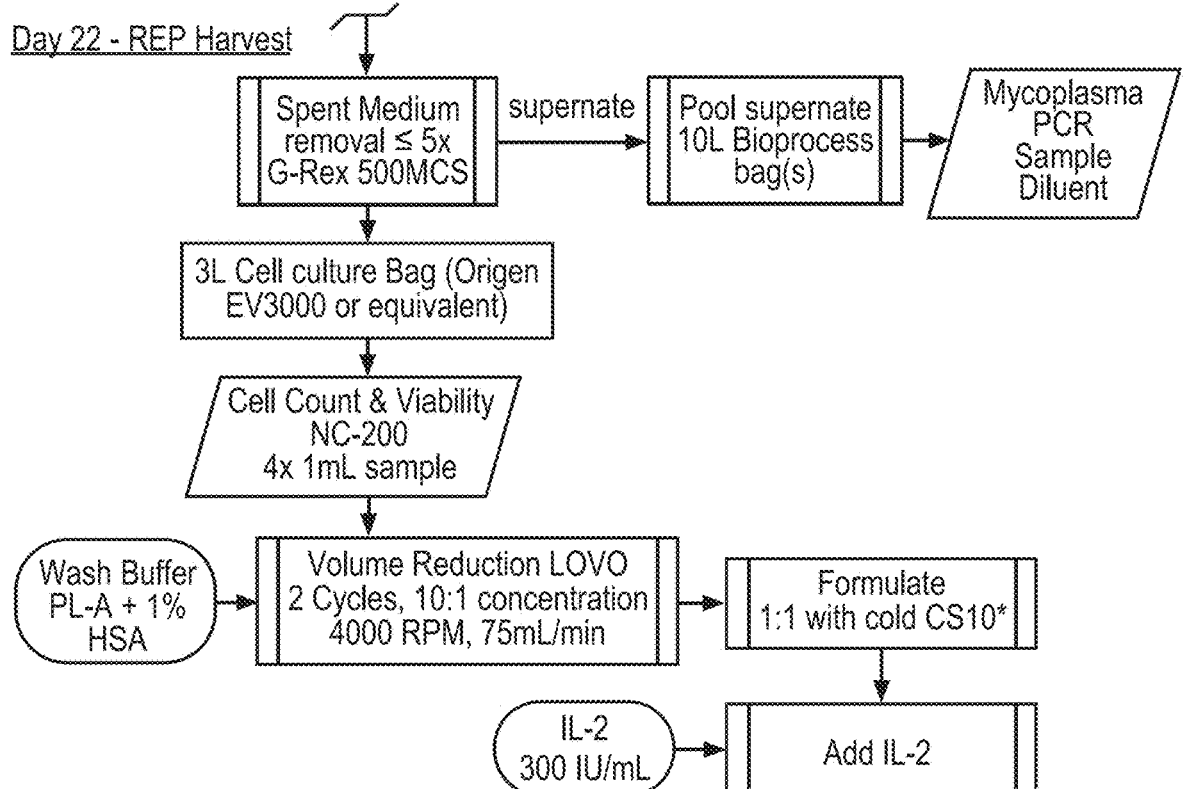
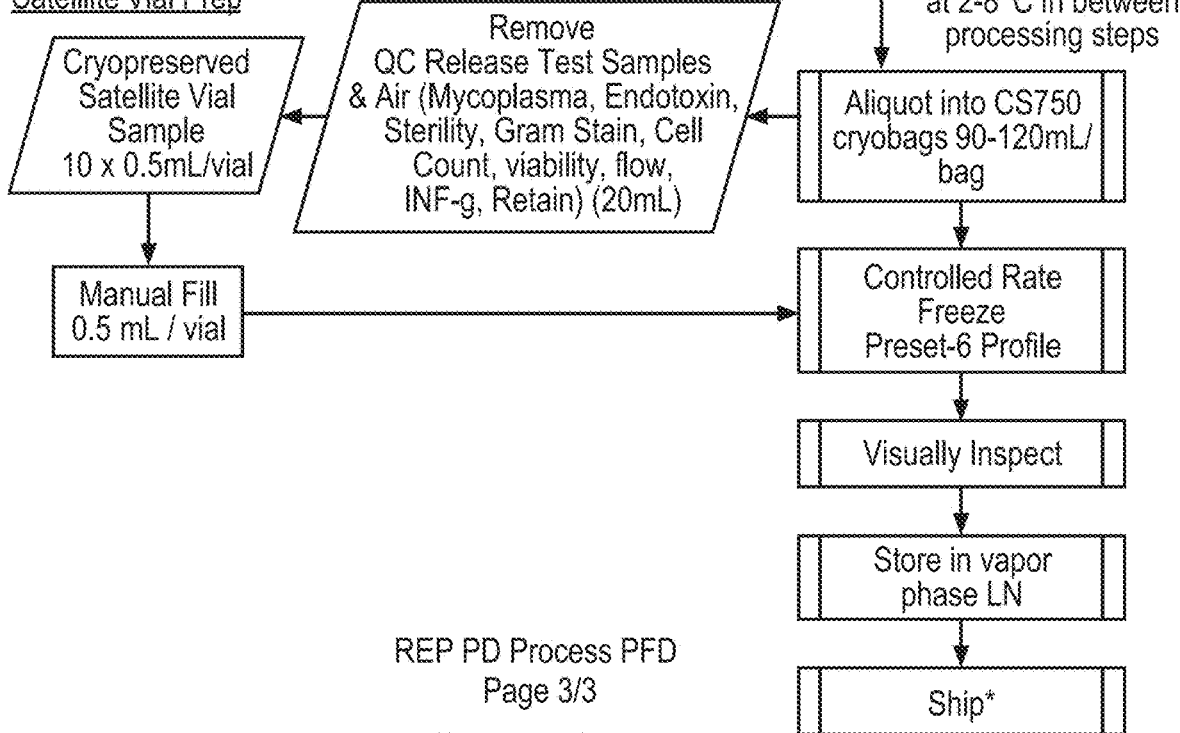
Figure 28C

| Normal Blood Values | |
|---|---|
| Glucose | 0.7-1g/l |
| Glutamine | 0.3-0.65mmol/l |
| Sodium | 135-145mol/l |
| Potassium | 3.5-5.0mmol/l |
| Lactic Acid | 0.060-.16g/l |
| Ammonia | .023-.047mmol/l |

Figure 32

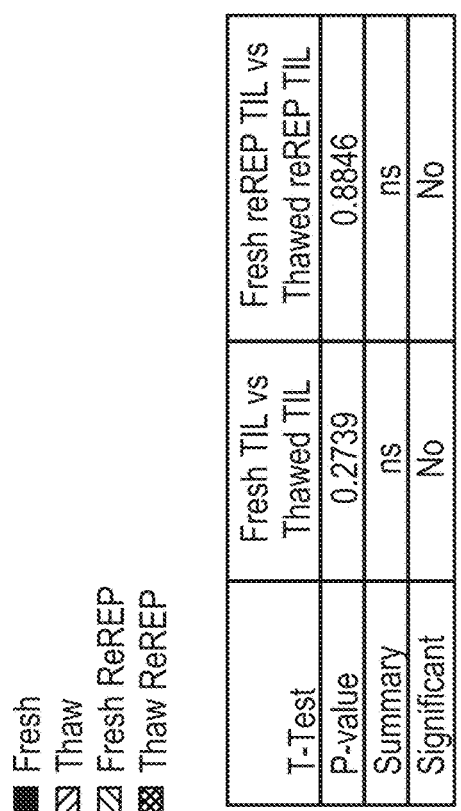
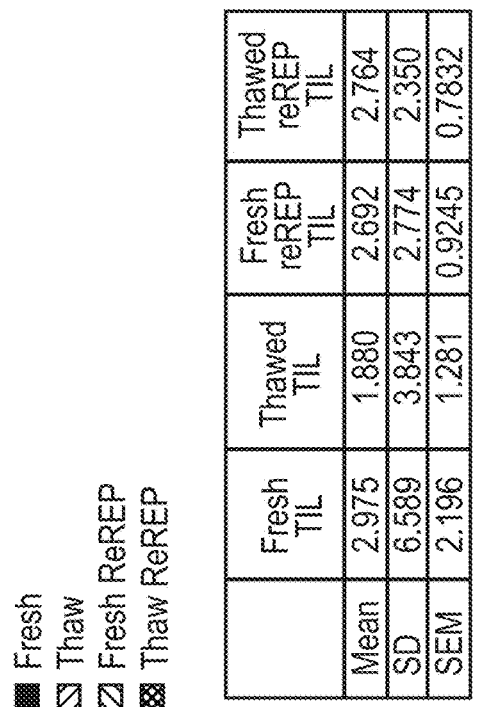
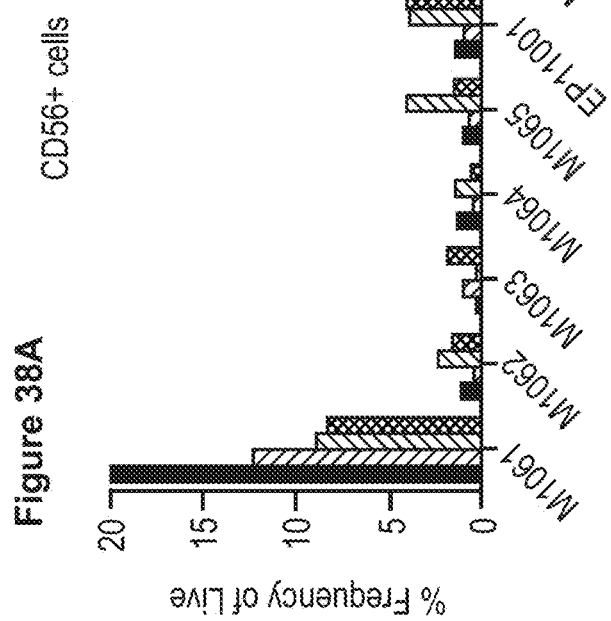
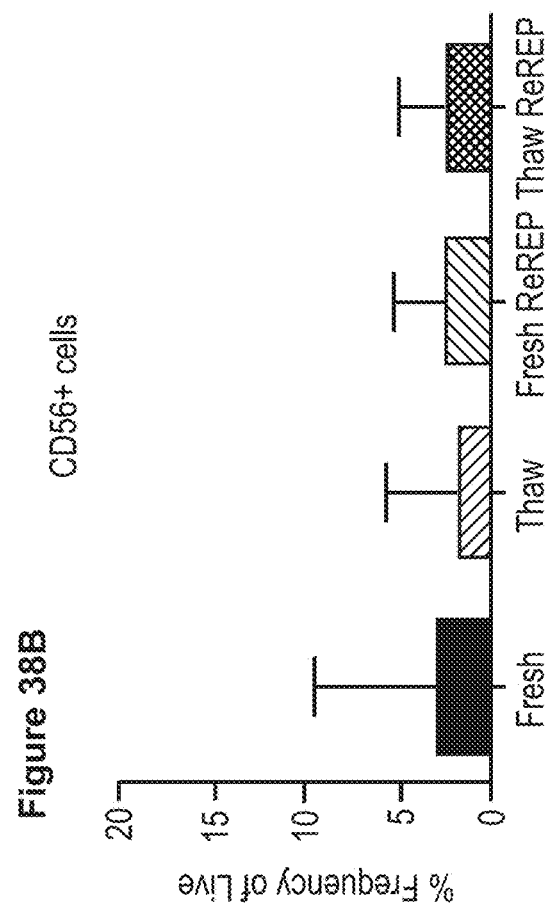
Figure 38A
Figure 38B

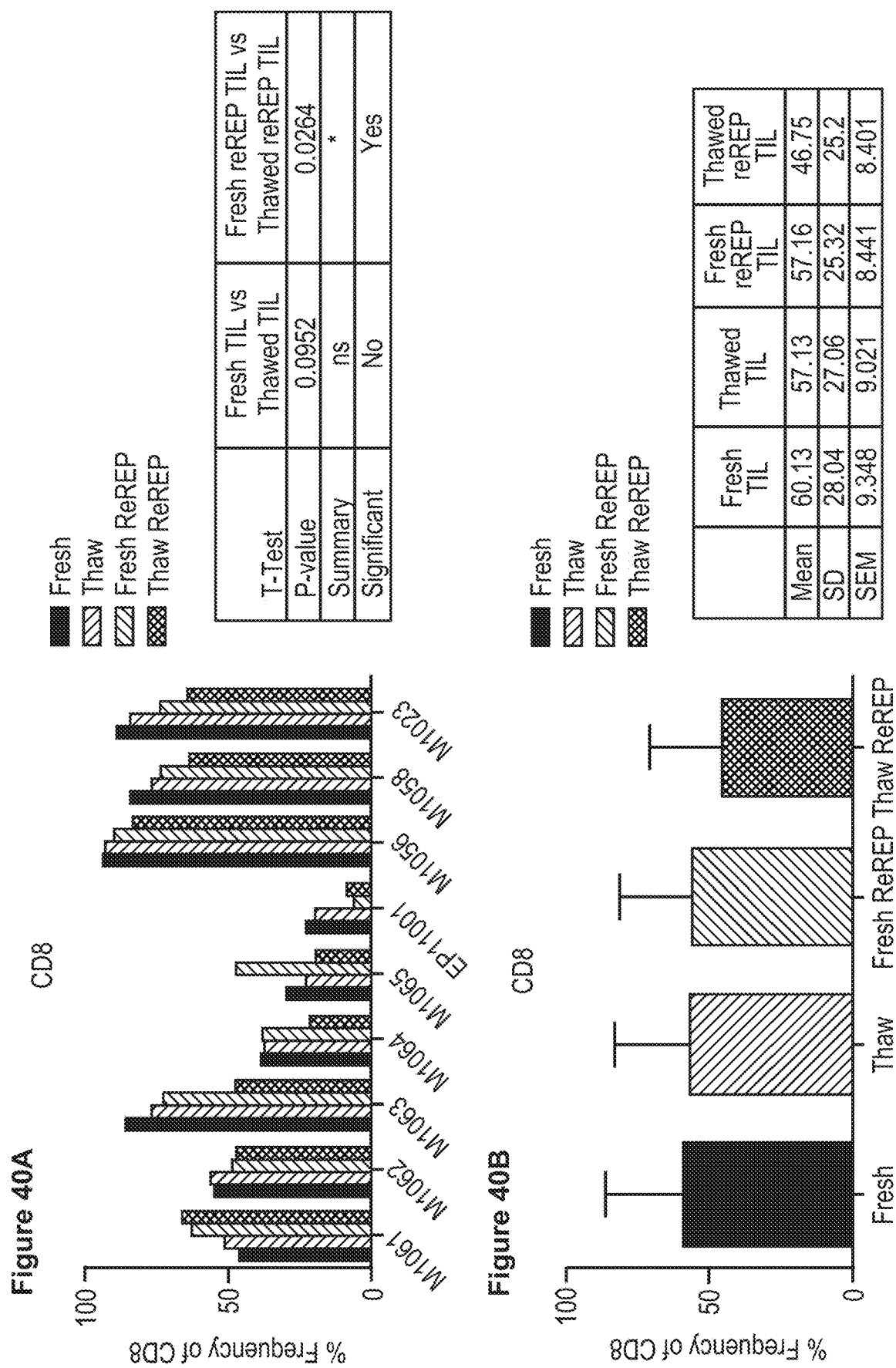

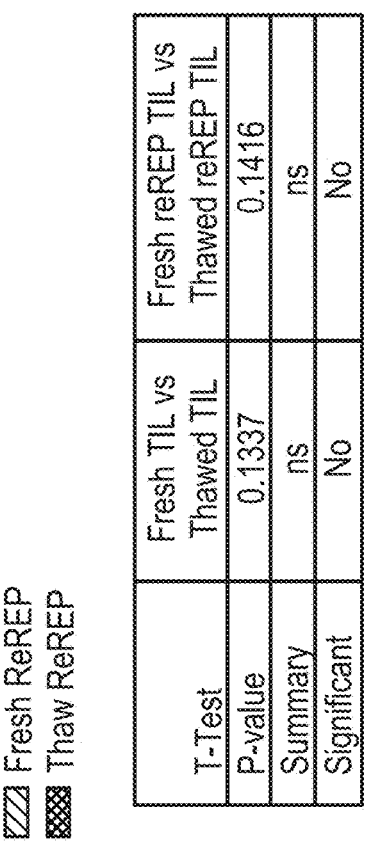
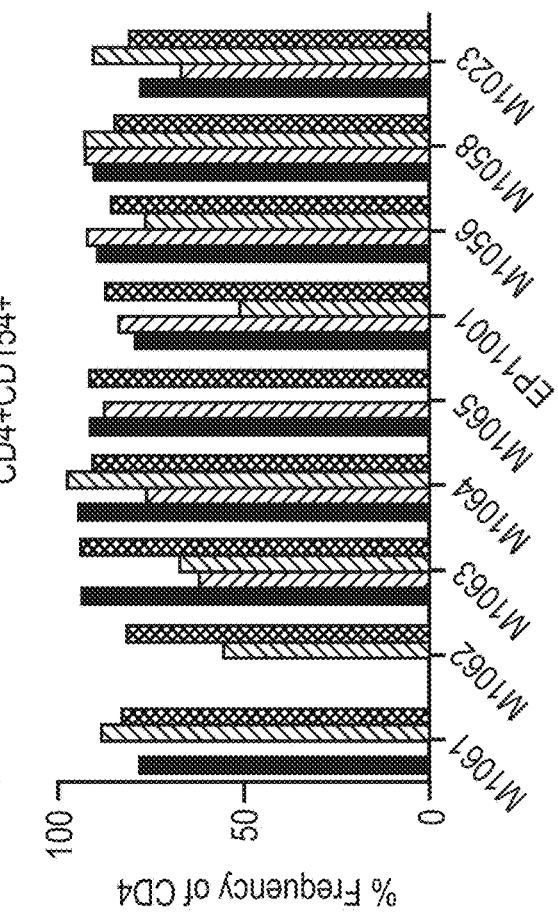
Figure 41A
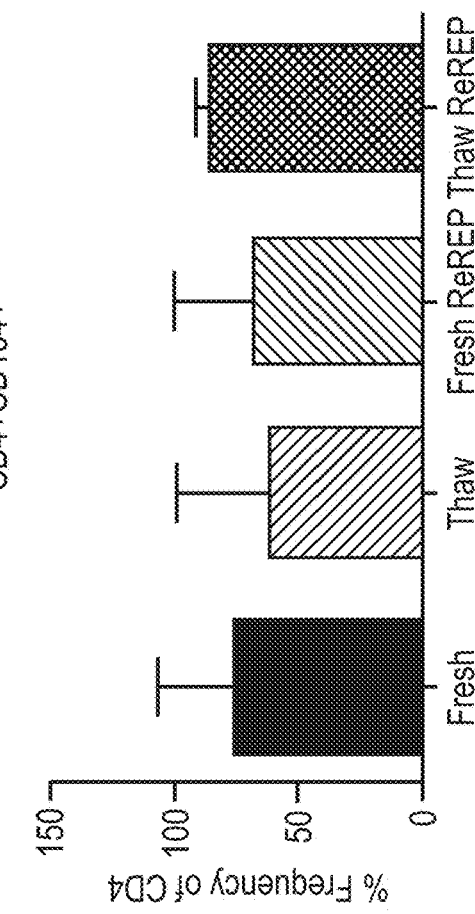
Figure 41B

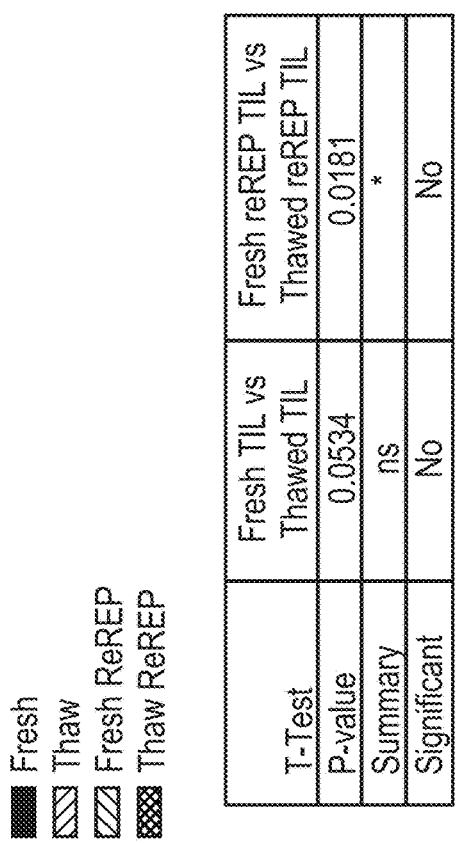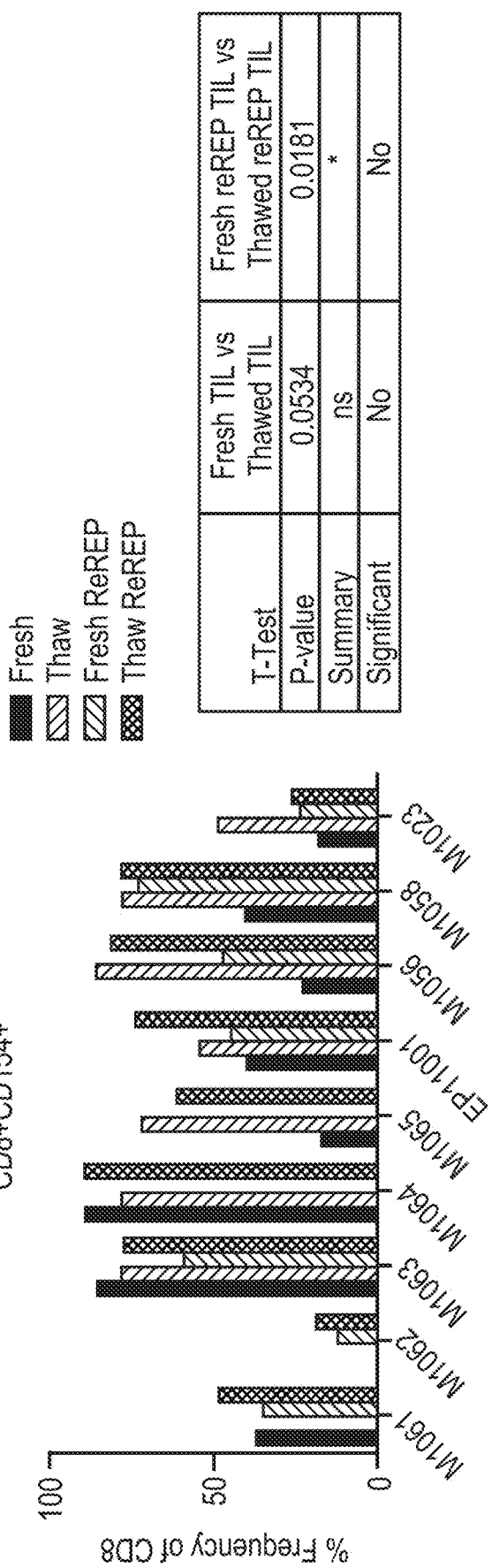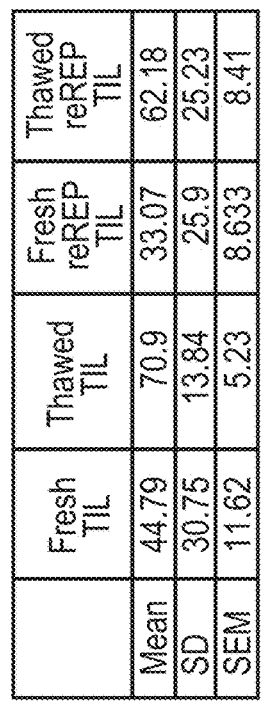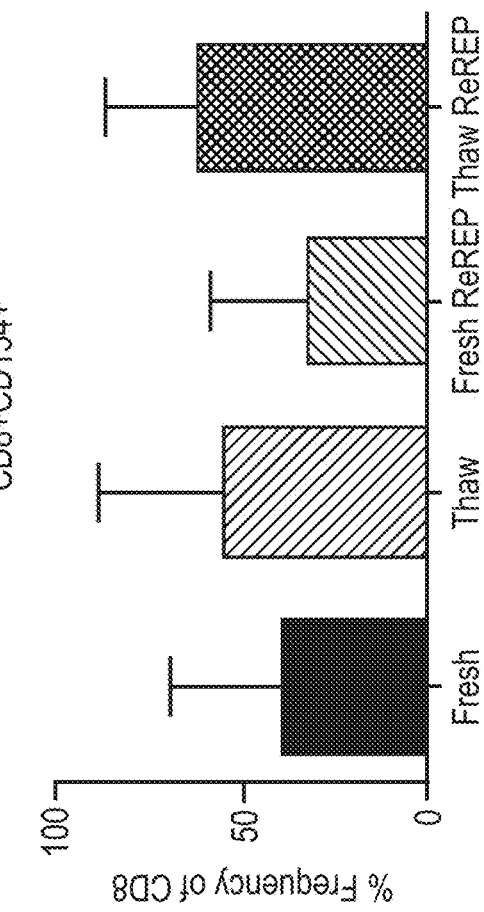
Figure 42A
Figure 42B

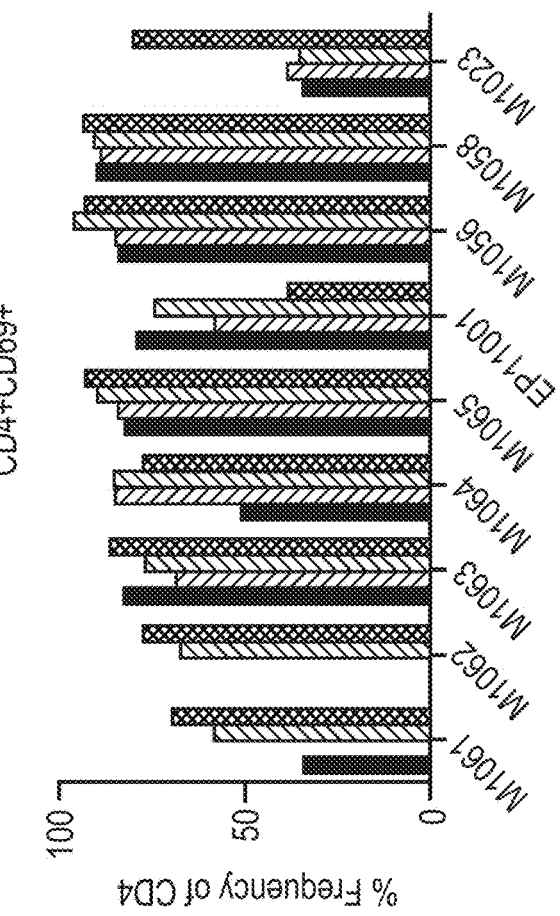
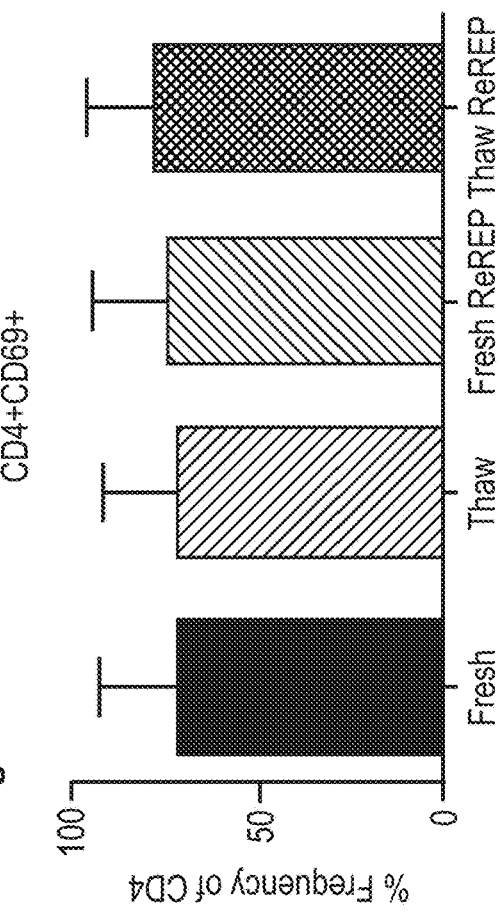
Figure 43A
Figure 43B

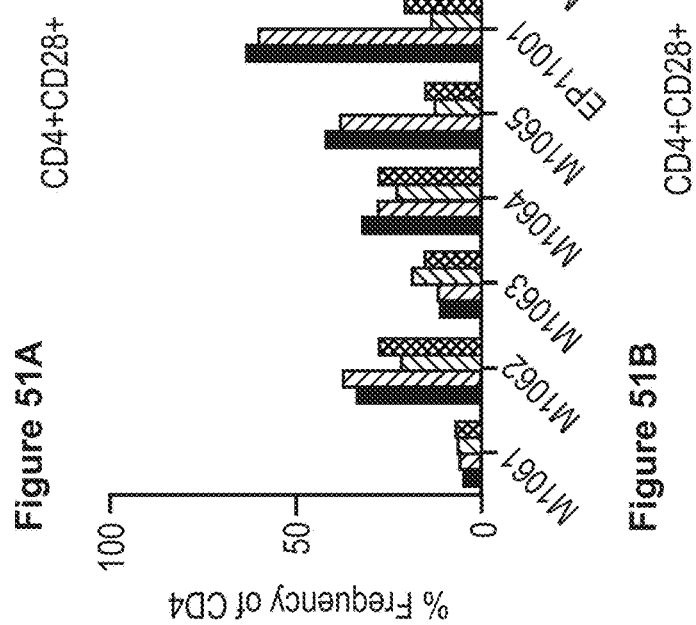
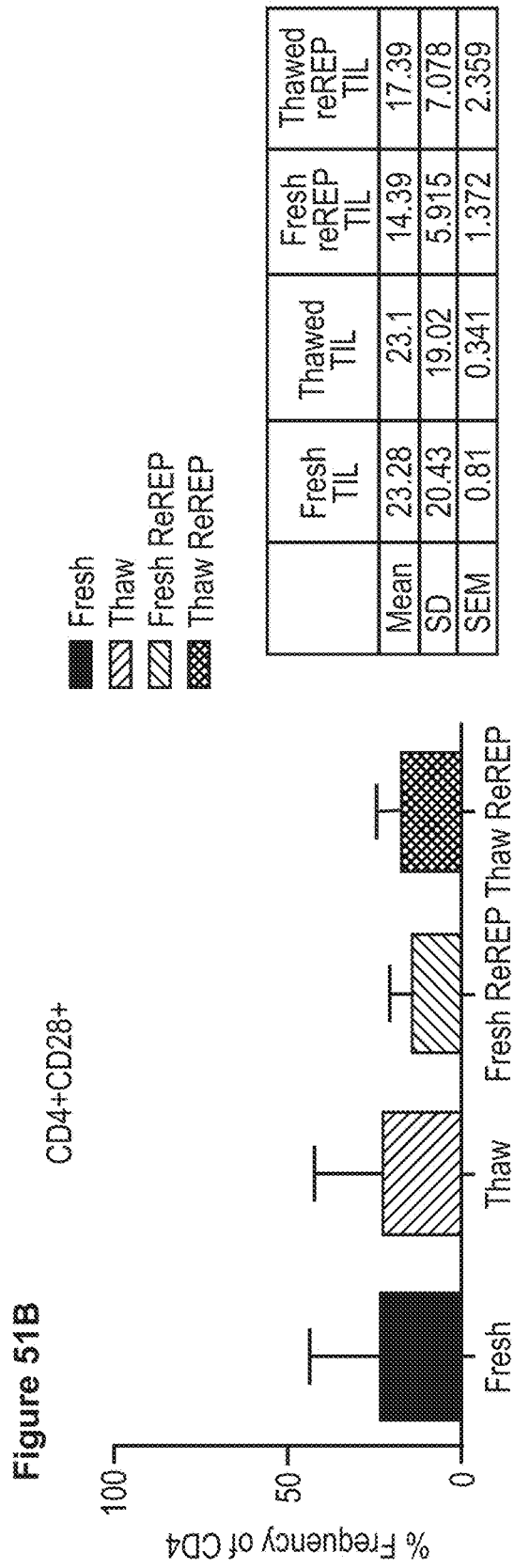
Figure 51A
Figure 51B

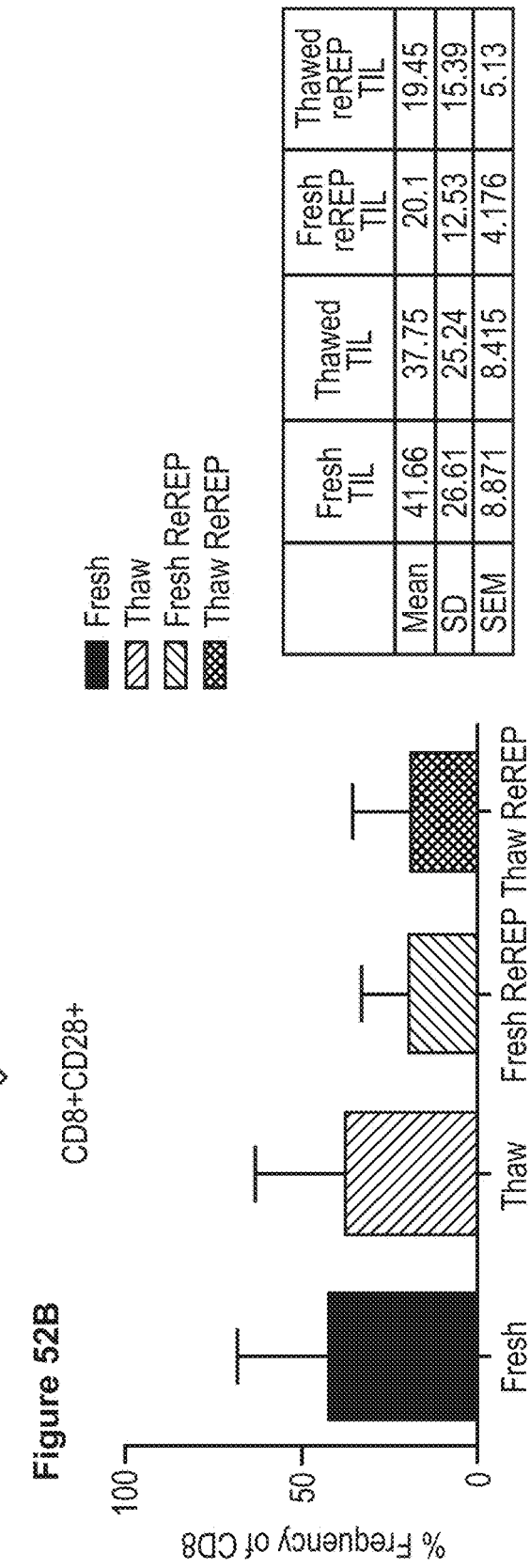
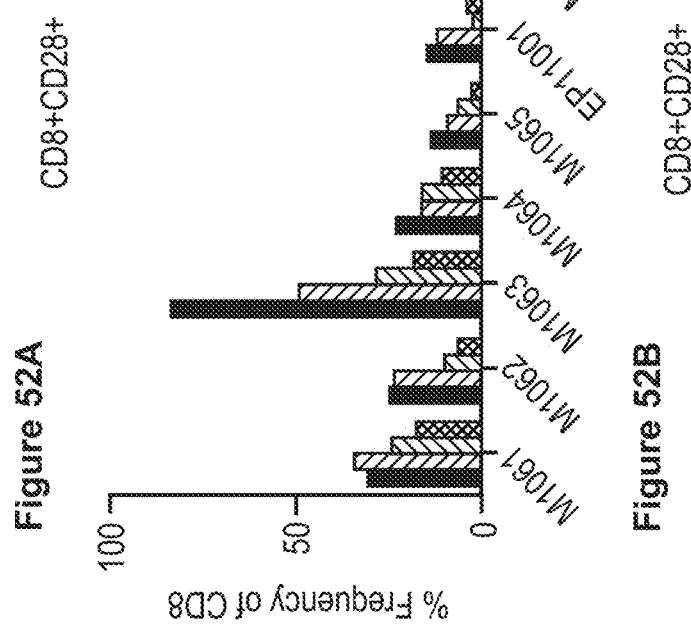
Figure 52A
Figure 52B

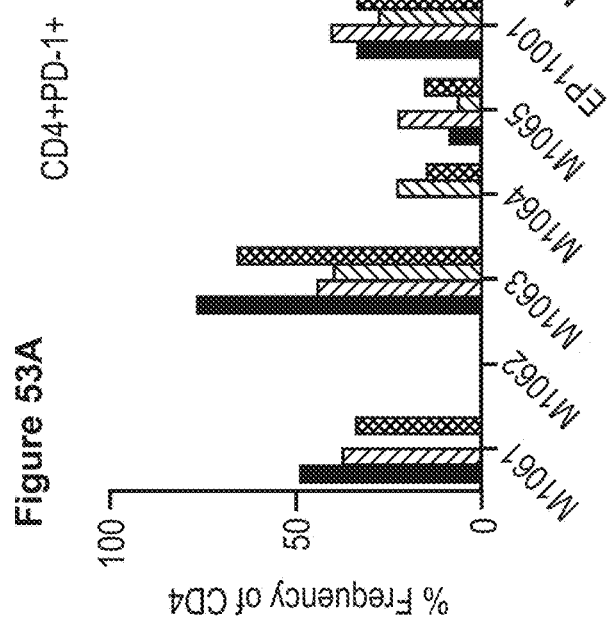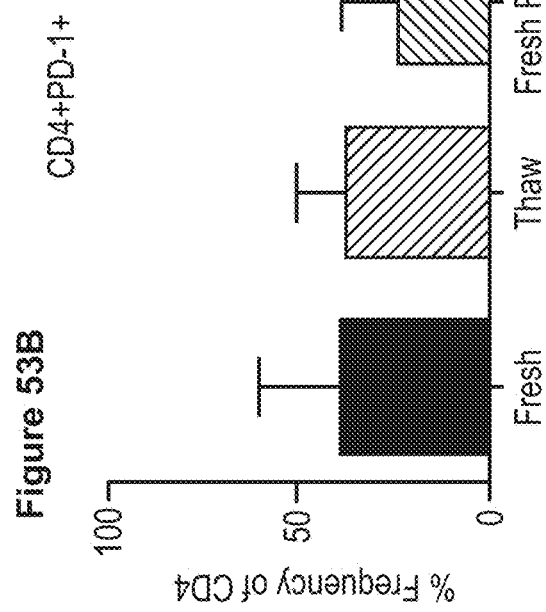
Figure 53A
Figure 53B

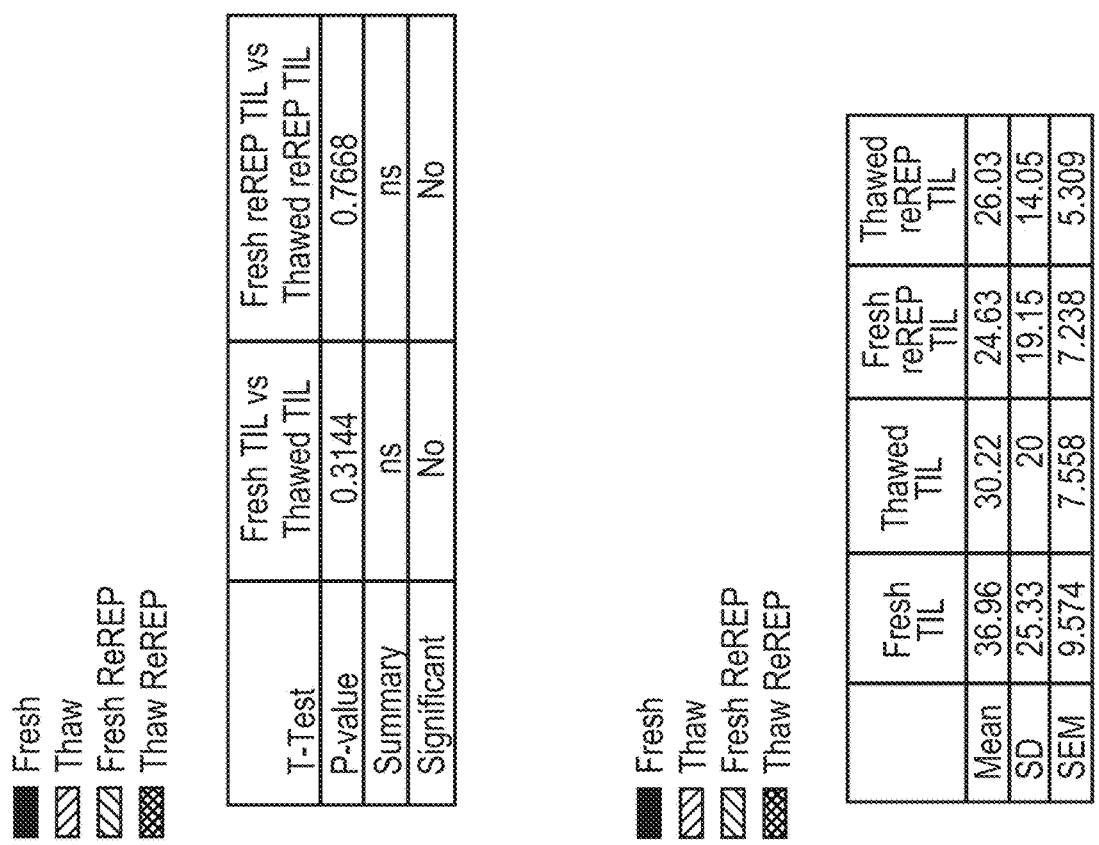
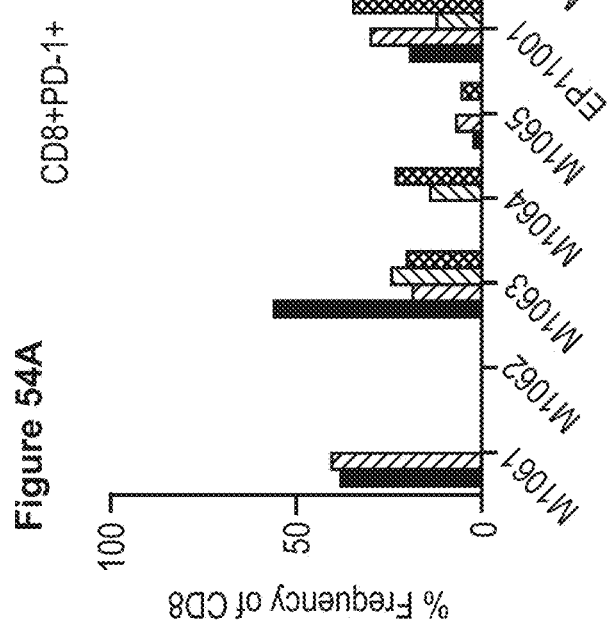
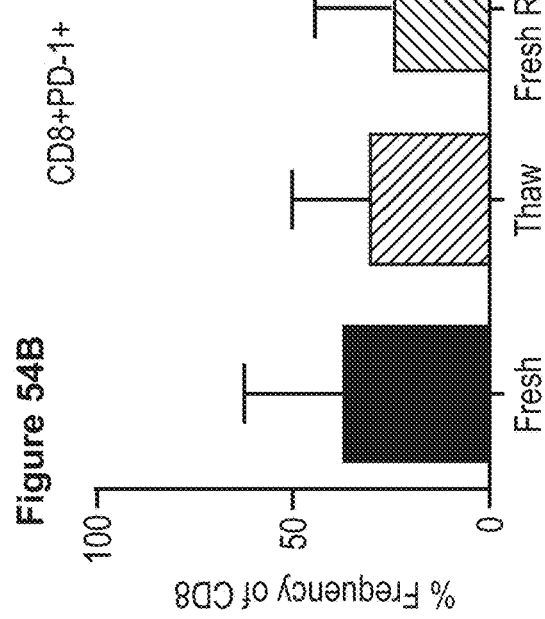
Figure 54A
Figure 54B

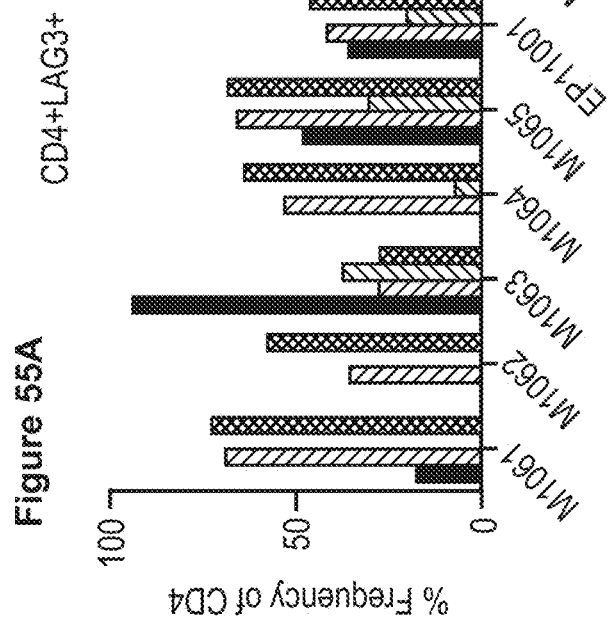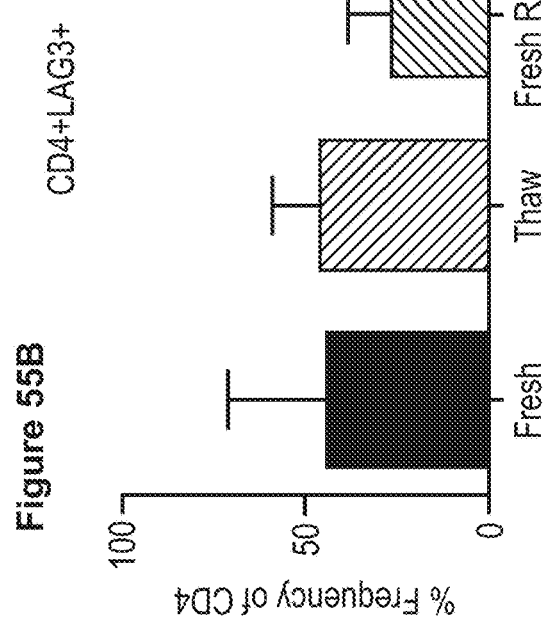
Figure 55A
Figure 55B

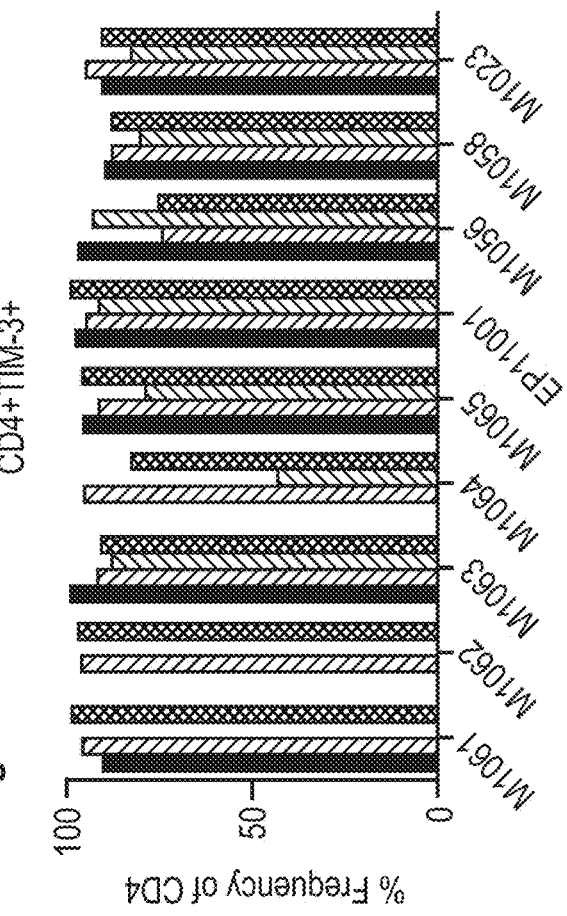
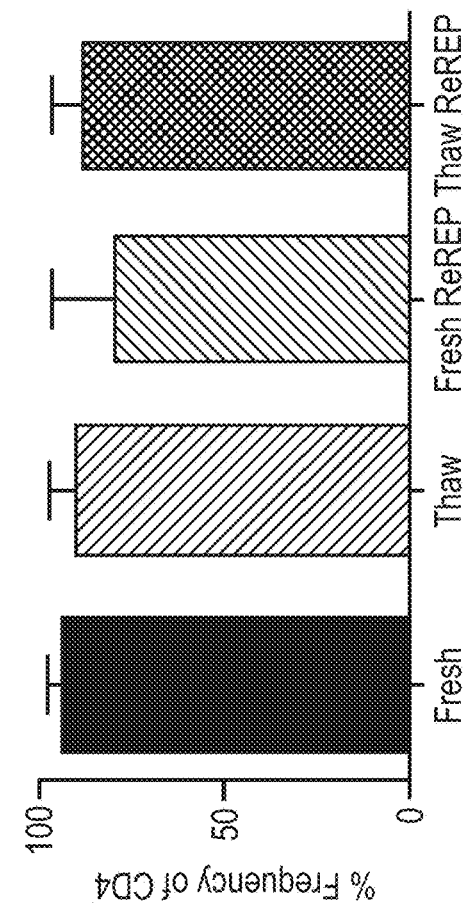
Figure 57A
Figure 57B

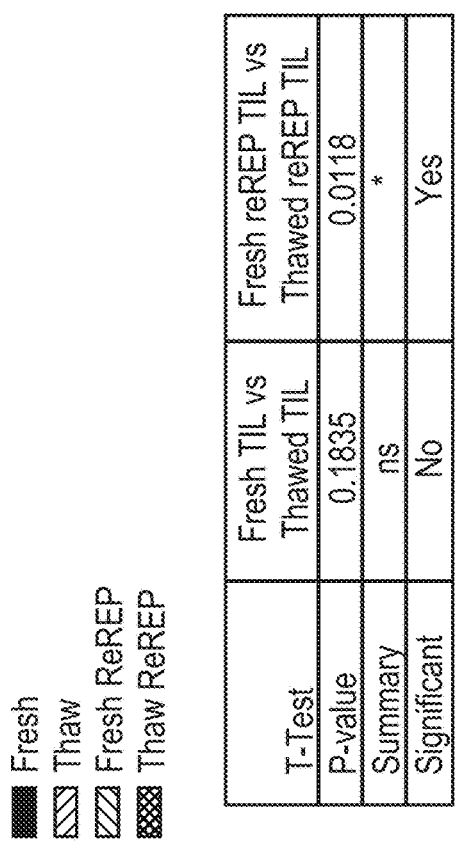
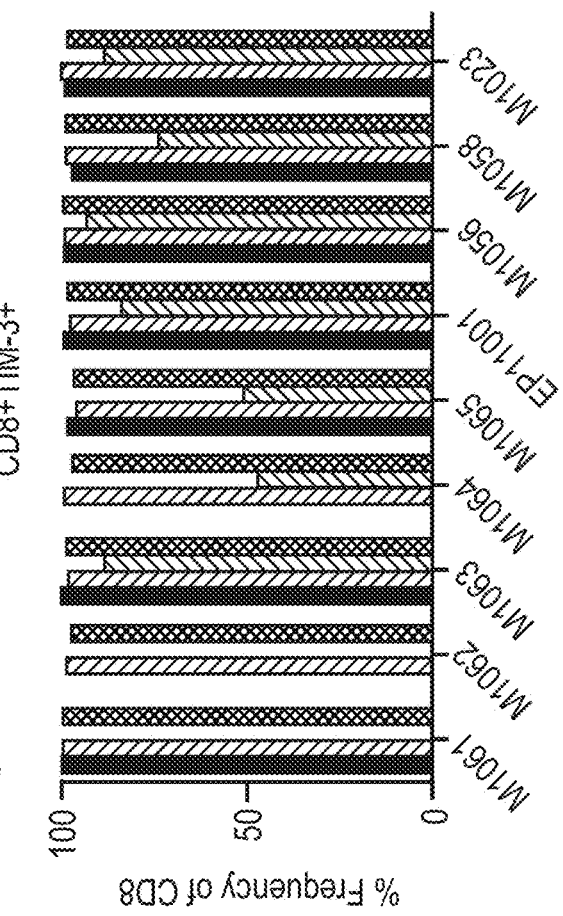
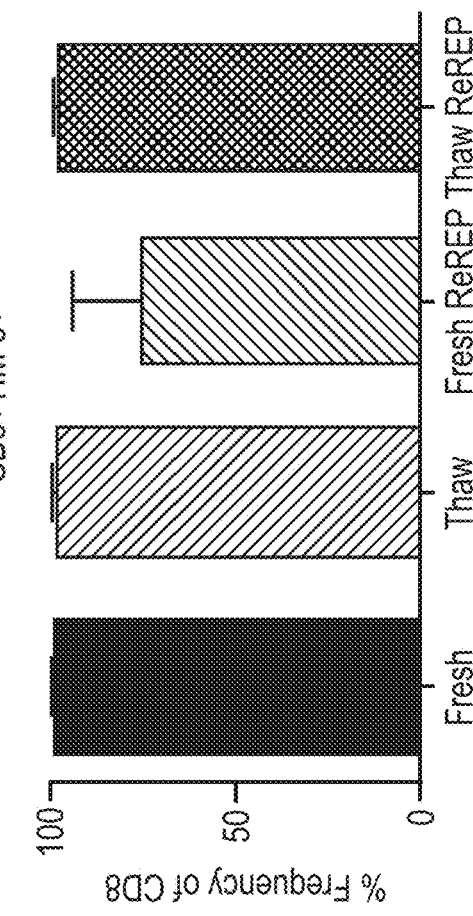
Figure 58A
Figure 58B

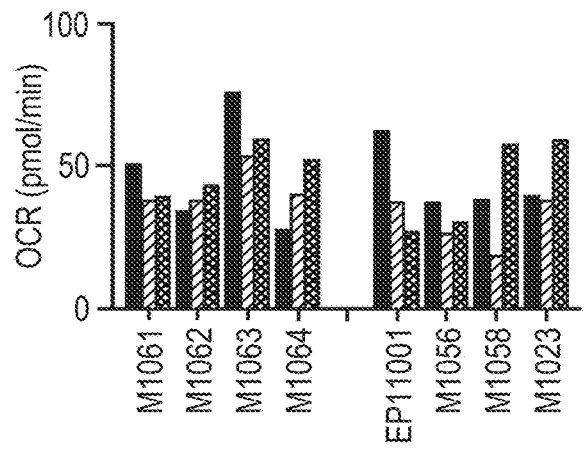
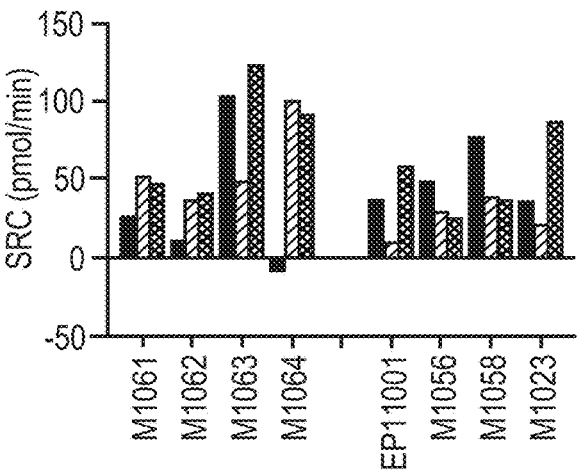
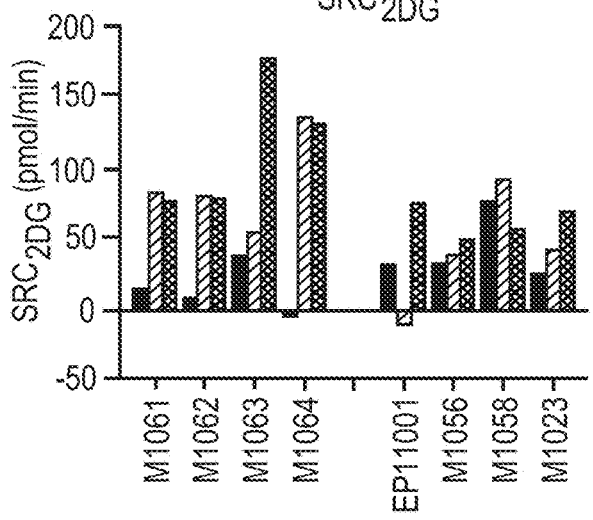
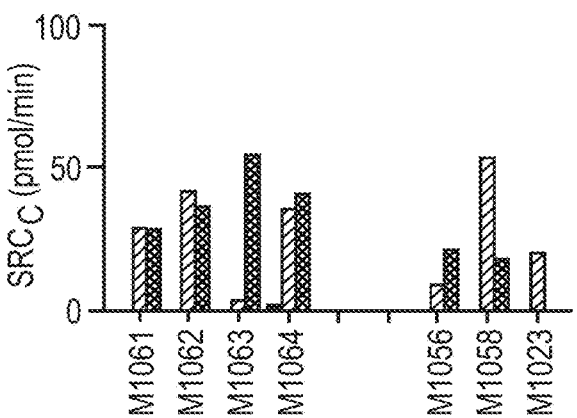
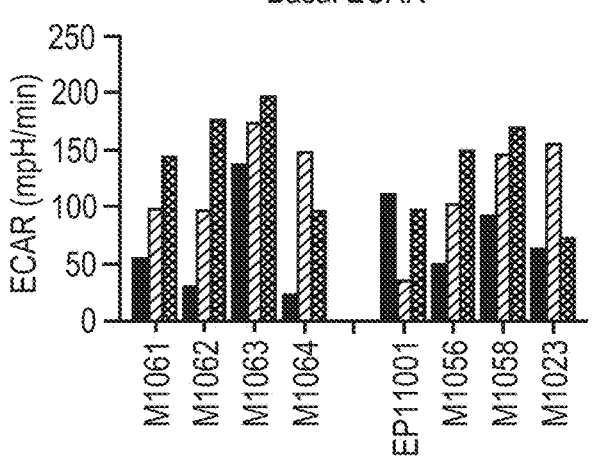
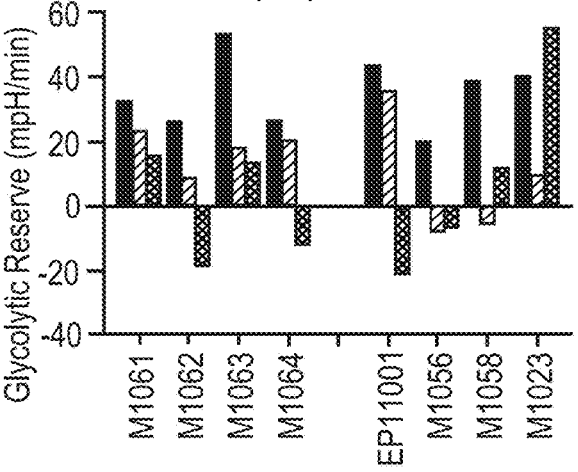

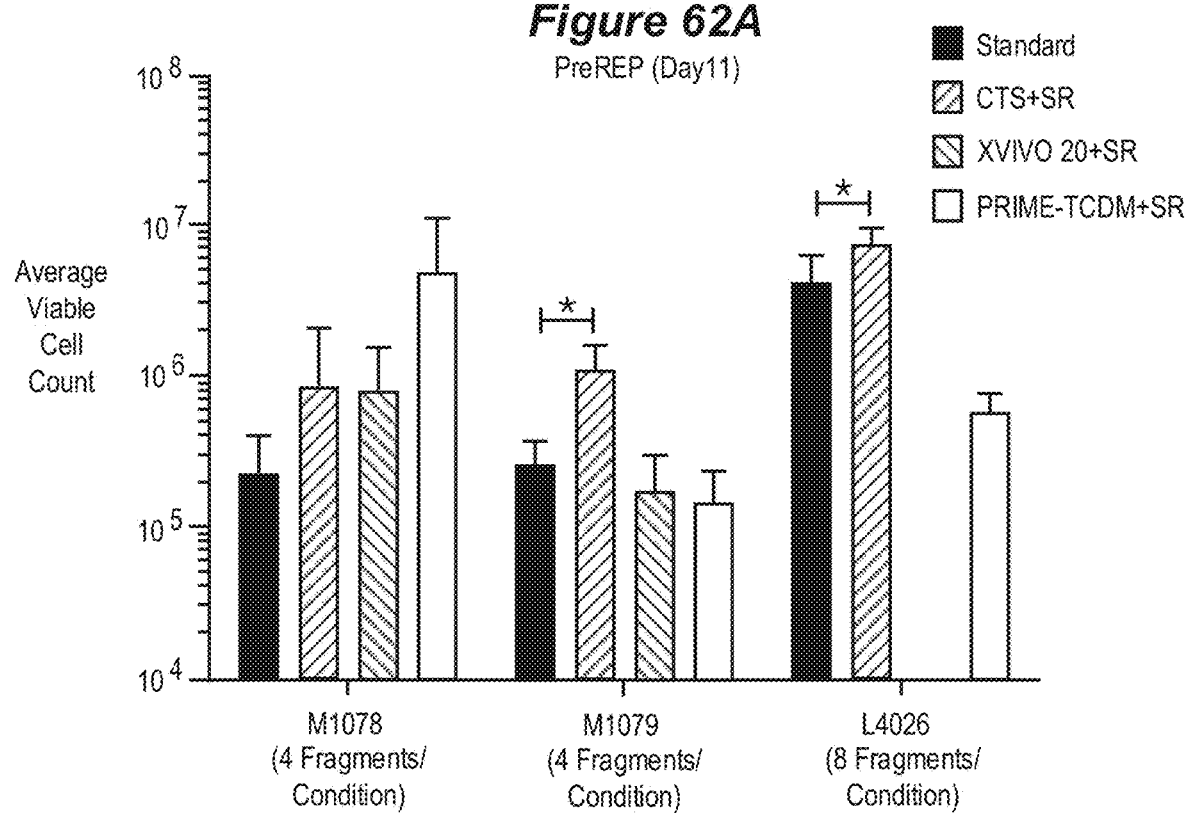
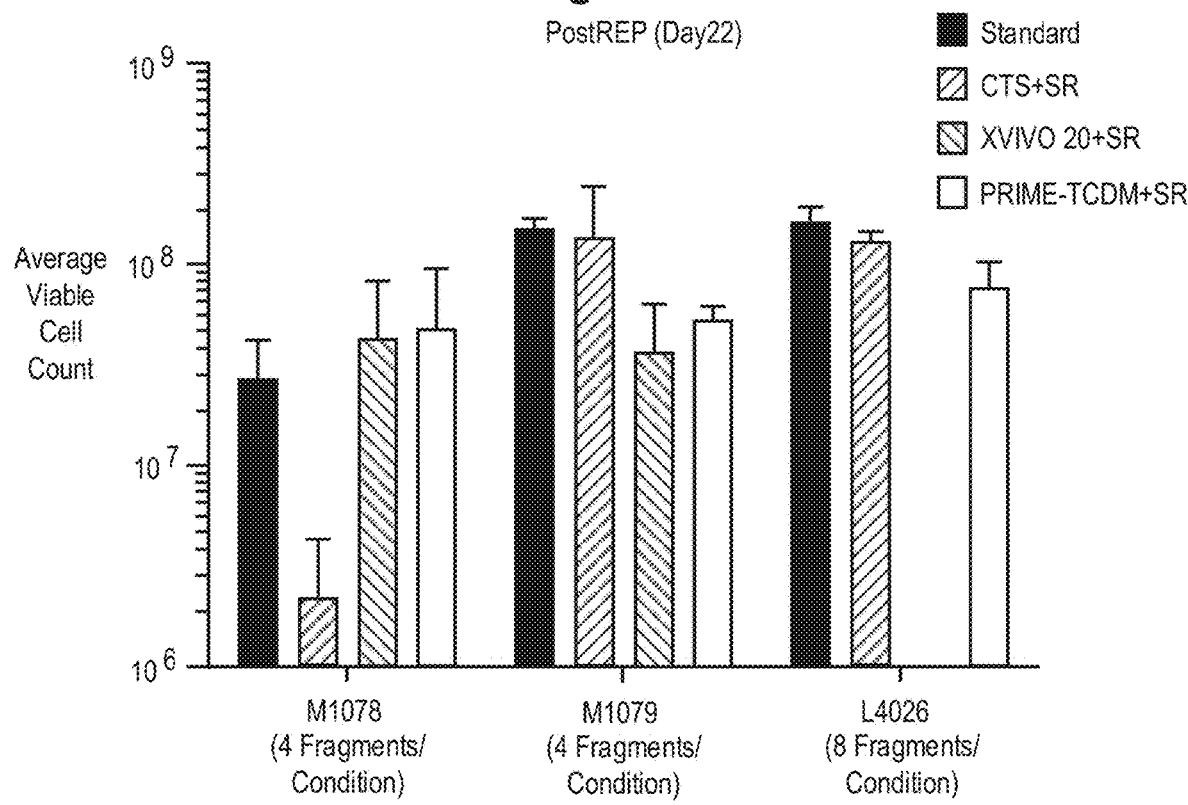

*Figure 65C*

|  | Pre-REP Cell count | | Post-REP Cell count | |
|---|---|---|---|---|
|  | Standard | CTS Optimizer +SR | Standard | CTS Optimizer +SR |
| M1078 | 6.82E+07 | 3.38E+08 | 3.46E+09 | 2.73E+08 |
| M1079 | 2.60E+06 | 1.09E+07 | 1.99E+10 | 5.61E+10 |
| M1080 |  |  |  |  |
| L4020 | 1.98E+08 | 1.27E+08 | 4.75E+10 | 3.99E+10 |
| L4026 | 1.68E+08 | 3.02E+08 | 8.63E+10 | 6.69E+10 |
| L4030 | 7.05E+07 | 7.48E+08 | 2.63E+10 | 5.96E+10 |
| EP11020 | 2.04E+06 | 1.06E+06 | 4.44E+10 | 7.14E+10 |
| T6030 | 1.61E+08 | 9.64E+08 | 2.98E+10 | 2.18E+10 |
| M1092 | 2.00E+07 | 7.05E+08 | 4.41E+09 | 2.02E+10 |
|  |  |  |  |  |

Figure 83

| Process 1C: 43-55 Days for Steps A - E | Process 2A: about 22 days from Steps A - E |
|---|---|
| 1. STEP A<br>Obtain Patient Tumor Sample | 1. STEP A<br>Obtain Patient Tumor Sample |
| 2. STEP B<br>Fragmentation and First Expansion<br>11 days to 21 days | 2. STEP B<br>Fragmentation and First Expansion<br>3 days to 14 days |
| 3. STEP C<br>First Expansion to Second Expansion Transition<br>Optional Storage until Selection | 3. STEP C<br>First Expansion to Second Expansion Transition<br>No Storage and Closed System |
| 4. STEP D<br>Second Expansion<br>IL-2, OKT-3, antigen-presenting feeder cells<br>Optionally repeat one or more times | 4. STEP D<br>Second Expansion<br>IL-2, OKT-3, and antigen-presenting feeder cells<br>Closed System |
| 5. STEP E<br>Harvest TILS from Step D | 5. STEP E<br>Harvest TILS from Step D<br>Closed System |
| 6. STEP F<br>Final Formulation and/or Transfer to Infusion Bag | 6. STEP F<br>Final Formulation and/or Transfer to Infusion Bag<br>(optionally cryopreserve) |

*Figure 84*

| Process Step | Process 1C Embodiment | Process 2A Embodiment | Advantages |
|---|---|---|---|
| Pre-REP | • 4 fragments per 10 GREX-10 flasks<br>• 11-21 day duration | • 40 fragments per 1 GREX-100M flask<br>• 11 day duration | • Increased tumor fragments per flask<br>• Shortened culture time<br>• Reduced number of steps<br>• Amenable to closed system |
| Pre-REP to REP Transition | • Pre-REP TIL are frozen until phenotyped for selection then thawed to proceed to the REP (~day 30)<br>• REP requires >40×10$^6$ TIL | • Pre-REP TIL directly move to REP on day 11<br>• REP requires 25-200×10$^6$ TIL | • Shortened pre-REP-to-REP process<br>• Reduced number of steps<br>• Eliminated phenotyping selection<br>• Amenable to closed system |
| REP | • 6 GREX-100M flasks on REP day 0<br>• 5×10$^6$ TIL and 5×10$^8$ PBMC feeders per flask on REP day 0<br>• Split to 18-36 flasks on REP day 7<br>• 14 day duration | • 1 GREX-500M flask on day 11<br>• 25-200×10$^6$ TIL and 5x10$^9$ PBMC feeders on day 11<br>• Split to ≤ 6 GREX-500M flasks on day 16<br>• 11 day duration | • Reduced number of steps<br>• Shorter REP duration<br>• Closed system transfer of TIL between flasks<br>• Closed system media exchanges |
| Harvest | • TIL harvested via centrifugation | • TIL harvested via LOVO automated cell washing system' | • Reduced number of steps<br>• Automated cell washing<br>• Closed system<br>• Reduced loss of product during wash |
| Final Formulation | • Fresh product in Hypothermosol<br>• Single infusion bag<br>• Limited shipping stability | • Cyropreserved product in PlasmaLyte-A + 1% HSA and CS10 stored in LN$_2$<br>• Multiple aliquots<br>• Longer shipping stability | • Shipping flexibility<br>• Flexible patient scheduling<br>• More timely release testing |
| Overall Estimated Process Time | • 43-55 days | • 22 days | • Faster turnaround to patient |

| DILUTION | AV | SD | UPPER LIMIT (AV + 3SD) | LOWER LIMIT (AV - 3SD) |
|---|---|---|---|---|
| 1 to 10 | 2976 | 203 | 3585 | 2367 |
| 1 to 100 | 322 | 39 | 440 | 204 |
| 1 to 1000 | 36 | 7 | 56 | 16 |

| DILUTION | RANGE (UPPER-LOWER) | EXP#1 (AV) | EXP#2 (AV) | EXP#3 (AV) |
|---|---|---|---|---|
| 1 to 10 | 3585-2367 | 2814 | 3282 | 2367 |
| 1 to 100 | 440-204 | 227 | 320 | 239 |
| 1 to 1000 | 56-16 | 27 | 25 | 32 |

Figure 94

| PROCESS STEP | GEN 1 | GEN 2 | IMPACT |
| --- | --- | --- | --- |
| Fragment Culture | ≤21 days, multiple bioreactors, multiple operator interventions | ≤11 days, single closed bioreactor, no intervention | Shortens culture, reduces interventions |
| TIL selection | IL-2 expanded TIL cryopreserved, tested, selection based on phenotype, thaw, rest, co-culture | Bulk TIL direct to co-culture | Reduces steps, eliminates testing, increases clonal diversity |
| Harvest/ Wash | Manual volume reduction and harvest. Manual wash and concentration | Closed semi-automated volume reduction and harvest. Automated wash and concentration | Reduces operator interventions, reduces processing time, maintains functionally closed system |
| Formulation | Fresh hypothermic product (2-8°C) | Cryopreserved product (≤ -150°C) | Allows for global trials through increased flexibility in shipping and patient scheduling |
| Manufacturing Time | 38 day process time | 22 day process time | Turnaround to patient, clean room throughput, lower cost of goods |

| Tumor Histology | # of studies demonstrating >20% enhancement of growth using IL-2/IL-15/IL-21 (compared to IL-2) |
|---|---|
| Melanoma | 1/5 (20%) |
| Lung | 3/8 (38%) |
| Colorectal | 7/11 (63%) |
| Cervical | 1/1 (100%) |
| Pancreatic | 2/2 (100%) |
| Glioblastoma | 1/1 (100%) |
| Triple Negative Breast | 1/2 (50%) |

Melanoma

Lung Carcinoma

Melanoma

Lung Carcinoma

Melanoma

Lung Carcinoma

*Figure 106A*
Melanoma
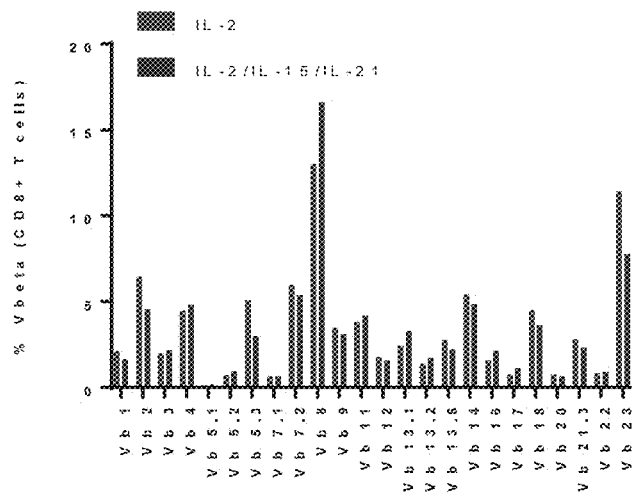
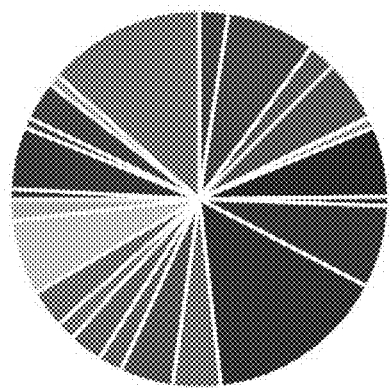
IL-2
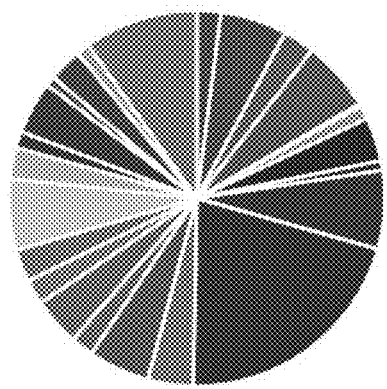
IL-2/IL-15/IL-21

Figure 106B
Lung Carcinoma
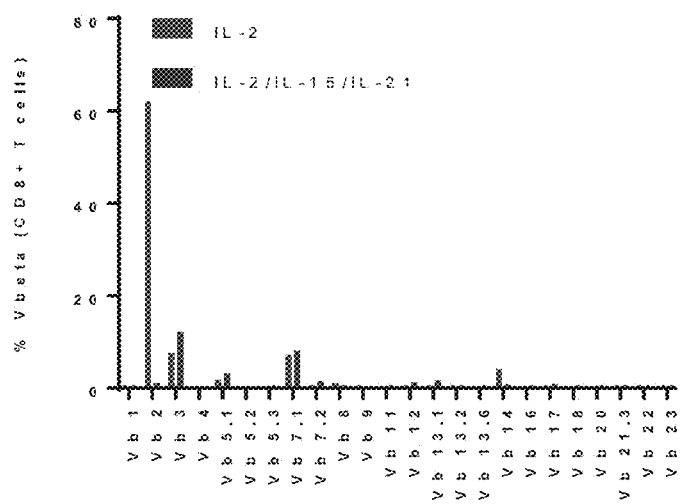
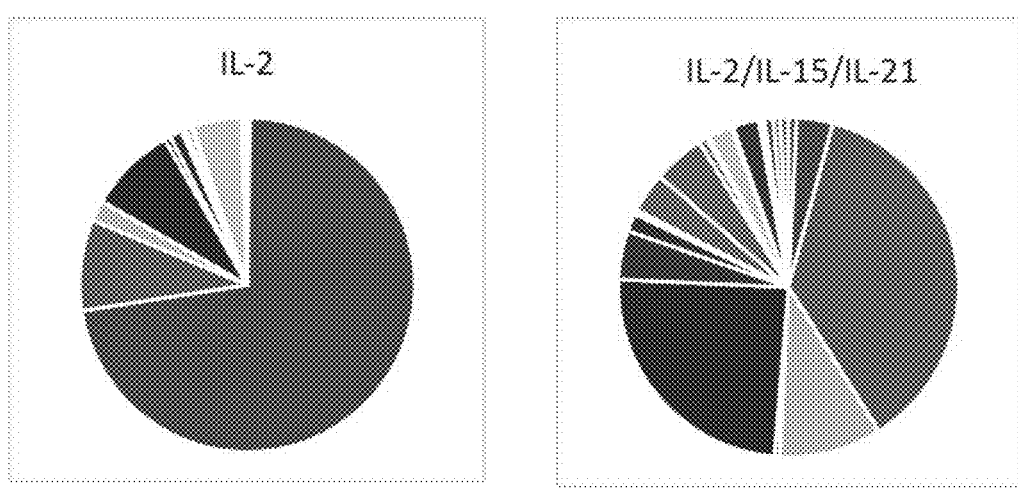

| CHARACTERISTIC | Historical Cohort 1* N = 16, (%) | Cohort 2 N = 13, (%) |
|---|---|---|
| Gender, n (%) | | |
| Male | 7 (44) | 5 (39) |
| Female | 9 (56) | 8 (62) |
| Age | | |
| Median | 55 | 54 |
| Min, Max | 41, 72 | 35, 66 |
| Prior therapies, n (%) | | |
| Mean # prior systemic therapies | 3 | 4 |
| Anti-CTLA-4 | 14 (88) | 13 (100) |
| Anti-PD-1 | 21 (100) | 13 (100) |
| Target Lesion Sum of Diameter (mm) | | |
| Mean (SD) | 104 (68) | 141 (102) |
| Min, Max | 15, 225 | 38, 342 |

| CHARACTERISTIC | Historical Cohort 1* N = 16, (%) | Cohort 2 N = 13, (%) |
|---|---|---|
| Baseline ECOG score, n (%) | | |
| 0 | 9 (56) | 8 (62) |
| 1 | 7 (44) | 5 (39) |
| BRAF Status, n (%) | | |
| Mutated | 9 (56) | 6 (46) |
| Wild Type | 7 (44) | 7 (54) |
| Baseline LDH (U/L [SD]) | | |
| 1-2 times ULN | 7 (44) | 7 (54) |
| Min, Max | 1 (6) | 2 (15) |
| Number of Target & Non-Target Lesions (at Base Line) | | |
| >3 | 12(75) | 10(77) |
| Mean | 5.6 | 5.5 |

*Figure 109*

|  | Historical Cohort 1 (N = 16) | | | Cohort 2 (N = 13) | | |
|---|---|---|---|---|---|---|
| PREFERRED TERM | Any Grade n (%) | Grade 3/4 n (%) | Grade 5 n (%) | Any Grade n (%) | Grade 3/4 n (%) | Grade 5 n (%) |
| Number of patients reporting at least one Treatment-Emergent AE | 14 (87.5) | 14 (87.5) | 0 | 12 (85.7) | 11 (78.6) | 0 |
| Nausea | 14 (87.5) | 0 | 0 | 7 (53.8) | 0 | 0 |
| Platelet count decreased | 12 (75.0) | 12 (75.0) | 0 | 7 (53.8) | 6 (46.2) | 0 |
| Anaemia | 11 (68.8) | 8 (50.0) | 0 | 8 (61.5) | 7 (53.8) | 0 |
| Neutrophil count decreased | 11 (68.8) | 11 (68.8) | 0 | 6 (46.2) | 6 (46.2) | 0 |
| Febril neutropenia | 10 (62.5) | 10 (62.5) | 0 | 7 (53.8) | 6 (46.2) | 0 |
| White blood count decreased | 10 (62.5) | 10 (62.5) | 0 | 6 (46.2) | 6 (46.2) | 0 |
| Chills | 9 (56.3) | 0 | 0 | 6 (46.2) | 1 (7.7) | 0 |
| Diarrhoea | 8 (50.0) | 1 (6.3) | 0 | 4 (30.8) | 0 | 0 |
| Fatigue | 7 (43.8) | 0 | 0 | 7 (53.8) | 0 | 0 |
| Vomiting | 7 (43.8) | 0 | 0 | 2 (15.4) | 0 | 0 |
| Constipation | 6 (37.5) | 0 | 0 | 3 (23.1) | 0 | 0 |
| Decreased appetite | 5 (31.3) | 0 | 0 | 4 (30.8) | 0 | 0 |
| Headache | 5 (31.3) | 0 | 0 | 3 (23.1) | 0 | 0 |
| Hypocalcaemia | 5 (31.3) | 0 | 0 | 1 (7.7) | 0 | 0 |
| Hypokalaemia | 5 (31.3) | 0 | 0 | 3 (23.1) | 0 | 0 |
| Hypophosphataemia | 5 (31.3) | 5 (31.3) | 0 | 4 (23.1) | 1 (7.7) | 0 |
| Hypotension | 5 (31.3) | 2 (12.5) | 0 | 3 (23.1) | 3 (7.7) | 0 |
| Lymphocyte count decreased | 5 (31.3) | 5 (31.3) | 0 | 3 (23.1) | 3 (23.1) | 0 |
| Nasal Congestion | 5 (31.3) | 0 | 0 | 0 | 0 | 0 |
| Pyrexia | 5 (31.3) | 0 | 0 | 9 (69.2) | 1 (7.7) | 0 |
| Cough | 4 (25.0) | 0 | 0 | 4 (30.8) | 0 | 0 |
| Oedema peripheral | 4 (25.0) | 0 | 0 | 4 (30.8) | 0 | 0 |
| Pruritus | 4 (25.0) | 0 | 0 | 4 (30.8) | 0 | 0 |

Notes: Adverse events are coded by MedDRA version 18.1.

Patients with multiple events for a given preferred term are counted only once using the maximum grade under each preferred term.

Events are sorted by decreasing frequency of preferred term under SOC per any grade.

Treatment-Emergent Adverse Events refer to all AEs starting on or after the first dose date of pre-treatment chemotherapy(Fludarabine and Cyclophosphamide) up to the last dose of IL2 + 30 days.

*Figure 110*

| CHARACTERISTIC | Cohort 2<br>N = 17, (%) |
|---|---|
| Gender, n (%) | |
|   Male | 8 (47) |
|   Female | 9 (53) |
| Age | |
|   Median | 54 |
|   Min, Max | 35, 66 |
| Prior therapies, n (%) | |
|   Mean # prior systemic therapies | 3.6 |
|   Anti-CTLA-4 | 15 (88) |
|   Anti-PD-1 | 16 (94) |
| Target Lesion Sum of Diameter (mm) | |
|   Mean (SD) | 140 (93) |
|   Min, Max | 38, 342 |

| CHARACTERISTIC | Cohort 2<br>N = 17, (%) |
|---|---|
| Baseline ECOG, n (%) | |
|   0 | 11 (65) |
|   1 | 6 (35) |
| BRAF Status, n (%) | |
|   Mutated | 5 (29) |
|   Wild Type | 9 (53) |
|   Unknown | 3 (18) |
| Baseline LDH (U/L [SD]) | |
|   1-2 times ULN | 8 (47) |
|   > 2 times ULN | 2 (12) |
| Number of Target & Non-Target Lesions (at Base Line) | |
|   > 3 | 12 (71) |
|   Mean | 5.9 |

Cohort 2 has:

3.6 median prior therapies

High tumor burden at baseline as reflected by 140 mm sum of diameters for target lesions

*Figure 116*

| PREFERRED TERM | Cohort 2 (N = 17) | | |
| --- | --- | --- | --- |
| | Any Grade n (%) | Grade 3/4 n (%) | Grade 5 n (%) |
| Number of patients reporting at least one Treatment-Emergent AE | 16 (94.1) | 16 (94.1) | 0 |
| Pyrexia | 13 (76.5) | 1 (5.9) | 0 |
| Anaemia | 11 (64.7) | 10 (58.8) | 0 |
| Neutrophil count decreased | 10 (58.8) | 10 (58.8) | 0 |
| Platelet count decreased | 10 (58.8) | 8 (47.1) | 0 |
| Februle neutropenia | 10 (58.8) | 8 (47.1) | 0 |
| Fatigue | 10 (58.8) | 0 | 0 |
| Chills | 9 (52.9) | 1 (5.9) | 0 |
| Nausea | 9 (52.9) | 0 | 0 |
| White blood cell count decreased | 8 (47.1) | 8 (47.1) | 0 |
| Lymphocyte count decreased | 6 (35.3) | 6 (35.3) | 0 |
| Diarroea | 6 (35.3) | 0 | 0 |
| Decreased appetite | 6 (35.3) | 0 | 0 |

Notes: Patients with multiple events for a given preferred term are counted only once using the maximum grade under each preferred term. Treatment-Emergent Adverse Events refer to all AEs starting on or after the first dose date of pre-treatment chemotherapy (Fludarabine and Cyclophosphamide) up to the last dose of IL-2 + 30 days.

| RESPONSE | PATIENTS, N=10 n (%) |
|---|---|
| Objective Response Rate | 4 (40%) |
| Disease Control Rate | 8 (80%) |
| Partial Response | 4 (40%) |
| Stable Disease | 4 (40%) |
| Progressive Disease | 1 (10%) |
| Non-Evaluable* | 1 (10%) |

Cervical Carcinoma (C-145-04)

| Pt No | INFUSION | # CELLS INFUSED | RESPONSE DAY 42 | RESPONSE DAY 84 | RESPONSE DAY 126 | RESPONSE AT 6 MONTHS | RESPONSE AT 9 MONTHS | BOR |
|---|---|---|---|---|---|---|---|---|
| 1 | 9-Aug-17 | 32.6 bil | PR | PR | - | - | - | - |
| 2 | 19-Sep-17 | 41.4 bil | SD (needs confirmation) | - | - | - | - | - |

HNSCC (C-145-03)

| Pt No | INFUSION | # CELLS INFUSED | RESPONSE DAY 28 | RESPONSE DAY 56 | RESPONSE DAY 84 | RESPONSE AT 4 MONTHS | RESPONSE AT 6 MONTHS | BOR |
|---|---|---|---|---|---|---|---|---|
| 1 | 31-May-17 | 21 bil | SD | PD | Discon. | - | - | SD |
| 2 | 20-Jun-17 | 21 bil | PR | SD | SD | Passed away. | - | SD |
| 3 | 1-Aug-17 | 30 bil | PR | PR | PR | PD | - | PR |
| 4 | 14-Sep-17 | 65 bil | PR | PR | - | - | - | PR |
| 5 | 03-Nov-17 | 10 bil | - | - | - | - | - | - |
| 6 | 07-Nov-17 | 37 bil | - | - | - | - | - | - |
| 7 | 08-Nov-17 | 21.5 bil | - | - | - | - | - | - |

Median Prior therapies for HNSCC: 4, all have had poor anti-PD-1. The data is live and subject to change.

*Figure 127*

PROCESSES FOR PRODUCTION OF TUMOR INFILTRATING LYMPHOCYTES AND USES OF SAME IN IMMUNOTHERAPY

CROSS-REFERENCE TO RELATED APPLICATIONS

This application is a continuation of U.S. patent application Ser. No. 17/147,412, filed on Jan. 12, 2021, which is a continuation of U.S. patent application Ser. No. 17/041,305, filed Sep. 24, 2020, which is a National Phase entry of International Patent Application No. PCT/US2018/040474, filed Jun. 29, 2018, which claims priority to U.S. patent application Ser. No. 15/940,901, filed on Mar. 29, 2018, which are hereby incorporated by reference in their entireties.

This application is a continuation of U.S. patent application Ser. No. 17/147,412, filed on Jan. 12, 2021, which continuation of U.S. patent application Ser. No. 17/110,179, filed Dec. 2, 2020, which is a continuation of U.S. patent application Ser. No. 15/940,901, filed Mar. 29, 2018, now U.S. Pat. No. 10,918,666, which is a continuation-in-part of U.S. patent application Ser. No. 15/863,634, filed on Jan. 5, 2018, now U.S. Pat. No. 10,894,063, which claims priority to U.S. Provisional Patent Application No. 62/478,506, filed on Mar. 29, 2017, U.S. Provisional Patent Application No. 62/539,410, filed on Jul. 31, 2017, U.S. Provisional Patent Application No. 62/548,306, filed on Aug. 21, 2017, U.S. Provisional Patent Application No. 62/554,538, filed on Sep. 5, 2017, U.S. Provisional Patent Application No. 62/559,374, filed on Sep. 15, 2017, U.S. Provisional Patent Application No. 62/567,121, filed on Oct. 2, 2017, U.S. Provisional Patent Application No. 62/577,655, filed on Oct. 26, 2017, U.S. Provisional Patent Application No. 62/582,874, filed on Nov. 7, 2017, and U.S. Provisional Patent Application No. 62/596,374, filed on Dec. 8, 2017, which are hereby incorporated by reference in their entireties.

SEQUENCE LISTING

The instant application contains a Sequence Listing which has been submitted electronically in XML file format and is hereby incorporated by reference in its entirety. Said XML file, created on Aug. 26, 2022, is named 116983-5036-US_Sequence_Listing.xml and is 72,616 bytes in size.

BACKGROUND OF THE INVENTION

Treatment of bulky, refractory cancers using adoptive transfer of tumor infiltrating lymphocytes (TILs) represents a powerful approach to therapy for patients with poor prognoses. Gattinoni, et al., *Nat. Rev. Immunol.* 2006, 6, 383-393. A large number of TILs are required for successful immunotherapy, and a robust and reliable process is needed for commercialization. This has been a challenge to achieve because of technical, logistical, and regulatory issues with cell expansion. IL-2-based TIL expansion followed by a "rapid expansion process" (REP) has become a preferred method for TIL expansion because of its speed and efficiency. Dudley, et al., *Science* 2002, 298, 850-54; Dudley, et al., *J. Clin. Oncol.* 2005, 23, 2346-57; Dudley, et al., *J. Clin. Oncol.* 2008, 26, 5233-39; Riddell, et al., *Science* 1992, 257, 238-41; Dudley, et al., *J. Immunother.* 2003, 26, 332-42. REP can result in a 1,000-fold expansion of TILs over a 14-day period, although it requires a large excess (e.g., 200-fold) of irradiated allogeneic peripheral blood mononuclear cells (PBMCs, also known as mononuclear cells (MNCs)), often from multiple donors, as feeder cells, as well as anti-CD3 antibody (OKT3) and high doses of IL-2. Dudley, et al., *J. Immunother.* 2003, 26, 332-42. TILs that have undergone an REP procedure have produced successful adoptive cell therapy following host immunosuppression in patients with melanoma. Current infusion acceptance parameters rely on readouts of the composition of TILs (e.g., CD28, CD8, or CD4 positivity) and on fold expansion and viability of the REP product.

Current TIL manufacturing processes are limited by length, cost, sterility concerns, and other factors described herein such that the potential to commercialize such processes is severely limited, and for these and other reasons, at the present time no commercial process has become available. There is an urgent need to provide TIL manufacturing processes and therapies based on such processes that are appropriate for commercial scale manufacturing and regulatory approval for use in human patients at multiple clinical centers.

BRIEF SUMMARY OF THE INVENTION

The present invention provides improved and/or shortened methods for expanding TILs and producing therapeutic populations of TILs.

The present invention provides a method for expanding tumor infiltrating lymphocytes (TILs) into a therapeutic population of TILs comprising:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2 and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) harvesting the therapeutic population of TILs obtained from step (d), wherein the transition from step (d) to step (e) occurs without opening the system; and
(f) transferring the harvested TIL population from step (e) to an infusion bag, wherein the transfer from step (e) to (f) occurs without opening the system.
In some embodiments, the method further comprises the step of cryopreserving the infusion bag comprising the harvested TIL population in step (f) using a cryopreservation process.

In some embodiments, the cryopreservation process is performed using a 1:1 ratio of harvested TIL population to cryopreservation media.

In some embodiments, the antigen-presenting cells are peripheral blood mononuclear cells (PBMCs). In some embodiments, the PBMCs are irradiated and allogeneic. In some embodiments, the PBMCs are added to the cell culture on any of days 9 through 14 in step (d). In some embodiments, the antigen-presenting cells are artificial antigen-presenting cells.

In some embodiments, the harvesting in step (e) is performed using a membrane-based cell processing system.

In some embodiments, the harvesting in step (e) is performed using a LOVO cell processing system.

In some embodiments, the multiple fragments comprise about 4 to about 50 fragments, wherein each fragment has a volume of about 27 mm$^3$.

In some embodiments, the multiple fragments comprise about 30 to about 60 fragments with a total volume of about 1300 mm$^3$ to about 1500 mm$^3$.

In some embodiments, the multiple fragments comprise about 50 fragments with a total volume of about 1350 mm$^3$.

In some embodiments, the multiple fragments comprise about 50 fragments with a total mass of about 1 gram to about 1.5 grams.

In some embodiments, the cell culture medium is provided in a container selected from the group consisting of a G-container and a Xuri cellbag.

In some embodiments, the cell culture medium in step (d) further comprises IL-15 and/or IL-21.

In some embodiments, the IL-2 concentration is about 10,000 IU/mL to about 5,000 IU/mL.

In some embodiments, the IL-15 concentration is about 500 IU/mL to about 100 IU/mL.

In some embodiments, the IL-21 concentration is about 20 IU/mL to about 0.5 IU/mL.

In some embodiments, the infusion bag in step (f) is a HypoThermosol-containing infusion bag.

In some embodiments, the cryopreservation media comprises dimethlysulfoxide (DMSO). In some embodiments, the cryopreservation media comprises 7% to 10% dimethlysulfoxide (DMSO).

In some embodiments, the first period in step (c) and the second period in step (e) are each individually performed within a period of 10 days, 11 days, or 12 days.

In some embodiments, the first period in step (c) and the second period in step (e) are each individually performed within a period of 11 days.

In some embodiments, steps (a) through (f) are performed within a period of about 10 days to about 22 days.

In some embodiments, steps (a) through (f) are performed within a period of about 20 days to about 22 days.

In some embodiments, steps (a) through (f) are performed within a period of about 15 days to about 20 days.

In some embodiments, steps (a) through (f) are performed within a period of about 10 days to about 20 days.

In some embodiments, steps (a) through (f) are performed within a period of about 10 days to about 15 days.

In some embodiments, steps (a) through (f) are performed in 22 days or less.

In some embodiments, steps (a) through (f) are performed in 20 days or less.

In some embodiments, steps (a) through (f) are performed in 15 days or less.

In some embodiments, steps (a) through (f) are performed in 10 days or less.

In some embodiments, steps (a) through (f) and cryopreservation are performed in 22 days or less.

In some embodiments, the therapeutic population of TILs harvested in step (e) comprises sufficient TILs for a therapeutically effective dosage of the TILs.

In some embodiments, the number of TILs sufficient for a therapeutically effective dosage is from about $2.3 \times 10^{10}$ to about $13.7 \times 10^{10}$.

In some embodiments, steps (b) through (e) are performed in a single container, wherein performing steps (b) through (e) in a single container results in an increase in TIL yield per resected tumor as compared to performing steps (b) through (e) in more than one container.

In some embodiments, the antigen-presenting cells are added to the TILs during the second period in step (d) without opening the system.

In some embodiments, the third population of TILs in step (d) provides for increased efficacy, increased interferon-gamma production, increased polyclonality, increased average IP-10, and/or increased average MCP-1 when administered to a subject.

In some embodiments, the third population of TILs in step (d) provides for at least a five-fold or more interferon-gamma production when adminstered to a subject.

In some embodiments, the third population of TILs in step (d) is a therapeutic population of TILs which comprises an increased subpopulation of effector T cells and/or central memory T cells relative to the second population of TILs, wherein the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells obtained from the third population of TILs exhibit increased CD57 expression and decreased CD56 expression relative to effector T cells and/or central memory T cells obtained from the second population of cells.

In some embodiments, the risk of microbial contamination is reduced as compared to an open system.

In some embodiments, the TILs from step (g) are infused into a patient.

In some embodiments, the multiple fragments comprise about 4 fragments.

The present invention also provides a method for treating a subject with cancer, the method comprising administering expanded tumor infiltrating lymphocytes (TILs) comprising:
(a) obtaining a first population of TILs from a tumor resected from a subject by processing a tumor sample obtained from the patient into multiple tumor fragments;
(b) adding the tumor fragments into a closed system;
(c) performing a first expansion by culturing the first population of TILs in a cell culture medium comprising IL-2 and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) optionally cryopreserving the infusion bag comprising the harvested TIL population from step (f) using a cryopreservation process; and (h) administering a therapeutically effective dosage of the third population of TILs from the infusion bag in step (g) to the patient.

In some embodiments, the therapeutic population of TILs harvested in step (e) comprises sufficient TILs for administering a therapeutically effective dosage of the TILs in step (h).

In some embodiments, the number of TILs sufficient for administering a therapeutically effective dosage in step (h) is from about $2.3 \times 10^{10}$ to about $13.7 \times 10^{10}$.

In some embodiments, the antigen presenting cells (APCs) are PBMCs.

In some embodiments, the PBMCs are added to the cell culture on any of days 9 through 14 in step (d).

In some embodiments, prior to administering a therapeutically effective dosage of TIL cells in step (h), a non-myeloablative lymphodepletion regimen has been administered to the patient.

In some embodiments, the non-myeloablative lymphodepletion regimen comprises the steps of administration of cyclophosphamide at a dose of 60 mg/m2/day for two days followed by administration of fludarabine at a dose of 25 mg/m2/day for five days.

In some embodiments, the method further comprises the step of treating the patient with a high-dose IL-2 regimen starting on the day after administration of the TIL cells to the patient in step (h).

In some embodiments, the high-dose IL-2 regimen comprises 600,000 or 720,000 IU/kg administered as a 15-minute bolus intravenous infusion every eight hours until tolerance.

In some embodiments, the third population of TILs in step (d) is a therapeutic population of TILs which comprises an increased subpopulation of effector T cells and/or central memory T cells relative to the second population of TILs, wherein the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells in the therapeutic population of TILs exhibit increased CD57 expression and decreased CD56 expression relative to effector T cells and/or central memory T cells obtained from the second population of cells.

In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma.

In some embodiments, the cancer is selected from the group consisting of melanoma, HNSCC, cervical cancers, and NSCLC.

In some embodiments, the cancer is melanoma.
In some embodiments, the cancer is HNSCC.
In some embodiments, the cancer is a cervical cancer.
In some embodiments, the cancer is NSCLC.

The present invention also provides methods for expanding tumor infiltrating lymphocytes (TILs) into a therapeutic population of TILs comprising:

(a) adding processed tumor fragments from a tumor resected from a patient into a closed system to obtain a first population of TILs;

(b) performing a first expansion by culturing the first population of TILs in a cell culture medium comprising IL-2 and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (a) to step (b) occurs without opening the system;

(c) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (b) to step (c) occurs without opening the system;

(d) harvesting the therapeutic population of TILs obtained from step (c), wherein the transition from step (c) to step (d) occurs without opening the system; and (e) transferring the harvested TIL population from step (d) to an infusion bag, wherein the transfer from step (d) to (e) occurs without opening the system.

In some embodiments, the therapeutic population of TILs harvested in step (d) comprises sufficient TILs for a therapeutically effective dosage of the TILs.

In some embodiments, the number of TILs sufficient for a therapeutically effective dosage is from about $2.3 \times 10^{10}$ to about $13.7 \times 10^{10}$.

In some embodiments, the method further comprises the step of cryopreserving the infusion bag comprising the harvested TIL population using a cryopreservation process.

In some embodiments, the cryopreservation process is performed using a 1:1 ratio of harvested TIL population to cryopreservation media.

In some embodiments, the antigen-presenting cells are peripheral blood mononuclear cells (PBMCs).

In some embodiments, the PBMCs are irradiated and allogeneic.

The method according to claim 68, wherein the PBMCs are added to the cell culture on any of days 9 through 14 in step (c).

In some embodiments, the antigen-presenting cells are artificial antigen-presenting cells.

In some embodiments, the harvesting in step (d) is performed using a LOVO cell processing system.

In some embodiments, the multiple fragments comprise about 4 to about 50 fragments, wherein each fragment has a volume of about 27 mm$^3$.

In some embodiments, the multiple fragments comprise about 30 to about 60 fragments with a total volume of about 1300 mm$^3$ to about 1500 mm$^3$.

In some embodiments, the multiple fragments comprise about 50 fragments with a total volume of about 1350 mm$^3$.

In some embodiments, the multiple fragments comprise about 50 fragments with a total mass of about 1 gram to about 1.5 grams.

In some embodiments, the multiple fragments comprise about 4 fragments.

In some embodiments, the second cell culture medium is provided in a container selected from the group consisting of a G-container and a Xuri cellbag.

In some embodiments, the infusion bag in step (e) is a HypoThermosol-containing infusion bag.

In some embodiments, the first period in step (b) and the second period in step (c) are each individually performed within a period of 10 days, 11 days, or 12 days.

In some embodiments, the first period in step (b) and the second period in step (c) are each individually performed within a period of 11 days.

In some embodiments, steps (a) through (e) are performed within a period of about 10 days to about 22 days.

In some embodiments, steps (a) through (e) are performed within a period of about 10 days to about 20 days.

In some embodiments, steps (a) through (e) are performed within a period of about 10 days to about 15 days.

In some embodiments, steps (a) through (e) are performed in 22 days or less.

In some embodiments, steps (a) through (e) and cryopreservation are performed in 22 days or less.

In some embodiments, steps (b) through (e) are performed in a single container, wherein performing steps (b) through (e) in a single container results in an increase in TIL yield per resected tumor as compared to performing steps (b) through (e) in more than one container.

In some embodiments, the antigen-presenting cells are added to the TILs during the second period in step (c) without opening the system.

In some embodiments, the third population of TILs in step (d) is a therapeutic population of TILs which comprises an increased subpopulation of effector T cells and/or central memory T cells relative to the second population of TILs, wherein the effector T cells and/or central memory T cells obtained in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells obtained in the therapeutic population of TILs exhibit increased CD57 expression and decreased CD56 expression relative to effector T cells, and/or central memory T cells obtained from the second population of cells.

In some embodiments, the risk of microbial contamination is reduced as compared to an open system.

In some embodiments, the TILs from step (e) are infused into a patient.

In some embodiments, the closed container comprises a single bioreactor.

In some embodiments, the closed container comprises a G-REX-10.

In some embodiments, the closed container comprises a G-REX-100.

In some embodiments, at step (d) the antigen presenting cells (APCs) are added to the cell culture of the second population of TILs at a APC:TIL ratio of 25:1 to 100:1.

In some embodiments, the cell culture has a ratio of $2.5 \times 10^9$ APCs to $100 \times 10^6$ TILs.

In some embodiments, at step (c) the antigen presenting cells (APCs) are added to the cell culture of the second population of TILs at a APC:TIL ratio of 25:1 to 100:1.

In some embodiments, the cell culture has ratio of $2.5 \times 10^9$ APCs to $100 \times 10^6$ TILs.

The present invention also provides a population of expanded TILs for use in the treatment of a subject with cancer, wherein the population of expanded TILs is a third population of TILs obtainable by a method comprising:
- (a) obtaining a first population of TILs from a tumor resected from a subject by processing a tumor sample obtained from the patient into multiple tumor fragments;
- (b) adding the tumor fragments into a closed system;
- (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
- (d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
- (e) harvesting the therapeutic population of TILs obtained from step (d), wherein the transition from step (d) to step (e) occurs without opening the system; and
- (f) transferring the harvested TIL population from step (e) to an infusion bag, wherein the transfer from step (e) to (f) occurs without opening the system; and
- (g) optionally cryopreserving the infusion bag comprising the harvested TIL population from step (f) using a cryopreservation process.

In some embodiments, the population of TILs is for use to treat a subject with cancer according the methods described above and herein, wherein the method further comprises one or more of the features recited above and herein. In some embodiments, the population of TILs is for use in the treatment of a subject with cancer according the methods described above and herein, wherein the method further comprises one or more of the features recited above and herein.

The present invention provides a method for expanding tumor infiltrating lymphocytes (TILs) into a therapeutic population of TILs comprising:
(a) obtaining a first population of TILs from a tumor resected from a patient by processing a tumor sample obtained from the patient into multiple tumor fragments;
(b) adding the tumor fragments into a closed system;
(c) performing a first expansion by culturing the first population of TILs in a cell culture medium comprising IL-2, optionally OKT-3, and optionally a tumor necrosis factor receptor superfamily (TNFRSF) agonist, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, optionally OKT-3, and optionally a tumor necrosis factor receptor superfamily (TNFRSF) agonist, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) harvesting the therapeutic population of TILs obtained from step (d), wherein the transition from step (d) to step (e) occurs without opening the system; and
(f) transferring the harvested TIL population from step (e) to an infusion bag, wherein the transfer from step (e) to (f) occurs without opening the system.

The present invention provides a method for treating a subject with cancer, the method comprising administering expanded tumor infiltrating lymphocytes (TILs) comprising:
(a) obtaining a first population of TILs from a tumor resected from a subject by processing a tumor sample obtained from the patient into multiple tumor fragments;
(b) adding the tumor fragments into a closed system;
(c) performing a first expansion by culturing the first population of TILs in a cell culture medium comprising IL-2, optionally OKT-3, and optionally a tumor necrosis factor receptor superfamily (TNFRSF) agonist, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, optionally OKT-3, and optionally a tumor necrosis factor receptor superfamily (TNFRSF) agonist, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) harvesting the therapeutic population of TILs obtained from step (d), wherein the transition from step (d) to step (e) occurs without opening the system; and
(f) transferring the harvested TIL population from step (e) to an infusion bag, wherein the transfer from step (e) to (f) occurs without opening the system;
(g) optionally cryopreserving the infusion bag comprising the harvested TIL population from step (f) using a cryopreservation process; and
(h) administering a therapeutically effective dosage of the third population of TILs from the infusion bag in step (g) to the patient.

In some embodiments, the tumor necrosis factor receptor superfamily (TNFRSF) agonist is a 4-1BB antibody. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof.

The present invention also provides a cryopreservation composition comprising a population of TILs as described above and herein, a cryoprotectant medium comprising dimethylsulfoxide (DMSO), and an electrolyte solution.

In some embodiments, the cryopreservation composition further comprises one or more stabilizers and one or more lymphocyte growth factors. In some embodiments, the one or more stabilizers comprise human serum albumin (HSA) and the one or more lymphocyte growth factors comprise IL-2. In some embodiments, the composition optionally comprises OKT-3.

In some embodiments, the DMSO and the electrolyte solution are present in a ratio of about 1.1:1 to about 1:1.1. In some embodiments, the DMSO and the electrolyte solution are present in a ratio of about 1:1.

In some embodiments, 100 mL of the cryopreservation composition comprises the population of TILs in an amount of about $1 \times 10^6$ to about $9 \times 10^{14}$, the cryoprotectant medium comprising DMSO in an amount of about 30 mL to about 70 mL, the electrolyte solution in an amount of about 30 mL to about 70 mL, HSA in an amount of about 0.1 g to about 1.0 g, and IL-2 in an amount of about 0.001 mg to about 0.005 mg.

In some embodiments, 100 mL of the cryopreservation composition comprises the population of TILs in an amount of about $1 \times 10^7$ to about $1 \times 10^{11}$; the cryoprotectant medium in an amount of about 30 mL to about 70 mL, wherein the cryoprotectant medium comprises about 10% DMSO; the electrolyte solution in an amount of about 30 mL to about 70 mL; HSA in an amount of about 0.3 g to about 0.7 g; and IL-2 in an amount of about 0.001 mg to about 0.003 mg.

In some embodiments, 100 mL of the cryopreservation composition consists essentially of the population of TILs in an amount of about $1 \times 10^7$ to about $1 \times 10^{11}$; the cryoprotectant medium in an amount of about 30 mL to about 70 mL, wherein the cryoprotectant medium consists essentially of about 10% DMSO; the electrolyte solution in an amount of about 30 mL to about 70 mL; HSA in an amount of about 0.3 g to about 0.7 g; and IL-2 in an amount of about 0.001 mg to about 0.003 mg.

In some embodiments, the composition is for use in treating a subject with cancer.

The present invention also provides a cryopreservation composition comprising a population of TILs, a cryoprotectant medium comprising dimethylsulfoxide (DMSO), and an electrolyte solution, wherein 100 mL of the composition comprises the population of TILs in an amount of about $1\times10^7$ to about $1\times10^{11}$; the cryoprotectant medium in an amount of about 30 mL to about 70 mL, wherein the cryoprotectant medium comprises about 10% DMSO; the electrolyte solution in an amount of about 30 mL to about 70 mL; HSA in an amount of about 0.3 g to about 0.7 g; and IL-2 in an amount of about 0.001 mg to about 0.003 mg.

The present invention also provides a cryopreservation composition consisting essentially of a population of TILs, a cryoprotectant medium comprising dimethylsulfoxide (DMSO), and an electrolyte solution, wherein 100 mL of the composition consists essentially of the population of TILs in an amount of about $1\times10^7$ to about $1\times10^{11}$; the cryoprotectant medium in an amount of about 30 mL to about 70 mL, wherein the cryoprotectant medium consists essentially of about 10% DMSO; the electrolyte solution in an amount of about 30 mL to about 70 mL; HSA in an amount of about 0.3 g to about 0.7 g; and IL-2 in an amount of about 0.001 mg to about 0.003 mg.

The present invention also provides an infusion bag comprising a cryopreservation composition as described above and herein.

In some embodiments, the infusion bag is a HypoThermosol-containing infusion bag.

The present invention also provides a storage bag comprising a cryopreservation composition as described above and herein.

In some embodiments, the storage bag of claim 54, wherein the storage bag is a CryoStore CS750 Freezing bag.

BRIEF DESCRIPTION OF THE DRAWINGS

FIG. 2: Shows a comparison between the 1C process and an embodiment of the 2A process for TIL manufacturing.

FIG. 11A-11C: Depicts the major steps of an embodiment of process 2A including the cryopreservation steps.

FIG. 27: Exemplary Process 2A chart providing an overview of Steps A through F.

FIG. 28A-28C: Process Flow Chart of Process 2A.

FIG. 32: Normal laboratory values of blood metabolites.

FIG. 38A-38B: TCRαβ-CD56+. Tumor infiltrating Natural Killer (NK) and NKT-cells also have the ability to lyse cells lacking MHC expression as well as CD1-presented lipid antigen and to provide immunoregulatory cytokines. However, an intense NK cell infiltration is associated with advanced disease and could facilitate cancer development. Figure A shows that in all instances, except in M1063, there was a modest, though not significant, decrease in NK population in thawed TIL compared to fresh TIL, (p=0.27). No significant difference was observed between the re-REP TIL population (p=0.88). Fresh TIL, fresh re-REP TIL, and thawed re-REP TIL demonstrate similar expression of CD56 as shown in Figure B. Thawed TIL product had less (1.9±1.3) NK-expressing cells than fresh TIL (3.0±2.2) possibly as a result of the cryo-freezing procedure.

FIG. 40A-40B: CD8+ cells. A) In all, except EP11001T, both fresh and thawed TIL showed comparable CD8+ populations (p=0.10, no significant difference). In most experiments, there was a slight decrease in the CD8+ expressing TIL in the fresh re-REP TIL product (exceptions were M1061T and M1065T). There was approximately a 10-30% decrease in the CD8+ population in the thawed re-REP TIL. Comparison of the re-REP TIL from both fresh and thawed TIL showed a significant difference (p=0.03, Student's t-test). Figure B shows the mean values of the CD8+ expressing TIL in all conditions. Both fresh and thawed TIL show similar results. However, there was a 10.8% decrease in the CD8+ population in the thawed re-REP TIL product in comparison to the fresh re-REP TIL.

FIG. 41A-41B: CD4+CD154+ cells. CD154, also known as CD40L is a marker for activated T-cells. Figure A: No substantial difference in the CD4+CD154+ population was observed in the different conditions, however, a decrease of 34.1% was observed in the EP11001T fresh re-REP CD4+ TILs. CD154 expression were not measured in M1061T and M1062T as these experiments were carried out before the extended phenotype panel was in place. Figure B: A slight decrease in thawed TIL condition could be attributed to CD154 not measured in M1061T and M1062T. All conditions show very comparable CD154 expression in the CD4 population suggesting activated CD4+ T cells.

FIG. 42A-42B: CD8+CD154+ cells. Activation marker CD154 expressed on CD8+ TIL was also analyzed. A) Overall, the CD154 expression was lower in the CD8+ population in the fresh and thawed TIL product. This is not surprising as CD154 is expressed mainly in the activated CD4+ T cells. In cases where the CD154 expression was measured in both fresh and thawed TIL product, either a no difference or an increase in the CD154 expression was observed in the thawed TIL products. Student's t-test showed the there was no significant difference between the two conditions. An increase in the CD154 expression in the thawed re-REP in comparison to the fresh re-REP was shown in all experiments (p=0.02). B) An increase in CD154 expression was observed in both the thawed TIL and thawed re-REP TIL products in comparison to their counterparts. Thawed re-REP TIL showed a 29.1% increase in CD154 expression compared to the fresh re-REP TIL.

FIG. 43A-43B: CD4+CD69+ cells. CD69 is the early activation marker in T cell following stimulation or activation. A) In all TIL except in EP11001T, both fresh and thawed re-REP showed a modest increase in CD69 expression, possibly due to the re-REP length (7 days rather than 11 days). No difference was observed between fresh and thawed TIL (p=0.89). A difference between fresh and thawed re-REP was also not observed (p=0.82). B) A minor increase in CD69 expression is observed in the re-REP TIL products. (Note: No CD69 staining was performed for either M1061T and M1062T thawed TIL product. CD69 expression of M1061T fresh TIL product was 33.9%).

FIG. 48B) An overall increase in CM population in the fresh TIL was observed in comparison to the thawed TIL. The numbers show that fresh TIL and re-REP TIL had only a difference of ~2%; the fresh TIL showed a very high standard deviation which could be attributed to M1064T; excluding the CM expression in M1064T resulted in very similar CM expression between the fresh and thawed TIL product (not shown).

FIG. 51A-51B: CD4+CD28+ cells. CD28 expression correlates with young TIL decreasing with age. A) Even though an increase in the CM population was observed in the re-REP TIL, a decrease in the CD28 expression was seen as a trend suggesting that CM-status alone could not determine the fate of TIL. A decrease in CD28 expression was observed in the—re-REP product, except for M1061T CD4+ TIL. B) A decrease of 8.89% in the fresh and 5.71% in the thawed TIL was seen compared to fresh and thawed TIL product, respectively.

FIG. 52A-52B: CD8+CD28+ cells. A) CD28 expression in the CD8+ TIL population was higher in the fresh and thawed TIL than re-REP product. In most cases, thawed re-REP TIL showed a drastic decrease when compared to thawed TIL and fresh re-REP TIL. However, Student's t-test showed no significant difference between fresh and thawed TIL (p=0.3668) and also between the fresh and thawed re-REP products (p-=0.7940). B) As seen in the CD4+ TIL population, there was a decrease in CD8+CD28+ populations in the fresh re-REP (21.5%) and thawed re-REP (18.2%) when compared to their non-restimulated counterparts.

FIG. 53A-53B: CD4+PD-1+ cells. PD-1 expression in TIL is correlated with antigen reactive and exhausted T cells. I Thus it is not surprising that an exhausted phenotype is observed in TIL which have undergone a REP for 11 days. A) This exhausted phenotype was either maintained or increased (specifically, EPI 1001T and M1056T) in the thawed TIL product. No significant difference between fresh and thawed TIL product was seen (p=0.9809). A similar trend was shown in the fresh compared to thawed re-REP TIL (p=0.0912). B) Fresh re-REP showed a modest decrease in PD-1 expression in the CD4+ TIL population. All the other conditions maintained a comparable PD-1 expression pattern. A decrease or no change in PD-1 expression was observed in fresh re-REP product compared to all other conditions. An increase in the PD-1 expression was seen in M1062T, M1063T (CD4+) and EP11001T (CD8+) in the thawed re-REP product. All other thawed re-REP product showed comparable results to the thawed product.

FIG. 54A-54B: CD8+PD-1+ cells. A) CD8+ population from the fresh TIL product showed a more exhausted phenotype associated with increased PD-1 expression. An exception was observed in EPI 1001T where CD8+ thawed TIL product had a modest increase in the PD-1 expression compared to fresh TIL product. There was a small, though non-significant difference in the PD-1 expression in the fresh TIL compared to thawed TIL (p=0.3144). B) Fresh TIL product showed a slight increase, but non-significant PD-1 expression compared to thawed TIL (6.74%, or 1.2-fold higher than thawed TIL) suggesting that the thawed TIL product was comparable based on the phenotype pattern.

FIG. 55A-55B: CD4+ LAG3+ cells. Exhausted T cells express high levels of inhibitory receptor LAG3 along with PD-1. A) The CD4+ thawed TIL showed slightly higher, but non-significant, levels of LAG3 expression in comparison to the fresh TIL (p=0.52). An exception was observed in M1063T. In experiments where LAG3 expression in the CD4+ fresh and fresh re-REP TIL were measured, a decrease in LAG3+ expression was observed in the fresh re-REP samples compared to fresh TIL. B) Overall, there is a modest decrease in the LAG3 expression in fresh re-REP TIL product. Please note that for Figure B to maintain consistent, M1061T, M1062T and M1064T were excluded as LAG3 expression were not measured in the fresh product.

FIG. 57A-57B: CD4+ TIM-3+ cells. A) As observed previously in the case of PD-1 and LAG3, a decrease in TIM-3 expression was seen in the fresh reREP TIL compared to thawed re-REP TIL. Regardless, no significant difference existed between fresh and thawed reREP TIL (p=0.2007). B) No major changes in TIM-3 expression was observed among fresh, thaw and thawed reREP TIL products. A modest decrease of 9.2% in TIM-3 expression was observed in the fresh reREP TIL in comparison to thawed reREP product.

FIG. 58A-58B: CD8+ TIM-3+ cells. A) A similar trend in TIM-3 expression that was seen in the CD4+ population was also seen in the CD8+ TIL. Fresh re-REP TIL had the least exhausted phenotype with low TIM-3 expression, showing a significant difference in comparison to thawed re-REP TIL (p=0.0147). Comparison of PD-1, LAG3 and TIM-3 suggests that fresh re-REP TIL had a less exhaustive phenotype with increased CM phenotype. B) In comparison to thawed re-REP TIL product, fresh re-REP TIL showed a significant 22% decrease in TIM-3 expression. Both fresh and thawed TIL show similar TIM-3 expression patterns.

FIG. 60A-60F: Metabolic respiration profile of fresh TIL, fresh re-REP TIL, and thawed re-REP TIL. Basal OCR (A), Overt SRC (B), SRC2DG (C), Covert SRC (D), Basal ECAR (E), and Glycolytic Reserve (F).

FIG. 62A-62B: Selection of Serum Free Media purveyor (Serum replacement). Each fragment were cultured in single well of G-Rex 24 well plate in quatraplicates. On Day 11, REP were initiated using $4^5$ TIL with $10^6$ Feeders to mimic 2A process. A) Bar graph showing average viable cell count recorded on Day 11 (preREP) for each conditions. B) Bar graph displaying average viable cell count recorded on Day 22 (postREP). P value were calculated using student 't'test. *P<0.05, P<0.01, *P<0.001 respectively.

FIG. 65A-65C: Summary of pre and post TIL expansion extrapolated comparing standard condition and CTS Optimizer. A) PreREP. B) PostREP. C) Summary of TIL expansion extrapolated to full scale run (Standard vs CTS Optimizer+SR).

FIG. 83: Comparison table of Steps A through F from exemplary embodiments of process 1C and process 2A.

FIG. 84: Detailed comparison of an embodiment of process 1C and an embodiment of process 2A.

FIG. 94: Table of process improvements from Gen 1 to Gen 2.

FIGS. 106A-106B: The TCRvβ repertoire (24 specificities) were assessed in the TIL derived from a (A) melanoma and (B) lung tumor using the Beckman Coulter kit for flow cytometry.

FIG. 109: Table illustrating the Comparison Patient Characteristics from Cohort 1 (ASCO 2017) vs Cohort 2.

FIG. 110: Table illustrating treatment emergent adverse events (≥30%).

FIG. 116: Updated patient characteristics for Cohort 2 of the phase 2 clinical trial in metastatic melanoma from the second data cut (N=17 patients).

FIG. 117: Treatment emergent adverse events for Cohort 2 (≥30%) from the second data cut (N=17 patients).

FIG. 120: Updated efficacy data for evaluable patients from Cohort 2 from the second data cut (N=17 patients). The * indicates a non-evaluable patient that did not reach the first assessment. All efficacy-evaluable patients had received prior anti-PD-1 and anti-CTLA-4 checkpoint inhibitor therapies.

Figure 121:
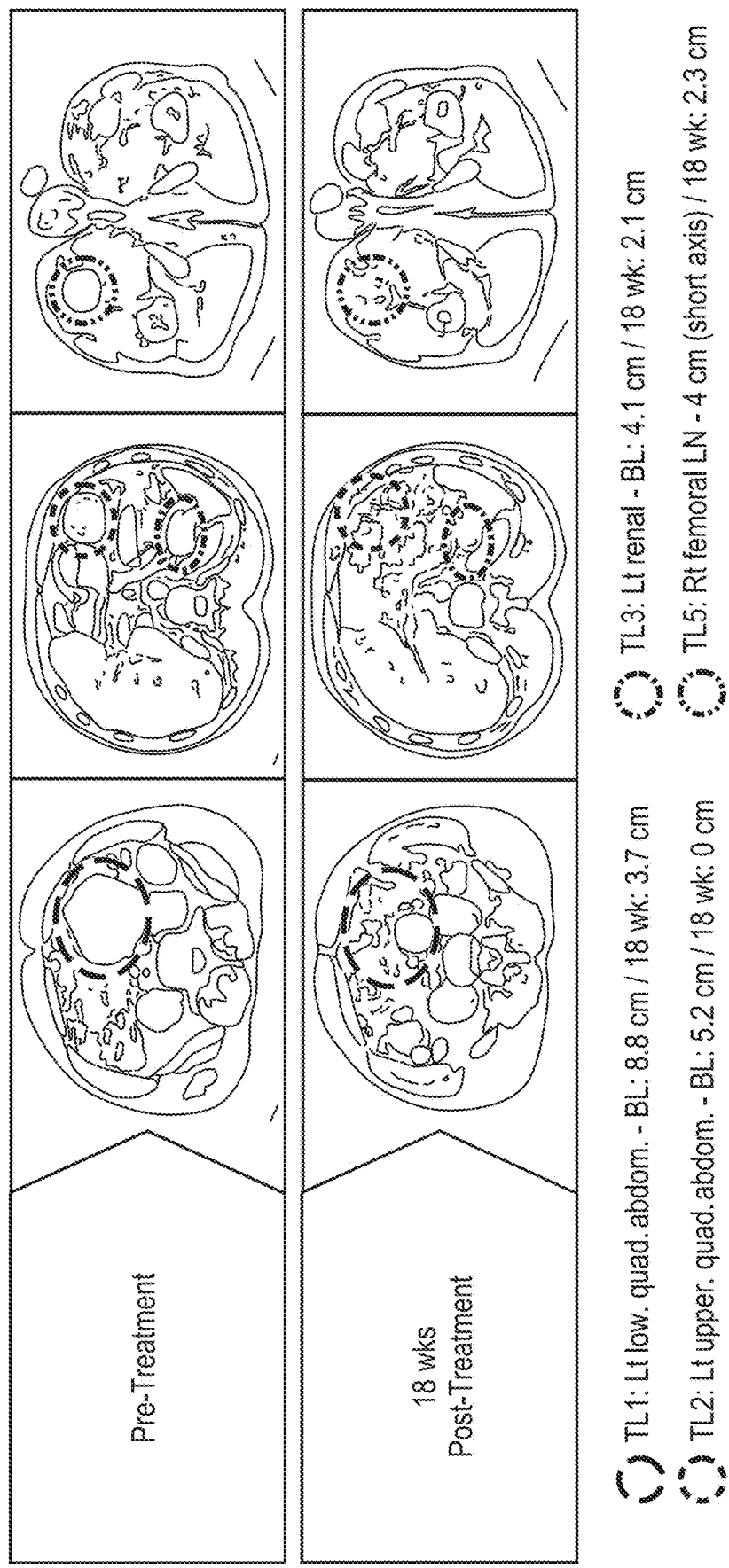

FIG. 121: Representative computed tomography scan of a patient (003-015) with a PR from Cohort 2, second data cut.

Figure 122:
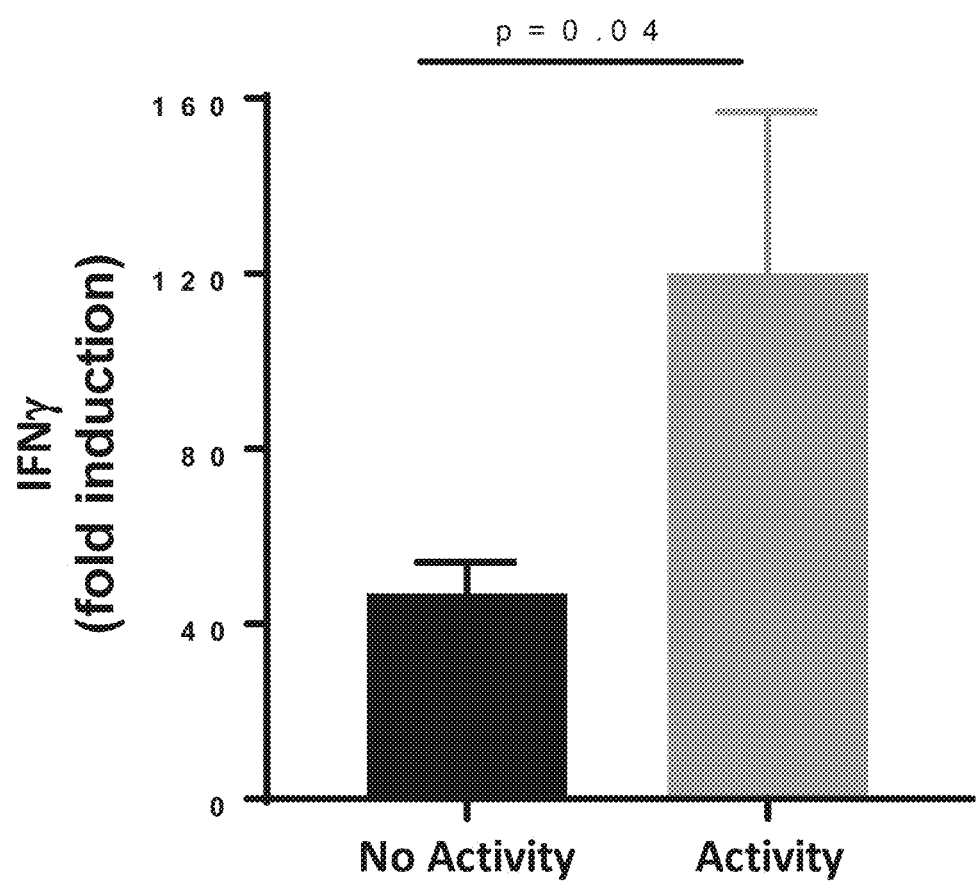

FIG. 122: Correlation of IFN-γ induction by TIL product prior to infusion with clinical reduction in tumor size on Day 42 post TIL infusion.

Figure 123:
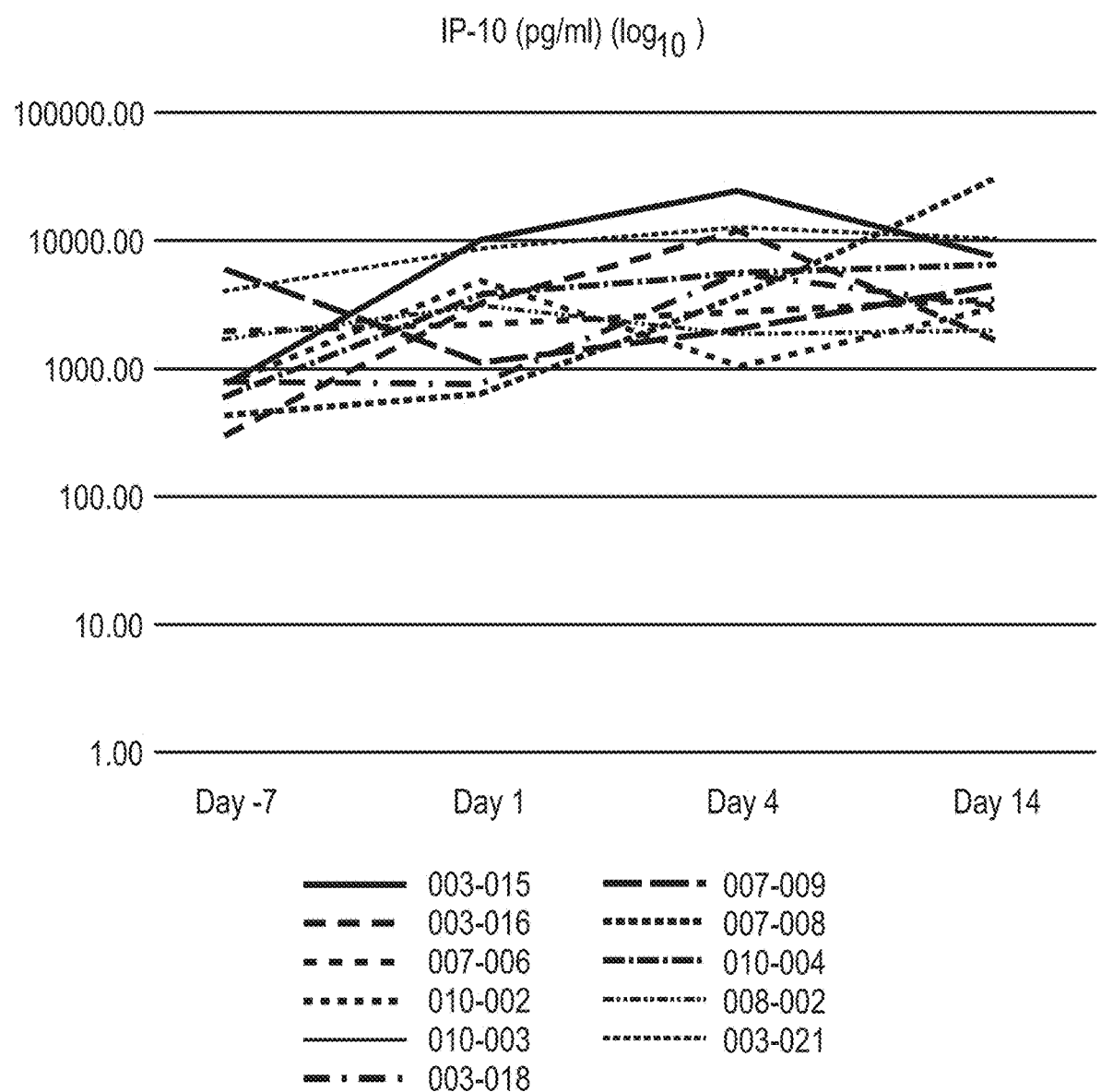

FIG. 123: IP-10 (CXCL10) levels (pg/mL, $\log_{10}$) pre- and post-infusion of an embodiment of Gen 2 TIL product. IP-10 is a marker of cell adhesion and homing.

Figure 124:
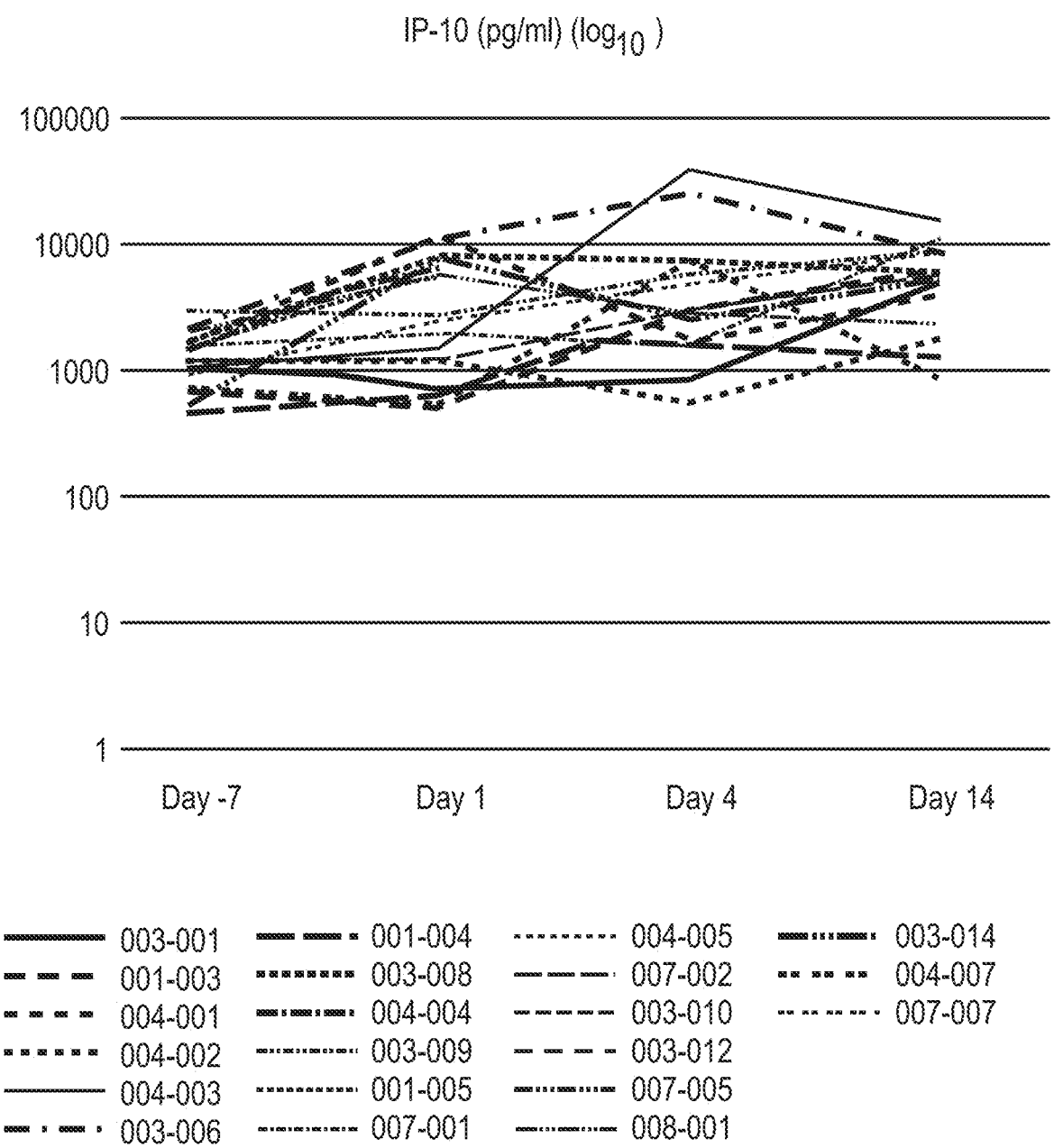

FIG. 124: IP-10 (CXCL10) levels (pg/mL, $\log_{10}$) pre- and post-infusion of an embodiment of Gen 1 TIL product.

Figure 125:
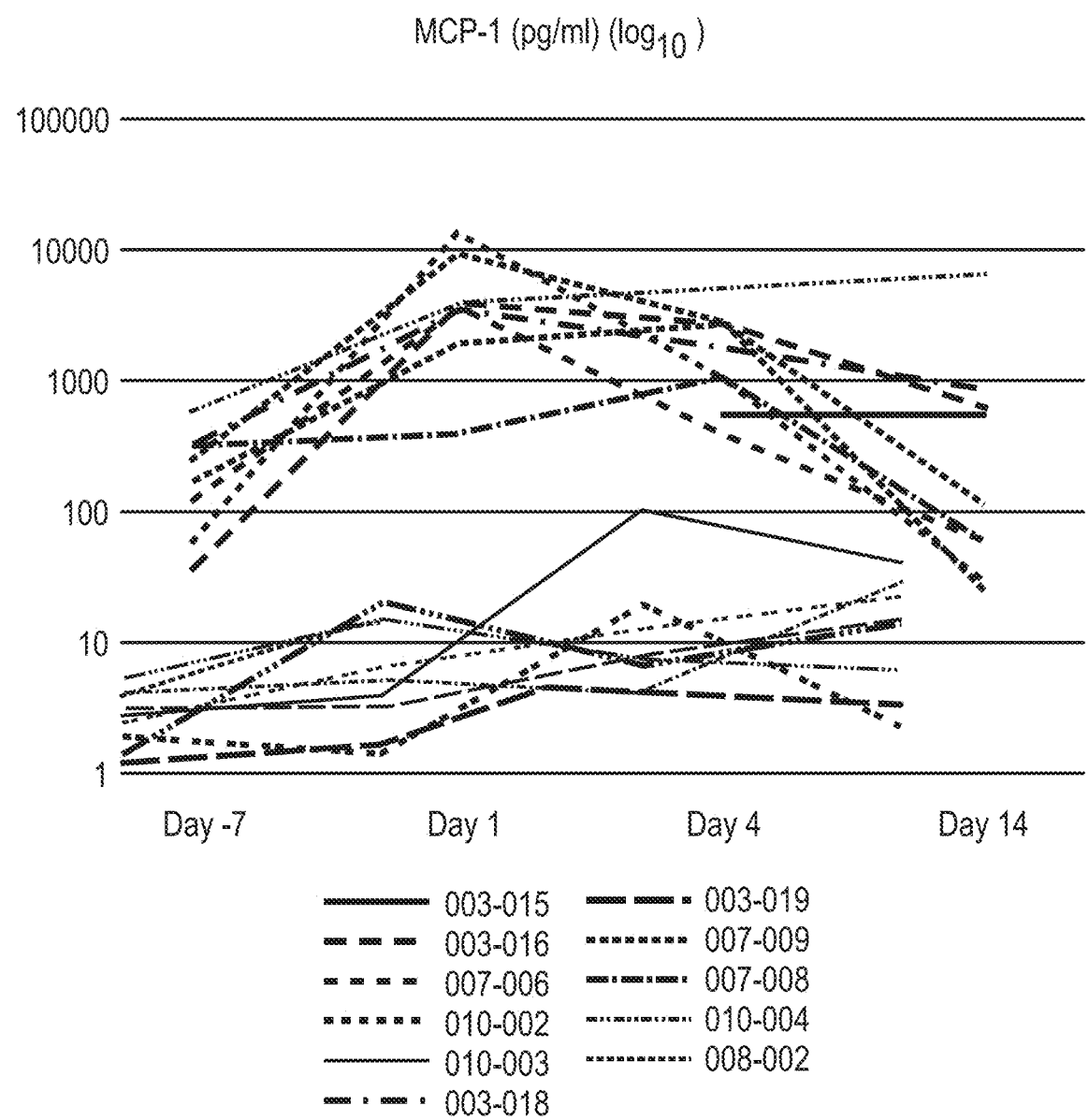

FIG. 125: MCP-1 levels (pg/mL, $\log_{10}$) pre- and post-infusion of an embodiment of Gen 2 TIL product. MCP-1 is a marker of cell adhesion and homing.

Figure 126:
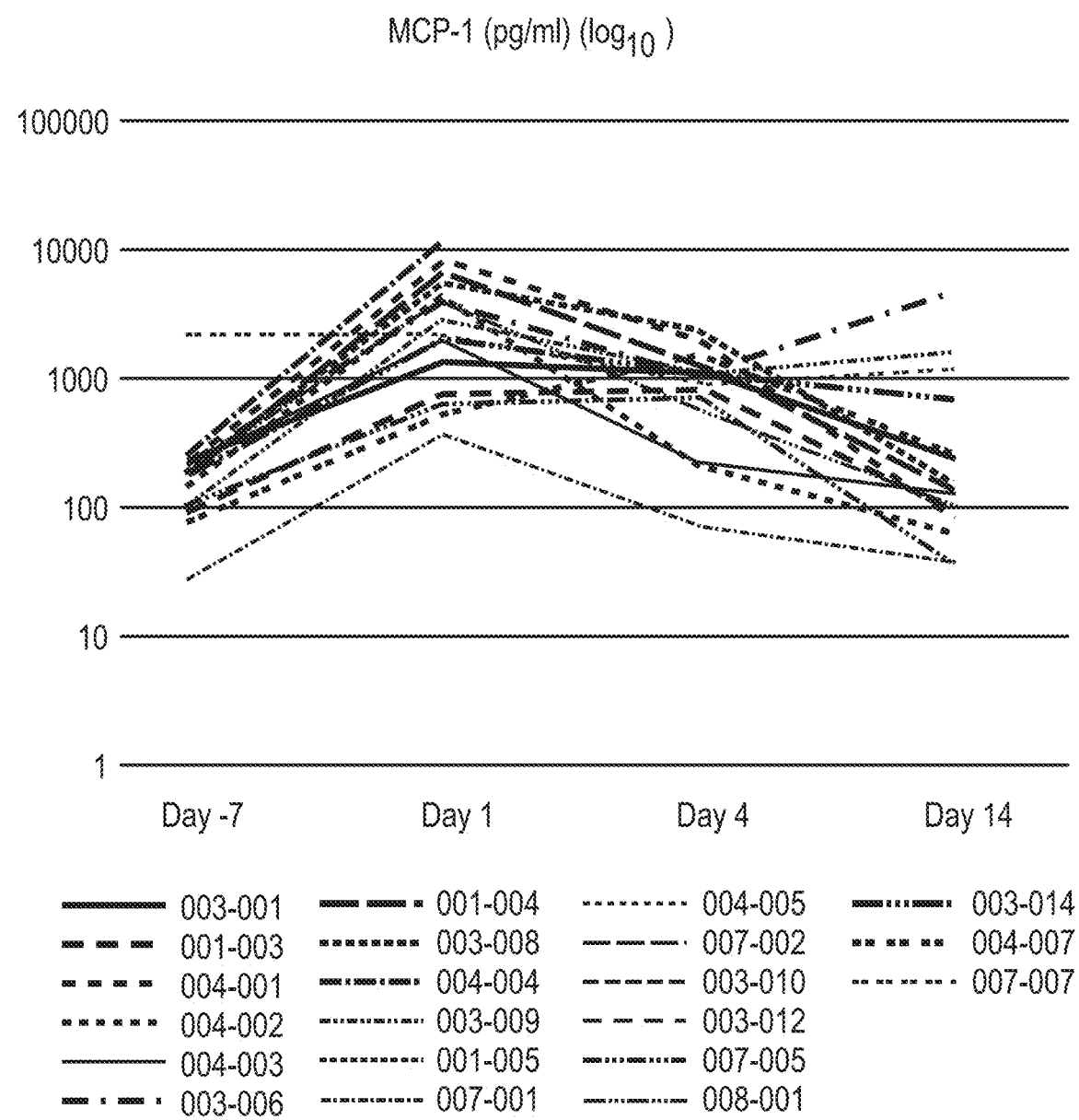

FIG. 126: MCP-1 levels (pg/mL, $\log_{10}$) pre- and post-infusion of an embodiment of Gen 1 TIL product.

FIG. 127: Data from Phase 2 studies in cervical carcinoma and head and neck squamous cell carcinoma (HNSCC). SD=stable disease. PR=progressive disease. PR=partial response.

Figure 128:
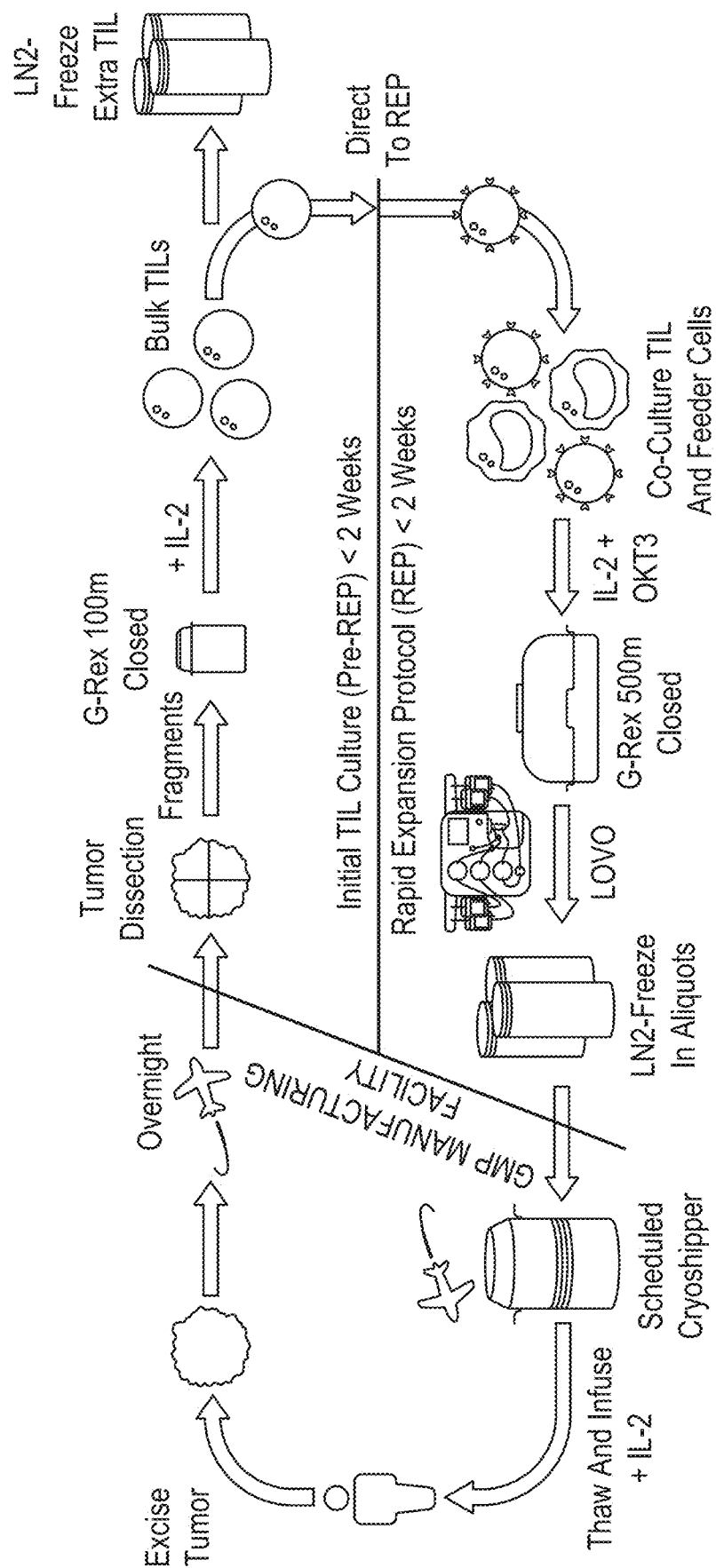

FIG. 128: Shows a diagram of an embodiment of process 2A, a 22-day process for TIL manufacturing.

Figure 129:
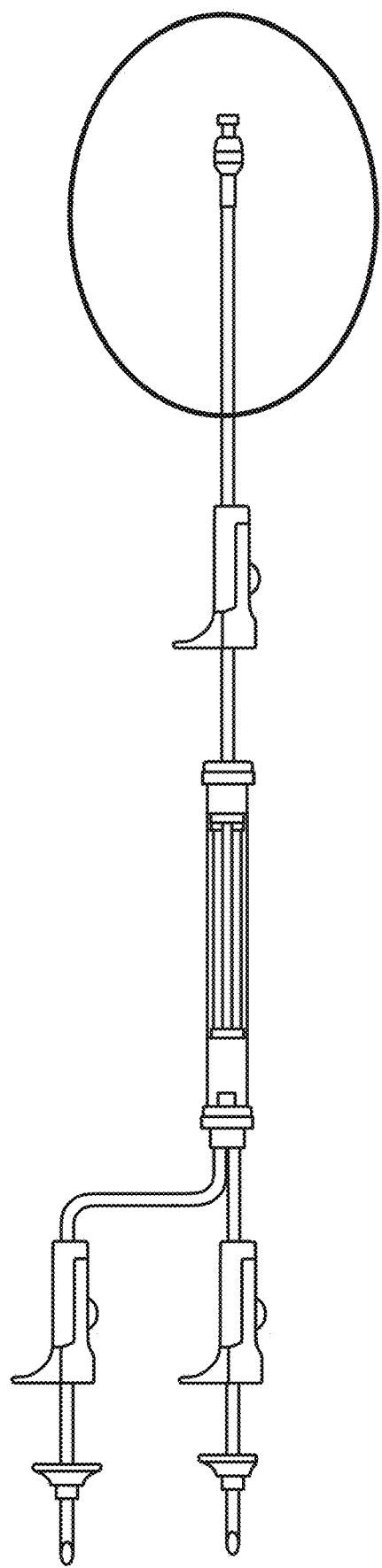

FIG. 129: Shows a schematic of the sterile weld (see, Process Note 5.11 in Example 30) the TIL Suspension transfer pack to the bottom (single line) of a Gravity Blood Filter.

Figure 130:
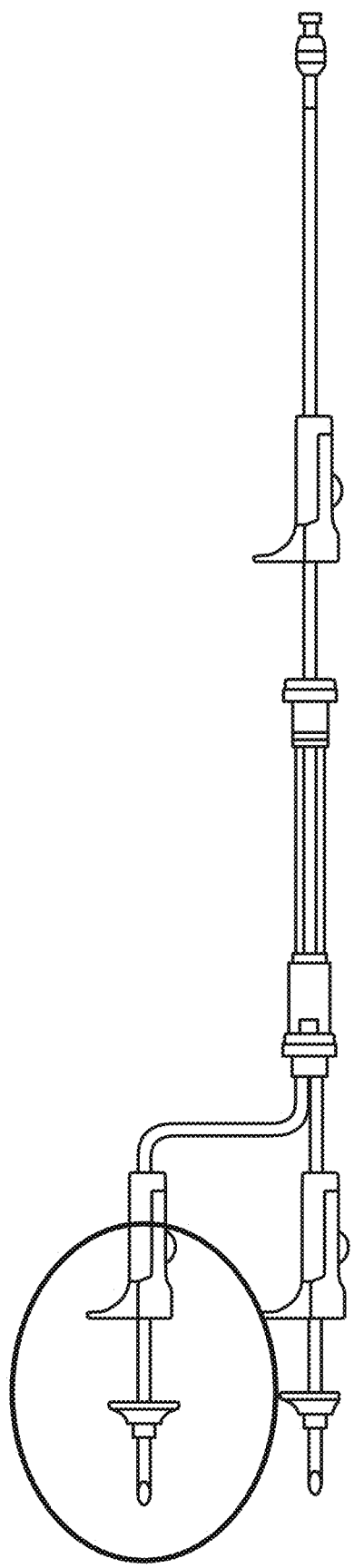

FIG. 130: Shows a schematic of the sterile weld (see, Process Note 5.11 in Example 30) the red media removal line from the GRex100MCS to the "Supernatant" transfer pack.

Figure 131:
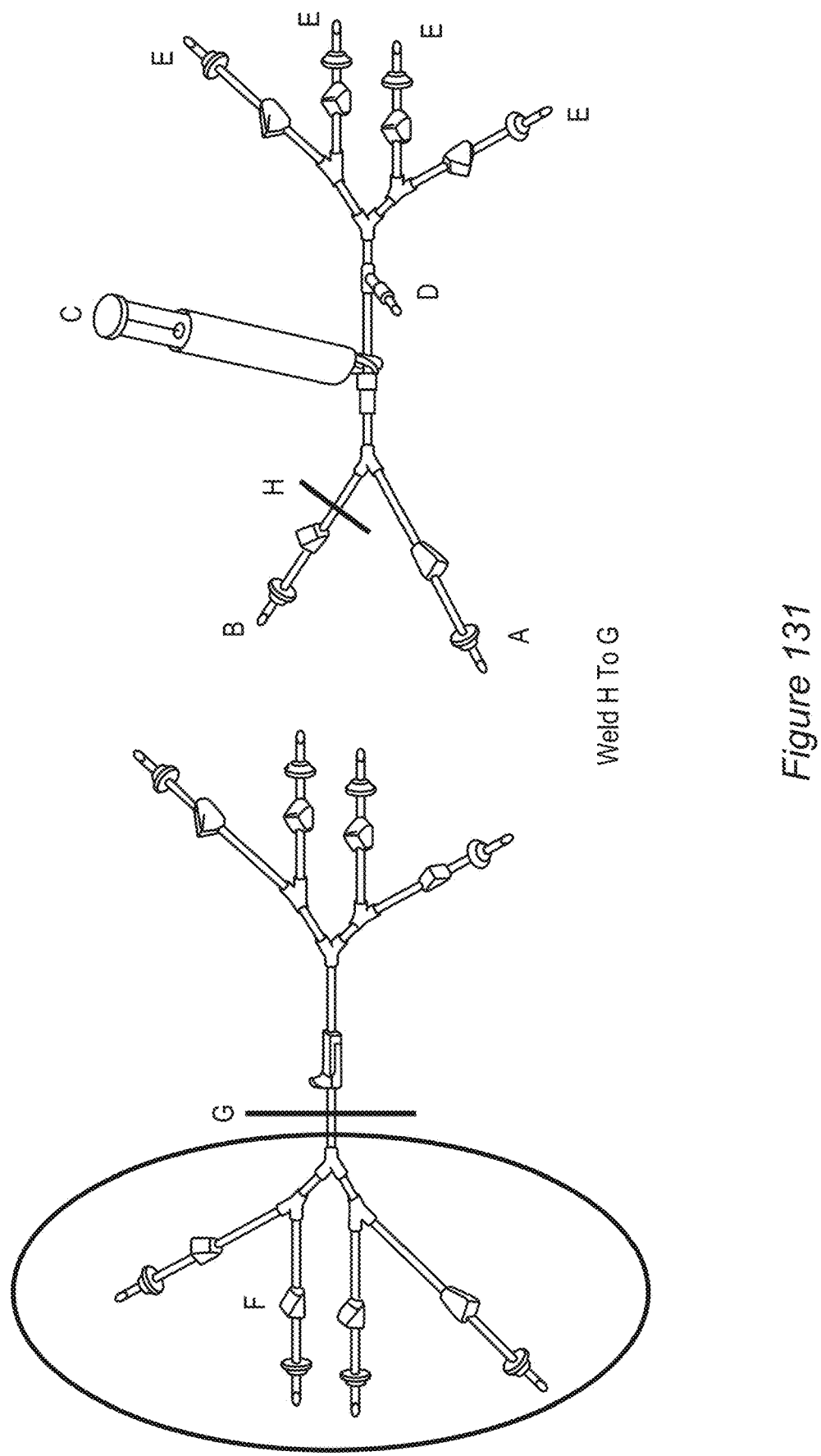

FIG. 131: Shows a schematic of the weld (see, Process Note 5.11 in Example 30) 4S-4M60 to a CC2 Cell Connect, replacing a single spike of the Cell Connect apparatus (B) with the 4-spike end of the 4S-4M60 manifold at (G).

Figure 132:
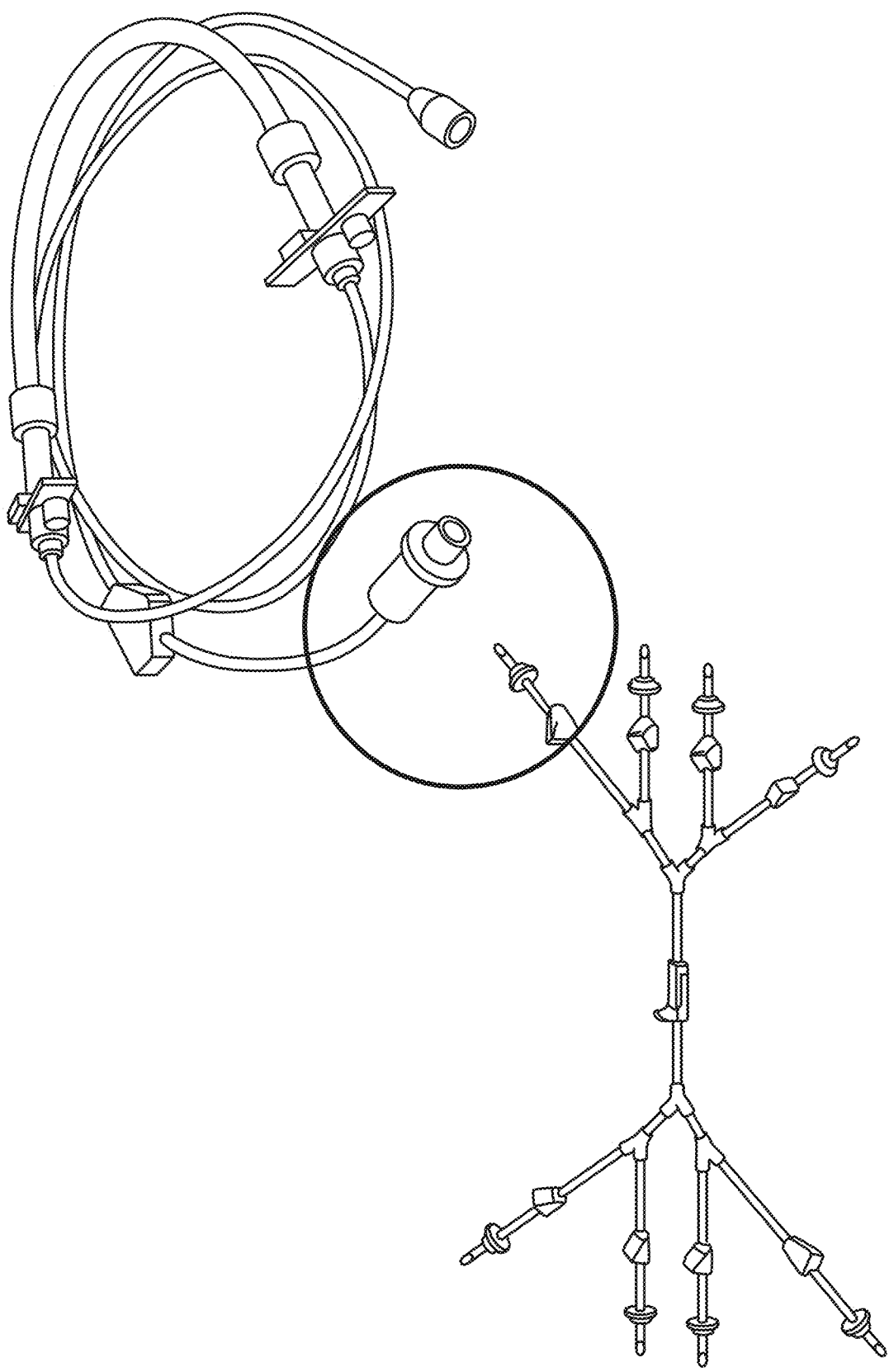

FIG. 132: Shows a schematic of the weld (see, Process Note 5.11 in Example 30) repeater fluid transfer set to one of the male luer ends of 4S-4M60.

Figure 133:
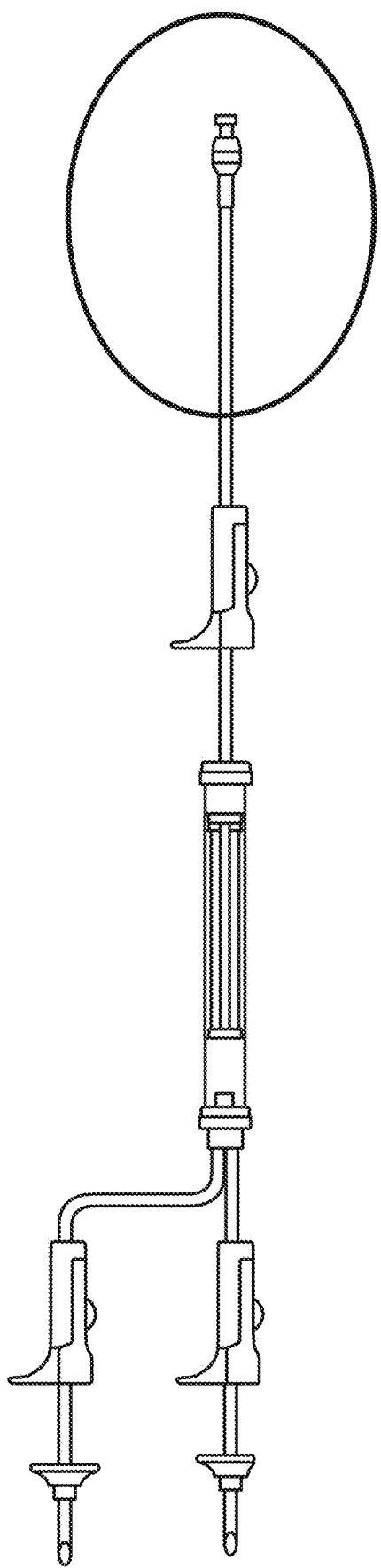

FIG. 133: Shows a schematic of the sterile weld (see, Process Note 5.11 in Example 30) the long terminal end of the gravity blood filter to the LOVO source bag.

Figure 134:
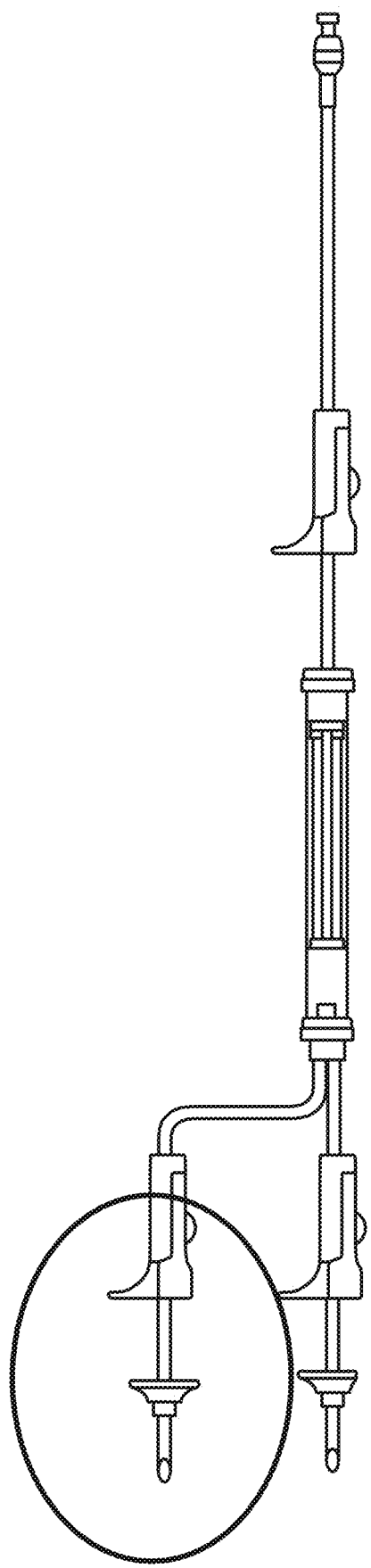

FIG. 134: Shows a schematic of the sterile weld (see, Process Note 5.11 in Example 30) one of the two source lines of the filter to "pooled TIL suspension" collection bag.

Figure 135:
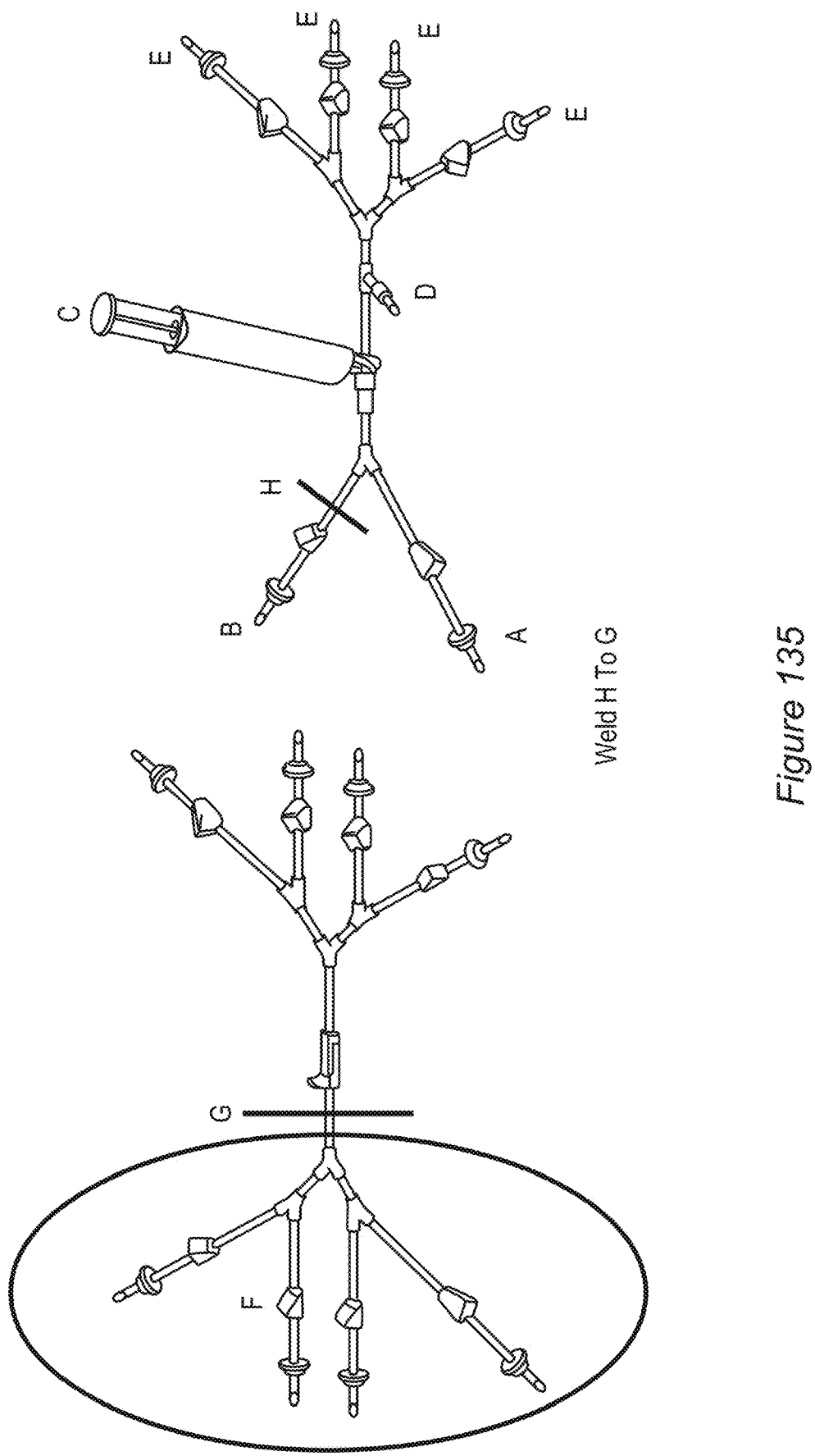

FIG. 135: Shows a schematic of the sterile weld (see, Process Note 5.11 in Example 30) a 4S-4M60 to a CC2 Cell Connect replacing a single spike of the Cell Connect apparatus (B) with the 4-spike end of the 4S-4M60 manifold at (G).

Figure 136:
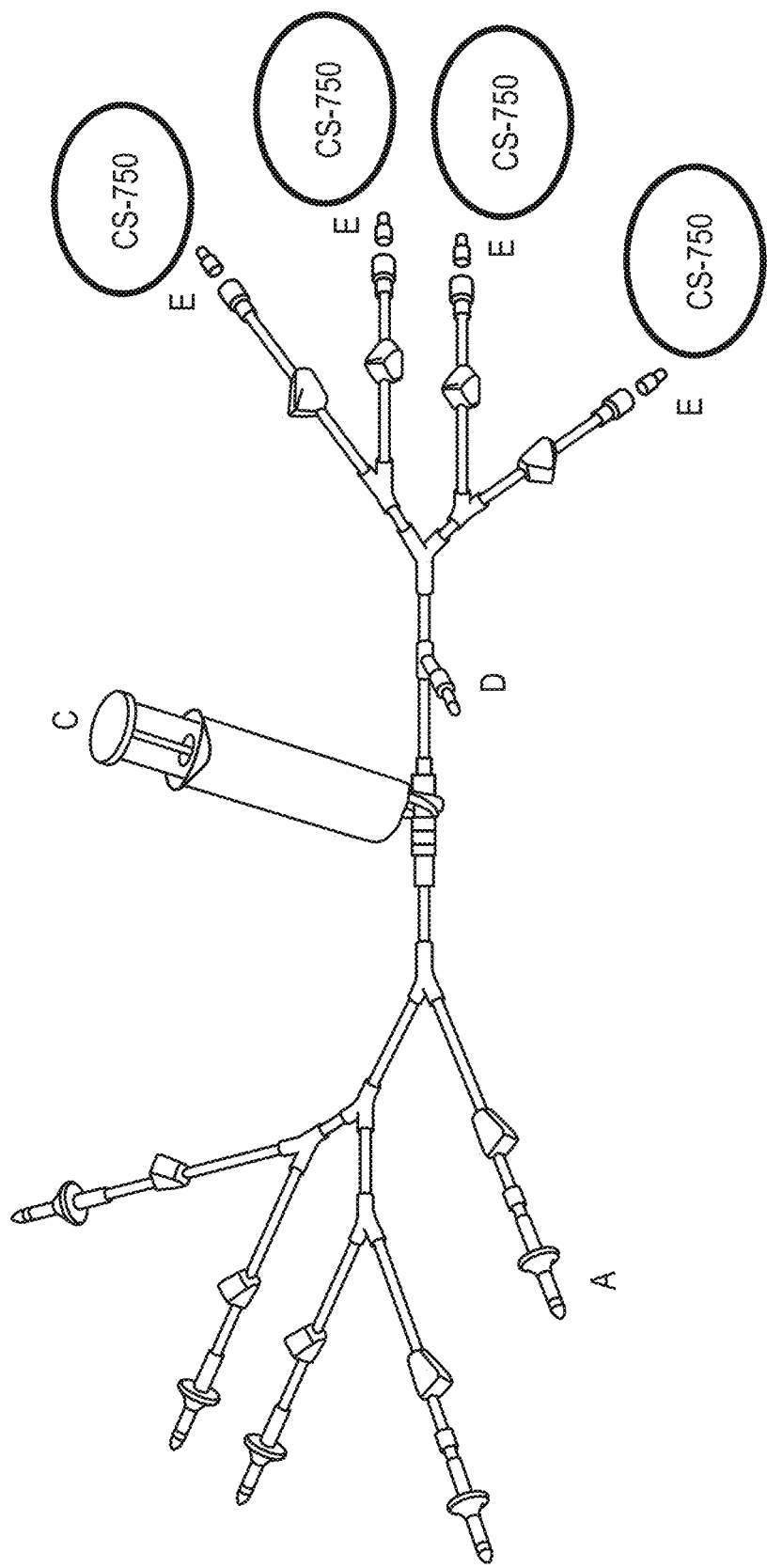

FIG. 136: Shows a schematic of the sterile weld (see, Process Note 5.11 in Example 30) the CS750 Cryobags to the harness prepared in Step 8.14.8, replacing one of the four male luer ends (E) with each bag.

Figure 137:
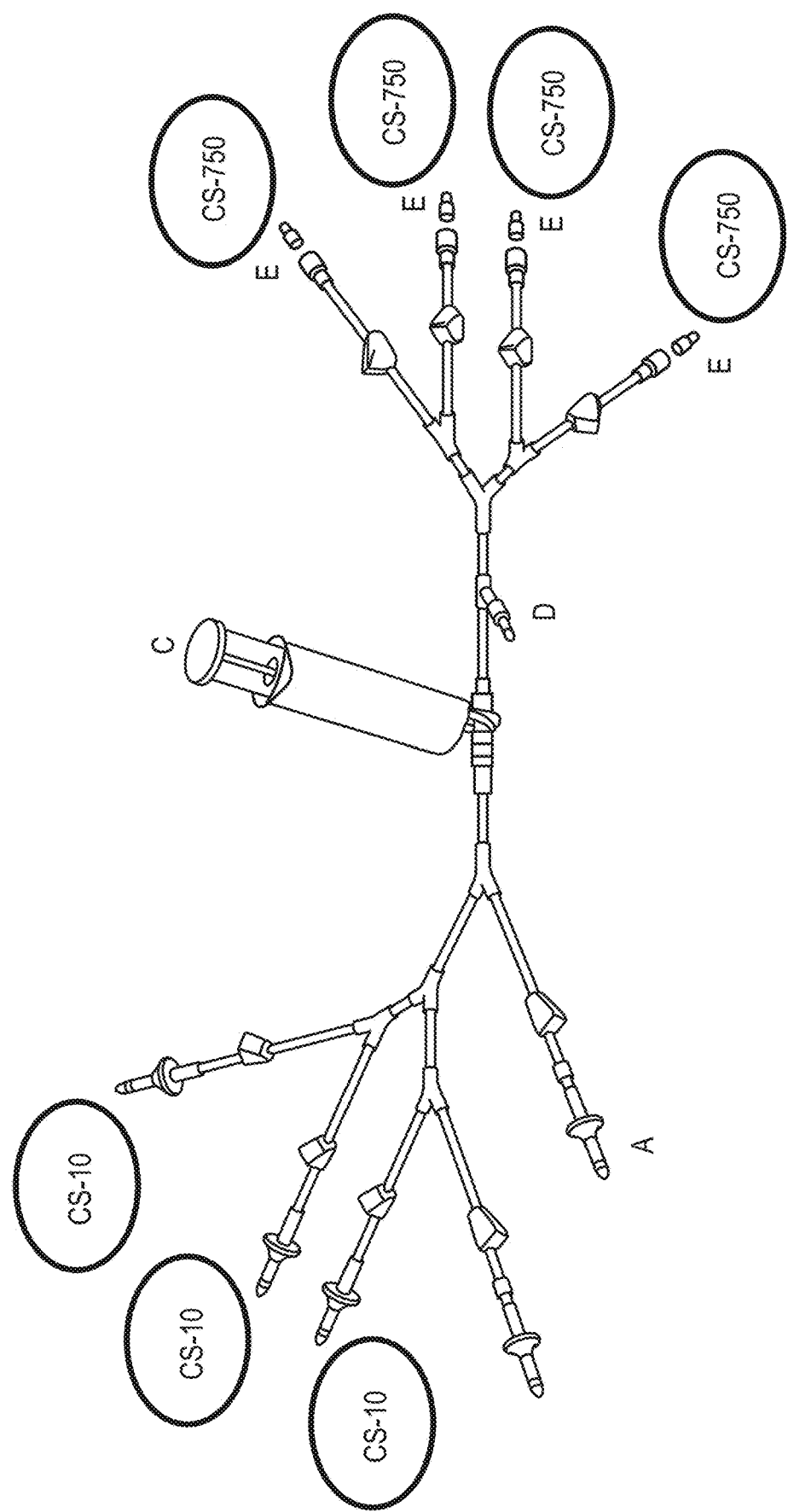

FIG. 137: Shows a schematic of the weld (see, Process Note 5.11 in Example 30) CS-10 bags to spikes of the 4S-4M60.

Figure 138:
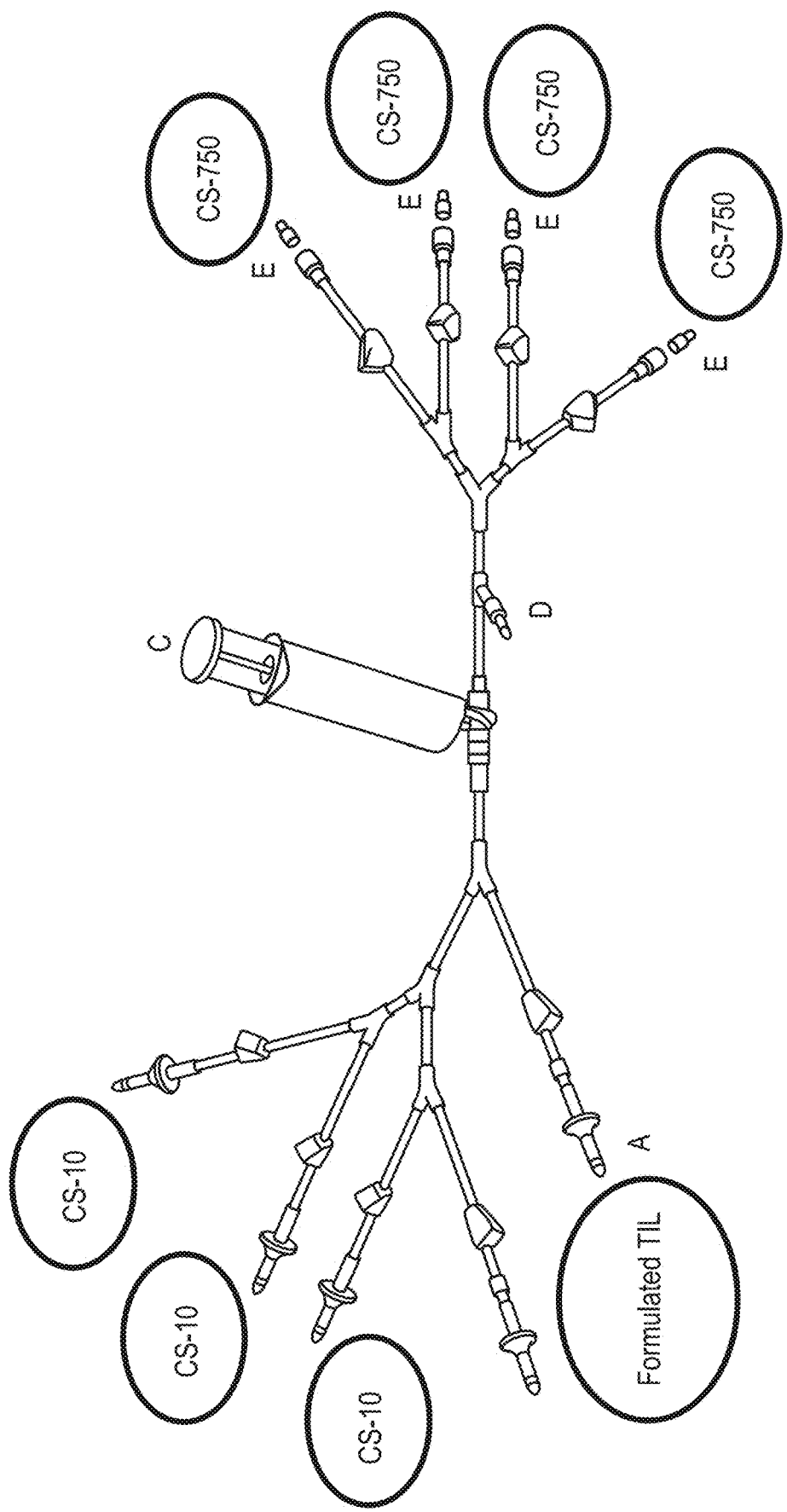

FIG. 138: Shows a schematic of the weld (see, Process Note 5.11 in Example 30) the "Formulated TIL" bag to the remaining spike (A) on the apparatus prepared in Step 8.14.10.

Figure 139:
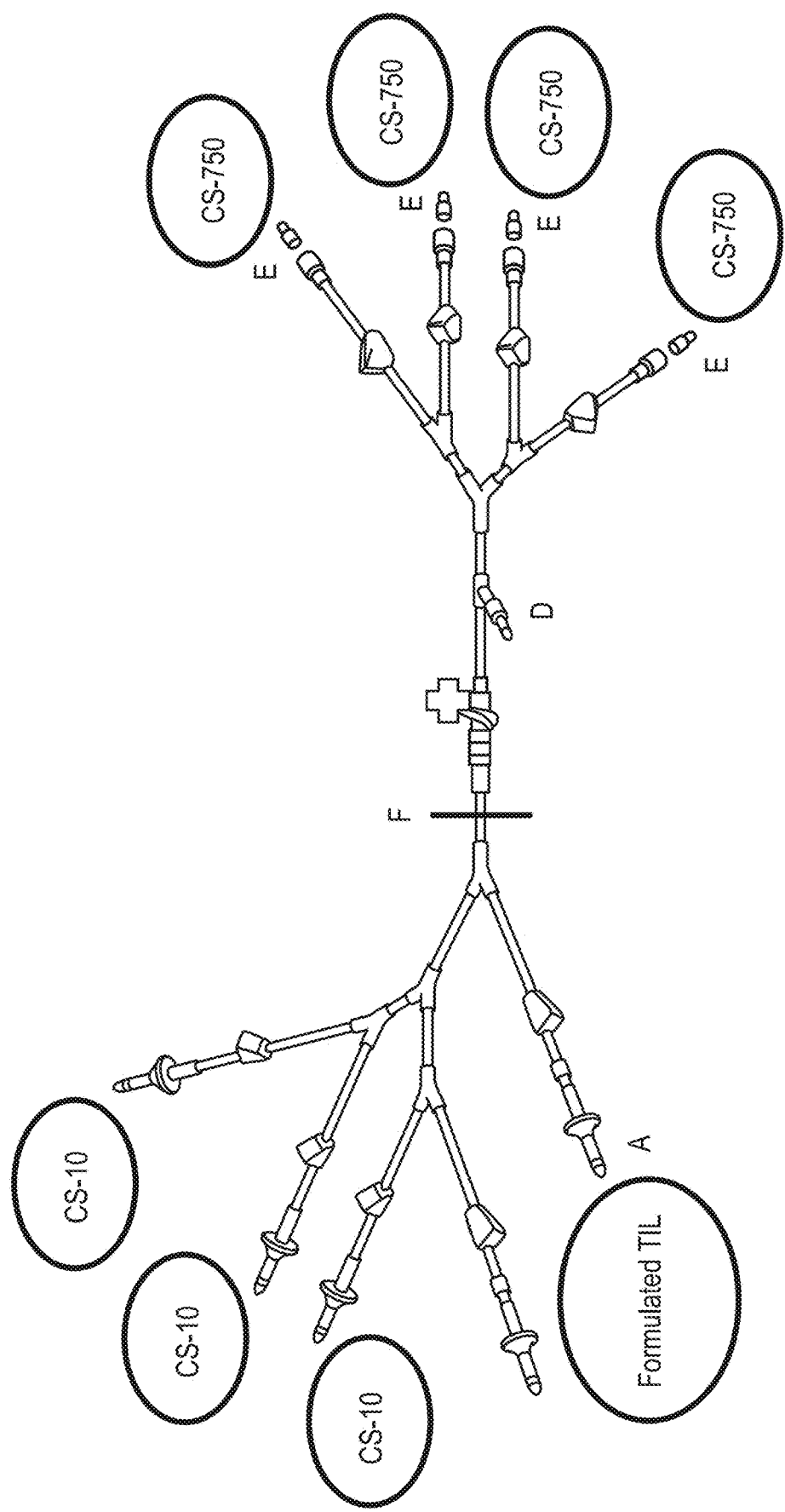

FIG. 139: Shows a diagram of the heat seal (see, Process Note 5.12 in Example 30) at F, removing the empty retentate bag and the CS-10 bags.

Figure 140:
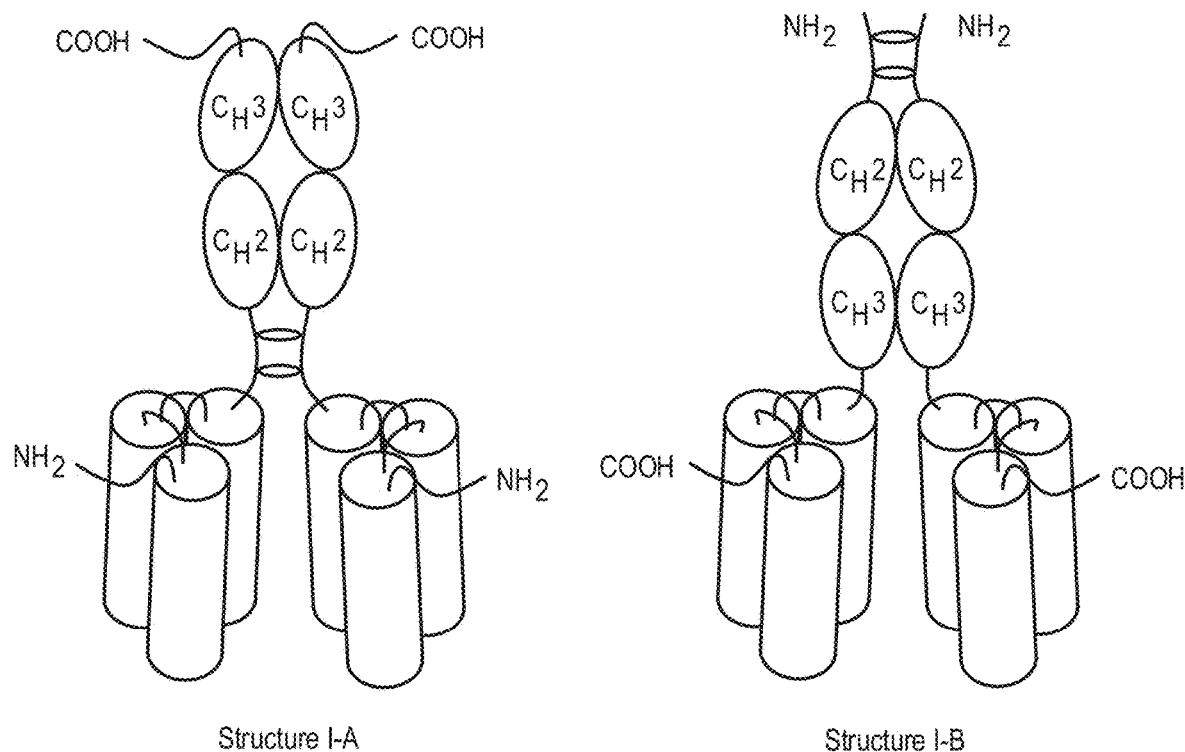

FIG. 140: Shows structures I-A and I-B, the cylinders refer to individual polypeptide binding domains. Structures I-A and I-B comprise three linearly-linked TNFRSF binding domains derived from e.g., 4-1BBL or an antibody that binds 4-1BB, which fold to form a trivalent protein, which is then linked to a second triavelent protein through IgG1-Fc (including $C_H3$ and $C_H2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex.

Figure 141:
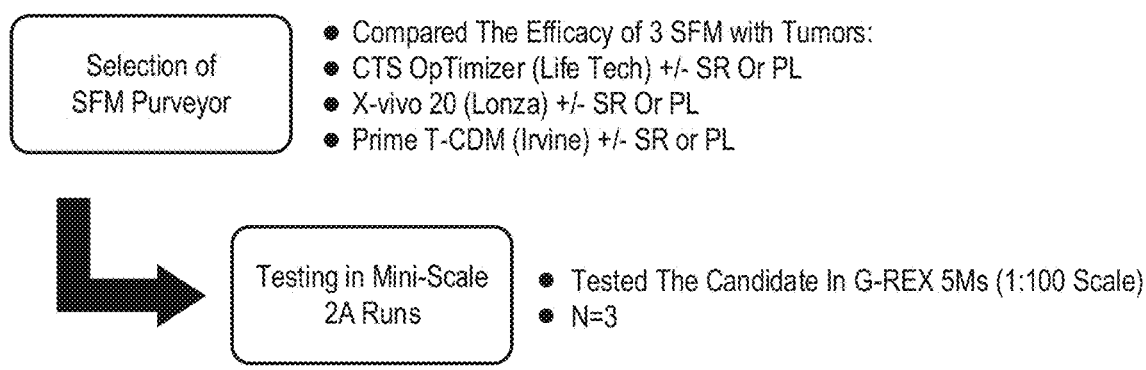

FIG. 141: Provides a chart showing the overview of the 3 phases of the experiment, as discussed in Example 21.

BRIEF DESCRIPTION OF THE SEQUENCE LISTING

SEQ ID NO:1 is the amino acid sequence of the heavy chain of muromonab.

SEQ ID NO:2 is the amino acid sequence of the light chain of muromonab.

SEQ ID NO:3 is the amino acid sequence of a recombinant human IL-2 protein.

SEQ ID NO:4 is the amino acid sequence of aldesleukin.

SEQ ID NO:5 is the amino acid sequence of a recombinant human IL-4 protein.

SEQ ID NO:6 is the amino acid sequence of a recombinant human IL-7 protein.

SEQ ID NO:7 is the amino acid sequence of a recombinant human IL-15 protein.

SEQ ID NO:8 is the amino acid sequence of a recombinant human IL-21 protein.

SEQ ID NO:9 is the amino acid sequence of human 4-1BB.

SEQ ID NO: 10 is the amino acid sequence of murine 4-1BB.

SEQ ID NO:11 is the heavy chain for the 4-1BB agonist monoclonal antibody utomilumab (PF-05082566).

SEQ ID NO:12 is the light chain for the 4-1BB agonist monoclonal antibody utomilumab (PF-05082566).

SEQ ID NO:13 is the heavy chain variable region ($V_H$) for the 4-1BB agonist monoclonal antibody utomilumab (PF-05082566).

SEQ ID NO:14 is the light chain variable region ($V_L$) for the 4-1BB agonist monoclonal antibody utomilumab (PF-05082566).

SEQ ID NO:15 is the heavy chain CDR1 for the 4-1BB agonist monoclonal antibody utomilumab (PF-05082566).

SEQ ID NO:16 is the heavy chain CDR2 for the 4-1BB agonist monoclonal antibody utomilumab (PF-05082566).

SEQ ID NO:17 is the heavy chain CDR3 for the 4-1BB agonist monoclonal antibody utomilumab (PF-05082566).

SEQ ID NO:18 is the light chain CDR1 for the 4-1BB agonist monoclonal antibody utomilumab (PF-05082566).

SEQ ID NO:19 is the light chain CDR2 for the 4-1BB agonist monoclonal antibody utomilumab (PF-05082566).

SEQ ID NO:20 is the light chain CDR3 for the 4-1BB agonist monoclonal antibody utomilumab (PF-05082566).

SEQ ID NO:21 is the heavy chain for the 4-1BB agonist monoclonal antibody urelumab (BMS-663513).

SEQ ID NO:22 is the light chain for the 4-1BB agonist monoclonal antibody urelumab (BMS-663513).

SEQ ID NO:23 is the heavy chain variable region ($V_H$) for the 4-1BB agonist monoclonal antibody urelumab (BMS-663513).

SEQ ID NO:24 is the light chain variable region ($V_L$) for the 4-1BB agonist monoclonal antibody urelumab (BMS-663513).

SEQ ID NO:25 is the heavy chain CDR1 for the 4-1BB agonist monoclonal antibody urelumab (BMS-663513).

SEQ ID NO:26 is the heavy chain CDR2 for the 4-1BB agonist monoclonal antibody urelumab (BMS-663513).

SEQ ID NO:27 is the heavy chain CDR3 for the 4-1BB agonist monoclonal antibody urelumab (BMS-663513).

SEQ ID NO:28 is the light chain CDR1 for the 4-1BB agonist monoclonal antibody urelumab (BMS-663513).

SEQ ID NO:29 is the light chain CDR2 for the 4-1BB agonist monoclonal antibody urelumab (BMS-663513).

SEQ ID NO:30 is the light chain CDR3 for the 4-1BB agonist monoclonal antibody urelumab (BMS-663513).

SEQ ID NO:46 is a 4-1BB ligand (4-1BBL) amino acid sequence.

SEQ ID NO:47 is a soluble portion of 4-1BBL polypeptide.

SEQ ID NO:48 is a heavy chain variable region ($V_H$) for the 4-1BB agonist antibody 4B4-1-1 version 1.

SEQ ID NO:49 is a light chain variable region ($V_L$) for the 4-1BB agonist antibody 4B4-1-1 version 1.

SEQ ID NO:50 is a heavy chain variable region ($V_H$) for the 4-1BB agonist antibody 4B4-1-1 version 2.

SEQ ID NO:51 is a light chain variable region ($V_L$) for the 4-1BB agonist antibody 4B4-1-1 version 2.

SEQ ID NO:52 is a heavy chain variable region ($V_H$) for the 4-1BB agonist antibody H39E3-2.

SEQ ID NO:53 is a light chain variable region ($V_L$) for the 4-1BB agonist antibody H39E3-2.

DETAILED DESCRIPTION OF THE INVENTION

I. Introduction

Adoptive cell therapy utilizing TILs cultured ex vivo by the Rapid Expansion Protocol (REP) has produced successful adoptive cell therapy following host immunosuppression in patients with melanoma. Current infusion acceptance parameters rely on readouts of the composition of TILs (e.g., CD28, CD8, or CD4 positivity) and on the numerical folds of expansion and viability of the REP product.

Current REP protocols give little insight into the health of the TIL that will be infused into the patient. T cells undergo a profound metabolic shift during the course of their maturation from naïve to effector T cells (see Chang, et al., *Nat. Immunol.* 2016, 17, 364, hereby expressly incorporated in its entirety, and in particular for the discussion and markers of anaerobic and aerobic metabolism). For example, naïve T cells rely on mitochondrial respiration to produce ATP, while mature, healthy effector T cells such as TIL are highly glycolytic, relying on aerobic glycolysis to provide the bioenergetics substrates they require for proliferation, migration, activation, and anti-tumor efficacy.

Previous papers report that limiting glycolysis and promoting mitochondrial metabolism in TILs prior to transfer is desirable as cells that are relying heavily on glycolysis will suffer nutrient deprivation upon adoptive transfer which results in a majority of the transferred cells dying. Thus, the art teaches that promoting mitochondrial metabolism might promote in vivo longevity and in fact suggests using inhibitors of glycolysis before induction of the immune response. See Chang et al. (Chang, et al., *Nat. Immunol.* 2016, 17(364).

The present invention is further directed in some embodiments to methods for evaluating and quantifying this increase in metabolic health. Thus, the present invention provides methods of assaying the relative health of a TIL population using one or more general evaluations of metabolism, including, but not limited to, rates and amounts of glycolysis, oxidative phosphorylation, spare respiratory capacity (SRC), and glycolytic reserve.

Furthermore, the present invention is further directed in some embodiments to methods for evaluating and quantifying this increase in metabolic health. Thus, the present invention provides methods of assaying the relative health of a TIL population using one or more general evaluations of metabolism, including, but not limited to, rates and amounts of glycolysis, oxidative phosphorylation, spare respiratory capacity (SRC), and glycolytic reserve.

In addition, optional additional evaluations include, but are not limited to, ATP production, mitochondrial mass and glucose uptake.

II. Definitions

Unless defined otherwise, all technical and scientific terms used herein have the same meaning as is commonly understood by one of skill in the art to which this invention belongs. All patents and publications referred to herein are incorporated by reference in their entireties.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "ex vivo" refers to an event which involves treating or performing a procedure on a cell, tissue and/or organ which has been removed from a subject's body. Aptly, the cell, tissue and/or organ may be returned to the subject's body in a method of surgery or treatment.

The term "rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 80-, or 90-fold) over a period of a week, or most preferably at least about 100-fold over a period of a week. A number of rapid expansion protocols are outlined below.

By "tumor infiltrating lymphocytes" or "TILs" herein is meant a population of cells originally obtained as white blood cells that have left the bloodstream of a subject and migrated into a tumor. TILs include, but are not limited to, CD8+ cytotoxic T cells (lymphocytes), Th1 and Th17 CD4+ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs and expanded TILs ("REP TILs" or "post-REP TILs"). TIL cell populations can include genetically modified TILs.

By "population of cells" (including TILs) herein is meant a number of cells that share common traits. In general, populations generally range from $1\times10^6$ to $1\times10^{10}$ in number, with different TIL populations comprising different numbers. For example, initial growth of primary TILs in the presence of IL-2 results in a population of bulk TILs of roughly $1\times10^8$ cells. REP expansion is generally done to provide populations of $1.5\times10^9$ to $1.5\times10^{10}$ cells for infusion.

By "cryopreserved TILs" herein is meant that TILs, either primary, bulk, or expanded (REP TILs), are treated and stored in the range of about $-150°$ C. to $-60°$ C. General methods for cryopreservation are also described elsewhere herein, including in the Examples. For clarity, "cryopreserved TILs" are distinguishable from frozen tissue samples which may be used as a source of primary TILs.

By "thawed cryopreserved TILs" herein is meant a population of TILs that was previously cryopreserved and then treated to return to room temperature or higher, including but not limited to cell culture temperatures or temperatures wherein TILs may be administered to a patient.

TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD95, PD-1, and CD25. Additionally and alternatively, TILs can be functionally defined by their ability to infiltrate solid tumors upon reintroduction into a patient.

The term "cryopreservation media" or "cryopreservation medium" refers to any medium that can be used for cryopreservation of cells. Such media can include media comprising 7% to 10% DMSO. Exemplary media include CryoStor CS10, Hyperthermasol, as well as combinations thereof. The term "CS10" refers to a cryopreservation medium which is obtained from Stemcell Technologies or from Biolife Solutions. The CS10 medium may be referred to by the trade name "CryoStor® CS10". The CS10 medium is a serum-free, animal component-free medium which comprises DMSO.

The term "central memory T cell" refers to a subset of T cells that in the human are CD45R0+ and constitutively express CCR7 ($CCR7^{hi}$) and CD62 L ($CD62^{hi}$). The surface phenotype of central memory T cells also includes TCR, CD3, CD127 (IL-7R), and IL-15R. Transcription factors for central memory T cells include BCL-6, BCL-6B, MBD2, and BMI1. Central memory T cells primarily secret IL-2 and CD40L as effector molecules after TCR triggering. Central memory T cells are predominant in the CD4 compartment in blood, and in the human are proportionally enriched in lymph nodes and tonsils.

The term "effector memory T cell" refers to a subset of human or mammalian T cells that, like central memory T cells, are CD45R0+, but have lost the constitutive expression of CCR7 (CCR7$^{lo}$) and are heterogeneous or low for CD62 L expression (CD62L$^{lo}$). The surface phenotype of central memory T cells also includes TCR, CD3, CD127 (IL-7R), and IL-15R. Transcription factors for central memory T cells include BLIMP1. Effector memory T cells rapidly secret high levels of inflammatory cytokines following antigenic stimulation, including interferon-γ, IL-4, and IL-5. Effector memory T cells are predominant in the CD8 compartment in blood, and in the human are proportionally enriched in the lung, liver, and gut. CD8+ effector memory T cells carry large amounts of perform.

The term "closed system" refers to a system that is closed to the outside environment. Any closed system appropriate for cell culture methods can be employed with the methods of the present invention. Closed systems include, for example, but are not limited to closed G-containers. Once a tumor segment is added to the closed system, the system is no opened to the outside environment until the TILs are ready to be administered to the patient.

The terms "fragmenting," "fragment," and "fragmented," as used herein to describe processes for disrupting a tumor, includes mechanical fragmentation methods such as crushing, slicing, dividing, and morcellating tumor tissue as well as any other method for disrupting the physical structure of tumor tissue.

The terms "peripheral blood mononuclear cells" and "PBMCs" refers to a peripheral blood cell having a round nucleus, including lymphocytes (T cells, B cells, NK cells) and monocytes. Preferably, the peripheral blood mononuclear cells are irradiated allogeneic peripheral blood mononuclear cells. PBMCs are a type of antigen-presenting cell.

The term "anti-CD3 antibody" refers to an antibody or variant thereof, e.g., a monoclonal antibody and including human, humanized, chimeric or murine antibodies which are directed against the CD3 receptor in the T cell antigen receptor of mature T cells. Anti-CD3 antibodies include OKT-3, also known as muromonab. Anti-CD3 antibodies also include the UHCT1 clone, also known as T3 and CD3ε. Other anti-CD3 antibodies include, for example, otelixizumab, teplizumab, and visilizumab.

The term "OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, CA, USA) and muromonab or variants, conservative amino acid substitutions, glycoforms, or biosimilars thereof. The amino acid sequences of the heavy and light chains of muromonab are given in Table 1 (SEQ ID NO:1 and SEQ ID NO:2). A hybridoma capable of producing OKT-3 is deposited with the American Type Culture Collection and assigned the ATCC accession number CRL 8001. A hybridoma capable of producing OKT-3 is also deposited with European Collection of Authenticated Cell Cultures (ECACC) and assigned Catalogue No. 86022706.

TABLE 1

| Identifier | Sequence (One-Letter Amino Acid Symbols) |
|---|---|
| SEQ ID NO: 1<br>Muromonab<br>heavy chain | QVQLQQSGAE LARPGASVKM SCKASGYTFT RYTMHWVKQR PGQGLEWIGY INPSRGYTNY 60<br>NQKFKDKATL TTDKSSSTAY MQLSSLTSED SAVYYCARYY DDHYCLDYWG QGTTLTVSSA 120<br>KTTAPSVYPL APVCGGTTGS SVTLGCLVKG YFPEPVTLTW NSGSLSSGVH TFPAVLQSDL 180<br>YTLSSSVTVT SSTWPSQSIT CNVAHPASST KVDKKIEPRP KSCDKTHTCP PCPAPELLGG 240<br>PSVFLFPPKP KDTLMISRTP EVTCVVVDVS HEDPEVKFNW YVDGVEVHNA KTKPREEQYN 300<br>STYRVVSVLT VLHQDWLNGK EYKCKVSNKA LPAPIEKTIS KAKGQPREPQ VYTLPPSRDE 360<br>LTKNQVSLTC LVKGFYPSDI AVEWESNGQP ENNYKTTPPV LDSDGSFFLY SKLTVDKSRW 420<br>QQGNVFSVSV MHEALHNHYT QKSLSLSPGK 450 |
| SEQ ID NO: 2<br>Muromonab<br>light chain | QIVLTQSPAI MSASPGEKVT MTCSASSSVS YMNWYQQKSG TSPKRWIYDT SKLASGVPAH 60<br>FRGSGSGTSY SLTISGMEAE DAATYYCQOW SSNPFTFGSG TKLEINRADT APTVSIFPPS 120<br>SEQLTSGGAS VVCFLNNFYP KDINVKWKID GSERQNGVLN SWTDQDSKDS TYSMSSTLTL 180<br>TKDEYERHNS YTCEATHKTS TSPIVKSFNR NEC 213 |

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, J. Immunol. 2004, 172, 3983-88 and Malek, Annu. Rev. Immunol. 2008, 26, 453-79, the disclosures of which are incorporated by reference herein. The amino acid sequence of recombinant human IL-2 suitable for use in the invention is given in Table 2 (SEQ ID NO:3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, NH, USA (CELL-GRO GMP) or ProSpec-Tany TechnoGene Ltd., East Brunswick, NJ, USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The amino acid sequence of aldesleukin suitable for use in the invention is given in Table 2 (SEQ ID NO:4). The term IL-2 also encompasses pegylated forms of IL-2, as described herein, including the pegylated IL2 prodrug NKTR-214, available from Nektar Therapeutics, South San Francisco, CA, USA. NKTR-214 and pegylated IL-2 suitable for use in the invention is described in U.S. Patent Application Publication No. US 2014/0328791 A1 and International Patent Application Publication No. WO 2012/065086 A1, the disclosures of which are incorporated by reference herein. Alternative forms of conjugated IL-2 suitable for use in the invention are described in U.S. Pat. Nos. 4,766,106, 5,206,344, 5,089,261 and 4902,502, the disclosures of which are incorporated by reference herein. Formulations of IL-2 suitable for use in the invention are described in U.S. Pat. No. 6,706,289, the disclosure of which is incorporated by reference herein.

recombinant human IL-7 suitable for use in the invention is given in Table 2 (SEQ ID NO:6).

The term "IL-15" (also referred to herein as "IL15") refers to the T cell growth factor known as interleukin-15, and

TABLE 2

Amino acid sequences of interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL<br>EEELKPLEEV LNLAQSKNFH LRPRDLISNI NVIVLELKGS ETTFMCEYAD ETATIVEFLN<br>RWITFCQSII STLT | 60<br>120<br>134 |
| SEQ ID NO: 4 Aldesleukin | PTSSSTKKTQ LQLEHLLLDL QMILNGINNY KNPKLTRMLT FKFYMPKKAT ELKHLQCLEE<br>ELKPLEEVLN LAQSKNFHLR PRDLISNINV IVLELKGSET TFMCEYADET ATIVEFLNRW<br>ITFSQSIIST LT | 60<br>120<br>132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH<br>EKDTRCLGAT AQQFHRHKQL IRFLKRLDRN LWGLAGLNSC PVKEANQSTL ENFLERLKTI<br>MREKYSKCSS | 60<br>120<br>130 |
| SEQ ID NO: 6 recombinant human IL-7 (rhIL-7) | MDCDIEGKDG KQYESVLMVS IDQLLDSMKE IGSNCLNNEF NFFKRHICDA NKEGMFLFRA<br>ARKLRQFLKM NSTGDFDLHL LKVSEGTTIL LNCTGQVKGR KPAALGEAQP TKSLEENKSL<br>KEQKKLNDLC FLKRLLQEIK TCWNKILMGT KEH | 60<br>120<br>153 |
| SEQ ID NO: 7 recombinant human IL-15 (rhIL-15) | MNWVNVISDL KKIEDLIQSM HIDATLYTES DVHPSCKVTA MKCVLLELQV ISLESGDASI<br>HDTVENLIIL ANNSLSSNGN VGESGCKECE ELEEKNIKEF LQSFVHIVQM FINTS | 60<br>115 |
| SEQ ID NO: 8 recombinant human IL-21 (rhIL-21) | MQDRHMIRMR QLIDIVDQLK NYVNDLVPEF LPAPEDVETN CEWSAFSCFQ KAQLKSANTG<br>NNERIINVSI KKLKRKPPST NAGRRQKHRL TCPSCDSYEK KPPKEFLERF KSLLQKMIHQ<br>HLSSRTHGSE DS | 60<br>120<br>132 |

The term "IL-4" (also referred to herein as "IL4") refers to the cytokine known as interleukin 4, which is produced by Th2 T cells and by eosinophils, basophils, and mast cells. IL-4 regulates the differentiation of naïve helper T cells (Th0 cells) to Th2 T cells. Steinke and Borish, Respir. Res. 2001, 2, 66-70. Upon activation by IL-4, Th2 T cells subsequently produce additional IL-4 in a positive feedback loop. IL-4 also stimulates B cell proliferation and class II MHC expression, and induces class switching to IgE and IgG$_1$ expression from B cells. Recombinant human IL-4 suitable for use in the invention is commercially available from multiple suppliers, including ProSpec-Tany TechnoGene Ltd., East Brunswick, NJ, USA (Cat. No. CYT-211) and ThermoFisher Scientific, Inc., Waltham, MA, USA (human IL-15 recombinant protein, Cat. No. Gibco CTP0043). The amino acid sequence of recombinant human IL-4 suitable for use in the invention is given in Table 2 (SEQ ID NO:5).

The term "IL-7" (also referred to herein as "IL7") refers to a glycosylated tissue-derived cytokine known as interleukin 7, which may be obtained from stromal and epithelial cells, as well as from dendritic cells. Fry and Mackall, Blood 2002, 99, 3892-904. IL-7 can stimulate the development of T cells. IL-7 binds to the IL-7 receptor, a heterodimer consisting of IL-7 receptor alpha and common gamma chain receptor, which in a series of signals important for T cell development within the thymus and survival within the periphery. Recombinant human IL-7 suitable for use in the invention is commercially available from multiple suppliers, including ProSpec-Tany TechnoGene Ltd., East Brunswick, NJ, USA (Cat. No. CYT-254) and ThermoFisher Scientific, Inc., Waltham, MA, USA (human IL-15 recombinant protein, Cat. No. Gibco PHC0071). The amino acid sequence of includes all forms of IL-2 including human and mammalian forms, conservative amino acid substitutions, glycoforms, biosimilars, and variants thereof. IL-15 is described, e.g., in Fehniger and Caligiuri, Blood 2001, 97, 14-32, the disclosure of which is incorporated by reference herein. IL-15 shares β and γ signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, NJ, USA (Cat. No. CYT-230-b) and ThermoFisher Scientific, Inc., Waltham, MA, USA (human IL-15 recombinant protein, Cat. No. 34-8159-82). The amino acid sequence of recombinant human IL-15 suitable for use in the invention is given in Table 2 (SEQ ID NO:7).

The term "IL-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. IL-21 is described, e.g., in Spolski and Leonard, Nat. Rev. Drug. Disc. 2014, 13, 379-95, the disclosure of which is incorporated by reference herein. IL-21 is primarily produced by natural killer T cells and activated human CD4+ T cells. Recombinant human IL-21 is a single, non-glycosylated polypeptide chain containing 132 amino acids with a molecular mass of 15.4 kDa. Recombinant human IL-21 is commercially available from multiple suppliers, including ProSpec-Tany TechnoGene Ltd., East Brunswick, NJ, USA (Cat. No. CYT-408-b) and ThermoFisher Scientific, Inc., Waltham, MA, USA (human IL-21 recombinant protein, Cat. No. 14-8219-80). The amino acid sequence of recombinant human IL-21 suitable for use in the invention is given in Table 2 (SEQ ID NO:8).

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, 105 to $10^{10}$, $10^5$ to $10^{11}$, $10^6$ to $10^{10}$, $10^6$ to $10^{11}$, $10^7$ to $10^{11}$, 107 to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., *New Eng. J. of Med.* 319: 1676, 1988). The optimal dosage and treatment regime for a particular patient can readily be determined by one skilled in the art of medicine by monitoring the patient for signs of disease and adjusting the treatment accordingly.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "solid tumor" refers to an abnormal mass of tissue that usually does not contain cysts or liquid areas. Solid tumors may be benign or malignant. The term "solid tumor cancer refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment.

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., *Cancer Res.*, 2012, 72, 2473. Although tumors express antigens that should be recognized by T cells, tumor clearance by the immune system is rare because of immune suppression by the microenvironment.

In an embodiment, the invention includes a method of treating a cancer with a population of TILs, wherein a patient is pre-treated with non-myeloablative chemotherapy prior to an infusion of TILs according to the invention. In some embodiments, the population of TILs may be provided wherein a patient is pre-treated with nonmyeloablative chemotherapy prior to an infusion of TILs according to the present invention. In an embodiment, the non-myeloablative chemotherapy is cyclophosphamide 60 mg/kg/d for 2 days (days 27 and 26 prior to TIL infusion) and fludarabine 25 mg/m2/d for 5 days (days 27 to 23 prior to TIL infusion). In an embodiment, after non-myeloablative chemotherapy and TIL infusion (at day 0) according to the invention, the patient receives an intravenous infusion of IL-2 intravenously at 720,000 IU/kg every 8 hours to physiologic tolerance.

Experimental findings indicate that lymphodepletion prior to adoptive transfer of tumor-specific T lymphocytes plays a key role in enhancing treatment efficacy by eliminating regulatory T cells and competing elements of the immune system ("cytokine sinks"). Accordingly, some embodiments of the invention utilize a lymphodepletion step (sometimes also referred to as "immunosuppressive conditioning") on the patient prior to the introduction of the rTILs of the invention.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source, or coding regions from different sources. Similarly, a heterologous protein indicates that the protein comprises two or more subsequences that are not found in the same relationship to each other in nature (e.g., a fusion protein).

The terms "sequence identity," "percent identity," and "sequence percent identity" (or synonyms thereof, e.g., "99% identical") in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by particular alignment software. In certain embodiments, the default parameters of the alignment software are used.

As used herein, the term "variant" encompasses but is not limited to antibodies or fusion proteins which comprise an amino acid sequence which differs from the amino acid sequence of a reference antibody by way of one or more substitutions, deletions and/or additions at certain positions within or adjacent to the amino acid sequence of the reference antibody. The variant may comprise one or more conservative substitutions in its amino acid sequence as compared to the amino acid sequence of a reference antibody. Conservative substitutions may involve, e.g., the substitution of similarly charged or uncharged amino acids. The variant retains the ability to specifically bind to the antigen of the reference antibody. The term variant also includes pegylated antibodies or proteins.

By "tumor infiltrating lymphocytes" or "TILs" herein is meant a population of cells originally obtained as white blood cells that have left the bloodstream of a subject and migrated into a tumor. TILs include, but are not limited to, $CD8^+$ cytotoxic T cells (lymphocytes), Th1 and Th17 $CD4^+$ T cells, natural killer cells, dendritic cells and M1 macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to bulk TILs, expanded TILs ("REP TILs") as well as "reREP TILs" as discussed herein. reREP TILs can include for example second expansion TILs or second additional expansion TILs (such as, for example, those described in Step D of FIG. 27, including TILs referred to as reREP TILs).

TILs can generally be defined either biochemically, using cell surface markers, or functionally, by their ability to infiltrate tumors and effect treatment. TILs can be generally categorized by expressing one or more of the following biomarkers: CD4, CD8, TCR $\alpha\beta$, CD27, CD28, CD56, CCR7, CD45Ra, CD95, PD-1, and CD25. Additionally, and alternatively, TILs can be functionally defined by their ability to infiltrate solid tumors upon reintroduction into a patient. TILS may further be characterized by potency—for example, TILS may be considered potent if, for example, interferon (IFN) release is greater than about 50 pg/mL, greater than about 100 pg/mL, greater than about 150 pg/mL, or greater than about 200 pg/mL.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study, and can be readily appreciated by one of ordinary skill in the art. Moreover, as used herein, the terms "about" and "approximately" mean that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compositions, methods, and kits described herein that embody the present invention can, in alternate embodiments, be more specifically defined by any of the transitional terms "comprising," "consisting essentially of," and "consisting of."

4-1BB (CD137) Agonists

In an embodiment, the TNFRSF agonist is a 4-1BB (CD137) agonist. The 4-1BB agonist may be any 4-1BB binding molecule known in the art. The 4-1BB binding molecule may be a monoclonal antibody or fusion protein capable of binding to human or mammalian 4-1BB. The 4-1BB agonists or 4-1BB binding molecules may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The 4-1BB agonist or 4-1BB binding molecule may have both a heavy and a light chain. As used herein, the term binding molecule also includes antibodies (including full length antibodies), monoclonal antibodies (including full length monoclonal antibodies), polyclonal antibodies, multispecific antibodies (e.g., bispecific antibodies), human, humanized or chimeric antibodies, and antibody fragments, e.g., Fab fragments, F(ab') fragments, fragments produced by a Fab expression library, epitope-binding fragments of any of the above, and engineered forms of antibodies, e.g., scFv molecules, that bind to 4-1BB. In an embodiment, the 4-1BB agonist is an antigen binding protein that is a fully human antibody. In an embodiment, the 4-1BB agonist is an antigen binding protein that is a humanized antibody. In some embodiments, 4-1BB agonists for use in the presently disclosed methods and compositions include anti-4-1BB antibodies, human anti-4-1BB antibodies, mouse anti-4-1BB antibodies, mammalian anti-4-1BB antibodies, monoclonal anti-4-1BB antibodies, polyclonal anti-4-1BB antibodies, chimeric anti-4-1BB antibodies, anti-4-1BB adnectins, anti-4-1BB domain antibodies, single chain anti-4-1BB fragments, heavy chain anti-4-1BB fragments, light chain anti-4-1BB fragments, anti-4-1BB fusion proteins, and fragments, derivatives, conjugates, variants, or biosimilars thereof. Agonistic anti-4-1BB antibodies are known to induce strong immune responses. Lee, et al., *PLOS One* 2013, 8, e69677. In a preferred embodiment, the 4-1BB agonist is an agonistic, anti-4-1BB humanized or fully human monoclonal antibody (i.e., an antibody derived from a single cell line). In an embodiment, the 4-1BB agonist is EU-101 (Eutilex Co. Ltd.), utomilumab, or urelumab, or a fragment, derivative, conjugate, variant, or biosimilar thereof. In a preferred embodiment, the 4-1BB agonist is utomilumab or urelumab, or a fragment, derivative, conjugate, variant, or biosimilar thereof.

In a preferred embodiment, the 4-1BB agonist or 4-1BB binding molecule may also be a fusion protein. In a preferred embodiment, a multimeric 4-1BB agonist, such as a trimeric or hexameric 4-1BB agonist (with three or six ligand binding domains), may induce superior receptor (4-1BBL) clustering and internal cellular signaling complex formation compared to an agonistic monoclonal antibody, which typically possesses two ligand binding domains. Trimeric (trivalent) or hexameric (or hexavalent) or greater fusion proteins comprising three TNFRSF binding domains and IgG1-Fc and optionally further linking two or more of these fusion proteins are described, e.g., in Gieffers, et al., *Mol. Cancer Therapeutics* 2013, 12, 2735-47.

Agonistic 4-1BB antibodies and fusion proteins are known to induce strong immune responses. In a preferred embodiment, the 4-1BB agonist is a monoclonal antibody or fusion protein that binds specifically to 4-1BB antigen in a manner sufficient to reduce toxicity. In some embodiments, the 4-1BB agonist is an agonistic 4-1BB monoclonal antibody or fusion protein that abrogates antibody-dependent cellular toxicity (ADCC), for example NK cell cytotoxicity. In some embodiments, the 4-1BB agonist is an agonistic 4-1BB monoclonal antibody or fusion protein that abrogates antibody-dependent cell phagocytosis (ADCP). In some embodiments, the 4-1BB agonist is an agonistic 4-1BB monoclonal antibody or fusion protein that abrogates complement-dependent cytotoxicity (CDC). In some embodiments, the 4-1BB agonist is an agonistic 4-1BB monoclonal antibody or fusion protein which abrogates Fc region functionality.

In some embodiments, the 4-1BB agonists are characterized by binding to human 4-1BB (SEQ ID NO:9) with high affinity and agonistic activity. In an embodiment, the 4-1BB agonist is a binding molecule that binds to human 4-1BB (SEQ ID NO:9). In an embodiment, the 4-1BB agonist is a binding molecule that binds to murine 4-1BB (SEQ ID NO:10). The amino acid sequences of 4-1BB antigen to which a 4-1BB agonist or binding molecule binds are summarized in Table 3.

TABLE 3

Amino acid sequences of 4-1BB antigens.

| Identifier | Sequence (One-Letter Amino Acid Symbols) | | | | | |
|---|---|---|---|---|---|---|
| SEQ ID NO: 9 human 4-1BB, Tumor necrosis factor receptor superfamily, member 9 (*Homo sapiens*) | MGNSCYNIVA TCDICRQCKG CFGTFNDQKR PGHSPQIISF CSCRFPEEEE | TLLLVLNFER VFRTRKECSS GICRPWTNCS FLALTSTALL GGCEL | TRSLQDPCSN TSNAECDCTP LDGKSVLVNG FLLFFLTLRF | CPAGTFCDNN GPHCLGAGCS TKERDVVCGP SVVKRGRKKL | RNQICSPCPP MCEQDCKQGQ SPADLSPGAS LYIFKQPFMR | NSFSSAGGQR ELTKKGCKDC SVTPPAPARE PVQTTQEEDG | 60 120 180 240 255 |

TABLE 3-continued

Amino acid sequences of 4-1BB antigens.

| Identifier | Sequence (One-Letter Amino Acid Symbols) | |
|---|---|---|
| SEQ ID NO: 10 murine 4-1BB, Tumor necrosis factor receptor superfamily, member 9 (Mus musculus) | MGNNCYNVVV IVLLLVGCEK VGAVQNSCDN CQPGTFCRKY NPVCKSCPPS TFSSIGGQPN<br>CNICRVCAGY FRFKKFCSST HNAECECIEG FHCLGPQCTR CEKDCRPGQE LTKQGCKTCS<br>LGTFNDQNGT GVCRPWTNCS LDGRSVLKTG TTEKDVVCGP PVVSFSPSTT ISVTPEGGPG<br>GHSLQVLTLF LALTSALLLA LIFITLLFSV LKWIRKKFPH IFKQPFKKTT GAAQEEDACS<br>CRCPQEEEGG GGGYEL | 60<br>120<br>180<br>240<br>256 |

In some embodiments, the compositions, processes and methods described include a 4-1BB agonist that binds human or murine 4-1BB with a $K_D$ of about 100 pM or lower, binds human or murine 4-1BB with a $K_D$ of about 90 pM or lower, binds human or murine 4-1BB with a $K_D$ of about 80 pM or lower, binds human or murine 4-1BB with a $K_D$ of about 70 pM or lower, binds human or murine 4-1BB with a $K_D$ of about 60 pM or lower, binds human or murine 4-1BB with a $K_D$ of about 50 pM or lower, binds human or murine 4-1BB with a $K_D$ of about 40 pM or lower, or binds human or murine 4-1BB with a $K_D$ of about 30 pM or lower.

In some embodiments, the compositions, processes and methods described include a 4-1BB agonist that binds to human or murine 4-1BB with a $k_{assoc}$ of about $7.5 \times 10^5$ 1/M·s or faster, binds to human or murine 4-1BB with a $k_{assoc}$ of about $7.5 \times 10^5$ 1/M·s or faster, binds to human or murine 4-1BB with a $k_{assoc}$ of about $8 \times 10^5$ 1/M·s or faster, binds to human or murine 4-1BB with a $k_{assoc}$ of about $8.5 \times 10^5$ 1/M·s or faster, binds to human or murine 4-1BB with a $k_{assoc}$ of about $9 \times 10^5$ 1/M·s or faster, binds to human or murine 4-1BB with a $k_{assoc}$ of about $9.5 \times 10^5$ 1/M·s or faster, or binds to human or murine 4-1BB with a $k_{assoc}$ of about $1 \times 10^6$ 1/M·s or faster.

In some embodiments, the compositions, processes and methods described include a 4-1BB agonist that binds to human or murine 4-1BB with a $k_{dissoc}$ of about $2 \times 10^{-5}$ 1/s or slower, binds to human or murine 4-1BB with a $k_{dissoc}$ of about $2.1 \times 10^{-5}$ 1/s or slower, binds to human or murine 4-1BB with a $k_{dissoc}$ of about $2.2 \times 10^{-5}$ 1/s or slower, binds to human or murine 4-1BB with a $k_{dissoc}$ of about $2.3 \times 10^{-5}$ 1/s or slower, binds to human or murine 4-1BB with a $k_{dissoc}$ of about $2.4 \times 10^{-5}$ 1/s or slower, binds to human or murine 4-1BB with a $k_{dissoc}$ of about $2.5 \times 10^{-5}$ 1/s or slower, binds to human or murine 4-1BB with a $k_{dissoc}$ of about $2.6 \times 10^{-5}$ 1/s or slower or binds to human or murine 4-1BB with a $k_{dissoc}$ of about $2.7 \times 10^{-5}$ 1/s or slower, binds to human or murine 4-1BB with a $k_{dissoc}$ of about $2.8 \times 10^{-5}$ 1/s or slower, binds to human or murine 4-1BB with a $k_{dissoc}$ of about $2.9 \times 10^{-5}$ 1/s or slower, or binds to human or murine 4-1BB with a $k_{dissoc}$ of about $3 \times 10^{-5}$ 1/s or slower.

In some embodiments, the compositions, processes and methods described include a 4-1BB agonist that binds to human or murine 4-1BB with an $IC_{50}$ of about 10 nM or lower, binds to human or murine 4-1BB with an $IC_{50}$ of about 9 nM or lower, binds to human or murine 4-1BB with an $IC_{50}$ of about 8 nM or lower, binds to human or murine 4-1BB with an $IC_{50}$ of about 7 nM or lower, binds to human or murine 4-1BB with an $IC_{50}$ of about 6 nM or lower, binds to human or murine 4-1BB with an $IC_{50}$ of about 5 nM or lower, binds to human or murine 4-1BB with an $IC_{50}$ of about 4 nM or lower, binds to human or murine 4-1BB with an $IC_{50}$ of about 3 nM or lower, binds to human or murine 4-1BB with an $IC_{50}$ of about 2 nM or lower, or binds to human or murine 4-1BB with an $IC_{50}$ of about 1 nM or lower.

In a preferred embodiment, the 4-1BB agonist is utomilumab, also known as PF-05082566 or MOR-7480, or a fragment, derivative, variant, or biosimilar thereof. Utomilumab is available from Pfizer, Inc. Utomilumab is an immunoglobulin G2-lambda, anti-[*Homo sapiens* TNFRSF9 (tumor necrosis factor receptor (TNFR) superfamily member 9, 4-1BB, T cell antigen ILA, CD137)], *Homo sapiens* (fully human) monoclonal antibody. The amino acid sequences of utomilumab are set forth in Table 4. Utomilumab comprises glycosylation sites at Asn59 and Asn292; heavy chain intrachain disulfide bridges at positions 22-96 ($V_H$-$V_L$), 143-199 ($C_H$1-$C_L$), 256-316 ($C_H$2) and 362-420 ($C_H$3); light chain intrachain disulfide bridges at positions 22'-87' ($V_H$-$V_L$) and 136'-195' ($C_H$1-$C_L$); interchain heavy chain-heavy chain disulfide bridges at IgG2A isoform positions 218-218, 219-219, 222-222, and 225-225, at IgG2A/B isoform positions 218-130, 219-219, 222-222, and 225-225, and at IgG2B isoform positions 219-130 (2), 222-222, and 225-225; and interchain heavy chain-light chain disulfide bridges at IgG2A isoform positions 130-213' (2), IgG2A/B isoform positions 218-213' and 130-213', and at IgG2B isoform positions 218-213' (2). The preparation and properties of utomilumab and its variants and fragments are described in U.S. Pat. Nos. 8,821,867; 8,337,850; and 9,468,678, and International Patent Application Publication No. WO 2012/032433 A1, the disclosures of each of which are incorporated by reference herein. Preclinical characteristics of utomilumab are described in Fisher, et al., *Cancer Immunolog. & Immunother.* 2012, 61, 1721-33. Current clinical trials of utomilumab in a variety of hematological and solid tumor indications include U.S. National Institutes of Health clinicaltrials.gov identifiers NCT02444793, NCT01307267, NCT02315066, and NCT02554812.

In an embodiment, a 4-1BB agonist comprises a heavy chain given by SEQ ID NO:11 and a light chain given by SEQ ID NO:12. In an embodiment, a 4-1BB agonist comprises heavy and light chains having the sequences shown in SEQ ID NO:11 and SEQ ID NO:12, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:11 and SEQ ID NO:12, respectively. In an embodiment, a 4-1BB agonist comprises heavy and light chains that are each at least 98% identical to the sequences shown in SEQ ID NO:11 and SEQ ID NO:12, respectively. In an embodiment, a 4-1BB agonist comprises heavy and light chains that are each at least 97% identical to the sequences shown in SEQ ID NO:11 and SEQ ID NO:12, respectively. In an embodiment, a 4-1BB agonist comprises heavy and light chains that are each at least 96% identical to the sequences shown in SEQ ID NO:11 and SEQ ID NO:12, respectively. In an embodiment, a 4-1BB agonist comprises heavy and light chains that are each at least 95% identical to the sequences shown in SEQ ID NO:11 and SEQ ID NO:12, respectively.

In an embodiment, the 4-1BB agonist comprises the heavy and light chain CDRs or variable regions (VRs) of utomilumab. In an embodiment, the 4-1BB agonist heavy chain variable region ($V_H$) comprises the sequence shown in SEQ ID NO:13, and the 4-1BB agonist light chain variable region ($V_L$) comprises the sequence shown in SEQ ID NO: 14, and conservative amino acid substitutions thereof. In an embodiment, a 4-1BB agonist comprises $V_H$ and $V_L$ regions that are each at least 99% identical to the sequences shown in SEQ ID NO:13 and SEQ ID NO:14, respectively. In an embodiment, a 4-1BB agonist comprises $V_H$ and $V_L$ regions that are each at least 98% identical to the sequences shown in SEQ ID NO:13 and SEQ ID NO:14, respectively. In an embodiment, a 4-1BB agonist comprises $V_H$ and $V_L$ regions that are each at least 97% identical to the sequences shown in SEQ ID NO:13 and SEQ ID NO:14, respectively. In an embodiment, a 4-1BB agonist comprises $V_H$ and $V_L$ regions that are each at least 96% identical to the sequences shown in SEQ ID NO:13 and SEQ ID NO:14, respectively. In an embodiment, a 4-1BB agonist comprises $V_H$ and $V_L$ regions that are each at least 95% identical to the sequences shown in SEQ ID NO:13 and SEQ ID NO:14, respectively. In an embodiment, a 4-1BB agonist comprises an scFv antibody comprising $V_H$ and $V_L$ regions that are each at least 99% identical to the sequences shown in SEQ ID NO:13 and SEQ ID NO:14.

In an embodiment, a 4-1BB agonist comprises heavy chain CDR1, CDR2 and CDR3 domains having the sequences set forth in SEQ ID NO:15, SEQ ID NO: 16, and SEQ ID NO:17, respectively, and conservative amino acid substitutions thereof, and light chain CDR1, CDR2 and CDR3 domains having the sequences set forth in SEQ ID NO:18, SEQ ID NO:19, and SEQ ID NO:20, respectively, and conservative amino acid substitutions thereof.

In an embodiment, the 4-1BB agonist is a 4-1BB agonist biosimilar monoclonal antibody approved by drug regulatory authorities with reference to utomilumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is utomilumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is utomilumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is utomilumab.

TABLE 4

Amino acid sequences for 4-1BB agonist antibodies related to utomilumab.

| Identifier | Sequence (One-Letter Amino Acid Symbols) |
|---|---|
| SEQ ID NO: 11<br>heavy chain for<br>utomilumab | EVQLVQSGAE VKKPGESLRI SCKGSGYSFS TYWISWVRQM PGKGLEWMGK IYPGDSYTNY 60<br>SPSFQGQVTI SADKSISTAY LQWSSLKASD TAMYYCARGY GIFDYWGQGT LVTVSSASTK 120<br>GPSVFPLAPC SRSTSESTAA LGCLVKDYFP EPVTVSWNSG ALTSGVHTFP AVLQSSGLYS 180<br>LSSVVTVPSS NFGTQTYTCN VDHKPSNTKV DKTVERKCCV ECPPCPAPPV AGPSVFLFPP 240<br>KPKDTLMISR TPEVTCVVVD VSHEDPEVQF NWYVDGVEVH NAKTKPREEQ FNSTFRVVSV 300<br>LTVVHQDWLN GKEYKCKVSN KGLPAPIEKT ISKTKGQPRE PQVYTLPPSR EEMTKNQVSL 360<br>TCLVKGFYPS DIAVEWESNG QPENNYKTTP PMLDSDGSFF LYSKLTVDKS RWQQGNVFSC 420<br>SVMHEALHNH YTQKSLSLSP G 441 |
| SEQ ID NO: 12<br>light chain for<br>utomilumab | SYELTQPPSV SVSPGQTASI TCSGDNIGDQ YAHWYQQKPG QSPVLVIYQD KNRPSGIPER 60<br>FSGSNSGNTA TLTISGTQAM DEADYYCATY TGFGSLAVFG GGTKLTVLGQ PKAAPSVTLF 120<br>PPSSEELQAN KATLVCLISD FYPGAVTVAW KADSSPVKAG VETTTPSKQS NNKYAASSYL 180<br>SLTPEQWKSH RSYSCQVTHE GSTVEKTVAP TECS 214 |
| SEQ ID NO: 13<br>heavy chain<br>variable region<br>for utomilumab | EVQLVQSGAE VKKPGESLRI SCKGSGYSFS TYWISWVRQM PGKGLEWMG KIYPGDSYTN 60<br>YSPSFQGQVT ISADKSISTA YLQWSSLKAS DTAMYYCARG YGIFDYWGQ GTLVTVSS 118 |
| SEQ ID NO: 14<br>light chain<br>variable region<br>for utomilumab | SYELTQPPSV SVSPGQTASI TCSGDNIGDQ YAHWYQQKPG QSPVLVIYQD KNRPSGIPER 60<br>FSGSNSGNTA TLTISGTQAM DEADYYCATY TGFGSLAVFG GGTKLTVL 108 |

TABLE 4-continued

Amino acid sequences for 4-1BB agonist antibodies related to utomilumab.

| Identifier | Sequence (One-Letter Amino Acid Symbols) | |
|---|---|---|
| SEQ ID NO: 15<br>heavy chain CDR1<br>for utomilumab | STYWIS | 6 |
| SEQ ID NO: 16<br>heavy chain CDR2<br>for utomilumab | KIYPGDSYTN YSPSFQG | 17 |
| SEQ ID NO: 17<br>heavy chain CDR3<br>for utomilumab | RGYGIFDY | 8 |
| SEQ ID NO: 18<br>light chain CDR1<br>for utomilumab | SGDNIGDQYA H | 11 |
| SEQ ID NO: 19<br>light chain CDR2<br>for utomilumab | QDKNRPS | 7 |
| SEQ ID NO: 20<br>light chain CDR3<br>for utomilumab | ATYTGFGSLA V | 11 |

In a preferred embodiment, the 4-1BB agonist is the monoclonal antibody urelumab, also known as BMS-663513 and 20H4.9.h4a, or a fragment, derivative, variant, or biosimilar thereof. Urelumab is available from Bristol-Myers Squibb, Inc., and Creative Biolabs, Inc. Urelumab is an immunoglobulin G4-kappa, anti-[*Homo sapiens* TNFRSF9 (tumor necrosis factor receptor superfamily member 9, 4-1BB, T cell antigen ILA, CD137)], *Homo sapiens* (fully human) monoclonal antibody. The amino acid sequences of urelumab are set forth in Table 5. Urelumab comprises N-glycosylation sites at positions 298 (and 298"); heavy chain intrachain disulfide bridges at positions 22-95 ($V_H$-$V_L$), 148-204 ($C_H1$-$C_L$), 262-322 ($C_H2$) and 368-426 ($C_H3$) (and at positions 22"-95", 148"-204", 262"-322", and 368"-426"); light chain intrachain disulfide bridges at positions 23'-88' ($V_H$-$V_L$) and 136'-196' ($C_H1$-$C_L$) (and at positions 23'''-88''' and 136'''-196'''); interchain heavy chain-heavy chain disulfide bridges at positions 227-227" and 230-230"; and interchain heavy chain-light chain disulfide bridges at 135-216' and 135"-216'". The preparation and properties of urelumab and its variants and fragments are described in U.S. Pat. Nos. 7,288,638 and 8,962,804, the disclosures of which are incorporated by reference herein. The preclinical and clinical characteristics of urelumab are described in Segal, et al., Clin. *Cancer Res.* 2016, available at http:/dx.doi.org/10.1158/1078-0432.CCR-16-1272. Current clinical trials of urelumab in a variety of hematological and solid tumor indications include U.S. National Institutes of Health clinicaltrials.gov identifiers NCT01775631, NCT02110082, NCT02253992, and NCT01471210.

In an embodiment, a 4-1BB agonist comprises a heavy chain given by SEQ ID NO:21 and a light chain given by SEQ ID NO:22. In an embodiment, a 4-1BB agonist comprises heavy and light chains having the sequences shown in SEQ ID NO:21 and SEQ ID NO:22, respectively, or antigen binding fragments, Fab fragments, single-chain variable fragments (scFv), variants, or conjugates thereof. In an embodiment, a 4-1BB agonist comprises heavy and light chains that are each at least 99% identical to the sequences shown in SEQ ID NO:21 and SEQ ID NO:22, respectively. In an embodiment, a 4-1BB agonist comprises heavy and light chains that are each at least 98% identical to the sequences shown in SEQ ID NO:21 and SEQ ID NO:22, respectively. In an embodiment, a 4-1BB agonist comprises heavy and light chains that are each at least 97% identical to the sequences shown in SEQ ID NO:21 and SEQ ID NO:22, respectively. In an embodiment, a 4-1BB agonist comprises heavy and light chains that are each at least 96% identical to the sequences shown in SEQ ID NO:21 and SEQ ID NO:22, respectively. In an embodiment, a 4-1BB agonist comprises heavy and light chains that are each at least 95% identical to the sequences shown in SEQ ID NO:21 and SEQ ID NO:22, respectively.

In an embodiment, the 4-1BB agonist comprises the heavy and light chain CDRs or variable regions (VRs) of urelumab. In an embodiment, the 4-1BB agonist heavy chain variable region ($V_H$) comprises the sequence shown in SEQ ID NO:23, and the 4-1BB agonist light chain variable region ($V_L$) comprises the sequence shown in SEQ ID NO:24, and conservative amino acid substitutions thereof. In an embodiment, a 4-1BB agonist comprises $V_H$ and $V_L$ regions that are each at least 99% identical to the sequences shown in SEQ ID NO:23 and SEQ ID NO:24, respectively. In an embodiment, a 4-1BB agonist comprises $V_H$ and $V_L$ regions that are each at least 98% identical to the sequences shown in SEQ ID NO:23 and SEQ ID NO:24, respectively. In an embodiment, a 4-1BB agonist comprises $V_H$ and $V_L$ regions that are each at least 97% identical to the sequences shown in SEQ ID NO:23 and SEQ ID NO:24, respectively. In an embodiment, a 4-1BB agonist comprises $V_H$ and $V_L$ regions that are each at least 96% identical to the sequences shown in SEQ ID NO:23 and SEQ ID NO:24, respectively. In an embodiment, a 4-1BB agonist comprises $V_H$ and $V_L$ regions that are each at least 95% identical to the sequences shown in SEQ ID NO:23 and SEQ ID NO:24, respectively. In an embodiment, a 4-1BB agonist comprises an scFv antibody comprising $V_H$ and $V_L$ regions that are each at least 99% identical to the sequences shown in SEQ ID NO:23 and SEQ ID NO:24.

In an embodiment, a 4-1BB agonist comprises heavy chain CDR1, CDR2 and CDR3 domains having the sequences set forth in SEQ ID NO:25, SEQ ID NO:26, and SEQ ID NO:27, respectively, and conservative amino acid substitutions thereof, and light chain CDR1, CDR2 and CDR3 domains having the sequences set forth in SEQ ID NO:28, SEQ ID NO:29, and SEQ ID NO:30, respectively, and conservative amino acid substitutions thereof.

In an embodiment, the 4-1BB agonist is a 4-1BB agonist biosimilar monoclonal antibody approved by drug regulatory authorities with reference to urelumab. In an embodiment, the biosimilar monoclonal antibody comprises an 4-1BB antibody comprising an amino acid sequence which has at least 97% sequence identity, e.g., 97%, 98%, 99% or 100% sequence identity, to the amino acid sequence of a reference medicinal product or reference biological product and which comprises one or more post-translational modifications as compared to the reference medicinal product or reference biological product, wherein the reference medicinal product or reference biological product is urelumab. In some embodiments, the one or more post-translational modifications are selected from one or more of: glycosylation, oxidation, deamidation, and truncation. In some embodiments, the biosimilar is a 4-1BB agonist antibody authorized or submitted for authorization, wherein the 4-1BB agonist antibody is provided in a formulation which differs from the formulations of a reference medicinal product or reference biological product, wherein the reference medicinal product or reference biological product is urelumab. The 4-1BB agonist antibody may be authorized by a drug regulatory authority such as the U.S. FDA and/or the European Union's EMA. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab. In some embodiments, the biosimilar is provided as a composition which further comprises one or more excipients, wherein the one or more excipients are the same or different to the excipients comprised in a reference medicinal product or reference biological product, wherein the reference medicinal product or reference biological product is urelumab.

TABLE 5

Amino acid sequences for 4-1BB agonist antibodies related to urelumab.

| Identifier | Sequence (One-Letter Amino Acid Symbols) | | | | | |
|---|---|---|---|---|---|---|
| SEQ ID NO: 21 heavy chain for urelumab | QVQLQQWGAG PSLESRVTIS SASTKGPSVF SGLYSLSSVV VFLFPPKPKD YRVVSVLTVL KNQVSLTCLV GNVFSCSVMH | LLKPSETLSL VDTSKNQFSL PLAPCSRSTS TVPSSSLGTK TLMISRTPEV HQDWLNGKEY KGFYPSDIAV EALHNHYTQK | TCAVYGGSFS KLSSVTAADT ESTAALGCLV TYTCNVDHKP TCVVVDVSQE KCKVSNKGLP EWESNGQPEN SLSLSLGK | GYYWSWIRQS AVYYCARDYG KDYPPEPVTV SNTKVDKRVE DPEVQFNWYV SSIEKTISKA NYKTTPPVLD | PEKGLEWIGE PGNYDWYFDL SWNSGALTSG SKYGPPCPPC DGVEVHNAKT KGQPREPQVY SDGSFFLYSR | INHGGYVTYN 60 WGRGTLVTVS 120 VHTFPAVLQS 180 PAPEFLGGPS 240 KPREEQFNST 300 TLPPSQEEMT 360 LTVDKSRWQE 420 448 |
| SEQ ID NO: 22 light chain for urelumab | EIVLTQSPAT RFSGSGSGTD PPSDEQLKSG LTLSKADYEK | LSLSPGERAT FTLTISSLEP TASVVCLLNN HKVYACEVTH | LSCRASQSVS EDFAVYYCQQ FYPREAKVQW QGLSSPVTKS | SYLAWYQQKP RSNWPPALTF KVDNALQSGN FNRGEC | GQAPRLLIYD CGGTKVEIKR SQESVTEQDS | ASNRATGIPA 60 TVAAPSVFIF 120 KDSTYSLSST 180 216 |
| SEQ ID NO: 23 variable heavy chain for urelumab | MKHLWFFLLL EKGLEWIGEI | VAAPRWVLSQ NHGGYVTYNP | VQLQQWGAGL SLESRVTISV | LKPSETLSLT DTSKNQFSLK | CAVYGGSFSG LSSVTAADTA | YYWSWIRQSP 60 VYYCARDYGP 120 |
| SEQ ID NO: 24 variable light chain for urelumab | MEAPAQLLFL GQAPRLLIYD | LLLWLPDTTG ASNRATGIPA | EIVLTQSPAT RFSGSGSGTD | LSLSPGERAT FTLTISSLEP | LSCRASQSVS EDFAVYYCQQ | SYLAWYQQKP 60 110 |
| SEQ ID NO: 25 heavy chain CDR1 for urelumab | GYYWS | | | | | 5 |
| SEQ ID NO: 26 heavy chain CDR2 for urelumab | EINHGGYVTY NPSLES | | | | | 16 |
| SEQ ID NO: 27 heavy chain CDR3 for urelumab | DYGPGNYDWY FDL | | | | | 13 |
| SEQ ID NO: 28 light chain CDR1 for urelumab | RASQSVSSYL A | | | | | 11 |
| SEQ ID NO: 29 light chain CDR2 for urelumab | DASNRAT | | | | | 7 |
| SEQ ID NO: 30 light chain CDR3 for urelumab | QQRSDWPPAL T | | | | | 11 |

In an embodiment, the 4-1BB agonist is selected from the group consisting of 1D8, 3Elor, 4B4 (BioLegend 309809), H4-1BB-M127 (BD Pharmingen 552532), BBK2 (Thermo Fisher MS621PABX), 145501 (Leinco Technologies B591), the antibody produced by cell line deposited as ATCC No. HB-11248 and disclosed in U.S. Pat. No. 6,974,863, 5F4 (BioLegend 31 1503), C65-485 (BD Pharmingen 559446), antibodies disclosed in U.S. Patent Application Publication No. US 2005/0095244, antibodies disclosed in U.S. Pat. No. 7,288,638 (such as 20H4.9-IgG1 (BMS-663031)), antibodies disclosed in U.S. Pat. No. 6,887,673 (such as 4E9 or BMS-554271), antibodies disclosed in U.S. Pat. No. 7,214, 493, antibodies disclosed in U.S. Pat. No. 6,303,121, antibodies disclosed in U.S. Pat. No. 6,569,997, antibodies disclosed in U.S. Pat. No. 6,905,685 (such as 4E9 or BMS-554271), antibodies disclosed in U.S. Pat. No. 6,362, 325 (such as 1D8 or BMS-469492; 3H3 or BMS-469497; or 3E1), antibodies disclosed in U.S. Pat. No. 6,974,863 (such as 53A2); antibodies disclosed in U.S. Pat. No. 6,210,669 (such as 1D8, 3B8, or 3E1), antibodies described in U.S. Pat. No. 5,928,893, antibodies disclosed in U.S. Pat. No. 6,303, 121, antibodies disclosed in U.S. Pat. No. 6,569,997, antibodies disclosed in International Patent Application Publication Nos. WO 2012/177788, WO 2015/119923, and WO 2010/042433, and fragments, derivatives, conjugates, variants, or biosimilars thereof, wherein the disclosure of each of the foregoing patents or patent application publications is incorporated by reference here.

In an embodiment, the 4-1BB agonist is a 4-1BB agonistic fusion protein described in International Patent Application Publication Nos. WO 2008/025516 A1, WO 2009/007120 A1, WO 2010/003766 A1, WO 2010/010051 A1, and WO 2010/078966 A1; U.S. Patent Application Publication Nos. US 2011/0027218 A1, US 2015/0126709 A1, US 2011/ 0111494 A1, US 2015/0110734 A1, and US 2015/0126710 A1; and U.S. Pat. Nos. 9,359,420, 9,340,599, 8,921,519, and 8,450,460, the disclosures of which are incorporated by reference herein.

In an embodiment, the 4-1BB agonist is a 4-1BB agonistic fusion protein as depicted in Structure I-A (C-terminal Fc-antibody fragment fusion protein) or Structure I-B (N-terminal Fc-antibody fragment fusion protein), or a fragment, derivative, conjugate, variant, or biosimilar thereof: In structures I-A and I-B, the cylinders refer to individual polypeptide binding domains (see, FIG. 140). Structures I-A and I-B comprise three linearly-linked TNFRSF binding domains derived from e.g., 4-1BBL or an antibody that binds 4-1BB, which fold to form a trivalent protein, which is then linked to a second trivalent protein through IgG1-Fc (including $C_H^3$ and $C_H^2$ domains) is then used to link two of the trivalent proteins together through disulfide bonds (small elongated ovals), stabilizing the structure and providing an agonists capable of bringing together the intracellular signaling domains of the six receptors and signaling proteins to form a signaling complex. The TNFRSF binding domains denoted as cylinders may be scFv domains comprising, e.g., a $V_H$ and a $V_L$ chain connected by a linker that may comprise hydrophilic residues and Gly and Ser sequences for flexibility, as well as Glu and Lys for solubility. Any scFv domain design may be used, such as those described in de Marco, *Microbial Cell Factories,* 2011, 10, 44; Ahmad, et al., *Clin. & Dev. Immunol.* 2012, 980250; Monnier, et al., *Antibodies,* 2013, 2, 193-208; or in references incorporated elsewhere herein. Fusion protein structures of this form are described in U.S. Pat. Nos. 9,359,420, 9,340,599, 8,921,519, and 8,450,460, the disclosures of which are incorporated by reference herein.

Amino acid sequences for the other polypeptide domains of structure I-A are given in Table 6. The Fc domain preferably comprises a complete constant domain (amino acids 17-230 of SEQ ID NO:31) the complete hinge domain (amino acids 1-16 of SEQ ID NO:31) or a portion of the hinge domain (e.g, amino acids 4-16 of SEQ ID NO:31). Preferred linkers for connecting a C-terminal Fc-antibody may be selected from the embodiments given in SEQ ID NO:32 to SEQ ID NO:41, including linkers suitable for fusion of additional polypeptides.

TABLE 6

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | |
|---|---|---|
| SEQ ID NO: 31<br>Fc domain | KSCDKTHTCP PCPAPELLGG PSVFLFPPKP KDTLMISRTP EVTCVVVDVS HEDPEVKFNW<br>YVDGVEVHNA KTKPREEQYN STYRVVSVLT VLHQDLWNGK EYKCKVSNKA LPAPIEKTIS<br>KAKGQPREPQ VYTLPPSREE MTKNQVSLTC LVKGFYPSDI AVEWESNGQP ENNYKTTPPV<br>LDSDGSFFLY SKLTVDKSRW QQGNVFSCSV MHEALHNHYT QKSLSLSPGK | 60<br>120<br>180<br>230 |
| SEQ ID NO: 32<br>linker | GGPGSSKSCD KTHTCPPCPA PE | 22 |
| SEQ ID NO: 33<br>linker | GGSGSSKSCD KTHTCPPCPA PE | 22 |
| SEQ ID NO: 34<br>linker | GGPGSSSSSS SKSCDKTHTC PPCPAPE | 27 |
| SEQ ID NO: 35<br>linker | GGSGSSSSSS SKSCDKTHTC PPCPAPE | 27 |
| SEQ ID NO: 36<br>linker | GGPGSSSSSS SSSKSCDKTH TCPPCPAPE | 29 |
| SEQ ID NO: 37<br>linker | GGSGSSSSSS SSSKSCDKTH TCPPCPAPE | 29 |
| SEQ ID NO: 38<br>linker | GGPGSSGSGS SDKTHTCPPC PAPE | 24 |

TABLE 6-continued

Amino acid sequences for TNFRSF fusion proteins, including 4-1BB fusion proteins, with C-terminal Fc-antibody fragment fusion protein design (structure I-A).

| Identifier | Sequence (One-Letter Amino Acid Symbols) | |
|---|---|---|
| SEQ ID NO: 39 linker | GGPGSSGSGS DKTHTCPPCP APE | 23 |
| SEQ ID NO: 40 linker | GGPSSSGSDK THTCPPCPAP E | 21 |
| SEQ ID NO: 41 linker | GGSSSSSSSS GSDKTHTCPP CPAPE | 25 |

Amino acid sequences for the other polypeptide domains of structure I-B are given in Table 7. If an Fc antibody fragment is fused to the N-terminus of an TNRFSF fusion protein as in structure I-B, the sequence of the Fc module is preferably that shown in SEQ ID NO:42, and the linker sequences are preferably selected from those embodiments set forth in SEQ ID NO:43 to SEQ ID NO:45.

TABLE 7

Amino acid sequences for TNFRSF fusion proteins, including 4-1BB fusion protiens, with N-terminal Fc-antibody fragment fusion protein design (structure I-B).

| Identifier | Sequence (One-Letter Amino Acid Symbols) | |
|---|---|---|
| SEQ ID NO: 42 Fc domain | METDTLLLWV LLLWVPAGNG DKTHTCPPCP APELLGGPSV FLFPPKPKDT LMISRTPEVT | 60 |
| | CVVVDVSHED PEVKFNWYVD GVEVHNAKTK PREEQYNSTY RVVSVLTVLH QDWLNGKEYK | 120 |
| | CKVSNKALPA PIEKTISKAK GQPREPQVYT LPPSREEMTK NQVSLTCLVK GFYPSDIAVE | 180 |
| | WESNGQPENN YKTTPPVLDS DGSFFLYSKL TVDKSRWQQG NVFSCSVMHE ALHNHYTQKS | 240 |
| | LSLSPG | 246 |
| SEQ ID NO: 43 linker | SGSGSGSGSG S | 11 |
| SEQ ID NO: 44 linker | SSSSSSGSGS GS | 12 |
| SEQ ID NO: 45 linker | SSSSSSGSGS GSGSGS | 16 |

In an embodiment, a 4-1BB agonist fusion protein according to structures I-A or I-B comprises one or more 4-1BB binding domains selected from the group consisting of a variable heavy chain and variable light chain of utomilumab, a variable heavy chain and variable light chain of urelumab, a variable heavy chain and variable light chain of utomilumab, a variable heavy chain and variable light chain selected from the variable heavy chains and variable light chains described in Table 8, any combination of a variable heavy chain and variable light chain of the foregoing, and fragments, derivatives, conjugates, variants, and biosimilars thereof.

In an embodiment, a 4-1BB agonist fusion protein according to structures I-A or I-B comprises one or more 4-1BB binding domains comprising a 4-1BBL sequence. In an embodiment, a 4-1BB agonist fusion protein according to structures I-A or I-B comprises one or more 4-1BB binding domains comprising a sequence according to SEQ ID NO:46. In an embodiment, a 4-1BB agonist fusion protein according to structures I-A or I-B comprises one or more 4-1BB binding domains comprising a soluble 4-1BBL sequence. In an embodiment, a 4-1BB agonist fusion protein according to structures I-A or I-B comprises one or more 4-1BB binding domains comprising a sequence according to SEQ ID NO:47.

In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO: 13 and SEQ ID NO:14, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the sequences shown in SEQ ID NO:23 and SEQ ID NO:24, respectively, wherein the $V_H$ and $V_L$ domains are connected by a linker. In an embodiment, a 4-1BB agonist fusion protein according to structures I-A or I-B comprises one or more 4-1BB binding domains that is a scFv domain comprising $V_H$ and $V_L$ regions that are each at least 95% identical to the $V_H$ and $V_L$ sequences given in Table 8, wherein the $V_H$ and $V_L$ domains are connected by a linker.

TABLE 8

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| SEQ ID NO: 46 4-1BBL | MEYASDASLD PEAPWPPAPR ARACRVLPWA LVAGLLLLLL LAAACAVFLA CPWAVSGARA | 60 |
| | SPGSAASPRL REGPELSPDD PAGLLDLRQG MFAQLVAQNV LLIDGPLSWY SDPGLAGVSL | 120 |
| | TGGLSYKEDT KELVVAKAGV YYVFFQLELR RVVAGEGSGS VSLALHLQPL RSAAGAAALA | 180 |

TABLE 8-continued

Additional polypeptide domains useful as 4-1BB binding domains in fusion proteins or as scFv 4-1BB agonist antibodies.

| Identifier | Sequence (One-Letter Amino Acid Symbols) | |
|---|---|---|
| | LTVDLPPASS EARNSAFGFQ GRLLHLSAGQ RLGVHLHTEA RARHAWQLTQ GATVLGLFRV | 240 |
| | TPEIPAGLPS PRSE | 254 |
| SEQ ID NO: 47<br>4-1BBL soluble<br>domain | LRQGMFAQLV AQNVLLIDGP LSWYSDPGLA GVSLTGGLSY KEDTKELVVA KAGVYYVFFQ<br>LELRRVVAGE GSGSVSLALH LQPLRSAAGA AALALTVDLP PASSEARNSA FGFQGRLLHL<br>SAGQRLGVHL HTEARARHAW QLTQGATVLG LFRVTPEIPA GLPSPRSE | 60<br>120<br>168 |
| SEQ ID NO: 48<br>variable heavy<br>chain for 4B4-1-1<br>version 1 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVS | 60<br>118 |
| SEQ ID NO: 49<br>variable light<br>chain for 4B4-1-1<br>version 1 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIK | 60<br>107 |
| SEQ ID NO: 50<br>variable heavy<br>chain for 4B4-1-1<br>version 2 | QVQLQQPGAE LVKPGASVKL SCKASGYTFS SYWMHWVKQR PGQVLEWIGE INPGNGHTNY<br>NEKFKSKATL TVDKSSSTAY MQLSSLTSED SAVYYCARSF TTARGFAYWG QGTLVTVSA | 60<br>119 |
| SEQ ID NO: 51<br>variable light<br>chain for 4B4-1-1<br>version 2 | DIVMTQSPAT QSVTPGDRVS LSCRASQTIS DYLHWYQQKS HESPRLLIKY ASQSISGIPS<br>RFSGSGSGSD FTLSINSVEP EDVGVYYCQD GHSFPPTFGG GTKLEIKR | 60<br>108 |
| SEQ ID NO: 52<br>variable heavy<br>chain for H39E3-2 | MDWTWRILFL VAAATGAHSE VQLVESGGGL VQPGGSLRLS CAASGFTFSD YWMSWVRQAP<br>GKGLEWVADI KNDGSYTNYA PSLTNRFTIS RDNAKNSLYL QMNSLRAEDT AVYYCARELT | 60<br>120 |
| SEQ ID NO: 53<br>variable light<br>chain for H39E3-2 | MEAPAQLLFL LLLWLPDTTG DIVMTQSPDS LAVSLGERAT INCKSSQSLL SSGNQKNYL<br>WYQQKPGQPP KLLIYYASTR QSGVPDRFSG SGSGTDFTLT ISSLQAEDVA | 60<br>110 |

In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, and wherein the additional domain is a Fab or Fc fragment domain. In an embodiment, the 4-1BB agonist is a 4-1BB agonistic single-chain fusion polypeptide comprising (i) a first soluble 4-1BB binding domain, (ii) a first peptide linker, (iii) a second soluble 4-1BB binding domain, (iv) a second peptide linker, and (v) a third soluble 4-1BB binding domain, further comprising an additional domain at the N-terminal and/or C-terminal end, wherein the additional domain is a Fab or Fc fragment domain, wherein each of the soluble 4-1BB domains lacks a stalk region (which contributes to trimerisation and provides a certain distance to the cell membrane, but is not part of the 4-1BB binding domain) and the first and the second peptide linkers independently have a length of 3-8 amino acids.

In an embodiment, the 4-1BB agonist is a 4-1BB agonistic single-chain fusion polypeptide comprising (i) a first soluble tumor necrosis factor (TNF) superfamily cytokine domain, (ii) a first peptide linker, (iii) a second soluble TNF superfamily cytokine domain, (iv) a second peptide linker, and (v) a third soluble TNF superfamily cytokine domain, wherein each of the soluble TNF superfamily cytokine domains lacks a stalk region and the first and the second peptide linkers independently have a length of 3-8 amino acids, and wherein each TNF superfamily cytokine domain is a 4-1BB binding domain.

In an embodiment, the 4-1BB agonist is a 4-1BB agonistic scFv antibody comprising any of the foregoing $V_H$ domains linked to any of the foregoing $V_L$ domains.

In an embodiment, the 4-1BB agonist agonist is BPS Bioscience 4-1BB agonist antibody catalog no. 79097-2, commercially available from BPS Bioscience, San Diego, CA, USA. In an embodiment, the 4-1BB agonist agonist is Creative Biolabs 4-1BB agonist antibody catalog no. MOM-18179, commercially available from Creative Biolabs, Shirley, NY, USA.

III. TIL Manufacturing Processes

Figure 1:
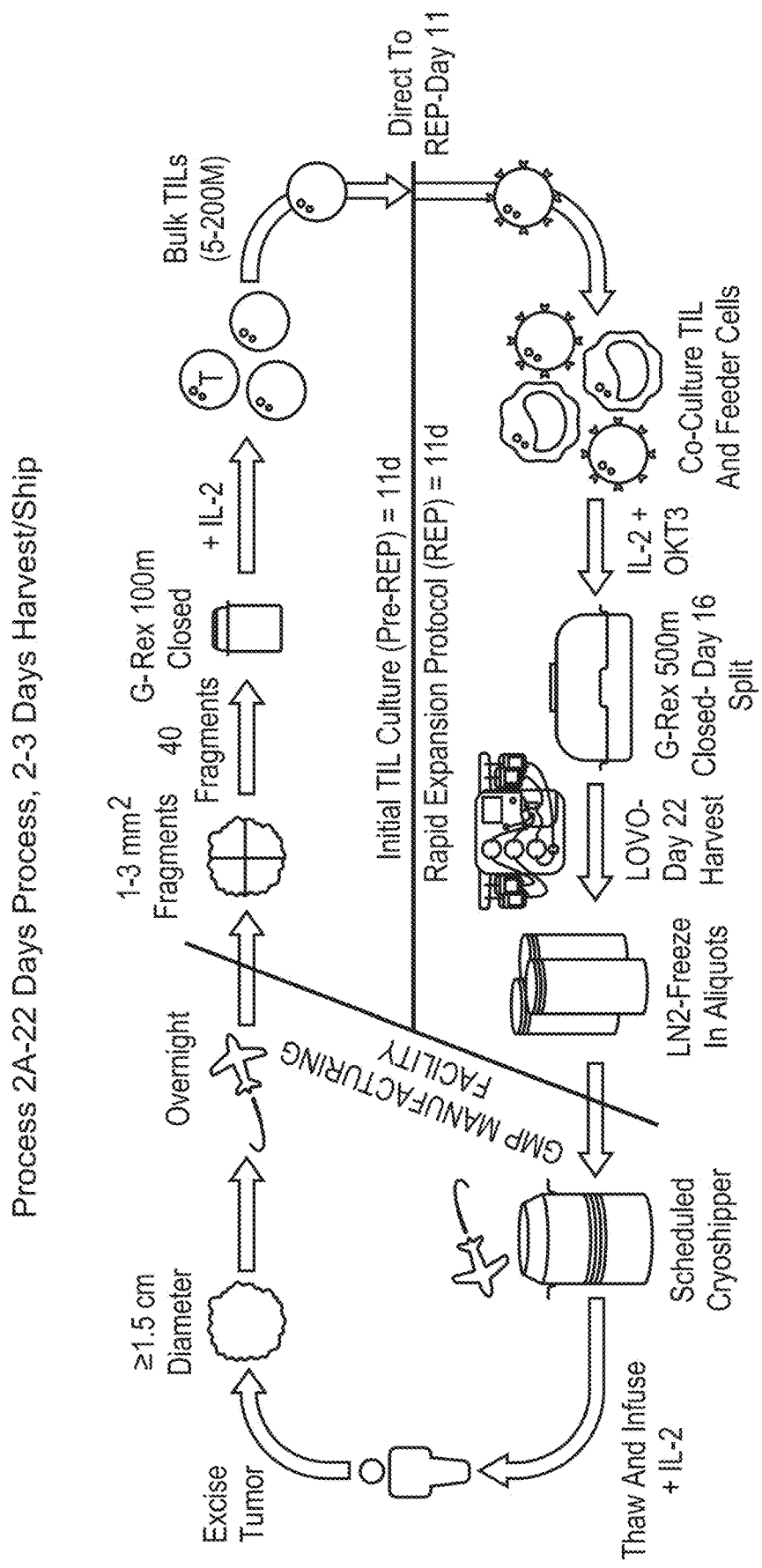
FIG. 1: Shows a diagram of an embodiment of process 2A, a 22-day process for TIL manufacturing.
Figure 3:
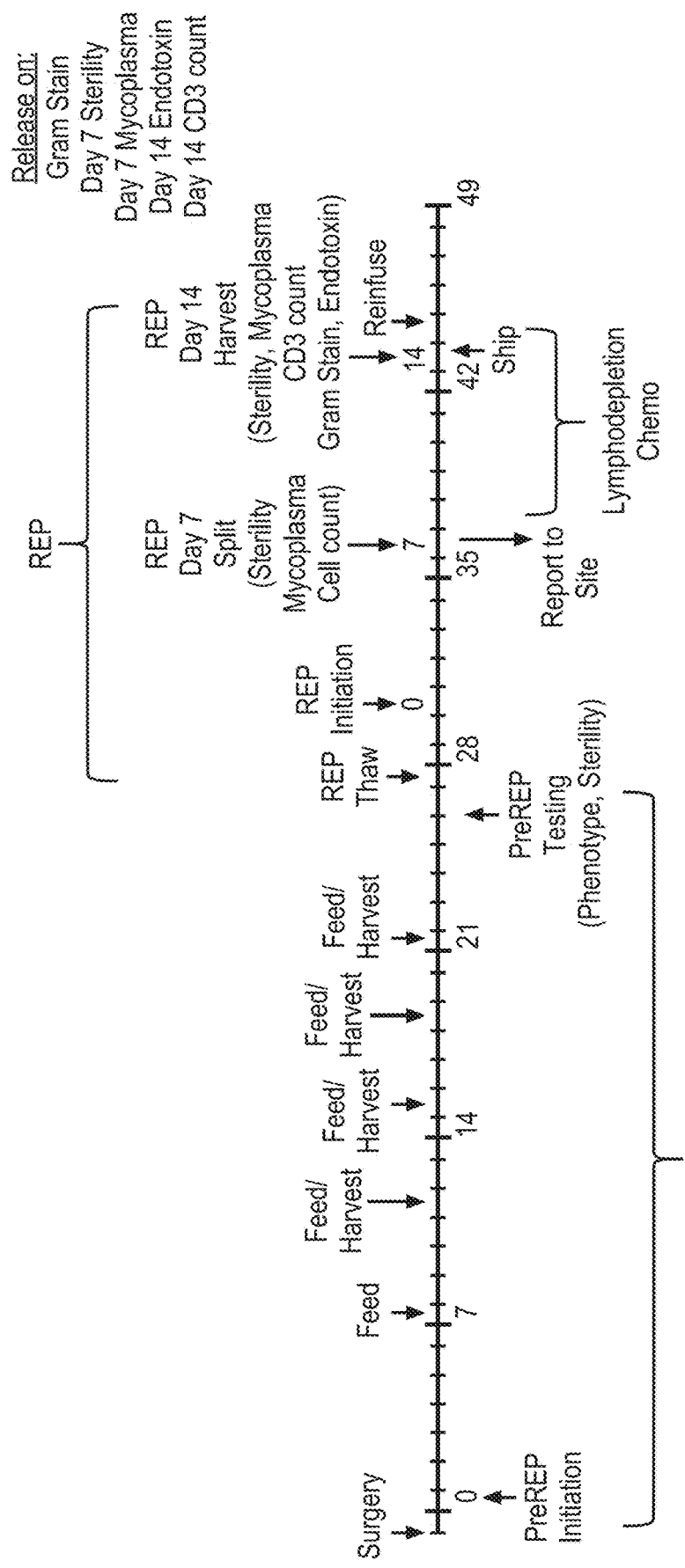
FIG. 3: Shows the 1C process timeline.
Figure 4:
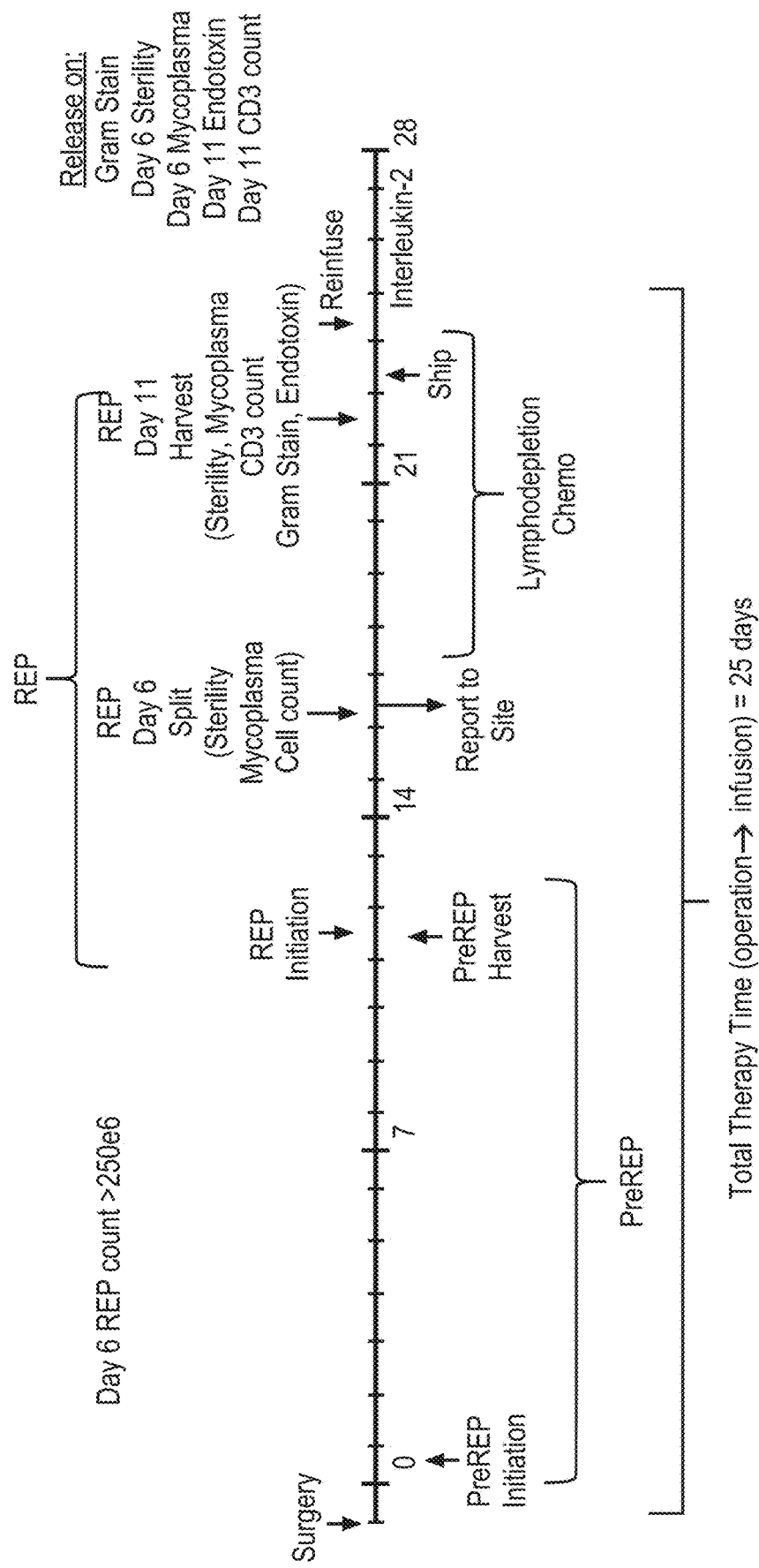
FIG. 4: Shows the process of an embodiment of TIL therapy using process 2A for TIL manufacturing, including administration and co-therapy steps, for higher cell counts.

An exemplary TIL process known as process 2A containing some of these features is depicted in FIG. 1, and some of the advantages of this embodiment of the present invention over process 1C are described in FIG. 2, as does FIG. 84. Process 1C is shown for comparison in FIG. 3. Two alternative timelines for TIL therapy based on process 2A are shown in FIG. 4 (higher cell counts) and FIG. 5 (lower cell counts). An embodiment of process 2A is shown in FIG. 6 as well as FIG. 27. FIGS. 83 and 84 further provides an exemplary 2A process compared to an exemplary 1C process.

As discussed herein, the present invention can include a step relating to the restimulation of cryopreserved TILs to increase their metabolic activity and thus relative health prior to transplant into a patient, and methods of testing said metabolic health. As generally outlined herein, TILs are generally taken from a patient sample and manipulated to expand their number prior to transplant into a patient. In some embodiments, the TILs may be optionally genetically manipulated as discussed below.

In some embodiments, the TILs may be cryopreserved. Once thawed, they may also be restimulated to increase their metabolism prior to infusion into a patient.

In some embodiments, the first expansion (including processes referred to as the preREP as well as processes shown in FIG. 27 as Step A) is shortened to 3 to 14 days and the second expansion (including processes referred to as the REP as well as processes shown in FIG. 27 as Step B) is shorted to 7 to 14 days, as discussed in detail below as well as in the examples and figures. In some embodiments, the first expansion (for example, an expansion described as Step B in FIG. 27) is shortened to 11 days and the second expansion (for example, an expansion as described in Step D in FIG. 27) is shortened to 11 days, as discussed in the Examples and shown in FIGS. 4, 5 and 27. In some embodiments, the combination of the first expansion and second expansion (for example, expansions described as Step B and Step D in FIG. 27) is shortened to 22 days, as discussed in detail below and in the examples and figures.

The "Step" Designations A, B, C, etc., below are in reference to FIG. 27 and in reference to certain embodiments described herein. The ordering of the Steps below and in FIG. 27 is exemplary and any combination or order of steps, as well as additional steps, repetition of steps, and/or omission of steps is contemplated by the present application and the methods disclosed herein.

A. Step A: Obtain Patient Tumor Sample

In general, TILs are initially obtained from a patient tumor sample ("primary TILs") and then expanded into a larger population for further manipulation as described herein, optionally cryopreserved, restimulated as outlined herein and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, pancreatic, prostate, colorectal, lung, brain, renal, stomach, and skin (including but not limited to squamous cell carcinoma, basal cell carcinoma, and melanoma). In some embodiments, useful TILs are obtained from malignant melanoma tumors, as these have been reported to have particularly high levels of TILs.

The term "solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, triple negative breast cancer, prostate, colon, rectum, and bladder. In some embodiments, the cancer is selected from cervical cancer, head and neck cancer (including, for example, head and neck squamous cell carcinoma (HNSCC)) glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

Once obtained, the tumor sample is generally fragmented using sharp dissection into small pieces of between 1 to about 8 mm$^3$, with from about 2-3 mm$^3$ being particularly useful. The TILs are cultured from these fragments using enzymatic tumor digests. Such tumor digests may be produced by incubation in enzymatic media (e.g., Roswell Park Memorial Institute (RPMI) 1640 buffer, 2 mM glutamate, 10 mcg/mL gentamicine, 30 units/mL of DNase and 1.0 mg/mL of collagenase) followed by mechanical dissociation (e.g., using a tissue dissociator). Tumor digests may be produced by placing the tumor in enzymatic media and mechanically dissociating the tumor for approximately 1 minute, followed by incubation for 30 minutes at 37° C. in 5% $CO_2$, followed by repeated cycles of mechanical dissociation and incubation under the foregoing conditions until only small tissue pieces are present. At the end of this process, if the cell suspension contains a large number of red blood cells or dead cells, a density gradient separation using FICOLL branched hydrophilic polysaccharide may be performed to remove these cells. Alternative methods known in the art may be used, such as those described in U.S. Patent Application Publication No. 2012/0244133 A1, the disclosure of which is incorporated by reference herein. Any of the foregoing methods may be used in any of the embodiments described herein for methods of expanding TILs or methods treating a cancer.

In general, the harvested cell suspension is called a "primary cell population" or a "freshly harvested" cell population.

In some embodiments, fragmentation includes physical fragmentation, including for example, dissection as well as digestion. In some embodiments, the fragmentation is physical fragmentation. In some embodiments, the fragmentation is dissection. In some embodiments, the fragmentation is by digestion. In some embodiments, TILs can be initially cultured from enzymatic tumor digests and tumor fragments obtained from patients. In an embodiment, TILs can be initially cultured from enzymatic tumor digests and tumor fragments obtained from patients.

In some embodiments, where the tumor is a solid tumor, the tumor undergoes physical fragmentation after the tumor sample is obtained in, for example, Step A (as provided in FIG. 27). In some embodiments, the fragmentation occurs before cryopreservation. In some embodiments, the fragmentation occurs after cryopreservation. In some embodiments, the fragmentation occurs after obtaining the tumor and in the absence of any cryopreservation. In some embodiments, the tumor is fragmented and 10, 20, 30, 40 or more fragments or pieces are placed in each container for the first expansion. In some embodiments, the tumor is fragmented and 30 or 40 fragments or pieces are placed in each container for the first expansion. In some embodiments, the tumor is fragmented and 40 fragments or pieces are placed in each container for the first expansion. In some embodiments, the multiple fragments comprise about 4 to about 50 fragments, wherein each fragment has a volume of about 27 mm$^3$. In some embodiments, the multiple fragments comprise about 30 to about 60 fragments with a total volume of about 1300 mm$^3$ to about 1500 mm$^3$. In some embodiments, the multiple fragments comprise about 50 fragments with a total volume of about 1350 mm$^3$. In some embodiments, the multiple fragments comprise about 50 fragments with a total mass of about 1 gram to about 1.5 grams. In some embodiments, the multiple fragments comprise about 4 fragments.

In some embodiments, the TILs are obtained from tumor fragments. In some embodiments, the tumor fragment is obtained by sharp dissection. In some embodiments, the tumor fragment is between about 1 mm$^3$ and 10 mm$^3$. In some embodiments, the tumor fragment is between about 1 mm$^3$ and 8 mm$^3$. In some embodiments, the tumor fragment is about 1 mm$^3$. In some embodiments, the tumor fragment is about 2 mm$^3$. In some embodiments, the tumor fragment is about 3 mm$^3$. In some embodiments, the tumor fragment is about 4 mm$^3$. In some embodiments, the tumor fragment is about 5 mm$^3$. In some embodiments, the tumor fragment is about 6 mm$^3$. In some embodiments, the tumor fragment is about 7 mm$^3$. In some embodiments, the tumor fragment is about 8 mm$^3$. In some embodiments, the tumor fragment is about 9 mm$^3$. In some embodiments, the tumor fragment is about 10 mm$^3$. In some embodiments, the tumors are 1-4 mm×1-4 mm×1-4 mm. In some embodiments, the tumors are 1 mm×1 mm×1 mm. In some embodiments, the tumors are 2 mm× 2 mm×2 mm. In some embodiments, the tumors are 3 mm× 3 mm×3 mm. In some embodiments, the tumors are 4 mm× 4 mm×4 mm.

In some embodiments, the tumors are resected in order to minimize the amount of hemorrhagic, necrotic, and/or fatty tissues on each piece. In some embodiments, the tumors are resected in order to minimize the amount of hemorrhagic tissue on each piece. In some embodiments, the tumors are resected in order to minimize the amount of necrotic tissue on each piece. In some embodiments, the tumors are resected in order to minimize the amount of fatty tissue on each piece.

In some embodiments, the tumor fragmentation is performed in order to maintain the tumor internal structure. In some embodiments, the tumor fragmentation is performed without preforming a sawing motion with a scapel. In some embodiments, the TILs are obtained from tumor digests. In some embodiments, tumor digests were generated by incubation in enzyme media, for example but not limited to RPMI 1640, 2 mM GlutaMAX, 10 mg/mL gentamicin, 30 U/mL DNase, and 1.0 mg/mL collagenase, followed by mechanical dissociation (GentleMACS, Miltenyi Biotec, Auburn, CA). After placing the tumor in enzyme media, the tumor can be mechanically dissociated for approximately 1 minute. The solution can then be incubated for 30 minutes at 37° C. in 5% $CO_2$ and it then mechanically disrupted again for approximately 1 minute. After being incubated again for 30 minutes at 37° C. in 5% $CO_2$, the tumor can be mechanically disrupted a third time for approximately 1 minute. In some embodiments, after the third mechanical disruption if large pieces of tissue were present, 1 or 2 additional mechanical dissociations were applied to the sample, with or without 30 additional minutes of incubation at 37° C. in 5% $CO_2$. In some embodiments, at the end of the final incubation if the cell suspension contained a large number of red blood cells or dead cells, a density gradient separation using Ficoll can be performed to remove these cells.

In some embodiments, the harvested cell suspension prior to the first expansion step is called a "primary cell population" or a "freshly harvested" cell population.

In some embodiments, cells can be optionally frozen after sample harvest and stored frozen prior to entry into the expansion described in Step B, which is described in further detail below, as well as exemplified in FIG. 27.

B. Step B: First Expansion

1. Young TILs

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, at al., *Scandinavian Journal of Immunology*, 75:157-167 (2012); Dudley et al., *Clin Cancer Res*, 16:6122-6131 (2010); Huang et al., *J Immunother*, 28(3):258-267 (2005); Besser et al., *Clin Cancer Res*, 19(17):OF1-OF9 (2013); Besser et al., *J Immunother* 32:415-423 (2009); Robbins, et al., *J. Immunol* 2004; 173: 7125-7130; Shen et al., *J Immunother*, 30:123-129 (2007); Zhou, et al., *J Immunother*, 28:53-62 (2005); and Tran, et al., *J Immunother*, 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide herein including for example, methods other than those embodied in FIG. 27. In some embodiments, the TILs obtained by the present method exhibit an increase in the T-cell repertoire diversity as compared to freshly harvested TILs and/or TILs prepared using methods referred to as process 1C, as exemplified in FIG. 83. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

After dissection or digestion of tumor fragments, for example such as described in Step A of FIG. 27, the resulting cells are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIL population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step (for example such as those described in Step B of FIG. 27, which can include processes referred to as pre-REP) as described below and herein, followed by a second expansion (Step D, including processes referred to as rapid expansion protocol (REP) steps) as described below under Step D and herein, followed by optional cryopreservation, and followed by a second Step D (including processes referred to as restimulation REP steps) as described below and herein. The TILs obtained from this process may be optionally characterized for phenotypic characteristics and metabolic parameters as described herein.

In embodiments where TIL cultures are initiated in 24-well plates, for example, using Costar 24-well cell culture cluster, flat bottom (Corning Incorporated, Corning, NY, each well can be seeded with $1\times10^6$ tumor digest cells or one tumor fragment in 2 mL of complete medium (CM) with IL-2 (6000 IU/mL; Chiron Corp., Emeryville, CA). In some embodiments, the tumor fragment is between about 1 mm³ and 10 mm³.

In some embodiments, the first expansion culture medium is referred to as "CM", an abbreviation for culture media. In some embodiments, CM for Step B consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm² gas-permeable silicon bottom (for example, G-Rex10; Wilson Wolf Manufacturing, New Brighton, MN) (FIG. 1), each flask was loaded with 10-40×10⁶ viable tumor digest cells or 5-30 tumor fragments in 10-40 mL of CM with IL-2. Both the G-Rex10 and 24-well plates were incubated in a humidified incubator at 37° C. in 5% CO₂ and 5 days after culture initiation, half the media was removed and replaced with fresh CM and IL-2 and after day 5, half the media was changed every 2-3 days.

After preparation of the tumor fragments, the resulting cells (i.e., fragments) are cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of aAPC cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\times10^6$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ IU/mg for a 1 mg vial. In some embodiments, the IL-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the IL-2 stock solution is prepare as described in Example 4. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of IL-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of IL-15 to about 100 IU/mL of IL-15. In some embodiments, the first expansion culture media comprises about 300 IU/mL of IL-15 to about 100 IU/mL of IL-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of IL-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 µg/mL and 100 µg/mL. In some embodiments, the TNFRSF agonist is added at a concentration sufficient to achieve a concentration in the cell culture medium of between 20 µg/mL and 40 µg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, the first expansion culture medium is referred to as "CM", an abbreviation for culture media. In some embodiments, it is referred to as CM1 (culture medium 1). In some embodiments, CM consists of RPMI 1640 with GlutaMAX, supplemented with 10% human AB serum, 25 mM Hepes, and 10 mg/mL gentamicin. In embodiments where cultures are initiated in gas-permeable flasks with a 40 mL capacity and a 10 cm$^2$ gas-permeable silicon bottom (for example, G-Rex10; Wilson Wolf Manufacturing, New Brighton, MN) (FIG. 1), each flask was loaded with 10-40× 10$^6$ viable tumor digest cells or 5-30 tumor fragments in 10-40 mL of CM with IL-2. Both the G-Rex10 and 24-well plates were incubated in a humidified incubator at 37° C. in 5% $CO_2$ and 5 days after culture initiation, half the media was removed and replaced with fresh CM and IL-2 and after day 5, half the media was changed every 2-3 days. In some embodiments, the CM is the CM1 described in the Examples, see, Example 5. In some embodiments, the first expansion occurs in an initial cell culture medium or a first cell culture medium. In some embodiments, the initial cell culture medium or the first cell culture medium comprises IL-2.

In some embodiments, the first expansion (including processes such as for example those described in Step B of FIG. 27, which can include those sometimes referred to as the pre-REP) process is shortened to 3-14 days, as discussed in the examples and figures. In some embodiments, the first expansion (including processes such as for example those described in Step B of FIG. 27, which can include those sometimes referred to as the pre-REP) is shortened to 7 to 14 days, as discussed in the Examples and shown in FIGS. 4 and 5, as well as including for example, an expansion as described in Step B of FIG. 27. In some embodiments, the first expansion of Step B is shortened to 10-14 days, as discussed in the Examples and shown in FIGS. 4 and 5. In some embodiments, the first expansion is shortened to 11 days, as discussed in the Examples and shown in FIGS. 4 and 5, as well as including for example, an expansion as described in Step B of FIG. 27.

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, IL-2, IL-7, IL-15, and/or IL-21 as well as any combinations thereof can be included during the first expansion, including for example during a Step B processes according to FIG. 27, as well as described herein. In some embodiments, a combination of IL-2, IL-15, and IL-21 are employed as a combination during the first expansion. In some embodiments, IL-2, IL-15, and IL-21 as well as any combinations thereof can be included during Step B processes according to FIG. 27 and as described herein.

In some embodiments, the first expansion (including processes referred to as the pre-REP; for example, Step B according to FIG. 27) process is shortened to 3 to 14 days, as discussed in the examples and figures. In some embodiments, the first expansion of Step B is shortened to 7 to 14 days, as discussed in the Examples and shown in FIGS. 4 and 5. In some embodiments, the first expansion of Step B is shortened to 10 to 14 days, as discussed in the Examples and shown in FIGS. 4, 5, and 27. In some embodiments, the first expansion is shortened to 11 days, as discussed in the Examples and shown in FIGS. 4, 5, and 27.

In some embodiments, the first expansion, for example, Step B according to FIG. 27, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

C. Step C: First Expansion to Second Expansion Transition

In some cases, the bulk TIL population obtained from the first expansion, including for example the TIL population obtained from for example, Step B as indicated in FIG. 27, can be cryopreserved immediately, using the protocols discussed herein below. Alternatively, the TIL population obtained from the first expansion, referred to as the second TIL population, can be subjected to a second expansion (which can include expansions sometimes referred to as REP) and then cryopreserved as discussed below. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

In some embodiments, the TILs obtained from the first expansion (for example, from Step B as indicated in FIG. 27) are stored until phenotyped for selection. In some embodiments, the TILs obtained from the first expansion (for example, from Step B as indicated in FIG. 27) are not stored and proceed directly to the second expansion. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days from when fragmentation occurs. In some embodiments, the transition from the first expansion to the second expansion occurs at about 3 days to 14 days from when fragmentation occurs. In some embodiments, the transition from the first expansion to the second expansion occurs at about 4 days to 14 days from when fragmentation occurs. In some embodiments, the transition from the first expansion to the second expansion occurs at about 4 days to 10 days from when fragmentation occurs. In some embodiments, the transition from the first expansion to the second expansion occurs at about 7 days to 14 days from when fragmentation occurs. In some embodiments, the transition from the first expansion to the second expansion occurs at about 14 days from when fragmentation occurs.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days from when fragmentation occurs. In some embodiments, the transition from the first expansion to the second expansion occurs 1 day to 14 days from when fragmentation occurs. In some embodiments, the first TIL expansion can proceed for 2 days to 14 days. In some embodiments, the transition from the first expansion to the second expansion occurs 3 days to 14 days from when fragmentation occurs. In some embodiments, the transition from the first expansion to the second expansion occurs 4 days to 14 days from when fragmentation occurs. In some embodiments, the transition from the first expansion to the second expansion occurs 5 days to 14 days from when fragmentation occurs. In some embodiments, the transition from the first expansion to the second expansion occurs 6 days to 14 days from when fragmentation occurs. In some embodiments, the transition from the first expansion to the second expansion occurs 7 days to 14 days from when fragmentation occurs. In some embodiments, the transition from the first expansion to the second expansion occurs 8 days to 14 days from when fragmentation occurs. In some embodiments, the transition from the first expansion to the second expansion occurs 9 days to 14 days from when fragmentation occurs. In some embodiments, the transition from the first expansion to the second expansion occurs 10 days to 14 days from when fragmentation occurs. In some embodiments, the transition from the first expansion to the second expansion occurs 11 days to 14 days from when fragmentation occurs. In some embodiments, the transition from the first expansion to the second expansion occurs 12 days to 14 days from when fragmentation occurs. In some embodiments, the transition from the first expansion to the second expansion occurs 13 days to 14 days from when fragmentation occurs. In some embodiments, the transition from the first expansion to the second expansion occurs 14 days from when fragmentation occurs. In some embodiments, the transition from the first expansion to the second expansion occurs 1 day to 11 days from when fragmentation occurs. In some embodiments, the transition from the first expansion to the second expansion occurs 2 days to 11 days from when fragmentation occurs. In some embodiments, the transition from the first expansion to the second expansion occurs 3 days to 11 days from when fragmentation occurs. In some embodiments, the transition from the first expansion to the second expansion occurs 4 days to 11 days from when fragmentation occurs. In some embodiments, the transition from the first expansion to the second expansion occurs 5 days to 11 days from when fragmentation occurs. In some embodiments, the transition from the first expansion to the second expansion occurs 6 days to 11 days from when fragmentation occurs. In some embodiments, the transition from the first expansion to the second expansion occurs 7 days to 11 days from when fragmentation occurs. In some embodiments, the transition from the first expansion to the second expansion occurs 8 days to 11 days from when fragmentation occurs. In some embodiments, the transition from the first expansion to the second expansion occurs 9 days to 11 days from when fragmentation occurs. In some embodiments, the transition from the first expansion to the second expansion occurs 10 days to 11 days from when fragmentation occurs. In some embodiments, the transition from the first expansion to the second expansion occurs 11 days from when fragmentation occurs.

In some embodiments, the TILs are not stored after the first expansion and prior to the second expansion, and the TILs proceed directly to the second expansion (for example, in some embodiments, there is no storage during the transition from Step B to Step D as shown in FIG. 27). In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion, for example, Step C according to FIG. 27, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

D. Step D: Second Expansion

In some embodiments, the TIL cell population is expanded in number after harvest and initial bulk processing for example, after Step A and Step B, and the transition referred to as Step C, as indicated in FIG. 27). This further expansion is referred to herein as the second expansion, which can include expansion processes generally referred to in the art as a rapid expansion process (REP; as well as processes as indicated in Step D of FIG. 27). The second expansion is generally accomplished using a culture media comprising a number of components, including feeder cells, a cytokine source, and an anti-CD3 antibody, in a gas-permeable container.

In some embodiments, the second expansion or second TIL expansion (which can include expansions sometimes referred to as REP; as well as processes as indicated in Step D of FIG. 27) of TIL can be performed using any TIL flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure (including for example, expansions referred to as REP; as well as processes as indicated in Step D of FIG. 27). For example, TILs can be rapidly expanded using non-specific T-cell receptor stimulation in the presence of interleukin-2 (IL-2) or interleukin-15 (IL-15). The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, NJ or Miltenyi Biotech, Auburn, CA) or UHCT-1 (commercially available from BioLegend, San Diego, CA, USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (HLA-A2) binding peptide, e.g., 0.3 μM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT-3 antibody. In some embodiments, the cell culture medium comprises about 30 ng/mL of OKT-3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 μg/mL of OKT-3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT-3 antibody. In some embodiments, the cell culture medium does not comprise OKT-3 antibody.

In some embodiments, the cell culture medium comprises one or more TNFRSF agonists in a cell culture medium. In some embodiments, the TNFRSF agonist comprises a 4-1BB agonist. In some embodiments, the TNFRSF agonist is a 4-1BB agonist, and the 4-1BB agonist is selected from the group consisting of urelumab, utomilumab, EU-101, a fusion protein, and fragments, derivatives, variants, biosimilars, and combinations thereof. In some embodiments, the TNFRSF agonist is added at a concentration sufficient to achieve a concentration in the cell culture medium of between 0.1 μg/mL and 100 μg/mL. In some embodiments, the TNFRSF agonist is added at a concentration sufficient to achieve a concentration in the cell culture medium of between 20 μg/mL and 40 μg/mL.

In some embodiments, in addition to one or more TNFRSF agonists, the cell culture medium further comprises IL-2 at an initial concentration of about 3000 IU/mL and OKT-3 antibody at an initial concentration of about 30 ng/mL, and wherein the one or more TNFRSF agonists comprises a 4-1BB agonist.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion, including for example during a Step D processes according to FIG. 27, as well as described herein. In some embodiments, a combination of IL-2, IL-15, and IL-21 are employed as a combination during the second expansion. In some embodiments, IL-2, IL-15, and IL-21 as well as any combinations thereof can be included during Step D processes according to FIG. 27 and as described herein.

In some embodiments, the second expansion can be conducted in a supplemented cell culture medium comprising IL-2, OKT-3, antigen-presenting feeder cells, and optionally a TNFRSF agonist. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally 2/3 media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., *J. Immunother.* 2008, 31, 742-51; Dudley, et al., *J Immunother.* 2003, 26, 332-42) or gas permeable cultureware (G-Rex flasks). In some embodiments, the second expansion (including expansions referred to as rapid expansions) is performed in T-175 flasks, and about $1 \times 10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% $CO_2$. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0 \times 10^6$ cells/mL.

In an embodiment, the second expansion (which can include expansions referred to as REP, as well as those referred to in Step D of FIG. 27) may be performed in 500 mL capacity gas permeable flasks with 100 cm gas-permeable silicon bottoms (G-Rex 100, commercially available from Wilson Wolf Manufacturing Corporation, New Brighton, MN, USA), 5×10$^6$ or 10×10$^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% CO$_2$. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% CO$_2$ and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 ml media. In some embodiments, media replacement is done until the cells are transferred to an alternative growth chamber. In some embodiments, ⅔ of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, the disclosures of which are incorporated herein by reference, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, MA). In some embodiments, viability is determined according to the Cellometer K2 Image Cytometer Automatic Cell Counter protocol described, for example, in Example 15.

In some embodiments, the second expansion (including expansions referred to as REP) of TIL can be performed using T-175 flasks and gas-permeable bags as previously described (Tran K Q, Zhou J, Durflinger K H, et al., 2008, *J Immunother.*, 31:742-751, and Dudley M E, Wunderlich J R, Shelton T E, et al. 2003, *J Immunother.*, 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about 1×10$^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% CO$_2$. In some embodiments, half the media is changed on day 5 using 50/50 medium with 3000 IU/mL of IL-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about 2.0×10$^6$ cells/mL.

In some embodiments, the second expansion (including expansions referred to as REP) are performed in 500 mL capacity flasks with 100 cm$^2$ gas-permeable silicon bottoms (G-Rex 100, Wilson Wolf) (FIG. 1), about 5×10$^6$ or 10×10$^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% CO$_2$. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% CO$_2$ and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

In some embodiments, the second expansion culture medium (e.g., sometimes referred to as CM2 or the second cell culture medium), comprises IL-2, OKT-3, as well as the antigen-presenting feeder cells (APCs), as discussed in more detail below.

In some embodiments, the second expansion, for example, Step D according to FIG. 27, is performed in a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

1. Feeder Cells and Antigen Presenting Cells

In an embodiment, the second expansion procedures described herein (for example including expansion such as those described in Step D from FIG. 27, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, as described in the examples, in particular example 14, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion). See, for example, Example 14.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2. See, for example, Example 13.

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/ml IL-2. In some embodiments, the PBMCs are cultured in the presence of 10-50 ng/ml OKT3 antibody and 2000-5000 IU/ml IL-2. In some embodiments, the PBMCs are cultured in the presence of 20-40 ng/ml OKT3 antibody and 2000-4000 IU/ml IL-2. In some embodiments, the PBMCs are cultured in the presence of 25-35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5 \times 10^9$ feeder cells to about $100 \times 10^6$ TILs. In another embodiment, the second expansion procedures described herein require a ratio of about $2.5 \times 10^9$ feeder cells to about $50 \times 10^6$ TILs. In yet another embodiment, the second expansion procedures described herein require about $2.5 \times 10^9$ feeder cells to about $25 \times 10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

Figure 5:
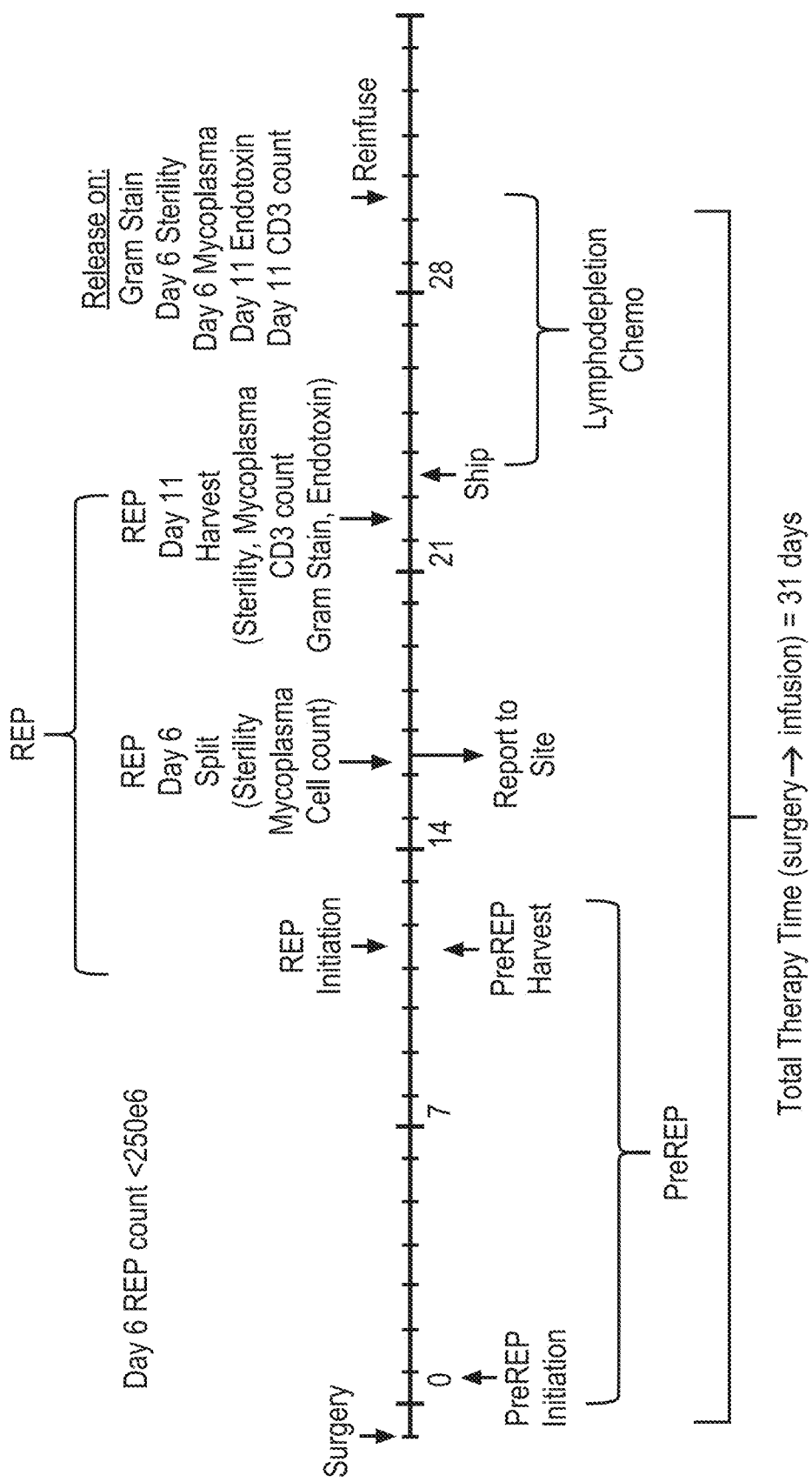
FIG. 5: Shows the process of an embodiment of TIL therapy using process 2A for TIL manufacturing, including administration and co-therapy steps, for lower cell counts.
Figure 6:
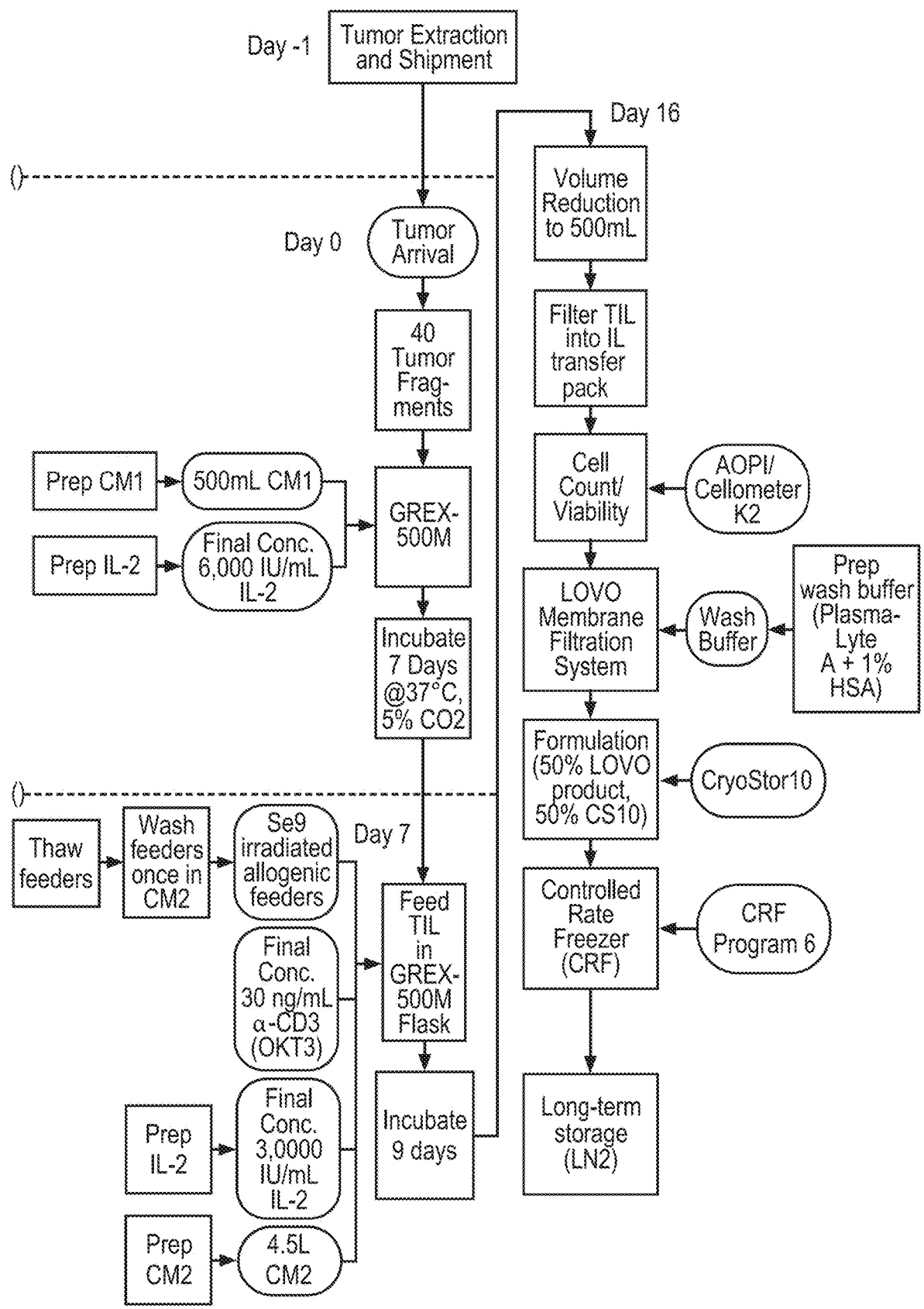
FIG. 6: Shows a detailed schematic for an embodiment of the 2A process.
Figure 7:
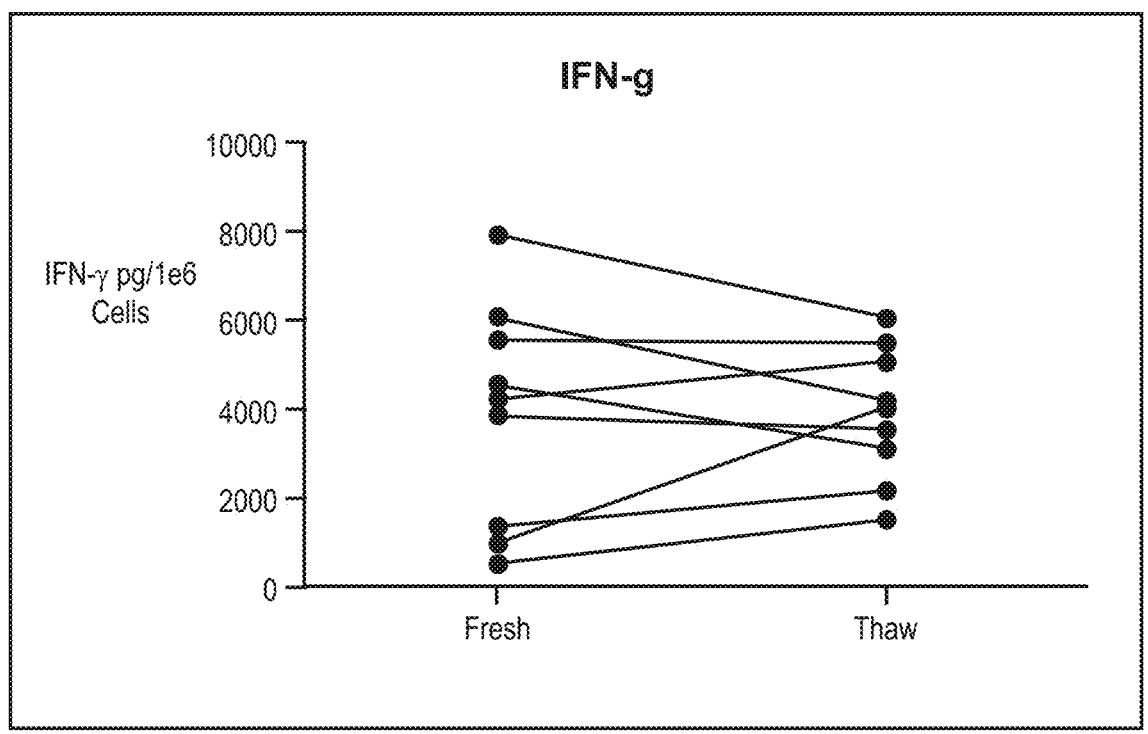
FIG. 7: Shows characterization of TILs prepared using an embodiment of the 2A process by comparing interferon-gamma (IFN-γ) expression between fresh TILs and thawed TILs.

In general, the allogenic PBMCs are inactivated, either via irradiation or heat treatment, and used in the TIL expansion procedures described herein, including the exemplary procedures described in FIGS. 4, 5, and 27.

In an embodiment, artificial antigen presenting cells are used in the second expansion as a replacement for, or in combination with, PBMCs.

2. Cytokines

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

3. Anti-CD3 Antibodies

In some embodiments, the culture media used in expansion methods described herein (including those referred to as REP, see for example, FIG. 27) also includes an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., *J. Immunol.* 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, NJ or Miltenyi Biotech, Auburn, CA).

E. Step E: Harvest TILS

After the second expansion step, cells can be harvested. In some embodiments the TILs are harvested after one, two, three, four or more expansion steps, for example as provided in FIG. 27. In some embodiments the TILs are harvested after two expansion steps, for example as provided in FIG. 27.

TILs can be harvested in any appropriate and sterile manner, including for example by centrifugation. Methods for TIL harvesting are well known in the art and any such know methods can be employed with the present process. In some embodiments, TILS are harvest using an automated system.

Cell harvesters and/or cell processing systems are commercially available from a variety of sources, including, for example, Fresenius Kabi, Tomtec Life *Science*, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest, for example, Step E according to FIG. 27, is performed from a closed system bioreactor. In some embodiments, a closed system is employed for the TIL expansion, as described herein. In some embodiments, a single bioreactor is employed. In some embodiments, the single bioreactor employed is for example a G-REX-10 or a G-REX-100. In some embodiments, the closed system bioreactor is a single bioreactor.

In some embodiments, Step E according to FIG. 27, is performed according to the processes described in Example 30. In some embodiments, the closed system is accessed via syringes under sterile conditions in order to maintain the sterility and closed nature of the system. In some embodiments, a closed system as described in Example 30 is employed.

In some embodiments, TILs are harvested according to the methods described in Example 30. In some embodiments, TILs between days 1 and 11 are harvested using the methods as described in Section 8.5 (referred to as the Day 11 TIL harvest in Example 30). In some embodiments, TILs between days 12 and 22 are harvested using the methods as described in Section 8.12 (referred to as the Day 22 TIL harvest in Example 30).

F. Step F: Final Formulation/Transfer to Infusion Bag

After Steps A through E as provided in an exemplary order in FIG. 27 and as outlined in detailed above and herein are complete, cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

1. Pharmaceutical Compositions, Dosages, and Dosing Regimens

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3\times10^{10}$ to about $13.7\times10^{10}$ TILs are administered, with an average of around $7.8\times10^{10}$ TILs, particularly if the cancer is melanoma. In an embodiment, about $1.2\times10^{10}$ to about $4.3\times10^{10}$ of TILs are administered. In some embodiments, about $3\times10^{10}$ to about $12\times10^{10}$ TILs are administered. In some embodiments, about $4\times10^{10}$ to about $10\times10^{10}$ TILs are administered. In some embodiments, about $5\times10^{10}$ to about $8\times10^{10}$ TILs are administered. In some embodiments, about $6\times10^{10}$ to about $8\times10^{10}$ TILs are administered. In some embodiments, about $7\times10^{10}$ to about $8\times10^{10}$ TILs are administered. In some embodiments, the therapeutically effective dosage is about $2.3\times10^{10}$ to about $13.7\times10^{10}$. In some embodiments, the therapeutically effective dosage is about $7.8\times10^{10}$ TILs, particularly of the cancer is melanoma. In some embodiments, the therapeutically effective dosage is about $1.2\times10^{10}$ to about $4.3\times10^{10}$ of TILs. In some embodiments, the therapeutically effective dosage is about $3\times10^{10}$ to about $12\times10^{10}$ TILs. In some embodiments, the therapeutically effective dosage is about $4\times10^{10}$ to about $10\times10^{10}$ TILs. In some embodiments, the therapeutically effective dosage is about $5\times10^{10}$ to about $8\times10^{10}$ TILs. In some embodiments, the therapeutically effective dosage is about $6\times10^{10}$ to about $8\times10^{10}$ TILs. In some embodiments, the therapeutically effective dosage is about $7\times10^{10}$ to about $8\times10^{10}$ TILs.

In some embodiments, the number of the TILs provided in the pharmaceutical compositions of the invention is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{13}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In an embodiment, the number of the TILs provided in the pharmaceutical compositions of the invention is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.00010% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.00010% w/w, w/v, or v/v of the pharmaceutical composition.

In some embodiments, the concentration of the TILs provided in the pharmaceutical compositions of the invention is in the range from about 0.00010% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.0010% to about 10%, about 0.010% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In some embodiments, an effective dosage of TILs is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$, $1 \times 10^{12}$ to $5 \times 10^{12}$, and $5 \times 10^{12}$ to $1 \times 10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by intra-arterial injection, intravenously, intraperitoneally, parenterally, intramuscularly, subcutaneously, topically, by transplantation, or by inhalation.

G. Optional Cell Viability Analyses

Optionally, a cell viability assay can be performed after the Step B first expansion, using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining.

In some embodiments, the TILs are analyzed for CD3+ cell population percentages. In some embodiments, the TILs for use in treatment are analyzed for CD3+ cell population percentages. In some embodiments, the TILs are CD3+/CD45+ TILs. In some embodiments, the CD3+ percentage is between about 70% and about 99.9%. In some embodiments, the CD3+ percentage is between about 74% and about 99.9%. In some embodiments, the CD3+ percentage is between about 74% and about 99.9%. In some embodiments, the CD3+ percentage is between about 74% and about 97.1%. In some embodiments, the CD3+ percentage is between about 80% and about 99.9%. In some embodiments, the CD3+ percentage is between about 85% and about 99.9%. In some embodiments, the CD3+ percentage is between about 90% and about 99.9%. In some embodiments, the CD3+ percentage is between about 85% and about 95%. In some embodiments, the CD3+ percentage is between about 80% and about 95%. In some embodiments, the CD3+ percentage is between about 95% and about 99.9%. In some embodiments, the CD3+/CD45+ percentage is between about 70% and about 99.9%. In some embodiments, the CD3+/CD45+ percentage is between about 74% and about 99.9%. In some embodiments, the CD3+/CD45+ percentage is between about 74% and about 99.9%. In some embodiments, the CD3+/CD45+ percentage is between about 74% and about 97.1%. In some embodiments, the CD3+/CD45+ percentage is between about 80% and about 99.9%. In some embodiments, the CD3+/CD45+ percentage is between about 85% and about 99.9%. In some embodiments, the CD3+/CD45+ percentage is between about 90% and about 99.9%. In some embodiments, the CD3+/CD45+ percentage is between about 85% and about 95%. In some embodiments, the CD3+/CD45+ percentage is between about 80% and about 95%. In some embodiments, the CD3+/CD45+ percentage is between about 95% and about 99.9%.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs may include using about 5,000 mL to about 25,000 mL of cell medium, about 5,000 mL to about 10,000 mL of cell medium, or about 5,800 mL to about 8,700 mL of cell medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise adding fresh cell culture media to the cells (also referred to as feeding the cells) no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using aAPCs for a duration of about 14 to about 42 days, e.g., about 28 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L. In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this expansion is conducted without adding fresh cell culture media to the cells (also referred to as feeding the cells). In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., J. Immunotherapy, 2012, 35:283-292.

Optional Genetic Engineering of TILs

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

H. Optional Cryopreservation of TILs

As discussed above, and exemplified in Steps A through E as provided in FIG. 27, cryopreservation can occur at numerous points throughout the TIL expansion process. In some embodiments, the expanded population of TILs after the second expansion (as provided for example, according to Step D of FIG. 27) can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986. In some embodiments, the TILs are cryopreserved in 5% DMSO. In some embodiments, the TILs are cryopreserved in cell culture media plus 5% DMSO. In some embodiments, the TILs are cryopreserved according to the methods provided in Examples 8 and 9.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

I. Phenotypic Characteristics of Expanded TILs

In some embodiment, the TILs are analyzed for expression of numerous phenotype markers after expansion, including those described herein and in the Examples. In an embodiment, expression of one or more phenotypic markers is examined. In some embodiments, the phenotypic characteristics of the TILs are analyzed after the first expansion in Step B. In some embodiments, the phenotypic characteristics of the TILs are analyzed during the transition in Step C. In some embodiments, the phenotypic characteristics of the TILs are analyzed during the transition according to Step C and after cryopreservation. In some embodiments, the phenotypic characteristics of the TILs are analyzed after the second expansion according to Step D. In some embodiments, the phenotypic characteristics of the TILs are analyzed after two or more expansions according to Step D. In some embodiments, the marker is selected from the group consisting of TCRab (i.e., TCRα/β), CD57, CD28, CD4, CD27, CD56, CD8a, CD45RA, CD8a, CCR7, CD4, CD3, CD38, and HLA-DR. In some embodiments, the marker is selected from the group consisting of TCRab (i.e., TCRα/β), CD57, CD28, CD4, CD27, CD56, and CD8a. In an embodiment, the marker is selected from the group consisting of CD45RA, CD8a, CCR7, CD4, CD3, CD38, and HLA-DR. In some embodiments, expression of one, two, three, four, five, six, seven, eight, nine, ten, eleven, twelve, thirteen, or fourteen markers is examined. In some embodiments, the expression from one or more markers from each group is examined. In some embodiments, one or more of HLA-DR, CD38, and CD69 expression is maintained (i.e., does not exhibit a statistically significant difference) in fresh TILs as compared to thawed TILs. In some embodiments, the activation status of TILs is maintained in the thawed TILs.

In an embodiment, expression of one or more regulatory markers is measured. In some embodiments, the regulatory marker is selected from the group consisting of CD137, CD8a, Lag3, CD4, CD3, PD-1, TIM-3, CD69, CD8a, TIGIT, CD4, CD3, KLRG1, and CD154. In some embodiments, the regulatory marker is selected from the group consisting of CD137, CD8a, Lag3, CD4, CD3, PD-1, and TIM-3. In some embodiments, the regulatory marker is selected from the group consisting of CD69, CD8a, TIGIT, CD4, CD3, KLRG1, and CD154. In some embodiments, regulatory molecule expression is decreased in thawed TILs as compared to fresh TILs. In some embodiments, expression of regulatory molecules LAG-3 and TIM-3 is decreased in thawed TILs as compared to fresh TILs. In some embodiments, there is no significant difference in CD4, CD8, NK, TCRαβ expression. In some embodiments, there is no significant difference in CD4, CD8, NK, TCRαβ expression, and/or memory markers in fresh TILs as compared to thawed TILs. In some embodiments, there is no significant difference in CD4, CD8, NK, TCRαβ expression between the TILs produced by the methods provided herein, as exemplified for example in FIG. 27, and/or TILs prepared using other methods than those provide herein including for example, methods other than those embodied in FIG. 27.

In some embodiments, no selection of the first population of TILs, second population of TILs, third population of TILs, harvested TIL population, and/or the therapeutic TIL population based on CD4, CD8, and/or NK, TCRαβ expression is performed during any of steps, including those discussed above or as provided for example in FIG. 27. In some embodiments, no selection of the first population of TILs based on CD4, CD8, and/or NK, TCRαβ is performed. In some embodiments, no selection of the second population of TILs based on CD4, CD8, and/or NK, TCRαβ expression is performed. In some embodiments, no selection of the third population of TILs based on CD4, CD8, and/or NK, TCRαβ expression is performed. In some embodiments, no selection of the harvested population of TILs based on CD4, CD8, and/or NK, TCRαβ expression is performed. In some embodiments, no selection of the therapeutic population of TILs based on CD4, CD8, and/or NK, TCRαβ expression is performed.

In an embodiment, no selection of the first population of TILs, second population of TILs, third population of TILs, or harvested TIL population based on CD4, CD8, and/or NK, TCRαβ expression is performed during any of steps (a) to (f) of the method for expanding tumor infiltrating lymphocytes (TILs) into a therapeutic population of TILs comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T cells and/or central memory T cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system.

In an embodiment, no selection of the first population of TILs, second population of TILs, third population of TILs, or harvested TIL population based on CD4, CD8, and/or NK, TCRαβ expression is performed during any of steps (a) to (h) of the method for treating a subject with cancer, the method comprising administering expanded tumor infiltrating lymphocytes (TILs) comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T cells and/or central memory T cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) optionally cryopreserving the infusion bag comprising the harvested TIL population from step (f) using a cryopreservation process; and (h) administering a therapeutically effective dosage of the third population of TILs from the infusion bag in step (g) to the patient.

In some embodiments the memory marker is selected from the group consisting of CCR7 and CD62L In some embodiments, the viability of the fresh TILs as compared to the thawed TILs is at least 70%, at least 75%, at least 80%, at least 85%, at least 90%, at least 95%, or at least 98%. In some embodiments, the viability of both the fresh and thawed TILs is greater than 70%, greater than 75%, greater than 80%, greater than 85%, greater than 90%, greater than 95%, or greater than 98%. In some embodiments, the viability of both the fresh and thawed product is greater than 80%, greater than 81%, greater than 82%, greater than 83%, greater than 84%, greater than 85%, greater than 86%, greater than 87%, greater than 88%, greater than 89%, or greater than 90%. In some embodiments, the viability of both the fresh and thawed product is greater than 86%.

In an embodiment, restimulated TILs can also be evaluated for cytokine release, using cytokine release assays. In some embodiments, TILs can be evaluated for interferon-γ (IFN-γ) secretion in response to stimulation either with OKT3 or co-culture with autologous tumor digest. For example, in embodiments employing OKT3 stimulation, TILs are washed extensively, and duplicate wells are prepared with 1×10⁵ cells in 0.2 mL CM in 96-well flat-bottom plates precoated with 0.1 or 1.0 μg/mL of OKT3 diluted in phosphate-buffered saline. After overnight incubation, the supernatants are harvested and IFN-γ in the supernatant is measured by ELISA (Pierce/Endogen, Woburn, MA). For the co-culture assay, 1×10⁵ TIL cells are placed into a 96-well plate with autologous tumor cells. (1:1 ratio). After a 24-hour incubation, supernatants are harvested and IFN-γ release can be quantified, for example by ELISA.

Flow cytometric analysis of cell surface biomarkers: TIL samples were aliquoted for flow cytometric analysis of cell surface markers see, for Example see Examples 7, 8, and 9.

In some embodiments, the TILs are being evaluated for various regulatory markers. In some embodiments, the regulatory marker is selected from the group consisting of TCR α/β, CD56, CD27, CD28, CD57, CD45RA, CD45RO, CD25, CD127, CD95, IL-2R-, CCR7, CD62L, KLRG1, and CD122. In some embodiments, the regulatory marker is TCR (X/β. In some embodiments, the regulatory marker is CD56. In some embodiments, the regulatory marker is CD27. In some embodiments, the regulatory marker is CD28. In some embodiments, the regulatory marker is CD57. In some embodiments, the regulatory marker is CD45RA. In some embodiments, the regulatory marker is CD45RO. In some embodiments, the regulatory marker is CD25. In some embodiments, the regulatory marker is CD127. In some embodiments, the regulatory marker is CD95. In some embodiments, the regulatory marker is IL-2R-. In some embodiments, the regulatory marker is CCR7. In some embodiments, the regulatory marker is CD62L. In some embodiments, the regulatory marker is KLRG1. In some embodiments, the regulatory marker is CD122.

In an embodiment, the expanded TILs are analyzed for expression of numerous phenotype markers, including those described herein and in the Examples. In an embodiment, expression of one or more phenotypic markers is examined. In some embodiments, the marker is selected from the group consisting of TCRab (i.e., TCRα/β), CD57, CD28, CD4, CD27, CD56, CD8a, CD45RA, CD8a, CCR7, CD4, CD3, CD38, and HLA-DR. In some embodiments, the marker is selected from the group consisting of TCRab (i.e., TCRα/β), CD57, CD28, CD4, CD27, CD56, and CD8a. In an embodiment, the marker is selected from the group consisting of CD45RA, CD8a, CCR7, CD4, CD3, CD38, and HLA-DR. In some embodiments, expression of one, two, three, four, five, six, seven, eight, nine, ten, eleven, twelve, thirteen, or fourteen markers is examined. In some embodiments, the expression from one or more markers from each group is examined. In some embodiments, one or more of HLA-DR, CD38, and CD69 expression is maintained (i.e., does not exhibit a statistically significant difference) in fresh TILs as compared to thawed TILs. In some embodiments, the activation status of TILs is maintained in the thawed TILs.

In an embodiment, expression of one or more regulatory markers is measured. In some embodiments, the regulatory marker is selected from the group consisting of CD137, CD8a, Lag3, CD4, CD3, PD1, TIM-3, CD69, CD8a, TIGIT, CD4, CD3, KLRG1, and CD154. In some embodiments, the regulatory marker is selected from the group consisting of CD137, CD8a, Lag3, CD4, CD3, PD1, and TIM-3. In some embodiments, the regulatory marker is selected from the group consisting of CD69, CD8a, TIGIT, CD4, CD3, KLRG1, and CD154. In some embodiments, regulatory molecule expression is decreased in thawed TILs as compared to fresh TILs. In some embodiments, expression of regulatory molecules LAG-3 and TIM-3 is decreased in thawed TILs as compared to fresh TILs. In some embodiments, there is no significant difference in CD4, CD8, NK, TCRαβ expression. In some embodiments, there is no significant difference in CD4, CD8, NK, TCRαβ expression, and/or memory markers in fresh TILs as compared to thawed TILs.

In some embodiments the memory marker is selected from the group consisting of CCR7 and CD62L.

In some embodiments, the viability of the fresh TILs as compared to the thawed TILs is at least 70%, at least 75%, at least 80%, at least 85%, at least 90%, at least 95%, or at least 98%. In some embodiments, the viability of both the fresh and thawed TILs is greater than 70%, greater than 75%, greater than 80%, greater than 85%, greater than 90%, greater than 95%, or greater than 98%. In some embodiments, the viability of both the fresh and thawed product is greater than 80%, greater than 81%, greater than 82%, greater than 83%, greater than 84%, greater than 85%, greater than 86%, greater than 87%, greater than 88%, greater than 89%, or greater than 90%. In some embodiments, the viability of both the fresh and thawed product is greater than 86%.

In an embodiment, restimulated TILs can also be evaluated for cytokine release, using cytokine release assays. In some embodiments, TILs can be evaluated for interferon-γ (IFN-γ) secretion in response to stimulation either with OKT3 or coculture with autologous tumor digest. For example, in embodiments employing OKT3 stimulation, TILs are washed extensively, and duplicate wells are prepared with $1 \times 10^5$ cells in 0.2 mL CM in 96-well flat-bottom plates precoated with 0.1 or 1.0 µg/mL of OKT3 diluted in phosphate-buffered saline. After overnight incubation, the supernatants are harvested and IFN-γ in the supernatant is measured by ELISA (Pierce/Endogen, Woburn, MA). For the coculture assay, $1 \times 10^5$ TIL cells are placed into a 96-well plate with autologous tumor cells. (1:1 ratio). After a 24-hour incubation, supernatants are harvested and IFN-γ release can be quantified, for example by ELISA.

In some embodiments, the phenotypic characterization is examined after cryopreservation.

J. Metabolic Health of Expanded TILs

The restimulated TILs are characterized by significant enhancement of basal glycolysis as compared to either freshly harvested TILs and/or post-thawed TILs. In an embodiment, no selection of the first population of TILs, second population of TILs, third population of TILs, harvested TIL population, and/or the therapeutic TIL population based on CD8 expression is performed during any of steps, including those discussed above or as provided for example in FIG. 27. In some embodiments, no selection of the first population of TILs based on CD8 expression is performed. In some embodiments, no selection of the second population of TILs based on CD8 expression is performed. In some embodiments, no selection of the third population of TILs based on CD8 expression is performed. In some embodiments, no selection of the harvested population of TILs based on CD8 expression is performed. In some embodiments, no selection of the therapeutic population of TILs based on CD8 expression is performed.

In an embodiment, no selection of the first population of TILs, second population of TILs, third population of TILs, or harvested TIL population based on CD8 expression is performed during any of steps (a) to (f) of the method for expanding tumor infiltrating lymphocytes (TILs) into a therapeutic population of TILs comprising:

(a) obtaining a first population of TILs from a tumor resected from a patient by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased sub-population of effector T cells and/or central memory T cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system.

In an embodiment, no selection of the first population of TILs, second population of TILs, third population of TILs, or harvested TIL population based on CD8 expression is performed during any of steps (a) to (h) of the method for treating a subject with cancer, the method comprising administering expanded tumor infiltrating lymphocytes (TILs) comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased sub-population of effector T cells and/or central memory T cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) optionally cryopreserving the infusion bag comprising the harvested TIL population from step (f) using a cryopreservation process; and (h) administering a therapeutically effective dosage of the third population of TILs from the infusion bag in step (g) to the patient.

The TILs prepared by the methods described herein are characterized by significant enhancement of basal glycolysis as compared to, for example, freshly harvested TILs and/or TILs prepared using other methods than those provide herein including for example, methods other than those embodied in FIG. 27. In an embodiment, no selection of the first population of TILs, second population of TILs, third population of TILs, harvested TIL population, and/or the therapeutic TIL population based on CD8 expression is performed during any of steps, including those discussed above or as provided for example in FIG. 27. In some embodiments, no selection of the first population of TILs based on CD8 expression is performed. In some embodiments, no selection of the second population of TILs based on CD8 expression is performed. In some embodiments, no selection of the third population of TILs based on CD8 expression is performed. In some embodiments, no selection of the harvested population of TILs based on CD8 expression is performed. In some embodiments, no selection of the therapeutic population of TILs based on CD8 expression is performed. In an embodiment, no selection of the first population of TILs, second population of TILs, third population of TILs, or harvested TIL population based on CD8 expression is performed during any of steps (a) to (h).

Spare respiratory capacity (SRC) and glycolytic reserve can be evaluated for TILs expanded with different methods of the present disclosure. The Seahorse XF Cell Mito Stress Test measures mitochondrial function by directly measuring the oxygen consumption rate (OCR) of cells, using modulators of respiration that target components of the electron transport chain in the mitochondria. The test compounds (oligomycin, FCCP, and a mix of rotenone and antimycin A, described below) are serially injected to measure ATP production, maximal respiration, and non-mitochondrial respiration, respectively. Proton leak and spare respiratory capacity are then calculated using these parameters and basal respiration. Each modulator targets a specific component of the electron transport chain. Oligomycin inhibits ATP synthase (complex V) and the decrease in OCR following injection of oligomycin correlates to the mitochondrial respiration associated with cellular ATP production. Carbonyl cyanide-4 (trifluoromethoxy) phenylhydrazone (FCCP) is an uncoupling agent that collapses the proton gradient and disrupts the mitochondrial membrane potential. As a result, electron flow through the electron transport chain is uninhibited and oxygen is maximally consumed by complex IV. The FCCP-stimulated OCR can then be used to calculate spare respiratory capacity, defined as the difference between maximal respiration and basal respiration. Spare respiratory capacity (SRC) is a measure of the ability of the cell to respond to increased energy demand. The third injection is a mix of rotenone, a complex I inhibitor, and antimycin A, a complex III inhibitor. This combination shuts down mitochondrial respiration and enables the calculation of nonmitochondrial respiration driven by processes outside the mitochondria. In some embodiments, the comparison is to, for example, freshly harvested TILs and/or TILs prepared using other methods than those provide herein including for example, methods other than those embodied in FIG. 27.

In some embodiments, the metabolic assay is basal respiration. In general, second expansion TILs have a basal respiration rate that is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 27. In some embodiments, the basal respiration rate is from about 50% to about 99% of the basal respiration rate of freshly harvested TILs and/or TILs prepared using other methods than those provide herein including for example, methods other than those embodied in FIG. 27. In some embodiments, the basal respiration rate is from about 60% to about 99% of the basal respiration rate of freshly harvested TILs and/or TILs prepared using other methods than those provide herein including for example, methods other than those embodied in FIG. 27. In some embodiments, the basal respiration rate is from about 70% to about 99% of the basal respiration rate of freshly harvested TILs and/or TILs prepared using other methods than those provide herein including for example, methods other than those embodied in FIG. 27. In some embodiments, the basal respiration rate is from about 80% to about 99% of the basal respiration rate of freshly harvested TILs and/or TILs prepared using other methods than those provide herein including for example, methods other than those embodied in FIG. 27. In some embodiments, the basal respiration rate is from about 90% to about 99% of the basal respiration rate of freshly harvested TILs and/or TILs prepared using other methods than those provide herein including for example, methods other than those embodied in FIG. 27. In some embodiments, the basal respiration rate is from about 95% to about 99% of the basal respiration rate of freshly harvested TILs and/or TILs prepared using other methods than those provide herein including for example, methods other than those embodied in FIG. 27. In some embodiments, the second expansion TILs or second additional expansion TILs (such as, for example, those described in Step D of FIG. 27, including TILs referred to as reREP TILs) have a basal respiration rate that is not statistically significantly different than the basal respiration rate of freshly harvested TILs and/or TILs prepared using other methods than those provide herein including for example, methods other than those embodied in FIG. 27. In some embodiments, the comparison is to, for example, freshly harvested TILs and/or TILs prepared using other methods than those provide herein including for example, methods other than those embodied in FIG. 27.

In some embodiments, the metabolic assay is spare respiratory capacity. In general, the second expansion TILs or second additional expansion TILs (such as, for example, those described in Step D of FIG. 27, including TILs referred to as reREP TILs) have a spare respiratory capacity that is at least is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 27. In some embodiments, the spare respiratory capacity is from about 50% to about 99% of the basal respiration rate of freshly harvested TILs. In some embodiments, the spare respiratory capacity is from about 50% to about 99% of the basal respiration rate of freshly harvested TILs and/or TILs prepared using other methods than those provide herein including for example, methods other than those embodied in FIG. 27. In some embodiments, the spare respiratory capacity is from about 60% to about 99% of the basal respiration rate of freshly harvested TILs and/or TILs prepared using other methods than those provide herein including for example, methods other than those embodied in FIG. 27. In some embodiments, the spare respiratory capacity is from about 70% to about 99% of the basal respiration rate of freshly harvested TILs and/or TILs prepared using other methods than those provide herein including for example, methods other than those embodied in FIG. 27. In some embodiments, the spare respiratory capacity is from about 80% to about 99% of the basal respiration rate of freshly harvested TILs. In some embodiments, the spare respiratory capacity is from about 90% to about 99% of the basal respiration rate of freshly harvested TILs and/or TILs prepared using other methods than those provide herein including for example, methods other than those embodied in FIG. 27. In some embodiments, the spare respiratory capacity is from about 95% to about 99% of the basal respiration rate of freshly harvested TILs and/or TILs prepared using other methods than those provide herein including for example, methods other than those embodied in FIG. 27. In some embodiments, the second expansion TILs or second additional expansion TILs (such as, for example, those described in Step D of FIG. 27, including TILs referred to as reREP TILs) have a spare respiratory capacity that is not statistically significantly different than the basal respiration rate of freshly harvested TILs and/or TILs prepared using other methods than those provide herein including for example, methods other than those embodied in FIG. 27.

In general, second expansion TILs or second additional expansion TILs (such as, for example, those described in Step D of FIG. 27, including TILs referred to as reREP TILs) have a spare respiratory capacity that is at least is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 27. In some embodiments, the metabolic assay measured is glycolytic reserve. In some embodiments, the metabolic assay is spare respiratory capacity. To measure cellular (respiratory) metabolism cells were treated with inhibitors of mitochondrial respiration and glycolysis to determine a metabolic profile for the TIL consisting of the following measures: baseline oxidative phosphorylation (as measured by OCR), spare respiratory capacity, baseline glycolytic activity (as measured by ECAR), and glycolytic reserve. Metabolic profiles were performed using the Seahorse Combination Mitochondrial/Glycolysis Stress Test Assay (including the kit commercially available from Agilent®), which allows for determining a cells' capacity to perform glycolysis upon blockage of mitochondrial ATP production. In some embodiments, cells are starved of glucose, then glucose is injected, followed by a stress agent. In some embodiments, the stress agent is selected from the group consisting of oligomycin, FCCP, rotenone, antimycin A and/or 2-deoxyglucose (2-DG), as well as combinations thereof. In some embodiments, oligomycin is added at 10 mM. In some embodiments, FCCP is added at 10 mM. In some embodiments, rotenone is added at 2.5 mM. In some embodiments, antimycin A is added at 2.5 mM. In some embodiments, 2-deoxyglucose (2-DG) is added at 500 mM. In some embodiments, glycolytic capacity, glycolytic reserve, and/or non-glycolytic acidification are measured. In general, TILs have a glycolytic reserve that is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 27. In some embodiments, the glycolytic reserve is from about 50% to about 99% of the basal respiration rate of freshly harvested TILs and/or TILs prepared using other methods than those provide herein including for example, methods other than those embodied in FIG. 27. In some embodiments, the glycolytic reserve is from about 60% to about 99% of the basal respiration rate of freshly harvested TILs and/or TILs prepared using other methods than those provide herein including for example, methods other than those embodied in FIG. 27. In some embodiments, the glycolytic reserve is from about 70% to about 99% of the basal respiration rate of freshly harvested TILs and/or TILs prepared using other methods than those provide herein including for example, methods other than those embodied in FIG. 27. In some embodiments, the glycolytic reserve is from about 80% to about 99% of the basal respiration rate of freshly harvested TILs and/or TILs prepared using other methods than those provide herein including for example, methods other than those embodied in FIG. 27. In some embodiments, the glycolytic reserve is from about 90% to about 99% of the basal respiration rate of freshly harvested TILs and/or TILs prepared using other methods than those provide herein including for example, methods other than those embodied in FIG. 27. In some embodiments, the glycolytic reserve is from about 95% to about 99% of the basal respiration rate of freshly harvested TILs and/or TILs prepared using other methods than those provide herein including for example, methods other than those embodied in FIG. 27.

In some embodiments, the metabolic assay is basal glycolysis. In some embodiments, second expansion TILs or second additional expansion TILs (such as, for example, those described in Step D of FIG. 27, including TILs referred to as reREP TILs) have an increase in basal glycolysis of at least two-fold, at least three-fold, at least four-fold, at least five-fold, at least six-fold, at least 7-fold, at least eight-fold, at least nine-fold, or at least ten-fold as compared to freshly harvested TILs and/or TILs prepared using other methods than those provide herein including for example, methods other than those embodied in FIG. 27. In some embodiments, the second expansion TILs or second additional expansion TILs (such as, for example, those described in Step D of FIG. 27, including TILs referred to as reREP TILs) have an increase in basal glycolysis of about two-fold to about ten-fold as compared to freshly harvested TILs and/or TILs prepared using other methods than those provide herein including for example, methods other than those embodied in FIG. 27. In some embodiments, the second expansion TILs or second additional expansion TILs (such as, for example, those described in Step D of FIG. 27, including TILs referred to as reREP TILs) have an increase in basal glycolysis of about two-fold to about eight-fold as compared to freshly harvested TILs and/or TILs prepared using other methods than those provide herein including for example, methods other than those embodied in FIG. 27. In some embodiments, second expansion TILs or second additional expansion TILs (such as, for example, those described in Step D of FIG. 27, including TILs referred to as reREP TILs) have an increase in basal glycolysis of about three-fold to about seven-fold as compared to freshly harvested TILs and/or TILs prepared using other methods than those provide herein including for example, methods other than those embodied in FIG. 27. In some embodiments, the second expansion TILs or second additional expansion TILs (such as, for example, those described in Step D of FIG. 27, including TILs referred to as reREP TILs) have an increase in basal glycolysis of about two-fold to about four-fold as compared to freshly harvested TILs and/or TILs prepared using other methods than those provide herein including for example, methods other than those embodied in FIG. 27. In some embodiments, the second expansion TILs or second additional expansion TILs (such as, for example, those described in Step D of FIG. 27, including TILs referred to as reREP TILs) have an increase in basal glycolysis of about two-fold to about three-fold as compared to freshly harvested TILs and/or TILs prepared using other methods than those provide herein including for example, methods other than those embodied in FIG. 27.

In general, the second expansion TILs or second additional expansion TILs (such as, for example, those described in Step D of FIG. 27, including TILs referred to as reREP TILs) have a glycolytic reserve that is at least 50%, at least 55%, at least 60%, at least 65%, at least 70%, at least 75%, at least 80%, at least 85%, at least 90%, at least 95%, at least 97%, at least 98%, or at least 99% of the basal respiration rate of freshly harvested TILs and/or TILs prepared using other methods than those provide herein including for example, methods other than those embodied in FIG. 27. In some embodiments, the glycolytic reserve is from about 50% to about 99% of the basal respiration rate of freshly harvested TILs. In some embodiments, the glycolytic reserve is from about 60% to about 99% of the basal respiration rate of freshly harvested TILs and/or TILs prepared using other methods than those provide herein including for example, methods other than those embodied in FIG. 27. In some embodiments, the glycolytic reserve is from about 70% to about 99% of the basal respiration rate of freshly harvested TILs and/or TILs prepared using other methods than those provide herein including for example, methods other than those embodied in FIG. 27. In some embodiments, the glycolytic reserve is from about 80% to about 99% of the basal respiration rate of freshly harvested TILs and/or TILs prepared using other methods than those provide herein including for example, methods other than those embodied in FIG. 27. In some embodiments, the glycolytic reserve is from about 90% to about 99% of the basal respiration rate of freshly harvested TILs and/or TILs prepared using other methods than those provide herein including for example, methods other than those embodied in FIG. 27. In some embodiments, the glycolytic reserve is from about 95% to about 99% of the basal respiration rate of freshly harvested TILs.

Granzyme B Production: Granzyme B is another measure of the ability of TIL to kill target cells. Media supernatants restimulated as described above using antibodies to CD3, CD28, and CD137/4-1BB were also evaluated for their levels of Granzyme B using the Human Granzyme B DuoSet ELISA Kit (R & D Systems, Minneapolis, MN) according to the manufacturer's instructions. In some embodiments, the second expansion TILs or second additional expansion TILs (such as, for example, those described in Step D of FIG. 27, including TILs referred to as reREP TILs) have increased Granzyme B production. In some embodiments, the second expansion TILs or second additional expansion TILs (such as, for example, those described in Step D of FIG. 27, including TILs referred to as reREP TILs) have increased cytotoxic activity.

In some embodiments, telomere length can be used as a measure of cell viability and/or cellular function. In some embodiments, the telomeres are surprisingly the same length in the TILs produced by the present invention as compared to TILs prepared using other methods than those provide herein including for example, methods other than those embodied in FIG. 27. Telomere length measurement: Diverse methods have been used to measure the length of telomeres in genomic DNA and cytological preparations. The telomere restriction fragment (TRF) analysis is the gold standard to measure telomere length (de Lange et al., 1990). However, the major limitation of TRF is the requirement of a large amount of DNA (1.5 ˆg). Two widely used techniques for the measurement of telomere lengths namely, fluorescence in situ hybridization (FISH; Agilent Technologies, Santa Clara, CA) and quantitative PCR can be employed with the present invention. In some embodiments, there is no change in telomere length between the initially harvest TILs in Step A and the expanded TILs from for example Step D as provided in FIG. 27.

In some embodiments, TIL health is measured by IFN-gamma (IFN-γ) secretion. In some embodiments, IFN-γ secretion is indicative of active TILs. In some embodiments, a potency assay for IFN-γ production is employed. IFN-γ production is another measure of cytotoxic potential. IFN-γ production can be measured by determining the levels of the cytokine IFN-γ in the media of TIL stimulated with antibodies to CD3, CD28, and CD137/4-1BB. IFN-γ levels in media from these stimulated TIL can be determined using by measuring IFN-γ release. In some embodiments, an increase in IFN-γ production in for example Step D as provided in FIG. 27 TILs as compared to initially harvested TILs in for example Step A as provided in FIG. 27 is indicative of an increase in cytotoxic potential of the Step D TILs. In some embodiments, IFN-γ secretion is increased one-fold, two-fold, three-fold, four-fold, or five-fold or more. In some embodiments, IFN-γ secretion is increased one-fold. In some embodiments, IFN-γ secretion is increased two-fold. In some embodiments, IFN-γ secretion is increased three-fold. In some embodiments, IFN-γ secretion is increased four-fold. In some embodiments, IFN-γ secretion is increased five-fold. In some embodiments, IFN-γ is measured using a Quantikine ELISA kit. In some embodiments, IFN-γ is measured in TILs ex vivo. In some embodiments, IFN-γ is measured in TILs ex vivo, including TILs produced by the methods of the present invention, including for example FIG. 27 methods, as well as freshly harvested TILs or those TILs produced by other methods, such as those provided for example in FIG. 83 (such as for example process 1C TILs).

In some embodiments, the cytotoxic potential of TIL to lyse target cells was assessed using a co-culture assay of TIL with the bioluminescent cell line, P815 (Clone G6), according to a bioluminescent redirected lysis assay (potency assay) for TIL assay which measures TIL cytotoxicity in a highly sensitive dose dependent manner.

In some embodiments, the present methods provide an assay for assessing TIL viability, using the methods as described above. In some embodiments, the TILs are expanded as discussed above, including for example as provided in FIG. 27. In some embodiments, the TILs are cryopreserved prior to being assessed for viability. In some embodiments, the viability assessment includes thawing the TILs prior to performing a first expansion, a second expansion, and an additional second expansion. In some embodiments, the present methods provide an assay for assessing cell proliferation, cell toxicity, cell death, and/or other terms related to viability of the TIL population. Viability can be measured by any of the TIL metabolic assays described above as well as any methods know for assessing cell viability that are known in the art. In some embodiments, the present methods provide as assay for assessment of cell proliferation, cell toxicity, cell death, and/or other terms related to viability of the TILs expanded using the methods described herein, including those exemplified in FIG. 27.

The present invention also provides assay methods for determining TIL viability. In some embodiments, the TILs have equal viability as compared to freshly harvested TILs and/or TILs prepared using other methods than those provide herein including for example, methods other than those embodied in FIG. 27. In some embodiments, the TILs have increased viability as compared to freshly harvested TILs and/or TILs prepared using other methods than those provide herein including for example, methods other than those embodied in FIG. 27. The present disclosure provides methods for assaying TILs for viability by expanding tumor infiltrating lymphocytes (TILs) into a larger population of TILs comprising:
(i) obtaining a first population of TILs which has been previously expanded;
(ii) performing a first expansion by culturing the first population of TILs in a cell culture medium comprising IL-2 to produce a second population of TILs; and
(iii) performing a second expansion by supplementing the cell culture medium of the second population of TILs with additional IL-2, OKT-3, and antigen presenting cells (APCs), to produce a third population of TILs, wherein the third population of TILs is at least 100-fold greater in number than the second population of TILs, and wherein the second expansion is performed for at least 14 days in order to obtain the third population of TILs, wherein the third population of TILs comprises an increased subpopulation of effector T cells and/or central memory T cells relative to the second population of TILs, and wherein the third population is further assayed for viability.

In some embodiments, the method further comprises:
(iv) performing an additional second expansion by supplementing the cell culture medium of the third population of TILs with additional IL-2, additional OKT-3, and additional APCs, wherein the additional second expansion is performed for at least 14 days to obtain a larger population of TILs than obtained in step (iii), wherein the larger population of TILs comprises an increased subpopulation of effector T cells and/or central memory T cells relative to the third population of TILs, and wherein the third population is further assayed for viability.

In some embodiments, prior to step (i), the cells are cryopreserved.

In some embodiments, the cells are thawed prior to performing step (i).

In some embodiments, step (iv) is repeated one to four times in order to obtain sufficient TILs for analysis.

In some embodiments, steps (i) through (iii) or (iv) are performed within a period of about 40 days to about 50 days.

In some embodiments, steps (i) through (iii) or (iv) are performed within a period of about 42 days to about 48 days.

In some embodiments, steps (i) through (iii) or (iv) are performed within a period of about 42 days to about 45 days.

In some embodiments, steps (i) through (iii) or (iv) are performed within about 44 days.

In some embodiments, the cells from steps (iii) or (iv) express CD4, CD8, and TCR αβ at levels similar to freshly harvested cells.

In some embodiments, the antigen presenting cells are peripheral blood mononuclear cells (PBMCs).

In some embodiments, the PBMCs are added to the cell culture on any of days 9 through 17 in step (iii).

In some embodiments, the effector T cells and/or central memory T cells in the larger population of TILs in step (iv) exhibit one or more characteristics selected from the group consisting of expression of CD27, expression of CD28, longer telomeres, increased CD57 expression, and decreased CD56 expression, relative to effector T cells, and/or central memory T cells in the third population of cells.

In some embodiments, the effector T cells and/or central memory T cells exhibit increased CD57 expression and decreased CD56 expression.

In some embodiments, the APCs are artificial APCs (aAPCs).

In some embodiments, the method further comprises the step of transducing the first population of TILs with an expression vector comprising a nucleic acid encoding a high-affinity T cell receptor.

In some embodiments, the step of transducing occurs before step (i).

In some embodiments, the method further comprises the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability.

In some embodiments, the TILs are assayed for viability after cryopreservation.

In some embodiments, the TILs are assayed for viability after cryopreservation and after step (iv).

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity (sometimes referred to as polyclonality). In some embodiments, the increase in T-cell repertoire diversity is as compared to freshly harvested TILs and/or TILs prepared using other methods than those provide herein including for example, methods other than those embodied in FIG. 27. In some embodiments, the TILs obtained by the present method exhibit an increase in the T-cell repertoire diversity. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRα/β).

According to the present disclosure, a method for assaying TILs for viability and/or further use in administration to a subject. In some embodiments, the method for assay tumor infiltrating lymphocytes (TILs) comprises:
 (i) obtaining a first population of TILs;
 (ii) performing a first expansion by culturing the first population of TILs in a cell culture medium comprising IL-2 to produce a second population of TILs; and
 (iii) performing a second expansion by supplementing the cell culture medium of the second population of TILs with additional IL-2, OKT-3, and antigen presenting cells (APCs), to produce a third population of TILs, wherein the third population of TILs is at least 50-fold greater in number than the second population of TILs;
 (iv) harvesting, washing, and cryopreserving the third population of TILs;
 (v) storing the cryopreserved TILs at a cryogenic temperature;
 (vi) thawing the third population of TILs to provide a thawed third population of TILs; and
 (vii) performing an additional second expansion of a portion of the thawed third population of TILs by supplementing the cell culture medium of the third population with IL-2, OKT-3, and APCs for an additional expansion period (sometimes referred to as a reREP period) of at least 3 days, wherein the third expansion is performed to obtain a fourth population of TILs, wherein the number of TILs in the fourth population of TILs is compared to the number of TILs in the third population of TILs to obtain a ratio;
 (viii) determining based on the ratio in step (vii) whether the thawed population of TILs is suitable for administration to a patient;
 (ix) administering a therapeutically effective dosage of the thawed third population of TILs to the patient when the ratio of the number of TILs in the fourth population of TILs to the number of TILs in the third population of TILs is determined to be greater than 5:1 in step (viii).

In some embodiments, the additional expansion period (sometimes referred to as a reREP period) is performed until the ratio of the number of TILs in the fourth population of TILs to the number of TILs in the third population of TILs is greater than 50:1.

In some embodiments, the number of TILs sufficient for a therapeutically effective dosage is from about $2.3 \times 10^{10}$ to about $13.7 \times 10^{10}$.

In some embodiments, steps (i) through (vii) are performed within a period of about 40 days to about 50 days. In some embodiments, steps (i) through (vii) are performed within a period of about 42 days to about 48 days. In some embodiments, steps (i) through (vii) are performed within a period of about 42 days to about 45 days. In some embodiments, steps (i) through (vii) are performed within about 44 days.

In some embodiments, the cells from steps (iii) or (vii) express CD4, CD8, and TCR α β at levels similar to freshly harvested cells. In some embodiments the cells are TILs.

In some embodiments, the antigen presenting cells are peripheral blood mononuclear cells (PBMCs). In some embodiments, the PBMCs are added to the cell culture on any of days 9 through 17 in step (iii).

In some embodiments, the effector T cells and/or central memory T cells in the larger population of TILs in steps (iii) or (vii) exhibit one or more characteristics selected from the group consisting of expression of CD27, expression of CD28, longer telomeres, increased CD57 expression, and decreased CD56 expression, relative to effector T cells, and/or central memory T cells in the third population of cells.

In some embodiments, the effector T cells and/or central memory T cells exhibit increased CD57 expression and decreased CD56 expression.

In some embodiments, the APCs are artificial APCs (aAPCs).

In some embodiments, the step of transducing the first population of TILs with an expression vector comprising a nucleic acid encoding a high-affinity T cell receptor.

In some embodiments, the step of transducing occurs before step (i).

In some embodiments, the step of transducing the first population of TILs with an expression vector comprising a nucleic acid encoding a chimeric antigen receptor (CAR) comprising a single chain variable fragment antibody fused with at least one endodomain of a T-cell signaling molecule.

In some embodiments, the step of transducing occurs before step (i).

In some embodiments, the TILs are assayed for viability after step (vii).

The present disclosure also provides further methods for assaying TILs. In some embodiments, the disclosure provides a method for assaying TILs comprising:
(i) obtaining a portion of a first population of cryopreserved TILs;
(ii) thawing the portion of the first population of cryopreserved TILs;
(iii) performing a first expansion by culturing the portion of the first population of TILs in a cell culture medium comprising IL-2, OKT-3, and antigen presenting cells (APCs) for an additional expansion period (sometimes referred to as a reREP period) of at least 3 days, to produce a second population of TILs, wherein the portion from the first population of TILs is compared to the second population of TILs to obtain a ratio of the number of TILs, wherein the ratio of the number of TILs in the second population of TILs to the number of TILs in the portion of the first population of TILs is greater than 5:1;
(iv) determining based on the ratio in step (iii) whether the first population of TILs is suitable for use in therapeutic administration to a patient;
(v) determining the first population of TILs is suitable for use in therapeutic administration when the ratio of the number of TILs in the second population of TILs to the number of TILs in the first population of TILs is determined to be greater than 5:1 in step (iv).

In some embodiments, the ratio of the number of TILs in the second population of TILs to the number of TILs in the portion of the first population of TILs is greater than 50:1.

In some embodiments, the method further comprises performing expansion of the entire first population of cryopreserved TILs from step (i) according to the methods as described in any of the embodiments provided herein.

In some embodiments, the method further comprises administering the entire first population of cryopreserved TILs from step (i) to the patient.

K. Closed Systems for TIL Manufacturing

The present invention provides for the use of closed systems during the TIL culturing process. Such closed systems allow for preventing and/or reducing microbial contamination, allow for the use of fewer flasks, and allow for cost reductions. In some embodiments, the closed system uses two containers.

Such closed systems are well-known in the art and can be found, for example, at http://www.fda.gov/cber/guidelines.htm and https://www.fda.gov/BiologicsBloodVaccines/GuidanceComplianceRegulatoryInformation/Guidances/Blood/ucm076779.htm.

In some embodiments, the closed systems include luer lock and heat sealed systems as described in for example, Example 30. In some embodiments, the closed system is accessed via syringes under sterile conditions in order to maintain the sterility and closed nature of the system. In some embodiments, a closed system as described in Example 30 is employed. In some embodiments, the TILs are formulated into a final product formulation container according to the method described in Example 30, section 8.14 "Final Formulation and Fill".

As provided on the FDA website, closed systems with sterile methods are known and well described. See, https://www.fda.gov/BiologicsBloodVaccines/GuidanceComplianceRegulatoryInformation/Guidances/Blood/ucm076779.htm, as referenced above and provided in pertinent part below.

Introduction

Sterile connecting devices (STCDs) produce sterile welds between two pieces of compatible tubing. This procedure permits sterile connection of a variety of containers and tube diameters. This guidance describes recommended practices and procedures for use of these devices. This guidance does not address the data or information that a manufacturer of a sterile connecting device must submit to FDA in order to obtain approval or clearance for marketing. It is also important to note that the use of an approved or cleared sterile connecting device for purposes not authorized in the labeling may cause the device to be considered adulterated and misbranded under the Federal Food, Drug and Cosmetic Act.

1. FDA Recommendations

Manufacturers of blood products who propose to routinely use an FDA-cleared STCD should incorporate information regarding such use in standard operating procedure (SOP) manuals for each blood product. These entries should include record keeping, product tracking, tube weld quality control, lot numbers of software and disposables (including source(s) of elements to be added). Quality control procedures should include a test of the integrity of each weld.

2. Applications of the STCD

The user should be aware that use of the device may create a new product or significantly modify the configuration of a regulated product for which safety and efficacy have not been demonstrated. For those "new products" subject to licensure, applications, or application supplements must be submitted to FDA in addition to submission of a SOP. In general, pooling or mixing that involves cellular components represents a change in the product that requires submission and approval of a license application or application supplement. Such applications and application supplements should contain data and descriptions of manufacturing procedures that demonstrate that the "new product" is safe and effective for its intended use throughout the proposed dating period.

The following comments are provided as guidance on the more common uses of an FDA cleared or approved STCD:

L. Adding a New or Smaller Needle to a Blood Collection Set

Using the STCD to add a needle prior to the initiation of a procedure (whole blood collection, plateletpheresis or source plasma collection) is not consideredto open a functionally closed system. If a needle is added during a procedure, only an STCD approved to weld liquid-filled tubing should be used. If the test of weld integrity is satisfactory, the use of an STCD is not considered to open a functionally closed system.

Platelets, Pheresis prepared in an open system should be labeled with a 24 hour outdate and Platelets, Pheresis products prepared in a functionally closed system should be labeled with a five day outdate (See Revised Guideline for Collection of Platelets, Pheresis, Oct. 7, 1988).

The source and specifications of added tubing and needles should be addressed in the blood center's SOP and records. Using the STCD to add needles does not represent a major change in manufacturing for which licensed establishments need preapproval.

M. Using the STCD to Prepare Components

When the STCD is used to attach additional component preparation bags, records should be properly maintained identifying the source of the transfer packs and the appropriate verification of blood unit number and ABO/Rh. All blood and blood components must be appropriately labeled (21 CFR 606.121).

EXAMPLES

Adding a fourth bag to a whole blood collection triplepack for the production of Cryoprecipitated AHF from Fresh Frozen Plasma.
Connection of an additive solution to a red blood cell unit.
Addition of an in-line filter that has been FDA cleared for use in manufacturing components.
Addition of a third storage container to a plateletpheresis harness.
For the above stated uses, procedures should be developed and records maintained, but licensees need not have FDA approval in order to institute the procedures.
1. Using the STCD to Pool Blood Products Appropriate use of an STCD to pool Platelets prepared from Whole Blood collection may obviate potential contamination from the spike and port entries commonly used. Pooling performed immediately before transfusion is an example of such appropriate use. Pooled Platelets should be administered not more than 4 hours after pooling (See 21 CFR 606.122(1)(2)).

However, pooling and subsequent storage may increase the risk compared to administration of random donor units; if one contaminated unit is pooled with others and stored before administration, the total bacterial inoculum administered may be increased as a result of replication in the additional volume. Accordingly, the proposed use of an STCD to pool and store platelets for more than 4 hours should be supported by data which satisfactorily addresses whether such pooling is associated with increased risk.

Such platelet pooling constitutes manufacture of a new product.

Pooling or mixing that involves platelets is considered the manufacture of a new product that requires submission and approval of a license application or application supplement if the storage period is to exceed four hours.

2. Using the STCD to Prepare an Aliquot for Pediatric Use and Divided Units

Pediatric units and divided units for Whole Blood, Red Blood Cells, and Fresh Frozen Plasma prepared using an STCD will not be considered a new product for which a biologics license application (BLA) supplement is required providing the following conditions are met:

The manufacturer should have an approved biologics license or license supplement, for the original (i.e., undivided) product, including approval for each anticoagulant used.

Labels should be submitted for review and approval before distribution. A notation should be made under the comments section of FDA Form 2567, Transmittal of Labels and *Circulars*.

Final product containers approved for storage of the component being prepared should be used.

Platelets manufactured under licensure must contain at least $5.5 \times (10)^{10}$ platelets (21 CFR 640.24 (c)). Platelets, Pheresis manufactured under licensure should contain at least $3.0 \times (10)^{11}$ platelets (See Revised Guideline for the Collection of Platelets, Pheresis, Oct. 7, 1988).

Procedures to be followed regarding the use of an STCD to prepare divided products from Whole Blood collections and from plasma and platelets prepared by automated hemapheresis procedures should include descriptions of:

How the apheresis harness or collection container will be modified with an FDA-cleared STCD;
the minimum volume of the split plasma or whole blood products;
the volume and platelet concentration of the split plateletpheresis products;
storage time of the product. The product should be in an approved container and should be consistent with the storage time on the label of such container;
method(s) to be used to label and track divided products in the blood center's records.

NOTE: Procedures for labeling the aliquots should be clearly stated in the procedure record keeping should be adequate to permit tracking and recall of all components, if necessary.

3. Using an STCD to Connect Additional Saline or Anticoagulant Lines During an Automated Plasmapheresis Procedure Procedures should be developed and records maintained consistent with the instrument manufacturer's directions for use, but licensees need not have FDA approval in order to institute the procedures.

4. Using the STCD to Attach Processing Solutions

When using an STCD to attach containers with processing solutions to washed or frozen red blood cell products, the dating period for the resulting products is 24 hours, unless data are provided in the form of license applications or application supplements to CBER to support a longer dating period (21 CFR 610.53(c)). Exemptions or modifications must be approved in writing from the Director, CBER (21 CFR 610.53(d)).

5. Using an STCD to Add an FDA-Cleared Leukocyte Reduction Filter

Some leuko-reduction filters are not integrally attached to the Whole Blood collection systems. Procedures for use of an STCD for pre-storage filtration should be consistent with filter manufacturers' directions for use.

Leukocyte reduction prior to issue constitutes a major manufacturing change. Therefore, for new leukocyte-reduced products prepared using an STCD, manufacturers must submit biologics license applications (21 CFR 601.2) or prior approval application supplements to FDA (21 CFR 601.12).

Using an STCD to remove samples from blood product containers for testing (e.g., using an STCD to obtain a sample of platelets from a container of Platelets or Platelets, Pheresis for cross matching).

If the volume and/or cell count of the product after sample withdrawal differ from what is stated on the original label or in the circular of information, the label on the product should be modified to reflect the new volume and/or cell count. For example, samples may not be removed that reduce the platelet count of a unit of Platelets to less than $5.5 \times (10)^{10}$ platelets (21 CFR 640.24 (c)).

6. Additional Information from FDA Guidance

The FDA guidance presents general guidance as well as specific information and examples concerning specifications for submission of applications and application supplements to FDA addressing use of an STCD. If further questions arise concerning appropriate use of an STCD, concerns should be directed to the Office of Blood Research and Review, Center for Biologics Evaluation and Research.

In some embodiments, the closed system uses one container from the time the tumor fragments are obtained until the TILs are ready for administration to the patient or cryopreserving. In some embodiments when two containers are used, the first container is a closed G-container and the population of TILs is centrifuged and transferred to an infusion bag without opening the first closed G-container. In some embodiments, when two containers are used, the infusion bag is a HypoThermosol-containing infusion bag. A closed system or closed TIL cell culture system is characterized in that once the tumor sample and/or tumor fragments have been added, the system is tightly sealed from the outside to form a closed environment free from the invasion of bacteria, fungi, and/or any other microbial contamination.

In some embodiments, the reduction in microbial contamination is between about 5% and about 100%. In some embodiments, the reduction in microbial contamination is between about 5% and about 95%. In some embodiments, the reduction in microbial contamination is between about 5% and about 90%. In some embodiments, the reduction in microbial contamination is between about 10% and about 90%. In some embodiments, the reduction in microbial contamination is between about 15% and about 85%. In some embodiments, the reduction in microbial contamination is about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, about 99%, or about 100%.

The closed system allows for TIL growth in the absence and/or with a significant reduction in microbial contamination.

Moreover, pH, carbon dioxide partial pressure and oxygen partial pressure of the TIL cell culture environment each vary as the cells are cultured. Consequently, even though a medium appropriate for cell culture is circulated, the closed environment still needs to be constantly maintained as an optimal environment for TIL proliferation. To this end, it is desirable that the physical factors of pH, carbon dioxide partial pressure and oxygen partial pressure within the culture liquid of the closed environment be monitored by means of a sensor, the signal whereof is used to control a gas exchanger installed at the inlet of the culture environment, and the that gas partial pressure of the closed environment be adjusted in real time according to changes in the culture liquid so as to optimize the cell culture environment. In some embodiments, the present invention provides a closed cell culture system which incorporates at the inlet to the closed environment a gas exchanger equipped with a monitoring device which measures the pH, carbon dioxide partial pressure and oxygen partial pressure of the closed environment, and optimizes the cell culture environment by automatically adjusting gas concentrations based on signals from the monitoring device.

In some embodiments, the pressure within the closed environment is continuously or intermittently controlled. That is, the pressure in the closed environment can be varied by means of a pressure maintenance device for example, thus ensuring that the space is suitable for growth of TILs in a positive pressure state, or promoting exudation of fluid in a negative pressure state and thus promoting cell proliferation. By applying negative pressure intermittently, moreover, it is possible to uniformly and efficiently replace the circulating liquid in the closed environment by means of a temporary shrinkage in the volume of the closed environment.

In some embodiments, optimal culture components for proliferation of the TILs can be substituted or added, and including factors such as IL-2 and/or OKT3, as well as combination, can be added.

C. Cell Cultures

In an embodiment, a method for expanding TILs, including those discuss above as well as exemplified in FIG. 27, may include using about 5,000 mL to about 25,000 mL of cell medium, about 5,000 mL to about 10,000 mL of cell medium, or about 5,800 mL to about 8,700 mL of cell medium. In some embodiments, the media is a serum free medium, as described for example in Example 21. In some embodiments, the media in the first expansion is serum free. In some embodiments, the media in the second expansion is serum free. In some embodiments, the media in the first expansion and the second are both serum free. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium for a duration of about 7 to 14 days, e.g., about 11 days. In some embodiments pre-REP is about 7 to 14 days, e.g., about 11 days. In some embodiments, REP is about 7 to 14 days, e.g., about 11 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5 \times 10^5$ cells/cm$^2$ to between $10 \times 10^6$ and $30 \times 10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., J. Immunotherapy, 2012, 35:283-292.

D. Optional Genetic Engineering of TILs

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

E. Optional Cryopreservation of TILs

Either the bulk TIL population or the expanded population of TILs can be optionally cryopreserved. In some embodiments, cryopreservation occurs on the therapeutic TIL population. In some embodiments, cryopreservation occurs on the TILs harvested after the second expansion. In some embodiments, cryopreservation occurs on the TILs in exemplary Step F of FIG. 27. In some embodiments, the TILs are cryopreserved in the infusion bag. In some embodiments, the TILs are cryopreserved prior to placement in an infusion bag. In some embodiments, the TILs are cryopreserved and not placed in an infusion bag. In some embodiments, cryopreservation is performed using a cryopreservation medium. In some embodiments, the cryopreservation media contains dimethylsulfoxide (DMSO). This is generally accomplished by putting the TIL population into a freezing solution, e.g. 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See, Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In a preferred embodiment, a population of TILs is cryopreserved using CS10 cryopreservation media (CryoStor 10, BioLife Solutions). In a preferred embodiment, a population of TILs is cryopreserved using a cryopreservation media containing dimethylsulfoxide (DMSO). In a preferred embodiment, a population of TILs is cryopreserved using a 1:1 (vol:vol) ratio of CS10 and cell culture media. In a preferred embodiment, a population of TILs is cryopreserved using about a 1:1 (vol:vol) ratio of CS10 and cell culture media, further comprising additional IL-2.

As discussed above in Steps A through E, cryopreservation can occur at numerous points throughout the TIL expansion process. In some embodiments, the bulk TIL population after the first expansion according to Step B or the expanded population of TILs after the one or more second expansions according to Step D can be cryopreserved. Cryopreservation can be generally accomplished by placing the TIL population into a freezing solution, e.g., 85% complement inactivated AB serum and 15% dimethyl sulfoxide (DMSO). The cells in solution are placed into cryogenic vials and stored for 24 hours at −80° C., with optional transfer to gaseous nitrogen freezers for cryopreservation. See Sadeghi, et al., *Acta Oncologica* 2013, 52, 978-986.

When appropriate, the cells are removed from the freezer and thawed in a 37° C. water bath until approximately ⅘ of the solution is thawed. The cells are generally resuspended in complete media and optionally washed one or more times. In some embodiments, the thawed TILs can be counted and assessed for viability as is known in the art.

In some cases, the Step B TIL population can be cryopreserved immediately, using the protocols discussed below. Alternatively, the bulk TIL population can be subjected to Step C and Step D and then cryopreserved after Step D. Similarly, in the case where genetically modified TILs will be used in therapy, the Step B or Step D TIL populations can be subjected to genetic modifications for suitable treatments.

F. Optional Cell Viability Analyses

Optionally, a cell viability assay can be performed after the first expansion (sometimes referred to as the initial bulk expansion), using standard assays known in the art. For example, a trypan blue exclusion assay can be done on a sample of the bulk TILs, which selectively labels dead cells and allows a viability assessment. Other assays for use in testing viability can include but are not limited to the Alamar blue assay; and the MTT assay.

1. Cell Counts, Viability, Flow Cytometry

In some embodiments, cell counts and/or viability are measured. The expression of markers such as but not limited CD3, CD4, CD8, and CD56, as well as any other disclosed or described herein, can be measured by flow cytometry with antibodies, for example but not limited to those commercially available from BD Bio-sciences (BD Biosciences, San Jose, CA) using a FACSCanto™ flow cytometer (BD Biosciences). The cells can be counted manually using a disposable c-chip hemocytometer (VWR, Batavia, IL) and viability can be assessed using any method known in the art, including but not limited to trypan blue staining.

In some cases, the bulk TIL population can be cryopreserved immediately, using the protocols discussed below. Alternatively, the bulk TIL population can be subjected to REP and then cryopreserved as discussed below. Similarly, in the case where genetically modified TILs will be used in therapy, the bulk or REP TIL populations can be subjected to genetic modifications for suitable treatments.

2. Cell Cultures

In an embodiment, a method for expanding TILs may include using about 5,000 mL to about 25,000 mL of cell medium, about 5,000 mL to about 10,000 mL of cell medium, or about 5,800 mL to about 8,700 mL of cell medium. In an embodiment, expanding the number of TILs uses no more than one type of cell culture medium. Any suitable cell culture medium may be used, e.g., AIM-V cell medium (L-glutamine, 50 µM streptomycin sulfate, and 10 µM gentamicin sulfate) cell culture medium (Invitrogen, Carlsbad CA). In this regard, the inventive methods advantageously reduce the amount of medium and the number of types of medium required to expand the number of TIL. In an embodiment, expanding the number of TIL may comprise feeding the cells no more frequently than every third or fourth day. Expanding the number of cells in a gas permeable container simplifies the procedures necessary to expand the number of cells by reducing the feeding frequency necessary to expand the cells.

In an embodiment, the cell medium in the first and/or second gas permeable container is unfiltered. The use of unfiltered cell medium may simplify the procedures necessary to expand the number of cells. In an embodiment, the cell medium in the first and/or second gas permeable container lacks beta-mercaptoethanol (BME).

In an embodiment, the duration of the method comprising obtaining a tumor tissue sample from the mammal; culturing the tumor tissue sample in a first gas permeable container containing cell medium therein; obtaining TILs from the tumor tissue sample; expanding the number of TILs in a second gas permeable container containing cell medium therein using aAPCs for a duration of about 14 to about 42 days, e.g., about 28 days.

In an embodiment, TILs are expanded in gas-permeable containers. Gas-permeable containers have been used to expand TILs using PBMCs using methods, compositions, and devices known in the art, including those described in U.S. Patent Application Publication No. 2005/0106717 A1, the disclosures of which are incorporated herein by reference. In an embodiment, TILs are expanded in gas-permeable bags. In an embodiment, TILs are expanded using a cell expansion system that expands TILs in gas permeable bags, such as the Xuri Cell Expansion System W25 (GE Healthcare). In an embodiment, TILs are expanded using a cell expansion system that expands TILs in gas permeable bags, such as the WAVE Bioreactor System, also known as the Xuri Cell Expansion System W5 (GE Healthcare). In an embodiment, the cell expansion system includes a gas permeable cell bag with a volume selected from the group consisting of about 100 mL, about 200 mL, about 300 mL, about 400 mL, about 500 mL, about 600 mL, about 700 mL, about 800 mL, about 900 mL, about 1 L, about 2 L, about 3 L, about 4 L, about 5 L, about 6 L, about 7 L, about 8 L, about 9 L, and about 10 L.

In an embodiment, TILs can be expanded in G-Rex flasks (commercially available from Wilson Wolf Manufacturing). Such embodiments allow for cell populations to expand from about $5\times10^5$ cells/cm$^2$ to between $10\times10^6$ and $30\times10^6$ cells/cm$^2$. In an embodiment this is without feeding. In an embodiment, this is without feeding so long as medium resides at a height of about 10 cm in the G-Rex flask. In an embodiment this is without feeding but with the addition of one or more cytokines. In an embodiment, the cytokine can be added as a bolus without any need to mix the cytokine with the medium. Such containers, devices, and methods are known in the art and have been used to expand TILs, and include those described in U.S. Patent Application Publication No. US 2014/0377739A1, International Publication No. WO 2014/210036 A1, U.S. Patent Application Publication No. us 2013/0115617 A1, International Publication No. WO 2013/188427 A1, U.S. Patent Application Publication No. US 2011/0136228 A1, U.S. Pat. No. 8,809,050 B2, International publication No. WO 2011/072088 A2, U.S. Patent Application Publication No. US 2016/0208216 A1, U.S. Patent Application Publication No. US 2012/0244133 A1, International Publication No. WO 2012/129201 A1, U.S. Patent Application Publication No. US 2013/0102075 A1, U.S. Pat. No. 8,956,860 B2, International Publication No. WO 2013/173835 A1, U.S. Patent Application Publication No. US 2015/0175966 A1, the disclosures of which are incorporated herein by reference. Such processes are also described in Jin et al., *J. Immunotherapy*, 2012, 35:283-292.

Optional Genetic Engineering of TILs

In some embodiments, the TILs are optionally genetically engineered to include additional functionalities, including, but not limited to, a high-affinity T cell receptor (TCR), e.g., a TCR targeted at a tumor-associated antigen such as MAGE-1, HER2, or NY-ESO-1, or a chimeric antigen receptor (CAR) which binds to a tumor-associated cell surface molecule (e.g., mesothelin) or lineage-restricted cell surface molecule (e.g., CD19).

IV. Methods of Treating Patients

Methods of treatment begin with the initial TIL collection and culture of TILs. Such methods have been both described in the art by, for example, Jin et al., J Immunotherapy, 2012, 35(3):283-292, incorporated by reference herein in its entirety. Embodiments of methods of treatment are described throughout the sections below, including the Examples.

The expanded TILs produced according the methods described herein, including for example as described in Steps A through F above or according to Steps A through F above (also as shown, for example, in FIG. 27) find particular use in the treatment of patients with cancer (for example, as described in Goff, et al., *J. Clinical Oncology*, 2016, 34(20):2389-239, as well as the supplemental content; incorporated by reference herein in its entirety. In some embodiments, TIL were grown from resected deposits of metastatic melanoma as previously described (see, Dudley, et al., *J Immunother.*, 2003, 26:332-342; incorporated by reference herein in its entirety). Fresh tumor can be dissected under sterile conditions. A representative sample can be collected for formal pathologic analysis. Single fragments of 2 mm$^3$ to 3 mm$^3$ may be used. In some embodiments, 5, 10, 15, 20, 25 or 30 samples per patient are obtained. In some embodiments, 20, 25, or 30 samples per patient are obtained.

In some embodiments, 20, 22, 24, 26, or 28 samples per patient are obtained. In some embodiments, 24 samples per patient are obtained. Samples can be placed in individual wells of a 24-well plate, maintained in growth media with high-dose IL-2 (6,000 IU/mL), and monitored for destruction of tumor and/or proliferation of TIL. Any tumor with viable cells remaining after processing can be enzymatically digested into a single cell suspension and cryopreserved, as described herein.

In some embodiments, successfully grown TIL can be sampled for phenotype analysis (CD3, CD4, CD8, and CD56) and tested against autologous tumor when available. TIL can be considered reactive if overnight coculture yielded interferon-gamma (IFN-γ) levels >200 pg/mL and twice background. (Goff, et al., *J Immunother.*, 2010, 33:840-847; incorporated by reference herein in its entirety). In some embodiments, cultures with evidence of autologous reactivity or sufficient growth patterns can be selected for a second expansion (for example, a second expansion as provided in according to Step D of FIG. 27), including second expansions that are sometimes referred to as rapid expansion (REP). In some embodiments, expanded TILs with high autologous reactivity (for example, high proliferation during a second expansion), are selected for an additional second expansion. In some embodiments, TILs with high autologous reactivity (for example, high proliferation during second expansion as provided in Step D of FIG. 27), are selected for an additional second expansion according to Step D of FIG. 27.

In some embodiments, the patient is not moved directly to ACT (adoptive cell transfer), for example, in some embodiments, after tumor harvesting and/or a first expansion, the cells are not utilized immediately. In such embodiments, TILs can be cryopreserved and thawed 2 days before administration to a patient. In such embodiments, TILs can be cryopreserved and thawed 1 day before administration to a patient. In some embodiments, the TILs can be cryopreserved and thawed immediately before the administration to a patient.

Cell phenotypes of cryopreserved samples of infusion bag TIL can be analyzed by flow cytometry (e.g., FlowJo) for surface markers CD3, CD4, CD8, CCR7, and CD45RA (BD BioSciences), as well as by any of the methods described herein. Serum cytokines were measured by using standard enzyme-linked immunosorbent assay techniques. A rise in serum IFN-g was defined as >100 pg/mL and greater than 4 3 baseline levels.

In some embodiments, the TILs produced by the methods provided herein, for example those exemplified in FIG. 27, provide for a surprising improvement in clinical efficacy of the TILs. In some embodiments, the TILs produced by the methods provided herein, for example those exemplified in FIG. 27, exhibit increased clinical efficacy as compared to TILs produced by methods other than those described herein, including for example, methods other than those exemplified in FIG. 27. In some embodiments, the methods other than those described herein include methods referred to as process 1C and/or Generation 1 (Gen 1). In some embodiments, the increased efficacy is measured by DCR, ORR, and/or other clinical responses. In some embodiments, the TILS produced by the methods provided herein, for example those exemplified in FIG. 27, exhibit a similar time to response and safety profile compared to TILs produced by methods other than those described herein, including for example, methods other than those exemplified in FIG. 27, for example the Gen 1 process.

In some embodiments, IFN-gamma (IFN-γ) is indicative of treatment efficacy and/or increased clinical efficacy. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood, serum, or TILs ex vivo of a subject treated with TILs prepared by the methods of the present invention, including those as described for example in FIG. 27. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 27. In some embodiments, IFN-γ secretion is increased one-fold as compared to an untreated patient and/or as compared to a patient treated with TILs prepared using other methods than those provide herein including for example, methods other than those embodied in FIG. 27. In some embodiments, IFN-γ secretion is increased two-fold as compared to an untreated patient and/or as compared to a patient treated with TILs prepared using other methods than those provide herein including for example, methods other than those embodied in FIG. 27. In some embodiments, IFN-γ secretion is increased three-fold as compared to an untreated patient and/or as compared to a patient treated with TILs prepared using other methods than those provide herein including for example, methods other than those embodied in FIG. 27. In some embodiments, IFN-γ secretion is increased four-fold as compared to an untreated patient and/or as compared to a patient treated with TILs prepared using other methods than those provide herein including for example, methods other than those embodied in FIG. 27. In some embodiments, IFN-γ secretion is increased five-fold as compared to an untreated patient and/or as compared to a patient treated with TILs prepared using other methods than those provide herein including for example, methods other than those embodied in FIG. 27. In some embodiments, IFN-γ is measured using a Quantikine ELISA kit. In some embodiments, IFN-γ is measured in TILs ex vivo of a subject treated with TILs prepared by the methods of the present invention, including those as described for example in FIG. 27. In some embodiments, IFN-γ is measured in blood of a subject treated with TILs prepared by the methods of the present invention, including those as described for example in FIG. 27. In some embodiments, IFN-γ is measured in TILs serum of a subject treated with TILs prepared by the methods of the present invention, including those as described for example in FIG. 27.

In some embodiments, higher average IP-10 is indicative of treatment efficacy and/or increased clinical efficacy. In some embodiments, higher average IP-10 in the blood of subjects treated with TILs is indicative of active TILs. IP-10 production can be measured by determining the levels of the IP-10 in the blood of a subject treated with TILs prepared by the methods of the present invention, including those as described for example in FIG. 27. In some embodiments, higher average IP-10 is indicative of treatment efficacy in a patient treated with the TILs produced by the methods of the present invention. In some embodiments, higher average IP-10 correlates to an increase of one-fold, two-fold, three-fold, four-fold, or five-fold or more as compared to an untreated patient and/or as compared to a patient treated with TILs prepared using other methods than those provide herein including for example, methods other than those embodied in FIG. 27. In some embodiments, higher average IP-10 correlates to an increase of one-fold as compared to an untreated patient and/or as compared to a patient treated with TILs prepared using other methods than those provide herein including for example, methods other than those embodied in FIG. 27. In some embodiments, higher average IP-10 correlates to an increase of two-fold as compared to an untreated patient and/or as compared to a patient treated with TILs prepared using other methods than those provide herein including for example, methods other than those embodied in FIG. 27. In some embodiments, higher average IP-10 correlates to an increase of three-fold as compared to an untreated patient and/or as compared to a patient treated with TILs prepared using other methods than those provide herein including for example, methods other than those embodied in FIG. 27. In some embodiments, higher average IP-10 correlates to an increase of four-fold as compared to an untreated patient and/or as compared to a patient treated with TILs prepared using other methods than those provide herein including for example, methods other than those embodied in FIG. 27. In some embodiments, higher average IP-10 correlates to an increase of five-fold as compared to an untreated patient and/or as compared to a patient treated with TILs prepared using other methods than those provide herein including for example, methods other than those embodied in FIG. 27. In some embodiments, IP-10 is measured in blood of a subject treated with TILs prepared by the methods of the present invention, including those as described for example in FIG. 27. In some embodiments, IP-10 is measured in TILs serum of a subject treated with TILs prepared by the methods of the present invention, including those as described for example in FIG. 27.

In some embodiments, higher average MCP-1 is indicative of treatment efficacy and/or increased clinical efficacy. In some embodiments, higher average MCP-1 in the blood of subjects treated with TILs is indicative of active TILs. MCP-1 production can be measured by determining the levels of the MCP-1 in the blood of a subject treated with TILs prepared by the methods of the present invention, including those as described for example in FIG. 27. In some embodiments, higher average MCP-1 is indicative of treatment efficacy in a patient treated with the TILs produced by the methods of the present invention. In some embodiments, higher average MCP-1 correlates to an increase of one-fold, two-fold, three-fold, four-fold, or five-fold or more as compared to an untreated patient and/or as compared to a patient treated with TILs prepared using other methods than those provide herein including for example, methods other than those embodied in FIG. 27. In some embodiments, higher average MCP-1 correlates to an increase of one-fold as compared to an untreated patient and/or as compared to a patient treated with TILs prepared using other methods than those provide herein including for example, methods other than those embodied in FIG. 27. In some embodiments, higher average MCP-1 correlates to an increase of two-fold as compared to an untreated patient and/or as compared to a patient treated with TILs prepared using other methods than those provide herein including for example, methods other than those embodied in FIG. 27. In some embodiments, higher average MCP-1 correlates to an increase of three-fold as compared to an untreated patient and/or as compared to a patient treated with TILs prepared using other methods than those provide herein including for example, methods other than those embodied in FIG. 27. In some embodiments, higher average MCP-1 correlates to an increase of four-fold as compared to an untreated patient and/or as compared to a patient treated with TILs prepared using other methods than those provide herein including for example, methods other than those embodied in FIG. 27. In some embodiments, higher average MCP-1 correlates to an increase of five-fold as compared to an untreated patient and/or as compared to a patient treated with TILs prepared using other methods than those provide herein including for example, methods other than those embodied in FIG. 27. In some embodiments, MCP-1 is measured in blood of a subject treated with TILs prepared by the methods of the present invention, including those as described for example in FIG. 27. In some embodiments, MCP-1 is measured in TILs serum of a subject treated with TILs prepared by the methods of the present invention, including those as described for example in FIG. 27.

In some embodiments, the TILs prepared by the methods of the present invention, including those as described for example in FIG. 27, exibit increased polyclonality as compared to TILs produced by other methods, including those not exemplified in FIG. 27, such as for example, methods referred to as process 1C methods. In some embodiments, significantly improved polyclonality and/or increased polyclonality is indicative of treatment efficacy and/or increased clinical efficacy. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 27. In some embodiments, polyclonality is increased one-fold as compared to an untreated patient and/or as compared to a patient treated with TILs prepared using other methods than those provide herein including for example, methods other than those embodied in FIG. 27. In some embodiments, polyclonality is increased two-fold as compared to an untreated patient and/or as compared to a patient treated with TILs prepared using other methods than those provide herein including for example, methods other than those embodied in FIG. 27. In some embodiments, polyclonality is increased ten-fold as compared to an untreated patient and/or as compared to a patient treated with TILs prepared using other methods than those provide herein including for example, methods other than those embodied in FIG. 27. In some embodiments, polyclonality is increased 100-fold as compared to an untreated patient and/or as compared to a patient treated with TILs prepared using other methods than those provide herein including for example, methods other than those embodied in FIG. 27. In some embodiments, polyclonality is increased 500-fold as compared to an untreated patient and/or as compared to a patient treated with TILs prepared using other methods than those provide herein including for example, methods other than those embodied in FIG. 27. In some embodiments, polyclonality is increased 1000-fold as compared to an untreated patient and/or as compared to a patient treated with TILs prepared using other methods than those provide herein including for example, methods other than those embodied in FIG. 27.

Measures of efficacy can include The disease control rate (DCR) measurements as well as overall response rate (ORR), as known in the art as well as described in the Examples provided herein, including Example 28.

1. Methods of Treating Cancers and Other Diseases

The compositions and methods described herein can be used in a method for treating diseases. In an embodiment, they are for use in treating hyperproliferative disorders. They may also be used in treating other disorders as described herein and in the following paragraphs.

In some embodiments, the hyperproliferative disorder is cancer. In some embodiments, the hyperproliferative disorder is a solid tumor cancer. In some embodiments, the solid tumor cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma. In some embodiments, the hyperproliferative disorder is a hematological malignancy. In some embodiments, the solid tumor cancer is selected from the group consisting of chronic lymphocytic leukemia, acute lymphoblastic leukemia, diffuse large B cell lymphoma, non-Hodgkin's lymphoma, Hodgkin's lymphoma, follicular lymphoma, and mantle cell lymphoma.

In an embodiment, the invention includes a method of treating a cancer with a population of TILs, wherein a patient is pre-treated with non-myeloablative chemotherapy prior to an infusion of TILs according to the present disclosure. In an embodiment, the non-myeloablative chemotherapy is cyclophosphamide 60 mg/kg/d for 2 days (days 27 and 26 prior to TIL infusion) and fludarabine 25 mg/m$^2$/d for 5 days (days 27 to 23 prior to TIL infusion). In an embodiment, after non-myeloablative chemotherapy and TIL infusion (at day 0) according to the present disclosure, the patient receives an intravenous infusion of IL-2 intravenously at 720,000 IU/kg every 8 hours to physiologic tolerance.

Efficacy of the compounds and combinations of compounds described herein in treating, preventing and/or managing the indicated diseases or disorders can be tested using various models known in the art, which provide guidance for treatment of human disease. For example, models for determining efficacy of treatments for ovarian cancer are described, e.g., in Mullany, et al., *Endocrinology* 2012, 153, 1585-92; and Fong, et al., *J. Ovarian Res.* 2009, 2, 12. Models for determining efficacy of treatments for pancreatic cancer are described in Herreros-Villanueva, et al., *World J Gastroenterol.* 2012, 18, 1286-1294. Models for determining efficacy of treatments for breast cancer are described, e.g., in Fantozzi, *Breast Cancer Res.* 2006, 8, 212. Models for determining efficacy of treatments for melanoma are described, e.g., in Damsky, et al., *Pigment Cell & Melanoma Res.* 2010, 23, 853-859. Models for determining efficacy of treatments for lung cancer are described, e.g., in Meuwissen, et al., *Genes & Development,* 2005, 19, 643-664. Models for determining efficacy of treatments for lung cancer are described, e.g., in Kim, *Clin. Exp. Otorhinolaryngol.* 2009, 2, 55-60; and Sano, *Head Neck Oncol.* 2009, 1, 32.

In some embodiments, IFN-gamma (IFN-γ) is indicative of treatment efficacy for hyperproliferative disorder treatment. In some embodiments, IFN-γ in the blood of subjects treated with TILs is indicative of active TILs. In some embodiments, a potency assay for IFN-γ production is employed. IFN-γ production is another measure of cytotoxic potential. IFN-γ production can be measured by determining the levels of the cytokine IFN-γ in the blood of a subject treated with TILs prepared by the methods of the present invention, including those as described for example in FIG. 27. In some embodiments, the TILs obtained by the present method provide for increased IFN-γ in the blood of subjects treated with the TILs of the present method as compared subjects treated with TILs prepared using methods referred to as process 1C, as exemplified in FIG. 83. In some embodiments, an increase in IFN-γ is indicative of treatment efficacy in a patient treated with the TILs produced by the methods of the present invention. In some embodiments, IFN-γ is increased one-fold, two-fold, three-fold, four-fold, or five-fold or more as compared to an untreated patient and/or as compared to a patient treated with TILs prepared using other methods than those provide herein including for example, methods other than those embodied in FIG. 27. In some embodiments, IFN-γ secretion is increased one-fold as compared to an untreated patient and/or as compared to a patient treated with TILs prepared using other methods than those provide herein including for example, methods other than those embodied in FIG. 27. In some embodiments, IFN-γ secretion is increased two-fold as compared to an untreated patient and/or as compared to a patient treated with TILs prepared using other methods than those provide herein including for example, methods other than those embodied in FIG. 27. In some embodiments, IFN-γ secretion is increased three-fold as compared to an untreated patient and/or as compared to a patient treated with TILs prepared using other methods than those provide herein including for example, methods other than those embodied in FIG. 27. In some embodiments, IFN-γ secretion is increased four-fold as compared to an untreated patient and/or as compared to a patient treated with TILs prepared using other methods than those provide herein including for example, methods other than those embodied in FIG. 27. In some embodiments, IFN-γ secretion is increased five-fold as compared to an untreated patient and/or as compared to a patient treated with TILs prepared using other methods than those provide herein including for example, methods other than those embodied in FIG. 27. In some embodiments, IFN-γ is measured using a Quantikine ELISA kit. In some embodiments, IFN-γ is measured using a Quantikine ELISA kit. In some embodiments, IFN-γ is measured in TILs ex vivo from a patient treated with the TILs produced by the methods of the present invention. In some embodiments, IFN-γ is measured in blood in a patient treated with the TILs produced by the methods of the present invention. In some embodiments, IFN-γ is measured in serum in a patient treated with the TILs produced by the methods of the present invention.

In some embodiments, higher average IP-10 is indicative of treatment efficacy and/or increased clinical efficacy for hyperproliferative disorder treatment. In some embodiments, higher average IP-10 in the blood of subjects treated with TILs is indicative of active TILs. In some embodiments, the TILs obtained by the present method provide for higher average IP-10 in the blood of subjects treated with the TILs of the present method as compared subjects treated with TILs prepared using methods referred to as process 1C, as exemplified in FIG. 83. IP-10 production can be measured by determining the levels of the IP-10 in the blood of a subject treated with TILs prepared by the methods of the present invention, including those as described for example in FIG. 27. In some embodiments, higher average IP-10 is indicative of treatment efficacy in a patient treated with the TILs produced by the methods of the present invention. In some embodiments, higher average IP-10 correlates to an increase of one-fold, two-fold, three-fold, four-fold, or five-fold or more as compared to an untreated patient and/or as compared to a patient treated with TILs prepared using other methods than those provide herein including for example, methods other than those embodied in FIG. 27. In some embodiments, higher average IP-10 correlates to an increase of one-fold as compared to an untreated patient and/or as compared to a patient treated with TILs prepared using other methods than those provide herein including for example, methods other than those embodied in FIG. 27. In some embodiments, higher average IP-10 correlates to an increase of two-fold as compared to an untreated patient and/or as compared to a patient treated with TILs prepared using other methods than those provide herein including for example, methods other than those embodied in FIG. 27. In some embodiments, higher average IP-10 correlates to an increase of three-fold as compared to an untreated patient and/or as compared to a patient treated with TILs prepared using other methods than those provide herein including for example, methods other than those embodied in FIG. 27. In some embodiments, higher average IP-10 correlates to an increase of four-fold as compared to an untreated patient and/or as compared to a patient treated with TILs prepared using other methods than those provide herein including for example, methods other than those embodied in FIG. 27. In some embodiments, higher average IP-10 correlates to an increase of five-fold as compared to an untreated patient and/or as compared to a patient treated with TILs prepared using other methods than those provide herein including for example, methods other than those embodied in FIG. 27.

In some embodiments, higher average MCP-1 is indicative of treatment efficacy and/or increased clinical efficacy for hyperproliferative disorder treatment. In some embodiments, higher average MCP-1 in the blood of subjects treated with TILs is indicative of active TILs. In some embodiments, the TILs obtained by the present method provide for higher average MCP-1 in the blood of subjects treated with the TILs of the present method as compared subjects treated with TILs prepared using methods referred to as process 1C, as exemplified in FIG. 83. MCP-1 production can be measured by determining the levels of the MCP-1 in the blood of a subject treated with TILs prepared by the methods of the present invention, including those as described for example in FIG. 27. In some embodiments, higher average MCP-1 is indicative of treatment efficacy in a patient treated with the TILs produced by the methods of the present invention. In some embodiments, higher average MCP-1 correlates to an increase of one-fold, two-fold, three-fold, four-fold, or five-fold or more as compared to an untreated patient and/or as compared to a patient treated with TILs prepared using other methods than those provide herein including for example, methods other than those embodied in FIG. 27. In some embodiments, higher average MCP-1 correlates to an increase of one-fold as compared to an untreated patient and/or as compared to a patient treated with TILs prepared using other methods than those provide herein including for example, methods other than those embodied in FIG. 27. In some embodiments, higher average MCP-1 correlates to an increase of two-fold as compared to an untreated patient and/or as compared to a patient treated with TILs prepared using other methods than those provide herein including for example, methods other than those embodied in FIG. 27. In some embodiments, higher average MCP-1 correlates to an increase of three-fold as compared to an untreated patient and/or as compared to a patient treated with TILs prepared using other methods than those provide herein including for example, methods other than those embodied in FIG. 27. In some embodiments, higher average MCP-1 correlates to an increase of four-fold as compared to an untreated patient and/or as compared to a patient treated with TILs prepared using other methods than those provide herein including for example, methods other than those embodied in FIG. 27. In some embodiments, higher average MCP-1 correlates to an increase of five-fold as compared to an untreated patient and/or as compared to a patient treated with TILs prepared using other methods than those provide herein including for example, methods other than those embodied in FIG. 27.

In some embodiments, the TILs prepared by the methods of the present invention, including those as described for example in FIG. 27, exhibit increased polyclonality as compared to TILs produced by other methods, including those not exemplified in FIG. 27, such as for example, methods referred to as process 1C methods. In some embodiments, significantly improved polyclonality and/or increased polyclonality is indicative of treatment efficacy and/or increased clinical efficacy for cancer treatment. In some embodiments, polyclonality refers to the T-cell repertoire diversity. In some embodiments, an increase in polyclonality can be indicative of treatment efficacy with regard to administration of the TILs produced by the methods of the present invention. In some embodiments, polyclonality is increased one-fold, two-fold, ten-fold, 100-fold, 500-fold, or 1000-fold as compared to TILs prepared using methods than those provide herein including for example, methods other than those embodied in FIG. 27. In some embodiments, polyclonality is increased one-fold as compared to an untreated patient and/or as compared to a patient treated with TILs prepared using other methods than those provide herein including for example, methods other than those embodied in FIG. 27. In some embodiments, polyclonality is increased two-fold as compared to an untreated patient and/or as compared to a patient treated with TILs prepared using other methods than those provide herein including for example, methods other than those embodied in FIG. 27. In some embodiments, polyclonality is increased ten-fold as compared to an untreated patient and/or as compared to a patient treated with TILs prepared using other methods than those provide herein including for example, methods other than those embodied in FIG. 27. In some embodiments, polyclonality is increased 100-fold as compared to an untreated patient and/or as compared to a patient treated with TILs prepared using other methods than those provide herein including for example, methods other than those embodied in FIG. 27. In some embodiments, polyclonality is increased 500-fold as compared to an untreated patient and/or as compared to a patient treated with TILs prepared using other methods than those provide herein including for example, methods other than those embodied in FIG. 27. In some embodiments, polyclonality is increased 1000-fold as compared to an untreated patient and/or as compared to a patient treated with TILs prepared using other methods than those provide herein including for example, methods other than those embodied in FIG. 27.

2. Methods of Co-Administration

In some embodiments, the TILs produced as described herein, including for example TILs derived from a method described in Steps A through F of FIG. 27, can be administered in combination with one or more immune checkpoint regulators, such as the antibodies described below. For example, antibodies that target PD-1 and which can be co-administered with the TILs of the present invention include, e.g., but are not limited to nivolumab (BMS-936558, Bristol-Myers Squibb; Opdivo®), pembrolizumab (lambrolizumab, MK03475 or MK-3475, Merck; Keytruda®), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)—BioXcell cat #BP0146. Other suitable antibodies suitable for use in co-administration methods with TILs produced according to Steps A through F as described herein are anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in co-administration methods with TILs produced according to Steps A through F as described herein. For example, antibodies that target PD-L1 and are in clinical trials, include BMS-936559 (Bristol-Myers Squibb) and MPDL3280A (Genentech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, are suitable for use in co-administration methods with TILs produced according to Steps A through F as described herein. In some embodiments, the subject administered the combination of TILs produced according to Steps A through F is co administered with a and anti-PD-1 antibody when the patient has a cancer type that is refractory to administration of the anti-PD-1 antibody alone. In some embodiments, the patient is administered TILs in combination with and anti-PD-1 when the patient has refractory melanoma. In some embodiments, the patient is administered TILs in combination with and anti-PD-1 when the patient has non-small-cell lung carcinoma (NSCLC).

3. Optional Lymphodepletion Preconditioning of Patients

In an embodiment, the invention includes a method of treating a cancer with a population of TILs, wherein a patient is pre-treated with non-myeloablative chemotherapy prior to an infusion of TILs according to the present disclosure. In an embodiment, the invention includes a population of TILs for use in the treatment of cancer in a patient which has been pre-treated with non-myeloablative chemotherapy. In an embodiment, the population of TILs is for administration by infusion. In an embodiment, the non-myeloablative chemotherapy is cyclophosphamide 60 mg/kg/d for 2 days (days 27 and 26 prior to TIL infusion) and fludarabine 25 mg/m²/d for 5 days (days 27 to 23 prior to TIL infusion). In an embodiment, after non-myeloablative chemotherapy and TIL infusion (at day 0) according to the present disclosure, the patient receives an intravenous infusion of IL-2 (aldesleukin, commercially available as PROLEUKIN) intravenously at 720,000 IU/kg every 8 hours to physiologic tolerance. In certain embodiments, the population of TILs is for use in treating cancer in combination with IL-2, wherein the IL-2 is administered after the population of TILs.

Experimental findings indicate that lymphodepletion prior to adoptive transfer of tumor-specific T lymphocytes plays a key role in enhancing treatment efficacy by eliminating regulatory T cells and competing elements of the immune system ('cytokine sinks'). Accordingly, some embodiments of the invention utilize a lymphodepletion step (sometimes also referred to as "immunosuppressive conditioning") on the patient prior to the introduction of the TILs of the invention.

In general, lymphodepletion is achieved using administration of fludarabine or cyclophosphamide (the active form being referred to as mafosfamide) and combinations thereof. Such methods are described in Gassner, et al., *Cancer Immunol. Immunother.* 2011, 60, 75-85, Muranski, et al., *Nat. Clin. Pract. Oncol.*, 2006, 3, 668-681, Dudley, et al., *J Clin. Oncol.* 2008, 26, 5233-5239, and Dudley, et al., *J Clin. Oncol.* 2005, 23, 2346-2357, all of which are incorporated by reference herein in their entireties.

In some embodiments, the fludarabine is administered at a concentration of 0.5 µg/mL-10 µg/mL fludarabine. In some embodiments, the fludarabine is administered at a concentration of 1 µg/mL fludarabine. In some embodiments, the fludarabine treatment is administered for 1 day, 2 days, 3 days, 4 days, 5 days, 6 days, or 7 days or more. In some embodiments, the fludarabine is administered at a dosage of 10 mg/kg/day, 15 mg/kg/day, 20 mg/kg/day, 25 mg/kg/day, 30 mg/kg/day, 35 mg/kg/day, 40 mg/kg/day, or 45 mg/kg/day. In some embodiments, the fludarabine treatment is administered for 2-7 days at 35 mg/kg/day. In some embodiments, the fludarabine treatment is administered for 4-5 days at 35 mg/kg/day. In some embodiments, the fludarabine treatment is administered for 4-5 days at 25 mg/kg/day.

In some embodiments, the mafosfamide, the active form of cyclophosphamide, is obtained at a concentration of 0.5 µg/mL-10 µg/mL by administration of cyclophosphamide. In some embodiments, mafosfamide, the active form of cyclophosphamide, is obtained at a concentration of 1 µg/mL by administration of cyclophosphamide. In some embodiments, the cyclophosphamide treatment is administered for 1 day, 2 days, 3 days, 4 days, 5 days, 6 days, or 7 days or more. In some embodiments, the cyclophosphamide is administered at a dosage of 100 mg/m²/day, 150 mg/m²/day, 175 mg/m²/day, 200 mg/m²/day, 225 mg/m²/day, 250 mg/m²/day, 275 mg/m²/day, or 300 mg/m²/day. In some embodiments, the cyclophosphamide is administered intravenously (i.e., i.v.) In some embodiments, the cyclophosphamide treatment is administered for 2-7 days at 35 mg/kg/day. In some embodiments, the cyclophosphamide treatment is administered for 4-5 days at 250 mg/m²/day i.v. In some embodiments, the cyclophosphamide treatment is administered for 4 days at 250 mg/m²/day i.v.

In some embodiments, lymphodepletion is performed by administering the fludarabine and the cyclophosphamide together to a patient. In some embodiments, fludarabine is administered at 25 mg/m²/day i.v. and cyclophosphamide is administered at 250 mg/m²/day i.v. over 4 days.

In an embodiment, the lymphodepletion is performed by administration of cyclophosphamide at a dose of 60 mg/m²/day for two days followed by administration of fludarabine at a dose of 25 mg/m²/day for five days.

4. IL-2 Regimens

In an embodiment, the IL-2 regimen comprises a high-dose IL-2 regimen, wherein the high-dose IL-2 regimen comprises aldesleukin, or a biosimilar or variant thereof, administered intravenously starting on the day after administering a therapeutically effective portion of the therapeutic population of TILs, wherein the aldesleukin or a biosimilar or variant thereof is administered at a dose of 0.037 mg/kg or 0.044 mg/kg IU/kg (patient body mass) using 15-minute bolus intravenous infusions every eight hours until tolerance, for a maximum of 14 doses. Following 9 days of rest, this schedule may be repeated for another 14 doses, for a maximum of 28 doses in total.

In an embodiment, the IL-2 regimen comprises a decrescendo IL-2 regimen. Decrescendo IL-2 regimens have been described in O'Day, et al., *J. Clin. Oncol.* 1999, 17, 2752-61 and Eton, et al., Cancer 2000, 88, 1703-9, the disclosures of which are incorporated herein by reference. In an embodiment, a decrescendo IL-2 regimen comprises $18 \times 10^6$ IU/m$^2$ administered intravenously over 6 hours, followed by $18 \times 10^6$ IU/m$^2$ administered intravenously over 12 hours, followed by $18 \times 10^6$ IU/m$^2$ administered intravenously over 24 hrs, followed by $4.5 \times 10^6$ IU/m$^2$ administered intravenously over 72 hours. This treatment cycle may be repeated every 28 days for a maximum of four cycles. In an embodiment, a decrescendo IL-2 regimen comprises 18,000,000 IU/m$^2$ on day 1, 9,000,000 IU/m$^2$ on day 2, and 4,500,000 IU/m$^2$ on days 3 and 4.

In an embodiment, the IL-2 regimen comprises administration of pegylated IL-2 every 1, 2, 4, 6, 7, 14 or 21 days at a dose of 0.10 mg/day to 50 mg/day.

5. Adoptive Cell Transfer

Adoptive cell transfer (ACT) is a very effective form of immunotherapy and involves the transfer of immune cells with antitumor activity into cancer patients. ACT is a treatment approach that involves the identification, in vitro, of lymphocytes with antitumor activity, the in vitro expansion of these cells to large numbers and their infusion into the cancer-bearing host. Lymphocytes used for adoptive transfer can be derived from the stroma of resected tumors (tumor infiltrating lymphocytes or TILs). TILs for ACT can be prepared as described herein. In some embodiments, the TILs are prepared, for example, according to a method as described in FIG. 27. They can also be derived or from blood if they are genetically engineered to express antitumor T-cell receptors (TCRs) or chimeric antigen receptors (CARs), enriched with mixed lymphocyte tumor cell cultures (MLTCs), or cloned using autologous antigen presenting cells and tumor derived peptides. ACT in which the lymphocytes originate from the cancer-bearing host to be infused is termed autologous ACT. U.S. Publication No. 2011/0052530 relates to a method for performing adoptive cell therapy to promote cancer regression, primarily for treatment of patients suffering from metastatic melanoma, which is incorporated by reference in its entirety for these methods. In some embodiments, TILs can be administered as described herein. In some embodiments, TILs can be administered in a single dose. Such administration may be by injection, e.g., intravenous injection. In some embodiments, TILs and/or cytotoxic lymphocytes may be administered in multiple doses. Dosing may be once, twice, three times, four times, five times, six times, or more than six times per year. Dosing may be once a month, once every two weeks, once a week, or once every other day. Administration of TILs and/or cytotoxic lymphocytes may continue as long as necessary.

6. Exemplary Treatment Embodiments

In some embodiments, the present disclosure provides a method of treating a cancer with a population of tumor infiltrating lymphocytes (TILs) comprising the steps of (a) obtaining a first population of TILs from a tumor resected from a patient; (b) performing an initial expansion of the first population of TILs in a first cell culture medium to obtain a second population of TILs, wherein the second population of TILs is at least 5-fold greater in number than the first population of TILs, and wherein the first cell culture medium comprises IL-2; (c) performing a rapid expansion of the second population of TILs using a population of myeloid artificial antigen presenting cells (myeloid aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; (d) administering a therapeutically effective portion of the third population of TILs to a patient with the cancer. In some embodiments, the present disclosure a population of tumor infiltrating lymphocytes (TILs) for use in treating cancer, wherein the population of TILs are obtainable by a method comprising the steps of (b) performing an initial expansion of a first population of TILs obtained from a tumor resected from a patient in a first cell culture medium to obtain a second population of TILs, wherein the second population of TILs is at least 5-fold greater in number than the first population of TILs, and wherein the first cell culture medium comprises IL-2; (c) performing a rapid expansion of the second population of TILs using a population of myeloid artificial antigen presenting cells (myeloid aAPCs) in a second cell culture medium to obtain a third population of TILs, wherein the third population of TILs is at least 50-fold greater in number than the second population of TILs after 7 days from the start of the rapid expansion; and wherein the second cell culture medium comprises IL-2 and OKT-3; (d) administering a therapeutically effective portion of the third population of TILs to a patient with the cancer. In some embodiments, the method comprises a first step (a) of obtaining the first population of TILs from a tumor resected from a patient. In some embodiments, the IL-2 is present at an initial concentration of about 3000 IU/mL and OKT-3 antibody is present at an initial concentration of about 30 ng/mL in the second cell culture medium. In some embodiments, first expansion is performed over a period not greater than 14 days. In some embodiments, the first expansion is performed using a gas permeable container. In some embodiments, the second expansion is performed using a gas permeable container. In some embodiments, the ratio of the second population of TILs to the population of aAPCs in the rapid expansion is between 1 to 80 and 1 to 400. In some embodiments, the ratio of the second population of TILs to the population of aAPCs in the rapid expansion is about 1 to 300. In some embodiments, the cancer for treatment is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HN-SCC)), renal cancer, and renal cell carcinoma. In some embodiments, the cancer for treatment is selected from the group consisting of melanoma, ovarian cancer, and cervical cancer. In some embodiments, the cancer for treatment is melanoma. In some embodiments, the cancer for treatment is ovarian cancer. In some embodiments, the cancer for treatment is cervical cancer. In some embodiments, the method of treating cancer further comprises the step of treating the patient with a non-myeloablative lymphodepletion regimen prior to administering the third population of TILs to the patient. In some embodiments, the non-myeloablative lymphodepletion regimen comprises the steps of administration of cyclophosphamide at a dose of 60 mg/m2/day for two days followed by administration of fludarabine at a dose of 25 mg/m2/day for five days. In some embodiments, the high dose IL-2 regimen comprises 600,000 or 720,000 IU/kg of aldesleukin, or a biosimilar or variant thereof, administered as a 15-minute bolus intravenous infusion every eight hours until tolerance.

V. Exemplary Embodiments

In some embodiments, the present invention provides a method for treating a subject with cancer, the method comprising administering expanded tumor infiltrating lymphocytes (TILs) comprising:
(a) obtaining a first population of TILs from a tumor resected from a subject by processing a tumor sample obtained from the patient into multiple tumor fragments;
(b) adding the tumor fragments into a closed system;
(c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 11 days to obtain the second population of TILs, wherein the second population of TILs is at least 50-fold greater in number than the first population of TILs, and wherein the transition from step (b) to step (c) occurs without opening the system;
(d) performing a second expansion by supplementing the cell culture medium of the second population of TILs with additional IL-2, OKT-3, and antigen presenting cells (APCs), to produce a third population of TILs, wherein the second expansion is performed for about 11 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
(e) harvesting the therapeutic population of TILs obtained from step (d), wherein the transition from step (d) to step (e) occurs without opening the system; and
(f) transferring the harvested TIL population from step (e) to an infusion bag, wherein the transfer from step (e) to (f) occurs without opening the system;
(g) cryopreserving the infusion bag comprising the harvested TIL population from step (f) using a cryopreservation process; and
(h) administering a therapeutically effective dosage of the third population of TILs from the infusion bag in step (g) to the patient.

In some embodiment, the cryopreservation process comprises cryopreservation in a media comprising DMSO. In some embodiments, the cryopreservation media comprises 7% to 10% DMSO. In some embodiments, the cryopreservation medium in CS10.

In some embodiments, the therapeutic population of TILs harvested in step (e) comprises sufficient TILs for administering a therapeutically effective dosage of the TILs in step (h).

In some embodiments, the number of TILs sufficient for administering a therapeutically effective dosage in step (h) is from about $2.3 \times 10^{10}$ to about $13.7 \times 10^{10}$.

In some embodiments, the antigen presenting cells (APCs) are PBMCs.

In some embodiments, the PBMCs are added to the cell culture on any of days 9 through 11 in step (d).

In some embodiments, prior to administering a therapeutically effective dosage of TIL cells in step (h), a non-myeloablative lymphodepletion regimen has been administered to the patient.

In some embodiments, the non-myeloablative lymphodepletion regimen comprises the steps of administration of cyclophosphamide at a dose of 60 mg/m²/day for two days followed by administration of fludarabine at a dose of 25 mg/m²/day for five days.

In some embodiments, the method further comprises the step of treating the patient with a high-dose IL-2 regimen starting on the day after administration of the TIL cells to the patient in step (h).

In some embodiments, the high-dose IL-2 regimen comprises 600,000 or 720,000 IU/kg administered as a 15-minute bolus intravenous infusion every eight hours until tolerance.

In some embodiments, the third population of TILs in step (d) provides for increased efficacy, increased interferon-gamma (IFN-γ) production, increased polyclonality, increased average IP-10, and/or increased average MCP-1 when adminstered to a subject. In some embodiments, the increase in IFN-γ, increased average IP-10, and/or increased average MCP-1 is measured in the blood of the subject treated with the TILs.

In some embodiments, the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma. In some embodiments, the cancer is selected from the group consisting of melanoma, HNSCC, cervical cancers, and NSCLC. In some embodiments, the cancer is melanoma. In some embodiments, the cancer is HNSCC. In some embodiments, the cancer is a cervical cancer. In some embodiments, the cancer is NSCLC.

In an embodiment, the invention provides a method for expanding tumor infiltrating lymphocytes (TILs).

The present invention provides a method for expanding tumor infiltrating lymphocytes (TILs) comprising: (a) obtaining a tumor sample from a patient, wherein said tumor sample comprises a first population of TILs; (b) processing said tumor sample into multiple tumor fragments; (c) adding said tumor fragments into a closed container; (d) performing an initial expansion of said first population of TILs in a first cell culture medium to obtain a second population of TILs, wherein said first cell culture medium comprises IL-2, wherein said initial expansion is performed in said closed container providing at least 100 cm² of gas-permeable surface area, wherein said initial expansion is performed in a first period of about 7-14 days to obtain a second population of TILs, wherein said second population of TILs is at least 50-fold greater in number than said first population of TILs, and wherein the transition from step (c) to step (d) occurs without opening the system; (e) expanding said second population of TILs in a second cell culture medium, wherein said second cell culture medium comprises IL-2, OKT-3, and peripheral blood mononuclear cells (PBMCs, also known as mononuclear cells (MNCs)), wherein said expansion is performed within a second period of about 7-14 days to obtain a third population of TILs, wherein said third population of TILs exhibits an increased subpopulation of effector T cells and/or central memory T cells relative to the second population of TILs, wherein said expansion is performed in a closed container providing at least 500 cm² of gas-permeable surface area, and wherein the transition from step (d) to step (e) occurs without opening the system; (f) harvesting said third population of TILs obtained from step (e), wherein the transition from step (e) to step (f) occurs without opening the system; and (g) transferring said harvested TIL population from step (f) to an infusion bag, wherein said transfer from step (f) to (g) occurs without opening the system. In some embodiments, the method is an in vitro or an ex vivo method.

In some embodiments, the method further comprises harvesting in step (f) via a cell processing system, such as the LOVO system manufactured by Fresenius Kabi. The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some cases, the cell processing system can perform cell separation, washing, fluid-exchange, concentration, and/or other cell processing steps in a closed, sterile system.

In some embodiments, the closed container is selected from the group consisting of a G-container and a Xuri cellbag.

In some embodiments, the infusion bag in step (g) is a HypoThermosol-containing infusion bag.

In some embodiments, the first period in step (d) and said second period in step (e) are each individually performed within a period of 10 days, 11 days, or 12 days.

In some embodiments, the first period in step (d) and said second period in step (e) are each individually performed within a period of 11 days.

In some embodiments, steps (a) through (g) are performed within a period of about 25 days to about 30 days.

In some embodiments, steps (a) through (g) are performed within a period of about 20 days to about 25 days.

In some embodiments, steps (a) through (g) are performed within a period of about 20 days to about 22 days.

In some embodiments, steps (a) through (g) are performed in 22 days or less.

In some embodiments, steps (c) through (f) are performed in a single container, wherein performing steps (c) through (f) in a single container results in an increase in TIL yield per resected tumor as compared to performing steps (c) through (f) in more than one container.

In some embodiments, the PBMCs are added to the TILs during the second period in step (e) without opening the system.

In some embodiments, the effector T cells and/or central memory T cells obtained from said third population of TILs exhibit one or more characteristics selected from the group consisting of expressing CD27+, expressing CD28+, longer telomeres, increased CD57 expression, and decreased CD56 expression relative to effector T cells and/or central memory T cells obtained from said second population of cells.

In some embodiments, the effector T cells and/or central memory T cells obtained from said third population of TILs exhibit increased CD57 expression and decreased CD56 expression relative to effector T cells and/or central memory T cells obtained from said second population of cells.

In some embodiments, the risk of microbial contamination is reduced as compared to an open system.

In some embodiments, the TILs from step (g) are infused into a patient.

The present invention also provides a method of treating cancer in a patient with a population of tumor infiltrating lymphocytes (TILs) comprising the steps of: (a) obtaining a tumor sample from a patient, wherein said tumor sample comprises a first population of TILs;
(b) processing said tumor sample into multiple tumor fragments; (c) adding said tumor fragments into a closed container; (d) performing an initial expansion of said first population of TILs in a first cell culture medium to obtain a second population of TILs, wherein said first cell culture medium comprises IL-2, wherein said initial expansion is performed in said closed container providing at least 100 cm$^2$ of gas-permeable surface area, wherein said initial expansion is performed within a first period of about 7-14 days to obtain a second population of TILs, wherein said second population of TILs is at least 50-fold greater in number than said first population of TILs, and wherein the transition from step (c) to step (d) occurs without opening the system; (e) expanding said second population of TILs in a second cell culture medium, wherein said second cell culture medium comprises IL-2, OKT-3, and peripheral blood mononuclear cells (PBMCs), wherein said expansion is performed within a second period of about 7-14 days to obtain a third population of TILs, wherein said third population of TILs exhibits an increased subpopulation of effector T cells and/or central memory T cells relative to the second population of TILs, wherein said expansion is performed in a closed container providing at least 500 cm$^2$ of gas-permeable surface area, and wherein the transition from step (d) to step (e) occurs without opening the system; (f) harvesting said third population of TILs obtained from step (e), wherein the transition from step (e) to step (f) occurs without opening the system; (g) transferring said harvested TIL population from step (f) to an infusion bag, wherein said transfer from step (f) to (g) occurs without opening the system; and (h) administering a therapeutically effective amount of TIL cells from said infusion bag in step (g) to said patient.

In some embodiments, the present invention also comprises a population of tumor infiltrating lymphocytes (TILs) for use in treating cancer, wherein the population of TILs is obtainable from a method comprising the steps of: (b) processing a tumor sample obtained from a patient wherein said tumour sample comprises a first population of TILs into multiple tumor fragments; (c) adding said tumor fragments into a closed container; (d) performing an initial expansion of said first population of TILs in a first cell culture medium to obtain a second population of TILs, wherein said first cell culture medium comprises IL-2, wherein said initial expansion is performed in said closed container providing at least 100 cm$^2$ of gas-permeable surface area, wherein said initial expansion is performed within a first period of about 7-14 days to obtain a second population of TILs, wherein said second population of TILs is at least 50-fold greater in number than said first population of TILs, and wherein the transition from step (c) to step (d) occurs without opening the system; (e) expanding said second population of TILs in a second cell culture medium, wherein said second cell culture medium comprises IL-2, OKT-3, and peripheral blood mononuclear cells (PBMCs), wherein said expansion is performed within a second period of about 7-14 days to obtain a third population of TILs, wherein said third population of TILs exhibits an increased subpopulation of effector T cells and/or central memory T cells relative to the second population of TILs, wherein said expansion is performed in a closed container providing at least 500 cm$^2$ of gas-permeable surface area, and wherein the transition from step (d) to step (e) occurs without opening the system; (f) harvesting said third population of TILs obtained from step (e), wherein the transition from step (e) to step (f) occurs without opening the system; (g) transferring said harvested TIL population from step (f) to an infusion bag, wherein said transfer from step (f) to (g) occurs without opening the system. In some embodiments, the method comprises a first step (a) obtaining the tumor sample from a patient, wherein said tumor sample comprises the first population of TILs. In some embodiments, the population of TILs is for administration from said infusion bag in step (g) in a therapeutically effective amount.

In some embodiments, prior to administering a therapeutically effective amount of TIL cells in step (h), a non-myeloablative lymphodepletion regimen has been administered to said patient. In some embodiments, the populations of TILs is for administration to a patient who has undergone a non-myeloablative lymphodepltion regimen.

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In some embodiments, the method further comprises the step of treating said patient with a high-dose IL-2 regimen starting on the day after administration of said TIL cells to said patient in step (h). In some embodiments, the populations of TILs is for administration prior to a high-dose IL-2 regimen. In some embodiments, the population of TILs is for administration one day before the start of the high-dose IL-2 regimen.

In some embodiments, the high-dose IL-2 regimen comprises 600,000 or 720,000 IU/kg administered as a 15-minute bolus intravenous infusion every eight hours until tolerance.

In some embodiments, the effector T cells and/or central memory T cells obtained from said third population of TILs exhibit one or more characteristics selected from the group consisting of expressing CD27+, expressing CD28+, longer telomeres, increased CD57 expression, and decreased CD56 expression relative to effector T cells and/or central memory T cells obtained from said second population of cells.

In some embodiments, the effector T cells and/or central memory T cells obtained from said third population of TILs exhibit increased CD57 expression and decreased CD56 expression relative to effector T cells and/or central memory T cells obtained from said second population of cells.

The present invention also provides a method for expanding tumor infiltrating lymphocytes (TILs) comprising the steps of (a) adding processed tumor fragments into a closed system; (b) performing a first expansion of said first population of TILs in a first cell culture medium to obtain a second population of TILs, wherein said first cell culture medium comprises IL-2, wherein said first expansion is performed in a closed container providing a first gas-permeable surface area, wherein said first expansion is performed within a first period of about 3-14 days to obtain a second population of TILs, wherein said second population of TILs is at least 50-fold greater in number than said first population of TILs, and wherein the transition from step (a) to step (b) occurs without opening the system; (c) expanding said second population of TILs in a second cell culture medium, wherein said second cell culture medium comprises IL-2, OKT-3, and antigen-presenting cells, wherein said expansion is performed within a second period of about 7-14 days to obtain a third population of TILs, wherein said third population of TILs exhibits an increased subpopulation of effector T cells and/or central memory T cells relative to the second population of TILs, wherein said expansion is performed in a closed container providing a second gas-permeable surface area, and wherein the transition from step (b) to step (c) occurs without opening the system; (d) harvesting said third population of TILs obtained from step (c), wherein the transition from step (c) to step (d) occurs without opening the system; and (e) transferring said harvested TIL population from step (d) to an infusion bag, wherein said transfer from step (d) to (e) occurs without opening the system.

In some embodiments, the method further comprises the step of cryopreserving the infusion bag comprising the harvested TIL population using a cryopreservation process. In some embodiments, the cryopreservation process is performed using a 1:1 ratio of harvested TIL population to CS10 media.

In some embodiments, the antigen-presenting cells are peripheral blood mononuclear cells (PBMCs). In some embodiments, the antigen-presenting cells are artificial antigen-presenting cells.

In some embodiments, the harvesting in step (d) is performed using a LOVO cell processing system.

In some embodiments, the multiple fragments comprise about 50 fragments, wherein each fragment has a volume of about 27 mm$^3$. In some embodiments, the multiple fragments comprise about 30 to about 60 fragments with a total volume of about 1300 mm$^3$ to about 1500 mm$^3$. In some embodiments, the multiple fragments comprise about 50 fragments with a total volume of about 1350 mm$^3$. In some embodiments, the multiple fragments comprise about 50 fragments with a total mass of about 1 gram to about 1.5 grams.

In some embodiments, the second cell culture medium is provided in a container selected from the group consisting of a G-container and a Xuri cellbag.

In some embodiments, the infusion bag in step (e) is a HypoThermosol-containing infusion bag.

In some embodiments, the first period in step (b) and said second period in step (c) are each individually performed within a period of 10 days, 11 days, or 12 days. In some embodiments, the first period in step (b) and said second period in step (c) are each individually performed within a period of 11 days.

In some embodiments, the steps (a) through (e) are performed within a period of about 25 days to about 30 days. In some embodiments, the steps (a) through (e) are performed within a period of about 20 days to about 25 days. In some embodiments, the steps (a) through (e) are performed within a period of about 20 days to about 22 days. In some embodiments, the steps (a) through (e) are performed in 22 days or less. In some embodiments, the steps (a) through (e) and cryopreservation are performed in 22 days or less.

In some embodiments, the steps (b) through (e) are performed in a single closed system, wherein performing steps (b) through (e) in a single container results in an increase in TIL yield per resected tumor as compared to performing steps (b) through (e) in more than one container.

In some embodiments, the antigen-presenting cells are added to the TILs during the second period in step (c) without opening the system.

In some embodiments, the effector T cells and/or central memory T cells obtained from said third population of TILs exhibit one or more characteristics selected from the group consisting of expressing CD27+, expressing CD28+, longer telomeres, increased CD57 expression, and decreased CD56 expression relative to effector T cells and/or central memory T cells obtained from said second population of cells.

In some embodiments, the effector T cells and/or central memory T cells obtained from said third population of TILs exhibit increased CD57 expression and decreased CD56 expression relative to effector T cells and/or central memory T cells obtained from said second population of cells.

In some embodiments, the risk of microbial contamination is reduced as compared to an open system.

In some embodiments, the TILs from step (e) are infused into a patient.

In some embodiments, the closed container comprises a single bioreactor. In some embodiments, the closed container comprises a G-REX-10. In some embodiments, the closed container comprises a G-REX-100. In some embodiments, the closed container comprises a G-Rex 500. In some embodiments, the closed container comprises a Xuri or Wave bioreactor gas permeable bag.

In some embodiments, the present disclosure provides a method for expanding tumor infiltrating lymphocytes (TILs) into a therapeutic population of TILs comprising:
- (b) adding tumor fragments into a closed system wherein the tumour fragments comprise a first population of TILs;
- (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
- (d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased sub-population of effector T cells and/or central memory T cells relative to the second population of TILs, wherein the second expansion is performed in a closed container providing a second gas-permeable surface area, and wherein the transition from step (c) to step (d) occurs without opening the system;
- (e) harvesting the therapeutic population of TILs obtained from step (d), wherein the transition from step (d) to step (e) occurs without opening the system; and
- (f) transferring the harvested TIL population from step (e) to an infusion bag, wherein the transfer from step (e) to (f) occurs without opening the system.

In some embodiments, the method also comprises as a first step:
- (a) obtaining a first population of TILs from a tumor resected from a patient by processing a tumor sample obtained from the patient into multiple tumor fragments.

In an embodiment, the method is an in vitro or an ex vivo method.

In some embodiments, the present disclosure provides a method for expanding tumor infiltrating lymphocytes (TILs) into a therapeutic population of TILs comprising:
- (a) obtaining a first population of TILs from a tumor resected from a patient by processing a tumor sample obtained from the patient into multiple tumor fragments;
- (b) adding the tumor fragments into a closed system;
- (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
- (d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased sub-population of effector T cells and/or central memory T cells relative to the second population of TILs, wherein the second expansion is performed in a closed container providing a second gas-permeable surface area, and wherein the transition from step (c) to step (d) occurs without opening the system;
- (e) harvesting the therapeutic population of TILs obtained from step (d), wherein the transition from step (d) to step (e) occurs without opening the system; and
- (f) transferring the harvested TIL population from step (e) to an infusion bag, wherein the transfer from step (e) to (f) occurs without opening the system.

In an embodiment, the method is an in vitro or an ex vivo method.

In some embodiments, the method further comprises the step of cryopreserving the infusion bag comprising the harvested TIL population in step (f) using a cryopreservation process.

In some embodiments, the cryopreservation process is performed using a 1:1 ratio of harvested TIL population to cryopreservation media. In some embodiments, the cryopreservation media comprises dimethylsulfoxide. In some embodiments, the cryopreservation media is selected from the group consisting of Cryostor CS10, HypoThermasol, or a combination thereof.

In some embodiments, the antigen-presenting cells are peripheral blood mononuclear cells (PBMCs).

In some embodiments, the PBMCs are irradiated and allogeneic.

In some embodiments, the PBMCs are added to the cell culture on any of days 9 through 14 in step (d).

In some embodiments, the antigen-presenting cells are artificial antigen-presenting cells.

In some embodiments, the harvesting in step (e) is performing using a LOVO cell processing system.

In some embodiments, the tumor fragments are multiple fragments and comprise about 4 to about 50 fragments, wherein each fragment has a volume of about 27 $mm^3$. In some embodiments, the multiple fragments comprise about 30 to about 60 fragments with a total volume of about 1300 $mm^3$ to about 1500 $mm^3$. In some embodiments, the multiple fragments comprise about 50 fragments with a total volume of about 1350 $mm^3$. In some embodiments, the multiple fragments comprise about 50 fragments with a total mass of about 1 gram to about 1.5 grams.

In some embodiments, the cell culture medium is provided in a container selected from the group consisting of a G-container and a Xuri cellbag.

In some embodiments, the infusion bag in step (f) is a HypoThermosol-containing infusion bag.

In some embodiments, the first period in step (c) and the second period in step (e) are each individually performed within a period of 10 days, 11 days, or 12 days. In some embodiments, the first period in step (c) and the second period in step (e) are each individually performed within a period of 11 days. In some embodiments, steps (a) through (f) are performed within a period of about 25 days to about 30 days. In some embodiments, steps (a) through (f) are performed within a period of about 20 days to about 25 days. In some embodiments, steps (a) through (f) are performed within a period of about 20 days to about 22 days. In some embodiments, steps (a) through (f) are performed in 22 days or less. In some embodiments, steps (a) through (f) and cryopreservation are performed in 22 days or less.

In some embodiments, the therapeutic population of TILs harvested in step (e) comprises sufficient TILs for a therapeutically effective dosage of the TILs. In some embodiments, the number of TILs sufficient for a therapeutically effective dosage is from about $2.3 \times 10^{10}$ to about $13.7 \times 10^{10}$.

In some embodiments, steps (b) through (e) are performed in a single container, wherein performing steps (b) through (e) in a single container results in an increase in TIL yield per resected tumor as compared to performing steps (b) through (e) in more than one container.

In some embodiments, the antigen-presenting cells are added to the TILs during the second period in step (d) without opening the system.

In some embodiments, the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells obtained from the third population of TILs exhibit increased CD57 expression and decreased CD56 expression relative to effector T cells and/or central memory T cells obtained from the second population of cells.

In some embodiments, the risk of microbial contamination is reduced as compared to an open system.

In some embodiments, the TILs from step (f) are infused into a patient.

In some embodiments, the multiple fragments comprise about 4 fragments. In some embodiments, the 4 fragments are placed into a G-REX-100. In some embodiments, the 4 fragments are about 0.5 cm in diameter. In some embodiments, the 4 fragments are placed into a G-REX-100. In some embodiments, the 4 fragments are about 0.1 cm, 0.2 cm, 0.3 cm, 0.4 cm, 0.5 cm, 0.6 cm, 0.7 cm, 0.8 cm, 0.9 cm, or 1 cm in diameter. In some embodiments, the 4 fragments are about 0.1 cm, 0.2 cm, 0.3 cm, 0.4 cm, 0.5 cm, 0.6 cm, 0.7 cm, 0.8 cm, 0.9 cm, or 1 cm in diameter and are placed into a G-REX-100. In some embodiments, the 4 fragments are about 0.1 cm, 0.2 cm, 0.3 cm, 0.4 cm, 0.5 cm, 0.6 cm, 0.7 cm, 0.8 cm, 0.9 cm, or 1 cm in diameter are placed into a container with an equivalent volume to a G-REX-100. In some embodiments, the 4 fragments are about 0.5 cm in diameter and are placed into a G-REX -100. In some embodiments, the 4 fragments are about 0.5 cm in diameter and are placed into a container with an equivalent volume to a G-REX-100.

Further details of steps (a), (b), (c), (d), (e) and (f) are provided herein below, including for example but not limited to the embodiments described under the headings "STEP A: Obtain Patient Tumor Sample", "STEP B: First Expansion", "STEP C: First Expansion to Second Expansion Transition", "STEP D: Second Expansion", "STEP E: Harvest TILS and "STEP F: Final Formulation/Transfer to Infusion Bag".

In some embodiments, the present disclosure provides methods for treating a subject with cancer, the method comprising administering expanded tumor infiltrating lymphocytes (TILs) comprising:
  (a) obtaining a first population of TILs from a tumor resected from a subject by processing a tumor sample obtained from the patient into multiple tumor fragments;
  (b) adding the tumor fragments into a closed system;
  (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
  (d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T cells and/or central memory T cells relative to the second population of TILs, wherein the second expansion is performed in a closed container providing a second gas-permeable surface area, and wherein the transition from step (c) to step (d) occurs without opening the system;
  (e) harvesting the therapeutic population of TILs obtained from step (d), wherein the transition from step (d) to step (e) occurs without opening the system; and
  (f) transferring the harvested TIL population from step (e) to an infusion bag, wherein the transfer from step (e) to (f) occurs without opening the system;
  (g) optionally cryopreserving the infusion bag comprising the harvested TIL population from step (f) using a cryopreservation process; and
  (h) administering a therapeutically effective dosage of the third population of TILs from the infusion bag in step (g) to the patient.

In some embodiments, the invention provides a therapeutic population of tumor infiltrating lymphocytes (TILs) for use in treating cancer, wherein the population is obtainable from a method comprising the steps of:
  (b) adding tumor fragments into a closed system wherein the tumour fragments comprise a first population of TILs;
  (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T cells and/or central memory T cells relative to the second population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system; and (g) optionally cryopreserving the infusion bag comprising the harvested TIL population from step (f) using a cryopreservation process.

In some embodiments, the population is obtainable by a method also comprising as a first step:

(a) obtaining a first population of TILs from a tumor resected from a patient by processing a tumor sample obtained from the patient into multiple tumor fragments.

In an embodiment, the method is an in vitro or an ex vivo method.

In some embodiments, any of steps (a) to (f) comprise one or more features disclosed herein, e.g. one or more features disclosed under the headings "STEP A: Obtain Patient Tumor Sample", "STEP B: First Expansion", "STEP C: First Expansion to Second Expansion Transition", "STEP D: Second Expansion", "STEP E: Harvest TILs and "STEP F: Final Formulation/Transfer to Infusion Bag".

In some embodiments, step (g) comprises one or more features disclosed herein, e.g. one or more features disclosed under the heading "STEP H: Optional Cryopreservation of TILs". In some embodiments, step (h) comprise one or more features disclosed herein, e.g. one or more features disclosed under the heading "STEP F:1 Pharmaceutical Compositions, Dosages and Dosing Regimens".

In some embodiments, the therapeutic population of TILs harvested in step (e) comprises sufficient TILs for administering a therapeutically effective dosage of the TILs in step (h).

In some embodiments, the number of TILs sufficient for administering a therapeutically effective dosage in step (h) is from about $2.3 \times 10^{10}$ to about $13.7 \times 10^{10}$.

In some embodiments, the antigen presenting cells (APCs) are PBMCs.

In some embodiments, the PBMCs are added to the cell culture on any of days 9 through 14 in step (d).

In some embodiments, prior to administering a therapeutically effective dosage of TIL cells in step (h), a non-myeloablative lymphodepletion regimen has been administered to the patient.

In some embodiments, there is provided a therapeutic population of tumor infiltrating lymphocytes (TILs) for use in treating cancer and in combination with a non-myeloablative lymphodepletion regimen. In some embodiments, the non-myeloablative lymphodepletion regimen is administered prior to administering the therapeutic population of tumor infiltrating lymphocytes (TILs).

In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In some embodiments, the step of treating the patient with a high-dose IL-2 regimen starting on the day after administration of the TIL cells to the patient in step (h).

In some embodiments, there is provided a therapeutic population of tumor infiltrating lymphocytes (TILs) for use in treating cancer and in combination with high-dose IL-2 regimen. In some embodiments, the high-dose IL-2 regimen starts on the day after administration of the therapeutic population of TIL cells.

In some embodiments, the high-dose IL-2 regimen comprises 600,000 or 720,000 IU/kg administered as a 15-minute bolus intravenous infusion every eight hours until tolerance.

In some embodiments, the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells in the therapeutic population of TILs exhibit increased CD57 expression and decreased CD56 expression relative to effector T cells and/or central memory T cells obtained from the second population of cells.

The present disclosure also provides methods for expanding tumor infiltrating lymphocytes (TILs) into a therapeutic population of TILs comprising:

(a) adding processed tumor fragments from a tumor resected from a patient into a closed system to obtain a first population of TILs;

(b) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (a) to step (b) occurs without opening the system;

(c) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T cells and/or central memory T cells relative to the second population of TILs, wherein the second expansion is performed in a closed container providing a second gas-permeable surface area, and wherein the transition from step (b) to step (c) occurs without opening the system;

(d) harvesting the therapeutic population of TILs obtained from step (c), wherein the transition from step (c) to step (d) occurs without opening the system; and (e) transferring the harvested TIL population from step (d) to an infusion bag, wherein the transfer from step (d) to (e) occurs without opening the system.

In some embodiments, the therapeutic population of TILs harvested in step (d) comprises sufficient TILs for a therapeutically effective dosage of the TILs.

In some embodiments, the number of TILs sufficient for a therapeutically effective dosage is from about $2.3 \times 10^{10}$ to about $13.7 \times 10^{10}$.

In some embodiments, the method further comprises the step of cryopreserving the infusion bag comprising the harvested TIL population using a cryopreservation process.

In some embodiments, the cryopreservation process is performed using a 1:1 ratio of harvested TIL population to CS10 media.

In some embodiments, the present disclosure provides methods for treating a subject with cancer, the method comprising administering expanded tumor infiltrating lymphocytes (TILs) comprising:
- (a) obtaining a first population of TILs from a tumor resected from a subject by processing a tumor sample obtained from the patient into multiple tumor fragments;
- (b) adding the tumor fragments into a closed system;
- (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
- (d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T cells and/or central memory T cells relative to the second population of TILs, wherein the second expansion is performed in a closed container providing a second gas-permeable surface area, and wherein the transition from step (c) to step (d) occurs without opening the system;
- (e) harvesting the therapeutic population of TILs obtained from step (d), wherein the transition from step (d) to step (e) occurs without opening the system; and
- (f) transferring the harvested TIL population from step (e) to an infusion bag, wherein the transfer from step (e) to (f) occurs without opening the system;
- (g) optionally cryopreserving the infusion bag comprising the harvested TIL population from step (f) using a cryopreservation process; and
- (h) administering a therapeutically effective dosage of the third population of TILs from the infusion bag in step (g) to the patient.

wherein no selection of TIL population is performed during any of steps (a) to (h). In an embodiment, no selection of the second population of TILs (the pre-REP population) based on phenotype is performed prior to performing the second expansion of step (d). In an embodiment, no selection of the first population of TILs, second population of TILs, third population of TILs, or harvested TIL population based on CD8 expression is performed during any of steps (a) to (h).

In some embodiments, the present disclosure provides methods for treating a subject with cancer, the method comprising administering expanded tumor infiltrating lymphocytes (TILs) comprising:
- (a) obtaining a first population of TILs from a tumor resected from a subject by processing a tumor sample obtained from the patient into multiple tumor fragments;
- (b) adding the tumor fragments into a closed system;
- (c) performing a first expansion by culturing the first population of TILs in a cell culture medium comprising IL-2 to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
- (d) performing a second expansion by supplementing the cell culture medium of the second population of TILs with additional IL-2, OKT-3, and antigen presenting cells (APCs), to produce a third population of TILs, wherein the second expansion is performed for about 7-14 days to obtain the third population of TILs, wherein the third population of TILs is a therapeutic population of TILs which comprises an increased subpopulation of effector T cells and/or central memory T cells relative to the second population of TILs, wherein the second expansion is performed in a closed container providing a second gas-permeable surface area, and wherein the transition from step (c) to step (d) occurs without opening the system;
- (e) harvesting the therapeutic population of TILs obtained from step (d), wherein the transition from step (d) to step (e) occurs without opening the system; and
- (f) transferring the harvested TIL population from step (e) to an infusion bag, wherein the transfer from step (e) to (f) occurs without opening the system;
- (g) cryopreserving the infusion bag comprising the harvested TIL population from step (f) using a cryopreservation process, wherein the cryopreservation process comprises mixing of a cryopreservation media with the harvested TIL population;
- (h) administering a therapeutically effective dosage of the third population of TILs from the infusion bag in step (g) to the patient.

wherein no selection of TIL population is performed during any of steps (a) to (h). In an embodiment, no selection of the second population of TILs (for example, the pre-REP population) based on phenotype is performed prior to performing the second expansion of step (d). In an embodiment, no selection of the first population of TILs, second population of TILs, third population of TILs, or harvested TIL population based on CD8 expression is performed during any of steps (a) to (h). In some embodiments, the non-myeloablative lymphodepletion regimen is administered prior to administering the harvested TIL population. In some embodiments, the non-myeloablative lymphodepletion regimen comprises the steps of administration of cyclophosphamide at a dose of 60 mg/m$^2$/day for two days followed by administration of fludarabine at a dose of 25 mg/m$^2$/day for five days.

In some embodiments, the antigen-presenting cells are peripheral blood mononuclear cells (PBMCs). In some embodiments, the PBMCs are irradiated and allogeneic. In some embodiments, the PBMCs are added to the cell culture on any of days 9 through 14 in step (c).

In some embodiments, the antigen-presenting cells are artificial antigen-presenting cells.

In some embodiments, the harvesting in step (d) is performed using a LOVO cell processing system.

In some embodiments, the method comprises harvesting in step (d) is via a LOVO cell processing system, such as the LOVO system manufactured by Fresenius Kabi. The term "LOVO cell processing system" also refers to any instrument or device that can pump a solution comprising cells through a membrane or filter such as a spinning membrane or spinning filter in a sterile and/or closed system environment, allowing for continuous flow and cell processing to remove supernatant or cell culture media without pelletization. In some cases, the cell processing system can perform cell separation, washing, fluid-exchange, concentration, and/or other cell processing steps in a closed, sterile system.

In some embodiments, the tumor fragments are multiple fragments and comprise about 4 to about 50 fragments, wherein each fragment has a volume of about 27 mm$^3$. In some embodiments, the multiple fragments comprise about 30 to about 60 fragments with a total volume of about 1300 mm$^3$ to about 1500 mm$^3$. In some embodiments, the multiple fragments comprise about 50 fragments with a total volume of about 1350 mm$^3$. In some embodiments, the multiple fragments comprise about 50 fragments with a total mass of about 1 gram to about 1.5 grams.

In some embodiments, the multiple fragments comprise about 4 fragments. In some embodiments, the 4 fragments are placed into a G-REX-100. In some embodiments, the 4 fragments are about 0.1 cm, 0.2 cm, 0.3 cm, 0.4 cm, 0.5 cm, 0.6 cm, 0.7 cm, 0.8 cm, 0.9 cm, or 1 cm in diameter. In some embodiments, the 4 fragments are about 0.1 cm, 0.2 cm, 0.3 cm, 0.4 cm, 0.5 cm, 0.6 cm, 0.7 cm, 0.8 cm, 0.9 cm, or 1 cm in diameter and are placed into a G-REX-100. In some embodiments, the 4 fragments are about 0.1 cm, 0.2 cm, 0.3 cm, 0.4 cm, 0.5 cm, 0.6 cm, 0.7 cm, 0.8 cm, 0.9 cm, or 1 cm in diameter are placed into a container with an equivalent volume to a G-REX-100. In some embodiments, the 4 fragments are about 0.5 cm in diameter and are placed into a G-REX-100. In some embodiments, the 4 fragments are about 0.5 cm in diameter and are placed into a container with an equivalent volume to a G-REX-100.

In some embodiments, the cell culture medium is provided in a container selected from the group consisting of a G-container and a Xuri cellbag.

In some embodiments, the infusion bag in step (e) is a HypoThermosol-containing infusion bag.

In some embodiments, the first period in step (b) and the second period in step (c) are each individually performed within a period of 10 days, 11 days, or 12 days. In some embodiments, the first period in step (b) and the second period in step (c) are each individually performed within a period of 11 days. In some embodiments, steps (a) through (e) are performed within a period of about 25 days to about 30 days. In some embodiments, steps (a) through (e) are performed within a period of about 20 days to about 25 days. In some embodiments, steps (a) through (e) are performed within a period of about 20 days to about 22 days. In some embodiments, steps (a) through (e) are performed in 22 days or less. In some embodiments, steps (a) through (e) and cryopreservation are performed in 22 days or less.

In some embodiments, steps (b) through (e) are performed in a single container, wherein performing steps (b) through (e) in a single container results in an increase in TIL yield per resected tumor as compared to performing steps (b) through (e) in more than one container.

In some embodiments, the antigen-presenting cells are added to the TILs during the second period in step (c) without opening the system.

In some embodiments, the effector T cells and/or central memory T cells obtained in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

In some embodiments, the effector T cells and/or central memory T cells obtained in the therapeutic population of TILs exhibit increased CD57 expression and decreased CD56 expression relative to effector T cells, and/or central memory T cells obtained from the second population of cells.

In some embodiments, the risk of microbial contamination is reduced as compared to an open system.

In some embodiments, the TILs from step (e) are infused into a patient.

In some embodiments, the closed container comprises a single bioreactor. In some embodiments, the closed container comprises a G-REX-10. In some embodiments, the closed container comprises a G-REX-100.

VI. Further Exemplary Embodiments

1. A method for expanding tumor infiltrating lymphocytes (TILs) into a therapeutic population of TILs comprising:
   (a) obtaining a first population of TILs from a tumor resected from a patient by processing a tumor sample obtained from the patient into multiple tumor fragments;
   (b) adding the tumor fragments into a closed system;
   (c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
   (d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
   (e) harvesting the therapeutic population of TILs obtained from step (d), wherein the transition from step (d) to step (e) occurs without opening the system; and
   (f) transferring the harvested TIL population from step (e) to an infusion bag, wherein the transfer from step (e) to (f) occurs without opening the system.

2. The method according to claim 56, further comprising the step of cryopreserving the infusion bag comprising the harvested TIL population in step (f) using a cryopreservation process.
3. The method according to claim 56, wherein the cryopreservation process is performed using a 1:1 ratio of harvested TIL population to cryopreservation media.
4. The method according to claim 56, wherein the antigen-presenting cells are peripheral blood mononuclear cells (PBMCs).
5. The method according to claim 4, wherein the PBMCs are irradiated and allogeneic.
6. The method according to claim 4, wherein the PBMCs are added to the cell culture on any of days 9 through 14 in step (d).
7. The method according to claim 56, wherein the antigen-presenting cells are artificial antigen-presenting cells.
8. The method according to claim 56, wherein the harvesting in step (e) is performed using a membrane-based cell processing system.
9. The method according to claim 56, wherein the harvesting in step (e) is performed using a LOVO cell processing system.
10. The method according to claim 56, wherein the multiple fragments comprise about 4 to about 50 fragments, wherein each fragment has a volume of about 27 mm$^3$.
11. The method according to claim 56, wherein the multiple fragments comprise about 30 to about 60 fragments with a total volume of about 1300 mm$^3$ to about 1500 mm$^3$.
12. The method according to claim 9, wherein the multiple fragments comprise about 50 fragments with a total volume of about 1350 mm$^3$.
13. The method according to claim 56, wherein the multiple fragments comprise about 50 fragments with a total mass of about 1 gram to about 1.5 grams.
14. The method according to claim 56, wherein the cell culture medium is provided in a container selected from the group consisting of a G-container and a Xuri cellbag.
15. The method according to claim 56, wherein the cell culture medium in step (d) further comprises IL-15 and/or IL-21.
16. The method according to claim any of the preceding claims, wherein the IL-2 concentration is about 10,000 IU/mL to about 5,000 IU/mL.
17. The method according to claim 565,wherein the IL-15 concentration is about 500 IU/mL to about 100 IU/mL.
18. The method according to claim 56, wherein the IL-21 concentration is about 20 IU/mL to about 0.5 IU/mL.
19. The method according to claim 56, wherein the infusion bag in step (f) is a HypoThermosol-containing infusion bag.
20. The method according to claim 3, wherein the cryopreservation media comprises dimethylsulfoxide (DMSO).
21. The method according to claim 567, wherein the wherein the cryopreservation media comprises 7% to 10% DMSO.
22. The method according to claim 56, wherein the first period in step (c) and the second period in step (e) are each individually performed within a period of 10 days, 11 days, or 12 days.
23. The method according to claim 56, wherein the first period in step (c) and the second period in step (e) are each individually performed within a period of 11 days.
24. The method according to claim 56, wherein steps (a) through (f) are performed within a period of about 10 days to about 22 days.
25. The method according to claim 56, wherein steps (a) through (f) are performed within a period of about 20 days to about 22 days.
26. The method according to claim 56, wherein steps (a) through (f) are performed within a period of about 15 days to about 20 days.
27. The method according to claim 56, wherein steps (a) through (f) are performed within a period of about 10 days to about 20 days.
28. The method according to claim 56, wherein steps (a) through (f) are performed within a period of about 10 days to about 15 days.
29. The method according to claim 56, wherein steps (a) through (f) are performed in 22 days or less.
30. The method according to claim 56, wherein steps (a) through (f) are performed in 20 days or less.
31. The method according to claim 56, wherein steps (a) through (f) are performed in 15 days or less.
32. The method according to claim 56, wherein steps (a) through (f) are performed in 10 days or less.
33. The method according to claim 2, wherein steps (a) through (f) and cryopreservation are performed in 22 days or less.
34. The method according to any one of claims 1 to 33, wherein the therapeutic population of TILs harvested in step (e) comprises sufficient TILs for a therapeutically effective dosage of the TILs.
35. The method according to claim 34, wherein the number of TILs sufficient for a therapeutically effective dosage is from about $2.3 \times 10^{10}$ to about $13.7 \times 10^{10}$.
36. The method according to any one of claims 1 to 35, wherein steps (b) through (e) are performed in a single container, wherein performing steps (b) through (e) in a single container results in an increase in TIL yield per resected tumor as compared to performing steps (b) through (e) in more than one container.
37. The method according to any one of claims 1 to 36, wherein the antigen-presenting cells are added to the TILs during the second period in step (d) without opening the system.
38. The method according to any one of claims 1 to 37, wherein the third population of TILs in step (d) provides for increased efficacy, increased interferon-gamma production, increased polyclonality, increased average IP-10, and/or increased average MCP-1 when adiminstered to a subject.
39. The method according to any one of claims 1 to 38, wherein the third population of TILs in step (d) provides for at least a five-fold or more interferon-gamma production when adiminstered to a subject.
40. The method according to any one of claims 1 to 39, wherein the third population of TILs in step (d) is a therapeutic population of TILs which comprises an increased subpopulation of effector T cells and/or central memory T cells relative to the second population of TILs, wherein the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.
41. The method according to any one of claims 1 to 40, wherein the effector T cells and/or central memory T cells obtained from the third population of TILs exhibit increased CD57 expression and decreased CD56 expression relative to effector T cells and/or central memory T cells obtained from the second population of cells.

42. The method according to any one of claims 1 to 41, wherein the risk of microbial contamination is reduced as compared to an open system.

43. The method according to any one of claims 1 to 42, wherein the TILs from step (g) are infused into a patient.

44. The method according to any one of claims 1 to 43, wherein the multiple fragments comprise about 4 fragments.

45. A method for treating a subject with cancer, the method comprising administering expanded tumor infiltrating lymphocytes (TILs) comprising:
   (a) obtaining a first population of TILs from a tumor resected from a subject by processing a tumor sample obtained from the patient into multiple tumor fragments;
   (b) adding the tumor fragments into a closed system;
   (c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
   (d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
   (e) harvesting the therapeutic population of TILs obtained from step (d), wherein the transition from step (d) to step (e) occurs without opening the system; and
   (f) transferring the harvested TIL population from step (e) to an infusion bag, wherein the transfer from step (e) to (f) occurs without opening the system;
   (g) optionally cryopreserving the infusion bag comprising the harvested TIL population from step (f) using a cryopreservation process; and
   (h) administering a therapeutically effective dosage of the third population of TILs from the infusion bag in step (g) to the patient.

46. The method according to claim 45, wherein the therapeutic population of TILs harvested in step (e) comprises sufficient TILs for administering a therapeutically effective dosage of the TILs in step (h).

47. The method according to claim 46, wherein the number of TILs sufficient for administering a therapeutically effective dosage in step (h) is from about $2.3 \times 10^{10}$ to about $13.7 \times 10^{10}$.

48. The method according to claim 47, wherein the antigen presenting cells (APCs) are PBMCs.

49. The method according to claim 48, wherein the PBMCs are added to the cell culture on any of days 9 through 14 in step (d).

50. The method according to any of claims 45 to 49, wherein prior to administering a therapeutically effective dosage of TIL cells in step (h), a non-myeloablative lymphodepletion regimen has been administered to the patient.

51. The method according to claim 50, where the non-myeloablative lymphodepletion regimen comprises the steps of administration of cyclophosphamide at a dose of 60 mg/m2/day for two days followed by administration of fludarabine at a dose of 25 mg/m2/day for five days.

52. The method according to any of claims 45 to 51, further comprising the step of treating the patient with a high-dose IL-2 regimen starting on the day after administration of the TIL cells to the patient in step (h).

53. The method according to claim 52, wherein the high-dose IL-2 regimen comprises 600,000 or 720,000 IU/kg administered as a 15-minute bolus intravenous infusion every eight hours until tolerance.

54. The method according to any of the preceding claims, wherein the third population of TILs in step (d) is a therapeutic population of TILs which comprises an increased subpopulation of effector T cells and/or central memory T cells relative to the second population of TILs, wherein the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

55. The method according to any of the preceding claims, wherein the effector T cells and/or central memory T cells in the therapeutic population of TILs exhibit increased CD57 expression and decreased CD56 expression relative to effector T cells and/or central memory T cells obtained from the second population of cells.

56. The method according to any of the preceding claims, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma.

57. The method according to any of the preceding claims, wherein the cancer is selected from the group consisting of melanoma, HNSCC, cervical cancers, and NSCLC.

58. The method according to any of the preceding claims, wherein the cancer is melanoma.

59. The method according to any of the preceding claims, wherein the cancer is HNSCC.

60. The method according to any of the preceding claims, wherein the cancer is a cervical cancer.

61. The method according to any of the preceding claims, wherein the cancer is NSCLC.

62. A method for expanding tumor infiltrating lymphocytes (TILs) into a therapeutic population of TILs comprising:
   (a) adding processed tumor fragments from a tumor resected from a patient into a closed system to obtain a first population of TILs;
   (b) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (a) to step (b) occurs without opening the system;

(c) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (b) to step (c) occurs without opening the system;

(d) harvesting the therapeutic population of TILs obtained from step (c), wherein the transition from step (c) to step (d) occurs without opening the system; and (e) transferring the harvested TIL population from step (d) to an infusion bag, wherein the transfer from step (d) to (e) occurs without opening the system.

63. The method according to claim 62, wherein the therapeutic population of TILs harvested in step (d) comprises sufficient TILs for a therapeutically effective dosage of the TILs.

64. The method according to claim 63, where the number of TILs sufficient for a therapeutically effective dosage is from about $2.3 \times 10^{10}$ to about $13.7 \times 10^{10}$.

65. The method according to claim 64, further comprising the step of cryopreserving the infusion bag comprising the harvested TIL population using a cryopreservation process.

66. The method according to claim 65, wherein the cryopreservation process is performed using a 1:1 ratio of harvested TIL population to cryopreservation media.

67. The method according to claim 62, wherein the antigen-presenting cells are peripheral blood mononuclear cells (PBMCs).

68. The method according to claim 67, wherein the PBMCs are irradiated and allogeneic.

69. The method according to claim 68, wherein the PBMCs are added to the cell culture on any of days 9 through 14 in step (c).

70. The method according to claim 62, wherein the antigen-presenting cells are artificial antigen-presenting cells.

71. The method according to claim 62, wherein the harvesting in step (d) is performed using a LOVO cell processing system.

72. The method according to claim 62, wherein the multiple fragments comprise about 4 to about 50 fragments, wherein each fragment has a volume of about 27 mm³.

73. The method according to claim 62, wherein the multiple fragments comprise about 30 to about 60 fragments with a total volume of about 1300 mm³ to about 1500 mm³.

74. The method according to claim 63, wherein the multiple fragments comprise about 50 fragments with a total volume of about 1350 mm³.

75. The method according to claim 62, wherein the multiple fragments comprise about 50 fragments with a total mass of about 1 gram to about 1.5 grams.

76. The method according to claim 62, wherein the multiple fragments comprise about 4 fragments.

77. The method according to claim 62, wherein the second cell culture medium is provided in a container selected from the group consisting of a G-container and a Xuri cellbag.

78. The method according to claim 62, wherein the infusion bag in step (e) is a HypoThermosol-containing infusion bag.

79. The method according to claim 62, wherein the first period in step (b) and the second period in step (c) are each individually performed within a period of 10 days, 11 days, or 12 days.

80. The method according to claim 62, wherein the first period in step (b) and the second period in step (c) are each individually performed within a period of 11 days.

81. The method according to claim 62, wherein steps (a) through (e) are performed within a period of about 10 days to about 22 days.

82. The method according to claim 62, wherein steps (a) through (e) are performed within a period of about 10 days to about 20 days.

83. The method according to claim 62, wherein steps (a) through (e) are performed within a period of about 10 days to about 15 days.

84. The method according to claim 62, wherein steps (a) through (e) are performed in 22 days or less.

85. The method according to claim 65, wherein steps (a) through (e) and cryopreservation are performed in 22 days or less.

86. The method according to any one of claims 62 to 85, wherein steps (b) through (e) are performed in a single container, wherein performing steps (b) through (e) in a single container results in an increase in TIL yield per resected tumor as compared to performing steps (b) through (e) in more than one container.

87. The method according to any one of claims 62 to 86, wherein the antigen-presenting cells are added to the TILs during the second period in step (c) without opening the system.

88. The method according to any one of claims 62 to 87, wherein the third population of TILs in step (d) is a therapeutic population of TILs which comprises an increased subpopulation of effector T cells and/or central memory T cells relative to the second population of TILs, wherein the effector T cells and/or central memory T cells obtained in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

89. The method according to any one of claims 62 to 88, wherein the effector T cells and/or central memory T cells obtained in the therapeutic population of TILs exhibit increased CD57 expression and decreased CD56 expression relative to effector T cells, and/or central memory T cells obtained from the second population of cells.

90. The method according to any one of claims 62 to 89, wherein the risk of microbial contamination is reduced as compared to an open system.

91. The method according to any one of claims 62 to 90, wherein the TILs from step (e) are infused into a patient.

92. The method according to any of the preceding claims wherein the closed container comprises a single bioreactor.

93. The method according to claim 92, wherein the closed container comprises a G-REX-10.

94. The method according to claim 92, wherein the closed container comprises a G-REX -100.

95. The method according to any one of claims 1 to 61, wherein at step (d) the antigen presenting cells (APCs) are added to the cell culture of the second population of TILs at a APC:TIL ratio of 25:1 to 100:1.

96. The method according to claim 95, wherein the cell culture has a ratio of $2.5 \times 10^9$ APCs to $100 \times 10^6$ TILs.

97. The method according to any one of claims 62 to 94, wherein at step (c) the antigen presenting cells (APCs) are added to the cell culture of the second population of TILs at a APC:TIL ratio of 25:1 to 100:1.

98. The method according to claim 97, wherein the cell culture has ratio of $2.5 \times 10^9$ APCs to $100 \times 10^6$ TILs.

99. A population of expanded TILs for use in the treatment of a subject with cancer, wherein the population of expanded TILs is a third population of TILs obtainable by a method comprising:
   (a) obtaining a first population of TILs from a tumor resected from a subject by processing a tumor sample obtained from the patient into multiple tumor fragments;
   (b) adding the tumor fragments into a closed system;
   (c) performing a first expansion by culturing the first population of TILs in a cell culture medium comprising IL-2, and optionally OKT-3, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
   (d) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
   (e) harvesting the therapeutic population of TILs obtained from step (d), wherein the transition from step (d) to step (e) occurs without opening the system; and
   (f) transferring the harvested TIL population from step (e) to an infusion bag, wherein the transfer from step (e) to (f) occurs without opening the system; and
   (g) optionally cryopreserving the infusion bag comprising the harvested TIL population from step (f) using a cryopreservation process.

100. The population of TILs for use to treat a subject with cancer according to claim 99, wherein the method further comprises one or more of the features recited in any of claims 1 to 99.

101. A method for expanding tumor infiltrating lymphocytes (TILs) into a therapeutic population of TILs comprising:
   (a) obtaining a first population of TILs from a tumor resected from a patient by processing a tumor sample obtained from the patient into multiple tumor fragments;
   (b) adding the tumor fragments into a closed system;
   (c) performing a first expansion by culturing the first population of TILs in a cell culture medium comprising IL-2, optionally OKT-3, and optionally a tumor necrosis factor receptor superfamily (TNFRSF) agonist, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;
   (d) performing a second expansion by supplementing the cell culture medium of the second population of TILs with additional IL-2, optionally OKT-3, and optionally a tumor necrosis factor receptor superfamily (TNFRSF) agonist, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;
   (e) harvesting the therapeutic population of TILs obtained from step (d), wherein the transition from step (d) to step (e) occurs without opening the system; and
   (f) transferring the harvested TIL population from step (e) to an infusion bag, wherein the transfer from step (e) to (f) occurs without opening the system.

102. The method according to claim 5601, further comprising the step of cryopreserving the infusion bag comprising the harvested TIL population in step (f) using a cryopreservation process.

103. The method according to claim 5601, wherein the cryopreservation process is performed using a 1:1 ratio of harvested TIL population to cryopreservation media.

104. The method according to claim 5601, wherein the antigen-presenting cells are peripheral blood mononuclear cells (PBMCs).

105. The method according to claim 5604, wherein the PBMCs are irradiated and allogeneic.

106. The method according to claim 5604, wherein the PBMCs are added to the cell culture on any of days 9 through 14 in step (d).

107. The method according to claim 5601, wherein the antigen-presenting cells are artificial antigen-presenting cells.

108. The method according to claim 5601, wherein the harvesting in step (e) is performed using a membrane-based cell processing system.

109. The method according to claim 5601, wherein the harvesting in step (e) is performed using a LOVO cell processing system.

110. The method according to claim 5601, wherein the multiple fragments comprise about 4 to about 50 fragments, wherein each fragment has a volume of about 27 mm$^3$.

111. The method according to claim 5601, wherein the multiple fragments comprise about 30 to about 60 fragments with a total volume of about 1300 mm$^3$ to about 1500 mm$^3$.

112. The method according to claim 5609, wherein the multiple fragments comprise about 50 fragments with a total volume of about 1350 mm$^3$.

113. The method according to claim 5601, wherein the multiple fragments comprise about 50 fragments with a total mass of about 1 gram to about 1.5 grams.

114. The method according to claim 5601, wherein the cell culture medium is provided in a container selected from the group consisting of a G-container and a Xuri cellbag.

115. The method according to claim 5601, wherein the cell culture medium in step (d) further comprises IL-15 and/or IL-21.

116. The method according to claim any of claims 101 to 115, wherein the IL-2 concentration is about 10,000 IU/mL to about 5,000 IU/mL.

117. The method according to claim 5615, wherein the IL-15 concentration is about 500 IU/mL to about 100 IU/mL.

118. The method according to claim 5601, wherein the IL-21 concentration is about 20 IU/mL to about 0.5 IU/mL.

119. The method according to claim 5601, wherein the infusion bag in step (f) is a HypoThermosol-containing infusion bag.

120. The method according to claim 5603, wherein the cryopreservation media comprises dimethlysulfoxide (DMSO).

121. The method according to claim 5617, wherein the wherein the cryopreservation media comprises 7% to 10% DMSO.

122. The method according to claim 5601, wherein the first period in step (c) and the second period in step (e) are each individually performed within a period of 10 days, 11 days, or 12 days.

123. The method according to claim 5601, wherein the first period in step (c) and the second period in step (e) are each individually performed within a period of 11 days.

124. The method according to claim 5601, wherein steps (a) through (f) are performed within a period of about 10 days to about 22 days.

125. The method according to claim 5601, wherein steps (a) through (f) are performed within a period of about 20 days to about 22 days.

126. The method according to claim 5601, wherein steps (a) through (f) are performed within a period of about 15 days to about 20 days.

127. The method according to claim 5601, wherein steps (a) through (f) are performed within a period of about 10 days to about 20 days.

128. The method according to claim 5601, wherein steps (a) through (f) are performed within a period of about 10 days to about 15 days.

129. The method according to claim 5601, wherein steps (a) through (f) are performed in 22 days or less.

130. The method according to claim 5601, wherein steps (a) through (f) are performed in 20 days or less.

131. The method according to claim 5601, wherein steps (a) through (f) are performed in 15 days or less.

132. The method according to claim 5601, wherein steps (a) through (f) are performed in 10 days or less.

133. The method according to claim 5602, wherein steps (a) through (f) and cryopreservation are performed in 22 days or less.

134. The method according to any one of claims 101 to 133, wherein the therapeutic population of TILs harvested in step (e) comprises sufficient TILs for a therapeutically effective dosage of the TILs.

135. The method according to claim 5634, wherein the number of TILs sufficient for a therapeutically effective dosage is from about $2.3 \times 10^{10}$ to about $13.7 \times 10^{10}$.

136. The method according to any one of claims 101 to 135, wherein steps (b) through (e) are performed in a single container, wherein performing steps (b) through (e) in a single container results in an increase in TIL yield per resected tumor as compared to performing steps (b) through (e) in more than one container.

137. The method according to any one of claims 101 to 136, wherein the tumor necrosis factor receptor superfamily (TNFRSF) agonist is a 4-1BB antibody.

138. The method according to any one of claims 101 to 137, wherein the antigen-presenting cells are added to the TILs during the second period in step (d) without opening the system.

139. The method according to any one of claims 101 to 138, wherein the third population of TILs in step (d) provides for increased efficacy, increased interferon-gamma production, increased polyclonality, increased average IP-10, and/or increased average MCP-1 when adminstered to a subject.

140. The method according to any one of claims 101 to 139, wherein the third population of TILs in step (d) provides for at least a five-fold or more interferon-gamma production when adminstered to a subject.

141. The method according to any one of claims 101 to 140, wherein the third population of TILs in step (d) is a therapeutic population of TILs which comprises an increased subpopulation of effector T cells and/or central memory T cells relative to the second population of TILs, wherein the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

142. The method according to any one of claims 101 to 141, wherein the effector T cells and/or central memory T cells obtained from the third population of TILs exhibit increased CD57 expression and decreased CD56 expression relative to effector T cells and/or central memory T cells obtained from the second population of cells.

143. The method according to any one of claims 101 to 142, wherein the risk of microbial contamination is reduced as compared to an open system.

144. The method according to any one of claims 101 to 143, wherein the TILs from step (g) are infused into a patient.

145. The method according to any one of claims 101 to 144, wherein the multiple fragments comprise about 4 fragments.

146. A method for treating a subject with cancer, the method comprising administering expanded tumor infiltrating lymphocytes (TILs) comprising:

(a) obtaining a first population of TILs from a tumor resected from a subject by processing a tumor sample obtained from the patient into multiple tumor fragments;

(b) adding the tumor fragments into a closed system;

(c) performing a first expansion by culturing the first population of TILs in a cell culture medium comprising IL-2, optionally OKT-3, and optionally a tumor necrosis factor receptor superfamily (TNFRSF) agonist, to produce a second population of TILs, wherein the first expansion is performed in a closed container providing a first gas-permeable surface area, wherein the first expansion is performed for about 3-14 days to obtain the second population of TILs, wherein the second population of TILs is at least 50-fold greater in number than the first population of TILs, and wherein the transition from step (b) to step (c) occurs without opening the system;

(d) performing a second expansion by supplementing the cell culture medium of the second population of TILs with additional IL-2, optionally OKT-3, and optionally a tumor necrosis factor receptor superfamily (TNFRSF) agonist, and antigen presenting cells (APCs), to produce a third population of TILs, wherein the second expansion is performed for about 7-14 days to obtain the third population of TILs, wherein the third population of TILs is a therapeutic population of TILs, wherein the second expansion is performed in a closed container providing a second gas-permeable surface area, and wherein the transition from step (c) to step (d) occurs without opening the system;

(e) harvesting the therapeutic population of TILs obtained from step (d), wherein the transition from step (d) to step (e) occurs without opening the system; and (f) transferring the harvested TIL population from step (e) to an infusion bag, wherein the transfer from step (e) to (f) occurs without opening the system;

(g) optionally cryopreserving the infusion bag comprising the harvested TIL population from step (f) using a cryopreservation process; and (h) administering a therapeutically effective dosage of the third population of TILs from the infusion bag in step (g) to the patient.

147. The method according to claim 5646, wherein the therapeutic population of TILs harvested in step (e) comprises sufficient TILs for administering a therapeutically effective dosage of the TILs in step (h).

148. The method according to claim 5647, wherein the number of TILs sufficient for administering a therapeutically effective dosage in step (h) is from about $2.3 \times 10^{10}$ to about $13.7 \times 10^{10}$.

149. The method according to claim 5648, wherein the antigen presenting cells (APCs) are PBMCs.

150. The method according to claim 5649, wherein the PBMCs are added to the cell culture on any of days 9 through 14 in step (d).

151. The method according to any one of claims 146 to 150, wherein the tumor necrosis factor receptor superfamily (TNFRSF) agonist is a 4-1BB antibody.

152. The method according to any of claims 146 to 151, wherein prior to administering a therapeutically effective dosage of TIL cells in step (h), a non-myeloablative lymphodepletion regimen has been administered to the patient.

153. The method according to claim 5652, where the non-myeloablative lymphodepletion regimen comprises the steps of administration of cyclophosphamide at a dose of 60 mg/m²/day for two days followed by administration of fludarabine at a dose of 25 mg/m²/day for five days.

154. The method according to any of claims 146 to 153, further comprising the step of treating the patient with a high-dose IL-2 regimen starting on the day after administration of the TIL cells to the patient in step (h).

155. The method according to claim 5654, wherein the high-dose IL-2 regimen comprises 600,000 or 720,000 IU/kg administered as a 15-minute bolus intravenous infusion every eight hours until tolerance.

156. The method according to any of claims 146 to 155, wherein the third population of TILs in step (d) is a therapeutic population of TILs which comprises an increased subpopulation of effector T cells and/or central memory T cells relative to the second population of TILs, wherein the effector T cells and/or central memory T cells in the therapeutic population of TILs exhibit one or more characteristics selected from the group consisting of expressing CD27+, expressing CD28+, longer telomeres, increased CD57 expression, and decreased CD56 expression relative to effector T cells, and/or central memory T cells obtained from the second population of cells.

157. The method according to any of claims 146 to 156, wherein the effector T cells and/or central memory T cells in the therapeutic population of TILs exhibit increased CD57 expression and decreased CD56 expression relative to effector T cells and/or central memory T cells obtained from the second population of cells.

158. The method according to any of claims 146 to 157, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma.

159. The method according to any of claims 146 to 158, wherein the cancer is selected from the group consisting of melanoma, HNSCC, cervical cancers, and NSCLC.

160. The method according to any of claims 146 to 159, wherein the cancer is melanoma.

161. The method according to any of claims 146 to 160, wherein the cancer is HNSCC.

162. The method according to any of claims 146 to 161, wherein the cancer is a cervical cancer.

163. The method according to any of claims 146 to 162, wherein the cancer is NSCLC.

164. A cryopreservation composition comprising the population of TILs according to any one of the preceding claims, a cryoprotectant medium comprising dimethylsulfoxide (DMSO), and an electrolyte solution.

165. The cryopreservation composition according to claim 5664, further comprising one or more stabilizers and one or more lymphocyte growth factors.

166. The cryopreservation composition according to claim 5665, wherein the one or more stabilizers comprise human serum albumin (HSA) and the one or more lymphocyte growth factors comprise IL-2.

167. The cryopreservation composition according to claim 5666, wherein the composition optionally comprises OKT-3.

168. The cryopreservation composition according to claim 5664, wherein the cryoprotectant medium comprising DMSO and the electrolyte solution are present in a ratio of about 1.1:1 to about 1:1.1.

169. The cryopreservation composition according to claim 5668, wherein the cryoprotectant medium comprising DMSO and the electrolyte solution are present in a ratio of about 1:1.

170. The cryopreservation composition according to claim 5664, wherein 100 mL of the composition comprises the population of TILs in an amount of about $1 \times 10^6$ to about $9 \times 10^{14}$; the cryoprotectant medium comprising DMSO in an amount of about 30 mL to about 70 mL, the electrolyte solution in an amount of about 30 mL to about 70 mL; HSA in an amount of about 0.1 g to about 1.0 g; and IL-2 in an amount of about 0.001 mg to about 0.005 mg.

171. The cryopreservation composition according to claim 5664, wherein 100 mL of the composition comprises the population of TILs in an amount of about $1 \times 10^7$ to about $1 \times 10^{11}$; the cryoprotectant medium in an amount of about 30 mL to about 70 mL, wherein the cryoprotectant medium comprises about 10% DMSO; the electrolyte solution in an amount of about 30 mL to about 70 mL;

HSA in an amount of about 0.3 g to about 0.7 g; and IL-2 in an amount of about 0.001 mg to about 0.003 mg.

172. The cryopreservation composition according to claim 5664, wherein 100 mL of the composition consists essentially of the population of TILs in an amount of about $1\times10^7$ to about $1\times10^{11}$; the cryoprotectant medium in an amount of about 30 mL to about 70 mL, wherein the cryoprotectant medium consists essentially of about 10% DMSO; the electrolyte solution in an amount of about 30 mL to about 70 mL; HSA in an amount of about 0.3 g to about 0.7 g; and IL-2 in an amount of about 0.001 mg to about 0.003 mg.

173. The cryopreservation composition according to claim 5664, wherein the composition is for use in treating a subject with cancer.

174. A cryopreservation composition comprising a population of TILs, a cryoprotectant medium comprising dimethylsulfoxide (DMSO), and an electrolyte solution, wherein 100 mL of the composition comprises the population of TILs in an amount of about $1\times10^7$ to about $1\times10^{11}$; the cryoprotectant medium in an amount of about 30 mL to about 70 mL, wherein the cryoprotectant medium comprises about 10% DMSO; the electrolyte solution in an amount of about 30 mL to about 70 mL; HSA in an amount of about 0.3 g to about 0.7 g; and IL-2 in an amount of about 0.001 mg to about 0.003 mg.

175. A cryopreservation composition consisting essentially of a population of TILs, a cryoprotectant medium comprising dimethylsulfoxide (DMSO), and an electrolyte solution, wherein 100 mL of the composition consists essentially of the population of TILs in an amount of about $1\times10^7$ to about $1\times10^{11}$; the cryoprotectant medium in an amount of about 30 mL to about 70 mL, wherein the cryoprotectant medium consists essentially of about 10% DMSO; the electrolyte solution in an amount of about 30 mL to about 70 mL; HSA in an amount of about 0.3 g to about 0.7 g; and IL-2 in an amount of about 0.001 mg to about 0.003 mg.

176. An infusion bag comprising a cryopreservation composition according to any one of claims 164 to 175.

177. The infusion bag of claim 5676, wherein the infusion bag is a HypoThermosol-containing infusion bag.

178. A storage bag comprising a cryopreservation composition according to any one of claims 164 to 175.

179. The storage bag of claim 5678, wherein the storage bag is a CryoStore CS750 Freezing bag.

Examples

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: Closed System Assays

As discussed herein, protocols and assays were developed for generating TIL from patient tumors in a closed system.
This Example describes a novel abbreviated procedure for generating clinically relevant numbers of TILs from patients' resected tumor tissue in G-REX devices and cryopreservation of the final cell product. Additional aspects of this procedure are described in Examples 2 to 8.

Definitions/Abbreviations

BSC—Biological Safety Cabinet
° C.—degrees Celsius
$CO_2$—Carbon dioxide
CD3—Cluster of Differentiation 3
CM1—Complete Medium 1
CM2—Complete Medium 2
TIWB—Tumor Isolation Wash Buffer
CM4—Complete Medium 4
CRF—Control Rate Freezer
EtOH—ethanol
GMP—Good Manufacturing Practice
IL-2, rIL-2-Interleukin-2, Recombinant human Interleukin-2,
IU—International Unit
L—Liter
LN2—liquid nitrogen
mL—milliliter
µl—microliter
mM—millimolar
µm—micrometer
NA—Not Applicable
PBMC—Peripheral Blood Mononuclear Cell
PPE—Personal Protective Equipment
Pre-REP—Initial TIL cultures originating from tumor fragments
REP—Rapid Expansion Protocol
TIL—Tumor Infiltrating Lymphocytes
TIWB—TIL Isolation Wash Buffer
SOP—Standard Operating Procedure Procedure 1. Advanced preparation: Day 0 (Performed up to 36 hours in advance)
    1.1 Prepared TIL Isolation Wash Buffer (TIWB) by supplementing 500 mL Hanks Balanced Salt Solution with 50 µg/mL Gentamicin. For 10 mg/mL Gentamicin stock solution transferred 2.5 mL to HBSS. For 50 mg/mL stock solution transferred 0.5 mL to HBSS.
    1.2. Prepared CM1 media with GlutaMax™ per LAB-005 "Preparation of media for PreREP and REP" for CM2 instructions". Store at 4° C. up to 24 hours. Allowed to warm at 37° C. for at least 1 hour prior to use.
    1.3. Removed IL-2 aliquot(s) from −20° C. freezer and placed aliquot(s) in 2-8° C. refrigerator.
2. Receipt of tumor tissue
    2.1. Kept all paperwork received with tumor tissue and obtained photos of transport container and tumor tissue.
    2.2. If TempTale was provided printed and saved the associated document; saved the PDF.
    2.3. Removed tumor specimen and secondary container (zip top bag) from shipper and stored at 4° C. until ready for processing.
    2.4 Shipped unused tumor either in HypoThermosol or as frozen fragments in CryoStor CS10 (both commercially available from BioLife Solutions, Inc.).
3. Tumor processing for TIL
    3.1. Aseptically transferred the following materials to the BSC, as needed, and labeled according to Table 3 below.

TABLE 3

Materials for tumor isolation.

| Item | Minimum Quantity | In-Process Label |
|---|---|---|
| Tumor | 1 | N/A |
| Petri dish, 150 mm | 1 | Dissection |
| Petri dish, 100 mm | 4 | Wash 1, 2, 3, 4 |
| Petri dish, 100 mm | 1 | Unfavorable Tissue |
| 6 well plate | 2 | Lid Label - "Tumor Fragments" Plate Bottom - "Favorable Tissue" |
| Ruler | 2 | N/A |
| Wash Buffer | 1 | N/A |
| Forceps | 1 | N/A |
| Long forceps | 1 | N/A |
| Scalpel | As needed | N/A |

3.2. Labeled the circles of the Tumor Fragments Dishes with the letters A-J.

3.3. Labeled the undersides of the wells of the Favorable Tissue Dishes with the letters A-J.

3.4. Transferred 5 mL Gentamicin to the HBSS bottle. Labeled as TIWB.

3.5. Swirled to mix.

3.6. Pipetted 50 mL TIWB to each of the following:
1. Wash 1 dish
2. Wash 2 dish
3. Wash 3 dish
4. Wash 4 dish 3.7. Pipetted 2 mL TIWB into wells A-J of the Favorable Tissue Dish.

3.8. Covered the Favorable Tissue Dishes (6-well plate bottom) with the corresponding Tumor Fragments Dish (6-well plate lid).

3.9. Using long forceps, removed the tumor(s) from the Specimen bottle and transferred to the Wash 1 dish.

3.10. Incubated the tumor at ambient temperature in the Wash 1 dish for 3 minutes.

3.11. During the incubation, relabeled the Specimen bottle "Bioburden" and stored at 2-8° C. until submitted to Quality Control for testing.

3.12. Discarded long forceps and used short forceps for further manipulations.

3.13. Using forceps transferred the tumor to the Wash 2 dish.

3.14. Incubated the tumor at ambient temperature in the Wash 2 dish for 3 minutes.

3.15. Using forceps transferred the tumor to the Wash 3 dish.

3.16. Incubated the tumor at ambient in the Wash 3 dish for 3 minutes.

3.17. Removed the Tumor Fragment Dishes (6-well plate lids) from the Favorable Tissue Dishes (6-well plate bottoms) and placed the Tumor Fragments Dishes upside down on the BSC surface.

3.18. Using a transfer pipette, added approximately 4 evenly-spaced, individual drops of TIWB to each circle of the Tumor Fragments dishes.

3.19. Placed a ruler underneath the Dissection dish.

3.20. Using forceps transferred the tumor to the Dissection dish.

3.21. Using the ruler under the Dissection dish, measured and recorded the length of the tumor.

3.22. For tumors greater than 1 cm additional Favorable Tissue Dishes were made.

3.23. Performed an initial dissection of the tumor pieces in the Dissection dish into 10 intermediate pieces and care was taken to conserve the tumor structure of each intermediate piece.

3.24. Transferred any intermediate tumor pieces not being actively dissected into fragments to the Wash 4 dish to ensure the tissue remained hydrated during the entire dissection procedure.

3.25. Working with one intermediate tumor piece at a time, carefully sliced the tumor into up to 3×3×3 mm fragments in the Dissection Dish, using the ruler underneath the dish for reference. When scalpel became dull, replaced with a new scalpel.

3.26. Continued dissecting fragments from the intermediate tumor piece until all tissue in the intermediate piece had been evaluated.

3.27. Selected favorable fragments and using a transfer pipette transferred up to 4 favorable fragments into the TIWB drops in one circle in the Tumor Fragments dish.

3.28. Using a transfer pipette transferred any remaining favorable fragments from the tumor piece, when available, to the corresponding well in the Favorable Tissue Dish.

3.29. Using a transfer pipette transferred as much as possible of the unfavorable tissue and waste product to the Unfavorable Tissue dish to clear the dissection dish. Unfavorable tissue was indicated by yellow adipose tissue or necrotic tissue.

3.30. Continued processing by repeating step 7.3.25-7.3.30 for the remaining intermediate tumor pieces, working one intermediate piece at a time until all of the tumor had been processed.

3.31. If fewer than 4 tumor fragments were available in the corresponding circle of the Tumor Fragments Dish, it was acceptable to use fragments from a non-corresponding well of the Favorable Tissue Dish as available to achieve the 40 fragment goal. When less than 40 fragments, 10-40 were placed in a singled G-Rex 100M flask.

4. Seeding G-Rex 100M flask 4.1. Aseptically transferred the following materials to the BSC, as needed, and labeled according to the Table 4 below.

TABLE 4

Additional Materials for Seeding Flasks.

| Item | Minimum Quantity | In-Process Label |
|---|---|---|
| G-Rex 100M flask | As Needed | Lot# |
| Warm CM1 | As Needed | Lot# |
| IL-2 Aliquots | As Needed | Lot# |

4.2. Supplemented each liter of CM1 with 1 mL of IL-2 stock solution ($6\times10^6$ IU/mL).

4.3. Placed 1000 mL of pre-warmed CM1 containing 6,000 IU/mL of IL-2 in each G-REX 100M bioreactor needed as determined by Table 5 below.

4.4. Using a transfer pipette, transferred the appropriate number of tumor fragments to each G-Rex 100M flask, distributing fragments per Table 5.

4.5. When one or more tumor fragments transferred to the G-Rex 100M flask float, obtained one additional tumor fragment if available from the Favorable Tissue Dish and transferred it to the G-Rex 100M flask.

4.6. Recorded the total number of fragments added to each flask.

4.7. Discarded the Unfavorable Tissue dish.
4.8. Placed each G-REX 100M bioreactor in 37° C., 5% $CO_2$ incubator.
4.9. When more than 40 fragments were available:
    4.9.1. When >41 fragments were obtained, placed 1000 mL of pre-warmed complete CM1 in a second G-REX 100M bioreactor.

TABLE 5

Number of G-REX bioreactors needed.

| Number of Fragments | G-REX | Number of G-REX | CM1 needed |
|---|---|---|---|
| 1-40 | G-REX 100M | 1 | 1000 mL |
| 41-80 distribute between flasks | G-REX 100M | 2 | 2000 mL |
| >80 | Freeze fragments in CS10 after 15 minute pre-incubation | | |

5. Advanced Preparation: Day 11 (Prepared up to 24 hours in advance)
  5.1. Prepared 6 L of CM2 with GlutaMax. Used reference laboratory procedures for "Preparation of media for PreREP and REP for CM2 instructions". Warmed at 37° C. 1 hour prior to use.
  5.2. Thawed IL-2 aliquots: Removed IL-2 aliquots from freezer and placed at 4° C.
6. Harvest TIL (Day 11)
  6.1. Carefully removed G-REX-100M flasks from incubator and placed in BSC2. Were careful to not disturb the cells on the bottom of the flask.
  6.2. Using GatherRex or peristaltic pump aspirated ~900 mL of cell culture supernatant from flask(s).
  6.3. Resuspended TIL by gently swirling flask. Observed that all cells have been liberated from the membrane.
  6.4. Using peristaltic pump or GatherRex transferred the residual cell suspension to an appropriately sized blood transfer pack (300-1000 mL). Was careful to not allow the fragments to be transferred to the blood transfer pack.
  6.5. Spiked the transfer pack with a 4" plasma transfer set (ensure clamp is closed).
  6.6. Massaged the pack to ensure the cell suspension was well mixed and using a 3 mL syringe, removed 1 mL TIL suspension for cell counts. Clamped the tubing and recapped female luer connector with a new sterile luer cap.
  6.7. Placed the transfer pack into a plastic zip top bag and replaced into the incubator until ready to use.
7. Media preparation
  7.1. Allowed media to warm at 37° C. for >1 hr.
  7.2. Added 3 mL of $6\times10^6$ IU/mL stock rhIL-2 to 6 L CM2 to reach a final concentration of 3,000 IU/mL rhIL-2. Label as "complete CM2".
  7.3. Sterile welded a 4" plasma transfer set with female luer to a 1 L Transfer pack.
  7.4. Transferred 500 mL complete CM2 to a 1 L transfer pack. Detached fluid transfer set or syringe and attached a sterile luer plug to the female luer port.
  7.5. Spiked the pack with a sample site coupler.
  7.6. Using a 1.0 mL syringe with needle drew up 150 µL of 1 mg/mL anti-CD3 (clone OKT3) and transferred to 500 mL "complete CM2" through sample site coupler. Drew back on the syringe to ensure all reagent was flushed from the line. Stored at 37° C. until use.
8. Flask preparation
  8.1. Transferred 4.5 L "complete CM2" to a G-REX-500M flask using the graduations on the flask for reference.
  8.2. Placed flask into 37° C. incubator until ready.
9. Thaw irradiated feeders
  9.1. Utilized $5.0\times10^9$ allogenic irradiated feeders from two or more donors for use.
  9.2. Removed feeders from LN2 freezer and placed in a biohazard transport bag.
  9.3. With feeder bags in the biohazard transport bag, thawed feeders in 37° C. incubator or bead bath. Kept bags static and submerged. Removed feeders from bath when almost completely thawed but still cold.
  9.4. Sprayed or wiped feeder bags with 70% EtOH and place in BSC2. Added each feeder bag directly to the open G-Rex 500M to assure sufficient number of irradiated cells ($5\times10^9$ cells, +/−20%).
  9.5. Closed both clamps on a fenwal Y type connector with male luer lock.
  9.6. Spiked each feeder bag with a leg of the Y connector.
  9.7. Removed 1 L transfer pack with 500 mL "complete CM2"+OKT3 and transferred to BSC.
  9.8. Aseptically attached a 60 mL syringe to a 3 way stopcock, and aseptically attached the transfer pack to the male end of the stopcock.
  9.9. Aseptically attached the Y connector to the 3 way stopcock.
  9.10. Drew the entire contents of the feeder bags into the syringe, recorded the volume, and dispensed $5.0\times10^9$ allogenic irradiated feeders into the transfer pack.
  9.11. Clamped and detached transfer pack from apparatus, and plug female luer lock with a new sterile luer plug.
  9.12. Using a needle and 3 mL syringe pulled 1 mL for cell counts from the sample site coupler.
  9.13. When +/−10% of the target cell number ($5.0\times10^9$) was reached with >70% viability, proceeded.
  9.14. When less than 90% of the target cell number ($5.0\times10^9$) was reached with >70% viability thawed another bag and repeated 7.9.4-7.9.12. When greater than 110% of the target cell number was achieved, calculated the proper volume required for desired cell dose and proceeded.
10. Co-culture TIL and feeders in G-REX 500M flask
  10.1. Removed the G-REX 500M flask containing prepared media from the incubator and placed in the BSC2.
  10.2. Attached feeder transfer pack to G-REX-500M and allowed contents of the bag to drain into the 500M.
  10.3. Removed TIL suspension from the incubator and placed in the BSC.
  10.4. Calculated volume of TIL suspension to add to achieve $200\times10^6$ total viable cells.

$$(TVC/mL)/200\times10^6 = mL$$

10.5. When TIL were between $5\text{-}200\times10^6$ total viable cells, added all TIL (total volume) to the G-REX-500M. When TIL count was greater than $200\times10^6$ total viable cells, added calculated volume necessary for 200×10⁶ TIL to be distributed to an individual G-REX-500M. Remaining TIL were spun down and frozen in at least two cryovials at up to $10^8$/mL in CS10, labeled with TIL identification and date frozen.

10.6. Placed the G-REX-500M in a 37° C., 5% $CO_2$ incubator for 5 days.

11. Advanced preparation: Day 16-18
    11.1. Warmed 1 10 L bag of AIM V for cultures initiated with less than 50×10⁶ TIL warmed 2 for those initiated with greater than 50×10⁶ TIL at 37° C. at least 1 hr or until ready to use.

12. Perform TIL cell count: Day 16-18
    12.1. Removed G-REX-500M flask from incubator and placed in BSC2. Were careful not to disturb the cell culture on the bottom of the flask.
    12.2. Aseptically removed 4 L of cell culture media from the G-REX-500M flask and placed into a sterile container.
    12.3. Swirled the G-REX-500M until all TIL had been resuspended from the membrane.
    12.4. Using GatherRex or peristaltic pump transferred cell suspension to a 2L transfer pack. Retained the 500M flask for later use. Sealed the port with the sample site coupler to avoid loss of TILs.
    12.5. Spiked the transfer pack with a sample site coupler and using a 3 mL syringe and needle removed 2×1 mL independent samples for a cell count.
    12.6. Calculated the total number of flasks required for subculture according to the following formula. Rounded fractions up.

Total viable cells/$1.0×10^9$=flask #

13. Prepare CM4
    13.1. Prepared a 10 L bag of AIM-V for every two 500M flasks needed. Warmed additional media as necessary.
    13.2. For every 10 L of AIM-V needed, added 100 mL of GlutaMAX to make CM4.
    13.3. Supplemented CM4 media with rhIL-2 for a final concentration of 3,000 IU/mL rhIL-2.

14. Split the cell culture
    14.1. Using the graduations on the flask, gravity filled each G-REX-500M to 5 L.
    14.2. Evenly distributed the TIL volume amongst the calculated number of G-REX −500 Ms.
    14.3. Placed flasks in a 37° C., 5% $CO_2$ incubator until harvest on Day 22 of REP.

15. Advanced Preparation: Day 22-24
    15.1. Prepared 2 L of 1% HSA wash buffer by adding 40 mL of 25% HSA to each of two 1 L bags of PlasmaLyte A 7.4. Pool into a LOVO ancillary bag.
    15.2. Supplemented 200 mL CS10 with IL-2 @ 600 IU/mL.
    15.3. Pre-cooled four 750 mL aluminum freezer canisters at 4° C.

16. Harvest TIL: Day 22-24
    16.1. Removed the G-REX-500M flasks from the 37° C. incubator and placed in the BSC2. Were careful to not disturb the cell culture on the bottom of the flask.
    16.2. Aspirated and discarded 4.5 L of cell culture supernatant from each flask.
    16.3. Swirled the G-REX-500M flask to completely resuspend the TIL.
    16.4. Weighed the 3-5 L bioprocess bag prior to use.
    16.5. Using GatherRex or peristaltic pump, harvested TIL into the bioprocess bag.
    16.6. Mixed bag well and using a 3 mL syringe take 2×2 mL samples from the syringe sample port for cell counting.
    16.7. Weighed the bag and found the difference between the initial and final weight. Used the following calculation to determine the volume of cell suspension.

Net weight of cell suspension (mL)/1.03=volume (mL)

17. Filter TIL and prepare LOVO Source bag
    17.1. Placed the bag containing cell culture into the BSC2.
    17.2. Placed a 170 μm blood filter into the BSC2 and closed all clamps.
    17.3. Sterile welded a source leg of the filter to the cell suspension.
    17.4. Weighed a new appropriately sized bioprocess bag (this was referred to as the LOVO source bag).
    17.5. Sterile welded the terminal end of the filter to the LOVO source bag.
    17.6. Elevated the cell suspension by hanging cells on an IV pole to set up a gravity-flow transfer of cells. Note: (Did not allow the source bag to hang from the filtration apparatus.)
    17.7. Opened all necessary clamps and allowed TIL to drain from the cell suspension bag through the filter and into the LOVO source bag.
    17.8. Once all cells were transferred to the LOVO source bag, closed all clamps and sealed the LOVO source bag tubing to remove filter.
    17.9. Weighed the LOVO source bag and calculate volume.
    17.10. The LOVO source bag was ready for the LOVO.
    17.11. Removed the LOVO final product bag from the disposable kit by sealing the tubing near the bag.

18. Formulate TIL 1:1 in cold CS10 supplemented with 600 IU/mL rhIL-2
    18.1. Calculated required number of cryobags needed. (volume of cell product×2) 100 number of required bags (round down)
    18.2. Calculated the volume to dispense into each bag. (volume of cell product×2) number of required bags volume to add to each bag
    18.3. Aseptically transferred the following materials in Table 6 to the BSC.

TABLE 6

Materials for TIL cryopreservation.

| Item | Minimum Quantity | In-Process Label |
| --- | --- | --- |
| Cell product | 1 | Lot# |
| Aluminum freezer cassette (750 ml) | 1 | n/a |
| Cold CS10 + IL-2 @600 IU/mL | As Needed | Lot# |
| Cell Connect CC1 device | 1 | n/a |
| 750 mL cryobags | calculated | Label aliquots 1- largest# |
| 100 mL syringe | #cryobags + 1 | n/a |
| 3 way stopcock | 1 | n/a |
| Cryovials | 5 | TIL Cryo-product satellite vials |

19. TIL formulation
  19.1. Closed all clamps on Cell Connect CC1.
  19.2. To the cell connect device aseptically attached the LOVO final product, CS10 bag luer lock and the appropriate number of cryobags. Replaced the 60 mL syringe with a 100 mL syringe.
  19.3. The amount of CS10 volume needed was equivalent to the volume of the LOVO final product bag.
  19.4. Opened the stopcock pathway and unclamp the line between the LOVO final product bag and syringe to pull CS10 into the syringe, reclamp CS10 path. Unclamped pathway to the cell bag to push CS10 into the LOVO final product bag. Used the syringe to measure the volume added to the LOVO final product bag. Repeated as necessary using a new syringe until desired amount of CS10 is transferred.
  19.5. Mixed LOVO final product bag by inversion.
  19.6. Replaced 100 mL syringe
  19.7. Opened clamps on 750 mL cryobags one at a time
  19.8. Only opened clamps that are directly associated with the formulated product and the cryobag in use.
  19.9. Used the 100 mL syringe to measure the volume of formulated product leading to the cryobag.
  19.10. Transferred 100 mL of formulated product into each cryobag.
  19.11. After addition to each bag pulled back on the syringe to remove all air bubbles from cryobags and reclamped the associated line.
  19.12. On the final bag pull back a 10 mL retain for QC testing.
  19.13. Sealed each cryobag, leaving as little tubing as possible.
  19.14. Removed the syringe containing the retained sample and transferred to a 50 mL conical tube; transferred 1.5 ml into individual cryovials and froze into a controlled rate freezer.
  19.15. Transferred sealed bags to 4° C. while labels were prepared.
  19.16. Labeled each cryobag with product description, name and date, volume, cell count, and viability.
  19.17. Placed each cryobag into pre-cooled aluminum freezer canisters.
20. Cryopreservation of TIL using Control Rate Freezer (CRF)
  20.1. Followed standard procedure for the controlled rate freezer.
  20.2. After using the CRF, stored cryobags in liquid nitrogen (LN2).
21. Determined expected results and measure acceptance criteria.

Example 2: Process Run on 8 Patient Tumors

The process of Example 1 was run using 8 patient tumors to produce 8 batches of TILs. Good recovery from culture, viability, cell counts, CD3+(indicating the % T cell content) and IFN-gamma (IFN-g or IFN-γ) release were obtained, as shown in Table 7 below and in FIG. 7 through FIG. 10.

TABLE 7

Results of Testing of Identity, Potency, and Viability/Recovery of the Process of Example 1.

| | IFNg (pg/1e6 cells/24 hr) | CD3 (%) | Cells/mL (Viable + Nonviable) | % Recovery Fresh/tovo | % Viability |
|---|---|---|---|---|---|
| M1061T | 4570 | 95.3 | 1.27E+08 | 103 | 88.1 |
| M1062T | 3921 | 99.7 | 1.65E+08 | 89 | 84.5 |

TABLE 7-continued

Results of Testing of Identity, Potency, and Viability/Recovery of the Process of Example 1.

| | IFNg (pg/1e6 cells/24 hr) | CD3 (%) | Cells/mL (Viable + Nonviable) | % Recovery Fresh/tovo | % Viability |
|---|---|---|---|---|---|
| M1063T | 5587 | 98.7 | 1.51E+08 | 112 | 82.1 |
| M1064T | 619 | 84.5 | 1.75E+08 | 83 | 86.8 |
| M1065T | 1363 | 96.8 | 3.42E+07 | 128 | 76.4 |
| EP11001T | 4253 | 90.4 | 1.82E+08 | 92 | 77.9 |
| M1056T | 6065 | 94.2 | 2.11E+08 | 85 | 84.8 |
| M105ST | 1007 | 99 | 2.72E+08 | 89 | 87.6 |

Example 3: Scalability of Modified TIL Process

The studies presented here were performed in a process development (PD) lab, and subsequently, a process qualification (PQ) study utilizing engineering runs was performed in the GMP clean room suite at a manufacturing facility. Three PQ/engineering runs were completed in the GMP facility clean room according to a qualification protocol, and a batch record based on the PD studies presented here. Acceptance criteria for the engineering runs were set prospectively. The PQ study is further summarized below, and test results obtained for the engineering batches are provided in the following sections.

The number of cells generated from pre-rapid expansion protocol (pre-REP) cultures often exceeded 100×10⁶ viable cells. In addition, including a freeze-thaw cycle between the Pre-REP and REP culture steps reduced the viable cell yield. By eliminating the in-process cryopreservation step, the REP could be reliably and regularly initiated with an increased number of TIL. This change allowed the duration of the REP to be decreased by a proportional amount of cell doubling times to roughly 11 days without impacting cell dose. In addition, the reduced culture time from activation to harvest results in a product that is less differentiated and potentially better able to persist in-vivo (Tran 2008).

The PD study validated the initiation of the REP culture with up to 200×10⁶ cells with a fixed number of feeder cells. The optimal time to harvest the REP culture was then evaluated over 9 to 14 days. Cultures were seeded at feeder to TIL ratios ranging from 100:1 to 25:1. Optimization of harvest time was determined by measuring total cell count, viability, immunophenotype, media consumption, metabolite analysis, interleukin-2 (IL-2) analysis, and the functional analyses described below.

Immunophenotyping of cells at the end of the REP culture was evaluated on the basis of the markers listed in Table 8 below. The phenotypic activation and differentiation state of the cells was evaluated. Statistical differences in phenotype were not observed among any of the experimental conditions.

TABLE 8

Markers of Activation and Differentiation Assayed on Process Optimization Cultures.

| Target | Label for Detection | Clone |
|---|---|---|
| Panel 1 | | |
| TCRab (i.e., TCRα/β) | PE/Cy7 | IP26 |
| CD57 | PerCP-Cy5.5 | HNK-1 |
| CD28 | PE | CD28.2 |

TABLE 8-continued

Markers of Activation and Differentiation
Assayed on Process Optimization Cultures.

| Target | Label for Detection | Clone |
|---|---|---|
| CD4 | FITC | OKT4 |
| CD27 | APC-H7 | M-T271 |
| CD56 | APC | N901 |
| CD8a | PB | RPA-T8 |
| Panel 2 | | |
| CD45RA | PE/Cy7 | HI100 |
| CD3 | PerCP/Cy5.5 | SP34-2 |
| CCR7 | PE | 150503 |
| CD8 | FITC | HIT8 |
| CD4 | APC/Cy7 | OKT4 |
| CD38 | APC | HB-7 |
| HLA-DR | PB | L243 |
| Panel 3 | | |
| CD137 | PE/Cy7 | 4B4-1 |
| CD3 | PerCP/Cy5.5 | SP34-2 |
| Lag3 | PE | 3DS223H |
| CD8 | FITC | HIT8 |
| CD4 | APCCy7 | OKT4 |
| PD1 | APC | EH12.2H7 |
| Tim-3 | BV421 | F38-2E2 |

Abbreviations:
PE/Cy7 = Phycoerythrin: Cy-7 Tandem Conjugate;
PerCP-Cy5.5 = Peridinin-chlorophyll-protein Complex: CY5.5 Conjugate;
PE = Phycoerythrin;
FITC = Fluorescein Isothiocyanate Conjugate;
APC-H7 = Allophycocyanin: H7 Tandem Conjugate;
APC = Allophycocyanin;
PB = Pacific Blue ™

Media consumption and metabolite production remained within tolerable limits for all conditions tested; and IL-2 levels remained greater than 150 IU/mL of culture supernatant (data not shown).

Tumor cell killing by T-cells is understood to be mediated by activation of the T-cell receptor on the effector T-cell in response to peptides presented on the surface of tumor cells. Ex vivo expanded T-cells must retain the ability to be activated and proliferate in response to TCR activation if they are to persist in vivo upon infusion and mediate tumor regression.

To assess the activation potential of the cultured cells, TIL harvested at different time points were reactivated with irradiated allogeneic PBMC loaded with OKT3. TIL cultures were harvested after 7 days and assayed for fold-expansion. The results of this study are summarized in TABLE 9.

TABLE 9

Summary of Results: Proliferation of Post-REP TIL
Upon Re-culture with OKT3 Loaded Allogeneic PBMC.

| Harvest Day | Fold-Expansion | SD | P-value (Student 't'test) |
|---|---|---|---|
| Experiment 1 | | | |
| Day 9 | 43 | 6.088 | NA |
| Day 10 | 48 | 3.105 | NA |
| Day 11 | 71 | 11.137 | 0.135 |
| Day 14 | 60 | 6.995 | |
| Experiment 2 | | | |
| Day 9 | 44 | 6.276 | NA |
| Day 10 | 27 | 4.762 | NA |
| Day 11 | 72 | 18.795 | 0.045 |
| Day 14 | 41 | 7.050 | |

TABLE 9-continued

Summary of Results: Proliferation of Post-REP TIL
Upon Re-culture with OKT3 Loaded Allogeneic PBMC.

| Harvest Day | Fold-Expansion | SD | P-value (Student 't'test) |
|---|---|---|---|
| Experiment 3 | | | |
| Day 9 | 54 | 5.810 | NA |
| Day 10 | 54 | 9.468 | NA |
| Day 11 | 65 | 1.674 | 0.071 |
| Day 14 | 50 | 8.541 | |

This study demonstrated that the potential for TIL to be activated in this assay increased with each day of culture through Day 11 (harvest Days 9-11). Cells harvested on Day 11 of the modified process performed similarly to control TIL maintained in culture for 14 days similar to the current process.

These studies demonstrated the scalability of the modified TIL process and established an acceptable range of seeding ratios of TIL to feeder cells. In addition, the growth characteristics were found to persist through Day 14 of culture, while culture conditions remained optimal through Day 11. The conditions tested showed no measurable effect on TIL phenotype. Cells harvested on REP culture Day 11 demonstrated the best ability to respond to reactivation while the cell culture conditions remained within tolerances. These changes were adopted and validated at full scale with the culture split occurring on Day 5 and harvest on Day 11.

Engineering runs were implemented at the process development facility in order to gain experience in manufacturing and testing the TIL product prior to the GMP manufacturing of autologous TIL product for administration to patients. The manufacturing procedure used for the engineering runs was at the same scale as that to be used in the manufacturing of GMP TIL product. Experience in growing TIL from various types of tumors including metastases of melanoma, breast, head and neck squamous cell carcinoma (HNSCC), cervical carcinoma, and lung cancer has determined that the dissection and outgrowth of TIL from metastatic tumor samples is similar for these cancers (Sethuraman 2016, JITC P42). Because the initial isolation of tumor fragments and outgrowth of lymphocytes appears to be similar between tumor histologies, these engineering runs are sufficient to qualify the process for the production of TIL from HNSCC, cervical and melanoma tumors.

Table 10 shows the source and characteristics of tumor samples used for the engineering runs.

TABLE 10

Tumor Samples Tested for Engineering Runs.

| Tumor Sample | Engineering Run 1 | Engineering Run 2 | Engineering Run 3 |
|---|---|---|---|
| Patient ID | 1001185 | 600-D455 | 40231 |
| Source | Biotheme Research | BioOptions | Moffitt |
| Tissue | Lung, Left | Breast, ERPR+Her2− | Melanoma |
| Date Processed | Jan. 5, 2017 | Jan. 12, 2017 | Jan. 26, 2017 |

Release testing of the three engineering runs of TIL at the process development facility was completed (Table 11) as described below. Product was tested on Day 16 and Day 22. IFN-γ secretion was also determined for the three engineering runs (Table 12) as detailed elsewhere.

TABLE 11

Product Release Test Results for Engineering Runs at Process Development Facility.

|  | Parameter | Test Method | Acceptance Criteria | Run 1 | Run 2 | Run 3 |
|---|---|---|---|---|---|---|
| Day 16 | Sterility* | BacT Alert | No Grwoth | No growth | No growth | No growth |
|  | Mycoplasma | PCR | Negative from Day 7 split | Negative | Negative | Negative |
| Day 22 | Viability (%) | AOPI | ≥70% | 82.3% | 85.13% | 84.6% |
|  | Total Viable Cells | AOPI | Report results | $2.6 \times 10^{10}$ | $1 \times 10^{10}$ | $1.4 \times 10^{11}$ |
|  | Sterility | Gram Stain | Negative | Negative | Negative | Negative |
|  | Sterility Final Product* | BacT/Alert | No Growth | Negative | Negative | Pending |
|  | % CD45$^+$CD3$^+$ | Flow cytometey | ≥90% | 99.3% | 96.3% | 99.8% |
|  | Endotoxin | Endo Safe | ≤0.7 EU/mL | <0.5 EU/mL | <0.5 EU/mL | <0.5 EU/mL |
|  | Mycoplasma Final Product | PCR | Negative | Negative | Negative | Negative |
|  | Appearance | Visual Inspection | Intact bag with no visible clumps | Intact bag, no visible clumps | Intact bag, no visible clumps | Intact bag, no visible clumps |

*Final sterility results for Day 16 and Day 22 are not available until after final product release for shipment. The gram stain results from Day 22 are used for sterility shipment release.

TABLE 12

Additional Functional Characterization: Measurement of IFN-γ Secretion.

| Functional Characterization | Method | Expected Results | Run 1 | Run 2 | Run 3 |
|---|---|---|---|---|---|
| IFN-γ Stimulation with anti-CD3, CD28, CD137 (pg/million cells) | ELISA | >2 standard deviations over non-stimulated | 3085 +/− 182 | 2363 +/− 437 | pending |
| IFN-γ Non-stimulated (pg/million cells) | ELISA | Not applicable | 34 +/− 5 | 27 +/− 10 | pending |

In conclusion, the data from the engineering runs demonstrate that TIL drug product can be manufactured for the purpose of autologous administration to patients.

Example 4: Lymphodepletion

Cell counts can be taken at day 7 and prior to lymphodepletion. The final cell product included up to approximately 150×10$^9$ viable cells formulated in a minimum of 50% HypoThermosol™ in Plasma-Lyte A™ (volume/volume) and up to 0.5% HSA (compatible for human infusion) containing 300 IU/mL IL2. The final product was available for administration in one of two volumes for infusion:
1) 250 mL (in a 300-mL capacity infusion bag) when the total TIL harvested are ≤75×10$^9$
OR
2) 500 mL (in a 600-mL capacity infusion bag) when the total TIL harvested are <150×10$^9$ The total number of cells that could be generated for the final TIL infusion product for each patient due to patient-to-patient variation in T-cell expansion rates during the REP step cannot be predicted. A lower limit of cells on day 3, 4, 5, 6, 7 of the 3 to 14-day REP is set based on the minimum number of cells needed in order to make a decision to lymphodeplete the patient using the cyclophosphamide plus fludarabine chemotherapy regimen. Once we have begun lymphodepletion based on this minimal attained cell number, we are committed to treating the patient with the available number of TIL we generate in the REP by any of days 3 to 14, and in many cases day 7. The upper limit of the range for infusion (150×10$^9$ viable cells) is based on the known published upper limit safely infused where a clinical response has been attained. Radvanyi, et al., Clin *Cancer Res* 2012, 18, 6758-6770.

Example 5: Process 2A—Day 0

This example describes the detailed day 0 protocol for the 2A process described in Examples 1 to 4.
Preparation.
1. Confirmed Tumor Wash Medium, CM1, and IL-2 are within expiration date.
2. Placed CM1 (cell media 1) in incubator.
Method.
1. Cleaned the biological safety cabinet (BSC).
2. Set up in-process surveillance plates and left in biosafety cabinet for 1-2 hours during procedure.
3. Placed the TIL media CM1 in the biological safety cabinet.
4. Prepared TIL media CM1 containing 6000 IU/mL IL-2:
  4.1. 1 L CM1
  4.2. 1 ml IL-2 (6,000,000 IU/mL)
  4.3. Placed 25 ml of CM1+IL2 into 50 ml conical to be used for fragments when adding to G-REX.
  4.4. Placed in 37° C. incubator to pre-warm 5. Wiped G-REX 100MCS package with 70% alcohol and place in biosafety cabinet. Closed all clamps except filter line.
6. Performed Acacia pump calibration.
7. Attached the red line of G-REX 100MCS flask to the outlet line of the acacia pump boot.
8. Attached pumpmatic to inlet line of pump boot and placed in bottle with media. Released clamps to pump boot.
9. Pumped remaining 975 ml of pre-warmed CM1 containing 6,000 IU/ml of IL-2 in each G-REX 100MCS bioreactor.
10. Heated seal red line, disconnect from pump boot.
11. Placed label on G-REX.
12. Placed G-REX 100MCS in incubator until needed.

Tissue Dissection
1. Recorded the start time of tumor processing.
2. Transferred Tumor Wash Medium to BSC.
3. Placed 5 100 mm petri dishes in biosafety cabinet, 3 for washes, 1 for holding and 1 for unfavorable tissue. Labeled dishes accordingly. Unfavorable tissue was indicated by yellow adipose tissue or necrotic tissue.
4. Placed three 6 well plates into biosafety cabinet.
5. Pipetted 3-5 mL of Tumor Wash Medium into each well of one six well plates for excess tumor pieces.
6. Pipetted 50 mL of Tumor Wash Medium to wash dishes 1-3 and holding dish.
7. Placed two 150 mm dissection dishes into biosafety cabinet.
8. Placed 3 sterile 50 mL conical tubes into the BSC.
9. Labeled one as forceps tumor wash medium, the second as scalpel tumor wash medium, and third for Tumor wash medium used in for lid drops.
10. Added 5-20 mL of tumor wash medium to each conical. The forceps and scalpels were dipped into the tumor wash media as needed during the tumor washing and dissection process.
11. Placed scapel and forceps in appropriate tubes.
12. Using long forceps removed the tumor(s) from the Specimen bottle and transferred to the Wash 1 dish.
13. Incubated the tumor at ambient in the Wash 1 dish for ≥3 minutes.
14. During the incubation, re-labeled the Specimen bottle "Bioburden" and stored at 2-8° C. until the final harvest or further sterility testing is required.
15. Using forceps transferred the tumor to the Wash 2 dish.
16. Incubated the tumor at ambient in the Wash 2 dish for ≥3 minutes.
17. During the incubation, using a transfer pipette, added approximately 4 evenly-spaced, individual drops of Tumor Wash Medium to each circle of the 6 well plate lids designated as Tumor Fragments dishes.
18. Using forceps transferred the tumor to the Wash 3 dish.
19. Incubated the tumor at ambient in the Wash 3 dish for ≥3 minutes.
20. The 150 mm dish lid was used for dissection. Placed a ruler underneath.
21. Using forceps transferred the tumor to the Dissection dish, measured and recorded the length of the tumor.
22. Took photograph of tumor.
23. Performed an initial dissection of the tumor pieces in the Dissection dish into intermediate pieces taking care to conserve the tumor structure of each intermediate piece.
24. Transferred any intermediate tumor pieces not being actively dissected into fragments to the tissue holding dish to ensure the tissue remained hydrated during the entire dissection procedure.
25. Worked with one intermediate tumor piece at a time, carefully sliced the tumor into approximately 3×3×3 mm fragments in the Dissection Dish, using the rule underneath the dish for reference
26. Continued dissecting fragments from the intermediate tumor piece until all tissue in the intermediate piece had been evaluated.
27. Selected favorable fragments and using a transfer pipette transferred up to 4 favorable fragments into the wash medium drops in one circle in the Tumor Fragments dish. Using a transfer pipette scalpel or forceps, transferred, as much as possible of the unfavorable tissue and waste product to the Unfavorable Tissue dish to clear the dissection dish. All remaining tissue was place into one of the wells of the six-well plate. (Unfavorable tissue was indicated by yellow adipose tissue or necrotic tissue.)
28. Continued processing by repeating step 23-26 for the remaining intermediate tumor pieces, working one intermediate piece at a time until the entire tumor had been processed. (Obtained a fresh scalpel or forceps as needed, to be decided by processing technician.)
29. Moved fragment plates toward rear of hood.
30. Using transfer pipette, the scapel, or the forceps, transferred up to 50 of the best tumor fragments to the 50 mL conical tube labeled tumor fragments containing the CM1.
31. Removed floaters from 50 mL conical with transfer pipet. Recorded number of fragments and floaters.
32. Removed all unnecessary items from hood, retaining the favorable tissue plates if they contain extra fragments. Wiped hood with alcohol wipe.
33. Removed G-REX 100MCS from incubator, wipe with 70% alcohol and place in biosafety cabinet.
34. Swirled conical with tumor fragments and poured the contents on the 50 ml conical into the G-Rex 100MCS flask
35. If one or more tumor fragments transferred to the G-Rex 100M flask float, obtained one additional tumor fragment when available from the Favorable Tissue Dish and transfer it to the G-Rex 100M flask.
36. Recorded incubator # (s) and total number of fragments added to each flask.
37. Placed the G-REX 100M bioreactor in 37° C., 5% $CO_2$ incubator
38. Any unused tumor were placed in 100 mL of Hypo-Thermosol and delivered to the laboratory.
39. Recorded the stop time of tumor processing.
40. Discarded any un-used TIL complete media containing IL-2 and any un-used aliquots of IL-2. 41. Cleaned biological safety cabinet.
42. Placed the Bioburden sample in the proper storage conditions.
43. Recorded data.
44. Saved the picture as file specimen ID #Tumor process Date to the prepared patient's file.
45. Ordered and ensured delivery of settle plates to the microbiology lab.

Example 6: Process 2A—Day 11

This example describes the detailed day 11 protocol for the 2A process described in Examples 1 to 4.

Prior Preparation.
1. Day before processing:
   1.1. CM2 could be prepared the day before processing occurred. Place at 4° C.
2. Day of processing.
   2.1. Prepared the feeder cell harness.
      2.1.1. Closed all clamps on a CC2 and 4S-4M60 connector sets.
      2.1.2. Sterile welded 4 spikes of 4S-4M60 harness to the spike line on the CC2 removing the spike.
      2.1.3. Set aside for feeder cell pooling.
   2.2. Prepared 5 mL of cryopreservation media per CTF-FORM-318 and place at 4° C. until needed.

Clean Room Environmental Monitoring—Pre-Processing
1. Recorded clean room information.
2. Biosafety Cabinets (BSC) were cleaned with large saturated alcohol wipes or alcohol spray.
3. Verified Particle Counts for 10 minutes before beginning processing.
4. Set up in-process surveillance plates and left in biosafety cabinet for 1-2 hours during procedure.

Prepare G-Rex 500MCS Flask:
1. Using 10 mL syringe aseptically transferred 0.5 mL of IL-2 (stock is $6 \times 10^6$ IU/mL) for each liter of CM2 (cell media 2) into the bioprocess bag through an unused sterile female luer connector.
2. Used excess air in the syringe to clear the line, drew up some media from the bag and expel back into back. This ensured all the IL-2 has been mixed with the media. Mixed well.
3. Opened exterior packaging and place G-Rex 500MCS in the BSC. Closed all clamps on the device except large filter line.
4. Sterile welded the red harvest line from the G-Rex 500MCS to the pump tubing outlet line.
5. Connected bioprocess bag female luer to male luer of the Pump boot.
6. Hung the bioprocess bag on the IV pole, opened the clamps and pump 4.5 Liters of the CM2 media into the G-Rex 500MCS. Cleared the line, clamp, and heat seal.
7. Retained the line from pump to media. It was used when preparing feeder cells.
8. Placed G-Rex 500MCS in the incubator.

Prepare Irradiated Feeder Cells
1. Sealed and removed spike(s) from IL TP. Clamped both lines.
2. Recorded the dry weight of a 1 L transfer pack (TP).
3. Sterile welded the 1 L transfer pack to the acacia pump boot ~12" from bag.
4. The other end of the pump tubing was still connected to the 10 L labtainer.
5. Pumped 500 mL CM2 by weight into the TP.
6. Closed clamp and sealed close to weld joint.
7. Placed in incubator.
8. Verified and Logged out feeder cell bags.
9. Recorded feeder lot used.
10. Wiped bags with alcohol.
11. Placed in zip lock bags.
12. Thawed feeder cells in the 37° C. (+/−1° C.) water bath. Recorded temperature of water bath.
13. Removed and dried with gauze.
14. Passed feeder cells through pass thru into Prep Room.
15. Transferred to BSC in Clean Room.
16. Using the previously prepared feeder harness, welded the 1 L TP with media to one of the unused lines on the sample port side of the 3 way stopcock as close as possible to the seal junction loosing as little tubing as possible.
17. Put feeder harness into BSC.
18. Spiked each of the 3 feeder bags with the spike from the feeder harness into the single port of the feeder bag.
19. Rotated the stopcock valve so the 1 L TP is in the "OFF" position.
20. Working with one bag at a time, opened the clamps on the line to the feeder bag, expel air in syringe and draw the contents of the feeder bag into the syringe. Expelled air from syringe helped in recovering cells. Closed clamp to feeder bag.
21. Recorded the volume recovered of thawed feeder cells in each bag.
22. Rotated the stopcock valve so that the feeder bag is in the "OFF" position
23. Opened the clamp on the TP and dispense the contents of the syringe into the TP.
24. Ensured the line has been cleared and re-clamp the TP. You may have had to draw some air into syringe from TP for use in clearing the line.
25. Mixed the cells well.
26. Closed clamp to feeder bag.
27. Rotated stopcock so syringe port is in the "OFF" position. Disconnected the 60 mL syringe from the stopcock.
28. Replaced with new syringe for each feeder bag.
29. Left syringe on after final bag.
30. Mixed final feeder formulation well.
31. Rotated stopcock so feeder cell suspension is in the "OFF" position.
32. Mixed cells cell and using a 5 mL syringe and needless port, rinsed port with some cell solution to ensure accurate sampling and remove 1 ml of cells, placed into tube labeled for counting.
33. Repeated with second syringe. These two independent samples each had a single cell count performed.
34. Turned stopcock so feeder suspension is in the "OPEN" position and using the 60 ml syringe attached to harness expelled air into the TP to clear the line.
35. Removed syringe and covered luer port with a new sterile cap.
36. Heated seal the TP close to weld joint, removed the harness.
37. Recorded mass of transfer pack with cell suspension and calculated the volume of cell suspension.
38. Placed in incubator.
39. Performed a single cell counts on the feeder cell sample and record data and attach counting raw data to batch record.
40. Documented the Cellometer counting program.
41. Verified the correct dilution was entered into the Cellometer.
42. Calculated the total viable cell density in the feeder transfer pack.
43. If cell count was $<5 \times 10^9$, thawed more cells, count, and added to feeder cells.
44. Re-weighed feeder bag and calculated volume.
45. Calculated volume of cells to remove.

Addition of Feeder to G-REX
1. Sterile welded a 4" transfer set to feeder TP.
2. In the BSC attached an appropriately sized syringe to the female luer welded to the feeder transfer pack.
3. Mixed cells well and removed the volume calculated in step 40 or 41 to achieve $5.0 \times 10^9$ cells. Discarded unneeded cells.

4. Using a 1 mL syringe and 18G needle draw up 0.150 mL of OKT3, removed needle and transferred to the feeder TP through the female luer.
5. Rinsed tubing and syringe with feeder cell and mixed bag well. Cleared the line with air from syringe.
6. Removed the G-Rex 500MCS from the incubator, wiped with alcohol wipes and placed beside the SCD.
7. Sterile welded the feeder bag to the red line on the G-Rex 500MCS. Unclamped the line and allowed the feeder cells to flow into the flask by gravity.
8. Ensured the line has been completely cleared then heat sealed the line close to the original weld and removed the feeder bag.
9. Returned the G-Rex 500MCS to the incubator and recorded time.

Prepare TIL: Record Time Initiation of TIL Harvest

1. Carefully removed G-Rex 100MCS from incubator and closed all clamps except large filter line.
2. Welded a 1 L transfer pack to the redline on the G-REX 100MCS.
3. Closed clamp on a 300 ml TP. Heat seal ~12 inches from the bag removing the spike. Recorded dry weight/mass.
4. Sterile welded the 300 mL transfer pack to the cell collection line on the 100MCS close to the heat seal. Clamped the line.
5. Released all clamps leading to the 1 L TP.
6. Using the GatheRex transferred ~900 mL of the culture supernatant to the 1 L transfer pack. Gatherex stopped when air entered the line. Clamped the line and heat seal.
7. Swirled the flask until all the cells had been detached from the membrane. Checked the membrane to make sure all cells are detached.
8. Tilted flask away from collection tubing and allowed tumor fragments to settle along edge.
9. Slowly tipped flask toward collection tubing so fragments remain on opposite side of flask.
10. Using the GatheRex transferred the residual cell suspension into the 300 mL transferred pack avoiding tumor fragments.
11. Rechecked that all cells had been removed from the membrane.
12. If necessary, back washed by releasing clamps on GatheRex and allowed some media to flow into the G-Rex 100MCS flask by gravity.
13. Vigorously tapped flask to release cells and pumped into 300 ml TP.
14. After collection was complete, closed the red line and heat seal.
15. Heated seal the collection line leaving roughly the same length of tubing as when dry weight was recorded.
16. Recorded mass (including dry mass) of the 300 ml TP containing the cell suspension and calculated the volume of cell suspension.
17. In the BSC spike the 300 mL TP with a 4" plasma transferred set. Mixed cells well. Aseptically attached a 5 mL syringe draw 1 mL, placed in cryo vial. Repeated with second syringe. These were used for cell counting, viability.
18. Re-clamped and replaced luer cap with new sterile luer cap.
19. Placed in incubator and recorded time place in incubator.
20. Performed a single cell count on each sample and recorded data and attach counting raw data to batch record.
21. Documented the Cellometer counting program.
22. Verified the correct dilution was entered into the Cellometer.
23. If necessary adjusted total viable TIL density to ≤2×10$^8$ viable cells.
24. Calculated volume to remove or note adjustment not necessary.
25. In the BSC aseptically attached an appropriately sized syringe to the 300 mL TP.
26. If required, removed the calculated volume of cells calculated in the "Calculate volume to remove" table.
27. Clamped and heat sealed the 300 ml TP.
28. Transferred excess cells to an appropriately sized conical tube and placed in the incubator with cap loosened for later cryopreservation.
29. Removed the G-Rex 500MCS from the incubator and place beside the SCD.
30. Sterile welded the 300 ml TP to the inlet line of the Acacia pump.
31. Sterile welded the red line of the G-Rex 500MCS to the outlet line of the Acacia pump.
32. Pumped cells into flask.
33. Ensured the line has been completely cleared then heat sealed the red line close to the original weld.
34. Checked that all clamps on the G-Rex 500MCS were closed except the large filter line.
35. Returned the G-Rex 500MCS to the incubator and record the time placed in the G-Rex incubator.
36. Ordered and ensured delivery of settle plates to the microbiology lab.

Cryopreservation of Excess

Calculated amount of freezing media to add to cells:

TABLE 13

| Target cell concentration was 1 × 10$^8$/ml | |
|---|---|
| A. Total cells removed (from step 15) | mL |
| B. Target cell concentration | 1 × 10$^8$ cells/mL |
| Volume of freezing media to add (A/B) | mL |

37. Spun down TIL at 400×g for 5 min at 20° C. with full brake and full acceleration.
38. Aseptically aspirated supernatant.
39. Gently tapped bottom of tube to resuspend cells in remaining fluid.
40. While gently tapping the tube slowly added prepared freezing media.
41. Aliquoted into appropriate size cryo tubes and record time cells placed into −80° C.

Example 7: Process 2A—Day 16

This example describes the detailed day 16 protocol for the 2A process described in Examples 1 to 4.

Clean Room Environmental Monitoring—Pre-Processing.

1. Biosafety Cabinets were cleaned with large saturated alcohol wipes or alcohol spray.
2. Verified Particle Counts for 10 minutes before beginning processing.
3. Set up in-process surveillance plates and left in biosafety cabinet for 1-2 hour during procedure.

Harvest and Count TIL.
1. Warmed one 10 L bag of CM4 for cultures initiated with less than 50×10$^6$ TIL in a 37° C. incubator at least 30 minutes or until ready to use.
2. In the BSC aseptically attached a Baxter extension set to a 10 L Labtainer bag.
3. Removed the G-Rex 500MCS flask from the incubator and placed on the benchtop adjacent the GatheRex. Checked all clamps were closed except large filter line. Moved the clamp on the quick connect line close to the "T" junction.
4. Sterile welded a 10 L Labtainer to the red harvest line on the G-Rex 500MCS via the weldable tubing on the Baxter extension.
5. Heat sealed a 2 L transfer pack 2" below the "Y removing the spike and recorded dry weight. Sterile welded the 2 L TP to the clear collection line on the G-Rex 500MCS.
6. Set the G-Rex 500MCS on a level surface.
7. Unclamped all clamps leading to the 10 L Labtainer and using the GatheRex transferred ~4 L of culture supernatant to the 10 L Labtainer.
8. Harvested according to appropriate GatheRex harvesting instructions.
9. Clamped the red line and recorded time TIL harvest initiated.
10. GatheRex stopped when air entered the line. Clamped the red line.
11. After removal of the supernatant, swirled the flask until all the cells had been detached from the membrane. Tilted the flask to ensure hose was at the edge of the flask.
12. Released all clamps leading to the 2 L TP and using the GatheRex transfer the residual cell suspension into the 2 L TP maintaining the tilted edge until all cells were collected.
13. Inspected membrane for adherent cells.
14. If necessary, back washed by releasing clamps on red line and allowed some media to flow into the flask by gravity.
15. Closed the red line and triple heat seal.
16. Vigorously tapped flask to release cells.
17. Added cells to 2 L TP.
18. Heated seal the 2 L transfer pack leaving roughly the same length of tubing as when dry weight was recorded.
19. Retained G-Rex 500MCS, it was reused in the split.
20. Recorded mass of transfer pack with cell suspension and calculated the volume of cell suspension.
21. Determined cell suspension volume, including dry mass.
22. Sterile welded a 4" transfer set to the cell suspension bag.
23. In the BSC mixed the cells gently and with 20 cc syringe draw up 11 ml and aliquoted as shown in Table 14:

TABLE 14

| Testing parameters. | | |
|---|---|---|
| Test | Sample volume | Vessel |
| Cell Count and viability | 2-2 mL samples | Cryovials |
| Mycoplasma | 1 mL | Cryovial stored at 4° C. until testing completed. |
| Sterility | 1 mL | Inoculated 0.5 mL into one each anaerobic and aerobic culture bottles |
| Flow | 2-2 mL | Unused cell count (Cryopreserved for future batch testing) |
| Remainder of cells | | Discarded |

24. Heat sealed. Closed the luer connection retaining the clamp
25. Labeled and placed the cell suspension in the incubator and recorded time placed in the incubator.
26. Calculated new volume.
27. Recorded Volume in 2 L transfer pack based on volume of cell suspension and volume removed for QC (11 mL).
28. Inoculated and ordered sterility testing.
29. Stored the *mycoplasma* sample at 4° C. in the pending rack for *mycoplasma* testing.
30. Set aside until TIL was seeded.
Cell Count:
Performed single cell counts and recorded data and attach counting raw data to batch record. Documented Dilution. Documented the Cellometer counting program. Verified the correct dilution was entered into the Cellometer.
Method Continued:
31. Calculated the total number of flasks required for subculture
   **Re-used the original vessel and rounded fractions of additional vessels up.
IL-2 Addition to CM
1. Placed 10 L bag of Aim V with Glutamax in the BSC.
2. Spiked the media bag with a 4" plasma transfer set.
3. Attached an 18G needle to a 10 mL syringe and draw 5 mL of IL-2 into the syringe (final concentration is 3000 IU/ml).
4. Removed the needle and aseptically attach the syringe to the plasma transfer set and dispensed IL-2 into the bag.
5. Flushed the line with air, draw up some media and dispense into the bag. This insured all IL-2 is in the media.
6. Repeated for remaining bags of Aim V.
Prepare G-REX500MCS Flasks
1. Determined amount of CM4 to add to flasks. Recorded volume of cells added per flask and volume of CM4 5000 mL-A.
2. Closed all clamps except the large filter line.
3. Sterile welded the inlet line of the Acacia pump to the 4" plasma transfer set on the media bag containing CM4.
4. Sterile welded the outlet line of the pump to the G-Rex 500MCS via the red collection line.
5. Pump determined amount of CM4 into the G-Rex 500MCS using lines on flask as guide.
6. Heated seal the G-Rex 500MCS red line.
7. Repeated steps 4-6 for each flask. Multiple flasks could be filled at the same time using gravity fill or multiple pumps. A "Y" connector could be welded to the outlet line of the pump and the two arms welded to two G-Rex 500MCS flasks filling both at the same time.
8. Placed flasks in a 37° C., 5% $CO_2$.

Seed Flasks With TIL
1. Closed all clamps on G-Rex 500MCS except large filter line
2. Sterile welded cell product bag to inlet line of the Acacia pump.
3. Sterile welded the other end of the pump to the red line on the G-Rex 500MCS.
4. Placed pump boot in pump.
5. Placed the cell product bag on analytical balance and recorded time TIL added to G-REX flask.
6. Zeroed the balance.
7. Unclamped lines and pump required volume of cells into G-Rex 500MCS by weight assuming 1 g=1 mL.
8. Turned cell bag upside down and pump air to clear the line. Heated seal red line of G-Rex 500MCS. Placed flask in incubator.
9. Sterile welded the outlet line of the pump to the next G-Rex 500MCS via the red collection line
10. Mixed cells well.
11. Repeated cell transfer for all flasks.
12. Placed flasks in a 37° C., 5% $CO_2$ and recorded time TIL added to G_REX flask.
13. Ordered testing for settle plates to the microbiology lab.
14. Recorded accession numbers.
15. Ordered testing for aerobic and anaerobic sterility.
16. Ensured delivery of plates and bottles to the microbiology lab.

Cryopreservation of Flow or Excess Cells:
1. Calculated amount of freezing media required:
   a. Target cell concentration was $1 \times 10^8$/ml; record total cells removed. Target cell concentration was $1 \times 10^8$ cells/mL. Calculated total volume of freezing media to add.
2. Prepared cryo preservation media and placed at 40° C. until needed.
3. Spun down TIL at 400×g for 5 min at 20° C. with full brake and full acceleration.
4. Aseptically aspirated supernatant.
5. Gently tapped bottom of tube to resuspend cells in remaining fluid.
6. While gently tapping the tube slowly added prepared freezing media.
7. Aliquoted into appropriate sized labelled cryo tubes.
8. Placed vial in a Mr. Frosty or equivalent and placed in a −80° C. freezer.
9. Within 72 hours transferred to permanent storage location and documented and recorded date and time placed in −80° C. freezer.

Example 8: Process 2A—Day 22

This example describes the detailed day 22 protocol for the 2A process described in Examples 1 to 4.

Document Negative In-Process Sterility Results
Before beginning harvest, obtained the Day 16 preliminary sterility results from Microbiology lab. Contacted the Laboratory Director or designee for further instructions if the results were positive.

Clean Room Environmental Monitoring—Pre-Processing
1. Verified Particle Counts for 10 minutes before beginning processing.
2. Biosafety Cabinets were cleaned with large saturated alcohol wipes or alcohol spray.
3. Set up in-process surveillance plates and left in biosafety cabinet for 1-2 hour during procedure.

Advanced Preparation
1. In BSC aseptically attached a Baxter extension set to a 10 L labtainer bag or equivalent. Label LOVO filtrate bag.
2. Placed three 1 L bags of PlasmaLyte A in the BSC
3. Prepared pool and labeled the PlasmaLyte A bags with 1% HSA:
   3.1. Closed all clamps on a 4S-4M60 Connector set and spiked each of the PlasmaLyte bags.
   3.2. Welded one of the male ends of the 4S-4M60 to the inlet line of the Acacia pump boot.
   3.3. Welded the outlet line of the pump boot to a 3 liter collection bag. Closed all clamps on 3 L bag except the line to pump.
   3.4. Pumped the 3 liters of Plasmalyte into the 3 liter bag. If necessary removed air from 3 L bag by reversing the pump.
   3.5. Closed all clamps except line with female luer.
   3.6. Using two 100 mL syringes and 16-18G needles, load 120 mL of 25% HSA. Red capped syringes.
   3.7. Attached one syringe to the female luer on the 3 liter bag and transferred HSA to 3 L PlasmaLyte bag. Mix well.
   3.8. Repeated with second syringe.
   3.9. Mixed well.
   3.10. Closed all clamps.
   3.11. Using a 10 mL syringe, removed 5 mL of PlasmaLyte with 1% HSA from the needleless port on the 3 liter bag.
   3.12. Capped syringe and kept in BSC for IL-2 dilution.
   3.13. Closed all clamps.
   3.14. Heated seal removing the female luer line from the pump boot.
   3.15. Labeled LOVO Wash buffer and date. Expired within 24 hrs at ambient temperature.

IL-2 Preparation
1. Dispensed Plasmalyte/1% HSA from 5 mL syringe into a labeled 50 ml sterile conical tube.
2. Added 0.05 mL IL-2 stock to the tube containing PlasmaLyte.
3. Labeled IL-2 $6 \times 10^4$
4. Capped label and store at 2-8° C. Record volumes.

Preparation of Cells
1. Closed all clamps on a 10 L Labtainer bag. At Attach Baxter extension set to the 10 L bag via luer connection.
2. Removed the G-REX 500M flasks from the 37° C.
3. Sterile welded the red media removal line from the G-Rex 500MCS to the extension set on the 10 L bioprocess bag.
4. Sterile welded the clear cell removal line from the G-Rex 500MCS to a 3 L collection bag and labeled "pooled cell suspension".
5. Unclamped red line and 10 L bag.
6. Used the GatheRex pump, volume reduced the first flask.
Note: If an air bubble was detected then the pump could stop prematurely. If full volume reduction was not complete reactivated GatheRex pump.
7. Closed the clamp on the supernatant bag and red line.
8. Swirled the G-REX 500M flask until the TIL were completely resuspended while avoiding splashing or foaming. Made sure all cells have been dislodged from the membrane.
9. Opened clamps on clear line and 3 L cell bag.
10. Tilted the G-Rex flask such that the cell suspension was pooled in the side of the flask where the collection straw was located.

11. Started GatherRex to collect the cell suspension. Note: If the cell collection straw was not at the junction of the wall and bottom membrane, rapping the flask while tiled at a 450 angle was usually sufficient to properly position the straw.
12. Ensured all cells had been removed from the flask.
13. If cells remained in the flask, added 100 mL of supernatant back to the flask, swirled, and collected into the cell suspension bag.
14. Closed clamp on the line to the cell collection bag. Released clamps on GatheRex.
15. Heated seal clear line of G-Rex 500MCS.
16. Heated seal red line of G-Rex 500MCS.
17. Repeated steps 3-16 for additional flasks.
18. It was necessary to replace 10 L supernatant bag as needed after every 2nd flask.
19. Multiple GatherRex could be used.
20. Documented number of G-Rex 500MCS processed.
21. Heated seal cell collection bag. Recorded number of G-REX harvested.
22. With a marker made a mark ~2" from one of the female luer connectors on a new 3 liter collection bag.
23. Heated seal and removed the female luer just below the mark.
24. Labeled as LOVO Source Bag
25. Recorded the dry weight.
26. Closed all clamps of a 170 µm blood filter.
27. Sterile welded the terminal end of the filter to the LOVO source bag just below the mark.
28. Sterile welded a source line of the filter to the bag containing the cell suspension.
29. Elevated the cell suspension by hanging cells on an IV pole to initiate gravity-flow transfer of cells. (Note: Did not allow the source bag to hang from the filtration apparatus.)
30. Opened all necessary clamps and allow TIL to drain from the cell suspension bag through the filter and into the LOVO source bag.
31. Once all cells were transferred to the LOVO source bag, closed all clamps, heated seal just above the mark and detached to remove filter.
32. Mixed bag well and using a two 3 mL syringe take 2 independent 2 mL samples from the syringe sample port for cell counting and viability.
33. Weighed the bag and determined the difference between the initial and final weight.
34. Recorded data and place in incubator, including dry mass.

Cell Count.

Performed a single cell count on each sample and recorded data and attach counting raw data to batch record. Documented the Cellometer counting program. Verified the correct dilution was entered into the Cellometer. Determined total number of nucleated cells. Determined number of TNC to remove to retain=$1.5 \times 10^{11}$ cells for LOVO processing. Place removed cell into appropriate size container for disposal.

LOVO Harvest

The 10 L Labtainer with Baxter extension set in Prior Preparation was the replacement filtrate bag welded to the LOVO kit later on. Turned LOVO on and follow the screen displays.

Check weigh scales and pressure sensor

To access the Instrument Operation Profile:
1. Touched the information button.
2. Touched the instrument settings tab.
3. Touched the Instrument Operation Profile button.
4. The Instrument Operation Profile displayed.

Check the Weigh Scales
1. Made sure there was nothing hanging on any of the weigh scales and reviewed the reading for each scale.
2. If any of the scales read outside of a range of 0+/−2 g, performed weigh scale calibration as described in the Weigh Scale Calibration Manual from the manufacturer.
3. If all scales were in tolerance with no weight hanging, proceed to hang a 1-kg weight on each scale (#1-4) and reviewed the reading.
4. If any of the scales read outside of a range of 1000+/− 10 g when a 1-kg weight was hanging, performed weigh scale calibration as described in the LOVO Operator's Manual from the manufacturer.

Check the Pressure Sensor
1. Reviewed the pressure sensor reading on the Instrument Operation Profile Screen.
2. N/A: If the pressure sensor reading was outside 0+/−10 mmHg, stored a new atmospheric pressure setting in Service Mode as described in the LOVO Operator's Manual from the manufacturer.
   a. Touched the check button on the Instrument Operation Profile screen.
   b. Touched the check button on the Instrument Settings tab.
3. If weigh scale calibration had been performed or a new atmospheric pressure setting had been stored, repeated the relevant sections.

To start the procedure, selected the "TIL G-Rex Harvest" protocol from the drop-down menu on the Protocol Selection Screen and press Start.
1. The Procedure Setup Screen displayed.
2. Touched the Solutions Information button.
3. The Solution 1 Screen displayed. Review the type of wash buffer required for Solution 1. (Should read PlasmaLyte.)
4. Touched the Next button to advance to the Solution 2 Screen. Reviewed the type of wash buffer required for Solution 2. (Should read "NONE", indicating that the protocol had been configured to only use one type of wash buffer, which was PlasmaLyte)
5. Touched the check button on the Solution 2 Information Screen to return to the Procedure Setup screen.
6. Touched the Procedure Information Button.
7. The Procedure Information Screen displayed.
8. Touched the User ID entry field. A keypad will display. Entered the initials of the performer and verifier. Touched the button to accept the entry.
9. Touched the Source ID entry field. A keypad will display. Entered the product lot #. Touched the button to accept the entry.
10. Touched the Procedure ID entry field. A keypad will display. Entered "TIL Harvest". Touched the button to accept the entry.
11. If there are extra notes to record, touched the Procedure Note entry field. A keypad displayed. Entered any notes. Touched the button to accept the entry.

NOTE: The Procedure Note entry field is optional and can be left blank.

12. Touched the check button on the Procedure Information Screen to return to the Procedure Setup Screen.
13. Verified that a "check" displays in the Procedure Information button. If no "check" displays, touched the Procedure Information button again and ensured that the User ID, Source ID, and Procedure ID fields all had entries.

14. Touched the Parameter Configuration Button.
15. The General Procedure Information Screen displayed.
16. Touched the Source Volume (mL) entry field. A numeric keypad displayed. Entered the Calculated volume of cell suspension (mL) from Table 1 17. Touched the button to accept the entry.
18. Touched the Source PCV (%) entry field. The TIL (viable+dead) screen displays.
19. Touched the Cell Concentration entry field. A numeric keypad displayed. Entered the Total Cellular concentration/mL from Table 14 in the Source product in units of "×$10^6$/mL". The entry could range from 00.0 to 99.9. Touched the button to accept the entry and return to the General Procedure Information Screen. NOTE: After the Cell Concentration was accepted, the Source PCV (%) entry field on the General Procedure Information Screen displayed the PCV % calculated by the LOVO, based on the Cell Concentration entry made by the operator.
20. On the General Procedure screen, touched the Next button to advance to screen 4 of 8, the Final Product Volume (Retentate Volume) screen. Note: Screens 2 and 3 did not have any entry fields for the operator to fill in.
21. The Final Product Volume (Retentate Volume) screen displayed.
22. Using the Total nucleated cells (TNC) value from Table 15, determined the final product target volume in the table below (Table 16). Entered the Final Product Volume (mL) associated with that Cell Range during LOVO Procedure setup.

TABLE 15

Determination of Final Product Target Volume.

| Cell Range | Final Product (Retentate) Volume to Target (mL) |
|---|---|
| 0 < Total (Viable + Dead) Cells ≤ 7.1E10 | 150 |
| 7.1E10 < Total (Viable + Dead) Cells ≤ 1.1E11 | 200 |
| 1.1E11 < Total (Viable + Dead) Cells ≤ 1.5E11 | 250 |

TABLE 16

Product target volume.

| Total nucleated cells (TNC) × $10^6$ | Final Product (Retentate) Target Volume (mL) |
|---|---|

23. To target the specified volume from Table 16 touched the Final Product Volume (mL) entry field. A numeric keypad displayed. Entered the desired Final Product Volume in unit of mL. Touched the button to accept the entry.
24. Touched on the Final Product Volume (Retentate Volume) screen to return to the Procedure Setup Screen. Note: Screens 5-8 did not have any entry fields for the operator to fill in.
25. Verified that a "Check" displays in the Parameter Configuration button. If no "check" displays, touched the Procedure Information button again and ensured that Source Volume and Source PCV on page 1 have entries. Also ensured that either the Target Minimum Final Product Volume checkbox was checked OR the Final Product Volume (mL) field had an entry on page 4.
26. Touched the Estimate Button at the top right corner of the screen.
27. The Estimation Summary Screen displayed. Confirmed sufficient and accurate values for Source and PlasmaLyte Wash Buffer.
28. Loaded the disposable kit: Followed screen directions for kit loading by selecting help button "(?)".
29. Made a note of the volumes displayed for Filtrate and Solution 1 (read PlasmaLyte)
30. Made a note of the volumes displayed for Filtrate and Solution 1 (read PlasmaLyte).
31. For instructions on loading the disposable kit touched the help button or followed instructions in operators manual for detailed instructions.
32. When the standard LOVO disposable kit had been loaded, touched the Next button. The Container Information and Location Screen displays. Removed filtrate bag from scale #3.
33. For this protocol, the Filtrate container was New and Off Scale
34. If the Filtrate container was already shown as New and Off-Scale, no changes were made.
35. If the Filtrate container type was shown as Original, touched the Original button to toggle to New.
36. If the Filtrate location was shown as On-Scale, touched the On-Scale button to toggle to Off-Scale.
37. If the volume of Filtrate to be generated was ≤2500 mL, the Filtrate Container Location was shown as On-Scale For consistency among runs, the Filtrate Container Location was changed to Off-Scale and container type was "new".
38. Touched the On-Scale button to toggle to Off-Scale. Attached transfer set Use sterile welding technique to replace the LOVO disposable kit Filtrate container with a 10-L bag. Opened the weld.
39. Placed the Filtrate container on the benchtop. Did NOT hang the Filtrate bag on weigh scale #3. Weigh scale #3 was empty during the procedure.
40. Opened any plastic clamps on the tubing leading to the Filtrate container. NOTE: If the tubing was removed from the F clamp during welding, replaced in clamp.
41. Touched the Filtrate Container Capacity entry field. A numeric keypad displayed. Entered the total new Filtrate capacity (10,000 mL). Touched the "check" button to accept the entry.
42. Used sterile welding technique to replace the LOVO disposable kit Filtrate container with a 10-L bag. Opened the weld. Note: If tubing was removed from the F clamp during welding, replaced in clamp.
43. Placed the new Filtrate container on the benchtop. Did NOT hang the Filtrate bag on weigh scale #3. Weigh scale #3 was empty during the procedure
44. Opened any plastic clamps on the tubing leading to the Filtrate container.
45. For the Retentate container, the screen displayed Original and On-Scale.
46. No changes were made to the Retentate container.
47. When all changes were made to the Filtrate container and appropriate information entered, touched the Next button.
48. The Disposable Kit Dry Checks overlay displays. Checked that the kit had been loaded properly, then pressed the Yes button.
49. All LOVO mechanical clamps closed automatically and the Checking Disposable Kit Installation screen displayed. The LOVO went through a series of pressurizing steps to check the kit.

50. After the disposable kit check passed successfully, the Connect Solutions screen displayed.
51. 3 L was the wash volume. Entered this value on screen.
52. Used sterile welding technique to attach the 3-L bag of PlasmaLyte to the tubing passing through Clamp 1. Opened the weld.
53. Hung the PlasmaLyte bag on an IV pole,
54. Opened any plastic clamps on the tubing leading to the PlasmaLyte bag.
55. Verified that the Solution Volume entry is 3000 mL. This was previously entered.
56. Touched the Next button. The Disposable Kit Prime overlay displayed. Verified that the PlasmaLyte was attached and any welds and plastic clamps on the tubing leading to the PlasmaLyte were open, then touched the Yes button. NOTE: Because only one type of wash buffer (PlasmaLyte) was used during the LOVO procedure, no solution was attached to the tubing passing through Clamp 2. The Roberts clamp on this tubing remained closed during the procedure.
57. Disposable kit prime started and the Priming Disposable Kit Screen displayed. Visually observed that PlasmaLyte moving through the tubing connected to the bag of PlasmaL Lyte. If no fluid was moving, pressed the Pause Button on the screen and determined if a clamp or weld was still closed. Once the problem had been solved, pressed the Resume button on the screen to resume the Disposable Kit Prime.
58. When disposable kit prime finished successfully, the Connect Source Screen displayed.
59. For this protocol, the Source container was New and Off-Scale
60. If the Source container was already shown as New and Off-Scale, no changes were made.
61. If the Source location was shown as On-Scale, touched the On-Scale button to toggle to Off-Scale.
62. Touched the Source Capacity (mL) entry field. A numeric keypad displayed. Enter the capacity of the container that held the Source product. Touched the check button to accept the entry. Note: The Source Capacity entry was used to make sure that the Source bag was able to hold the additional solution that was added to the bag during the Source Prime phase.
63. Used sterile welding technique to attach the Source container to the tubing passing through Clamp S. Opened the weld. Remove the tubing from the clamp as needed.
64. Made sure to replace source tubing into the S clamp.
65. Touched the Next button. The Source Prime overlay displayed. Verified that the Source was attached to the disposable kit and any welds and plastic clamps on the tubing leading to the Source were open, then touched the Yes button.
66. Source prime started and the Priming Source Screen displayed. Visually observed that PlasmaLyte was moving through the tubing attached to the Source bag. If no fluid was moving, pressed the Pause Button on the screen and determined if a clamp or weld was still closed. Once the problem had been solved, pressed the Resume button on the screen to resume the Source Prime.
67. When Source prime finished successfully, the Start Procedure Screen displayed.
68. Pressed the Start button. The "Pre-Wash Cycle 1" pause screen appeared, with the instructions to "Coat IP, Mix Source".
69. Pre-coated the IP bag.
70. Before pressing the Start button, removed the IP bag from weigh scale #2 (could also remove tubing from the IP top port tubing guide) and manually inverted it to allow the wash buffer added during the disposable kit prime step to coat all interior surfaces of the bag.
71. Re-hung the IP bag on weigh scale #2 (label on the bag faced to the left). Replaced the top port tubing in the tubing guide, if it was removed.
72. Mixed the Source bag.
73. Before pressing the Start button, removed the Source bag from weigh scale #1 and inverted it several times to create a homogeneous cell suspension.
74. Rehung the Source bag on weigh scale #1 or the IV pole. Made sure the bag was not swinging.
75. Pressed the Start button.
76. The LOVO started processing fluid from the Source bag and the Wash Cycle 1 Screen displayed.

During the LOVO procedure, the system automatically paused to allow the operator to interact with different bags. Different screens displayed during different pauses. Followed the corresponding instructions for each screen.

Source Rinse Pause

After draining the Source bag, the LOVO added wash buffer to the Source bag to rinse the bag. After the configured volume of wash buffer had been added to the Source bag, the LOVO paused automatically and displayed the Source Rinse Paused Screen.

When the Source Rinse Paused Screen displayed, the operator:

1. Removed the Source bag from weigh scale #1.
1. Inverted the Source bag several times to allow the wash buffer to touch the entire bag interior.
2. Re-hung the Source bag on weigh scale #1. Made sure the Source bag is not swinging on weigh scale #1.
3. Pressed the Resume button.

The LOVO processed the rinse fluid from the Source bag, then continued with the automated procedure.

Mix IP Bag Pause

To prepare cells for another pass through the spinner, the IP bag was diluted with wash buffer. After adding the wash buffer to the IP bag, the LOVO paused automatically and displayed the "Mix IP bag" Pause Screen.

When the "Mix IP bag" Pause Screen displayed, the operator:

1. Removed the IP bag from weigh scale #2. Could also remove the tubing from the IP top port tubing guide.
2. Inverted the IP bag several times to thoroughly mix the cell suspension.
3. Re-hung the IP bag on weigh scale #2. Also replaced the IP top port tubing in the tubing guide, if it was removed. Made sure the IP bag was not swinging on weigh scale #2.
4. Pressed the Resume button. The LOVO began processing fluid from the IP bag.

Massage IP Corners Pause

During the final wash cycle of the LOVO procedure, cells were pumped from the IP bag, through the spinner, and to the Retentate (Final Product) bag. When the IP bag was empty, 10 mL of wash buffers was added to the bottom port of the IP bag to rinse the bag. After adding the rinse fluid, the LOVO paused automatically and displayed the "Massage IP corners" Pause Screen.

When the "Massage IP corners" Pause Screen displayed, the operator:
1. Did NOT remove the IP bag from weigh scale #2.
2. With the IP bag still hanging on weigh scale #2, massaged the corners of the bag to bring any residual cells into suspension.
3. Made sure the IP bag was not swinging on weigh scale #2.
4. Pressed the Resume button.
5. The LOVO began pumping out the rinse fluid from the IP bag.

At the end of the LOVO procedure, the Remove Products Screen displayed. When this screen displayed, all bags on the LOVO kit could be manipulated.

Note: Did not touch any bags until the Remove Products Screen displays.

Placed a hemostat on the tubing very close to the port on the Retentate bag to keep the cell suspension from settling into the tubing and triple heat sealed below the hemostat.

Removed the retentate bag by breaking the middle seal and transferred to the BSC.

Followed the instructions on the Remove Products Screen

Touched the Next button. All LOVO mechanical clamps opened and the Remove Kit Screen displayed.

Followed the instructions on the Remove Kit screen. When completed proceeded.

Touched the Next button. All LOVO mechanical clamps closed and the Results Summary Screen displayed. Recorded the data from the results summary screen in Table 17. Closed all pumps and filtered support.

TABLE 17

LOVO results summary table.

| Elapsed Processing Time (parentheses #) | Elapsed Source Processing Time (parentheses #) | Pause Time | Source Volume (mL) | Retentate Volume (mL) | Filtrate Volume (mL) | Solution 1 Volume (mL) |
|---|---|---|---|---|---|---|
| A. | B. | C. | D. | E. | F. | G. |

Touched the Next button. The Protocol Selection Screen displayed.

LOVO Shutdown Procedure
1. Ensured all clamps were closed and filter support is in the upright position.
2. Touched the STOP button on the front of the LOVO.
3. The STOP Button Decision Overlay displayed.
4. The Shutdown Confirmation Overlay displayed.
5. Touched the Yes button. The Shutting Down Screen displayed.
6. After a few seconds, the Power Off Screen displayed. When this screen displayed, turned off the LOVO using the switch on the back left of the instrument.

Recorded final formulated product volume in a table.

Calculate Amount of IL-2 Required from Final Product Table

A. Calculated amount of IL-2 needed for final product. (300 IU/ml of IL-2 final product): Final product volume (ml) [Volume of Formulated Cell Product from Final Formulated Product Volume Table] × 300 IU/ml = IU of IL-2 required _____ mL × _____ 300 IU = _____ IU of IL-2 required B. IU IL-2 required ÷ working stock dilution (Concentration of $6 \times 10^4$ IU/mL) prepared in IL-2 preparation step = volume (ml) of IL-2 to add to final product.

_____ IU of IL-2 required from above] ÷ 60,000 IU/ml = _____ ml IL-2 working stock Determined the Number of Cryobags and Retain Volume Marked on the Target volume and retain table below the number of cryopreservation bags and volume of retention sample for product.

Targeted volume/bag calculation: (Final formulated volume—volume adjustment due to not getting 100% recovery=10 mL)/# bags.

Prepared cells with 1:1 (vol:vol) CS10 (CryoStor 10, BioLife Solutions) and IL-2.

1. Assemble Connect apparatus
   1.1. Sterile welded the CS750 cryobags to the CC2 Cell Connect apparatus replacing one of the distal male luer ends for each bag.
   1.2. Retained the clamps in the closed position.
   1.3. Labeled the bags 1-4.
2. Prepared cells with IL-2 and connected apparatus.
   2.1. In BSC spike the cell product bag with a 4" plasma transfer set with female luer connector. Be sure the clamp was closed on the transfer set.
   2.2. With an appropriate size syringe drew up the volume of IL-2 working dilution determined from the Final Product Table.
   2.3. Dispensed into LOVO product.
   2.4. Sterile welded LOVO product bag to CC2 single spike line removing the spike.
   2.5. Placed cells and apparatus in transport bag and place at 2-8° C. for ≤15 min.
3. Addition of CS10
   3.1. In BSC attached 3 way stopcock to male luer on bag of cold CS10.
   3.2. Attached appropriate size syringe to female luer of stopcock.
   3.3. Unclamped bag and drew up the amount of CS10 determined in the "Final Formulated Product Volume" table.
   3.4. Removed syringe and red capped.
   3.5. Repeated if multiple syringes were required.
   3.6. Removed cell/CC2 apparatus from 2-8° C. refrigerator and placed in BSC.
   3.7. Attached first syringe containing CS10 to middle luer of stopcock. Turned stopcock so line to CS750 bags is in "OFF" position.
   3.8. Slowly and with gentle mixing, added CS10 (1:1, vol:vol) to cells.
   3.9. Repeated for additional syringes of CS10.

Addition of Formulated Cell Product into Cryobags
1. Replaced syringe with appropriate size syringe for volume of cells to be placed in each cryo bag.
2. Mixed cell product.
3. Opened the clamp leading to the cell product bag and drew up appropriate volume
4. Turned stopcock so cell product bag is in "OFF" position and dispensed the contents of the syringe into cryobag #1. Cleared the line with air from syringe.

Record Final Product Volume
1. Using needless port and appropriate size syringe, drew up amount of retain determined previously.
2. Place retained in 50 mL conical tube labelled "Retain"
3. Using the syringe attached to the harness removed all air from bag drawing up cells to about 1" past bag into tubing. Clamped and heat sealed. Placed at 2-8° C.
4. Turned stopcock so cryo bags were in the "OFF" position
5. Mixed cells in cell product bag and repeat steps 3-8 for remaining CS750 bags using a new syringe on the stopcock and new syringe to obtain cell retain.
6. Retained should be set aside for processing once product was in CRF.

Controlled-Rate Freezer (CRF) Procedure (See Also Example 9)
1. Turned on the CRF (CryoMed Controlled Rate Freezer, Model 7454) and associated laptop computer.
2. Logged onto the computer using account and password
3. Opened Controlled Rate Freezer icon located on the desktop.
4. Clicked the Run button on the Main screen.
5. Clicked Open Profile, Click Open.
6. Entered the Run File Name followed by the date in this format: runMMDDYYYY.
7. Entered the Data Tag as the date with no dashes as MMDDYYY.
8. Closed door to the CRF.
9. Clicked Start Run.
10. Selected COM 6 on the pull down menu.
11. Clicked Ok. Waited about 30 seconds.
12. When "Profile Download," pops up, Clicked OK. Clicked Save. (See Example 9 for controlled-rate freezing profile details.)
13. Waited to press green button until the samples were in the CRF. The freezer was held at 4° C. until ready to add them.
14. Added samples to CRF.
15. Waited until CRF returns to 4° C. Once temperature was reached, clicked the green continue button. This initiated program to go to next step in program.
16. Performed a visual inspection of the cryobags for the following (Note: did not inspect for over or underfill): container integrity, port integrity, seal integrity, presence of cell clumps, and presence of particles.
17. Placed approved hang tag labels on each bag.
18. Verified final product label including: Lot number, product name, manufacturer date, product volume, other additives, storage temperature, and expiration.
19. Placed each cryobag (with hangtag) into an over-bag.
20. Heat sealed.
21. Placed in a cold cassette.
22. Repeated for each bag.
23. Placed the labeled cryobags into preconditioned cassettes and transferred to the CRF.
24. Evenly distributed the cassettes in the rack in the CRF.
25. Applied ribbon thermocouple to the center cassette, or place dummy bag in center position.
26. Closed the door to the CRF.
27. Once the chamber temperature reached 4° C.+/−1.5° C., Press Run on the PC Interface software.
28. Recorded the time and the chamber temperature that the product is transferred to the CRF.

Processing of Quality Control Sample
1. Aseptically transferred the following materials to the BSC, as needed, and labeled according to the table below:
2. Used a new pipette for pipette the following: QC and Retention Table
3. Delivered to QC: 1—Cell Count tube, 1—Endotoxin tube, 1—*Mycoplasma* tube, 1—Gram stain tube, 1 tube restimulation tube, and 1—flow tube to QC for immediate testing. The remaining duplicate tubes were placed in the controlled rate freezer.
4. Contacted the QC supervisor notifying of required testing.
5. See Table 18 for testing and storage instructions.

TABLE 18

Testing and storage instructions.

| Test | Vessel |
| --- | --- |
| Cell Count and viability | Cryovials. |
| Mycoplasma | Cryovial stored at 4° C. until testing completed. |
| Sterility | Inoculate 0.5 mL into an anaerobic and 0.5 mL into an aerobic culture bottle. |
| Gram Stain | Cryovial stored at 4° C. until testing completed. |
| Endotoxin | Cryovial stored at 4° C. until testing completed. |
| Flow | Cryovial stored at 4° C. until testing completed. |
| Post Formulation Retention | Cryopreserve for future testing: Consist of 5 satellite vial, 1 -Cell Count tube, 1- Endotoxin tube, 1-Mycoplasma tube, 1-Gram stain tube, and 1- flow tube to QC for immediate testing. |
| Restimulation | Sample is delivered at room temperature and assay must be started within 30 minutes of cell count results. |

Cell Count
Performed a single cell count on each sample and recorded data and attached counting raw data to batch record. Document the Cellometer counting program. Verified the correct dilution was entered into the Cellometer.

Cryopreservation of Post Formulation Retention Cells:
1. Placed vial in CRF.
2. Moved to storage location after completion of freeze and recorded date and time placed in CFR. Recorded date and time moved to LN2.

Microbiology Testing
1. Ordered testing for settle plates to the microbiology lab.
2. Recorded accession numbers.
3. Ordered testing for aerobic and anaerobic sterility.
4. Ensured delivery of plates and bottles to the microbiology lab.

Post-Cryopreservation of Cell Product Bags
1. Stopped the freezer after the completion of the run. Run could be stopped by clicking on the Stop button or pressing the Back key on the freezer keypad.
2. Removed cryobags from cassette
3. Transferred cassettes to vapor phase LN2.
4. Recorded storage location.
5. Entered any additional comments when the text entry window opens again. This window appeared regardless of the Run stop method.
6. Printed the profile report and attached to the batch record labeled with the lot number for the run.
7. Terminated Warm Mode and closed the Run screen with Exit button.

Example 9: Cryopreservation Process

This example describes the cryopreservation process method for TILs prepared with the abbreviated, closed procedure described above in Example 8 using the CryoMed Controlled Rate Freezer, Model 7454 (Thermo Scientific).

The equipment used, in addition to that described in Example 9, is as follows: aluminum cassette holder rack (compatible with CS750 freezer bags), cryostorage cassettes for 750 mL bags, low pressure (22 psi) liquid nitrogen tank, refrigerator, thermocouple sensor (ribbon type for bags), and CryoStore CS750 Freezing bags (OriGen Scientific).

The freezing process provides for a 0.5° C. rate from nucleation to −20° C. and 1° C. per minute cooling rate to −80° C. end temperature. The program parameters are as follows: Step 1—wait at 4° C.; Step 2: 1.0° C./min (sample temperature) to −4° C.; Step 3: 20.0° C./min (chamber temperature) to −45° C.; Step 4: 10.0° C./min (chamber temperature) to −10.0° C.; Step 5: 0.5° C./min (chamber temperature) to −20° C.; and Step 6: 1.0° C./min (sample temperature) to −80° C.

Figure 11A:
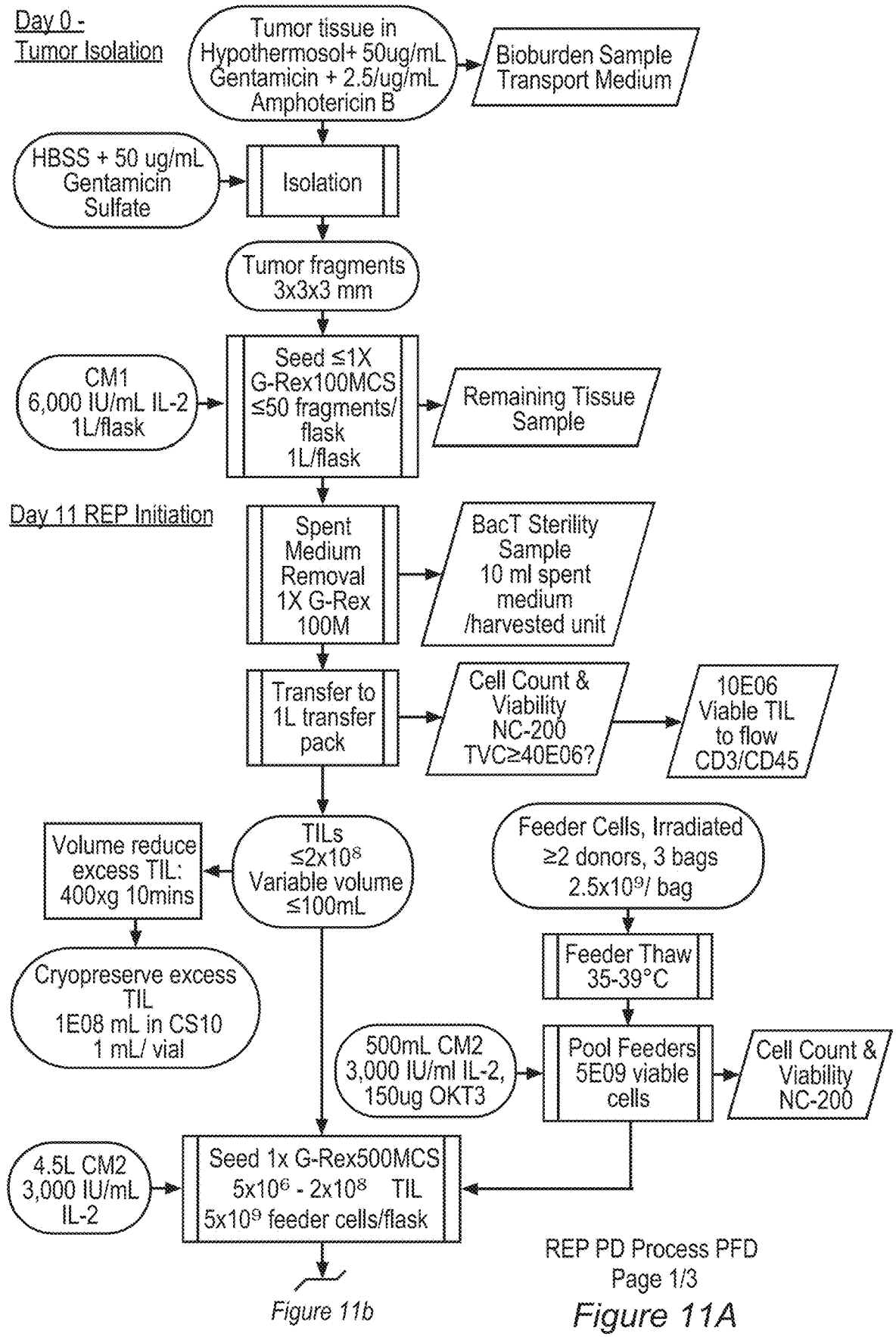
Figure 11B:
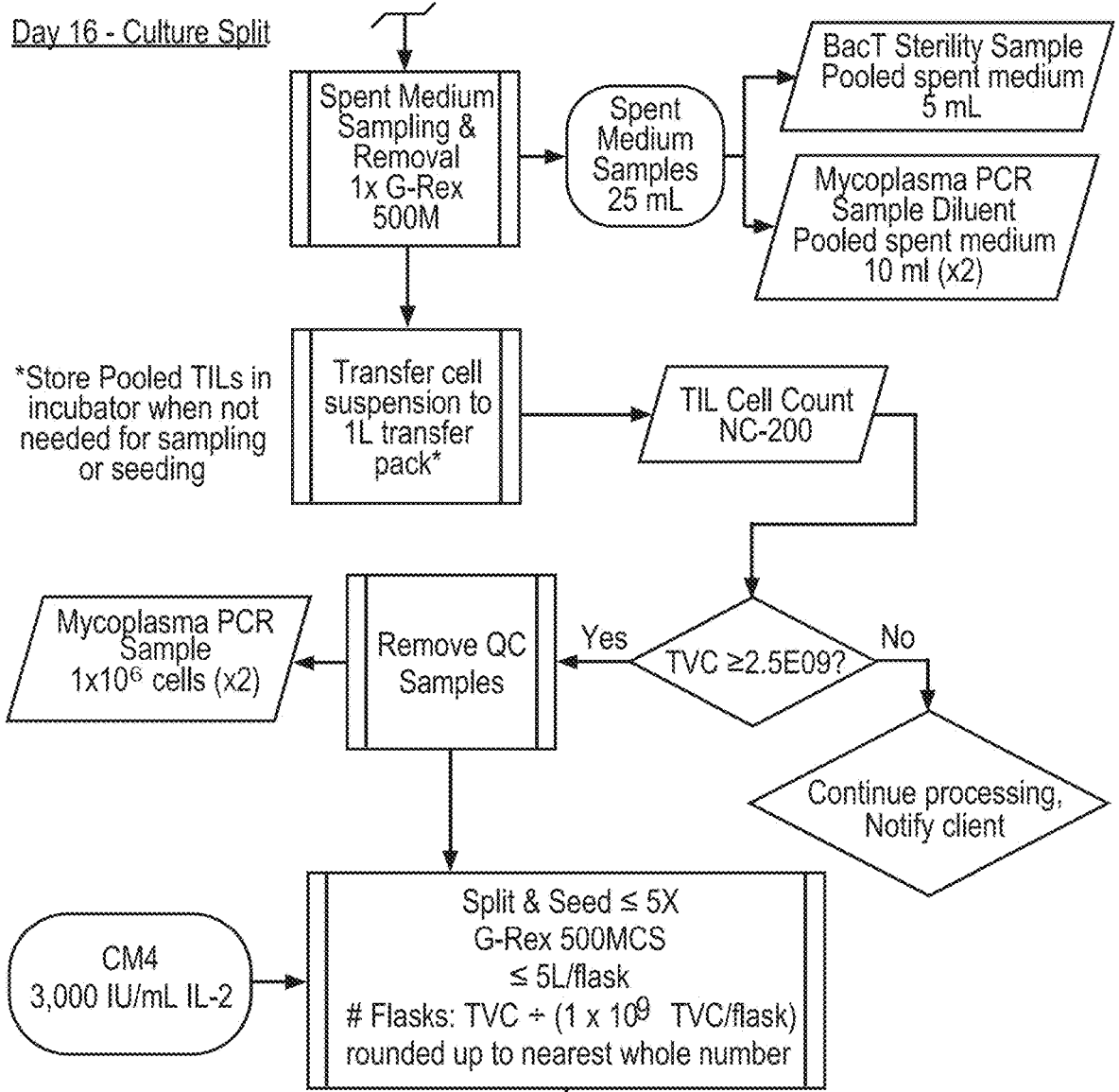

A depiction of the procedure of this example in conjunction with the process of Examples 1 to 8 is shown in FIG. 11.

Example 10: Characterization of Process 2A TILs

This example describes the characterization of TILs prepared with the abbreviated, closed procedure described above. In summary, the abbreviated, closed procedure (process 2A, described in Examples 1 to 9) had the advantages over prior TIL manufacturing processes given in Table 19. Advantages for the Pre-REP can include: increased tumor fragments per flask, shortened culture time, reduced number of steps, and/or being amenable to closed system. Advantages for the Pre-REP to REP transition can include: shortened pre-REP-to-REP process, reduced number of steps, eliminated phenotyping selection, and/or amenable to closed system. Advantages for the REP can include: reduced number of steps, shorter REP duration, closed system transfer of TIL between flasks, and/or closed system media exchanges. Advantages for the Harvest can include: reduced number of steps, automated cell washing, closed system, and reduced loss of product during wash. Advantages for the final formulation and/or product can include shipping flexibility.

A total of 9 experiments were performed using TILs derived from 9 tumors described in Table 20. All the data shown here was measured from thawed frozen TIL product from process TC and an embodiment of process 2A.

TABLE 20

Description of Tumor Donors, Processing Dates and Processing Locations

| Tumor ID | Tissue type | Source | Tissue |
|---|---|---|---|
| M1061 | Melanoma | MT group | Primary-left lateral foot |
| M1062 | Melanoma | Moffitt | N/A |
| M1063 | Melanoma | MT group | Metastatic C-right groin |
| M1064 | Melanoma | MT group | Metastatic C-left ankle |
| M1065 | Melanoma | Bio Options | Metastatic-Axillary lymph node |
| EP11001 | ER+PR+ | MT group | Primary-left breast invasive ductal carcinoma |
| M1056* | Melanoma | Moffitt | N/A |
| M1058* | Melanoma | MT group | Metastatic-Stage IIB Right scalp |
| M1023* | Melanoma | Atlantic Health | Primary-Right axilla |

The procedures described herein for process 2A were used to produce the TILs for characterization in this example. Briefly, for the REP, on Day 11, one G-REX-500M flask containing 5 L of CM2 supplemented with 3000 IU/ml rhIL-2, 30 ng/mL anti-CD3 (Clone OKT3) and 5×10$^9$ irradiated allogeneic feeder PBMC cells was prepared. TILs harvested from the pre-REP G-REX-100M flask after volume reduction were counted and seeded into the G-REX-500M flask at a density that ranged between 5×10$^6$ and 200×10$^6$ cells. The flask was then placed in a humidified 37° C., 5% $CO_2$ tissue Culture incubator for five days. On Day 16, volume of the G-REX-500M flask was reduced, TILs were counted and their viability determined. At this point, the TIL were expanded into multiple G-REX-500M flasks (up to a maximum of six flasks), each with a seeding density of 1×10$^9$ TILs/flask. All flasks were then placed in humidified 37° C., 500 $CO_2$ tissue Culture incubators for an

TABLE 19

Comparison of exemplary process 1C and an embodiment of process 2A.

| Process Step | Process 1C-Embodiment | Process 2A-Embodiment |
|---|---|---|
| Pre-REP | 4 fragments per 10 G-REX-10 flasks<br>11-21 day duration | 40 fragments per 1 G-REX-100M flask<br>11 day duration |
| Pre-REP to REP Transition | Pre-REP TIL are frozen until phenotyped for selection then thawed to proceed to the REP (~day 30)<br>REP requires >40 × 10$^6$ TIL | Pre-REP TIL directly move to REP on day 11<br>REP requires 25-200 × 10$^6$ TIL |
| REP | 6 G-REX-100M flasks on REP day 0<br>5 × 10$^6$ TIL and 5 × 10$^8$ PBMC feeders per flask on REP day 0<br>Split to 18-36 flasks on REP day 7<br>14 day duration | 1 G-REX-500M flask on day 11<br>25-200 × 10$^6$ TIL and 5 × 10$^9$ PBMC feeders on day 11<br>Split to ≤6 G-REX-500M flasks on day 16<br>11 day duration |
| Harvest | TIL harvested via centrifugation | TIL harvested via LOVO automated cell washing system' |
| Final Formulation | Fresh product in Hypothermosol<br>Single infusion bag<br>Limited shipping stability | Cryopreserved product in PlasmaLyte-A + 1% HSA and CS10 stored in $LN_2$<br>Multiple aliquots<br>Longer shipping stability |
| Overall Estimated Process Time | 43-55 days | 22 days | additional six days. On Day 22, the day of harvest, each flask was volume reduced by 90%, the cells were pooled together and filtered through a 170 μm blood filter, and then collected into a 3 L Origin EV3000 bag or equivalent in preparation for automated washing using the LOVO. TILs were washed using the LOVO automated cell processing system which replaced 99.99% of cell culture media with a wash buffer consisting of PlasmaLyte-A supplemented with 1% HSA. The LOVO operates using spinning filtration membrane technology that recovers over 92% of the TIL while virtually eliminating residual tissue culture components, including serum, growth factors, and cytokines, as well as other debris and particulates. After completion of the wash, a cell count was performed to determine the expansion of the TILs and their viability upon harvest. CS10 was added to the washed TIL at a 1:1 volume:volume ratio to achieve the Process 2A final formulation. The final formulated product was aliquoted into cryostorage bags, sealed, and placed in pre-cooled aluminum cassettes. Cryostorage bags containing TIL were then frozen using a CryoMed Controlled Rate Freezer (ThermoFisher Scientific, Waltham, MA) according to the procedures described herein, including in Example 9.

Figure 12:
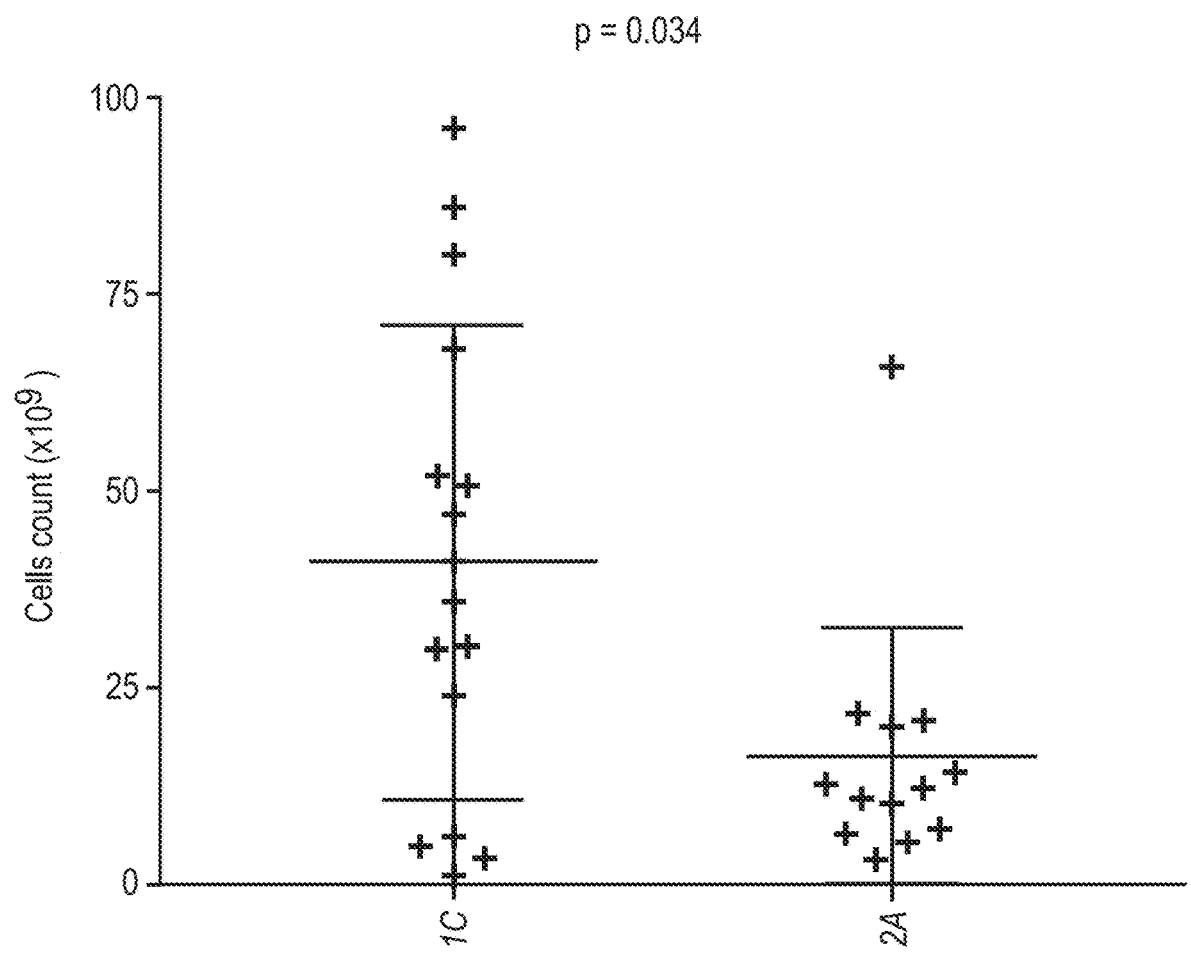
FIG. 12: Depicts cell counts obtained from the 1C process and an embodiment of the 2A process.
Figure 13:
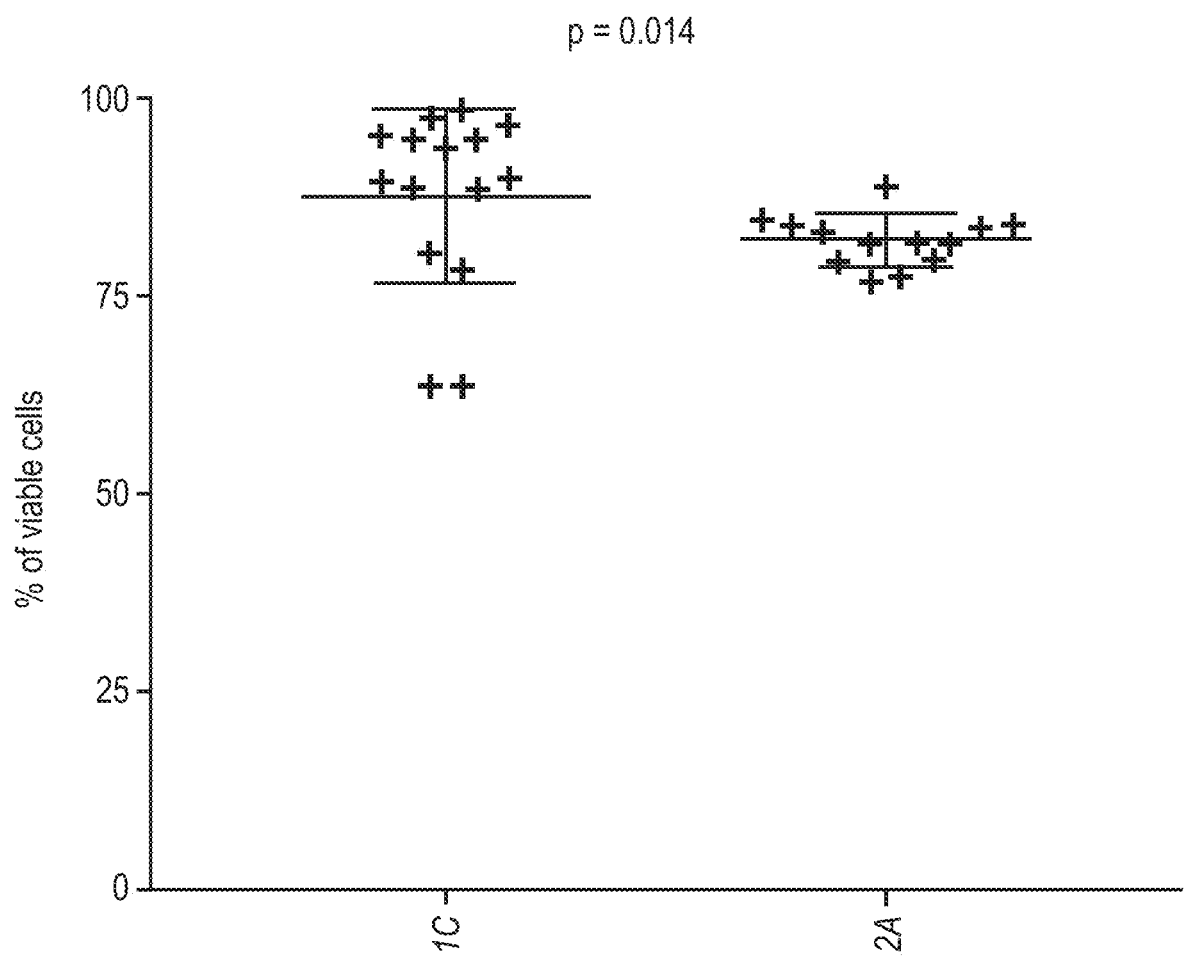
FIG. 13: Depicts percent cell viability obtained from the 1C process and an embodiment of the 2A process.
Figure 14:
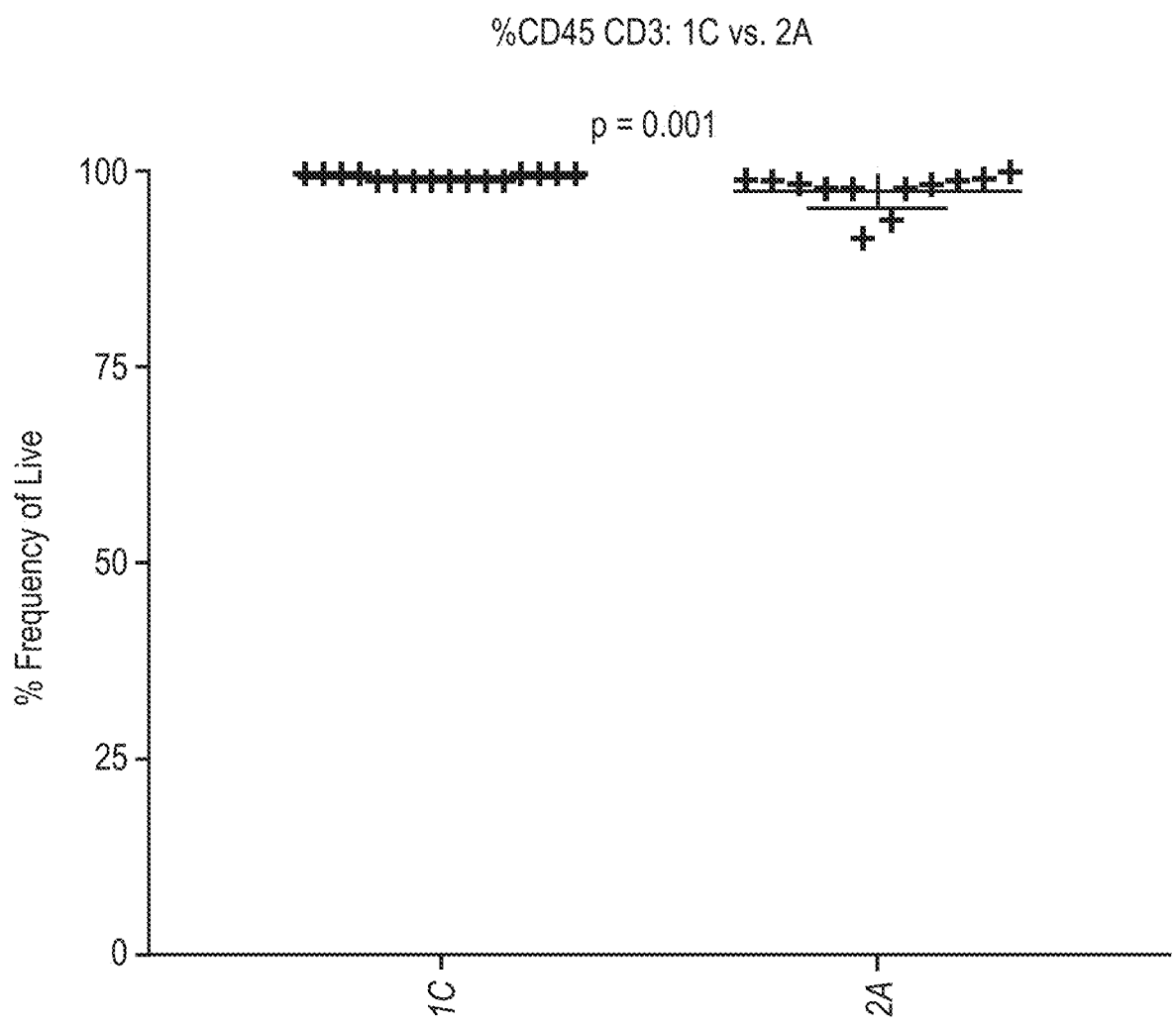
FIG. 14: Depicts percentages of CD45 and CD3 cells (i.e., T cells) measured by flow cytometry for TILs obtained for the 1C process and an embodiment of the 2A process.
Figure 15:
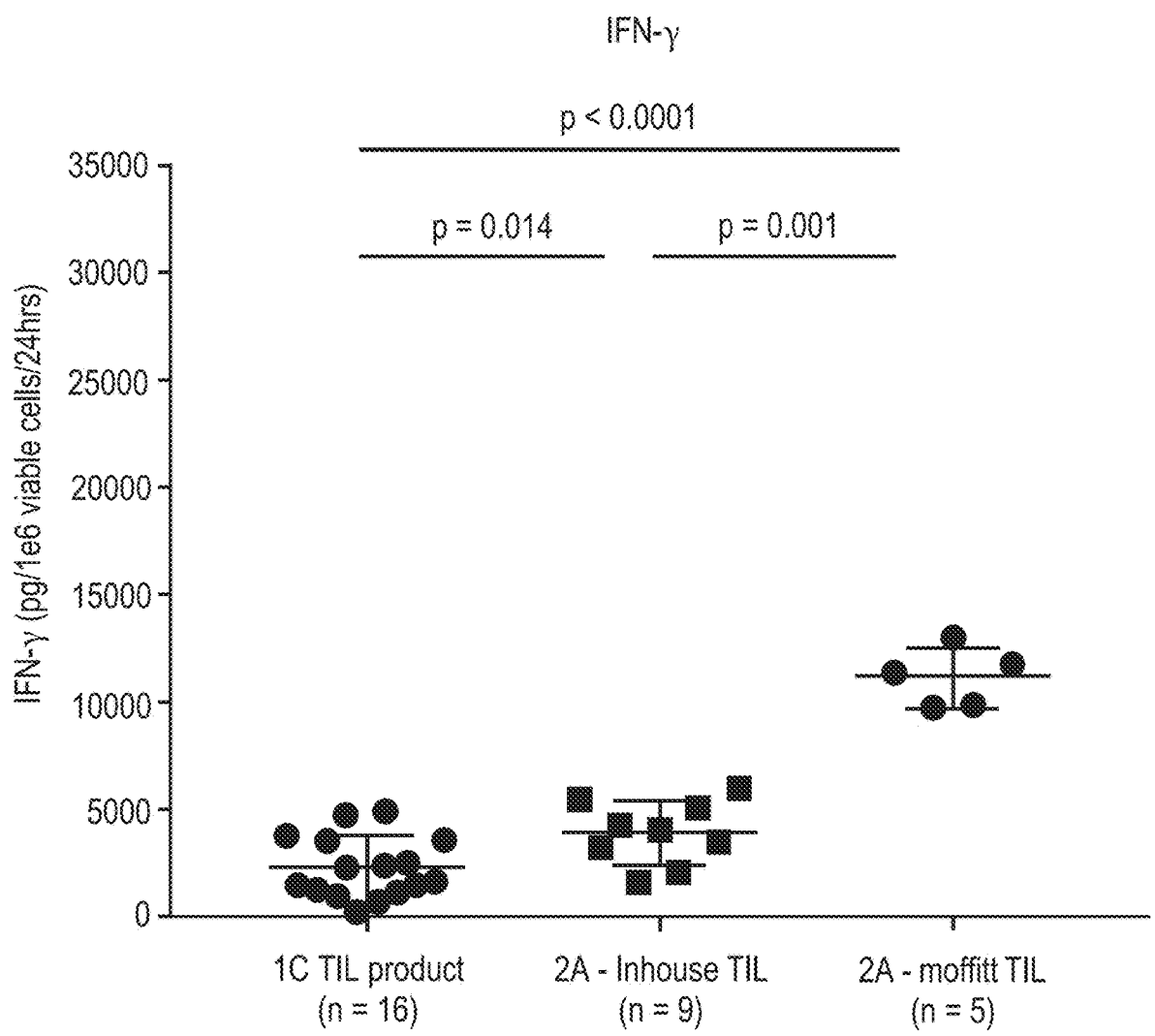
FIG. 15: Depicts IFN-γ release obtained for the 1C process and embodiments of the 2A process, as measured by an assay different than that used to generate the data in FIGS. 80 and 98.
Figure 16:
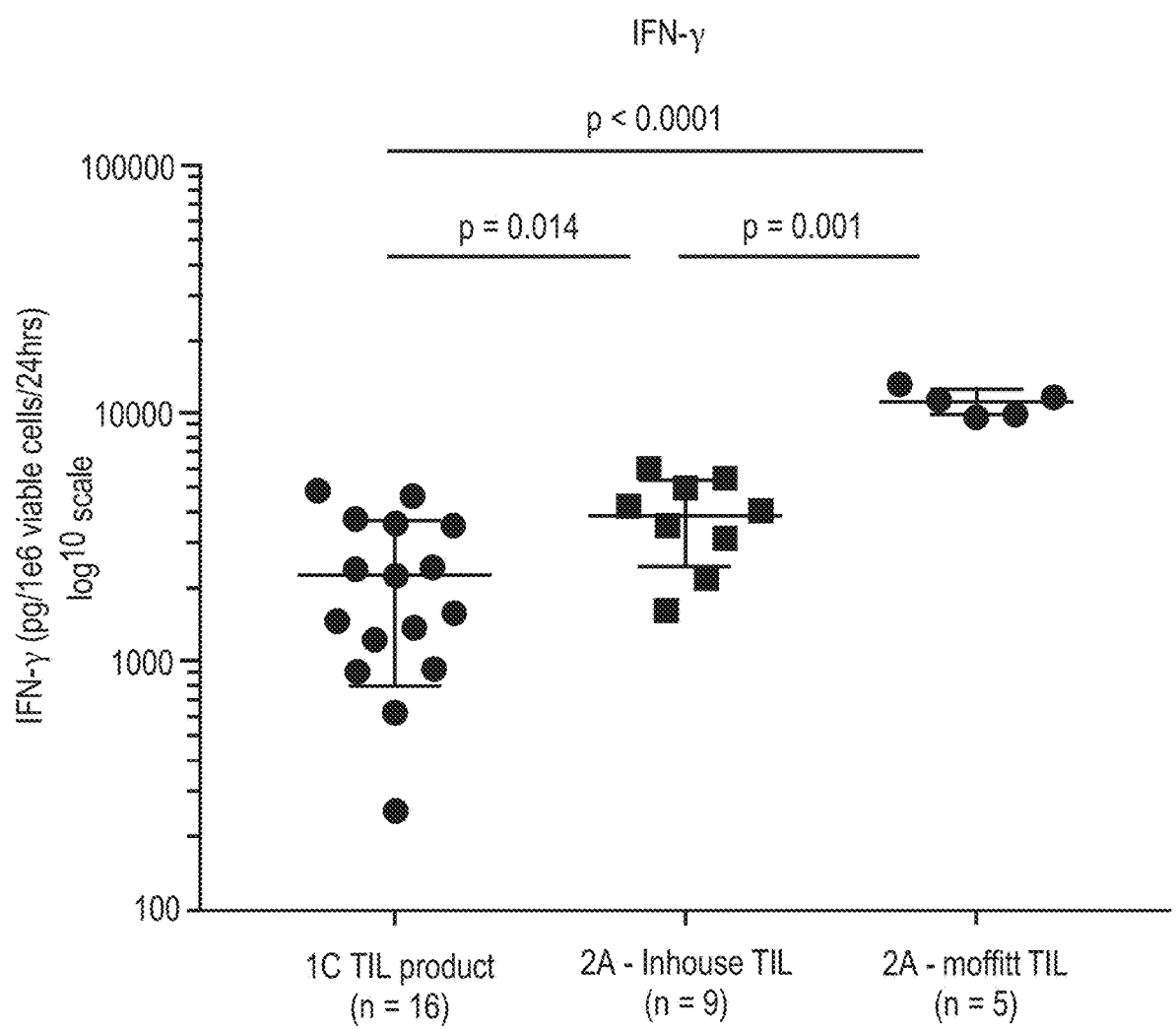
FIG. 16: Depicts IFN-γ release obtained for the 1C process and embodiments of the 2A process, as measured by an assay different than that used to generate the data in FIGS. 80 and 98.
Figure 17:
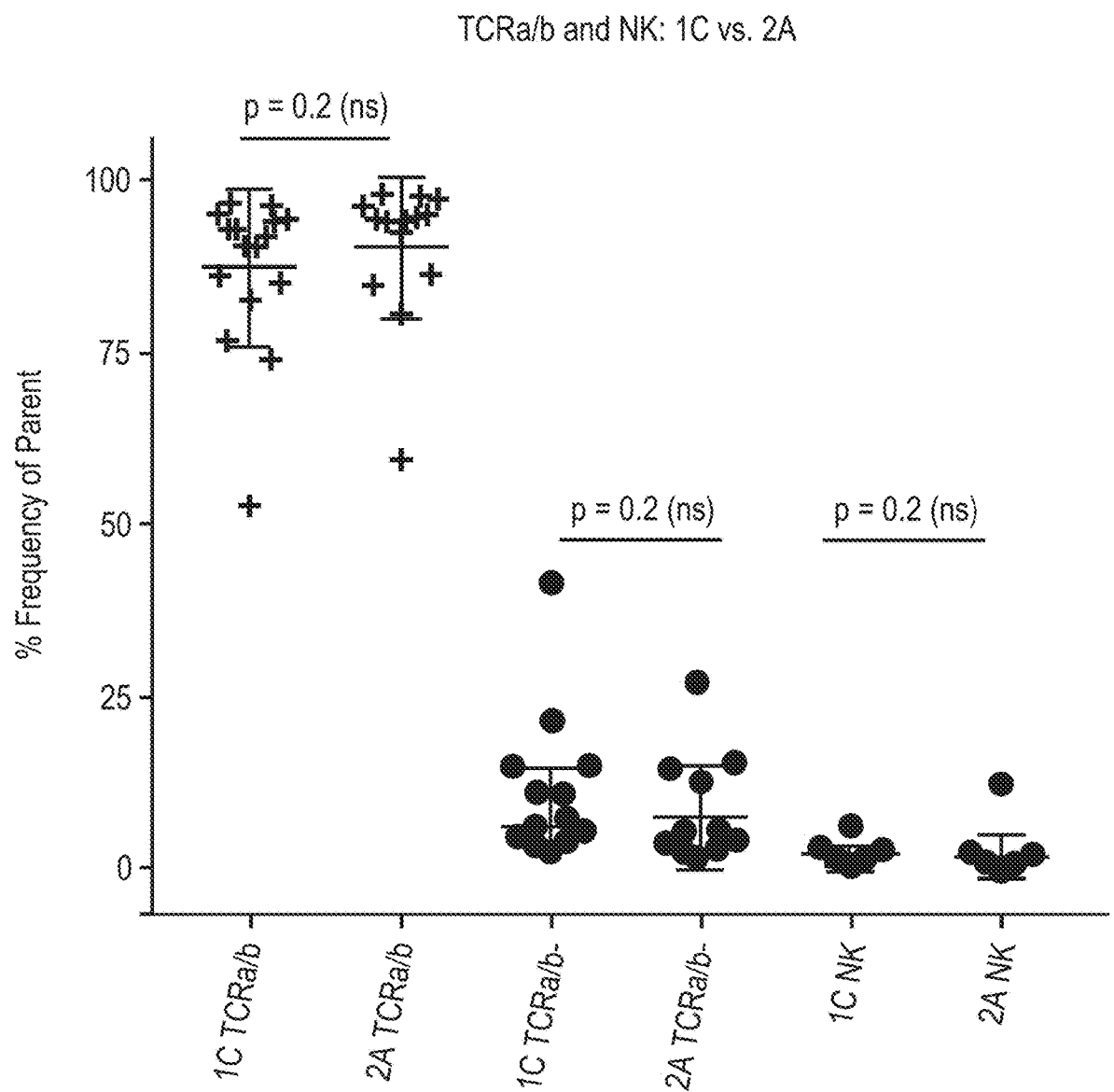
FIG. 17: Depicts percentages of TCR a/b and NK cells obtained from the 1C process and an embodiment of the 2A process.
Figure 18:
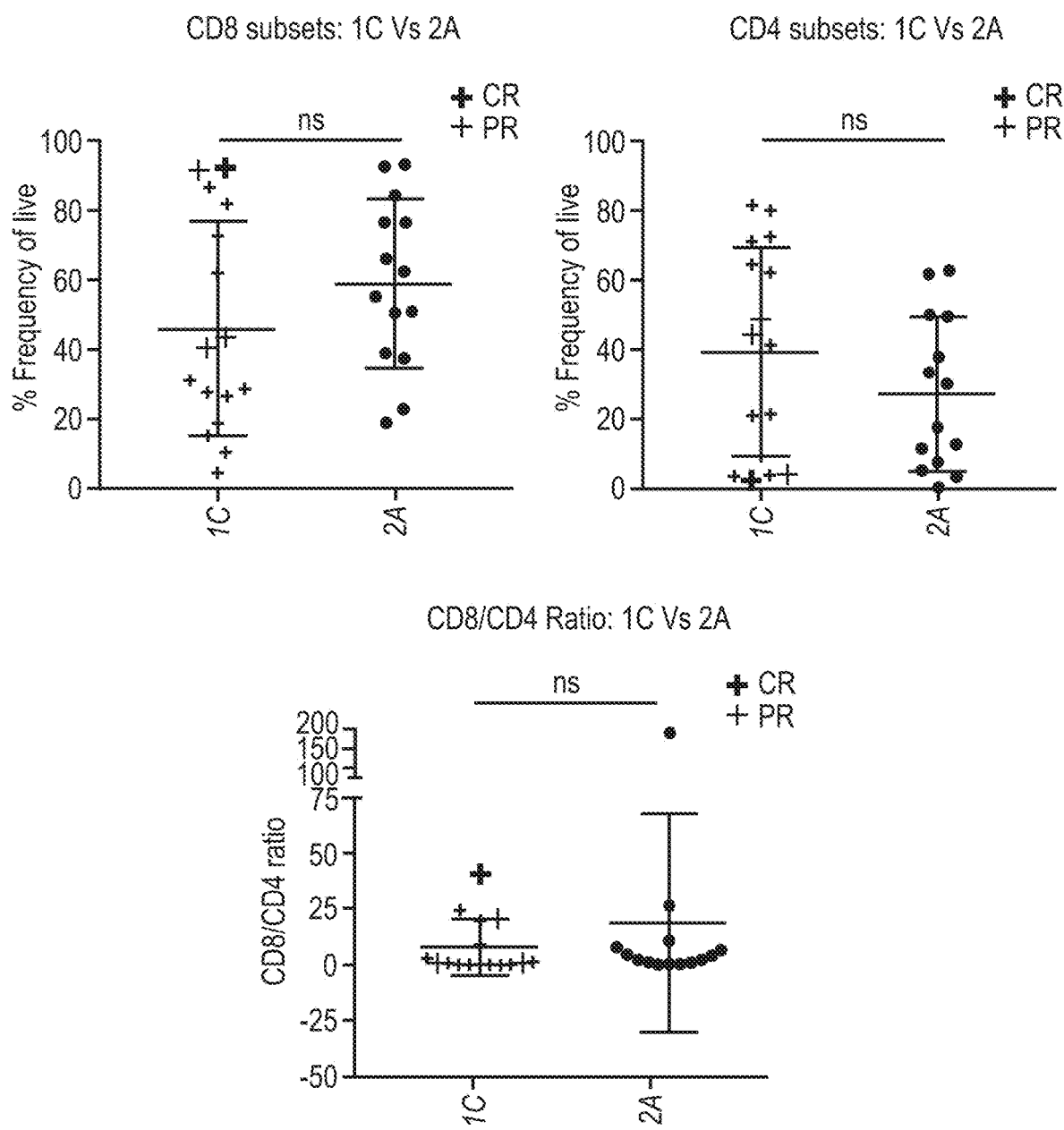
FIG. 18: Depicts percentages of $CD8^+$ and $CD4^+$ cells measured by flow cytometry for TILs obtained by the 1C process and an embodiment of the 2A process, as well as the ratio between each subset.
Figure 19:
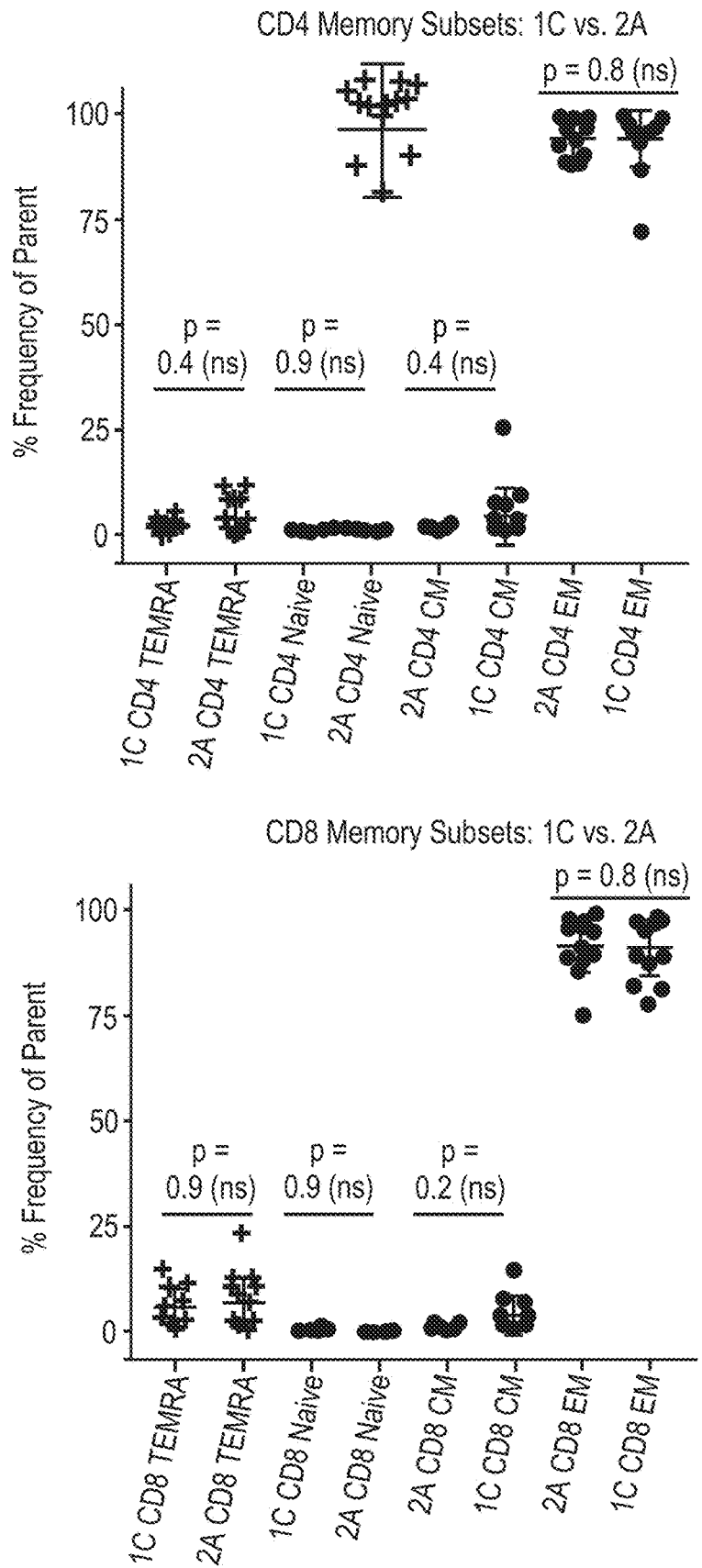
FIG. 19: Depicts percentages of memory subsets measured by flow cytometry for TILs obtained from the 1C process and an embodiment of the 2A process.
Figure 20:
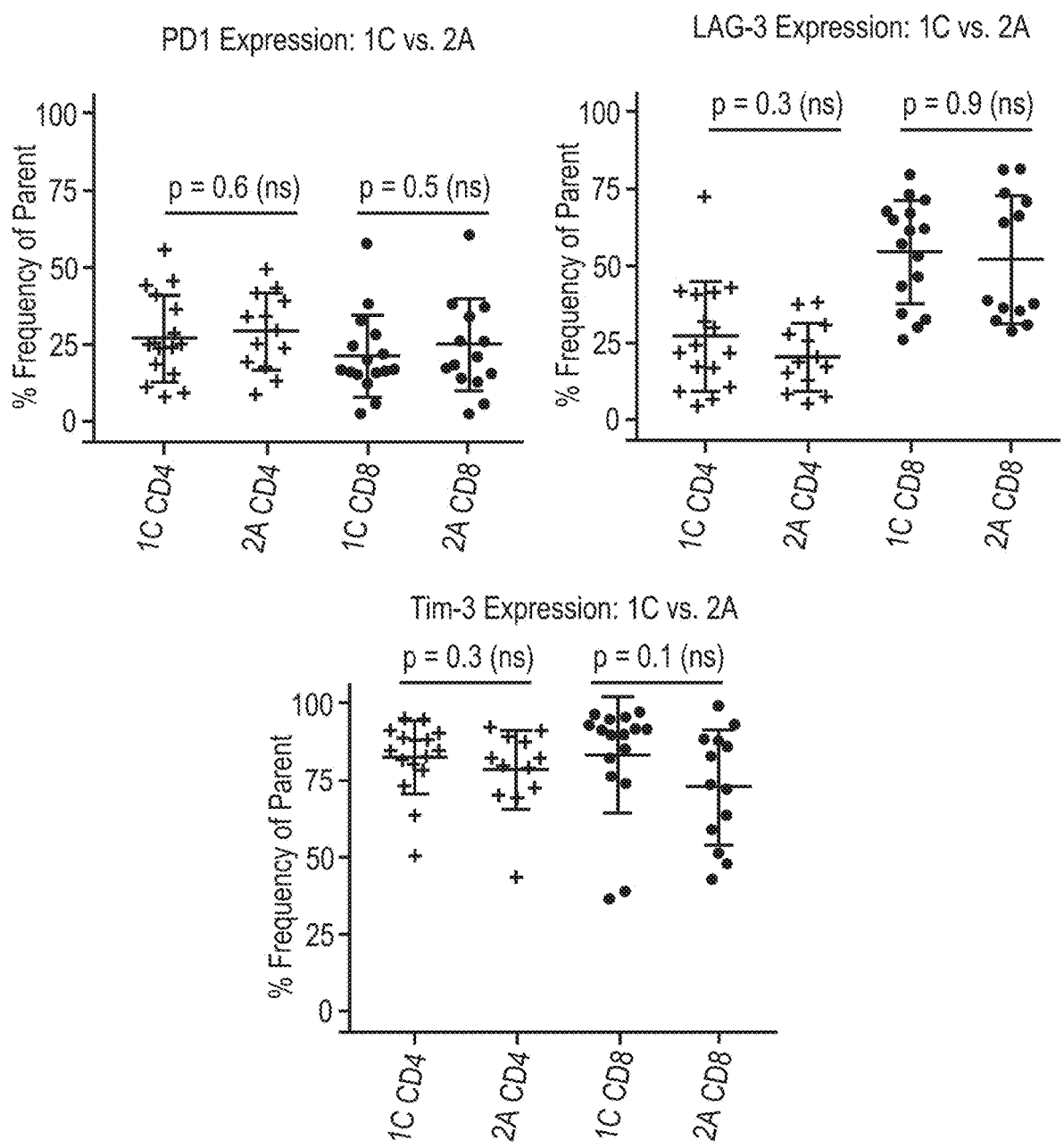
FIG. 20: Depicts percentages of PD-1, LAG-3, and TIM-3 expression by flow cytometry for TILs obtained from the 1C process and an embodiment of the 2A process.
Figure 21:
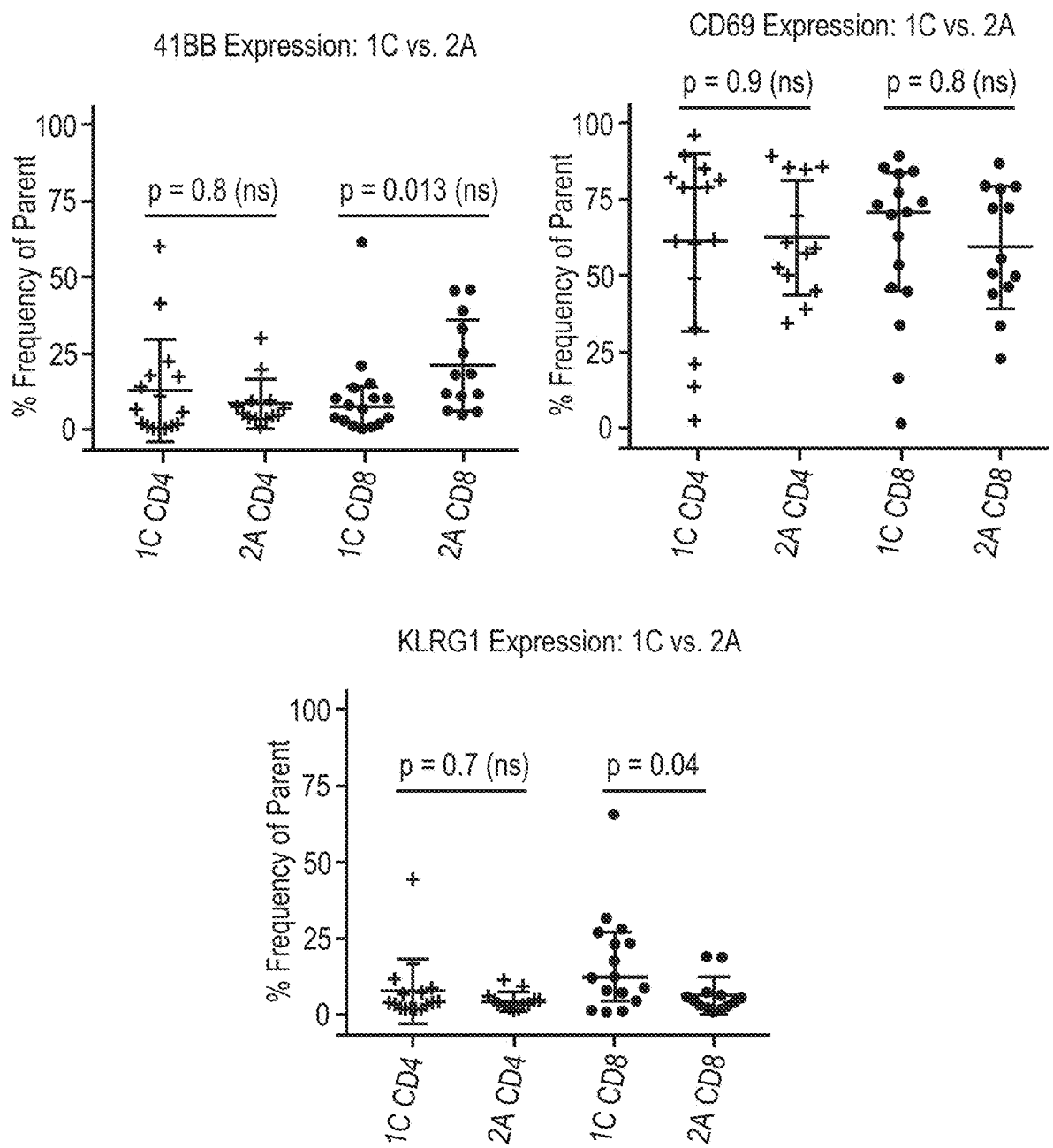
FIG. 21: Depicts percentages of 4-1BB, CD69, and KLRG1 expression by flow cytometry for TILs obtained from the 1C process and an embodiment of the 2A process.
Figure 22:
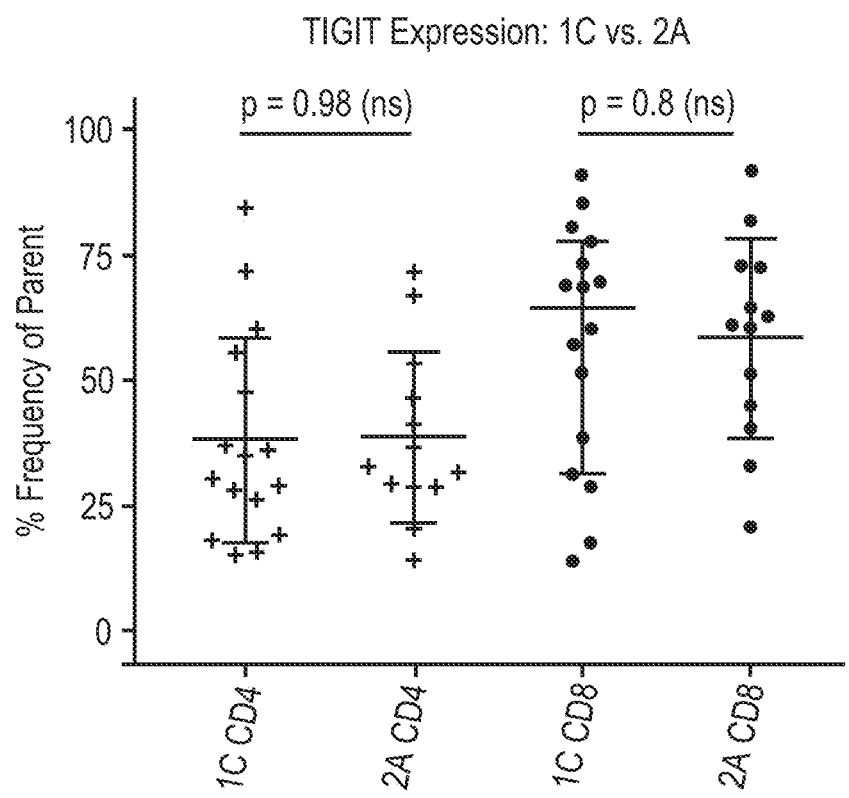
FIG. 22: Depicts percentages of TIGIT expression by flow cytometry for TILs obtained from the 1C process and an embodiment of the 2A process.
Figure 23:
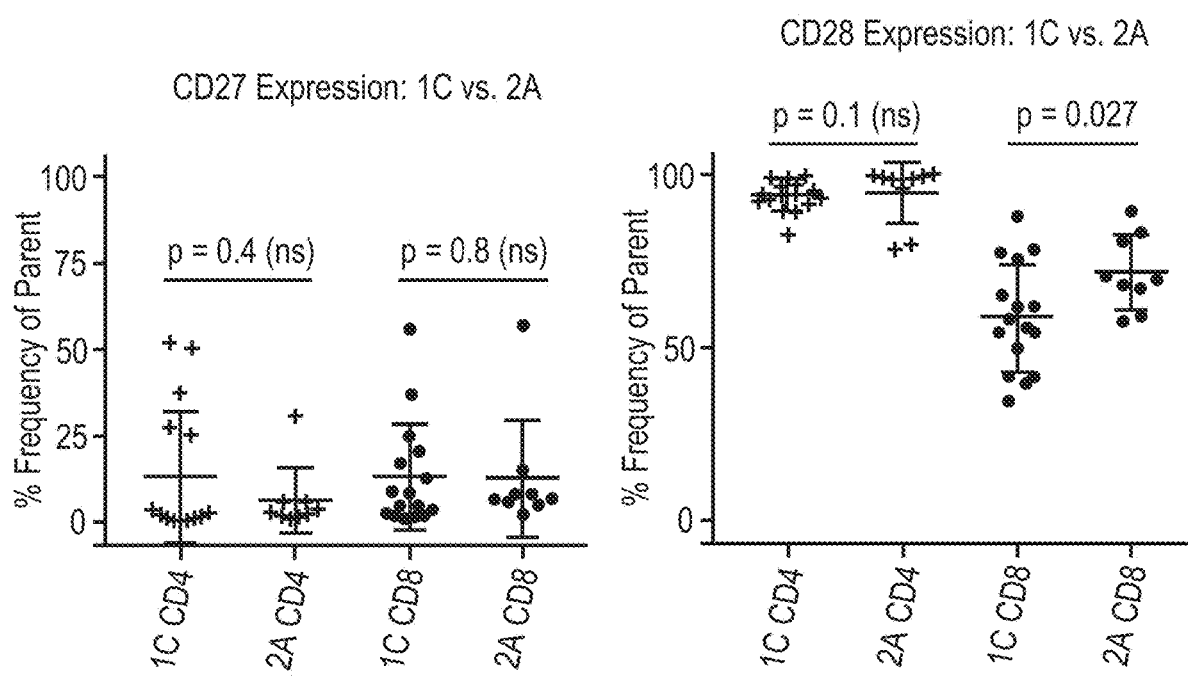
FIG. 23: Depicts percentages of CD27 and CD28 expression by flow cytometry for TILs obtained from the 1C process and an embodiment of the 2A process.

Cell counts and percentage viability for the nine runs were compared in FIGS. 12 and 13.

The cell surface markers shown in the following results were analyzed using flow cytometry (Canto II flow cytometer, Becton, Dickinson, and Co., Franklin Lakes, NJ, USA) using suitable commercially-available reagents. Results for markers of interest are shown in FIG. 14 through FIG. 23.

Diverse methods have been used to measure the length of telomeres in genomic DNA and cytological preparations. The telomere restriction fragment (TRF) analysis is the gold standard to measure telomere length (de Lange et al., 1990). However, the major limitation of TRF is the requirement of a large amount of DNA (1.5 μg). Here, two widely used techniques for the measurement of telomere lengths were applied, namely fluorescence in situ hybridization (FISH) and quantitative PCR.

Flow-FISH was performed using the Dako kit (K532711-8 RUO Code K5327 Telomere PNA Kit/FITC for Flow Cytometry, PNA FISH Kit/FITC. Flow, 20 tests) and the manufacturer's instructions were followed to measure average length of telomere repeat. Briefly, the cells were surface was stained with CD3 APC for 20 minutes at 4° C., followed by GAM Alexa 546 for 20 minutes. The antigen-antibody complex was then cross-linked with 2 mM BS3 (Fisher Scientific) chemical cross-linker. PNA-telomere probe binding in a standard population of T-cells with long telomeres, Jurkat 1301 T leukemia cell line (1301 cells) was used as an internal reference standard in each assay. Individual TILs were counted following antibody incubation and mixed with 1301 cells (ATCC) at a 1:1 cell ratio. $5 \times 10^5$ TILs were mixed with $5 \times 10^5$ 1301 cells. In situ hybridization was performed in hybridization solution (70% formamide, 1% BSA, 20 mM Tris pH 7.0) in duplicate and in the presence and absence of a FITC-conjugated Telomere PNA probe (Panagene), FITC-00-CCC-TAA-CCC-TAA-CCC-TAA, complementary to the telomere repeat sequence at a final concentration of 60 nM. After addition of the Telomere PNA probe, cells were incubated for 10 minutes at 81° C. in a shaking water bath. The cells were then placed in the dark at room temperature overnight. The next morning, excess telomere probe was removed by washing 2 times with PBS pre-warmed to 40° C. Following the washes, DAPI (Invitrogen, Carlsbad, CA) was added at a final concentration of 75 ng/mL. DNA staining with DAPI was used to gate cells in the G0/G1 population. Sample analysis was performed using our flow cytometer (BD Canto II, Mountain View, CA). Telomere fluorescence of the test sample was expressed as a percentage of the fluorescence (fl) of the 1301 cells per the following formula: Relative telomere length= [(mean FITC fl test cells w/probe-mean FITC fl test cells w/o probe)×DNA index 1301 cells×100]/[(mean FITC fl 1301 cells w/probe—mean FITC fl 1301 cells w/o probe)×DNA index test cell.

Real time qPCR was also used to measure relative telomere length (Nucleic Acids Res. 2002 May 15; 30(10): e47, 20, Leukemia, 2013, 27, 897-906). Briefly, the telomere repeat copy number to single gene copy number (T/S) ratio was determined using an BioRad PCR thermal cycler (Hercules, CA) in a 96-well format. Ten ng of genomic DNA was used for either the telomere or hemoglobin (hgb) PCR reaction and the primers used were as follows: Tel-1b primer (CGG TTT GTT TGG GTT TGG GTT TGG GTT TGG GTT TGG GTT), Tel-2b primer (GGC TTG CCT TAC CCT TAC CCT TAC CCT TAC CCT TAC CCT), hgb1 primer (GCTTCTGACACAACTGTGTTCACTAGC), and hgb2 primer (CACCAACTTCATCCACGTTCACC). All samples were analyzed by both the telomere and hemoglobin reactions, and the analysis was performed in triplicate on the same plate. In addition to the test samples, each 96-well plate contained a five-point standard curve from 0.08 ng to 250 ng using genomic DNA isolated from 1301 cell line. The T/S ratio (–dCt) for each sample was calculated by subtracting the median hemoglobin threshold cycle (Ct) value from the median telomere Ct value. The relative T/S ratio (–ddCt) was determined by subtracting the T/S ratio of the 10.0 ng standard curve point from the T/S ratio of each unknown sample.

Figure 24:
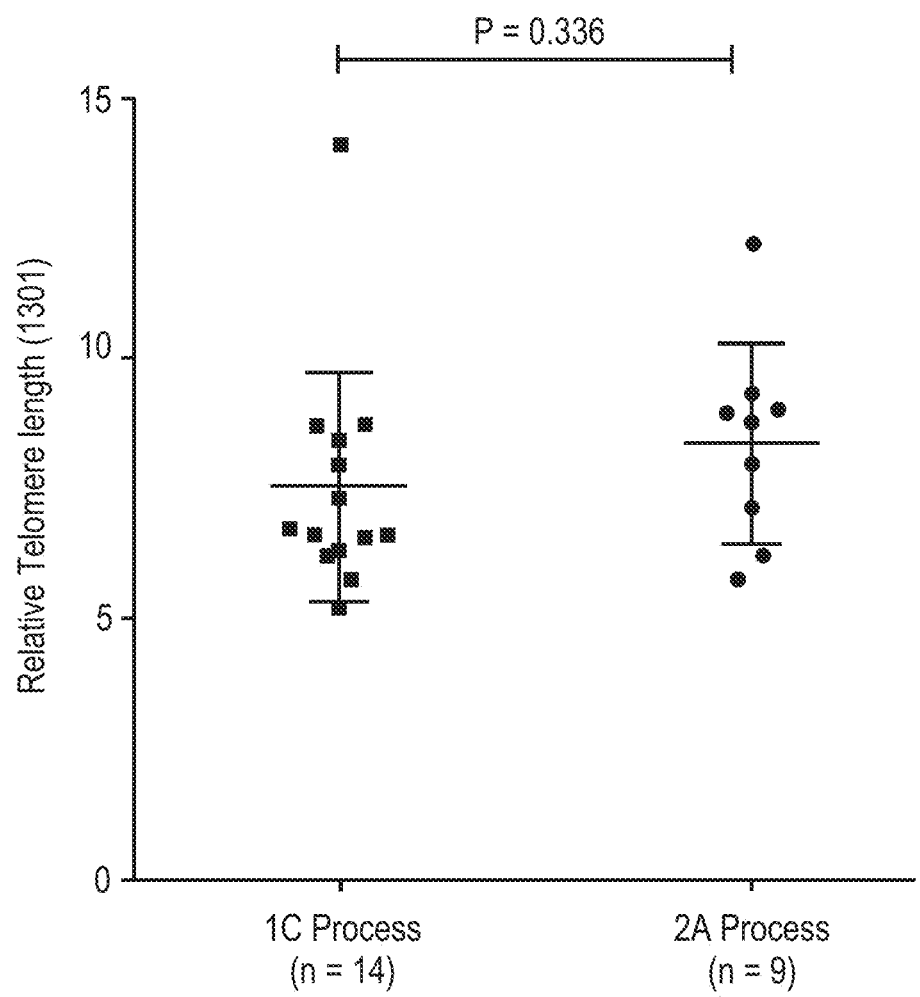
FIG. 24: Depicts the results of flow-FISH telomere length analysis.
Figure 25:
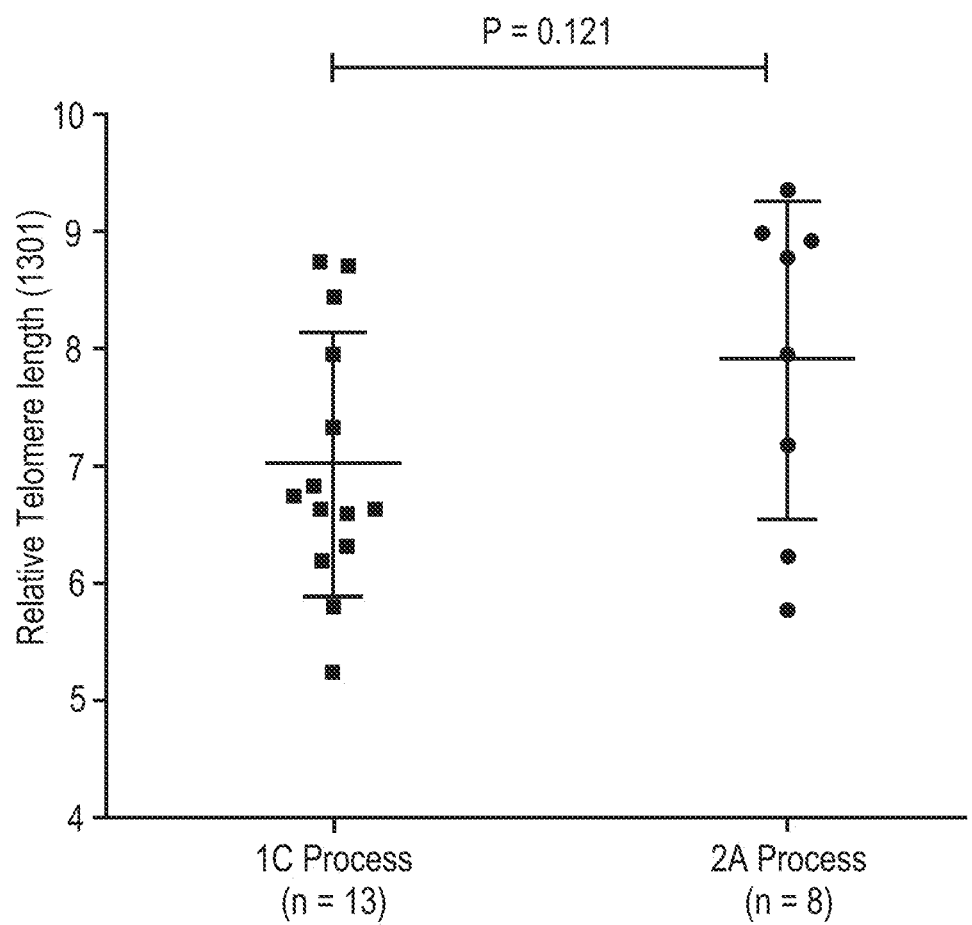
FIG. 25: Depicts the results of flow-FISH telomere length analysis (after removal of an outlier data point).

Flow-FISH results are shown in FIGS. 24 and 25, and no significant differences were observed between process 1C and process 2A, suggesting that the surprising properties of the TILs produced by process 2A were not predictable from the age of the TILs alone.

In conclusion, process 2A produced a potent TIL product with a "young" phenotype as defined by high levels of co-stimulatory molecules, low levels of exhaustion markers, and an increased capability to secrete cytokine upon reactivation. The abbreviated 22 day expansion platform allows for the rapid generation of clinical scale doses of TILs for patients in urgent need of therapy. The cryopreserved drug product introduces critical logistical efficiencies allowing rapid manufacture and flexibility in distribution. This expansion method overcomes traditional barriers to the wider application of TIL therapy.

Example 11: Use of IL-2, IL-15, and IL-21 Cytokine Cocktail

This example describes the use of IL-2, IL-15, and IL-21 cytokines, which serve as additional T cell growth factors, in combination with the TIL process of Examples 1 to 10.

Using the process of Examples 1 to 10, TILs were grown from colorectal, melanoma, cervical, triple negative breast, lung and renal tumors in presence of IL-2 in one arm of the experiment and, in place of IL-2, a combination of IL-2, IL-15, and IL-21 in another arm at the initiation of culture. At the completion of the pre-REP, cultures were assessed for expansion, phenotype, function (CD107a+ and IFN-γ) and TCR Vβ repertoire. IL-15 and IL-21 are described elsewhere herein and in Gruijl, et al., IL-21 promotes the expansion of CD27+CD28+ tumor infiltrating lymphocytes with high cytotoxic potential and low collateral expansion of regulatory T cells, *Santegoets*, S. J., J Transl Med., 2013, 11:37 (https://www.ncbi.nlm.nih.gov/pmc/articles/PMC3626797/).

The results showed that enhanced TIL expansion (>20%), in both $CD4^+$ and $CD8^+$ cells in the IL-2, IL-15, and IL-21 treated conditions were observed in multiple histologies relative to the IL-2 only conditions. There was a skewing towards a predominantly $CD8^+$ population with a skewed TCR Vβ repertoire in the TILs obtained from the IL-2, IL-15, and IL-21 treated cultures relative to the IL-2 only cultures. IFN-γ and CD107a were elevated in the IL-2, IL-15, and IL-21 treated TILs, in comparison to TILs treated only IL-2.

Example 12: Phase 2, Multicenter, Three-Cohort Study in Melanoma

Figure 26:
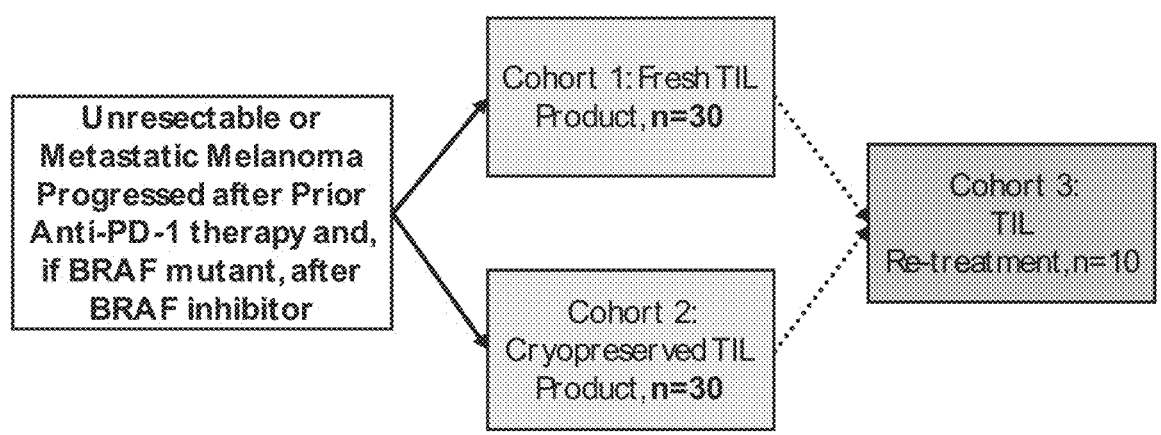
FIG. 26: Depicts the clinical trial design including cohorts treated with process 1C and an embodiment of process 2A.
Figure 28A:
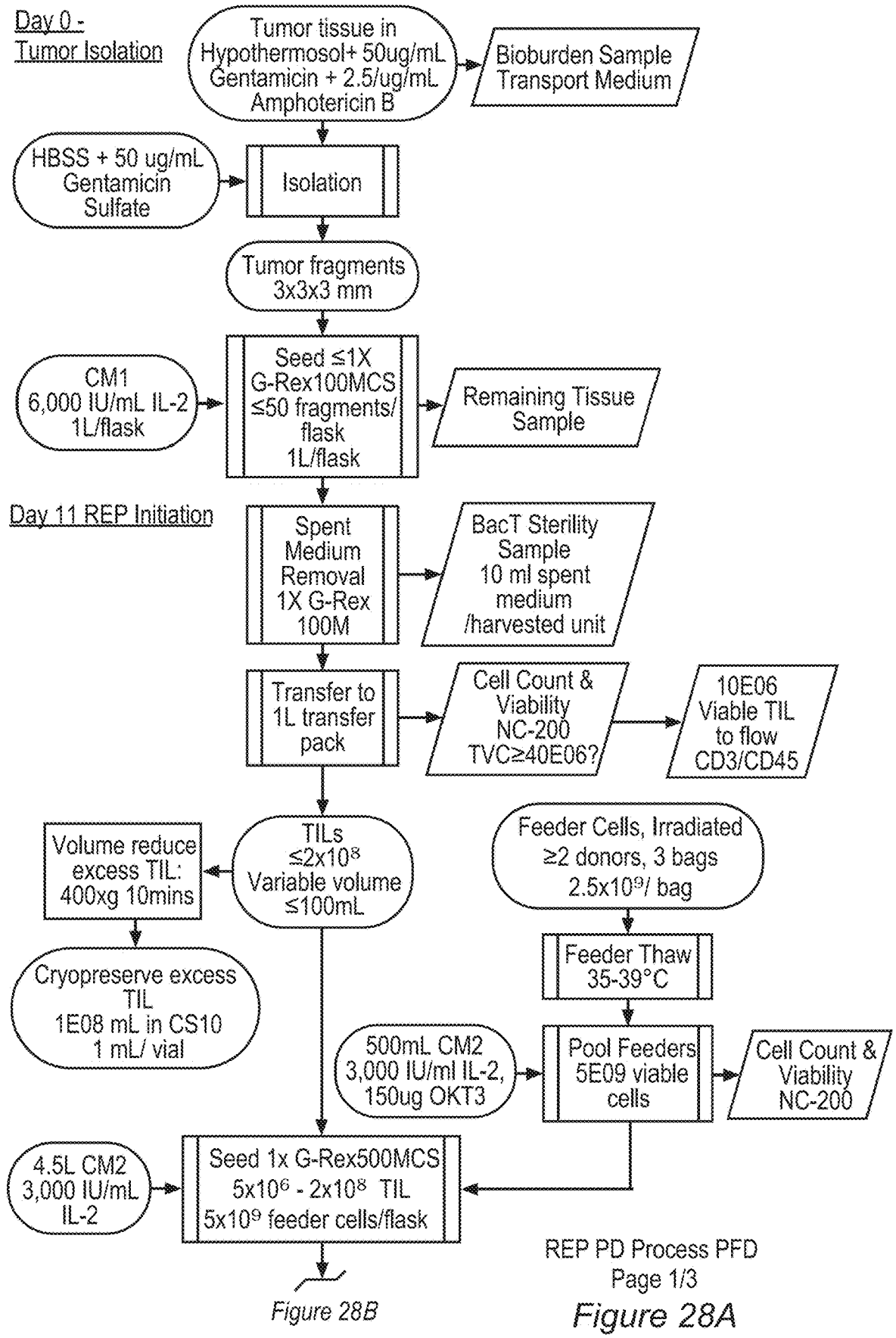
Figure 28B:
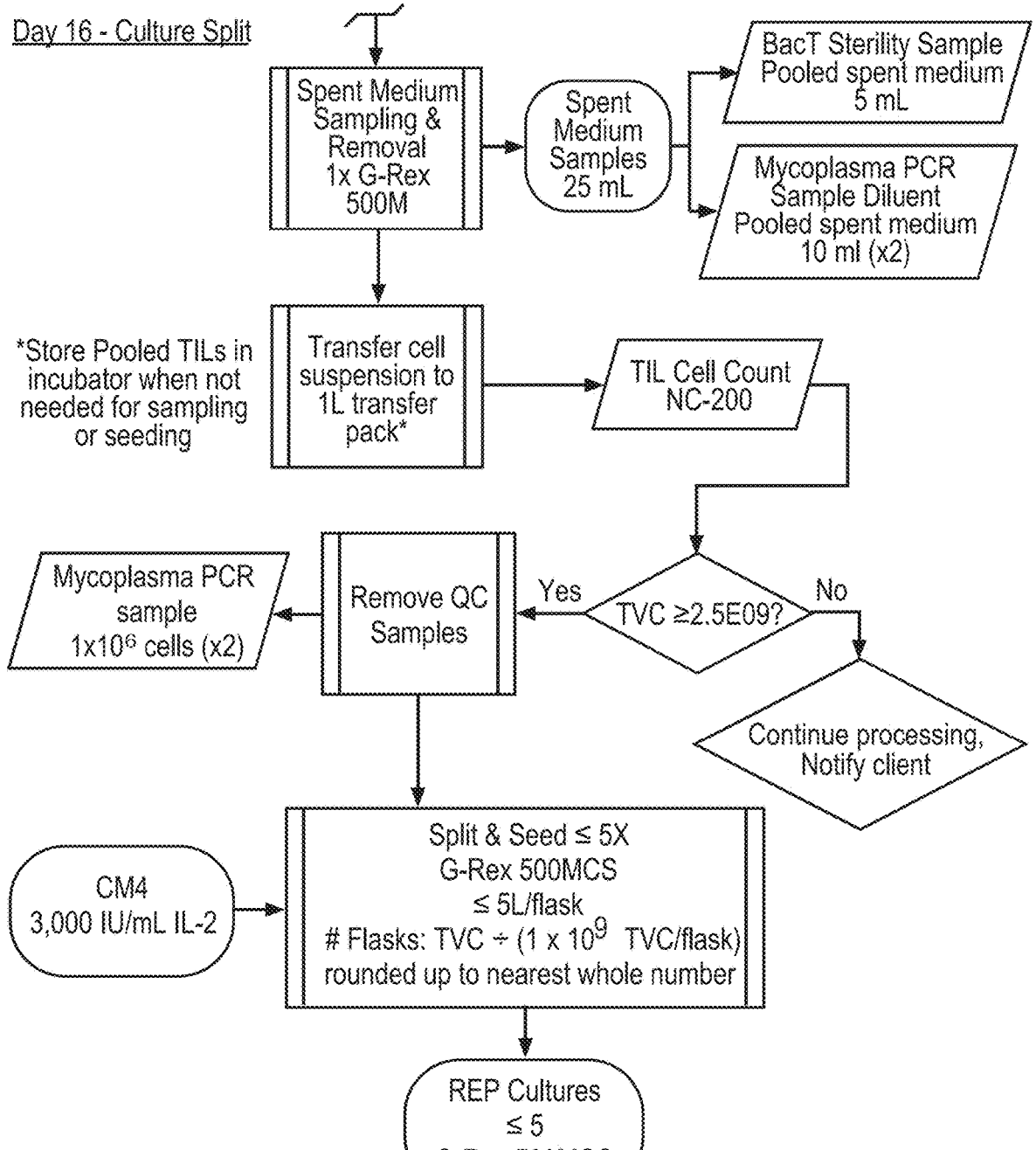

This Phase 2, multicenter, three-cohort study is designed to assess the safety and efficacy of a TIL therapy manufactured according to process 1C (as described herein) in patient with metastatic melanoma. Cohorts one and two will enroll up to 30 patients each and cohort three is a retreatment cohort for a second TIL infusion in up to ten patients. The first two cohorts are evaluating two different manufacturing processes: processes 1C and an embodiment of process 2A (described in Examples 1 to 10, respectively. Patients in cohort one receive fresh, non-cryopreserved TIL and cohort two patients receive product manufactured through the process described in Examples 1 to 10, yielding a cryopreserved product. The study design is shown in FIG. 26. The study is a Phase 2, multicenter, three cohort study to assess the safety and efficacy of autologous TILs for treatment of subpopulations of patients with metastatic melanoma. Key inclusion criteria include: measurable metastatic melanoma and >1 lesion resectable for TIL generation; at least one prior line of systemic therapy; age ≥18; and ECOG performance status of 0-1. Treatment cohorts include non-cryopreserved TIL product (prepared using process 1C), cryopreserved TIL product (prepared using an embodiment of process 2A), and retreatment with TIL product for patients without response or who progress after initial response. The primary endpoint is safety and the secondary endpoint is efficacy, defined as objective response rate (ORR), complete remission rate (CRR), progression free survival (PFS), duration of response (DOR), and overall survival (OS).

Example 13: Qualifying Individual Lots of Gamma-Irradiated Peripheral Mononuclear Cells This Example describes a novel abbreviated procedure for qualifying individual lots of gamma-irradiated peripheral mononuclear cells (PBMCs, also known as MNC) for use as allogeneic feeder cells in the exemplary methods described herein.

Each irradiated MNC feeder lot was prepared from an individual donor. Each lot or donor was screened individually for its ability to expand TIL in the REP in the presence of purified anti-CD3 (clone OKT3) antibody and interleukin-2 (IL-2). In addition, each lot of feeder cells was tested without the addition of TIL. to verify that the received dose of gamma radiation was sufficient to render them replication incompetent.

Definitions/Abbreviations

BSC—Biological Safety Cabinet
CD3—Cluster of Differentiation 3; surface marker protein T-lymphocytes
CF—Centrifugal
CM2—Complete Medium for TIL #
CMO—Contract Manufacturing Organization
$CO_2$—Carbon Dioxide
EtOH—Ethyl Alcohol
GMP—Good Manufacturing Practice
IL-2—Interleukin 2
IU—International Units
LN2—Liquid Nitrogen
mini-REP—Mini-Rapid Expansion Protocol
ml—Milliliter
MNC—Mononuclear Cells
NA—Not Applicable
OKT3—MACS GMP CD3 pure (clone OKT3) antibody
PPE—Personal Protective Equipment
Pre-REP—Before Rapid Expansion Protocol
QS—Quantum Satis; fill to this quantity
REP—Rapid Expansion Protocol
TIL—Tumor Infiltrating Lymphocytes
T25—25 $cm^2$ tissue culture flask
μg—Micrograms
μL—Microliter
Procedure
Background 7.1.1 Gamma-irradiated, growth-arrested MNC feeder cells were required for REP of TIL. Membrane receptors on the feeder MNCs bind to anti-CD3 (clone OKT3) antibody and crosslink to TIL in the REP flask, stimulating the TIL to expand. Feeder lots were prepared from the leukapheresis of whole blood taken from individual donors. The leukapheresis product was subjected to centrifugation over Ficoll-Hypaque, washed, irradiated, and cryopreserved under GMP conditions.

7.1.2 It is important that patients who received TIL therapy not be infused with viable feeder cells as this can result in Graft-Versus-Host Disease (GVHD). Feeder cells are therefore growth-arrested by dosing the cells with gamma-irradiation, resulting in double strand DNA breaks and the loss of cell viability of the MNC cells upon reculture.

Evaluation Criteria and Experimental Set-Up

Feeder lots were evaluated on two criteria: 1) their ability to expand TIL in co-culture >100-fold and 2) their replication incompetency.

7.2.2 Feeder lots were tested in mini-REP format utilizing two primary pre-REP TIL lines grown in upright T25 tissue culture flasks.

7.2.3 Feeder lots were tested against two distinct TIL lines, as each TIL line is unique in its ability to proliferate in response to activation in a REP.

7.2.4 As a control, a lot of irradiated MNC feeder cells which has historically been shown to meet the criteria of 7.2.1 was run alongside the test lots.

7.2.5 To ensure that all lots tested in a single experiment receive equivalent testing, sufficient stocks of the same pre-REP TIL lines were available to test all conditions and all feeder lots.

7.2.6 For each lot of feeder cells tested, there was a total of six T25 flasks:
  7.2.6.1 Pre-REP TIL line #1 (2 flasks)
  7.2.6.2 Pre-REP TIL line #2 (2 flasks)
  7.2.6.3 Feeder control (2 flasks)
  NOTE: Flasks containing TIL lines #1 and #2 evaluated the ability of the feeder lot to expand TIL. The feeder control flasks evaluated the replication incompetence of the feeder lot.

Experimental Protocol 7.3.1 Day −2/3, Thaw of TIL lines
  7.3.1.1 Prepared CM2 medium.
  7.3.1.2 Warmed CM2 in 37° C. water bath.
  7.3.1.3 Prepared 40 ml of CM2 supplemented with 3000 IU/ml IL-2. Keep warm until use.
  7.3.1.4 Placed 20 ml of pre-warmed CM2 without IL-2 into each of two 50 ml conical tubes labeled with names of the TIL lines used.
  7.3.1.5 Removed the two designated pre-REP TIL lines from LN2 storage and transferred the vials to the tissue culture room.
  7.3.1.6 Recorded TIL line identification.
  7.3.1.7 Thawed vials by placing them inside a sealed zipper storage bag in a 37° C. water bath until a small amount of ice remains.
  7.3.1.8 Sprayed or wiped thawed vials with 70% ethanol and transfer vials to BSC.
  7.3.1.9 Using a sterile transfer pipet, immediately transferred the contents of vial into the 20 ml of CM2 in the prepared, labeled 50 ml conical tube.
  7.3.1.10 QS to 40 ml using CM2 without IL-2 to wash cells.
  7.3.1.11 Centrifuged at 400×CF for 5 minutes.
  7.3.1.12 Aspirated the supernatant and resuspend in 5 ml warm CM2 supplemented with 3000 IU/ml IL-2.
  7.3.1.13 Removed small aliquot (20 µl) in duplicate for cell counting using an automated cell counter. Record the counts.
  7.3.1.14 While counting, placed the 50 ml conical tube with TIL cells into a humidified 37° C., 5% $CO_2$ incubator, with the cap loosened to allow for gas exchange.
  7.3.1.15 Determined cell concentration and dilute TIL to $1\times10^6$ cells/ml in CM2 supplemented with IL-2 at 3000 IU/ml.
  7.3.1.16 Cultured in 2 ml/well of a 24-well tissue culture plate in as many wells as needed in a humidified 37° C. incubator until Day 0 of the mini-REP.
  7.3.1.17 Cultured the different TIL lines in separate 24-well tissue culture plates to avoid confusion and potential cross-contamination.

7.3.2 Day 0, initiate Mini-REP
  7.3.2.1 Prepared enough CM2 medium for the number of feeder lots to be tested. (e.g., for testing 4 feeder lots at one time, prepared 800 ml of CM2 medium).
  7.3.2.2 Aliquoted a portion of the CM2 prepared in 7.3.2.1 and supplement it with 3000 IU/ml IL-2 for the culturing of the cells. (e.g., for testing 4 feeder lots at one time, prepare 500 ml of CM2 medium with 3000 IU/ml IL-2).
  7.3.2.3 The remainder of the CM2 with no IL-2 will be used for washing of cells as described below.
  7.3.2.4 Working with each TIL line separately to prevent cross-contamination, removed the 24-well plate with TIL culture from the incubator and transferred to the BSC.
  7.3.2.5 Using a sterile transfer pipet or 100-1000 µl Pipettor and tip, removed about 1 ml of medium from each well of TIL to be used and place in an unused well of the 24-well tissue culture plate. This was used for washing wells.
  7.3.2.6 Using a fresh sterile transfer pipet or 100-1000 µl Pipettor and tip, mixed remaining medium with TIL in wells to resuspend the cells and then transferred the cell suspension to a 50 ml conical tube labeled with the TIL name and recorded the volume.
  7.3.2.7 Washed the wells with the reserved media and transferred that volume to the same 50 ml conical tube.
  7.3.2.8 Spun the cells at 400×CF to collect the cell pellet.
  7.3.2.9 Aspirated off the media supernatant and resuspend the cell pellet in 2-5 ml of CM2 medium containing 3000 IU/ml IL-2, volume to be used based on the number of wells harvested and the size of the pellet—volume should be sufficient to ensure a concentration of $>1.3\times10^6$ cells/ml.
  7.3.2.10 Using a serological pipet, mixed the cell suspension thoroughly and recorded the volume.
  7.3.2.11 Removed 200 µl for a cell count using an automated cell counter.
  7.3.2.12 While counting, placed the 50 ml conical tube with TIL cells into a humidified, 5% $CO_2$, 37° C. incubator, with the cap loosened to allow gas exchange.
  7.3.2.13 Recorded the counts.
  7.3.2.14 Removed the 50 ml conical tube containing the TIL cells from the incubator and resuspend them cells at a concentration of $1.3\times10^6$ cells/ml in warm CM2 supplemented with 3000 IU/ml IL-2. Returned the 50 ml conical tube to the incubator with a loosened cap.
  7.3.2.15 If desired, kept the original 24-well plate to reculture any residual TIL.
  7.3.2.16 Repeated steps 7.3.2.4-7.3.2.15 for the second TIL line.
  7.3.2.17 Just prior to plating the TIL into the T25 flasks for the experiment, TIL were diluted 1:10 for a final concentration of $1.3\times10^5$ cells/ml as per step 7.3.2.35 below.

Prepare MACS GMP CD3 Pure (OKT3) Working Solution
  7.3.2.18 Took out stock solution of OKT3 (1 mg/ml) from 4° C. refrigerator and placed in BSC.
  7.3.2.19 A final concentration of 30 ng/ml OKT3 was used in the media of the mini-REP.
  7.3.2.20 600 ng of OKT3 were needed for 20 ml in each T25 flask of the experiment; this was the equivalent of 60 µl of a 10 µg/ml solution for each 20 ml, or 360 µl for all 6 flasks tested for each feeder lot.
  7.3.2.21 For each feeder lot tested, made 400 µl of a 1:100 dilution of 1 mg/ml OKT3 for a working concentration of 10 µg/ml (e.g., for testing 4 feeder lots at one time, make 1600 µl of a 1:100 dilution of 1 mg/ml OKT3: 16 µl of 1 mg/ml OKT3+1.584 ml of CM2 medium with 3000 IU/ml IL-2.)

Prepare T25 flasks
  7.3.2.22 Labeled each flask with the name of the TIL line tested, flask replicate number, feeder lot number, date, and initials of analyst.
  7.3.2.23 Filled flask with the CM2 medium prior to preparing the feeder cells.

7.3.2.24 Placed flasks into 37° C. humidified 5% $CO_2$ incubator to keep media warm while waiting to add the remaining components.

7.3.2.25 Once feeder cells were prepared, the components will be added to the CM2 in each flask.

Prepare MACS GMP CD3 Pure (OKT3) Working Solution.

TABLE 21

Solutions

| Component | Volume in co-culture flasks | Volume in control (feeder only) flasks |
|---|---|---|
| CM2 + 300 IU/ml IL-2 | 18 ml | 19 ml |
| MNC: $1.3 \times 10^7$ ml in CM2 + 3000 IU IL-2 (final concentration $1.3 \times 10^7$/flask) | 1 ml | 1 ml |
| OKT3: 10 μ/ml in CM2 + 3000 IU IL-2 | 60 μl | 60 μl |
| TIL: $1.3 \times 10^5$ ml in CM2 with 3000 IU IL-2 (final concentration $1.3 \times 10^5$ flask) | 1 ml | 0 |

Prepare Feeder Cells 7.3.2.26 A minimum of $78 \times 10^6$ feeder cells were needed per lot tested for this protocol. Each 1 ml vial frozen by SDBB had $100 \times 10^6$ viable cells upon freezing. Assuming a 50% recovery upon thaw from LN2 storage, it was recommended to thaw at least two 1 ml vials of feeder cells per lot giving an estimated $100 \times 10^6$ viable cells for each REP. Alternately, if supplied in 1.8 ml vials, only one vial provided enough feeder cells.

7.3.2.27 Before thawing feeder cells, pre-warmed approximately 50 ml of CM2 without IL-2 for each feeder lot to be tested.

7.3.2.28 Removed the designated feeder lot vials from LN2 storage, placed in zipper storage bag, and place on ice. Transferred vials to tissue culture room.

7.3.2.29 Thawed vials inside closed zipper storage bag by immersing in a 37° C. water bath.

7.3.2.30 Removed vials from zipper bag, spray or wipe with 70% EtOH and transferred vials to BSC.

7.3.2.31 Using a transfer pipet immediately transferred the contents of feeder vials into 30 ml of warm CM2 in a 50 ml conical tube. Washed vial with a small volume of CM2 to remove any residual cells in the vial.

7.3.2.32 Centrifuged at 400×CF for 5 minutes.

7.3.2.33 Aspirated the supernatant and resuspended in 4 ml warm CM2 plus 3000 IU/ml IL-2.

7.3.2.34 Removed 200 μl for cell counting using the Automated Cell Counter. Recorded the counts.

7.3.2.34 Resuspended cells at $1.3 \times 10^7$ cells/ml in warm CM2 plus 3000 IU/ml IL-2.

7.3.2.34 Diluted TIL cells from $1.3 \times 10^6$ cells/ml to $1.3 \times 10^5$ cells/ml. Worked with each TIL line independently to prevent cross-contamination.

Setup Co-Culture 7.3.2.36 Diluted TIL cells from $1.3 \times 10^6$ cells/ml to $1.3 \times 10^5$ cells/ml. Worked with each TIL line independently to prevent cross-contamination.

7.3.2.36.1 Added 4.5 ml of CM2 medium to a 15 ml conical tube.

7.3.2.36.2 Removed TIL cells from incubator and resuspended well using a 10 ml serological pipet.

7.3.2.36.3 Removed 0.5 ml of cells from the $1.3 \times 10^6$ cells/ml TIL suspension and added to the 4.5 ml of medium in the 15 ml conical tube. Returned TIL stock vial to incubator.

7.3.2.36.4 Mixed well.

7.3.2.36.5 Repeated steps 7.3.2.36.1-7.3.2.36.4 for the second TIL line.

7.3.2.36.6 If testing more than one feeder lot at one time, diluted the TIL to the lower concentration for each feeder lot just prior to plating the TIL.

7.3.2.37 Transferred flasks with pre-warmed media for a single feeder lot from the incubator to the BSC.

7.3.2.38 Mixed feeder cells by pipetting up and down several times with a 1 ml pipet tip and transferred 1 ml ($1.3 \times 10^7$ cells) to each flask for that feeder lot.

7.3.2.39 Added 60 μl of OKT3 working stock (10 μg/ml) to each flask.

7.3.2.40 Returned the two control flasks to the incubator.

7.3.2.41 Transferred 1 ml ($1.3 \times 10^5$) of each TIL lot to the correspondingly labeled T25 flask.

7.3.2.42 Returned flasks to the incubator and incubate upright. Did not disturb until Day 5.

7.3.2.43 Repeated 7.3.2.36-7.3.2.42 for all feeder lots tested.

Day 5, Media Change 7.3.3.1 Prepared CM2 with 3000 IU/ml IL-2. 10 ml is needed for each flask 7.3.3.2 To prevent cross-contamination, handled the flasks for a single feeder lot at a time. Removed flasks from the incubator and transfer to the BSC, care was taken not to disturb the cell layer on the bottom of the flask.

7.3.3.3 Repeated for all flasks including control flask.

7.3.3.4 With a 10 ml pipette, transferred 10 ml warm CM2 with 3000 IU/ml IL-2 to each flask.

7.3.3.5 Returned flasks to the incubator and incubate upright until Day 7. Repeated 7.3.3.1-7.3.3.6 for all feeder lots tested.

Day 7, Harvest 7.3.4.1 To prevent cross-contamination, handled the flasks for a single feeder lot at a time.

7.3.4.2 Removed flasks from the incubator and transfer to the BSC, care as taken not to disturb the cell layer on the bottom of the flask.

7.3.4.3 Without disturbing the cells growing on the bottom of the flasks, removed 10 ml of medium from each test flask and 15 ml of medium from each of the control flasks.

7.3.4.4 Using a 10 ml serological pipet, resuspended the cells in the remaining medium and mix well to break up any clumps of cells.

7.3.4.5 Recorded the volumes for each flask.

7.3.4.6 After thoroughly mixing cell suspension by pipetting, removed 200 μl for cell counting.

7.3.4.7 Counted the TIL using the appropriate standard operating procedure in conjunction with the automatic cell counter equipment.

7.3.4.8 Recorded counts in Day 7.

7.3.4.9 Repeated 7.3.4.1-7.3.4.8 for all feeder lots tested.

7.3.4.10 Feeder control flasks were evaluated for replication incompetence and flasks containing TIL were evaluated for fold expansion from Day 0 according to the criteria listed in Table 21 (below).

Day 7, Continuation of Feeder Control Flasks to Day 14

7.3.5.1 After completing the Day 7 counts of the feeder control flasks, added 15 ml of fresh CM2 medium containing 3000 IU/ml IL-2 to each of the control flasks.

7.3.5.2 Returned the control flasks to the incubator and incubated in an upright position until Day 14.

Day 14, Extended Non-Proliferation of Feeder Control Flasks
  7.3.6.1 To prevent cross-contamination, handled the flasks for a single feeder lot at a time.
  7.3.6.2 Removed flasks from the incubator and transfer to the BSC, care was taken not to disturb the cell layer on the bottom of the flask.
  7.3.6.3 Without disturbing the cells growing on the bottom of the flasks, removed approximately 17 ml of medium from each control flasks.
  7.3.6.4 Using a 5 ml serological pipet, resuspended the cells in the remaining medium and mixed well to break up any clumps of cells.
  7.3.6.5 Recorded the volumes for each flask.
  7.3.6.6 After thoroughly mixing cell suspension by pipetting, removed 200 µl for cell counting.
  7.3.6.7 Counted the TIL using the appropriate standard operating procedure in conjunction with the automatic cell counter equipment.
  7.3.6.8 Recorded counts.
  7.3.6.9 Repeated 7.3.4.1-7.3.4.8 for all feeder lots tested.

Results and Acceptance Criteria
  Results
  10.1.1 The dose of gamma irradiation was sufficient to render the feeder cells replication incompetent. All lots were expected to meet the evaluation criteria and also demonstrated a reduction in the total viable number of feeder cells remaining on Day 7 of the REP culture compared to Day 0.
  10.1.2 All feeder lots were expected to meet the evaluation criteria of 100-fold expansion of TIL growth by Day 7 of the REP culture.
  10.1.3 Day 14 counts of Feeder Control flasks were expected to continue the non-proliferative trend seen on Day 7.
  Acceptance Criteria
  10.2.1 The following acceptance criteria were met for each replicate TIL line tested for each lot of feeder cells
  10.2.2 Acceptance was two-fold, as follows (outlined in the Table below).

TABLE 22

Acceptance Criteria

| Test | Acceptance criteria |
| --- | --- |
| Irradiation of MNC/ Replication Incompetence | No growth observed at 7 and 14 days |
| TIL expansion | At least a 100-fold expansion of each TIL (minimum of $1.3 \times 10^7$ viable cells) |

10.2.2.1 Evaluated whether the dose of radiation was sufficient to render the MNC feeder cells replication incompetent when cultured in the presence of 30 ng/ml OKT3 antibody and 3000 IU/ml IL-2.
    10.2.2.1.1 Replication incompetence was evaluated by total viable cell count (TVC) as determined by automated cell counting on Day 7 and Day 14 of the REP.
    10.2.2.1.2 Acceptance criteria was "No Growth," meaning the total viable cell number has not increased on Day 7 and Day 14 from the initial viable cell number put into culture on Day 0 of the REP.
  10.2.2.2 Evaluated the ability of the feeder cells to support TIL expansion.
    10.2.2.2.1 TIL growth was measured in terms of fold expansion of viable cells from the onset of culture on Day 0 of the REP to Day 7 of the REP.
      10.2.2.2.1 On Day 7, TIL cultures achieved a minimum of 100-fold expansion, (i.e., greater than 100 times the number of total viable TIL cells put into culture on REP Day 0), as evaluated by automated cell counting.
  10.2.2.3 Should a lot fail to meet the two criteria above, the lot was retested according to the contingency plan outlined in Section 10.3 below.
  10.2.2.4 Following retesting of a failed lot, any MNC feeder lot that did not meet the two acceptance criteria in both the original evaluation and the contingency testing was excluded.
  10.2.2.5 Any MNC feeder lots that meet acceptance criteria but were judged to have poor performance in regard to the ability to expand TIL relative to other previous feeder lots tested in parallel with the same pre-REP TIL lines were excluded.

Contingency Testing of MNC Feeder Lots that do not Meet Acceptance Criteria
  10.3.1 In the event that an MNC feeder lot did not meet the either of the acceptance criteria outlined in Section 10.2 above, the following steps will be taken to retest the lot to rule out simple experimenter error as its cause.
  10.3.2 If there are two or more remaining satellite testing vials of the lot, then the lot was retested. If there were one or no remaining satellite testing vials of the lot, then the lot was failed according to the acceptance criteria listed in Section 10.2 above.
  10.3.3 Two trained personnel, include the original person who evaluated the lot in question, both tested the lot at the same time.
  10.3.4 Repeating Section 7.2-7.3 was done to re-evaluate the lot in question.
  10.3.5 Each person tested the lot in question as well as a control lot (as defined in Section 7.2.4 above).
  10.3.6 In order to be qualified, the lot in question and the control lot had to achieve the acceptance criteria of Section 10.2 for both of the personnel doing the contingency testing.
  10.3.7 Upon meeting these criteria, the lot was then released for CMO use as outlined in Section 10.2 above.

Example 14: Qualifying Individual Lots of Gamma-Irradiated Peripheral Blood Mononuclear Cells This Example describes a novel abbreviated procedure for qualifying individual lots of gamma-irradiated peripheral blood mononuclear cells (PBMC) for use as allogeneic feeder cells in the exemplary methods described herein. This example provides a protocol for the evaluation of irradiated PBMC cell lots for use in the production of clinical lots of TIL. Each irradiated PBMC lot was prepared from an individual donor. Over the course of more than 100 qualification protocols, it was been shown that, in all cases, irradiated PBMC lots from SDBB (San Diego Blood Bank) expand TIL >100-fold on Day 7 of a REP. This modified qualification protocol was intended to apply to irradiated donor PBMC lots from SDBB which were then further tested to verify that the received dose of gamma radiation was sufficient to render them replication incompetent. Once demonstrated that they maintained replication incompetence over the course of 14 days, donor PBMC lots were considered "qualified" for usage to produce clinical lots of TIL.

Key Terms and Definitions

μg—Microgram
μl—Microliter
AIM-V—commercially available cell culture medium
Biological Safety Cabinet
BSC—Cluster of Differentiation
CD—Complete Medium for TIL #2
CM2—CM2 supplemented with 3000 IU/ml IL-2
CM2IL2—Contract Manufacturing Organization
$CO_2$—Carbon Dioxide
EtOH—Ethanol
GMP—Good Manufacturing Practices
Gy—Gray
IL—Interleukin
IU—International Units
LN2—Liquid Nitrogen
MI—Milliliter
NA—Not Applicable
OKT3—anti-CD3 monoclonal antibody designation
P20—2-20 μl pipettor
P200—20-200 μl pipettor
PBMC—peripheral blood mononuclear cells
P1000—100-1000 μl pipettor
PPE—Personal Protective Equipment
REP—Rapid Expansion Protocol
SDBB—San Diego Blood Bank
TIL—Tumor Infiltrating Lymphocytes
T25—25 cm2 tissue culture flask
xg—"times gravity"—measure of relative centrifugal force
Specimens include Irradiated donor PBMC (SDBB).
Procedure
Background
7.1.1 Gamma-irradiated, growth-arrested PBMC were required for current standard REP of TIL. Membrane receptors on the PBMCs bind to anti-CD3 (clone OKT3) antibody and crosslink to TIL in culture, stimulating the TIL to expand. PBMC lots were prepared from the leukapheresis of whole blood taken from individual donors. The leukapheresis product was subjected to centrifugation over Ficoll-Hypaque, washed, irradiated, and cryopreserved under GMP conditions.
It is important that patients who received TIL therapy not be infused with viable PBMCs as this could result in Graft-Versus-Host Disease (GVHD). Donor PBMCs are therefore growth-arrested by dosing the cells with gamma-irradiation, resulting in double strand DNA breaks and the loss of cell viability of the PBMCs upon reculture.
Evaluation Criteria
7.2.1 Evaluation criterion for irradiated PBMC lots was their replication incompetency.
Experimental Set-Up
7.3.1 Feeder lots were tested in mini-REP format as if they were to be co-cultured with TIL, using upright T25 tissue culture flasks.
7.3.1.1 Control lot: One lot of irradiated PBMCs, which had historically been shown to meet the criterion of 7.2.1, was run alongside the experimental lots as a control.
7.3.2 For each lot of irradiated donor PBMC tested, duplicate flasks was run.

Experimental Protocol
All tissue culture work in this protocol was done using sterile technique in a BSC.
Day 0
7.4.1 Prepared ~90 ml of CM2 medium for each lot of donor PBMC to be tested. Kept CM2 warm in 37° C. water bath.
7.4.2 Thawed an aliquot of $6 \times 10^6$ IU/ml IL-2.
7.4.3 Returned the CM2 medium to the BSC, wiping with 70% EtOH prior to placing in hood. For each lot of PBMC tested, removed about 60 ml of CM2 to a separate sterile bottle. Added IL-2 from the thawed $6 \times 10^6$ IU/ml stock solution to this medium for a final concentration of 3000 IU/ml. Labeled this bottle as "CM2/IL2" (or similar) to distinguish it from the unsupplemented CM2.
7.4.4 Labeled two T25 flasks for each lot of PBMC to be tested. Minimal label included:
7.4.4.1 Lot number
7.4.4.2 Flask number (1 or 2)
7.4.4.3 Date of initiation of culture (Day 0)
Prepare OKT3
7.4.5 Took out the stock solution of anti-CD3 (OKT3) from the 4° C. refrigerator and placed in the BSC.
7.4.6 A final concentration of 30 ng/ml OKT3 was used in the media of the mini-REP.
7.4.7 Prepared a 10 μg/ml working solution of anti-CD3 (OKT3) from the 1 mg/ml stock solution. Placed in refrigerator until needed.
7.4.7.1 For each PBMC lot tested, prepare 150 μl of a 1:100 dilution of the anti-CD3 (OKT3) stock
E.g., for testing 4 PBMC lots at one time, prepare 600 μl of 10 μg/ml anti-CD3 (OKT3) by adding 6 μl of the 1 mg/ml stock solution to 594 μl of CM2 supplemented with 3000 IU/ml IL-2.
Prepare Flasks
7.4.8 Added 19 ml per flask of CM2/IL-2 to the labeled T25 flasks and placed flasks into 37° C., humidified, 5% $CO_2$ incubator while preparing cells.
Prepare Irradiate PBMC
7.4.9 Worked with each donor PBMC lot individually to avoid the potential cross-contamination of the lots.
7.4.10 Retrieved vials of PBMC lots to be tested from LN2 storage. These were placed at −80° C. or kept on dry ice prior to thawing.
7.4.11 Placed 30 ml of CM2 (without IL-2 supplement) into 50 ml conical tubes for each lot to be thawed. Labeled each tube with the different lot numbers of the PBMC to be thawed. Capped tubes tightly and place in 37° C. water bath prior to use. As needed, returned 50 ml conical tubes to the BSC, wiping with 70% EtOH prior to placing in the hood.
7.4.12 Removed a vial PBMC from cold storage and place in a floating tube rack in a 37° C. water bath to thaw. Allowed thaw to proceed until a small amount of ice remains in the vial.
7.4.13 Sprayed or wiped thawed vial with 70% EtOH and transfer to BSC.
7.4.14 Using a sterile transfer pipet, immediately transferred the contents of the vial into the 30 ml of CM2 in the 50 ml conical tube. Removed about 1 ml of medium from the tube to rinse the vial; returned rinse to the 50 ml conical tube. Capped tightly and swirl gently to wash cells.
7.4.15 Centrifuged at 400×g for 5 min at room temperature.
7.4.16 Aspirated the supernatant and resuspend the cell pellet in 1 ml of warm CM2/IL-2 using a 1000 μl pipet tip. Alternately, prior to adding medium, resuspended cell pellet by dragging capped tube along an empty tube rack. After resuspending the cell pellet, brought volume to 4 ml using CM2/IL-2 medium. Recorded volume.

7.4.17 Removed a small aliquot (e.g., 100 µl) for cell counting using an automated cell counter.

7.4.17.1 Performed counts in duplicate according to the particular automated cell counter SOP. It most likely was necessary to perform a dilution of the PBMC prior to performing the cell counts. A recommended starting dilution was 1:10, but this varied depending on the type of cell counter used.

7.4.17.2 Recorded the counts.

7.4.18 Adjusted concentration of PBMC to $1.3 \times 10^7$ cells/ml as per the worksheet in step 7.4.15.2 using CM2/IL-2 medium. Mixed well by gentle swirling or by gently aspirating up-and-down using a serological pipet.

Set Up Culture Flasks 7.4.19 Returned two labeled T25 flasks to the BSC from the tissue culture incubator.

7.4.20 Returned the 10 µg/ml vial of anti-CD3/OKT3 to the BSC.

7.4.21 Added 1 ml of the $1.3 \times 10^7$ PBMC cell suspension to each flask.

7.4.22 Added 60 µl of the 10 µg/ml anti-CD3/OKT3 to each flask.

7.4.23 Returned capped flasks to the tissue culture incubators for 14 days of growth without disturbance.

7.4.24 Placed anti-CD3/OKT3 vial back into the refrigerator until needed for the next lot.

7.4.25 Repeated steps 7.4.9-7.4.24 for each lot of PBMC to be evaluated.

Day 14, Measurement of Non-Proliferation of PBMC 7.4.26 Working with each lot independently, carefully returned the duplicate T25 flasks to the BSC.

7.4.27 For each flask, using a fresh 10 ml serological pipet, removed ~17 ml from each of the flasks, then carefully pulled up the remaining media to measure the volume remaining in the flasks. Recorded volume.

7.4.28 Mixed sample well by pipetting up and down using the same serological pipet.

7.4.29 Removed a 200 µl sample from each flask for counting.

7.4.30 Counted cells using an automated cell counter.

7.4.31 Repeated steps 7.4.26-7.4.31 for each lot of PBMC being evaluated.

Results and Acceptance Criterion

Results 10.1.1 The dose of gamma irradiation was expected to be sufficient to render the feeder cells replication incompetent. All lots were expected to meet the evaluation criterion, demonstrating a reduction in the total viable number of feeder cells remaining on Day 14 of the REP culture compared to Day 0.

Acceptance Criterion 10.2.1 The following acceptance criterion were met for each irradiated donor PBMC lot tested:

10.2.2 "No growth"—meant that the total number of viable cells on Day 14 was less than the initial viable cell number put into culture on Day 0 of the REP.

10.2.3 Should a lot fail to meet the criterion above, the lot was retested per the Contingency Testing Procedure outlined in the section 10.4.

10.2.4 Following retesting of a failed lot, any MNC feeder lot that did not meet the acceptance criterion in both the original evaluation and the contingency testing was excluded.

Contingency Testing of PBMC Lots which do not Meet Acceptance Criterion.

10.4.1 In the event than an irradiated donor PBMC lot did not meet the acceptance criterion above, the following steps were taken to retest the lot to rule out simple experimenter error as the cause of its failure.

10.4.2 If there were two or more remaining satellite vials of the lot, then the lot was retested. If there are one or no remaining satellite vials of the lot, then the lot was failed according to the acceptance criterion of section 10.2 above.

10.4.3 Whenever possible, two trained personnel (preferably including the original person who evaluated the lot in question) did the testing of the two separate vials independently. This was the preferred method of contingency testing. Aside from the separate vials of PBMC, the same reagents could be used by both personnel.

10.4.3.1. If two personnel were not available, one person did the testing of the two PBMC vials for the failed lot, working with each vial independently.

10.4.4 Repeating of section 7.4 "Experimental Protocol" was done to re-evaluated the lot in question.

10.4.5 In addition to the lot in question, a control lot was tested by each person carrying out the contingency testing.

10.4.5.1 If two personnel perform contingency testing, both personnel tested the control lot independently.

10.4.5.2 If only one person is available to perform contingency testing, it was not necessary for the control lot to be run in duplicate.

10.4.5.3 To be qualified, a PBMC lot going through contingency testing had both the control lot and both replicates of the lot in question achieve the acceptance criterion of Section 10.2 to pass.

10.4.5.4 Upon meeting this criterion, the lot was then released for CMO usage as outlined in section 10.2.

Example 15: Cellometer IC2 Image Cytometer Automatic Cell Counter

This Example describes the procedure for operation of the Cellometer K2 Image Cytometer automatic cell counter.

1. Definitions

µl Microliter
AOPI Acridine Orange Propidium Iodine
BSC Biological Safety Cabinet
DPBS Dulbecco's Phosphate Buffered Saline
ml Milliliter
MNC Mononuclear Blood Cells
NA Not Applicable
PBMC Peripheral Blood Mononuclear Cells
PPE Personal Protective Equipment
Pre-REP Initial TIL culture before Rapid Expansion Protocol of culture
REP Rapid Expansion Protocol
TIL Tumor Infiltrating Lymphocytes

7. Procedure

7.1 Cell suspension preparation
7.1.1 Trypan Blue Preparation
The final Trypan blue concentration was 0.10%. The manufacturer recommended preparing a stock solution of 0.2%.
  7.1.1.1 When using Trypan blue on the Cellometer K2, diluted the stock (0.4%) with PBS to 0.2%.
  7.1.1.2 Filtered the Trypan blue with a 0.2-0.4 micron filter and aliquot in small volumes into labeled, capped tubes.
  7.1.1.3 Mixed the cell suspension at 1:1 with 0.2% trypan blue.
7.1.2 AOPI Preparation
  7.1.2.1 When using AOPI on the Cellometer K2, obtained the AOPI solution.
  7.1.2.2 Stained cell sample at 1:1 with AOPI solution.
NOTE: When counting high concentration cultures, diluted the cell samples in cell culture medium prior to the final 1:1 dilution with Trypan Blue or AOPI.
Used manufacturer's suggested range of counting to determine the best dilution to use.

7.2 Cellometer K2 Set-Up
7.2.1 Turned on the Cellometer K2 equipment.
7.2.2 Selected the Cellometer Image Cytometer icon on the associated computer monitor.
7.2.3 On the main screen of the software, selected one of the Assays listed in the dropdown box.
  7.2.3.1 When selecting the appropriate Assay, the Cell Type and Image Mode self-populated.
  7.2.3.2 Under "Sample" section, clicked on Set User/Sample ID to open another screen to input operator's information for specimen.
    7.2.3.2.1 Entered "User ID". This will consist of the user's three letter initials.
    7.2.3.2.2 Entered "Sample ID". The sample ID is derived from incoming specimen information.
  7.2.3.3 Set up dilution parameters.
    7.2.3.3.1 If no other dilution was made besides the 1:1 mixture, the dilution factor was 2.
    7.2.3.3.2 If a dilution was made prior to the final 1:1 mixture, the dilution factor was 2 times of the prior dilution.
    7.2.3.3.3 Updated dilution factor according to the mixture used in the dilution section of the screen. Clicked on the pencil icon to bring up the dialog screens.
    7.2.3.3.4 Verified that F1 Image and F2 Image sections are identical to each other.
    7.2.3.3.5 Clicked on the "Save" button after set up has been completed.

7.3 Cell Counting
7.3.1 Removed the plastic backing from both sides of a Cellometer counting chamber slide (SD100) and placed it on top of a clean, lint-free wipe.
7.3.2 After preparing the cell suspension, removed a small aliquot of the sample and transferred it into a well of a multiwell cell culture plate or tube.
7.3.3 If diluting the sample, performed the dilution using cell culture medium.
7.3.4 Added 20 µl of cell suspension into a well of the multiwell cell culture plate or tube.
7.3.5 Added 20 111 of 0.2% trypan blue or the AOPI solution to the 20111 of cell suspension and mix sample thoroughly.
7.3.6 Measured 20 IA of the 1:1 solution and transferred it into one side of the counting chamber.
NOTE: Avoided touching the clear area of the slide.
7.3.7 If necessary, repeated the sample on the other side of the slide. 7.3.8. Inserted the chamber into the slot on the front of the Cellometer.
7.3.8 For the AOPI cell counting, clicked on "Preview F1" on the main screen to preview the green fluorescent image (live cell) image. For Trypan blue counting, clicked on "Preview Brightfield".
7.3.9 Using the focusing wheel, brought image into optimal focus. Cells had a bright center and a clearly-defined edge.
7.3.10 Clicked "Count" to begin the counting process.
7.3.11 Results were displayed in a counting results pop-up box on the computer screen showing the results of the counting process.

Example 16: Preparation of IL-2 Stock Solution (Cellgenix)

This Example describes the process of dissolving purified, lyophilized recombinant human interleukin-2 into stock samples suitable for use in further tissue culture protocols, including all of those described in the present application and Examples, including those that involve using rhIL-2.

3. Definitions/Abbreviations

µL: microliter
BSC: Biological Safety Cabinet
BSL2: Biosafety Level 2
D-PBS: Dulbecco's Phosphate Buffered Saline
G: Gauge
GMP: Good Manufacturing Processing
HAc: Acetic Acid
HSA: Human Serum Albumin
mL: Milliliter
NA: Not applicable
PPE: Personal Protective Equipment
rhIL-2; IL-2: Recombinant human Interleukin-2
COA: Certificate of Analysis

6. Procedure 6.1 Prepare 0.2% Acetic Acid solution (HAc).
6.1.1 Transferred 29 mL sterile water to a 50 mL conical tube.
6.1.2 Added 1 mL 1N acetic acid to the 50 mL conical tube.
6.1.3 Mixed well by inverting tube 2-3 times.
6.1.4 Sterilized the HAc solution by filtration using a Steriflip filter.
6.1.5 Capped, dated, and labeled the solution "Sterile 0.2% Acetic Acid Solution."
6.1.6 Solution expired after 2 months. Stored at room temperature.
6.2 Prepare 1% HSA in PBS.
6.2.1 Added 4 mL of 25% HSA stock solution to 96 mL PBS in a 150 mL sterile filter unit.
6.2.2 Filtered solution.
6.2.3 Capped, dated, and labeled the solution "1% HSA in PBS."
6.2.4 Solution expired after 2 months. Store 4° C.
6.3 For Each Vial of rhIL-2 Prepared, Fill Out Forms.
6.4 Prepared rhIL-2 Stock Solution ($6 \times 10^6$ IU/mL Final Concentration)

6.4.1 Each lot of rhIL-2 was different and required information found in the manufacturer's Certificate of Analysis (COA), such as:
6.4.1.1 Mass of rhIL-2 per vial (mg)
6.4.1.2 Specific activity of rhIL-2 (IU/mg)
6.4.1.3 Recommended 0.2% HAc reconstitution volume (mL)
6.4.2 Calculated the volume of 1% HSA required for rhIL-2 lot by using the equation below:

$$\left( \frac{\text{Vial Mass (mg)} \times \text{Biological Activity} \left( \frac{IU}{mg} \right)}{6 \times 10^6 \frac{IU}{mL}} \right) - HAc\ vol\ (mL) =$$

$$1\%\ HSA\ vol\ (mL)$$

6.4.2.1 For example, according to CellGenix's rhIL-2 lot 10200121 COA, the specific activity for the 1 mg vial is 25×10⁶ IU/mg. It recommends reconstituting the rhIL-2 in 2 mL 0.2% HAc.

$$\left( \frac{1\ mg \times 25 \times 10^6 \frac{IU}{mg}}{6 \times 10^6 \frac{IU}{mL}} \right) - 2\ mL = 2.167\ mL\ HSA$$

6.4.3 Wiped rubber stopper of IL-2 vial with alcohol wipe.
6.4.4 Using a 16G needle attached to a 3 mL syringe, injected recommended volume of 0.2% HAc into vial. Took care to not dislodge the stopper as the needle is withdrawn.
6.4.5 Inverted vial 3 times and swirled until all powder is dissolved.
6.4.6 Carefully removed the stopper and set aside on an alcohol wipe.
6.4.7 Added the calculated volume of 1% HSA to the vial.
6.4.8 Capped the vial with the rubber stopper.
6.5 Storage of rhIL-2 Solution
6.5.1 For short-term storage (<72 hrs), stored vial at 4° C.
6.5.2 For long-term storage (>72 hrs), aliquoted vial into smaller volumes and stored in cryovials at −20° C. until ready to use. Avoided freeze/thaw cycles. Expired 6 months after date of preparation.
6.5.3 Rh-IL-2 labels included vendor and catalog number, lot number, expiration date, operator initials, concentration and volume of aliquot.

Example 17: Preparation of Media for Pre-Rep and Rep Processes

This Example describes the procedure for the preparation of tissue culture media for use in protocols involving the culture of tumor infiltrating lymphocytes (TIL) derived from various tumor types including, but not limited to, metastatic melanoma, head and neck squamous cell carcinoma (HNSCC), ovarian carcinoma, triple-negative breast carcinoma, and lung adenocarcinoma. This media can be used for preparation of any of the TILs described in the present application and Examples.

3. Definition

µg microgram
µm micrometer
µM micromolar
AIM-V® serum-free tissue culture medium (Thermo Fisher Scientific)
BSC Biological Safety Cabinet
CM1 Complete Medium #1
CM2 Complete Medium #2
CM3 Complete Medium #3
CM4 Complete Medium #4
IU or U International units
ml milliliter
mM millimolar
NA not applicable
PPE personal protective equipment
Pre-REP pre-Rapid Expansion Process
REP Rapid Expansion Process
rhIL-2, IL-2 recombinant human Interleukin-2
RPMI1640 Roswell Park Memorial Institute medium, formulation 1640
SOP Standard Operating Procedure
TIL tumor infiltrating lymphocytes 7. Procedure 7.1 All Procedures are Done Using Sterile Technique in a BSC (Class II, Type A2).
7.1.1 Sprayed surface of hood with 70% ethanol prior to its use.
7.1.2 Sprayed all items and reagents with 70% ethanol prior to placing them into tissue culture hood.
7.2 Aliquotting of 200 mM L-Glutamine
7.2.1 L-glutamine was supplied in larger volumes than needed for the preparation of serum (e.g., 100 ml or 500 ml volumes).
7.2.2 Thawed bottle of L-glutamine in 37° C. water bath.
7.2.3 Mixed L-glutamine well after thawing, as it precipitates after thaw. Ensured that all precipitates have returned to solution prior to aliquotting.
7.2.4 Placed 5-10 ml aliquots of L-glutamine into sterile 15 ml conical tubes.
7.2.5 Labeled tubes with concentration, vendor, lot number, date aliquotted, and expiration date.
7.2.6 Tubes were then stored at −20° C. and pulled as needed for media preparation.
7.3 Preparation of CM1
7.3.1 Removed the following reagents from cold storage and warmed them in a 37° C. water bath:
7.3.1.1 RPMI1640
7.3.1.2 Human AB serum
7.3.1.3 200 mM L-glutamine
7.3.2 Removed the BME from 4° C. storage and place in tissue culture hood.
7.3.3 Placed the gentamycin stock solution from room temperature storage into tissue culture hood.
7.3.4 Prepared CM1 medium according to Table 23 below by adding each of the ingredients into the top section of a 0.2 um filter unit appropriate to the volume to be filtered.

TABLE 23

Preparation of CM1

| Ingredient | Final concentration | Final Volume 500 ml | Final Volume 1L |
|---|---|---|---|
| RPMI1640 | NA | 450 ml | 900 ml |
| Human AB serum, heat-inactivated 10% | 50 ml | 100 ml | |

TABLE 23-continued

Preparation of CM1

| Ingredient | Final concentration | Final Volume 500 ml | Final Volume 1L |
|---|---|---|---|
| 200 mM L-glutamine | 2 mM | 5 ml | 10 ml |
| 55 mM BME | 55 μM | 0.5 ml | 1 ml |
| 50 mg/ml gentamicin sulfate | 50 μg/ml | 0.5 ml | 1 ml |

7.3.5 Labeled the CM1 media bottle with its name, the initials of the preparer, the date it was filtered/prepared, the two week expiration date and store at 4° C. until needed for tissue culture. Media can be aliquotted into smaller volume bottles as required.

7.3.6 Any remaining RPMI1640, Human AB serum, or L-glutamine was stored at 4° C. until next preparation of media.

7.3.7 Stock bottle of BME was returned to 4° C. storage.

7.3.8 Stock bottle of gentamicin was returned to its proper RT storage location.

7.3.9 Because of the limited buffering capacity of the medium, CM1 was discarded no more than two weeks after preparation, or as the phenol red pH indicator showed an extreme shift in pH (bright red to pink coloration).

7.3.10 On the day of use, prewarmed required amount of CM1 in 37° C. water bath and add 6000 IU/ml IL-2.

7.3.11 Additional supplementation—as needed
   7.3.11.1 CM1 supplemented with GlutaMAX®
      7.3.11.1.1 CM1 could be prepared by substituting 2 mM GTutaMAX™ for 2 mM glutamine (final concentration, see Table 2.) If this was done, labeled the media bottle as in Step 7.3.5 above adding "2 mM GlutaMAX" to prevent confusion with the standard formulation of CM1.
   7.3.11.2 CM1 supplemented with extra antibiotic/antimycotic
      7.3.11.2.1 Some CM1 formulations required additional antibiotic or antimycotic to prevent contamination of pre-REP TIL grown from certain tumor types.
      7.3.11.2.2 Added antibiotic/antimycotic to the final concentrations shown in Table 24 below.
      7.3.11.2.3 If this was done, label the media bottle as in Step 7.3.1 above adding the name/s of the additional antibiotic/antimycotic to prevent confusion with the standard formulation of CM1.

TABLE 24

Additional supplementation of CM1, as needed.

| Supplement | Stock concentration | Dilution | Final concentration |
|---|---|---|---|
| GlutaMAXTm | 200 mM | 1:100 | 2mM |
| Penicillin/ streptomycin | 10,000 U/ml penicillin 10,000 μg/ml streptomycin | 1:100 | 100 U/ml penicillin 100 μg/ml streptomycin |
| Amphotericin B | 250 μg/ml | 1:100 | 2.5 μg/ml |

7.4 Preparation of CM2
7.4.1 Removed prepared CM1 from refrigerator or prepare fresh CM1 as per Section 7.3 above.
7.4.2 Removed AIM-V® from refrigerator.
7.4.3 Prepared the amount of CM2 needed by mixing prepared CM1 with an equal volume of AIM-V® in a sterile media bottle.
7.4.4 Added 3000 IU/ml IL-2 to CM2 medium on the day of usage.
7.4.5 Made sufficient amount of CM2 with 3000 IU/ml IL-2 on the day of usage.
7.4.6 Labeled the CM2 media bottle with its name, the initials of the preparer, the date it was filtered/prepared, the two week expiration date and store at 4° C. until needed for tissue culture. Media was aliquotted into smaller volume bottles as required.
7.4.7 Returned any CM2 without IL-2 to the refrigerator where it can be stored for up to two weeks, or until phenol red pH indicator shows an extreme shift in pH (bright red to pink coloration).
7.5 Preparation of CM3
7.5.1 Prepared CM3 on the day it was required for use.
7.5.2 CM3 was the same as AIM-V® medium, supplemented with 3000 IU/ml IL-2 on the day of use.
7.5.3 Prepared an amount of CM3 sufficient to experimental needs by adding IL-2 stock solution directly to the bottle or bag of AIM-V. Mixed well by gentle shaking. Label bottle with "3000 IU/ml IL-2" immediately after adding to the AIM-V. If there was excess CM3, stored it in bottles at 4° C. labeled with the media name, the initials of the preparer, the date the media was prepared, and its expiration date (7 days after preparation).
7.5.4 Discarded media supplemented with IL-2 after 7 days storage at 4° C.
7.6 Preparation of CM4
7.6.1 CM4 was the same as CM3, with the additional supplement of 2 mM GTutaMAX™ (final concentration).
   7.6.1.1 For every 1 L of CM3, added 10 ml of 200 mM GlutaMAX™.
7.6.2 Prepared an amount of CM4 sufficient to experimental needs by adding IL-2 stock solution and GTutaMAX™ stock solution directly to the bottle or bag of AIM-V. Mixed well by gentle shaking.
7.6.3 Labeled bottle with "3000 IL/nil IL-2 and GlutaMAX" immediately after adding to the AIM-V.
7.6.4 If there was excess CM4, stored it in bottles at 4° C. labeled with the media name, "GlutaMAX", the initials of the preparer, the date the media was prepared, and its expiration date (7 days after preparation).
7.6.5 Discarded media supplemented with IL-2 after 7 days storage at 4° C.

Example 18: Surface Antigen Staining of Post REP TIL

1. Purpose

The Example describes the procedure for cell surface staining of post-REP TILs by flow cytometry. This procedure can be applied to any TILs described in the application and Examples.

Key Terms and Definitions

α: Alpha
β: Beta
μl: Microliter
APC: Allophycocyanin
Ax647: Alex Fluor 647

BD: Becton Dickinson Company
BSA: Bovine Serum Albumin
BSC: Biological Safety Cabinet
BV421: Brilliant Violet 421
CD: Cluster of Differentiation
CST: Cytometer Setup and Tracking
Cy: Cyanine
DPBS: Dulbecco's Phosphate Buffered Saline
FACS: Fluorescence Activated Cell Sorter
FBS: Fetal Bovine Serum
FITC: Fluorescein Isothiocyanate
FMO: Fluorescence Minus One
G: Gram
H7: Analog of Cy7
Ml: Milliliter
PE: Phycoerythrin
PerCP-Cy5.5: Peridinin-Chlorophyll proteins
PPE: Personal Protective Equipment
REP: Rapid Expansion Protocol
SIT: Sample Injection Tube
TCR: T Cell Receptor
w/v: Weight to Volume
Flow Cytometry Antibodies and Stains

TABLE 25

Live/Dead Aqua Stain ThermoFisher Catalog # L34966.

| Target | Format | Clone | Supplier | Catalog Number |
|---|---|---|---|---|
| TCRab (i.e., TCRα/β) | PE/Cy7 | IP26 | BioLegend | 306720 |
| CD57 | PerCP-Cy5.5 | HNK-1 | BioLegend | 359622 |
| CD28 | PE | CD28.2 | BioLegend | 302908 |
| CD4 | FITC | OKT4 | eBioscience | 11-0048-42 |
| CD27 | APC-H7 | M-T271 | BD Biosciences | 560222 |
| CD56 | APC | N901 | Beckman Coulter | IM2474U |
| CD8a | PB | RPA-T8 | BioLegend | 301033 |
| CD45R A | PE-Cy7 | HI100 | BD Biosciences | 560675 |
| CD8a | PerCP/Cy5.5 | RPA-T8 | BioLegend | 301032 |
| CCR7 | PE | 150503 | BD Biosciences | 560765 |
| CD3 | APC/Cy7 | HIT3a | BioLegend | 300318 |
| CD38 | APC | HB-7 | BioLegend | 356606 |
| HLA-DR | PB | L243 | BioLegend | 307633 |
| CD69 | PE-Cy7 | FN50 | BD Biosciences | 557745 |
| TIGIT | PE | MBSA43 | eBioscience | 12-9500-42 |
| KLRG1 | Ax647 | SA231A2 | BioLegend | 367704 |
| CD154 | BV421 | TRAP1 | BD Biosciences | 563886 |
| CD137 | PE/Cy7 | 4B4-1 | BioLegend | 309818 |
| Lag3 | PE | 3DS223H | eBioscience | 12-2239-42 |
| PD1 | APC | EH12.2H 7 | BioLegend | 329908 |
| Tim-3 | BV421 | F38-2E2 | BioLegend | 345008 |

7. Procedure 7.1 Reagent Preparation
7.1.1 FACS Wash Buffer
  7.1.1.1 Added 2% (w/v) heat-inactivated FBS to DPBS (Add 10 ml FBS to 490 mLs of 1×dPBS).
  7.1.1.2 Added 0.1% (w/v) NaN$_3$ (76.9 ul to 500 mL bottle.)
  7.1.1.3 Solution was stored at 40° C. Discard after 30 days.
7.1.2 Aqua dye
  7.1.2.1 Added 50 μl of DMSO to the vial of reactive dye.
  7.1.2.2 Mixed well and visually confirm that all of the dye has dissolved.
  7.1.2.3 Dye that was not used for the procedure was aliquoted and frozen at 20° C. until the next use. Did not freeze/thaw a second time.
7.1.3 Antibody Cocktail Preparation.
  7.1.3.1 Cocktails were made up in polypropylene tubes such as an Eppendorf tube
  7.1.3.2 Cocktails were stored for up to 6 months.

TABLE 26

Differentiation Panel 1 (DF1):

| Target | Format | Clone | Supplier | Catalog Number | Titre |
|---|---|---|---|---|---|
| TCRab (i.e., TCRα/β) | PE/Cy7 | IP26 | BioLegend | 306720 | 3 |
| CD57* | PerCP-Cy5.5 | HNK-1 | BioLegend | 359622 | 2 |
| CD28* | PE | CD28.2 | BioLegend | 302908 | 2 |
| CD4 | FITC | OKT4 | eBioscience | 11-0048-42 | 2 |
| CD27* | APC-H7 | M-T271 | BD Biosciences | 560222 | 3 |
| CD56 | APC | N901 | Beckman Coulter | IM2474U | 3 |
| CD8a | PB | RPA-T8 | BioLegend | 301033 | 2 |
| FACS Buffer | | | | | 33 |

TABLE 27

Differentiation Panel 2 (DF2):

| Target | Format | Clone | Supplier | Catalog Number | Titre |
|---|---|---|---|---|---|
| CD45RA* | PE-Cy7 | HI100 | BD Biosciences | 560675 | 1 |
| CCD3 | PerCP/Cy5.5 | SP34-2 | BD Biosciences | 552852 | 2 |
| CCCR7* | PE | 150503 | BD Biosciences | 560765 | 5 |
| CCD8 | FITC | HIT8 | BioLegend | 300906 | 2 |
| CCD4 | APC/Cy7 | OKT4 | BioLegend | 317418 | 2 |
| CCD38* | APC | HB-7 | BioLegend | 356606 | 1 |
| HHLA-DR | PB | L243 | BioLegend | 307633 | 2 |
| FACS Buffer | | | | | 35 |

TABLE 28

T-cell Activation Panel 1 (Tact1)

| Target | Format | Clone | Supplier | Catalog Number | Titre |
|---|---|---|---|---|---|
| CD137* | PE/Cy7 | 4B4-1 | BioLegend | 309818 | 2 |
| CD3 | PerCP/Cy5.5 | SP34-2 | BD Biosciences | 552852 | 2 |
| Lag3* | PE | 3DS223H | eBioscience | 12-2239-42 | 5 |
| CD8 | FITC | HIT8 | BioLegend | 300906 | 2 |
| CD4 | APCCy7 | OKT4 | BioLegend | 317418 | 2 |
| PD1* | APC | EH12.2H7 | BioLegend | 329908 | 2 |
| Tim-3* | BV421 | F38-2E2 | BioLegend | 345008 | 2 |
| FACS Buffer | | | | | 33 |

TABLE 29

T-cell Activation Panel 2 (Tact2)

| Target | Format | Clone | Supplier | Catalog Number | Titre |
|---|---|---|---|---|---|
| CD69* | PE-Cy7 | FN50 | BD Biosciences | 557745 | 3 |
| CD3 | PerCP/Cy5.5 | SP34-2 | BD Biosciences | 552852 | 2 |
| TIGIT* | PE | MBSA43 | eBioscience | 12-9500-42 | 3 |
| CD8 | FITC | HIT8 | BioLegend | 300906 | 2 |
| CD4 | APCCy7 | OKT4 | BioLegend | 317418 | 2 |
| KLRG1* | Ax647 | SA231A2 | BioLegend | 367704 | 1 |
| CD154* | BV421 | TRAP1 | BD Biosciences | 563886 | 3 |
| FACS Buffer | | | | | 34 |

7.2 Flow Cytometry Assay Requirements
  7.2.1 Flow Cytometer Calibration
    7.2.1.1 The flow cytometer was calibrated on the day of the assay using CST beads following manufacturer's instructions.
    7.2.1.2 The operator ensured that the flow cytometer had passed calibration, where performance and baseline checks are valid.
  7.2.2 Compensation/FMO Controls
    7.2.2.1 Single color compensation samples were prepared using the BD compensation beads and the ArC™ Amine Reactive Compensation Bead Kit.
    7.2.2.2 FMO control, cell containing samples were stained with a cocktail of antibodies minus the following single antibody conjugate, CD27, CD28, and CD57.
  7.2.3 MFI Standardization
    7.2.3.1 Cytometer voltages was determined daily with a bead control and target voltage values.
7.3 Sample Staining
  7.3.1 Labeled FACS tube with the Sample ID-DF1, Sample ID-DF2, Sample ID-T1, Sample ID-T2.
  7.3.2 Labeled one set of FMO controls with CD27-APC-H7, CD28-PE, CD57-PerCPCy5.5, CD45RA-PECy7, CCR7-PE, CD38-APC, CD137-PE7, Lag3-PE, PD1 APC, Tim3-BV421, CD69-PE7, TIGIT-PE, KLRG1-Ax647, and CD154-BV421.
  7.3.3 Added 0.5 to 2 million cells to each tube.
  7.3.4 QS to 3 mLs of 1×PBS to each tube.
  7.3.5 Spun the tubes at 400×g, high acceleration and brake, for 5 minutes.
  7.3.6 While the samples were centrifuging, prepared the dead cell labeling Aqua dye.
  7.3.7 Removed an Aqua aliquot from the freezer and dilute 1/200 in PBS. Keep dark. Add 2 uL dye to 198 uL DPBS.
  7.3.8 Decanted or aspirated the supernatant from step 7.3.5.
  7.3.9 Added 25 uL of Aqua solution from above to samples and FMO controls.
  7.3.10 Incubated for 15 minutes at Room Temperature (RT) in the dark.
  7.3.11 Note: If cells were initially stored in a protein free media, then a blocking step should be added, such as 5 uL TruStain for 10 minutes at room temperature.
  7.3.12 Added 50 uL of antibody cocktails to appropriate tubes.
  7.3.13 Shook tube rack to mix.
  7.3.14 Incubated for 15 minutes at RT in the dark.
  7.3.15 Recording starting and ending times. Added 3 mL of FACS Wash buffer.
  7.3.16 Spun tubes at 400×g, high acceleration and brake, for 5 minutes.
  7.3.17 When centrifuge spin was complete, decanted or aspirated the supernatant.
  7.3.18 Resuspended cells by sliding the tubes along an empty rack.
  7.3.19 Added 100 uL of 1% ParaFormaldehyde to each tube.
  7.3.20 Stored at 40C in dark until ready to collect on Flow Cytometer.
    Note: Samples could be stored for up to 72 hours.
7.4 L/D Aqua Compensation Control.
  7.4.1 Labeled FACS tubes as L/D Aqua compensation control.
  7.4.2 Added one drop of Arc beads to the tube.
  7.4.3 Added 3 µl of L/D Aqua directly to the beads.
  7.4.4 Incubated the tubes at room temperature in the dark for 10 to 30 min.
  7.4.5 Recorded starting and ending incubation time on the worksheet
  7.4.6 After incubation, added 3 ml of FACS Wash to each tube.
  7.4.7 Spun tubes at 400×g, high acceleration and brake, for 5 minutes.
  7.4.8 Decanted or aspirated the supernatant.
  7.4.9 Resuspended the tubes with 500 µl of 1% PFA solution. Added 1 drop of negative bead. Placed at 40° C. in dark until collection.
7.5 Compensation Control Staining.
  7.5.1 Labeled FACS tubes as shown in the Post-REP TIL Phenotype worksheet.
  7.5.2 Added the antibodies as shown in the Post-REP TIL Phenotype worksheet.
  7.5.3 After incubation, added 3 mLs of FACS buffer to each tube.
  7.5.4 Spun tubes at 500 g, high acceleration and brake, for 2 minutes.
  7.5.5 Decanted or aspirated the supernatant.
  7.5.6 Resuspended the tubes with 500 µl of 1% PFA in PBS and stored at 2-80° C. in the dark.
7.6 Data Acquisition
  7.6.1 Opened FACSDiva software and login.
  7.6.2 In the cytometer mismatch dialog, clicked "Use CST Settings".
  7.6.3 Created a new experiment by clicking on "Experiment" tab and selecting the "Extended Phenotype" template.
  7.6.4 Double clicked on Target Values experiment and adjusted voltages to reach the target values determined by flow core operator.
  7.6.5 Copied instrument settings and pasted them onto the new experiment.
  7.6.6 Created a Specimen for each individual and named it appropriately.
  7.6.7 Created names for the samples according to the labels on their tubes.
  7.6.8 Gently vortexed or flick with finger before placing the tube in the SIT.
  7.6.9 Acquired the data under RECORD in the Acquisition board.
  7.6.10 Ran the samples at a speed of less than 7,500 events per second.

7.6.11 Collected between 50,000 to 100,000 live events excluding debris.

Example 19: Process 2A Verification Process Development

The experiments in this Example were completed to analyze Process 2A for the manufacture of TIL from patient-derived tumors of melanoma and a single breast cancer including the outgrowth of TIL from tumors in a pre-REP procedure, followed by a modified REP. Special emphasis was placed on the establishment of a frozen TIL product and a comparison of the performance of the frozen TIL product against the current fresh TIL product process (Process 1C). This report will demonstrate that similar profiles are observed in assessment of fresh and thawed critical quality attributes (cell number, % viability, % CD3+ T-cells, and bead-stimulated gamma interferon (IFN-γ) production) as well as a re-stimulation extended phenotype procedure (re-REP) whether the same TIL product is fresh or frozen. Data presented to support this conclusion include proliferation, viability, phenotype, IFN-γ release, potency, telomere length, and metabolic activity. The results characterize the Process 2A, a shortened pre-REP/REP process followed by the cryopreservation of TIL as well as compare the 2A process to the longer 1C process, as described herein.

Tumor donor descriptions, processing dates and processing locations can be found in Table 1 below (*indicates that REP was started using a frozen pre-REP TIL line):

TABLE 30

Description of Tumor Donors, Processing Dates And Processing Locations.

| Tumor ID | Tissue Type | Source | Tissue |
|---|---|---|---|
| M1061 | Melanoma | MT group | Primary-left lateral foot |
| M1062 | Melanoma | Moffitt | N/A |
| M1063 | Melanoma | MT group | Metastatic C-right groin |
| M1064 | Melanoma | MT group | Metastatic C-left ankle |
| M1065 | Melanoma | Bio Options | Metastatic-Axillary lymph node |
| EP11001 | ER+PR+ | MT group | Primary-left breast invasive ductal carcinoma |
| M1056* | Melanoma | Moffitt | N/A |
| M1058* | Melanoma | MT group | Metastatic-Stage IIB Right scalp |
| M1023* | Melanoma | Atlantic Health | Primary-Right axilla |

3. Background Information 3.1 LN-144 is an immunotherapeutic product for treating patients with metastatic melanoma. The product was composed of autologous tumor-infiltrating T lymphocytes (TIL) obtained from an individual patient following surgical resection of a tumor and expanded ex vivo through cell culture of morcellated tumor fragments (pre-REP) followed by Rapid Expansion of TIL in the presence of high dose IL-2, anti-CD3, and co-stimulatory APC. Following non-myeloablative lymphodepletion preconditioning, the patient received a single infusion of his/her TIL and subsequent intravenous infusions of aldesleukin (IL-2) every 8 hours for a maximum of 6 doses. Studies involving alternative methods of TIL expansion in the setting of Damage Associated Molecular Pattern Molecules (DAMPs) within the tumor microenvironment (TNE) have also demonstrated effective expansion of T-cells useful for therapy (Donia 2014; Sommerville, 2012).

The Process 1C which has been used for commercial production of TIL involves a production schedule that can take ~45-55 days to produce an infusible TIL product which is delivered to an immunodepleted patient within 24 hours. The immunodepletion of the recipient patient must be timed precisely with the harvest of the current TIL product. Delays in harvest or delivery of the fresh product can negatively impact an immunodepleted patient awaiting infusion. Process 2A improved upon Process 1C by decreasing manufacturing lead time and materials, due to the decreased lengths of both pre-REP and REP procedures. In addition, Process 2A increased flexibility for product shipment time. The differences between Process 1C and Process 2A in the pre-REP, REP and harvest of process (see Table 2) includes:

3.1.1 Larger flasks with increased tumor fragment capacity used in the pre-REP procedure.

3.1.2 Steps that made use of closed system or which are amenable to future adaptation to a closed system.

3.1.3 Decreased number of days in both pre-REP and REP procedures.

3.1.4 A direct-to-REP approach, which eliminated the need to phenotype pre-REP populations prior to selecting specific populations of pre-REP TIL to proceed to REP.

3.1.5 A co-culture with a pre-set number of irradiated, allogeneic PBMC APC in conjunction with anti-CD3 (clone OKT3) calculated for sufficient expansion of TIL.

3.1.6 An automated cell-washing system for harvest.

3.1.7 A CS10-based final formulation that was cryogenically-preserved prior to shipping.

TABLE 31

Impact of Process 2A on Process 1C.

| Process Step | Process 1C | Process 2A | Impact |
|---|---|---|---|
| STEP A: Obtain Patient tumor sample | After surgery, can be frozen after harvest and before Step B. | After surgery, can be frozen after harvest and before Step B. | Same. |
| STEP B: First Expansion | Physical fragmentation 4 fragments per 10 G-REX-10 flasks 11-21 day duration Growth media medium | Physical fragmentation 40 fragments per 1 G-REX-100M flask 11 day duration (3 days to 14 days range) | Increased tumor fragments per flask Shortened culture time Reduced number of steps Amenable to closed system |

TABLE 31-continued

Impact of Process 2A on Process 1C.

| Process Step | Process 1C | Process 2A | Impact |
|---|---|---|---|
| | comprises IL-2 | Growth media medium comprises IL-2 | |
| STEP C: First Expansion to Second Expansion Transition | Step B TILs are frozen until phenotyped for selection then thawed to proceed to Step D (~day 30) | Step B TILs directly move to Step D on Step B day 11 Step D requires 25-200 × $10^6$ TIL | Shortened pre-REP-to-REP process Reduced number of steps Eliminated phenotyping selection Amenable to closed system |
| | Step D requires >40 × $10^6$ TIL | | |
| STEP D: Second Expansion | 6 G-REX-100M flasks on Step D day 0 5 × $10^6$ TIL and 5 × $10^8$ antigen presenting cell feeders per flask on Step D day 0 Split to 18-36 flasks on Step D day 7 14 day duration for Step D Growth media medium comprises IL-2, OKT-3, and antigen-presenting cells | 1 G-REX-500M flask on Step B day 11 25-200 × $10^6$ TIL and 5 × $10^9$ antigen presenting cell feeders on Step B day 11 Split to ≤6 G-REX-500M flasks on day 16 11 day duration for Step D Growth media medium comprises IL-2, OKT-3, and antigen-presenting cells | Reduced number of steps Shorter REP duration Closed system transfer of TIL between flasks Closed system media exchanges |
| STEP E: Harvest TILS | TIL harvested via centrifugation | TIL harvested via LOVO automated cell washing system | Reduced number of steps Automated cell washing Closed system Reduced loss of product during wash |
| STEP F: Final Formulation/ Transfer to Infusion Bag | Fresh product in Hypothermosol Single infusion bag Limited shipping stability | Cryopreserved product in PlasmaLyte-A + 1% HSA and CS10 stored in LN2 Multiple aliquots Longer shipping stability | Shipping flexibility Flexible patient scheduling More timely release testing |
| Overall Estimated Process Time | 43-55 days from Step A through Step E | 22 days from Step A through Step E | Faster turnaround to patient Decreased clean room throughput Decreased Cost of Goods |

4. Abbreviations

μg microgram
μl microliter
μm micrometer
APC Antigen presenting cells
CD Cluster of Differentiation
CM Central memory
CM1, CM2, Culture Media 1, 2
$CO_2$ Carbon dioxide
CS10 CryoStor® CS10 cryopreservation medium (BioLife Solutions)
Ct PCR threshold cycle
DAMPs Damage Associated Molecular Pattern molecules
dCt Difference between reference Ct value and test Ct value
ddCt Difference between dCt and 10 ng standard Ct value
ECAR Extracellular acidification rate (measure of glycolysis)
EM Effector memory
ER+/PR+ Estrogen Receptor+/Progesterone Receptor+
GMP Good Manufacturing Practices
HBSS Hanks Balanced Salt Solution
HSA Human serum albumin
IFN-γ Interferon gamma
IL Interleukin
IU International units
LN2 Liquid nitrogen
Ml milliliter
Mm millimeter
ND Not determined
Ng Nanogram
° C. degrees Celsius
OCR Oxygen consumption rate (measure of oxidative phosphorylation)
OKT3 Clone designation of anti-CD3 monoclonal antibody
PBMC Peripheral Blood Mononuclear Cells
PD Process Development
REP Rapid Expansion Protocol
Rh Recombinant human
SOP Standard operating procedure
T/S Telomere repeat copy number to single gene copy number ratio
TIL Tumor Infiltrating Lymphocyte
VDJ Variable, diversity, and joining segments of the T cell receptor
Vα, Vβ The mature T cell receptor variable region segments in the predominant Tumor Infiltrating Lymphocyte
μg microgram
μl microliter
μm micrometer
APC Antigen presenting cells
CD Cluster of Differentiation
CM Central memory CM1, CM2, Culture Media 1, 2
CO2 Carbon dioxide
CS10 CryoStor® CS10 cryopreservation medium (BioLife Solutions)
Ct PCR threshold cycle
DAMPs Damage Associated Molecular Pattern molecules
dCt Difference between reference Ct value and test Ct value
ddCt Difference between dCt and 10 ng standard Ct value
ECAR Extracellular acidification rate (measure of glycolysis)
EM Effector memory
ER+/PR+ Estrogen Receptor+/Progesterone Receptor+
GMP Good Manufacturing Practices
HBSS Hanks Balanced Salt Solution
HSA Human serum albumin
IFN-γ Interferon gamma
IL Interleukin
IU International units
LN2 Liquid nitrogen
Ml milliliter
Mm millimeter
ND Not determined
Ng Nanogram
° C. degrees Celsius
OCR Oxygen consumption rate (measure of oxidative phosphorylation)
OKT3 Clone designation of anti-CD3 monoclonal antibody
PBMC Peripheral Blood Mononuclear Cells
PD Process Development
REP Rapid Expansion Protocol
Rh Recombinant human
SOP Standard operating procedure
T/S Telomere repeat copy number to single gene copy number ratio
TIL Tumor Infiltrating Lymphocyte
VDJ Variable, diversity, and joining segments of the T cell receptor
Vα, Vβ The mature T cell receptor variable region segments in the predominant Tumor Infiltrating Lymphocyte

5. Experimental Design 5.1 Process 2A 5.1.1 Pre-REP: Upon receipt, the tumor was transferred to a Biological Safety Cabinet (Class II, Type A2). Using sterile technique, the tumor is removed from the shipping container and washed in HBSS containing 50 μg/mL gentamicin. The technician morcellates the tumor into 40×3×3×3 mm fragments which are transferred to a G-REX –100M flask containing pre-warmed CM1 media supplemented with 6000 IU/mL rhIL-2. The flask is placed in a 37° C., 5% $CO_2$ humidified tissue culture incubator for 11 days. If the tumor generates more than 40 fragments, then more than one G-REX-100M may be set up. Cells are then harvested and prepared for the REP.

5.1.2 REP: On Day 11, one G-REX-500M flask containing 5 L of CM2 supplemented with 3000 IU/mL rhIL-2, 30 ng/mL anti-CD3 (Clone OKT3) and $5\times10^9$ irradiated allogeneic feeder PBMC cells is prepared. TIL harvested from the pre-REP G-REX-100M flask after volume reduction are counted and seeded into the G-REX-500M flask at a density that can range between $5\times10^6$ and $200\times10^6$ cells. The flask is then placed in a humidified 37° C., 5% $CO_2$ tissue culture incubator for five days. On Day 16, volume of the G-REX-500M flask is reduced, TIL are counted and their viability determined. At this point, the TIL are expanded into multiple G-REX-500M flasks (up to a maximum of six flasks), each with a seeding density of $1\times10^9$ TIL/flask. All flasks are then placed in humidified 37° C., 5% $CO_2$ tissue culture incubators for an additional six days. On Day 22, the day of harvest, each flask is volume reduced by 90%, the cells are pooled together and filtered through a 170 μm blood filter, and then collected into a 3 L Origin EV3000 bag or equivalent in preparation for automated washing using the LOVO.

5.1.3 Harvest and Final Formulation: TIL are washed using the LOVO automated cell processing system which replaces 99.99% of cell culture media with a wash buffer consisting of PlasmaLyte-A supplemented with 1% HSA. The LOVO operates using spinning filtration membrane technology that recovers over 92% of the TIL while virtually eliminating residual tissue culture components, including serum, growth factors, and cytokines, as well as other debris and particulates. After completion of the wash, a cell count is performed to determine the expansion of the TIL and their viability upon harvest. CS10 is added to the washed TIL at a 1:1 volume:volume ratio to achieve the Process 2A final formulation. The final formulated product is aliquoted into cryostorage bags, sealed, and placed in pre-cooled aluminum cassettes. Cryostorage bags containing TIL are then frozen using a CryoMed Controlled Rate Freezer (ThermoFisher Scientific, Waltham, MA) according to SOP LAB-018 Rev 000 Operation of Controlled Rate Freezer.

5.2 TIL Samples: Four Conditions of TIL were Collected for Characterization Comparison.

5.2.1 Fresh harvested TIL (direct from PlasmaLyte-A with 1% HSA wash buffer) Thawed TIL (direct from thawed final product bag)

5.2.2 Fresh Extended Phenotype reREP TIL (fresh harvested TIL cultured for 7-14 days with IL-2, PBMC feeders, and anti-CD3 clone OKT3)

5.2.3 Thawed Extended Phenotype TIL (thawed TIL cultured for 7-14 days with IL-2, PBMC feeders, and anti-CD3 clone OKT3)

5.3 Testing Overview (See FIG. 2)

5.3.1 Pre-REP testing includes evaluating the quantity of IL-2 and analyzing cell culture metabolites such as glucose, lactic acid, L-glutamine and ammonia throughout the pre-REP.

5.3.1.1 IL-2 quantification: media was periodically removed from pre-REP culture and tested by ELISA for IL-2 quantification. Reference R&D Systems Human IL-2 Quantikine ELISA Kit manufacturer's instructions.

5.3.1.2 Cell culture metabolite analysis: media was periodically removed from pre-REP culture and tested for the following metabolites: glucose, lactic acid, L-glutamine and ammonia. Reference the Roche Cedex Bioanalyzer user manual for instructions.

5.3.2 REP testing included extended assays such as cell counts, % viability, flow cytometric analysis of cell surface molecules, potency (IFN-γ production), bioluminescent redirected lysis assay, granzyme B production, cellular metabolism and telomere length measurement.

5.3.2.1 Cell counts and viability: TIL samples were counted and viability determined using a Cellometer K2 automated cell counter (Nexcelom Bioscience, Lawrence, MA) according to SOP LAB-003 Rev 000 Cellometer K2 Image Cytometer Automatic Cell Counter.

5.3.2.2 Flow cytometric analysis of cell surface biomarkers: TIL samples were aliquoted for flow cytometric analysis of cell surface markers using the procedure outlined in WRK LAB-041 Rev 000 Surface Antigen Staining of Post REP TIL 5.3.2.3 Potency Assay (IFN-γ production): Another measure of cytotoxic potential was measured by determining the levels of the cytokine IFN-γ in the media of TIL stimulated with antibodies to CD3, CD28, and CD137/4-1BB. IFN-γ levels in media from these stimulated TIL were determined using the WRK LAB-016 Rev 000 Stimulation of TIL to Measure IFN-γ Release 5.3.2.4 Bioluminescent Redirected Lysis Assay: The cytotoxic potential of TIL to lyse target cells was assessed using a co-culture assay of TIL with the bioluminescent cell line, P815 (Clone G6), according to the SOP outlined in WRK LAB-040 Bioluminescent Redirected Lysis Assay (Potency Assay) for TIL 5.3.2.5 Granzyme B Production: Granzyme B is another measure of the ability of TIL to kill target cells. Media supernatants restimulated as described in 5.2.5.3 were also evaluated for their levels of Granzyme B using the Human Granzyme B DuoSet ELISA Kit (R & D Systems, Minneapolis, MN) according to the manufacturer's instructions.

5.3.2.6 Cellular (Respiratory) metabolism: Cells were treated with inhibitors of mitochondrial respiration and glycolysis to determine a metabolic profile for the TIL consisting of the following measures: baseline oxidative phosphorylation (as measured by OCR), spare respiratory capacity, baseline glycolytic activity (as measured by ECAR), and glycolytic reserve. Metabolic profiles were performed using the procedure outlined in WRK LAB-029 Seahorse Combination Mitochondrial/Glycolysis Stress Test Assay.

5.3.2.7 Telomere length measurement: Diverse methods have been used to measure the length of telomeres in genomic DNA and cytological preparations. The telomere restriction fragment (TRF) analysis is the gold standard to measure telomere length (de Lange et al., 1990). However, the major limitation of TRF is the requirement of a large amount of DNA (1.5 ˆg). Two widely used techniques for the measurement of telomere lengths namely, fluorescence in situ hybridization (FISH; Agilent Technologies, Santa Clara, CA) and quantitative PCR.

5.3.3 Additional samples were taken for the following tests, and could be analyzed in the future as needed:
  5.3.3.1 In-depth cytokine analysis
  5.3.3.2 TCR sequencing

6. Results Achieved

A total of 9 experiments were performed using the TIL derived from the tumors described in section 2.3 the experimental design and harvest conditions in section 5.1. TIL harvested using Process 2A were subjected to the testing outlined in section 5.3.2 for the purpose of understanding their ability to expand, their viability, phenotype, cytotoxic potential, and metabolic profile. All measures were taken for the fresh harvested TIL product and the thawed frozen TIL product (Process 2A).

6.1 Cell Counts and Viability 6.1.1 Cell counts were taken at the end of the pre-REP, on Day 5 or 6 of the REP (expansion day), and at the end of the REP, both prior to LOVO wash and after LOVO wash. The cell counts were then used to determine the expansion of TIL during the REP and the recovery of TIL after washing on the LOVO. After thaw, the cells were counted again to determine the post-thaw recovery (based on the concentration at which the TIL were frozen) and the post-thaw viability prior to proceeding with other analytical assay. Table 3 summarizes all of these results for the nine Process 2A runs.

TABLE 32

Cell counts, % viability, and expansion of TIL from Process 2A runs.

|  | M1061T | M1062T | M1063T | M1064T | M1065T | EP11001T | M1056T | M1058T | M1023T |
|---|---|---|---|---|---|---|---|---|---|
| pre-REP Inoculum | $3.3 \times 10^7$ | $1 \times 10^8$ | $7.5 \times 10^7$ | $1.8 \times 10^8$ | $4.1 \times 10^6$ | $5.4 \times 10^5$ | $7 \times 10^7$ | $4.7 \times 10^7$ | $4.8 \times 10^7$ |
| Day 5/6 Count | $1.3 \times 10^9$ | $4 \times 10^9$ | $3 \times 10^9$ | $3.6 \times 10^9$ | $6.6 \times 10^8$ | $2.8 \times 10^9$ | $4.0 \times 10^9$ | $3.7 \times 10^9$ | $2.2 \times 10^9$ |
| Fold Expansion from Day 0 to Day 11 | 898 | 590 | 470 | 130 | 1900 | 522 | 771 | 1400 | 850 |
| Harvest | $2.8 \times 10^{10}$ | $5.6 \times 10^{10}$ | $3.5 \times 10^{10}$ | $2.3 \times 10^{10}$ | $7.8 \times 10^9$ | $2.63 \times 10^{10}$ | $5 \times 10^{10}$ | $6.7 \times 10^{10}$ | $4.1 \times 10^{10}$ |
| LOVO Recovery (%) | 100 | 68 | 100 | 100 | 92 | 95 | 100 | 90 | 99 |
| Cryostorage Bags | 3 × 30 ml | 2 × 100 ml | 2 × 100 ml | 2 × 50 ml | 3 × 100 ml | 2 × 65 ml | 2 × 100 ml | 2 × 100 ml | 2 × 100 ml |
| Post-thaw Recovery (%) | 103 | 84 | 90 | 88 | 101 | 82 | 82 | 86 | 78 |
| Post-thaw Viability (%) | 84.75 | 84.36 | 77.15 | 83.48 | 79.98 | 74.85 | 80.28 | 85.03 | 89.21 |

6.1.2 Process 2A SOP defines the starting number of TIL for a REP as a range of 5 200×10⁶ TIL. The range of nine TIL samples used to start the Process 2A REPs was from 4.1×106 (M1065T)—1.8×10⁸ (M1064T), with an average starting TIL number of $6.58 \times 10^7$. Interestingly, the REP plated with the lowest number of TIL expanded to the greatest degree at REP harvest (range of expansion for all 9 REPs: 130-1900-fold; average expansion, 840-fold). The average number of TIL harvested at the end of these nine Process 2A REPs was $4.49 \times 10^{10}$ (range $7.8 \times 10^9$-$6.7 \times 10^{10}$).

6.1.3 For comparative statistics of Process 1C, see Chemistry, Manufacturing, and Controls (CMC) Section of Investigational New Drug (IND) Application for LN144/LN-145.

6.1.4 Process 1C utilizes manual handling and centrifugation to wash the TIL product. This is time consuming, but more importantly can result in the loss of up to 25% of the product between harvest and final formulation. The automatic cell washing LOVO system provides a way to minimize cell loss and also introduces a closed system wash which decreases the risk of contamination of the product during the wash steps. The recovery of the product following the LOVO wash step of the protocol and showed an average of 93.8±10.4% recovery of the TIL product going into the wash step. This statistic includes TIL product for M1062T, which had a LOVO recovery of 68%, during which an operator error in the operation of the LOVO resulted in the need to centrifuge the sample and then restart the LOVO procedure (see Section 7, Deviations and Discrepancies). This represents a highly favorable improvement upon the Process 1C washing step on the REP harvest day.

6.1.5 Recovery of TIL after the thaw is also a major concern for a frozen TIL product. Recovery of the product was determined by measuring the number of cells recovered from the bag after the thaw compared to the number of cells placed into each freeze bag prior to cryopreservation. The range of recovery from thaw was 78-103%, with an average recovery of 88.2±8.6%.

6.1.6 Though there is a significant difference in the viability of the samples prior to or after thawing, on average, there is only a 2% loss in viability upon thaw. The viability of the TIL going into cryopreservation was 84.3±4.7%, and the same TIL after thawing had a viability of 82.1±4.4% (p=0.0742, paired Student's t-test, non-parametric). Release criteria for the fresh clinical TIL Process 1C product requires a minimum of 70% viability. Regardless of a small loss of viability upon thaw, all 9 runs of Process 2A met this release criterion following thaw of the cryogenic product. Table 4 and FIG. 3 show the viability of the TIL going into cryopreservation (Fresh+CS10) and the viability of the TIL upon thaw.

TABLE 33

Comparison of viability of fresh and thawed product.

| | M1061T | M1062T | M1063T | M1064T | M1065T | EP11001T | M1056T | M1058T | M1023T |
|---|---|---|---|---|---|---|---|---|---|
| Fresh + CS10 | 88.05 | 84.45 | 82.05 | 86.75 | 76.35 | 77.9 | 84.8 | 87.5 | 90.5 |
| Thaw | 84.75 | 84.36 | 77.15 | 83.48 | 79.98 | 74.85 | 80.28 | 85.03 | 89.21 |

6.2 Re-REP expansion of TIL. In addition to examining at the ability of the fresh product to expand in a REP, he ability of both the fresh and the thawed TIL product to expand upon restimulation with fresh irradiated allogeneic PBMC feeder APCs and fresh anti-CD3 was evaluated. After 7 days, these restimulated TIL products were analyzed for their ability to expand from initial culture conditions. FIG. 4 and Table 5 show the average expansion of re-REP TIL cells after 7 days of growth in culture. Analysis of the data using a paired Student's t-test shows that the ability of the TIL to expand in a re-REP is not significantly different whether starting the REP with a fresh TIL or thawed TIL product (p=0.81).

TABLE 34

Comparison of fresh and thawed TIL expansion in re-REP culture

| | M1061T | M1062T | M1063T | M1064T | M1065T | EP11001T | M1056T | M1058T | M1023T |
|---|---|---|---|---|---|---|---|---|---|
| Fresh + | 139.67 | 264 | 227 | 60.12 | 24.67 | 268.83 | 176 | 316.33 | 202.33 |
| Thaw | 177.33 | 110.33 | 220.67 | 177.6 | 220.2 | 302.5 | 114.77 | 190.67 | 73.82 |

6.3 Cell Culture Metabolites. One of the major premises of Lion 2A was that less tech time and process transfers would lead to cost savings and limit variability. Possible adverse consequences of this were increases in undesirable metabolites and decreases in nutrient sources. As shown in FIG. 5, normal blood values of electrolytes (sodium and potassium), nutrients (glutamine and glucose), and metabolites (lactic acid and ammonia) provide a range to consider when evaluating the results coming out of the 11 day pre-REP. As shown in FIG. 6, three TIL (M1061T, M1062T, and M1064T) were evaluated sequentially. In this setting, potassium and sodium were maintained at normal levels, glucose was at >1.0 g/L and glutamine >0.3 mmol/L, well above lower normal blood values. As expected lactate rose to as high as 0.8 g/L, about 5× the level found in blood normally and ammonia to as high as 3 mmol/L, as expected from rapidly expanded cells and also substantially higher than what is found normally in the blood.

6.4 IL-2 Quantification.

6.4.1 The main driver of TIL proliferation in the pre-REP in addition to supplemental glucose, glutamine and sufficient oxygenation, is the provision of high levels of rhIL-2. Following its addition to serum containing media, IL-2 levels were measured at 2-3.5×10³ IU/ml, only falling to about 1.0×103 IU/ml over the 11 days of culture. This is well above the 30-100 IU/ml necessary to sustain T-cell proliferation. Assessment of IL-2 concentrations using different sources of IL-2 (Prometheus, Akron, Cellgenix) is currently being tested in separate experiments (QP-17-010: Qualification of IL-2 from Cellgenix, Akron and Prometheus) at Lion Biotechnologies, Tampa.

Figure 8:
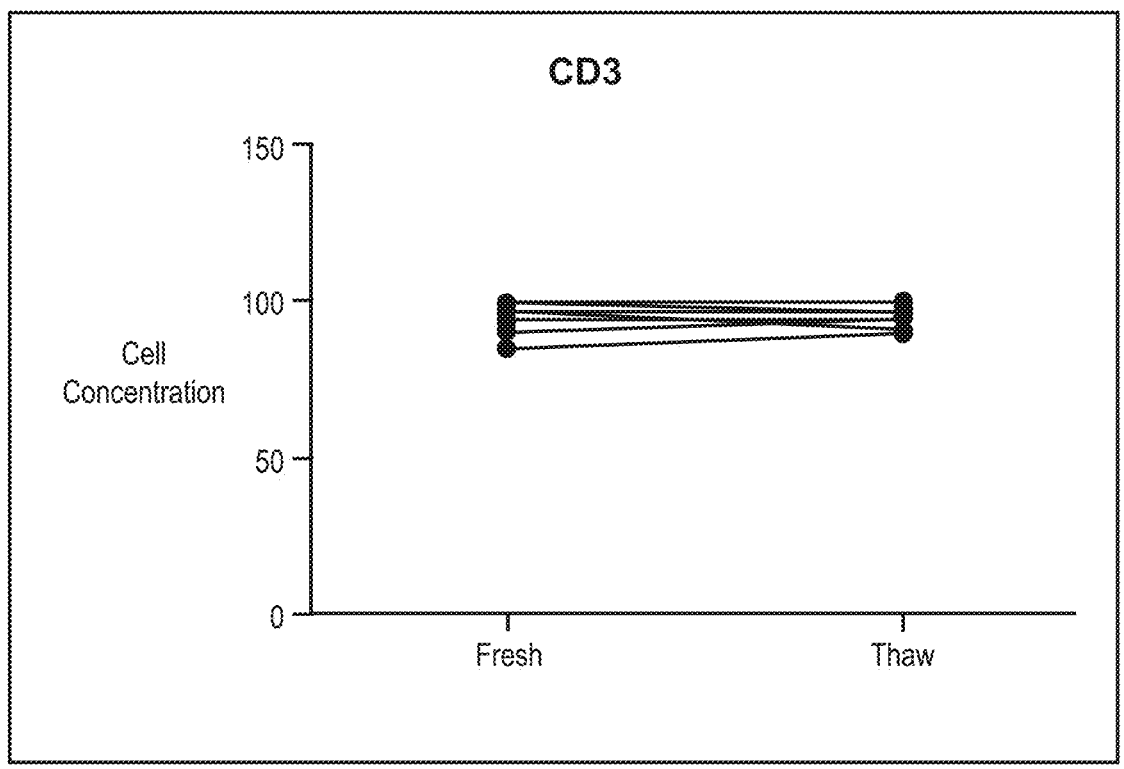
FIG. 8: Shows characterization of TILs prepared using an embodiment of the 2A process by examining CD3 expression in fresh TILs versus thawed TILs.

6.5 IFN-γ Production 6.5.1 After 24 hr stimulation of TIL with magnetic anti-CD3, CD28 and 4-1BB Dynabeads as described in sections 5.3.5.3, supernatant from cultures was collected and analyzed for IFN-γ using ELISA kits. All restimulated TIL produced more IFN-γ than their unstimulated counterparts, showing that the stimulation of the TIL resulted in their activation. FIG. 8 shows the ability of the four different TIL compositions (fresh, thaw, fresh re-REP and thaw re-REP TIL) tested to release IFN-γ into the surrounding medium upon restimulation.

Tables 6 and 7 show the average values of IFN-γ secretion in the 9 Process 2A runs. IFN-γ secretion into the surrounding medium upon restimulation is not different between the fresh TIL product and the thawed, cryopreserved TIL. Table 6 shows that fresh product produced an average of 4143±2285 pg IFN-γ/106 TIL while thawed product produced 3910±1487 pg IFN-γ/106 TIL (p=0.55 using paired Student's t-test). If normalized to total TIL product (Table 7), on average, stimulated fresh TIL produced 86±61 grams IFN-γ, while thawed stimulated TIL produced 68±40 grams IFN-γ (p=0.13). These findings indicate that both fresh and thawed TIL products produce IFN-γ and that there is no difference in the ability of either fresh or thawed matching TIL to produce IFN-γ upon stimulation with anti-CD3/anti-CD28/anti-4-1BB.

Figure 9:
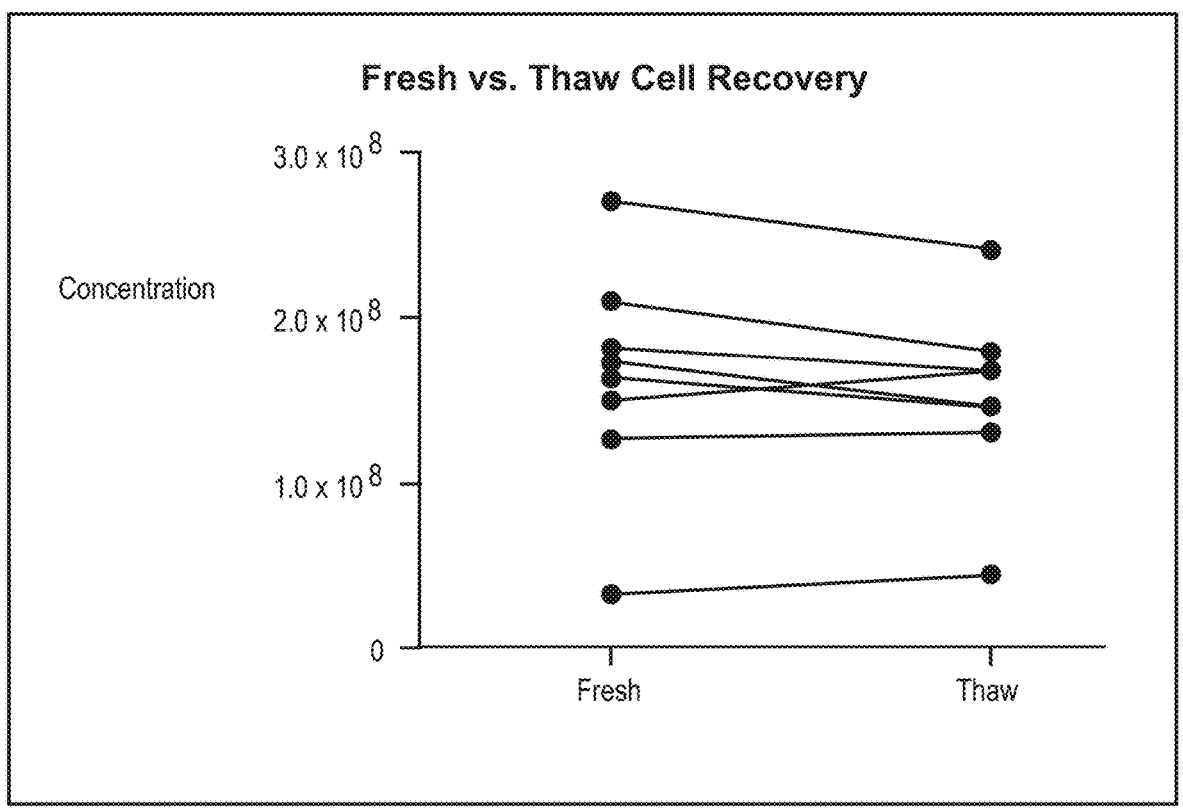
FIG. 9: Shows characterization of TILs prepared using an embodiment of the 2A process by examining recovery in fresh TILs versus thawed TILs.
Figure 10:
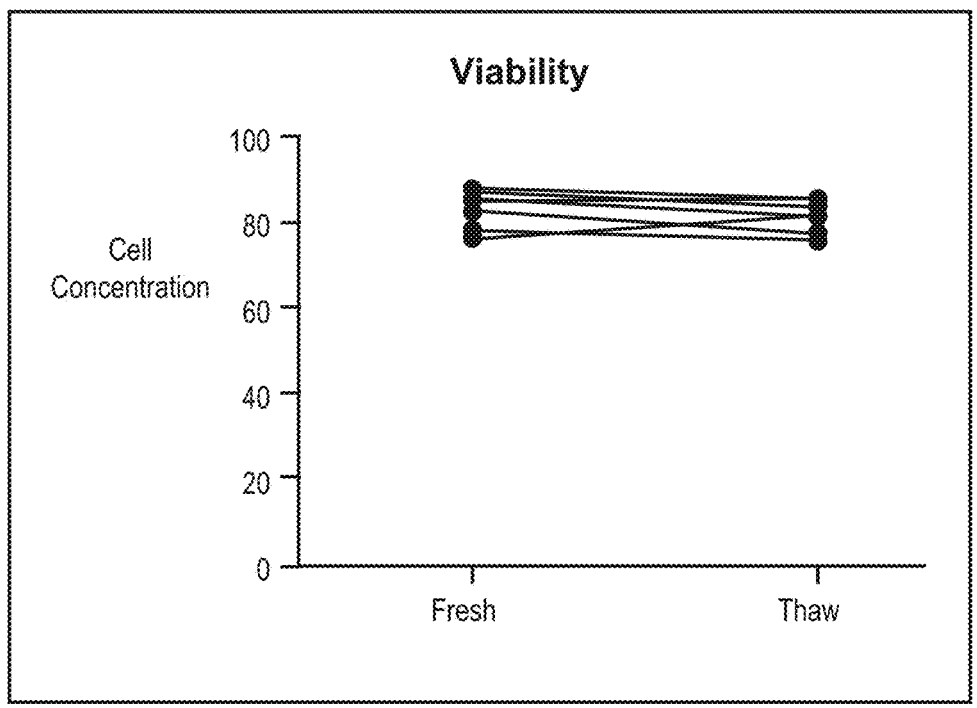
FIG. 10: Shows characterization of TILs prepared using an embodiment of the 2A process by examining viability of fresh TILs versus thawed TILs.

6.6 Granzyme B Production 6.6.1 TIL were stimulated with magnetic anti-CD3, CD28 and 4-1BB Dynabeads for 24 hr as described in 5.2.5.3, and supernatant from cultures was collected after 24 hr and analyzed Granzyme B levels by ELISA. All restimulated TIL produced more Granzyme B than their unstimulated counterparts, showing that the stimulation of the TIL resulted in their activation. FIG. 9 shows the ability of the fresh TIL, fresh re-REP TIL, and thawed re-REP TIL to release Granzyme B into the surrounding medium upon restimulation with the cytokine cocktail.

All products showed granzyme B production ranging from 9190 pg/$10^6$ viable cells to 262000 pg/$10^6$ viable cells (Table 8). Table 6 shows that fresh product produced an average of 60644+42959, while fresh and thawed re-REP produced 93600+67558 and 103878+84515 respectively. Comparison between the fresh re-REP and thawed re-REP showed that there is no difference in the ability of the TIL obtained from either conditions (p=0.7). Due to the lack of Granzyme B measurement in the thawed product, no statistical analysis were performed using the fresh TIL product.

TABLE 37

Granzyme B secretion in fresh TIL, fresh reREP TIL, and thawed reREP TIL (expressed as pg/$10^6$cells/24 hrs)

| | M1061T | M1062T | M1063T | M1064T | M1065T | EP11001T | M1056T | M1058T | M1023T |
|---|---|---|---|---|---|---|---|---|---|
| Fresh | 10600 | 108000 | 49100 | 28400 | 24300 | 17900 | 120000 | 12900 | 79100 |
| Fresh ReREP | 216000 | 37700 | 42400 | 91800 | 192000 | 22200 | 97300 | 73800 | 69200 |
| Thaw ReREP | 262000 | 113000 | 35100 | 65600 | 48700 | 9190 | 147000 | 201000 | 53300 |

6.7 Flow Cytometric Analysis of Cell Surface Biomarkers

Phenotypic profiling of TILs: Four antibody panels have been standardized at LION to broadly characterize the functional profile of T-cells. These panels were used to assess the immunophenotyping of fresh TIL, thawed TIL, fresh re-REP TIL, and thawed re-REP TIL. All the data used for graphical representation in this section are also provided in a table format (Tables 14-24) in the appendix section 10.

6.8 Bioluminescent Redirected Lysis Assay 6.8.1 To determine the potential ability of the Process 2A TIL to kill their target tumor cells, we developed a potency assay involving the co-culture of TIL with a bioluminescent surrogate target cell line P815, as

TABLE 35

IFN-γ secretion in fresh and thawed TIL (expressed as pg/$10^6$cells/24 hrs)

| | M1061T | M1062T | M1063T | M1064T | M1065T | EP11001T | M1056T | M1058T | M1023T |
|---|---|---|---|---|---|---|---|---|---|
| Fresh | 4570 | 3921 | 5589 | 619 | 1363 | 4263 | 6065 | 2983 | 7918 |
| Thaw | 3158 | 3543 | 5478 | 1563 | 2127 | 5059 | 4216 | 4033 | 6010 |
| Fresh Re-REP | 3638 | 1732 | 971 | 2676 | 2753 | 1461 | 2374 | 770 | 3512 |
| Thaw Re-REP | 2970 | 2060 | 1273 | 1074 | 1744 | 2522 | 5042 | 4038 | 923 |

TABLE 36

IFN-γ secretion in fresh and thawed TIL. All values are in 1012(expressed as grams/$10^6$cells/24 hrs)

| | M1061T | M1062T | M1063T | M1064T | M1065T | EP11001T | M1056T | M1058T | M1023T |
|---|---|---|---|---|---|---|---|---|---|
| Fresh | 67.1 | 78.4 | 99.6 | 8.4 | 4.8 | 66.1 | 157.0 | 109.0 | 187.0 |
| Thaw | 47.7 | 59.7 | 87.9 | 18.7 | 7.5 | 64.4 | 88.9 | 127.0 | 111.0 | described in section 5.3.2.4. A 4 hour co-culture of the different TIL compositions with P815 in the presence of anti-CD3 stimulation gives a measure of the cytotoxic potential of the TIL cells expressed as LU50, lytic units which can be defined as the number of TIL necessary to kill 50% of the target cells. This measure is then expressed as LU50/106 TIL. FIG. 32 below shows the cytotoxic potential of the TIL from the fresh product, and from the two re-REP TIL conditions, fresh re-REP and thaw re-REP.

6.8.2 Comparison of the fresh re-REP to the thaw re-REP shows that there is no significant difference in the ability either TIL to kill a target cell (p=0.3126). This data supports the conclusion that there is no difference between the fresh and the thawed product in terms of the cytotoxic potential of the TIL product. No comparison between fresh was performed as cytotoxic potential was not measured immediately after thawing TIL. Table 9 shows the lytic units of TIL needed to kill 50% of the P815 target cell line.

TABLE 38

Lytic units produced by TIL against P815 target cell line

|  | Fresh | Fresh reREP | Thaw reREP |
|---|---|---|---|
| M1061T | 21.7 | 42.3 | 342 |
| M1062T | 5.9 | 17.0 | 20.9 |
| M1063T | 14.2 | 161 | 12.5 |
| M10641 | 22.2 | 8.7 | 4.4 |
| M10651 | 42.6 | 411 | 128 8 |
| EP11001T | 1.8 | 4.3 | 147 |
| M1056T | 25.0 | 16.6 | 18.2 |
| M10513T | 76.9 | 13.8 | 16.6 |
| M1023T | 30.8 | 25.6 | 30.4 |
| avg ± sd | 26.8 ± 22.5 | 20.6 ± 13.3 | 31.1 ± 37.6 |

6.9 Cellular Metabolism Profile of TIL 6.9.1 To assess the metabolic health of post-REP TIL, we utilized the Seahorse metabolism analyzer instruments (XFp and XFe96) from Agilent Technologies (Santa Clara, CA) following the protocol outlined in section 5.3.2.6. Briefly, by treating cells with inhibitors that target certain aspects of either oxidative phosphorylation or glycolysis, cells are stressed in such a way that allows for the determination of their SRC and glycolytic reserve. In addition, basal levels of both oxidative phosphorylation (basal OCR) and glycolysis (basal ECAR) can be determined. Finally, because inhibitors of oxidative phosphorylation and glycolysis are combined in the same test, a potential hidden reserve of SRC can be discerned which is only apparent when the cells are treated with the competitive inhibitor of glycolysis, 2-deoxyglucose (2-DG), (labeled SRC2DG), resulting in an increase in SRC which would otherwise remain hidden. This extra respiratory capacity has been labeled as "Covert" SRC. Table 9 shows the metabolic profiles of the fresh harvested TIL, fresh re-REP TIL, and thawed re-REP TIL derived from the metabolic stress test performed on the cells.

6.9.2 FIGS. 55A-F show the data from Table 38 in graphical form. The fresh harvested REP product shows some statistical differences from the fresh re-REP and thawed re-REP products. This is not surprising since the re-REP product has been restimulated with fresh irradiated PBMC APC and fresh anti-CD3 antibody either immediately after the REP or upon thaw. However, in all cases, there is no significant difference between the fresh and thawed products when both are restimulated in a re-REP procedure (see p values of Table 9). This indicates that the cryopreservation process does not detrimentally affect the TIL product. Most notably, for oxidative phosphorylation, the re-REP products have higher SRC than their matching fresh harvest REP products. For glycolysis, the re-REP TIL have statistically significantly higher basal levels of glycolysis and conversely statistically lower levels of glycolytic reserve than fresh REP product. It is worth noting that this could indicate that the re-REP TIL are more highly activated than the freshly harvested TIL, as activated, healthy TIL are reported to possess high levels of glycolytic activity (Buck et al., JEM 212:1345-1360; 2015).

TABLE 39

Metabolic Profile of Process 2A TIL

|  | M1061 | M1062 | M1063 | Moff2 | Moff3 | Moff4 | EP11001T | M1064 | M1065 | avg | sd | p v. fresh | p v. fresh r REP |
|---|---|---|---|---|---|---|---|---|---|---|---|---|---|
| Basal OCR, pmol/min | | | | | | | | | | | | | |
| PLLA | 50.33 | 33.95 | 74.89 | 36.80 | 38.48 | 39.89 | 63.02 | | 55.89 | 49.16 | 14.56 | | |
| fresh re-REP | 38.92 | 38.48 | 54.35 | 25.98 | 18.68 | 38.61 | 37.33 | 41.04 | | 36.67 | 10.57 | 0.03 | |
| thaw re-REP | 39.25 | 43.28 | 60.05 | 30.68 | 57.90 | 59.08 | 27.85 | 52.58 | 32.82 | 44.83 | 12.90 | 0.48 | 0.11 |
| Overt SRC, pmol/min | | | | | | | | | | | | | |
| PLLA | 24.74 | 10.45 | 101.18 | 47.32 | 77.00 | 35.07 | 31.39 | | 3.02 | 41.27 | 33.22 | | |
| fresh re-REP | 51.72 | 36.46 | 48.24 | 28.34 | 37.69 | 21.02 | 9.93 | 99.71 | | 41.64 | 27.17 | 0.29 | |
| thaw re-REP | 47.38 | 40.40 | 121.86 | 26.04 | 37.32 | 86.47 | 58.45 | 89.59 | 56.45 | 62.66 | 30.75 | 0.16 | 0.12 |
| SRC2DG, pmol/min | | | | | | | | | | | | | |
| PLLA | 14.01 | 5.72 | 35.98 | 29.97 | 74.62 | 24.42 | 31.39 | | 20.70 | 29.60 | 20.67 | | |
| fresh re-REP | 81.80 | 78.82 | 52.73 | 38.69 | 92.37 | 42.35 | -12.81 | 137.15 | | 63.89 | 44.45 | 0.08 | |
| thaw re-REP | 76.97 | 77.72 | 177.48 | 48.27 | 56.57 | 69.05 | 74.14 | 130.76 | 85.89 | 88.54 | 40.59 | 0.00 | 0.25 |

TABLE 39-continued

Metabolic Profile of Process 2A TIL

| | M1061 | M1062 | M1063 | Moff2 | Moff3 | Moff4 | EP11001T | M1064 | M1065 | avg | sd | p v. fresh | p v. fresh r REP |
|---|---|---|---|---|---|---|---|---|---|---|---|---|---|
| Covert SRC, pmol/min | | | | | | | | | | | | | |
| PLLA | 0.00 | 0.00 | 0.00 | 0.00 | 0.00 | 0.00 | 0.00 | | 17.68 | 2.21 | 6.25 | | |
| fresh re-REP | 30.08 | 42.36 | 4.50 | 10.35 | 54.68 | 21.33 | 0.00 | 2.63 | | 20.74 | 20.13 | 0.02 | |
| thaw re-REP | 29.59 | 37.32 | 55.62 | 22.23 | 19.25 | 0.00 | 15.68 | 41.16 | 29.44 | 27.81 | 16.10 | 0.01 | 0.52 |
| Basal ECAR, mpH/min | | | | | | | | | | | | | |
| PLLA | 53.44 | 27.55 | 136.33 | 48.72 | 89.80 | 62.29 | 108.38 | | 72.07 | 74.82 | 35.20 | | |
| fresh re-REP | 96.48 | 96.63 | 171.47 | 102.87 | 145.19 | 153.97 | 35.60 | 147.02 | | 118.65 | 44.19 | 0.10 | |
| thaw re-REP | 143.35 | 173.93 | 193.39 | 149.19 | 169.21 | 73.17 | 98.64 | 96.37 | 90.55 | 131.98 | 43.15 | 0.01 | 0.38 |
| Glycolytic Reserve, mpH/min | | | | | | | | | | | | | |
| PLLA | 32.11 | 26.18 | 52.00 | 19.09 | 38.01 | 39.03 | 43.14 | | 76.43 | 40.75 | 17.61 | | |
| fresh re-REP | 24.06 | 8.75 | 18.17 | −8.28 | −5.89 | 10.31 | 35.34 | 20.80 | | 12.91 | 14.85 | 0.003 | |
| thaw re-REP | 15.50 | −18.94 | 13.56 | −6.78 | 11.45 | 54.84 | −21.37 | −12.66 | −5.47 | 3.35 | 23.75 | 0.01 | 0.47 |

Figure 36:
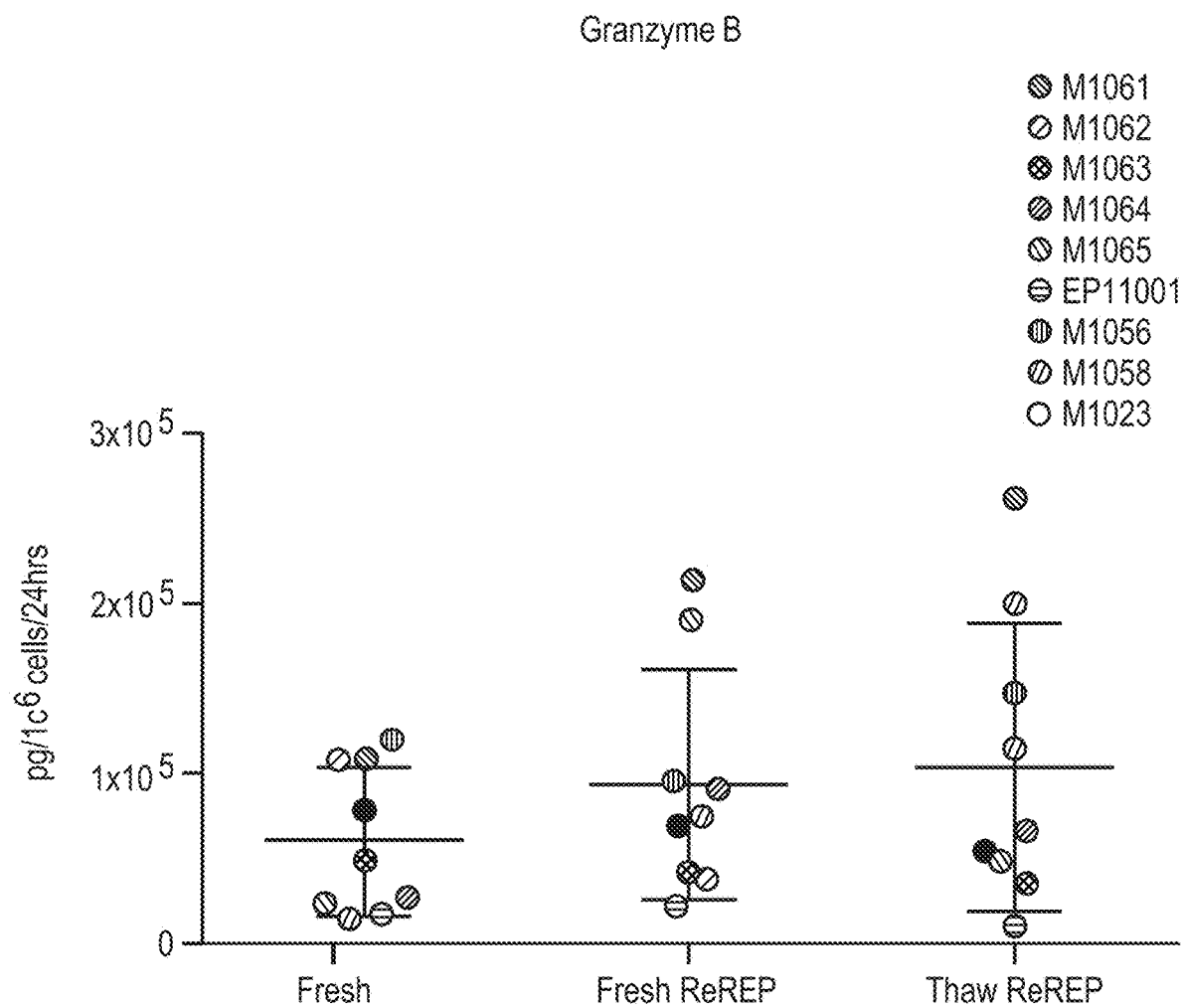
FIG. 36: Release of Granzyme B following anti-CD3, anti-CD28, and anti-4-1BB stimulation of TIL.
Figure 37A:
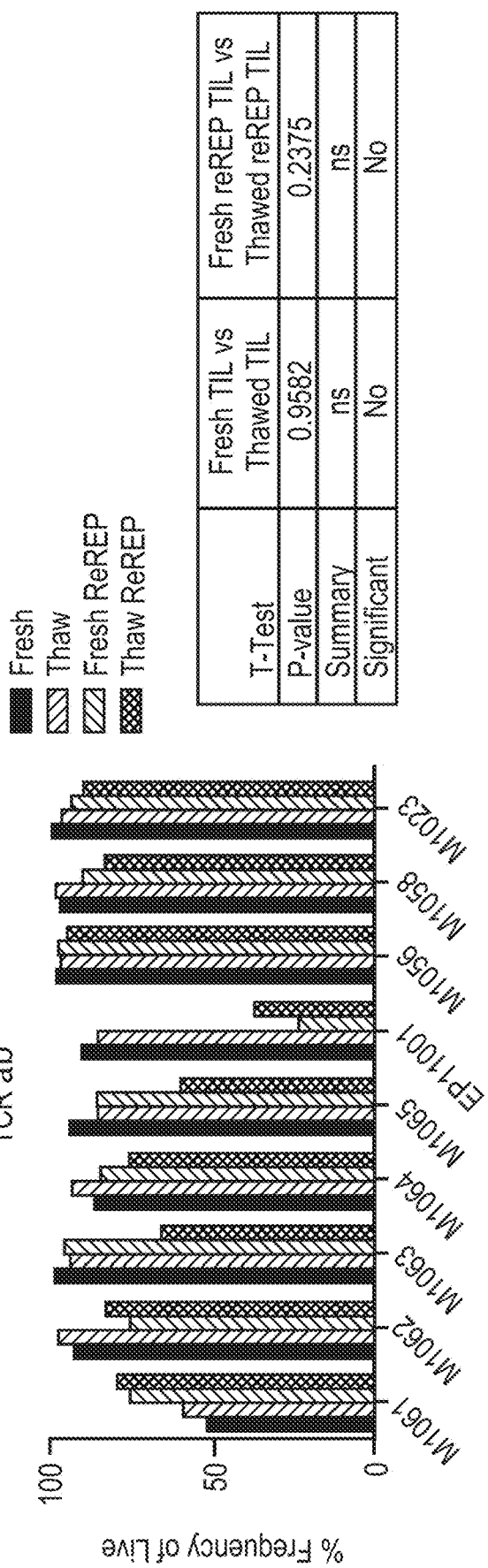
FIG. 37A-37B: TCR αβ+ TIL. Most human CD3+ T-cells express the receptors formed by α and β chains that recognize antigens in an MHC restricted manner. A) Except in M1061, fresh and thawed TIL product had 80% or more TCR αβ+ expressing TIL. Both fresh and thaw TIL had comparable expression of TCR αβ (p-value—0.9582). Even though a decrease in the TCR αβ+ expressing TIL after the Re-REP was observed, this decrease was not significant within the Re-REP TIL (p=0.24). B) There was a 9.2% and 15.7% decrease in the fresh and thaw RE-REP TIL expressing TCR αβ in comparison to fresh and thaw TIL respectively.
Figure 37B:
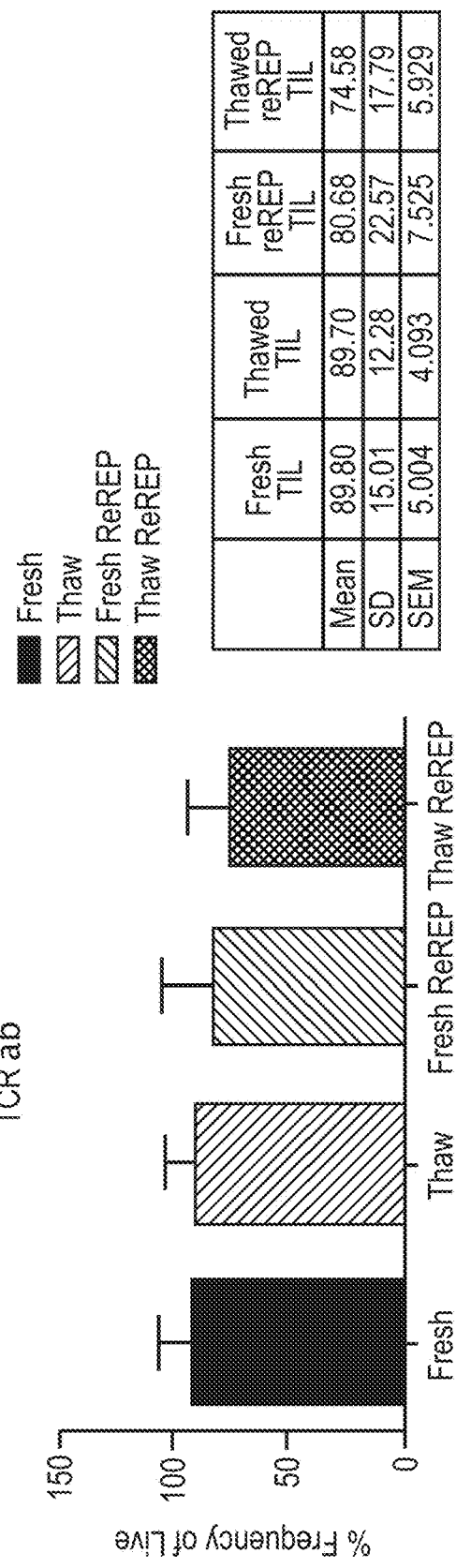

6.9.3 A direct comparison of fresh to frozen products using the re-REP procedure has enabled us to determine that both the fresh and frozen TIL products, upon identical stimulation conditions, result in metabolic profiles that are statistically indistinct. Both fresh re-REP and thawed re-REP TIL have similar levels of basal respiration (FIG. 60A, 36.7±10.6 and 44.8±12.9 pmol/min, respectively; p=0.11) as well as similar (overt) SRC (FIG. 60B, 41.6±27.2 and 62.7±30.8; p=0.12). Upon treatment of these re-REP cells with 2-DG, the competitive inhibitor to glucose, which results in an inhibition of glycolysis, we see that both fresh and thawed re-REP TIL show an extra, "hidden" spare respiratory capacity (SRC2DG; Covert SRC) that is mostly low or absent in the fresh harvested TIL sample (FIG. 60C); only one sample had high levels of SRC2DG (FIG. 60C) in the fresh harvested TIL, while conversely, only one of seven samples tested showed a lack Covert SRC upon re-REP. Covert SRC (FIG. 60D) for fresh re-REP averaged 20.7±20.1 while covert SRC (FIG. 60D) for thawed re-REP ranged from 27.8±16.1; p=0.52).

6.9.4 The most striking metabolic readout of the extended phenotype (re-REP) TIL is the consistently high levels of basal glycolysis of the extended phenotype (re-REP) samples. Basal glycolysis (FIG. 60E) is consistently high in re-REP samples, averaging 118.7±44.2 mpH/min in the fresh re-REP and 132.0±43.2 mpH/min in the thawed re-REP. These samples are not statistically different from each other (p=0.38). However, as mentioned above, the fresh harvested sample does not possess such high basal levels of glycolysis. Compared to fresh re-REP TIL, this difference is substantial, but not significant (p=0.10); however when compared to the thawed re-REP samples, the difference is significant (p 0.01). These re-REP cells are apparently heavily reliant on glycolysis for their energy needs, as they have little glycolytic reserve remaining when stressed in the Seahorse metabolic tests (FIG. 60F): fresh re-REP TIL average 12.9±14.9 mpH/min; thawed re-REP TIL, 3.35±23.8 mpH/min). These re-REPs are not different from each other (p=0.47) but both are statistically different than the glycolytic reserve found in fresh harvested TIL samples, which averages 40.8±17.6 mpH/min (p=0.003 and 0.01 compared to fresh re-REP and thawed re-REP TIL, respectively). Further studies should be conducted to determine the cause behind the differences seen in glycolysis between these fresh harvest and re-REP TIL samples.

6.10 Telomere Length Measurement 6.10.1 Measurement of Telomere Length of Post REP TIL by Flow Fish and qPCR.

6.10.1.1 Flow-FISH was performed using Dako/Agilent Pathology Solutions (Telomere PNA Kit/FITC for Flow Cytometry) kit and the manufacturer's instructions were followed to measure the average length of the Telomere repeat. 1301 T-cell leukemia cell line (Sigma-Aldrich, St. Louis, MO)) was used as an internal reference standard in each assay. Individual TIL were counted and mixed with 1301 cells at a 1:1 cell ratio. $2 \times 10^6$ TIL were mixed with $2 \times 10^6$ 1301 cells. In situ hybridization was performed in hybridization solution (70% formamide, 1% BSA, 20 mM Tris, pH 7.0) in duplicate and in the presence and absence of a FITC-conjugated Telomere PNA probe (FITC-00-CCCTAA-CCC-TAA-CCC-TAA) complementary to the telomere repeat sequence at a final concentration of 60 nM. After addition of the Telomere PNA probe, cells were incubated for 10 minutes at 82° C. in a heat block. The cells were then placed in the dark at room temperature overnight. The next morning, excess telomere probe was removed by washing 2 times for 10 minutes each on a heat block at 40° C. with Wash Solution. Following the washes, DAPI (Invitrogen, Carlsbad, CA) was added at a final concentration of 75 ng/ml. DNA staining with DAPI was used to gate cells in the G0/G1 population. Sample analysis was performed using a Yeti flow cytometer (Propel-Labs, Fort Collins, CO). Telomere fluorescence of the test sample was expressed as a percentage of the fluorescence (fl) of the 1301 cells per the following formula:Relative telomere length=[(mean FITC fl test cells w/probe-mean FITC fl test cells w/o probe)×DNA index of 1301 cells×100]/[(mean FITC fl 1301 cells w/probe—mean FITC fl 1301 cells w/o probe)×DNA index of test cells.

6.10.1.2 qPCR: Real time qPCR was used to measure relative telomere length. Briefly, the telomere repeat copy number to single gene copy number (T/S) ratio was determined using an Bio-Rad PCR thermal cycler (Bio-Rad Laboratories, Hercules, CA) in a 96-well format. Ten nanograms of genomic DNA was used for either telomere (Tel) or hemoglobin (hgb) PCR reaction and the primers used were as follows: Tel-1b primer (CGG TTT GTT TGG GTT TGG GTT TGG GTT TGG GTT TGG GTT), Tel-2b primer (GGC TTG CCT TAC CCT TAC CCT TAC CCT TAC CCT TAC CCT), hgb1 primer (GCTTCTGACACAACTGTGTTCACTAGC), and hgb2 primer (CACCAACTTCATCCACGTT-CACC). All samples were analyzed by both the telomere and hemoglobin reactions, and the analysis was performed in triplicate on the same plate. In addition to the test samples, each 96-well plate contained a five-point standard curve from 0.08 ng to 250 ng using genomic DNA isolated from 1301 cells. The T/S ratio (−dCt) for each sample was calculated by subtracting the median hemoglobin threshold cycle (Ct) value from the median telomere Ct value. The relative T/S ratio (−ddCt) was determined by subtracting the T/S ratio of the 10 ng standard curve point from the T/S ratio of each unknown sample.

6.10.1.3 Telomere Length Results and Discussion: Telomeres are caps (repetitive nucleotide sequences) at the end of the linear chromosomes which play a critical role in facilitating complete chromosome replication Telomere measurement is an emerging tool in the study of such conditions as degenerative diseases, cancer, and aging. Previous studies from NIH (J. Immunol. 2005, Nov. 15; 175(10):7046-52; Clin Cancer Res. 2011, Jul. 1; 17(13): 4550-4557) have shown that longer telomere length of TIL is associated with clinical response. Conversely, Radvanyi's group found no significant difference in the telomere length of TIL between responders and non-responders (Clin Cancer Res; 18(24); 6758-70). Thus far, there is no evidence to prove that telomere length is associated with the length of in vitro T cell culture. It is possible that post-REP TIL cultured by Process 2A (22 day culture) will have longer telomere length when compared to TIL cultured by Process 1C process (25-36 day culture).

Figure 35:
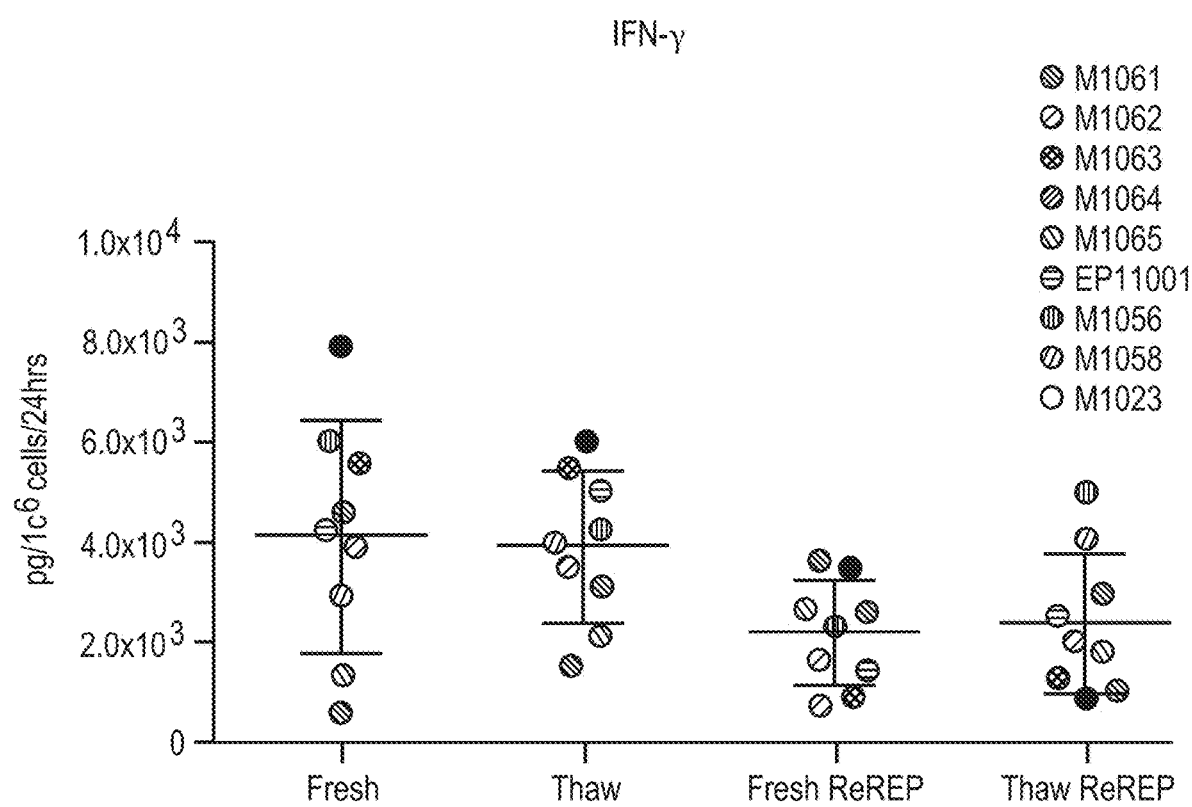
FIG. 35: Release of cytotoxic cytokines IFN-γ upon anti-CD3, anti-CD28 and anti-4-1BB stimulation of TIL.
Figure 59:
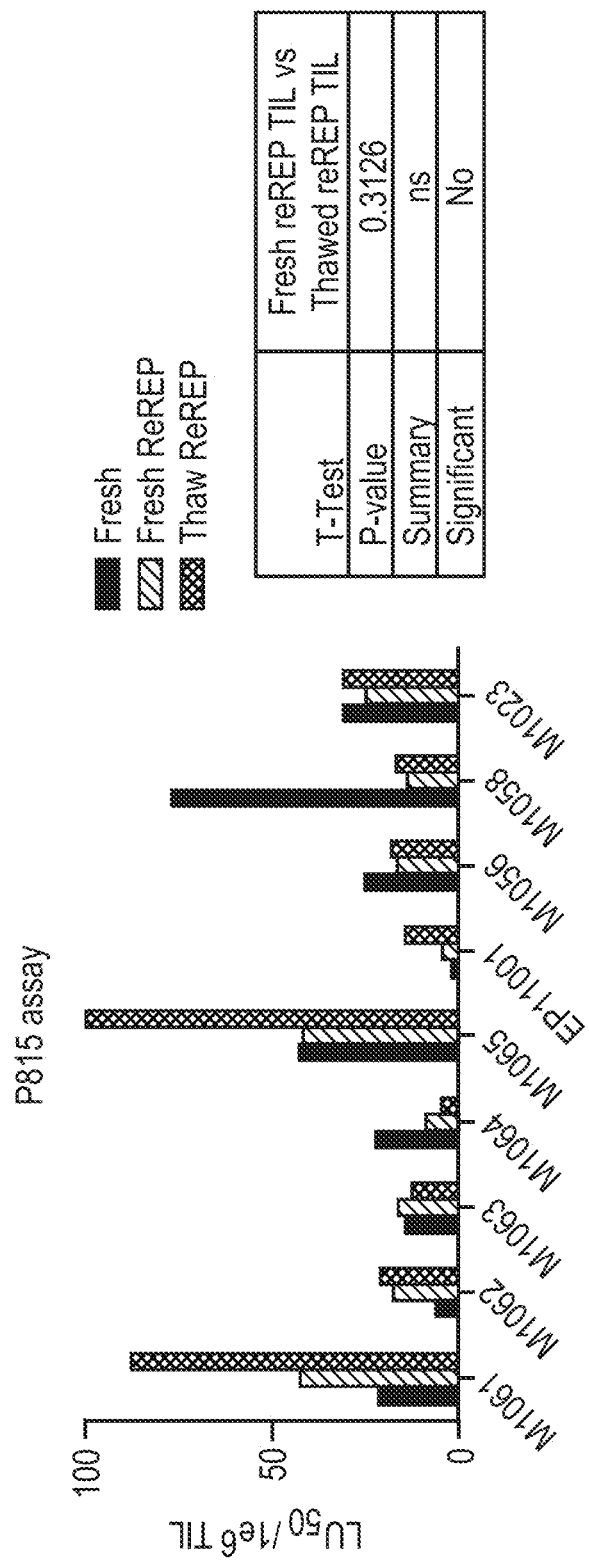
FIG. 59: Cytotoxic potential of TIL against P815 target cell line.

7. Discrepancies and Deviations
   7.1 Process Deviations
   7.1.1 M1061T: REP cells were split on Day 6 into 4 G-Rex500M flasks.
   7.1.2 M1062T: REP cells were split on Day 6 into 4 G-Rex500M flasks. Due to an operator error on the LOVO filtration system, an emergency stop occurred during the procedure which required a manual collection of the TIL from the disposable kit. The TIL were successfully filtered during a second LOVO run.
   7.1.3 M1063T: No deviations M1064T: No deviations
   7.1.4 M1065T: Pre-REP cells were below specification for cell count on Day 11 (<5×10$^6$ cells) but were continued into the REP. On REP Day 6, the cells were counted and placed back into the G-Rex500M and fed with 4.5 L fresh media. The TIL were not expanded on this day due to insufficient cell count (<1×10$^9$ cells on REP Day 6).
   7.1.5 EPI1001T: No deviations
   7.1.6 M1056T: Pre-REP cells were cultured at LION in a G-Rex 100 flask for up to 21 days. Tumor fragments were filtered out on pre-REP Day 11 and the TIL were frozen down on day of harvest in 100% CS10 at 30×106 cells per 1.5 ml vial. Frozen TIL were thawed at Moffitt PD in CM1 supplemented with 6000 IU/mL rhIL-2 and rested for 3 days before initiating Day 0 of the REP. On REP Day 6, TIL were expanded into 4 flasks which proceeded to harvest on REP Day 11.
   7.1.7 M1058T: Pre-REP cells were cultured at LION in a G-Rex 100 flask for up to 21 days. Tumor fragments were filtered out on pre-REP Day 11 and the TIL were frozen down on day of harvest in 100% CS10 at 30×106 cells per 1.5 ml vial. Frozen TIL were thawed at Moffitt PD in CM1 supplemented with 6000 IU/mL rhIL-2 and rested for 3 days before initiating Day 0 of the REP. On REP Day 6, cells were split into 4 flasks which proceeded to harvest on REP Day 11.
   7.1.8 M1023T: Pre-REP cells were cultured at LION in G-Rex10 flasks for up to 21 days. Tumor fragments were filtered out on pre-REP Day 11 and the TIL were frozen down on day of harvest in 100% CS10 at 30×106 cells per 1.5 ml vial. Frozen TIL were thawed at Moffitt PD in CM1 supplemented with 6000 IU/mL rhIL-2 and rested for 3 days prior to initiating Day 0 of the REP. On REP Day 6, cells were expanded into 4 flasks which proceeded to harvest on REP Day 11.
   7.2 Testing Deviations
   7.2.1 In-depth cytokine analysis and TCR sequencing were not performed 8. Conclusions and Recommendations
   8.1 Developing a More Robust Process. The challenge to Lion was to convert the earlier Lion Process 1C, which had a long processing time, to a potentially more commercializable Lion Process 2A which utilizes refinements resulting in shorter processing time and a cryopreserved final formulation of the TIL product. To this end, nine Process Development runs were conducted to confirm that the old and new processes demonstrated comparable cell yields and comparable TIL potency and phenotype. Of particular note was the markedly decreased complexity of the overall process, resulting in a 50% reduction in the overall length of the pre-REP and REP processes, yet still resulting in comparable TIL yields (7.8×10$^9$-67×10$^9$ cells) compared to the historic Lion Process 1C currently practiced at our contract manufacturer. This was recently updated for the June 2017 ASCO presentation (Mean: 41.04×109 cells with a range of 1.2-96×10$^9$ cells). In addition, Lion has successfully developed a cryopreserved TIL product which demonstrated a post-thaw recovery of 78-103% with >70% viability of TIL, consistent with current Process 1C release criteria (see Table 2).
   8.2 The Role of the Extended Phenotypic Analysis (Re-REP). The ability to proliferate in response to mitogenic stimulation (as in the experimental re-REPs presented in this report) is a critical quality attribute of TIL. The experiments presented here show that 8/9 thawed TIL products were able to expand >100-fold in one week compared to 7/9 matched fresh TIL products, supporting the comparability of the thawed TIL product to the fresh TIL product (Table 2). Two additional critical quality attributes of TIL are their ability to release IFN-γ and/or Granzyme B following cytokine (CD3/CD28/4-1BB) stimulation. Cytokine stimulation of both the fresh and thawed products resulted in IFN-γ release exceeding 2 ng/10$^6$ cells/24 hours in 7/9 fresh products and all thawed products (FIG. 35) (see section 6.2 of this report). Granzyme B release (FIG. 36) was observed in all 9 process runs. CD4 and CD8 levels (FIG. 39 and FIG. 40) demonstrated remarkable internal consistency between fresh and thawed TIL products. In addition, analysis of the ability of the TIL to kill a surrogate tumor target cell line (P815, FIG. 59) showed that the fresh and thawed TIL possessed similar cytotoxic potential.

8.3 A Metabolic Stress Test of TIL Reveals Robust Bioenergetics. An analysis of the metabolic profiles of fresh and thawed TIL products stimulated in a re-REP demonstrated that both fresh and thawed TIL responded similarly to metabolic stress testing and showed no substantive differences in a panel of metabolic characteristics (Table 39). Thus, the cryopreserved Process 2A TIL product can be considered comparable to the fresh Process 1C product based on the four quality attributes of identity, potency, cell number, and viability presented in this report. Assays comparing matched fresh and thawed cells were quite comparable in every assay outlined in this report.

8.4 Acceptance Criteria: The intrinsic heterogeneity of TIL products with personalized therapy for each patient reflects: (1) their unique major histocompatibility complex restricting molecules (the most polymorphic gene products in human biology); (2) the unique evolutionary trajectory of individual tumors arising in the tumor microenvironment with genomic instability and unique individual driver and passenger mutations; and (3) the heterogeneity conferred by allelic variation, N-region diversity, and VDJ rearrangements in the Vα and Vβ segments defining the T-cell receptors used for recognition of neoepitopes shared tumor-testis antigens, and virally encoded products. Assessing additional variation occurring as the result of process changes is thus a daunting task and requires assessment of as many parameters as possible to assure oneself that 'comparability' of an intrinsically heterogeneous material as possible. This has been accomplished by faithfully examining several acceptance criteria for feasibility and comparability as detailed in the Table 40 below.

TABLE 40

Acceptance criteria for feasibility and comparability

| Sampling Point | Parameter | Test Method | Acceptance Criteria for Feasibility | Acceptance Criteria for Comparability |
|---|---|---|---|---|
| Day 22 | Total Viable Cells | Automated Cell Counter with ACPI | ≥1.5 × 10% viable cells | No statistical significance between fresh and frozen ReREP arms (p-value < 0.05) |
| | % Viability | Automated Cell Counter with ACPI | ≥70% viable | No statistical significance between fresh and frozen ReREP arms (p-value < 0.05) |
| | Purity | Flow Cytometry | ≥90% T-cells | No statistical significance between fresh and frozen ReREP arms (p-value < 0.05) |
| | | TCR Sequencing | N/A | N/A |
| | Potency | IFNγ ELISA | ≥2x background and ≥400pg/1 × $10^6$ viable cells/24 hrs | No statistical significance between fresh and frozen ReREP arms (p-value < 0.05) |
| | | Granzyme B ELISA | ≥2x background | N/A |
| | | Bioluminescent Redirected Lysis Assay | N/A | N/A |
| | Respiration | Seahorse Stress Test | N/A | N/A |

Based on the feasibility criteria listed in Table 11, TIL will be evaluated on whether or not the requirements were met. All individual criteria were met for each experiment and each TIL line (n=9). Student t-test was used for statistical analysis. Non-parametric student T-test was used to calculate the p-value for % viability as viability measures will not be a Gaussian distribution. See, Table 41 below.

TABLE 41

Meeting Feasibility Acceptance Criteria.

| | Cell Count | | % Viability | | Purity (Flow Cytometry) | | Potency (IFNγ ELISA) pg/1 × $10^6$ cells/24 h | |
|---|---|---|---|---|---|---|---|---|
| TIL Line | Fresh | Thaw | Fresh | Thaw | Fresh | Thaw | Fresh | Thaw |
| M1061T | 6.48 × $10^9$ | 6.66 × $10^9$ | 88.05 | 84.93 | 95.3 | 91.5 | 4570 | 3158 |
| M1062T | 6.76 × $10^9$ | 5.70 × $10^9$ | 84.45 | 83.73 | 99.7 | 98.9 | 3921 | 3543 |

TABLE 41-continued

Meeting Feasibility Acceptance Criteria.

| TIL Line | Cell Count | | % Viability | | Purity (Flow Cytometry) | | Potency (IFNy ELISA) pg/1 × 10$^6$ cells/24 h | |
|---|---|---|---|---|---|---|---|---|
| | Fresh | Thaw | Fresh | Thaw | Fresh | Thaw | Fresh | Thaw |
| M1063T | 14.9 × 10$^9$ | 13.5 × 10$^9$ | 82.05 | 77.15 | 98.7 | 99.6 | 5589 | 5478 |
| M1064T | 8.06 × 10$^9$ | 7.08 × 10$^9$ | 86.75 | 83.36 | 84.5 | 89.8 | 619 | 1563 |
| M1065T | 3.06 × 10$^9$ | 3.10 × 10$^9$ | 76.35 | 80.90 | 96.8 | 91.4 | 1363 | 2127 |
| EP11001T | 14.9 × 10$^9$ | 12.2 × 10$^9$ | 77.9 | 74.85 | 90.4 | 94.3 | 4263 | 5059 |
| M1056T | 13.1 × 10$^9$ | 10.7 × 10$^9$ | 84.8 | 80.20 | 94.2 | 94.1 | 6065 | 4216 |
| M1058T | 23.4 × 10$^9$ | 20.1 × 10$^9$ | 87.5 | 85.07 | 99 | 96.2 | 2983 | 4033 |
| M1023T | 18.4 × 10$^9$ | 144 × 10$^9$ | 90.5 | 89.52 | 96.5 | 98.8 | 7918 | 6010 |
| P value | 0.1132 | | 0.0742 | | 0.9855 | | 0.5821 | |
| Significantly different | No | | No | | No | | No | |

Based on the acceptance criteria listed in Table 40, fresh and frozen re-REP TIL were evaluated on whether or not the requirements were met. (Viability not reported since the duration of re-REP was 7 days and residual irradiated PBMC could not be distinguished from TIL.) Numbers in parentheses denote the criteria that were not met. Based on the purity criteria measured using CD3+ expression, 6/9 fresh Re-REP TIL products met the stringent >90% criteria (M1061, M1065 and EP11001 did not) and 8/9 thawed products passed the acceptance criteria even following Re-REP. The low number of CD3+ TIL in EP11001T fresh re-REP might be attributed to extreme downregulation of T cell receptor. Measurement of CD3+ TIL as a measure of purity was not determined for M023T thaw re-REP TIL. For this TIL composition, purity was estimated using TCRαβ staining and is denoted by an asterisk (*). Student-t test was used for the statistical analysis. See, Table 42 below.

TABLE 42

Meeting Comparability Acceptance Criteria.

| TIL Line | Cell Count | | Purity (Flow Cytometry) | | Potency (IFNy ELISA) pg/1 × 10$^6$ cells/24 h | |
|---|---|---|---|---|---|---|
| | Fresh Re-REP | Thaw Re-REP | Fresh Re-REP | Thaw Re-REP | Fresh Re-REP | Thaw Re-REP |
| M1061T | 1.40 × 10$^6$ | 1.77 × 10$^6$ | (86.1) | 99.3 | 3638 | 2970 |
| M1062T | 2.64 × 10$^6$ | 1.10 × 10$^6$ | 99.3 | 97.1 | 1732 | 2060 |
| M1063T | 2.27 × 10$^6$ | 2.21 × 10$^6$ | 99.2 | 97.4 | 971 | 1273 |
| M1064T | 1.76 × 10$^6$ | 1.15 × 10$^6$ | 83.8 | 37.8 | 2676 | 1074 |
| M1065T | 3.16 × 10$^6$ | 1.91 × 10$^6$ | (78.1) | (75.8) | 2753 | 1744 |
| EP11001T | 2.02 × 10$^6$ | 0.738 × 10$^6$ | (18.2) | 85.4 | 1461 | 2522 |
| M1056T | 0.601 × 10$^6$ | 1.78 × 10$^6$ | 98.1 | 96.7 | 2374 | 5042 |
| M1058T | 0.740 × 10$^6$ | 2.20 × 10$^6$ | 98.4 | 99.2 | 770 | 4038 |
| M1023T | 2.69 × 10$^6$ | 3.03 × 10$^6$ | 97 | 39.9* | 3512 | 923 |
| P value | 0.6815 | | 0.3369 | | 0.7680 | |
| Significantly different | No | | No | | No | |

BIBLIOGRAPHY

Goff S L, Dudley M E, Citrin D E, Somerville R P, Wunderlich J R, Danforth D N, Zlott D A, Yang J C, Sherry R M, Kammula U S, Klebanoff C A, Hughes M S, Restifo N P, Langhan M M, Shelton T E, Lu L, Kwong M L, Ilyas S, Klemen N D, Payabyab E C, Morton K E, Toomey M A, Steinberg S M, White D E, Rosenberg S A. Randomized, Prospective Evaluation Comparing Intensity of Lymphodepletion Before Adoptive Transfer of Tumor-Infiltrating Lymphocytes for Patients With Metastatic Melanoma. J. Clin Oncol. 2016 Jul. 10; 34(20): 2389-97. doi: 10.1200/JCO.2016.66.7220. Epub 2016 May 23. PubMed PMID: 27217459; PubMed Central PMCID: PMC4981979.

Hinrichs C S, Rosenberg S A. Exploiting the curative potential of adoptive T-cell therapy for cancer. Immunol Rev. 2014 January; 257(1):56-71. doi:10.1111/imr.12132. Review. PubMed PMID: 24329789; PubMed Central PMCID: PMC3920180.

Jin J, Sabatino M, Somerville R, Wilson J R, Dudley M E, Stroncek D F, Rosenberg S A. Simplified method of the growth of human tumor infiltrating lymphocytes in gas-permeable flasks to numbers needed for patient treatment. J Immunother. 2012 April; 35(3):283-92. d10.1097/CJI.0b013e31824e801f. PubMed PMID: 22421946; PubMed Central PMCID: PMC3315105.

Somerville R P, Devillier L, Parkhurst M R, Rosenberg S A, Dudley M E. Clinical scale rapid expansion of lymphocytes for adoptive cell transfer therapy in the WAVER bioreactor. J Transl Med. 2012 Apr. 4; 10:69.

Donia M, Larsen S M, Met O, Svane I M. Simplified protocol for clinical-grade tumor-infiltrating lymphocyte manufacturing with use of the Wave bioreactor. Cytotherapy. 2014 August; 16(8):1117-20. doi: 10.1016/j.jcyt.2014.02.004; PubMed PMID: 24831841.

Henning A L, Levitt D E, Vingren J L, McFarlin B K. Measurement of T-Cell Telomere Length Using Amplified-Signal FISH Staining and Flow Cytometry. Curr Protoc Cytom. 2017 Jan. 5; 79:7.47.1-7.47.10. doi: 10.1002/cpcy.11. PubMed PMID 28055115

Kelesidis T, Schmid I. Assessment of Telomere Length, Phenotype, and DNA Content. Curr Protoc Cytom. 2017 Jan. 5; 79:7.26.1-7.26.23. doi: 10.1002/cpcy.12. PubMed PMID: 28055113.

Gardner M, Bann D, Wiley L, Cooper R, Hardy R, Nitsch D, Martin-Ruiz C, Shiels P, Sayer A A, Barbieri M, Bekaert S, Bischoff C, Brooks-Wilson A, Chen W, Cooper C, Christensen K, De Meyer T, Deary I, Der G, Diez Roux A, Fitzpatrick A, Hajat A, Halaschek-Wiener J, Harris S, Hunt S C, Jagger C, Jeon H S, Kaplan R, Kimura M, Lansdorp P, Li C, Maeda T, Mangino M, Nawrot T S, Nilsson P, Nordfjall K, Paolisso G, Ren F, Riabowol K, Robertson T, Roos G, Staessen J A, Spector T, Tang N, Unryn B, van der Harst P, Woo J, Xing C, Yadegarfar M E, Park J Y, Young N, Kuh D, von Zglinicki T, Ben-Shlomo Y; Halcyon study team. Gender and telomere length: systematic review and meta-analysis. Exp Gerontol. 2014 March; 51:15-27. doi:10.1016/j.exger.2013.12.004. Epub 2013 Dec. 21. Review. PubMed PMID: 24365661; PubMed Central PMCID: PMC4523138.

Carbonari M, Tedesco T, Fiorilli M. Correlation between terminal restriction fragments and flow-FISH measures in samples over wide range telomere lengths. Cell Prolif. 2014 February; 47(1):20-7. doi: 10.1111/cpr.12086. PubMed PMID: 24450811.

Rufer N, Dragowska W, Thornbury G, Roosnek E, Lansdorp P M. Telomere length dynamics in human lymphocyte subpopulations measured by flow cytometry. Nat Biotechnol. 1998 August; 16(8):743-7. PubMed PMID: 9702772.

Li Y, Liu S, Hemandez J, Vence L, Hwu P, Radvanyi L. MART-1-specific melanoma tumor-infiltrating lymphocytes maintaining CD28 expression have improved survival and expansion capability following antigenic restimulation in vitro. J. Immunol. 2010 Jan. 1; 184(1):452-65. doi: 10.4049/jimmunol.0901101. Epub 2009 Nov. 30. PubMed PMID: 19949105.

Rosenberg S A, Dudley M E. Adoptive cell therapy for the treatment of patients with metastatic melanoma. Curr Opin Immunol. 2009 April; 21(2):233-40. doi:10.1016/j.coi.2009.03.002. Epub 2009 Mar. 21. Review. PubMed PMID: 19304471; PubMed Central PMCID: PMC3459355.

Shen X, Zhou J, Hathcock K S, Robbins P, Powell D J Jr, Rosenberg S A, Hodes R J. Persistence of tumor infiltrating lymphocytes in adoptive immunotherapy correlates with telomere length. J Immunother. 2007 January; 30(1): 123-9. PubMed PMID:17198091; PubMed Central PMCID: PMC2151201.

Zhou J, Shen X, Huang J, Hodes R J, Rosenberg S A, Robbins P F. Telomere length of transferred lymphocytes correlates with in vivo persistence and tumor regression in melanoma patients receiving cell transfer therapy. J. Immunol. 2005 Nov. 15; 175(10):7046-52. PubMed PMID: 16272366; PubMed Central PMCID: PMC1351312.

Maciejowski J, de Lange T. Telomeres in cancer: tumour suppression and genome instability. Nat Rev Mol Cell Biol. 2017 March; 18(3):175-186. doi:10.1038/nrm.2016.171. Epub 2017 Jan. 18. Review. PubMed PMID: 28096526.

Erdel F, Kratz K, Willcox S, Griffith J D, Greene E C, de Lange T. Telomere Recognition and Assembly Mechanism of Mammalian Shelterin. Cell Rep. 2017 Jan. 3; 18(1):41-53. doi: 10.1016/j.celrep.2016.12.005. PubMed PMID: 28052260; PubMed Central PMCID: PMC5225662.

Cardenas M E, Bianchi A, de Lange T. A Xenopus egg factor with DNA-binding properties characteristic of terminus-specific telomeric proteins. Genes Dev.1993 May; 7(5): 883-94. PubMed PMID: 7684008.

de Lange T. Activation of telomerase in a human tumor. Proc Natl Acad Sci USA. 1994 Apr. 12; 91(8):2882-5. Review. PubMed PMID: 8159672; PubMed Central PMCID: PMC43476.

de Lange T, Shiue L, Myers R M, Cox D R, Naylor S L, Killery A M, Varmus H E. Structure and variability of human chromosome ends. Mol Cell Biol. 1990 February; 10(2):518-27. PubMed PMID: 2300052; PubMed Central PMCID: PMC360828.

9. Additional Tables

TABLE 43

Figure 39A:
FIG. 39A-39B: CD4+ cells. No substantial difference in the CD4 population was observed in individual conditions. Figure A represents the average CD4 population in each condition. The table in Figure B shows the SD and SEM values. There is a slight decrease in the CD4 population in the fresh re-REP population which is mostly due to a decrease in CD4 in the fresh re-REP population in EP11001T.
Figure 39B:
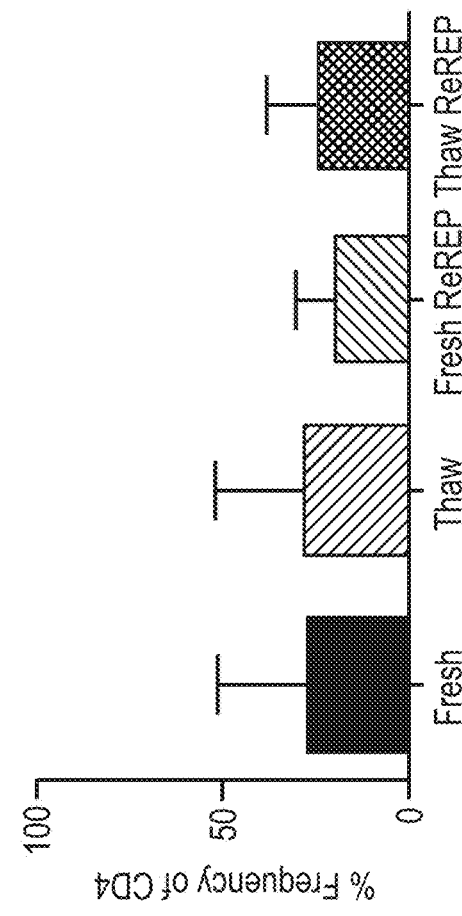
Figure 44A:
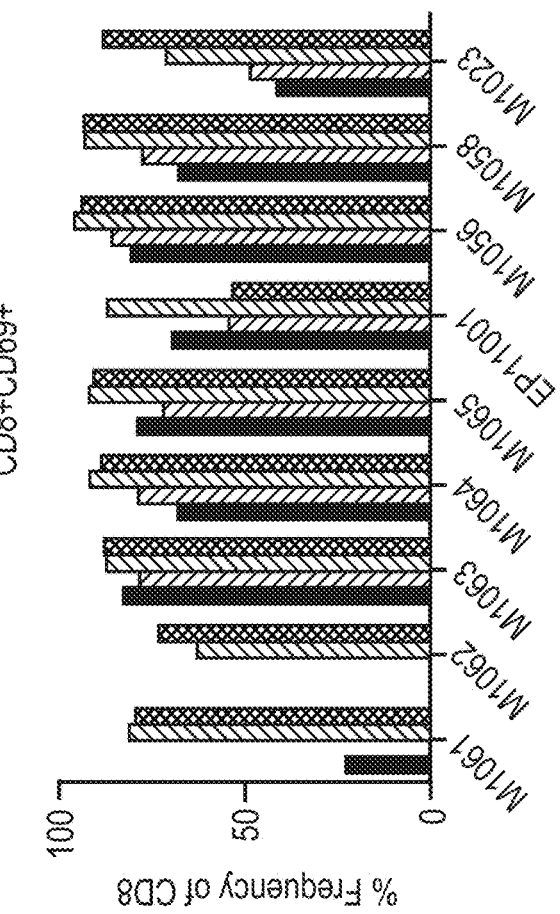
FIG. 44A-44B: CD8+CD69+ cells. As observed for the CD4+ population, Figure A shows an increase in the CD69 expression in the CD8+re-REP TIL. CD69 expression showed no significant difference between the fresh and thawed TIL (p=0.68) or the fresh and thawed re-REP TIL (p=0.76). Figure B supports the observation that there is a modest increase in the CD69 expression in the re-REP TIL product.
Figure 44B:
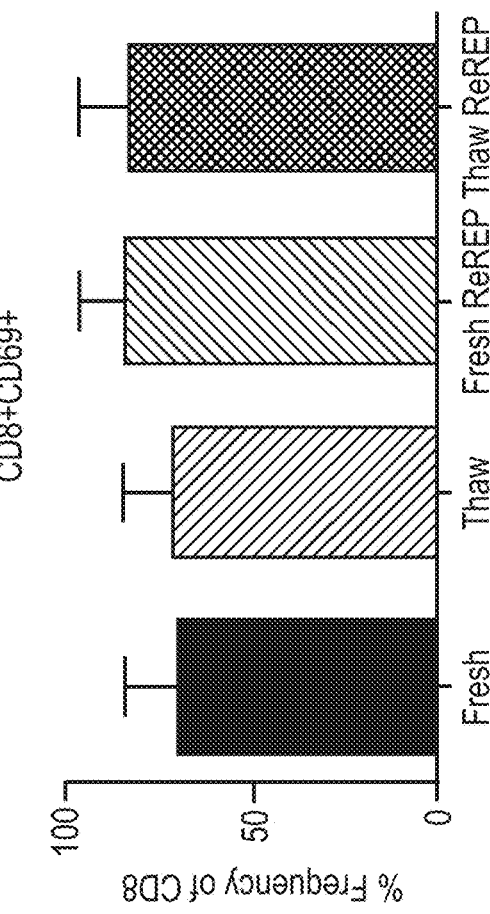

| FIG. 39: CD4+ cells | | | | | | | | | |
|---|---|---|---|---|---|---|---|---|---|
| Tumor ID | M1061 | M1062 | M1063 | M1064 | M1065 | EP11001 | M1056 | M1058 | M1023 |
| Fresh | 4.85 | 34 | 10.5 | 41.7 | 64.9 | 64.7 | 4.15 | 12.3 | 8.38 |
| Thaw | 5.68 | 33 | 11.3 | 49.5 | 61.7 | 62.6 | 3.46 | 17.9 | 7.6 |
| Fresh ReREP | 8.1 | 23.5 | 19.2 | 39/ | 31.9 | 16.3 | 6.46 | 12.9 | 16.7 |
| Thaw ReREP | 11 | 33 | 15.3 | 49.3 | 39.3 | 26.7 | 9.51 | 17.2 | 19.1 |

TABLE 44

| FIG. 40: CD8+ cells | | | | | | | | | |
|---|---|---|---|---|---|---|---|---|---|
| Tumor ID | M1061 | M1062 | M1063 | M1064 | M1065 | EP11001 | M1056 | M1058 | M1023 |
| Fresh | 45.6 | 54.7 | 85.8 | 38.2 | 28.6 | 22.3 | 93.2 | 84 | 88.8 |
| Thaw | 50.8 | 55.7 | 76.7 | 37 | 22.8 | 19 | 92.9 | 76.6 | 84.3 |
| Fresh ReREP | 63 | 48.3 | 72.4 | 37.9 | 47.8 | 5.87 | 90.3 | 74.5 | 74.4 |
| Thaw ReREP | 66.3 | 46.7 | 47 | 21.6 | 19.1 | 9.23 | 82.8 | 63.7 | 64.3 |

TABLE 45

FIG. 41: CD4+CD154+ cells and FIG. 105: CD8+CD154+ cells

| T cell | Markers | M1061 Fresh | M1061 Thawed | M1062 Fresh | M1062 Thawed | M1063 Fresh | M1063 Thawed | M1064 Fresh | M1064 Thawed |
|---|---|---|---|---|---|---|---|---|---|
| CD4 | CD154+ | 78.6 | nd | nd | nd | 93.3 | 62.1 | 94 | 76.2 |
| CD8 | CD154+ | 37.3 | nd | nd | nd | 85.8 | 19.9 | 89.3 | 61.1 |

| T cell | Markers | M1061 Fresh Re-REP | M1061 Thawed Re-REP | M1062 Fresh Re-REP | M1062 Thawed Re-REP | M1063 Fresh Re-REP | M1063 Thawed Re-REP | M1064 Fresh Re-REP | M1064 Thawed Re-REP |
|---|---|---|---|---|---|---|---|---|---|
| CD4 | CD154+ | 88.9 | 84 | 56 | 82.1 | 68.2 | 93.6 | 97 | 90.3 |
| CD8 | CD154+ | 35.6 | 49 | 12.5 | 19 | 59.1 | 77.88 | 0.025 | 90.1 |

| T cell | Markers | M1065 Fresh | M1065 Thawed | EP11001 Fresh | EP11001 Thawed | M1056 Fresh | M1056 Thawed | M1058 Fresh | M1058 Thawed | M1203 Fresh | M1203 Thawed |
|---|---|---|---|---|---|---|---|---|---|---|---|
| CD4 | CD154+ | 91 | 87.2 | 79.1 | 83.1 | 89.3 | 92 | 90.1 | 92.6 | 77.9 | 66.9 |
| CD8 | CD154+ | 17 | 20.3 | 40 | 36.9 | 23 | 27.6 | 40.5 | 52.1 | 17.9 | 13.7 |

| T cell | Markers | M1065 Fresh Re-REP | M1065 Thawed Re-REP | EP11001 Fresh Re-REP | EP11001 Thawed Re-REP | M1056 Fresh Re-REP | M1056 Thawed Re-REP | M1058 Fresh Re-REP | M1058 Thawed Re-REP | M1203 Fresh Re-REP | M1203 Thawed Re-REP |
|---|---|---|---|---|---|---|---|---|---|---|---|
| CD4 | CD154+ | 0 | 91.6 | 52.1 | 87.1 | 77 | 86.4 | 92.7 | 85.1 | 90.7 | 81.3 |
| CD8 | CD154+ | 0.00609 | 61.8 | 45.3 | 74.8 | 47.3 | 81.7 | 73.6 | 78.3 | 24.2 | 27.1 |

TABLE 46

FIG. 43: CD4+CD69+ cells and FIG. 17: CD8+CD69+ cells

| T cell | Markers | M1061 Fresh | M1061 Thawed | M1062 Fresh | M1062 Thawed | M1063 Fresh | M1063 Thawed | M1064 Fresh | M1064 Thawed |
|---|---|---|---|---|---|---|---|---|---|
| CD4 | CD69+ | 33.9 | nd | nd | nd | 82.2 | 68.8 | 51.3 | 84.8 |
| CD8 | CD69+ | 22.4 | nd | nd | nd | 83 | 78.3 | 67.8 | 78.6 |

| T cell | Markers | M1061 Fresh Re-REP | M1061 Thawed Re-REP | M1062 Fresh Re-REP | M1062 Thawed Re-REP | M1063 Fresh Re-REP | M1063 Thawed Re-REP | M1064 Fresh Re-REP | M1064 Thawed Re-REP |
|---|---|---|---|---|---|---|---|---|---|
| CD4 | CD69+ | 58.7 | 69.6 | 67.6 | 77.6 | 77.6 | 86.7 | 85.5 | 78.5 |
| CD8 | CD69+ | 80.9 | 80 | 62.7 | 73.2 | 87.6 | 87.9 | 92.2 | 88.3 |

| T cell | Markers | M1065 Fresh | M1065 Thawed | EP11001 Fresh | EP11001 Thawed | M1056 Fresh | M1056 Thawed | M1058 Fresh | M1058 Thawed | M1203 Fresh | M1203 Thawed |
|---|---|---|---|---|---|---|---|---|---|---|---|
| CD4 | CD69+ | 82.7 | 84.4 | 78.7 | 58.3 | 83.9 | 84.9 | 89.7 | 644.6 | 33.8 | 38.7 |
| CD8 | CD69+ | 78.9 | 72.3 | 69.5 | 54.5 | 80.3 | 86 | 68 | 77.8 | 41.3 | 48.8 |

| T cell | Markers | M1065 Fresh Re-REP | M1065 Thawed Re-REP | EP11001 Fresh Re-REP | EP11001 Thawed Re-REP | M1056 Fresh Re-REP | M1056 Thawed Re-REP | M1058 Fresh Re-REP | M1058 Thawed Re-REP | M1203 Fresh Re-REP | M1203 Thawed Re-REP |
|---|---|---|---|---|---|---|---|---|---|---|---|
| CD4 | CD69+ | 90.2 | 93.2 | 74.7 | 39.1 | 96.1 | 93.8 | 91.1 | 93.7 | 35.3 | 80.1 |
| CD8 | CD69+ | 91.3 | 90.5 | 87.6 | 52.9 | 95.4 | 94.2 | 93.1 | 93.6 | 71.1 | 88.1 |

TABLE 47

Figure 45A:
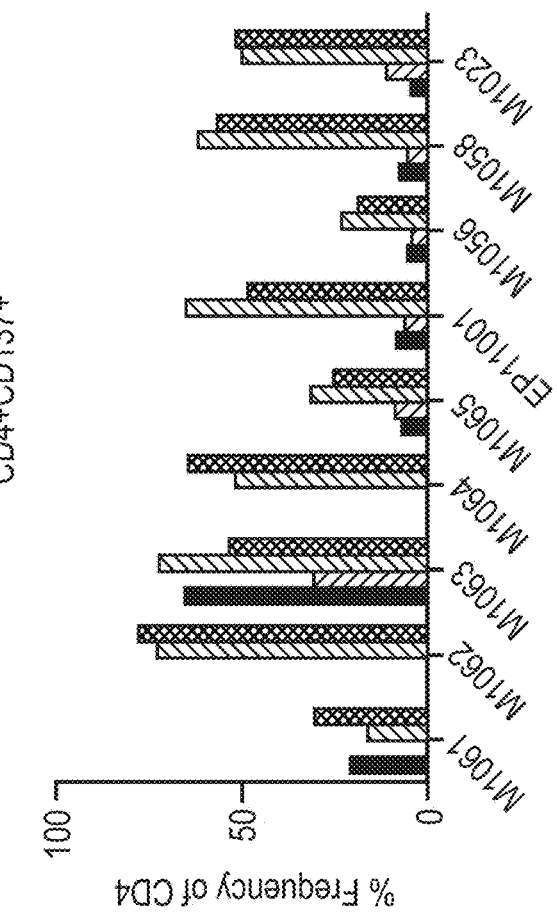
FIG. 45A-45B: CD4+CD137+ cells. CD137 (4-11313) is a T-cell costimulatory receptor induced upon TCR activation. It is activated on CD4+ and CD8+ T cells. A) CD137 expression showed a profound increase in the re-REP TIL population following 7 days of stimulation. However, no difference between the fresh and thawed TIL or fresh and thawed re-REP TIL were observed (p<0.05 in both cases Figure B supports this observation). Also, the thawed TIL showed a modest decrease in CD137 expression. The increase in CD137 expression in re-REP TIL could be attributed to the second round of stimulation of the 7-day re-REP.
Figure 45B:
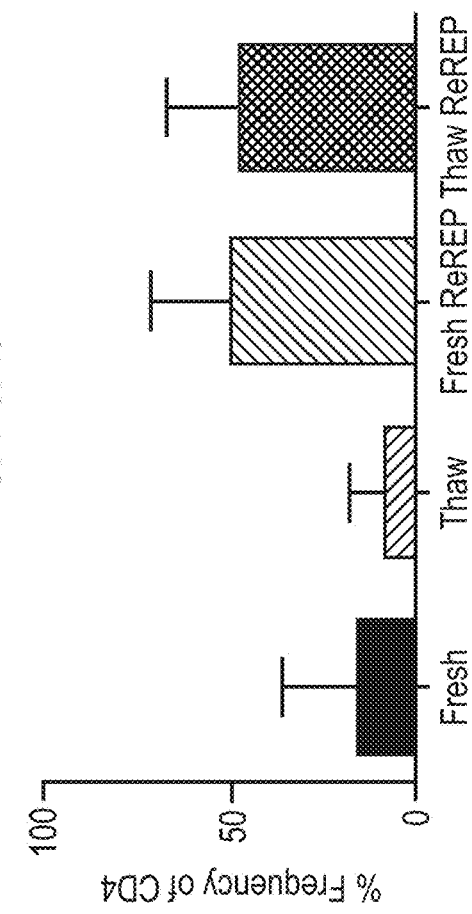
Figure 46A:
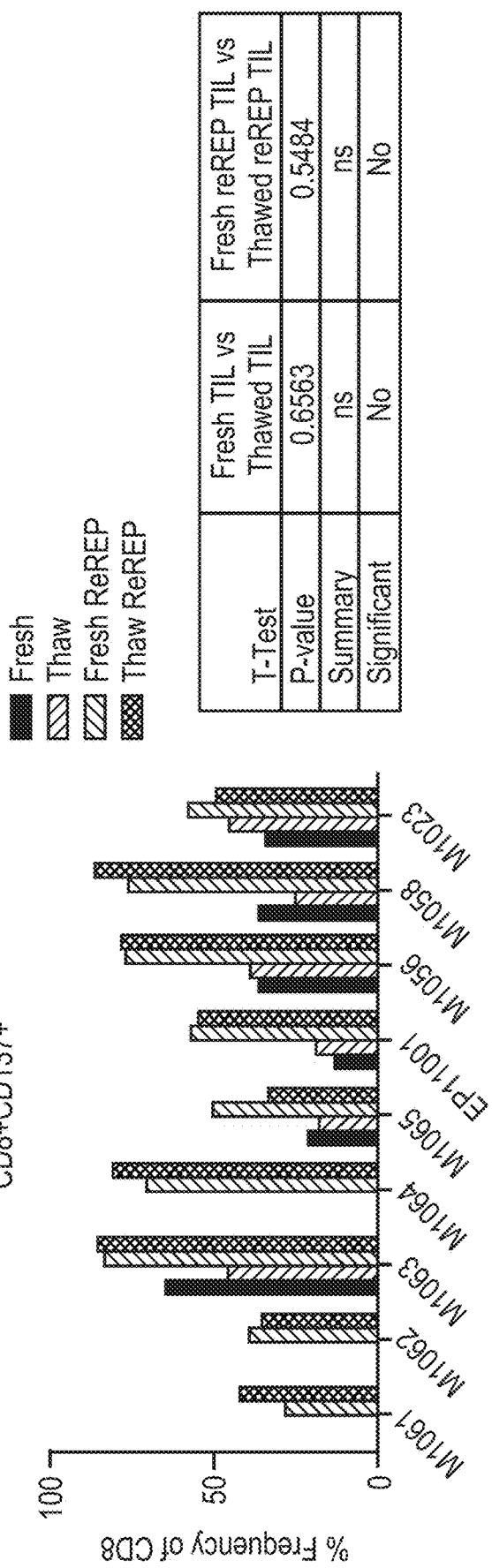
FIG. 46A-46B: CD8+CD137+ cells. A) CD8+ population showed an overall increase in the re-REP product. B) Fresh re-REP product had a 33.4% increase in CD8+CD137+ expression in comparison to fresh TIL product. Thawed re-REP product also showed a 33.15% increase in CD137 expression in the CD8+ population compared to thawed TIL. No significant differences were observed between fresh and thawed re-REP TIL. A similar observation can be seen comparing the fresh TIL to the thawed TIL product. This increase in CD137 expression could be due to the second round of activation of the re-REP. (Note that only 6 TIL were used for the analysis as CD137 expression were not measured for 3 of the experiments.)
Figure 46B:
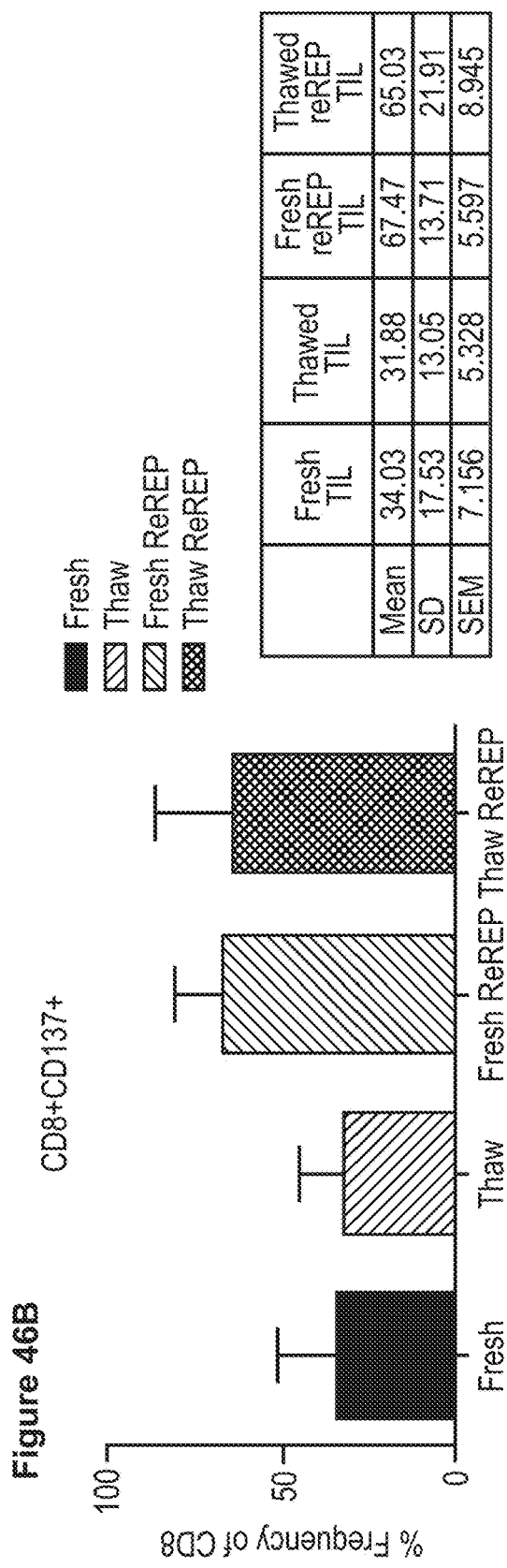

FIG. 45: CD4 +CD137+ cells and FIG. 19 CD8+CD137+ cells

| T cell | Markers | M1061 | | M1062 | | M1063 | | M1064 | |
|---|---|---|---|---|---|---|---|---|---|
| | | Fresh | Thawed | Fresh | Thawed | Fresh | Thawed | Fresh | Thawed |
| CD4 | CD137+ | 19.8 | nd | nd | nd | 65.4 | 30.4 | nd | 1.31 |
| CD8 | CD137+ | 19.8 | nd | nd | nd | 65.4 | 30.4 | nd | 1.31 |

| T cell | Markers | M1061 | | M1062 | | M1063 | | M1064 | |
|---|---|---|---|---|---|---|---|---|---|
| | | Fresh Re-REP | Thawed Re-REP | Fresh Re-REP | Thawed Re-REP | Fresh Re-REP | Thawed Re-REP | Fresh Re-REP | Thawed Re-REP |
| CD4 | CD137+ | 15.4 | 30.4 | 73 | 78.1 | 62.6 | 53.2 | 51.6 | 64.7 |
| CD8 | CD137+ | 28.8 | 43.1 | 39.3 | 35.3 | 84.4 | 85.7 | 71.1 | 81 |

| T cell | Markers | M1065 | | EP11001 | | M1056 | | M1058 | | M1203 | |
|---|---|---|---|---|---|---|---|---|---|---|---|
| | | Fresh | Thawed | Fresh | Thawed | Fresh | Thawed | Fresh | Thawed | Fresh | Thawed |
| CD4 | CD137+ | 524 | 7.26 | 7.78 | 5.4 | 4.28 | 3.65 | 6.89 | 4.6 | 4.28 | 9.67 |
| CD8 | CD137+ | 3.23 | 7.26 | 7.78 | 5.4 | 4.28 | 3.65 | 6.89 | 4.6 | 4.28 | 9.67 |

| T cell | Markers | M1065 | | EP11001 | | M1056 | | M1058 | | M1203 | |
|---|---|---|---|---|---|---|---|---|---|---|---|
| | | Fresh Re-REP | Thawed Re-REP | Fresh Re-REP | Thawed Re-REP | Fresh Re-REP | Thawed Re-REP | Fresh Re-REP | Thawed Re-REP | Fresh Re-REP | Thawed Re-REP |
| CD4 | CD137+ | 31.1 | 24.6 | 65.1 | 47.8 | 221 | 18.6 | 61.6 | 56.9 | 49.8 | 50.8 |
| CD8 | CD137+ | 50.9 | 33.8 | 57.3 | 54.6 | 77.3 | 78.8 | 76.9 | 87 | 58 | 50.3 |

TABLE 48

Figure 47A:
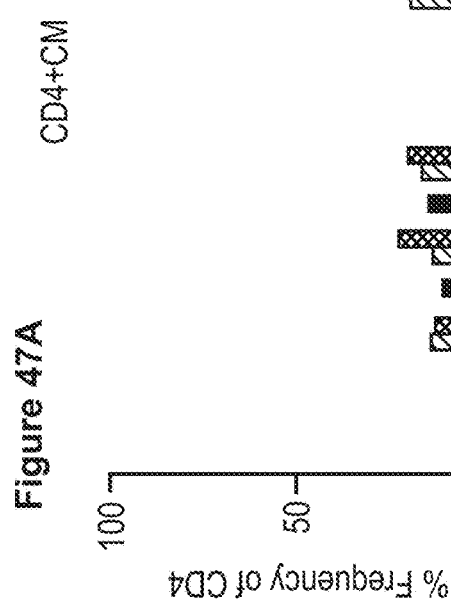
FIG. 47A-47B: CD4+CM cells. Central Memory (CM) population is defined by CD45RA− (negative) and CCR7+ (positive) expression. A) An increase in the CM population in the re-REP conditions were observed. M1063T and M1064T showed a decrease in the CM expression in the CD4+ population obtained from thawed TIL in comparison to fresh TIL product. Neither fresh and thawed TIL product (p=0.1658) nor fresh re-REP and thaw re-REP TIL (p=0.5535) showed a significant difference in CM population. B) A 14.4% and 15.4% increase in the CM population was observed in the fresh and thawed re-REP TIL in comparison to fresh and thawed TIL respectively.
Figure 47B:
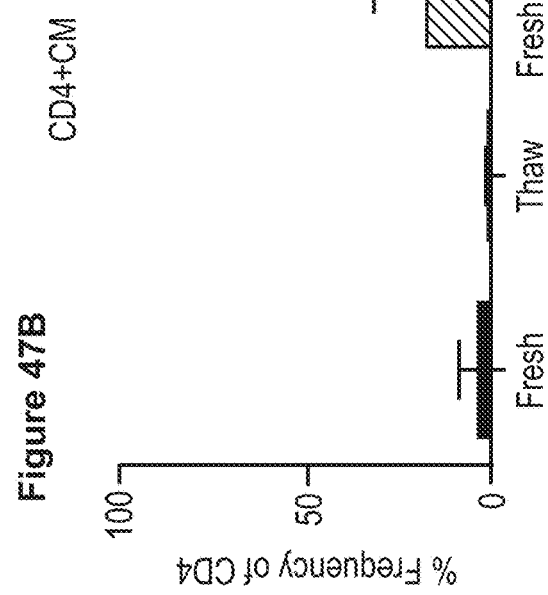
Figure 48A:
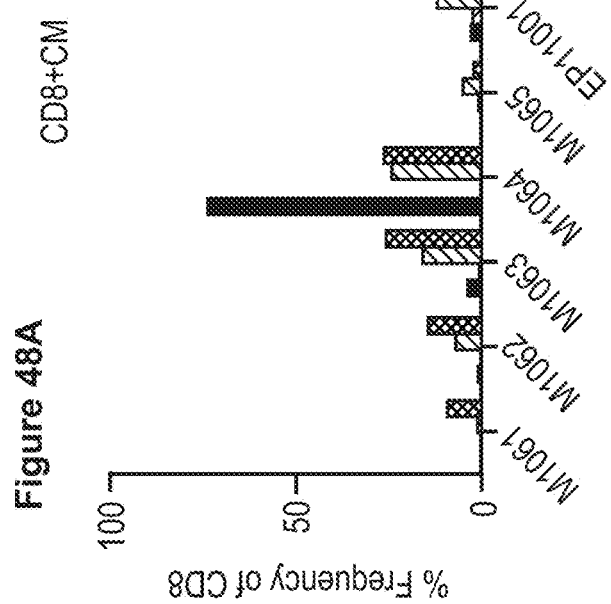
FIG. 48A-48B: CD8+CM cells. A) In the CD8+ population, a dramatic increase in CM expression in the fresh TIL product was seen, an observation not present in the TIL product. This increase did not affect the significance (p=0.3086), suggesting no difference between the fresh and thawed TIL. A similar trend was seen in the re-REP TIL products as well.
Figure 48B:
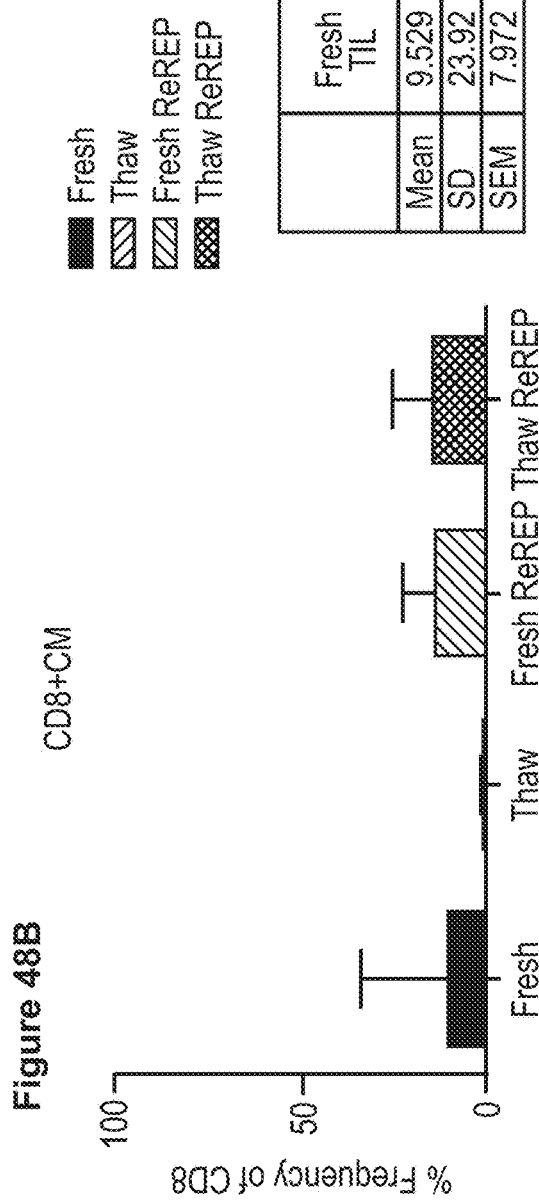

FIG. 47: CD4+CM cells and FIG. 21 CD8+CM cells

| TCell | Markers | M1061 | | M1062 | | M1063 | | M1064 | |
|---|---|---|---|---|---|---|---|---|---|
| | | Fresh | Thawed | Fresh | Thawed | Fresh | Thawed | Fresh | Thawed |
| CD4 | CM | 1.08 | n/d | 0.59 | 0.29 | 10.4 | 2.08 | 14.4 | 0.13 |
| CD8 | CM | 0.37 | n/d | 0.9 | 0.17 | 3.2 | 0.66 | 73.2 | 0.13 |

| T cell | Markers | M1061 | | M1062 | | M1063 | | M1064 | |
|---|---|---|---|---|---|---|---|---|---|
| | | Fresh Re-REP | Thawed Re-REP | Fresh Re-REP | Thawed Re-REP | Fresh Re-REP | Thawed Re-REP | Fresh Re-REP | Thawed Re-REP |
| CD4 | CM | 2.32 | 7.71 | 13.8 | 12.6 | 13.4 | 22.3 | 15.9 | 18.6 |
| CD8 | CM | 1.85 | 9.38 | 6.48 | 14.2 | 15.7 | 25.7 | 24.2 | 25.8 |

| T cell | Markers | M1065 | | EP11001 | | M1056 | | M1058 | | M1203 | |
|---|---|---|---|---|---|---|---|---|---|---|---|
| | | Fresh | Thawed | Fresh | Thawed | Fresh | Thawed | Fresh | Thawed | Fresh | Thawed |
| CD4 | CM | 0.42 | 0.53 | 0.48 | 1.17 | 1.83 | 1.5 | 1.36 | 1.8 | 2.45 | 1.79 |
| CD8 | CM | 0.21 | 0.67 | 2.65 | 1.79 | 0.33 | 0.72 | 0.91 | 0.67 | 1.99 | 2.22 |

| T cell | Markers | M1065 | | EP11001 | | M1056 | | M1058 | | M1203 | |
|---|---|---|---|---|---|---|---|---|---|---|---|
| | | Fresh Re-REP | Thawed Re-REP | Fresh Re-REP | Thawed Re-REP | Fresh Re-REP | Thawed Re-REP | Fresh Re-REP | Thawed Re-REP | Fresh Re-REP | Thawed Re-REP |
| CD4 | CM | 7.03 | 2.28 | 18.9 | 3.73 | 49.6 | 55.6 | 20.1 | 12.6 | 22.1 | 12.7 |
| CD8 | CM | 5.05 | 1.6 | 11.4 | 3.37 | 25.8 | 26.4 | 21.6 | 19.8 | 11.1 | 7.59 |

TABLE 49

Figures 49A, 49B:
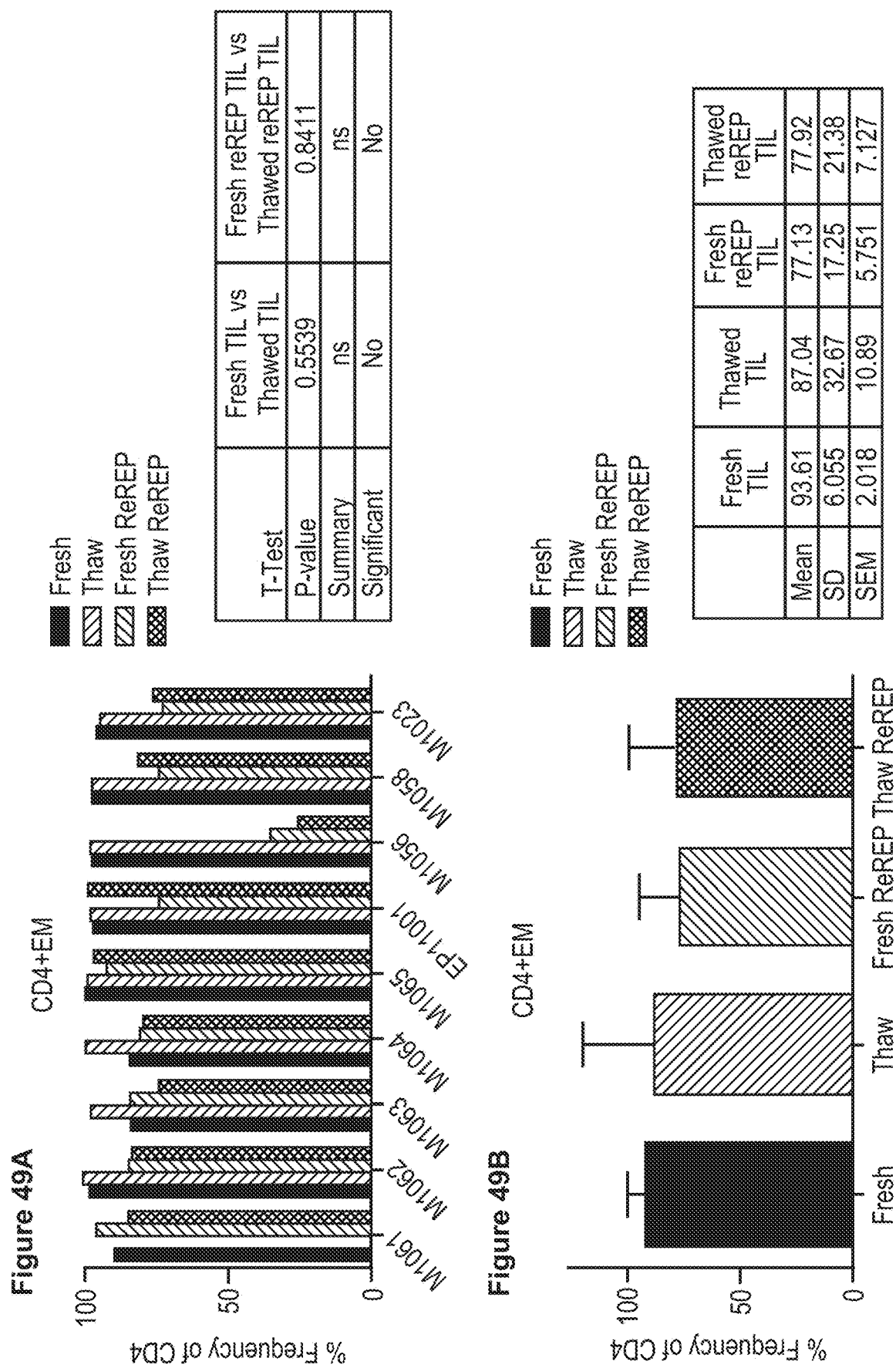
FIG. 49A-49B: CD4+EM cells. Effector memory (EM) population is defined by the lack of CCR7 and CD45RA expression. A) As expected the CD4+ population from fresh and thawed TIL had a high level of effector memory phenotype. A drastic decrease in the effector memory expression was found in the M1056T re-REP TIL population. Also, 5 other experiments showed a decrease in the effector memory phenotype in both fresh and thawed re-REP TIL. B) Both fresh and thawed TIL showed similar expression of effector memory phenotype. Comparison of fresh and fresh Re-REP TIL showed a decrease by 16% in the latter. A similar decrease was observed in the thawed Re-REP TIL (9%) when compared to the thawed TIL.
Figure 50A:
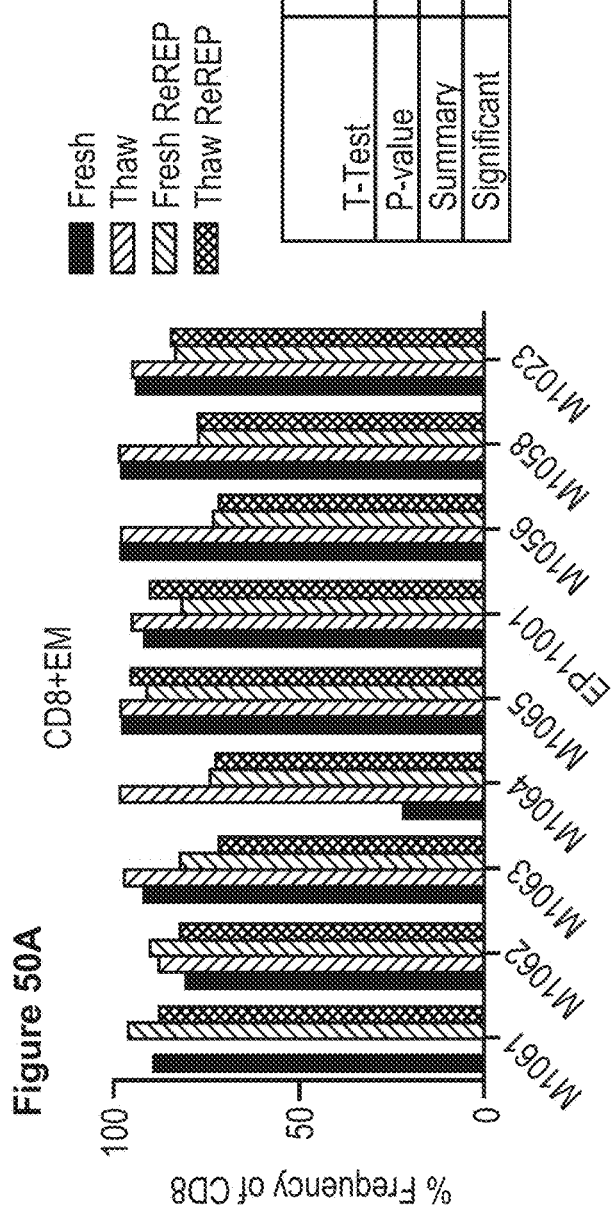
FIG. 50A-50B: CD8+EM cells. A) A similar pattern of increased effector memory in the fresh TIL was also seen in the CD8+ population. An exception was noted in the M1064T in which fresh TIL only had a 20% effector memory profile; this is due to the 73% of these TIL having a CM phenotype as described in A and B. All the samples showing a decrease in the effector memory population in their CD4+ TIL from the re-REP product followed the same trend in their CD8+ TIL. B) Unlike the CD4+ TIL population, CD8+ TIL showed a similar effector memory phenotype in fresh, thawed and re-REP products. (Note the high standard deviation in the fresh and thawed TIL, which are due to the low effector memory population in M1064T fresh and to no expression in M1061T thawed TIL samples.)
Figure 50B:
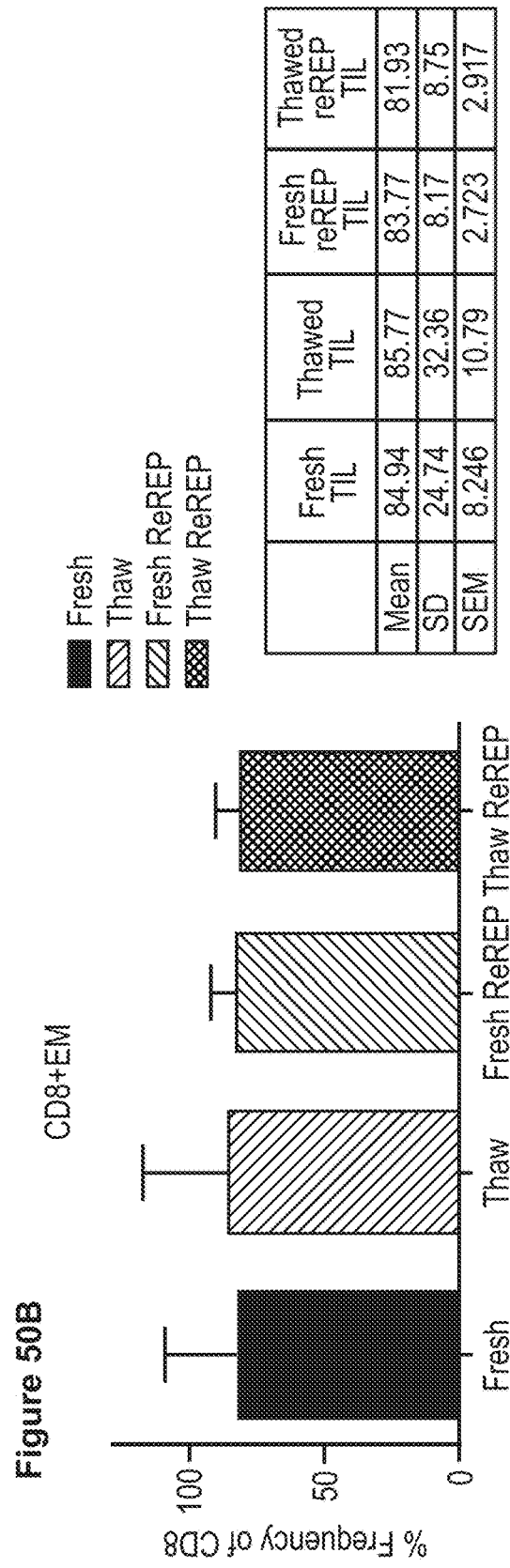
Figure 56A:
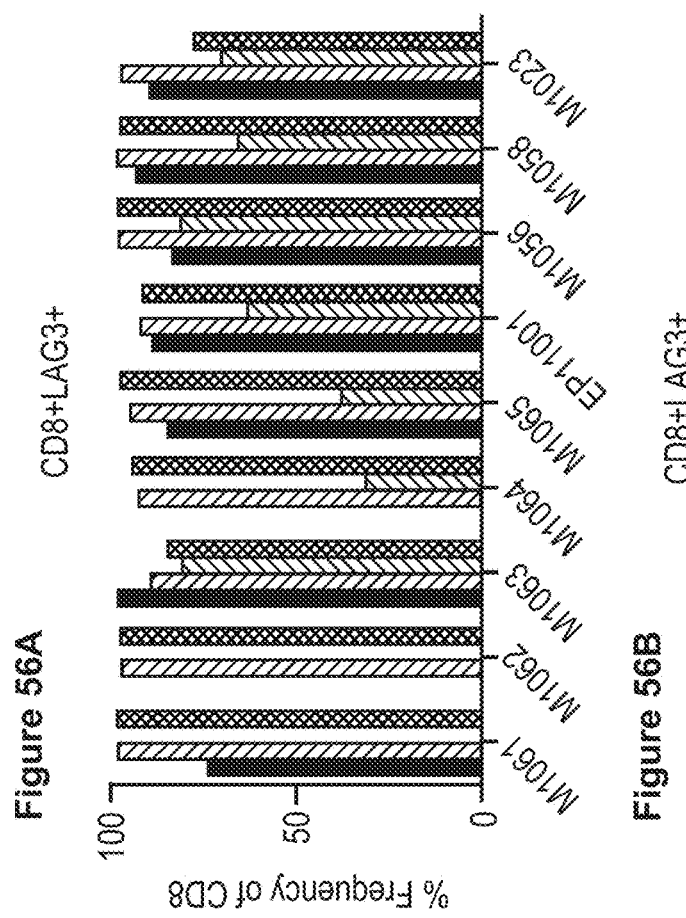
FIG. 56A-56B: CD8+ LAG3+ cells. A) CD8+ LAG3+ expressing TIL showed a modest decrease in the experiments, with the exception of M1063T in which a marked decrease in LAG3 expression was seen in the fresh re-REP TIL. Overall, thawed re-REP TIL showed a 1.5-fold, significant increase compared to fresh re-REP TIL for LAG3 expression (p=0.0154). However, no significant difference was observed between fresh TIL and thawed TIL products (p=0.0884). B) An approximate 30% decrease in LAG3 expression in the CD8+ TIL from fresh re-REP was observed in comparison to thawed TIL product. Both fresh and thawed TIL were comparable to thawed TIL showing a modest increase. (In this figure, M1061T, M1062T and M1064T were omitted as LAG3 expression was not measured in the either the fresh or fresh re-REP TIL samples.)
Figure 56B:
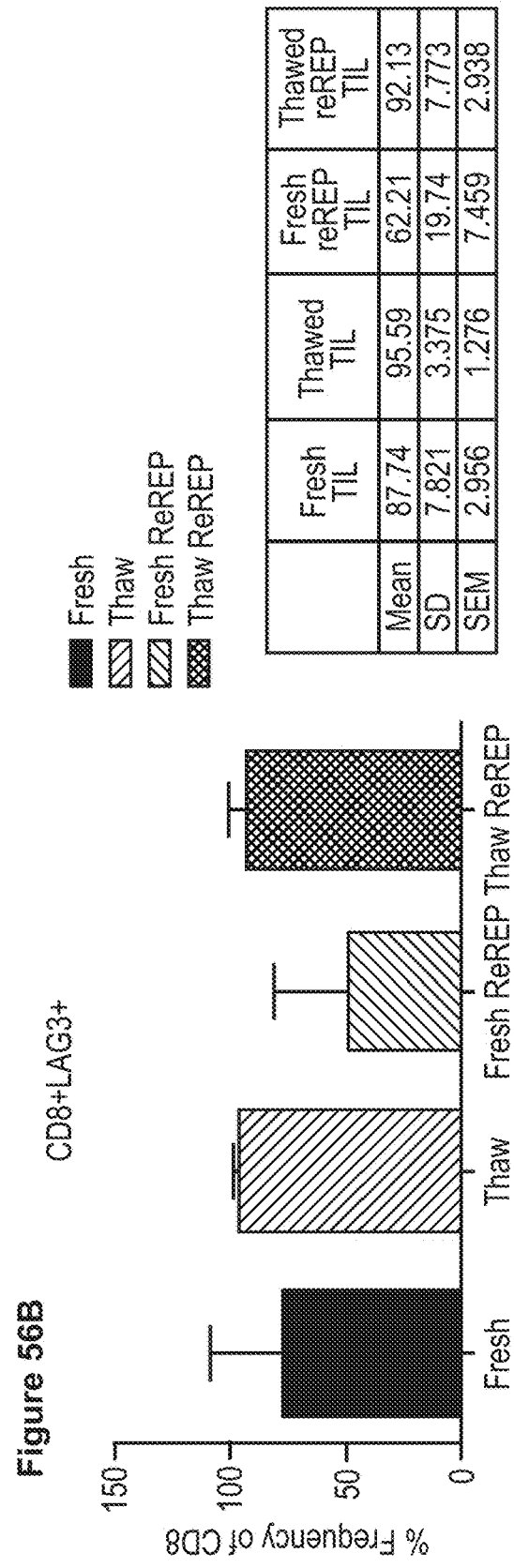

FIG. 49: CD4+EM cells and FIG. 23 CD8+EM cells

| T cell | Markers | M1061 Fresh | M1061 Thawed | M1062 Fresh | M1062 Thawed | M1063 Fresh | M1063 Thawed | M1064 Fresh | M1064 Thawed |
|---|---|---|---|---|---|---|---|---|---|
| CD4 | EM | 90 | n/d | 98.3 | 98.9 | 83.9 | 97.2 | 84.1 | 99.8 |
| CD8 | EM | 89.1 | n/d | 80.6 | 87.9 | 92.4 | 97.8 | 20.8 | 98.8 |

| T cell | Markers | M1061 Fresh Re-REP | M1061 Thawed Re-REP | M1062 Fresh Re-REP | M1062 Thawed Re-REP | M1063 Fresh Re-REP | M1063 Thawed Re-REP | M1064 Fresh Re-REP | M1064 Thawed Re-REP |
|---|---|---|---|---|---|---|---|---|---|
| CD4 | EM | 95.6 | 84.4 | 84.5 | 83.4 | 84.3 | 73.7 | 80.6 | 80.4 |
| CD8 | EM | 97.2 | 87.9 | 90.8 | 82.3 | 82.5 | 72.2 | 74.5 | 73 |

| T cell | Markers | M1065 Fresh | M1065 Thawed | EP11001 Fresh | EP11001 Thawed | M1056 Fresh | M1056 Thawed | M1058 Fresh | M1058 Thawed | M1203 Fresh | M1203 Thawed |
|---|---|---|---|---|---|---|---|---|---|---|---|
| CD4 | EM | 99.4 | 99.4 | 96.7 | 97.4 | 97.1 | 97.8 | 97.4 | 97.6 | 9.62 | 95.3 |
| CD8 | EM | 98.3 | 98.6 | 91.8 | 95.5 | 98.8 | 98.9 | 98.8 | 99.2 | 93.9 | 95.2 |

| T cell | Markers | M1065 Fresh Re-REP | M1065 Thawed Re-REP | EP11001 Fresh Re-REP | EP11001 Thawed Re-REP | M1056 Fresh Re-REP | M1056 Thawed Re-REP | M1058 Fresh Re-REP | M1058 Thawed Re-REP | M1203 Fresh Re-REP | M1203 Thawed Re-REP |
|---|---|---|---|---|---|---|---|---|---|---|---|
| CD4 | EM | 91.7 | 97 | 74.3 | 90.7 | 36.2 | 25.5 | 73.9 | 81.8 | 73.1 | 76.4 |
| CD8 | EM | 91.5 | 96.1 | 83 | 90.8 | 73.2 | 71.9 | 77.1 | 78.2 | 84.1 | 85.1 |

TABLE 50

FIG. 51: CD4+CD28+ cells and FIG. 25 CD8+CD28+ cells

| T cell | Markers | M1061 Fresh | M1061 Thawed | M1062 Fresh | M1062 Thawed | M1063 Fresh | M1063 Thawed | M1064 Fresh | M1064 Thawed |
|---|---|---|---|---|---|---|---|---|---|
| CD4 | CD28+ | 4.6 | 5.85 | 33.2 | 37 | 10.5 | 11.2 | 31.9 | 27.6 |
| CD8 | CD28+ | 30.1 | 34 | 24.5 | 23.1 | 83.8 | 49.3 | 22.5 | 15.5 |

| T cell | Markers | M1061 Fresh Re-REP | M1061 Thawed Re-REP | M1062 Fresh Re-REP | M1062 Thawed Re-REP | M1063 Fresh Re-REP | M1063 Thawed Re-REP | M1064 Fresh Re-REP | M1064 Thawed Re-REP |
|---|---|---|---|---|---|---|---|---|---|
| CD4 | CD28+ | 6.75 | 7.18 | 21.6 | 27.8 | 18.6 | 15 | 23 | 27.6 |
| CD8 | CD28+ | 24.6 | 17.9 | 10 | 6.4 | 28.6 | 18.9 | 15.7 | 11 |

| T cell | Markers | M1065 Fresh | M1065 Thawed | EP11001 Fresh | EP11001 Thawed | M1056 Fresh | M1056 Thawed | M1058 Fresh | M1058 Thawed | M1203 Fresh | M1203 Thawed |
|---|---|---|---|---|---|---|---|---|---|---|---|
| CD4 | CD28+ | 41.7 | 38.2 | 63.2 | 59.8 | 3.97 | 3.29 | 12.2 | 17.5 | 8.27 | 7.48 |
| CD8 | CD28+ | 13.4 | 8.52 | 14.5 | 12 | 53 | 54.4 | 56.5 | 62.1 | 76.5 | 80.8 |

| T cell | Markers | M1065 Fresh Re-REP | M1065 Thawed Re-REP | EP11001 Fresh Re-REP | EP11001 Thawed Re-REP | M1056 Fresh Re-REP | M1056 Thawed Re-REP | M1058 Fresh Re-REP | M1058 Thawed Re-REP | M1203 Fresh Re-REP | M1203 Thawed Re-REP |
|---|---|---|---|---|---|---|---|---|---|---|---|
| CD4 | CD28+ | 12.3 | 15.2 | 13.3 | 20 | 6.22 | 9.29 | 12.3 | 16.5 | 15.4 | 17.9 |
| CD8 | CD28+ | 6.9 | 2.43 | 2.07 | 3.75 | 24 | 34 | 27 | 36.9 | 42 | 43.9 |

TABLE 51

FIG. 53: CD4+PD-1+ cells and FIG. 27 CD8+PD-1+ cells

| T cell | Markers | M1061 | | M1062 | | M1063 | | M1064 | |
|---|---|---|---|---|---|---|---|---|---|
| | | Fresh | Thawed | Fresh | Thawed | Fresh | Thawed | Fresh | Thawed |
| CD4 | PD-1+ | 48.5 | nd | nd | nd | 77 | 40.6 | nd | 22.4 |
| CD8 | PD-1+ | 37.1 | nd | nd | nd | 56 | 24.6 | nd | 14 |

| T cell | Markers | M1061 | | M1062 | | M1063 | | M1064 | |
|---|---|---|---|---|---|---|---|---|---|
| | | Fresh Re-REP | Thawed Re-REP | Fresh Re-REP | Thawed Re-REP | Fresh Re-REP | Thawed Re-REP | Fresh Re-REP | Thawed Re-REP |
| CD4 | PD-1+ | 36.8 | 34.2 | 15.7 | 26.7 | 43.9 | 66 | 32.4 | 14.5 |
| CD8 | PD-1+ | 40.4 | 35.3 | 6.3 | 6.21 | 18 | 20.4 | 35.6 | 23.2 |

| T cell | Markers | M1065 | | EP11001 | | M1056 | | M1058 | | M1203 | |
|---|---|---|---|---|---|---|---|---|---|---|---|
| | | Fresh | Thawed | Fresh | Thawed | Fresh | Thawed | Fresh | Thawed | Fresh | Thawed |
| CD4 | PD-1+ | 7.87 | 7.23 | 33.3 | 28.2 | 33.9 | 32.8 | 41.7 | 38 | 22.7 | 23.8 |
| CD8 | PD-1+ | 1.61 | 0.72 | 19.2 | 12.5 | 23.8 | 24.7 | 78.4 | 59.8 | 42.6 | 36.1 |

| T cell | Markers | M1065 | | EP11001 | | M1056 | | M1058 | | M1203 | |
|---|---|---|---|---|---|---|---|---|---|---|---|
| | | Fresh Re-REP | Thawed Re-REP | Fresh Re-REP | Thawed Re-REP | Fresh Re-REP | Thawed Re-REP | Fresh Re-REP | Thawed Re-REP | Fresh Re-REP | Thawed Re-REP |
| CD4 | PD-1+ | 22.4 | 15.5 | 40.9 | 33.4 | 56 | 51.3 | 40.3 | 32.5 | 18.9 | 27.3 |
| CD8 | PD-1+ | 6.49 | 5.73 | 29.8 | 34.6 | 18.9 | 15.2 | 68.6 | 47 | 28.9 | 36.1 |

TABLE 52

Figure 29:
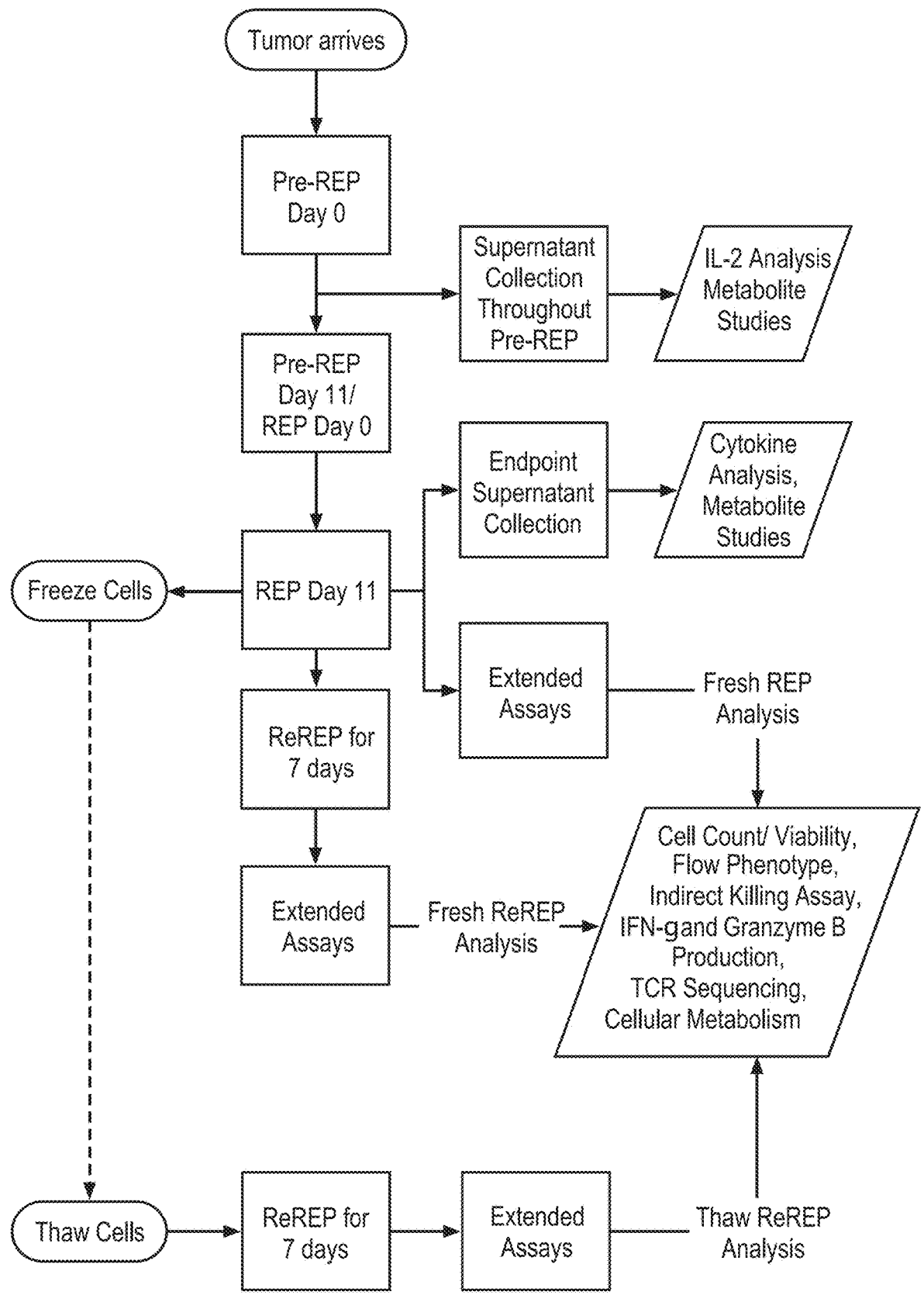
FIG. 29: Process Flow Chart on Process 2A Data Collection Plan
Figure 30:
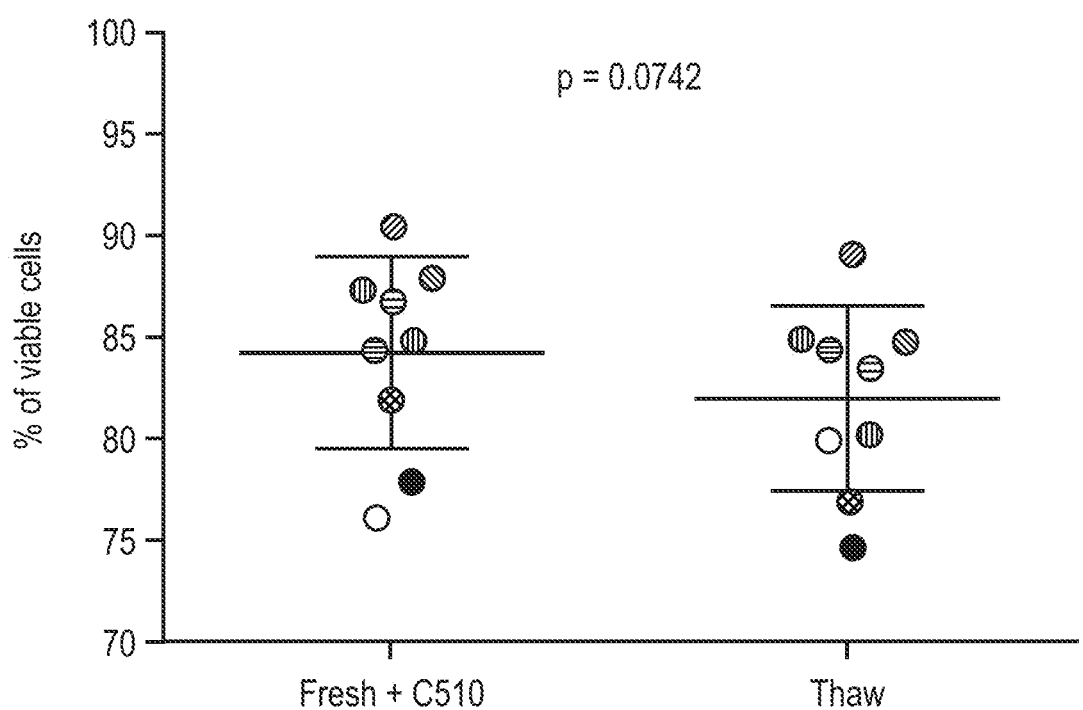
FIG. 30: Viability of fresh vs. thawed TIL

FIG. 55: CD4+LAG3+ cells and FIG. 29 CD8+LAG3+ cells

| T cell | Markers | M1061 | | M1062 | | M1063 | | M1064 | |
|---|---|---|---|---|---|---|---|---|---|
| | | Fresh | Thawed | Fresh | Thawed | Fresh | Thawed | Fresh | Thawed |
| CD4 | LAG3+ | 16.8 | nd | nd | nd | 93.5 | 37.3 | nd | 6.8 |
| CD8 | LAG3+ | 74 | nd | nd | nd | 98.4 | 81.5 | nd | 31.8 |

| T cell | Markers | M1061 | | M1062 | | M1063 | | M1064 | |
|---|---|---|---|---|---|---|---|---|---|
| | | Fresh Re-REP | Thawed Re-REP | Fresh Re-REP | Thawed Re-REP | Fresh Re-REP | Thawed Re-REP | Fresh Re-REP | Thawed Re-REP |
| CD4 | LAG3+ | 68.3 | 73.1 | 35.2 | 56.9 | 26.9 | 27.3 | 52.6 | 64 |
| CD8 | LAG3+ | 98.3 | 98.7 | 97.1 | 97.7 | 89.6 | 85.1 | 92.8 | 94.7 |

| T cell | Markers | M1065 | | EP11001 | | M1056 | | M1058 | | M1203 | |
|---|---|---|---|---|---|---|---|---|---|---|---|
| | | Fresh | Thawed | Fresh | Thawed | Fresh | Thawed | Fresh | Thawed | Fresh | Thawed |
| CD4 | LAG3+ | 47.2 | 30.5 | 35.5 | 20.1 | 25 | 27.4 | 48.6 | 38 | 14.5 | 7.65 |
| CD8 | LAG3+ | 85.3 | 38.7 | 89.6 | 64.2 | 83.4 | 81.9 | 93.2 | 66.3 | 90.3 | 71.1 |

| T cell | Markers | M1065 | | EP11001 | | M1056 | | M1058 | | M1203 | |
|---|---|---|---|---|---|---|---|---|---|---|---|
| | | Fresh Re-REP | Thawed Re-REP | Fresh Re-REP | Thawed Re-REP | Fresh Re-REP | Thawed Re-REP | Fresh Re-REP | Thawed Re-REP | Fresh Re-REP | Thawed Re-REP |
| CD4 | LAG3+ | 65.8 | 68.2 | 40.9 | 46 | 44.1 | 39.1 | 52.1 | 51 | 48.5 | 17.7 |
| CD8 | LAG3+ | 95.4 | 97.8 | 92.4 | 92.5 | 97.5 | 98.4 | 98.2 | 98.3 | 97.7 | 78.1 |

TABLE 53

Figure 31:
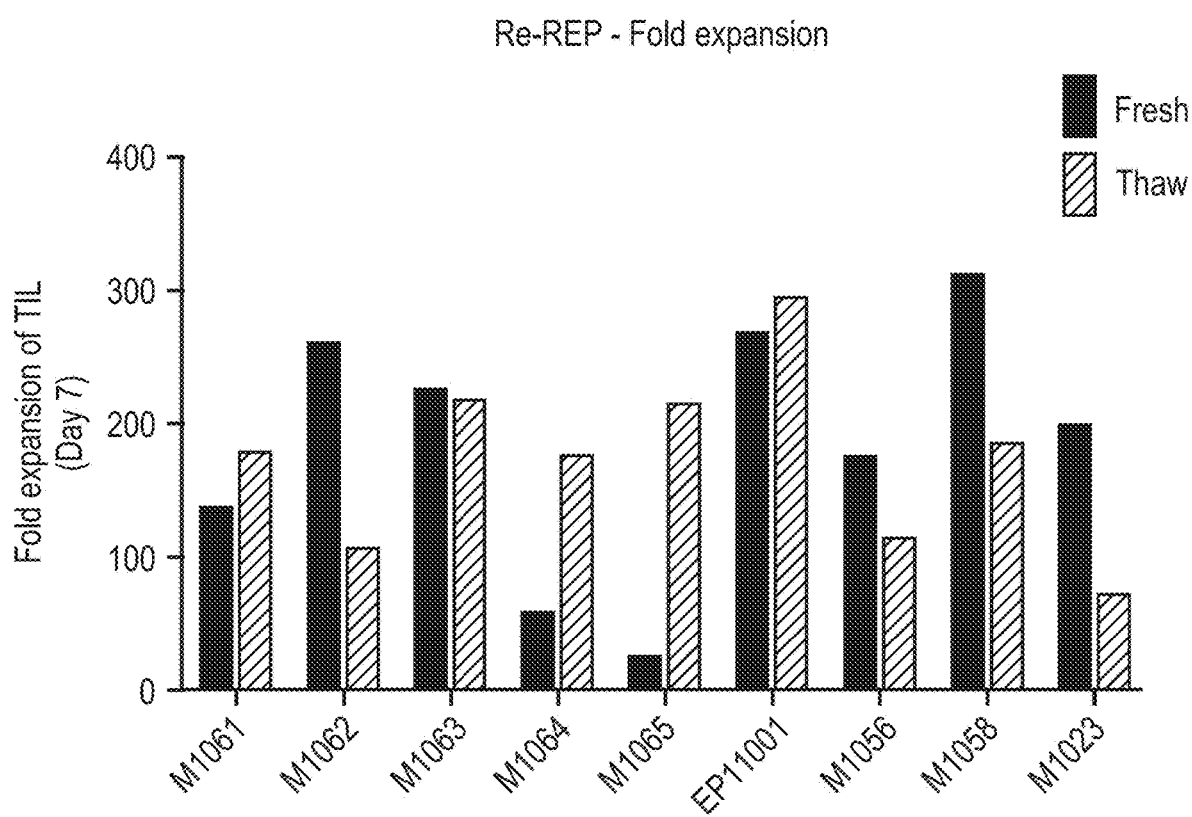
FIG. 31: Expansion of fresh and thawed TIL in re-REP culture
Figure 33A:
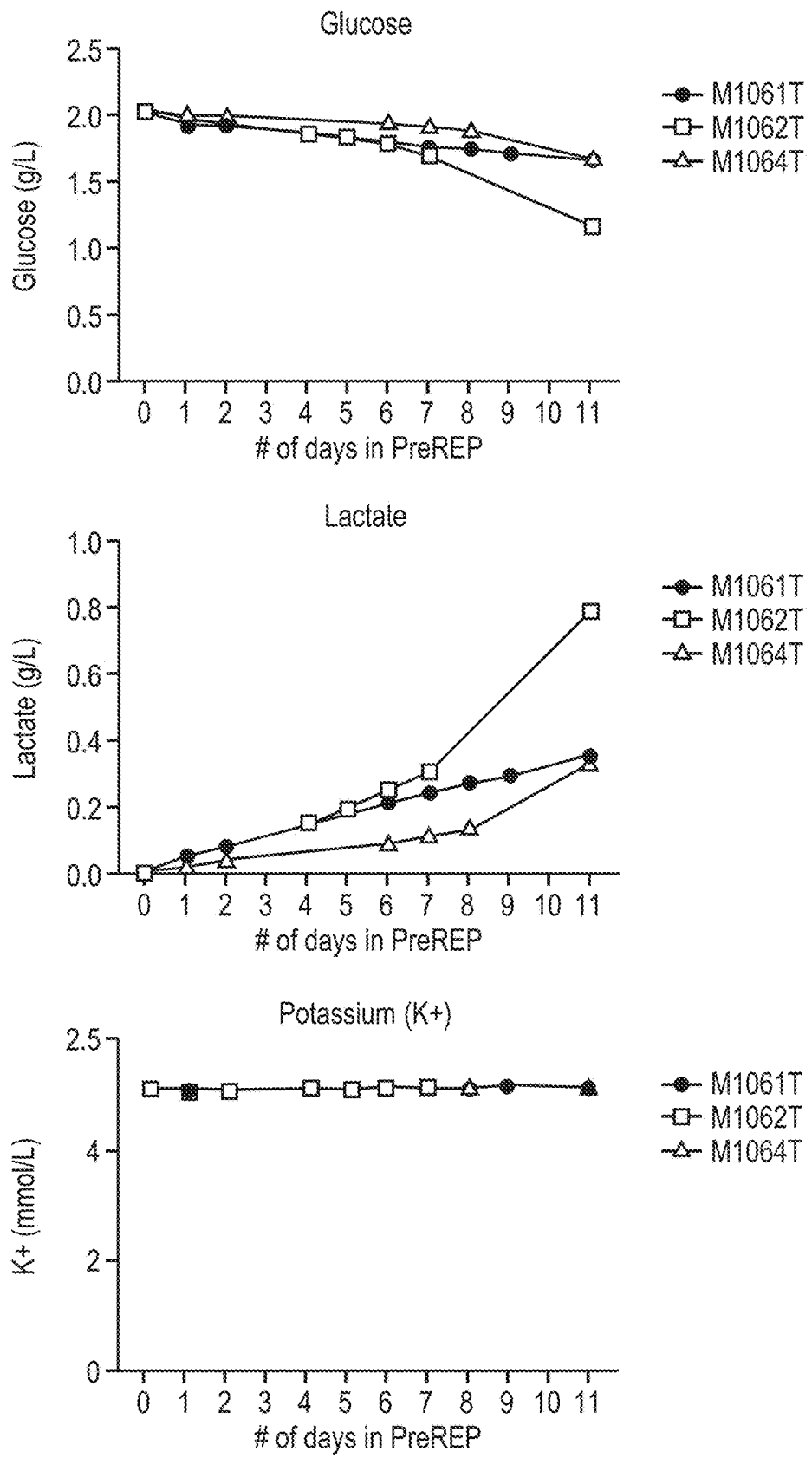
FIG. 33A-33B: Metabolite analysis of process 2A pre-REP TIL.
Figure 33B:
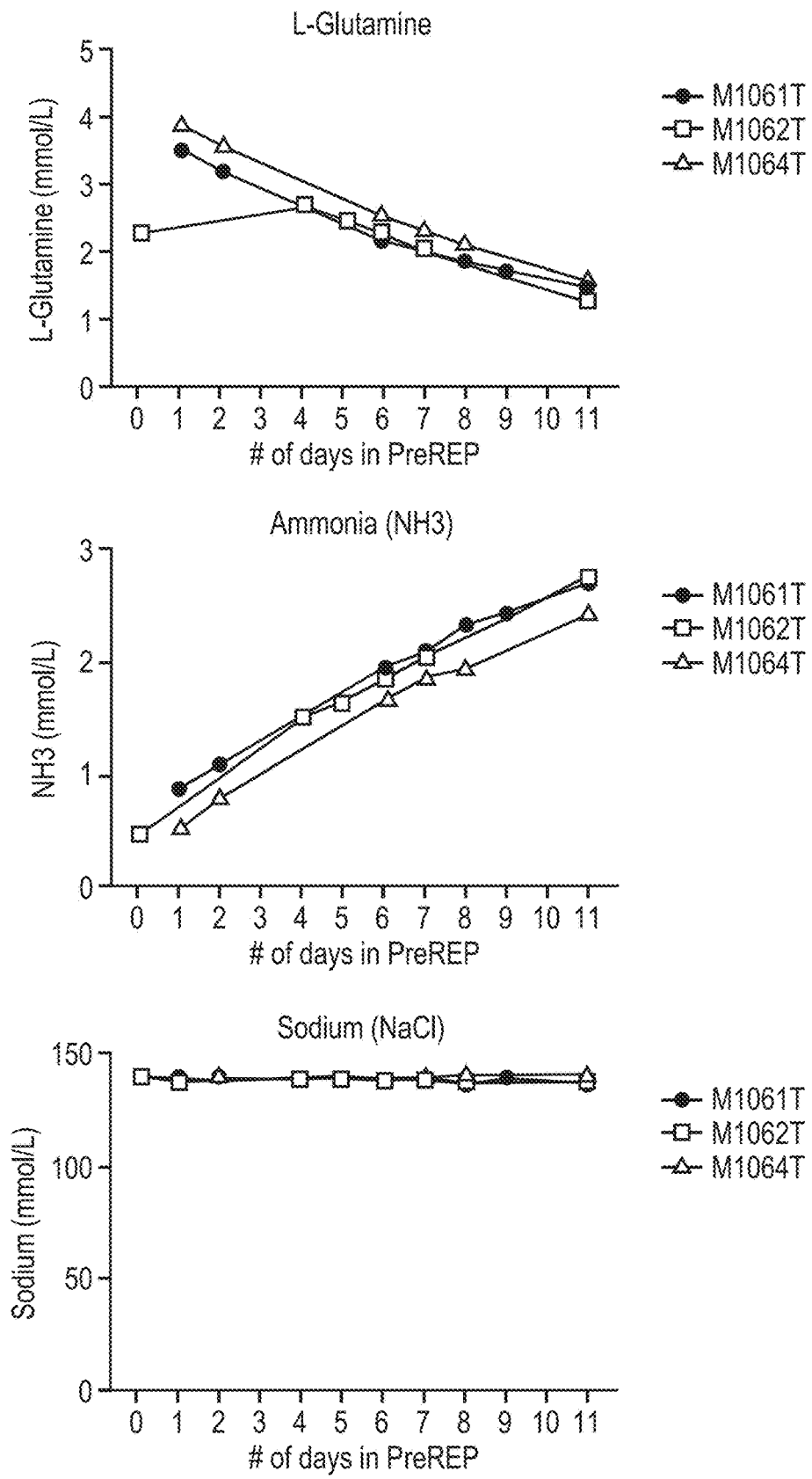
Figure 34:
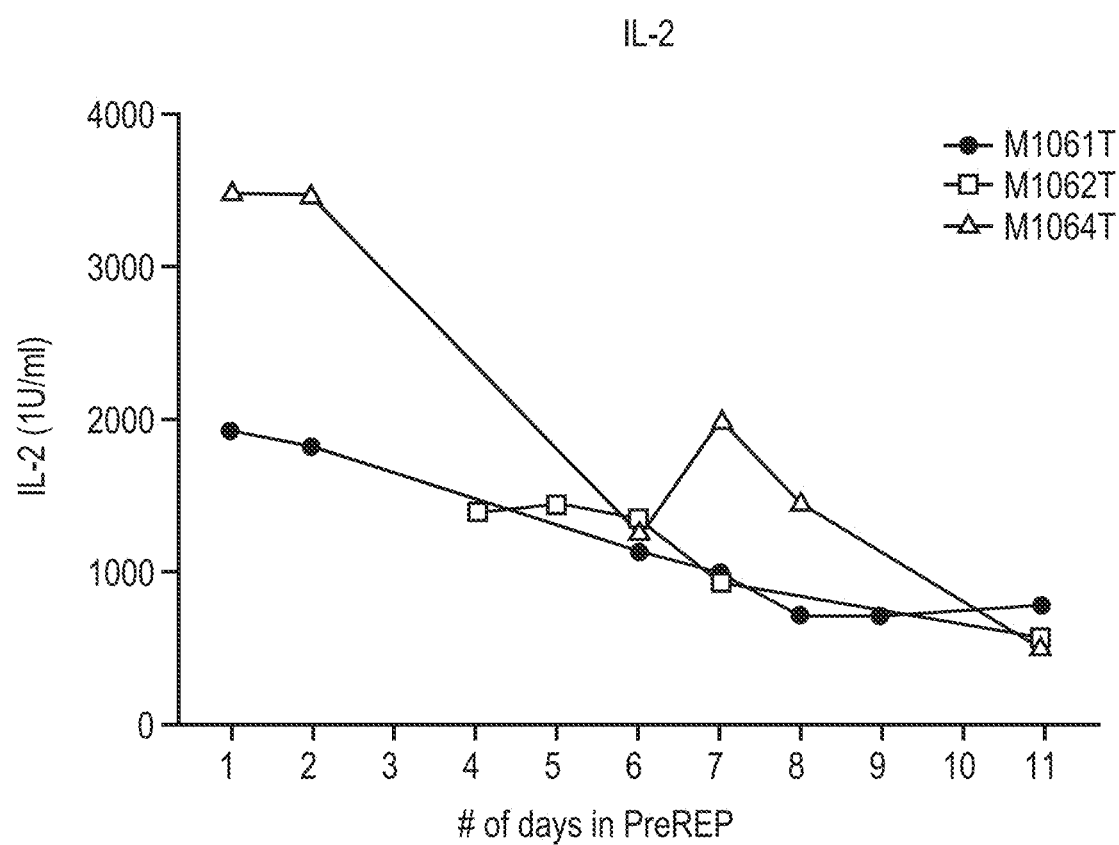
FIG. 34: Quantification of IL-2 in process 2A pre-REP TIL cell culture.

| FIG. 57: CD4+TIM-3+ cells and FIG. 31 CD8+TIM-3+ cells | | | | | | | | | |
|---|---|---|---|---|---|---|---|---|---|
| | | M1061 | | M1062 | | M1063 | | M1064 | |
| | | Fresh | Thawed | Fresh | Thawed | Fresh | Thawed | Fresh | Thawed |
| CD4 | TIM3+ | 89.7 | nd | nd | nd | 98.3 | 87.6 | nd | 43.2 |
| CD8 | TIM3+ | 99 | nd | nd | nd | 99.4 | 88.1 | nd | 47 |

| | | M1061 | | M1062 | | M1063 | | M1064 | |
|---|---|---|---|---|---|---|---|---|---|
| T cell | Markers | Fresh Re-REP | Thawed Re-REP | Fresh Re-REP | Thawed Re-REP | Fresh Re-REP | Thawed Re-REP | Fresh Re-REP | Thawed Re-REP |
| CD4 | TIM3+ | 95.3 | 98 | 94.5 | 96.9 | 90.8 | 90.2 | 94.2 | 82.6 |
| CD8 | TIM3+ | 98.9 | 98.9 | 97.3 | 96.7 | 97.1 | 97.7 | 98.2 | 95.7 |

| | | M1065 | | EP11001 | | M1056 | | M1058 | | M1203 | |
|---|---|---|---|---|---|---|---|---|---|---|---|
| T cell | Markers | Fresh | Thawed | Fresh | Thawed | Fresh | Thawed | Fresh | Thawed | Fresh | Thawed |
| CD4 | TIM3+ | 95 | 78.8 | 96.9 | 91.5 | 96.4 | 92.5 | 88.7 | 80.1 | 89.9 | 82.3 |
| CD8 | TIM3+ | 96.9 | 50.6 | 98.8 | 83 | 98.3 | 92.9 | 96.5 | 73.6 | 98.2 | 88.5 |

| | | M1065 | | EP11001 | | M1056 | | M1058 | | M1203 | |
|---|---|---|---|---|---|---|---|---|---|---|---|
| T cell | Markers | Fresh Re-REP | Thawed Re-REP | Fresh Re-REP | Thawed Re-REP | Fresh Re-REP | Thawed Re-REP | Fresh Re-REP | Thawed Re-REP | Fresh Re-REP | Thawed Re-REP |
| CD4 | TIM3+ | 91.1 | 95.4 | 94.3 | 98.7 | 74 | 75.4 | 86.5 | 87.3 | 94.4 | 90.6 |
| CD8 | TIM3+ | 94.9 | 96.5 | 96.3 | 98.3 | 98 | 99 | 97.3 | 98.6 | 99 | 97.7 |

TABLE 54

Figure 61A:
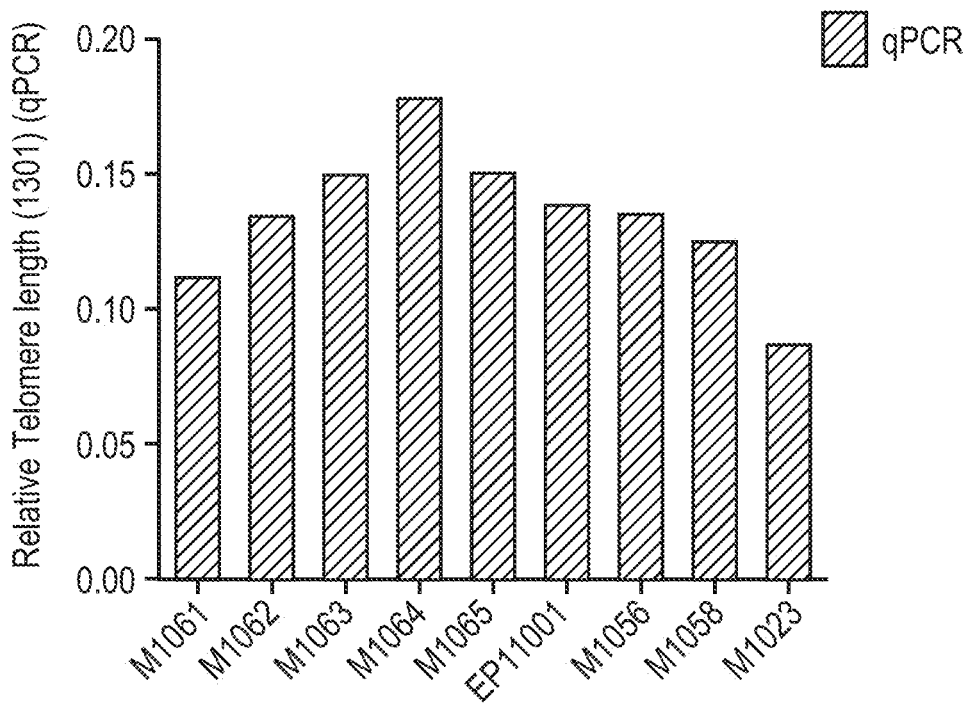
FIG. 61A-61B: Flow-FISH technology was used to measure average length of Telomere repeat in 9 post-REP Process 2A thawed TIL products. A) Data represents the telomere length measured by qPCR comparing TIL to 1301 cells B) Data shows the telomere length measured by Flow Fish Assay of TIL compared to 1301 cells. Data used for graphs are provided in a table format (Tables 25) in the appendix section 10. Overall, there was a rough similarity in the patterns of the results of the two telomere length assays, but experiments will continue to determine which method more accurately reflects the actual telomere length of the TIL. This technique could be applied to future clinical samples to determine a relationship between telomere length and patient response to TIL therapy.
Figure 61B:
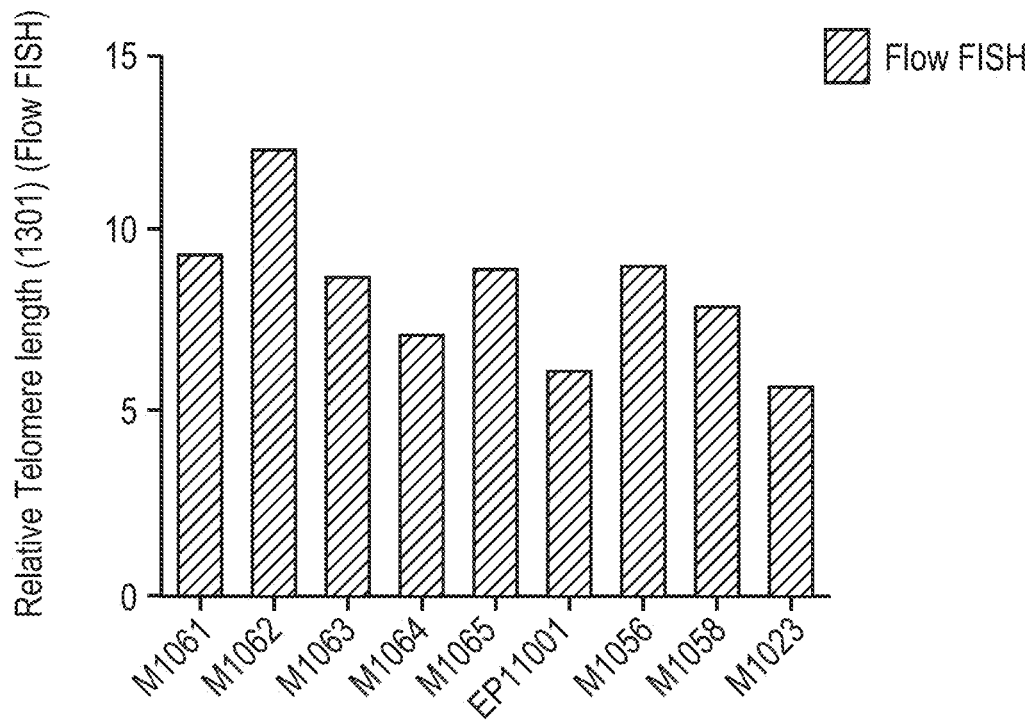
Figure 63A:
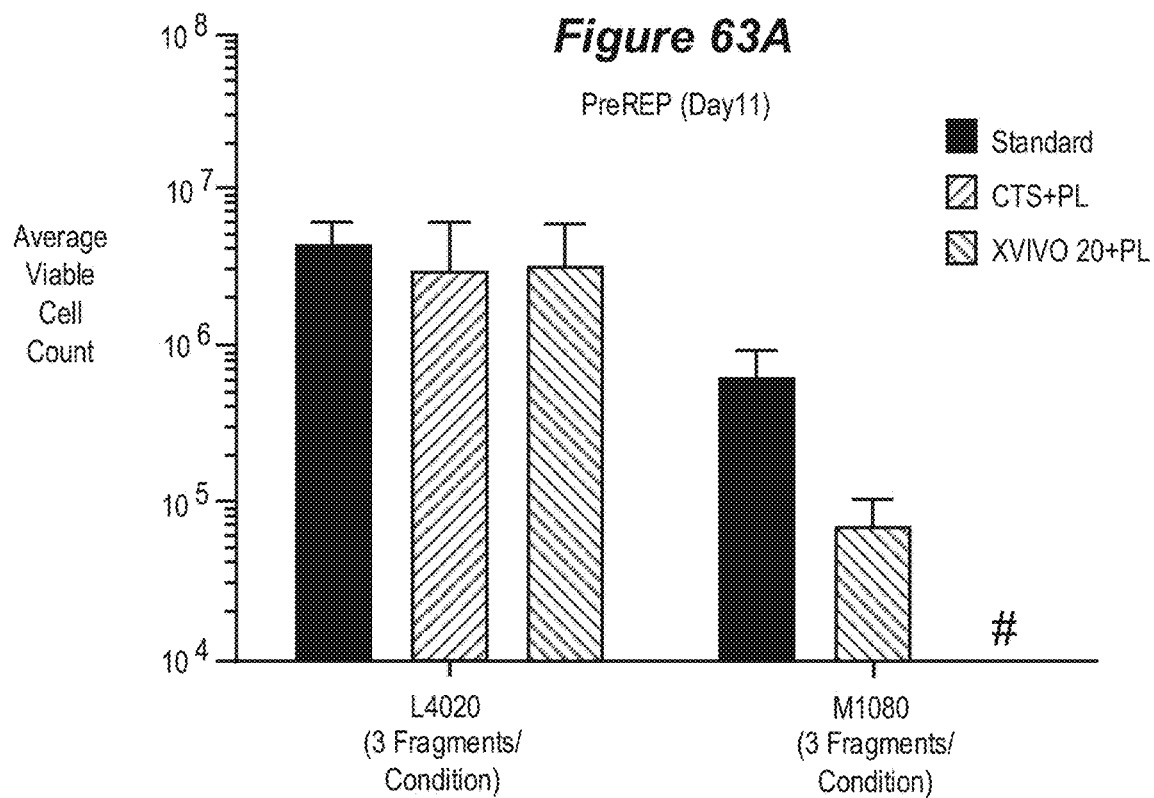
FIG. 63A-63B: Selection of Serum Free Media purveyor (Platelet Lysate serum). Each fragment were cultured in single well of G-Rex 24 well plate in triplicates. On Day 11, REP were initiated using 4e5 TIL with 10e6 Feeders to mimic 2A process. A) Bar graph showing average viable cell count recorded on Day 11 (preREP) for each conditions. B) Bar graph displaying average viable cell count recorded on Day 22 (postREP). P value were calculated using student 't'test. *P<0.05, P<0.01, *P<0.001 respectively. '#' Not enough tumor fragments.
Figure 63B:
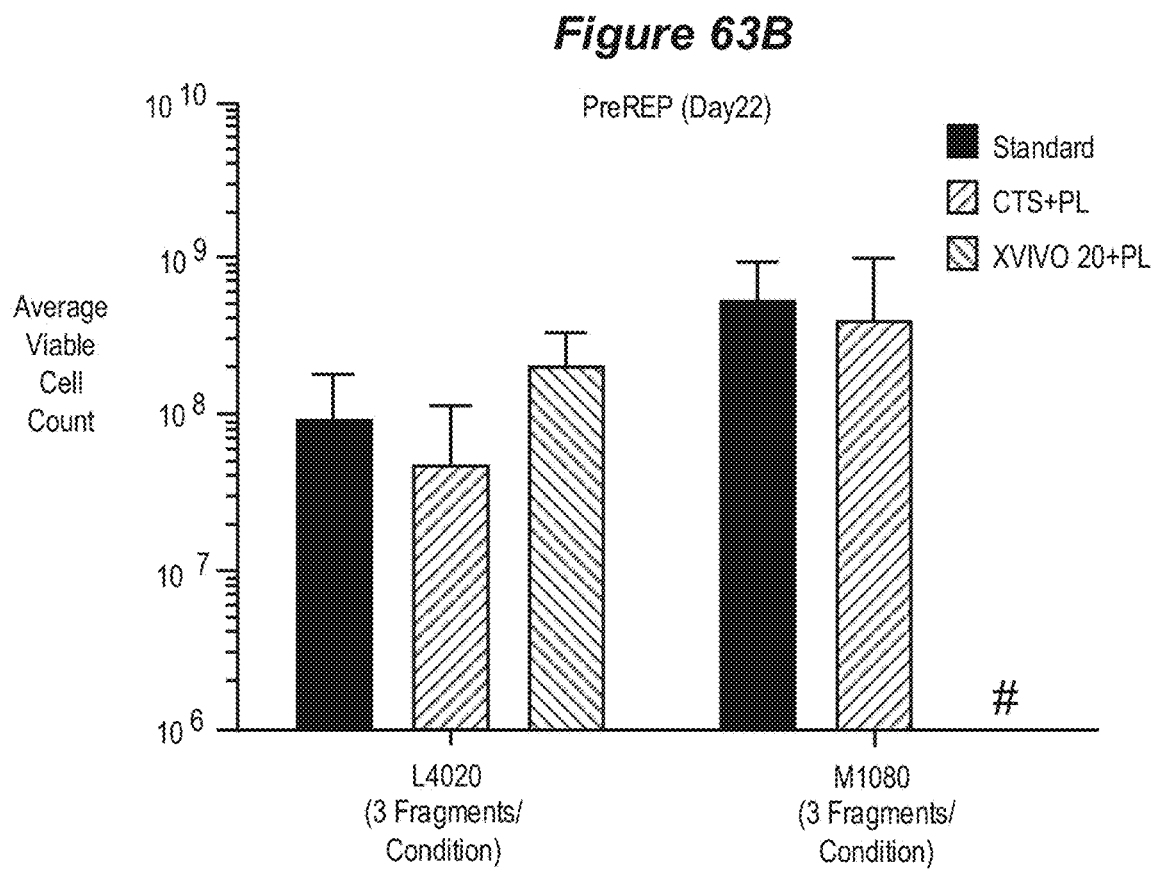
Figure 64A:
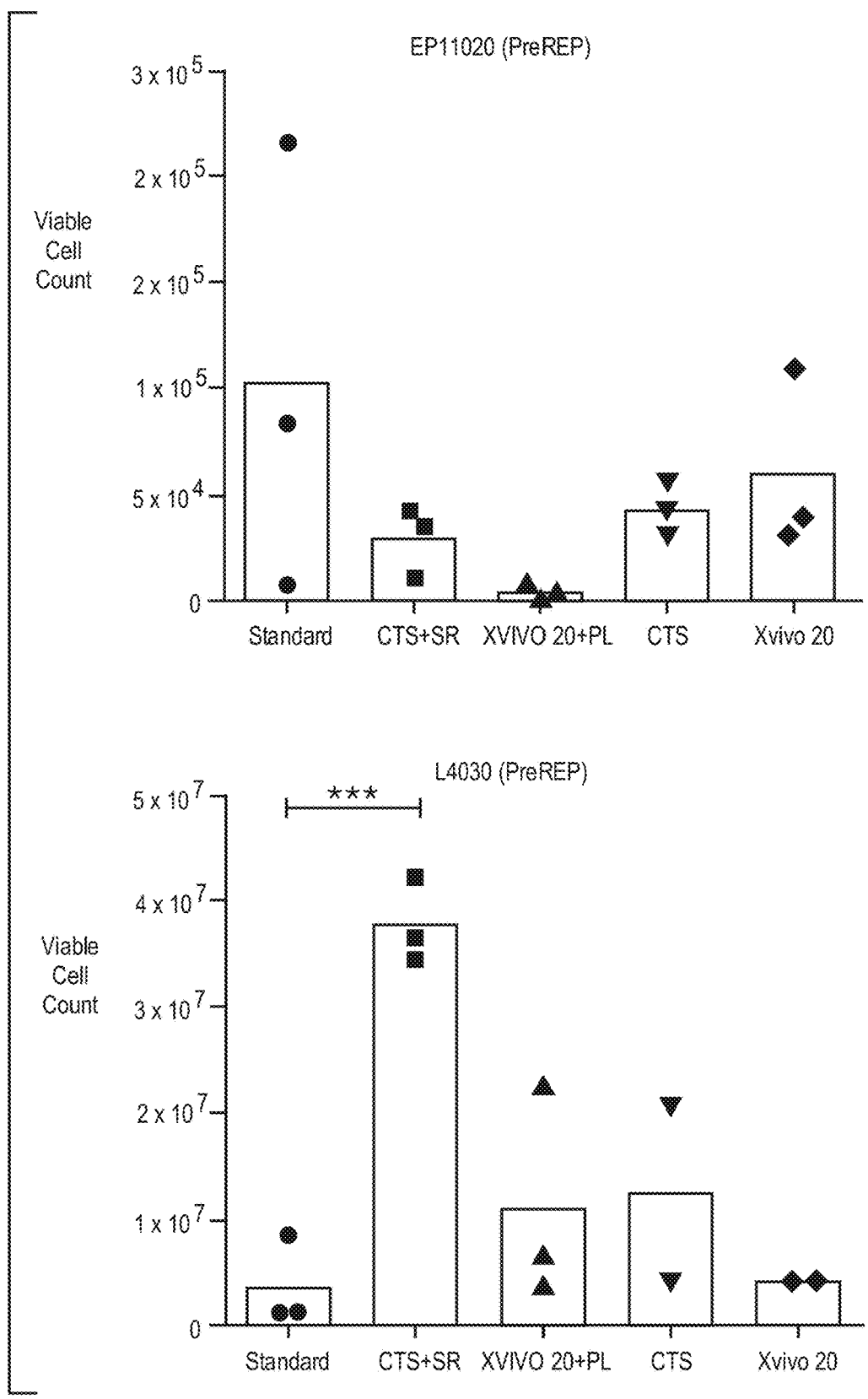
FIG. 64A-64B: Compare the efficacy of CTS Optimizer with standard condition using mini scale 2A process (G-Rex 5M). Two fragments/G-Rex 5M were cultured in triplicates, REP were initiated using $2^6$ TIL with $50^6$ Feeders to mimic 2A process. Bar presented above were average viable cell count obtained on Day 11 (A) or Day 22 (B).
Figure 64A:
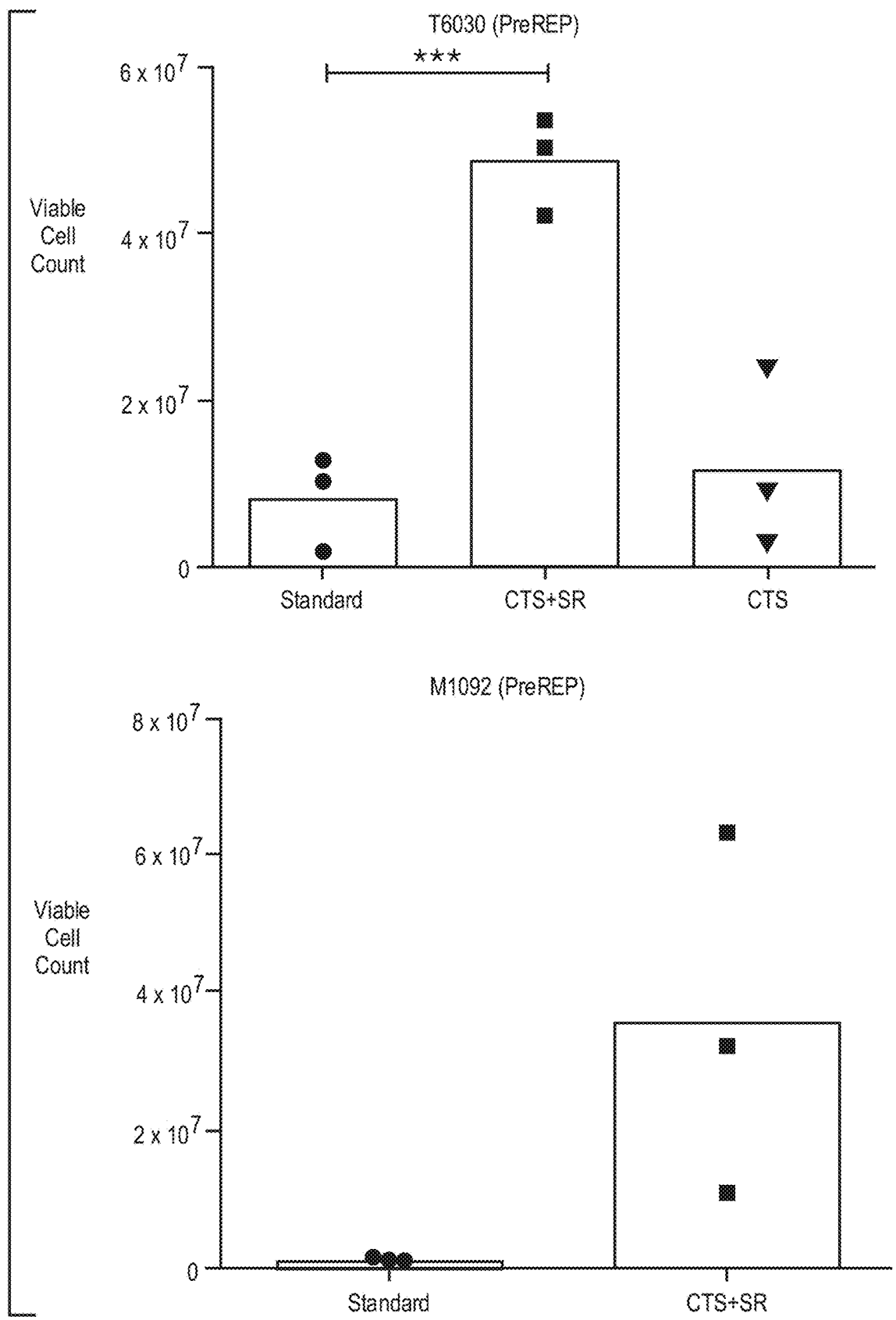
Figure 64B:
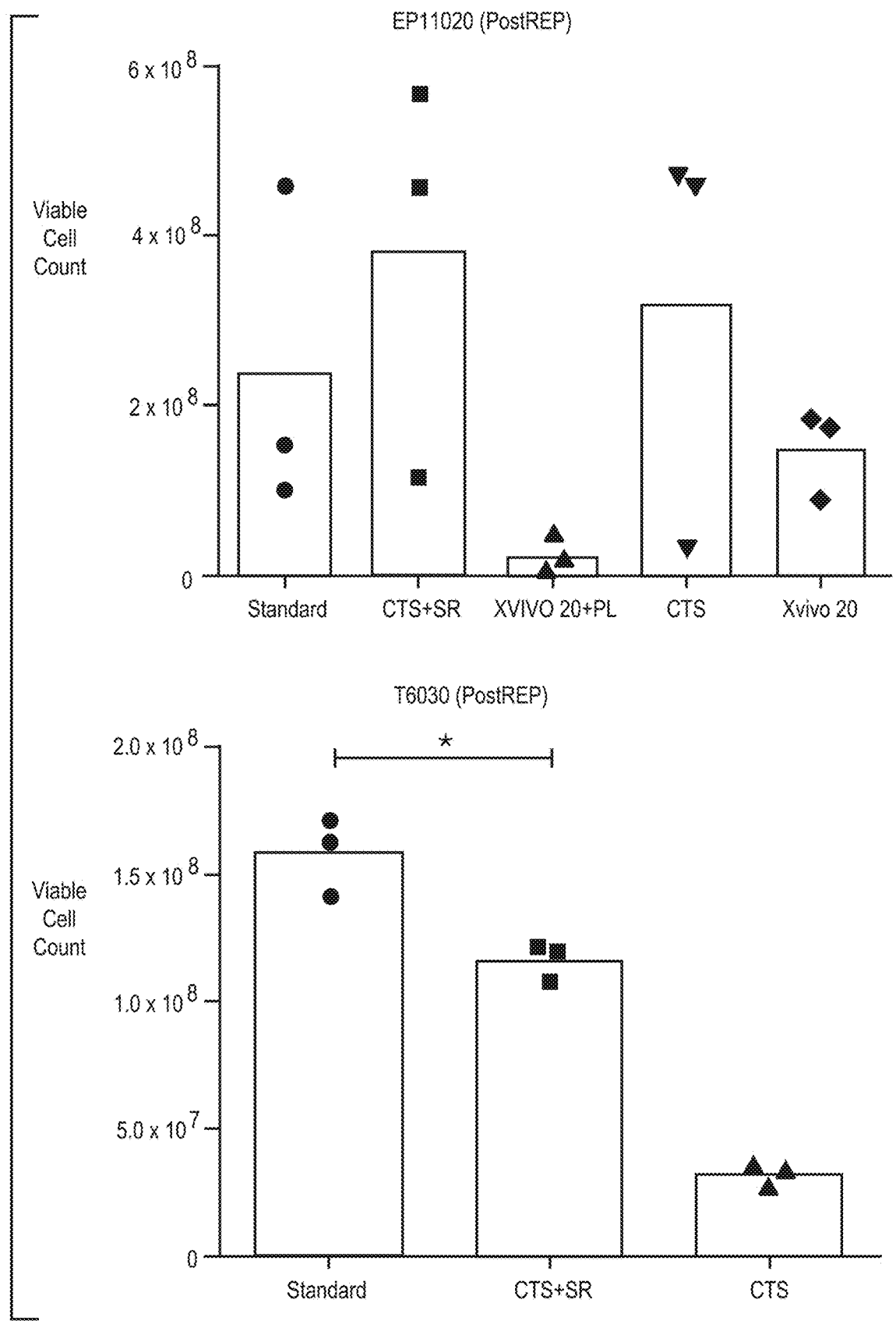
Figure 64B:
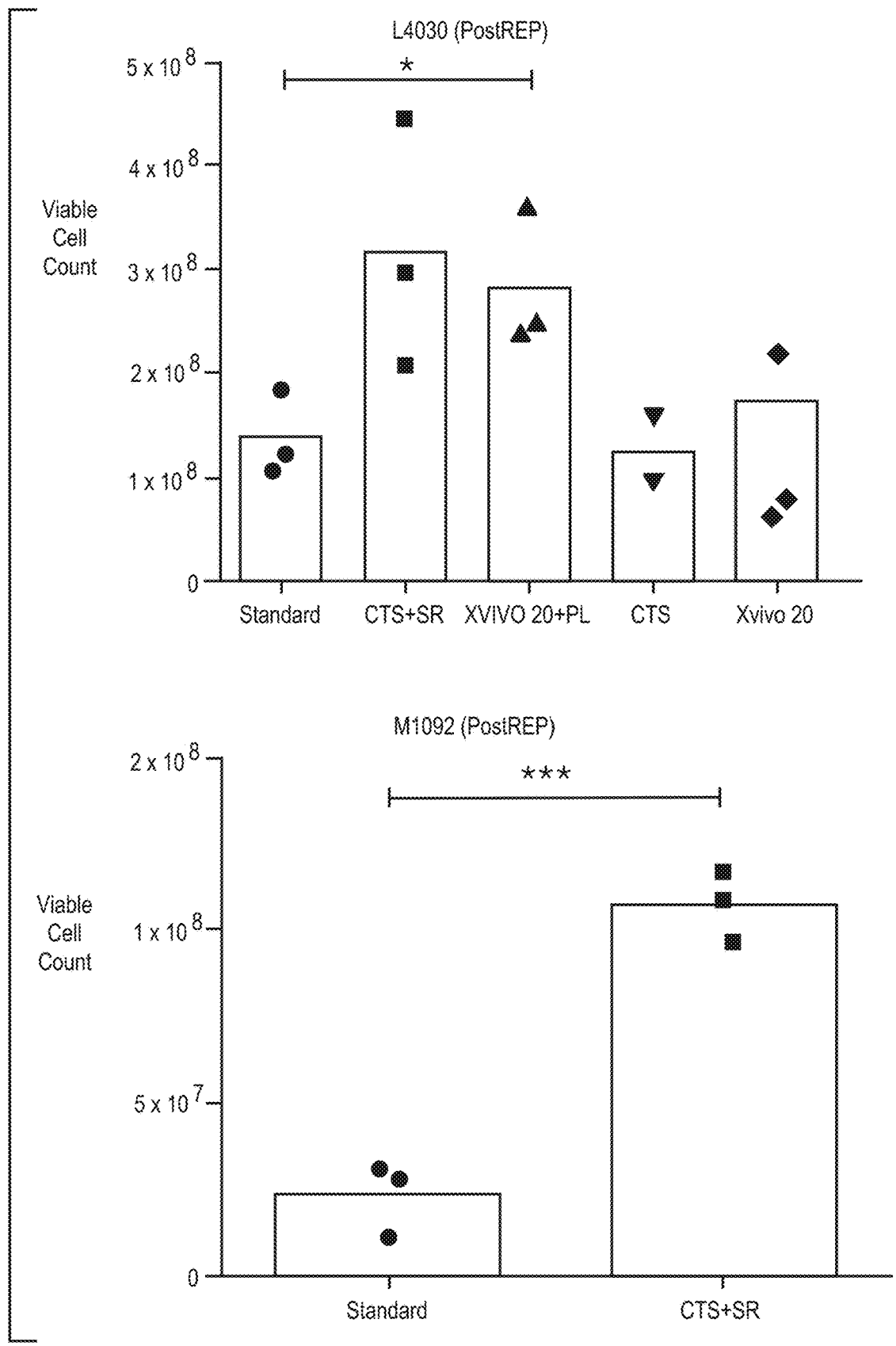
Figure 65A:
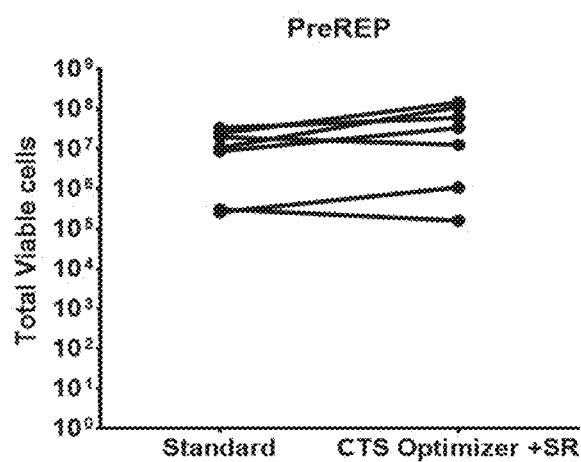
Figure 65B:
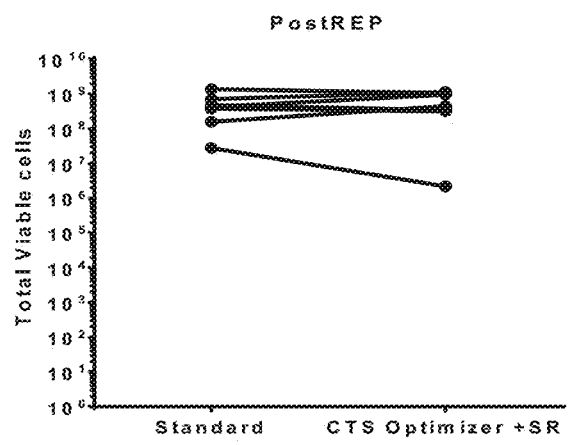

| FIG. 61: qPCR and Flow-FISH determination of telomere length repeat | | | | | | | | | |
|---|---|---|---|---|---|---|---|---|---|
| Tumor ID | M1061 | M1062 | M1063 | M1064 | M1065 | EP11001 | M1056 | M1058 | M1023 |
| qPCR | 0.111878 | 0.135842 | 0.149685 | 0.179244 | 0.151774 | 0.137738 | 0.134904 | 0.124137 | 0.086569 |
| Flow-FISH | 9.330236 | 1215041 | 8.782231 | 7.174627 | 8.961553 | 6112918 | 9.010615 | 7.944534 | 5.766692 |

Example 20: Novel Cryopreserved Tumor Infiltrating Lymphocytes (LN-144) Administered to Patients with Metastatic Melanoma Novel cryopreserved tumor infiltrating lymphocytes (LN-144) administered to patients with metastatic melanoma demonstrates efficacy and tolerability in a multicenter Phase 2 clinical trial Introduction The safety and efficacy of adoptive cell therapy (ACT) with non-cryopreserved tumor infiltrating lymphocytes (TIL) has been studied in hundreds of patients with metastatic melanoma. This multicenter clinical trial was initiated with centrally manufactured TILs (LN-144) as non-cryopreserved and cryopreserved infusion products. Our novel manufacturing process for the non-cryopreserved LN-144 is used in Cohort 1, and a shortened 3 weeks, cryopreserved LN-144 is used in Cohort 2. The Cohort 2 manufacturing offers a significantly shorter process, coupled with a cryopreserved TIL product which allows for flexibility of patient scheduling and dosing. The shorter manufacturing process reduces the wait time for the patient to receive their TIL product and cryopreservation adds convenience to logistics and delivery to the clinical sites.

Methods:

C-144-01 is a prospective, multicenter study evaluating metastatic melanoma patients who receive LN-144. Following a non-myeloablative lymphodepletion with Cy/Flu pre-conditioning regimen, patients receive a single infusion of LN-144 followed by the administration of IL-2 (600,000 IU/kg) up to 6 doses. Patients are evaluated for objective response as a primary endpoint for up to 24 months.

Results:

We characterize the cryopreserved LN-144 administered to a second cohort of patients, Cohort 2 (N=10) following the same pre- and post-TIL infusion treatment regimen as used for Cohort 1.

Cohort 2 patients were heavily pretreated with increased number of prior lines with all patients having anti-CTLA-4 and anti-PD-1 therapies, and larger tumor burden (mean SOD: 15.3, 10.9 cm for Cohorts 2, 1). Median number of prior systemic therapies is 4, 3 for Cohorts 2, 1, respectively. An initial analysis of safety data demonstrates comparable tolerability of cryopreserved LN-144. The safety profile for Cohort 1 patients receiving the non-cryopreserved LN-144 continues to be acceptable for this late stage patient population. The most common TEAEs observed in both cohorts by frequency are nausea, anaemia, febrile neutropenia, neutrophil count decreased, platelet count decreased. Early review of efficacy data indicates anti-tumor activity, including PR, to the TIL therapy observed in patients treated in Cohort 2.

Conclusions

This represents the first clinical trial in a multicenter setting with centrally manufactured TIL assessing a novel process for cryopreserved autologous product with a significantly shorter process (approximately 3 weeks). Preliminary results indicate the cryopreserved LN-144 as a safe and tolerable therapeutic option for patients with metastatic melanoma who've failed multiple prior therapies, including checkpoint inhibitors. The cryopreserved LN-144 provides greater flexibility for patients and caregivers and allows for more immediate treatment for patients with such high unmet medical need. NCT02360579.

Example 21: Evaluation of Serum-Free Media for Use in the 2A Process

This example provides data showing the evaluation of the efficacy of serum-free media as a replacement for the standard CM1, CM2, and CM4 media that is currently used in the 2A process. This study tested efficacy of available serum-free media (SFM) and serum free alternatives as a replacement in three phases;

Phase –1: Compared the efficacy of TIL expansion (n=3) using standard vs CTS Optimizer or Prime T CDM or Xvivo-20 serum free media with or without serum replacement or platelet lysate.

Phase-2: Tested the candidate serum free media condition in mini-scale 2A process using G-Rex 5M (n=3).

Background Information

Though the current media combination used in Pre and Post REP culture has proven to be effective, REP failures may be occurred with the AIM-V. If an effective serum-free alternative were identified, it would be make the process more straight-forward and simple to be performed in CMOs by reducing the number of media types used from 3 to 1. Additionally, SFM reduces the chance of adventitious disease by eliminating the use of human serum. This example provides data that showed supports the use of serum free media in the 2A processes.

Abbreviations

μl microliter
CM1,2,4 Complete Media 1,2,4
CTS OpTimizer SFM Cell Therapy System OpTimizer Serum Free Media
g Grams
Hr Hour
IFU Instructions for Use
IL-2 Interleukin-2 Cytokine
Min Minute
mL Milliliter
° C. degrees Celsius
PreREP Pre-Rapid Expansion Protocol
REP Rapid Expansion Protocol
RT Room Temperature
SR Serum Replacement
TIL Tumor Infiltrating Lymphocytes Experiment Design The Pre-REPs and REPs were initiated as mentioned in LAB-008. The overview of this 3 phases of experiment is shown FIG. 150.

As provide in FIG. 150, the project was intimated to test the serum free media and supplements in two steps.

Step 1. Selection of serum-free media purveyor. preREP and postREP were set up to mimic 2A process in G-Rex 24 well plate. PreREP were initiated by culturing each fragment/well of G-Rex 24 well plate in triplicates or quatraplicates per conditions. REP were initiated on Day 11 by culturing 4×10e5 TIL/well of G-Rex 24 well, split on Day 16, harvest on Day 22. CTS OpTimizer, X-Vivo 20, and Prime T-CDM were used as potential serum-free media alternatives for use in the PreREP and REP. CTS Immune SR Serum replacement (Life Technologies) or Platelet lysate serum (SDBB) were added at 3% to SFM. Each conditions were planned to test with at least 3 tumors in both preREP and postREP to mimic 2A process.

Step 2. Identified candidates were further tested on mini-scale 2A processes per protocol (TP-17-007). Briefly, pre-REP were initiated by culturing 2 fragments/G-Rex 5M flask in triplicates per condition. REP were initiated on Day 11 using 2×10e6/G-Rex 5M flask, split on Day 16, harvest on Day 22.

Note: Some tumors were processed and setup to measure multiple parameters in one experiment Observations Observed equivalent or statistically better results in cell growth when comparing a serum-free media to the standard used in the 2A process Observed similar phenotype, IFN-γ production, and metabolite analysis from the TIL grown in serum-free media when compared to the TIL grown in the standard media used in the 2A process.

Results

Testing the Efficacy of Serum Free Media on Pre and Post REP TIL Expansion.

CTS Optimizer+SR (Serum Replacement) showed enhanced preREP TIL expansion and comparable REP TIL expansion. CTS OpTimizer, X-Vivo 20, and Prime T-CDM were added with or without 3% CTS Immune CTS SR, were tested against standard condition. In M1079 and L4026, CTS OpTimizer+CSR condition showed significantly enhanced preREP TIL expansion (p<0.05) when compared with standard conditions (CM1, CM2, CM4) (FIG. 62A). Conversely, CTS Optimizer without CSR did not help preREP TIL expansion (Appendix –1,2,3). CTS Optimizer+ CSR showed comparable TIL expansion in PostREP in the two tumour of 3 tested (Figure-2B). A large amount of variation occurred in pre and post REP with the X-Vivo 20 and Prime T-CDM conditions, while CTS Optimizer was relatively consistent between quatraplicates. In addition, SFM added platelet lysate did not enhance preREP and postREP TIL expansion when compared to standards (FIG. 62A). This findings suggesting that serum replacement is certainly needed to provide a comparable growth to our standard, CTS optimizer+CSR may be a candidate.

Testing candidate condition in the G-Rex 5M mini scale (see FIG. 64).

Figure 66:
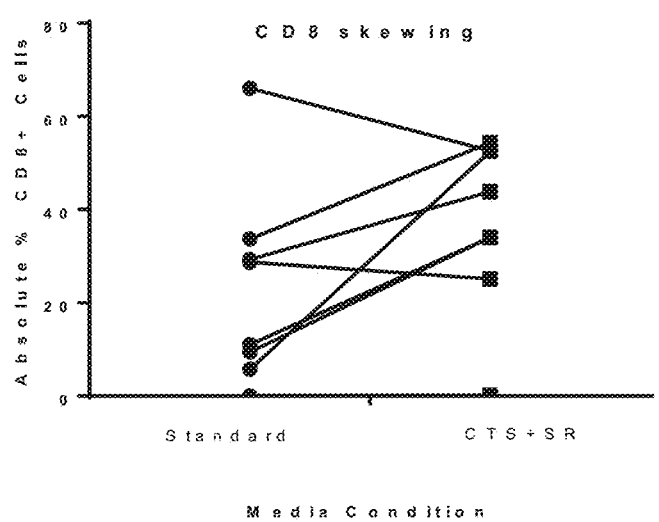
FIG. 66: CD8+ was gated on live cells. 7 of the 9 tumors show an increase in absolute CD8+ populations with the CTS+SR condition.

Phenotypic analysis of Post REP TIL. See FIG. 66 and Table 56 below.

TABLE 56

| CD8 skewing with CTS OpTimizer | | |
|---|---|---|
| | Average % CD8+ | |
| | Standard | CTS |
| M1078 | 11 | 34 |
| M1079 | 29.3 | 43.85 |
| M1080 | 33.67 | 54.37 |
| L4020 | 0.02 | 0.17 |
| EP11020 | 28.67 | 25.07 |

TABLE 56-continued

CD8 skewing with CTS OpTimizer

| | Average % CD8+ | |
|---|---|---|
| | Standard | CTS |
| L4030 | 0.13 | 0.09 |
| L4026 | 9.45 | 34.06 |
| Ml 092 | 5.75 | 52.47 |
| T6030 | 66 | 52.6 |

Interferon-Gamma Comparability

Figure 67:
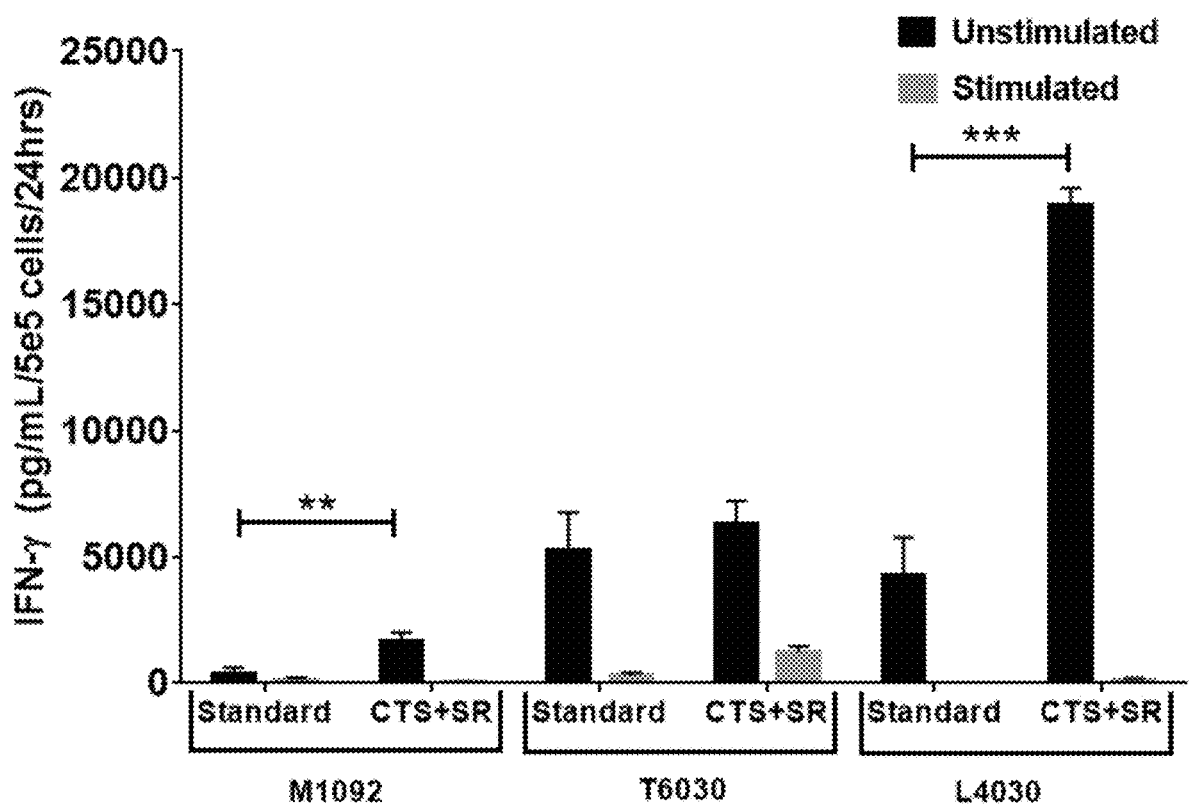
FIG. 67: Interferon-gamma Comparability. Interferon-gamma ELISA (Quantikine). Production of IFN-γ was measured using Quantikine ELISA kit by R&D systems. CTS+ SR produced comparable amounts of IFN-γ when compared to our standard condition.
Figure 68:
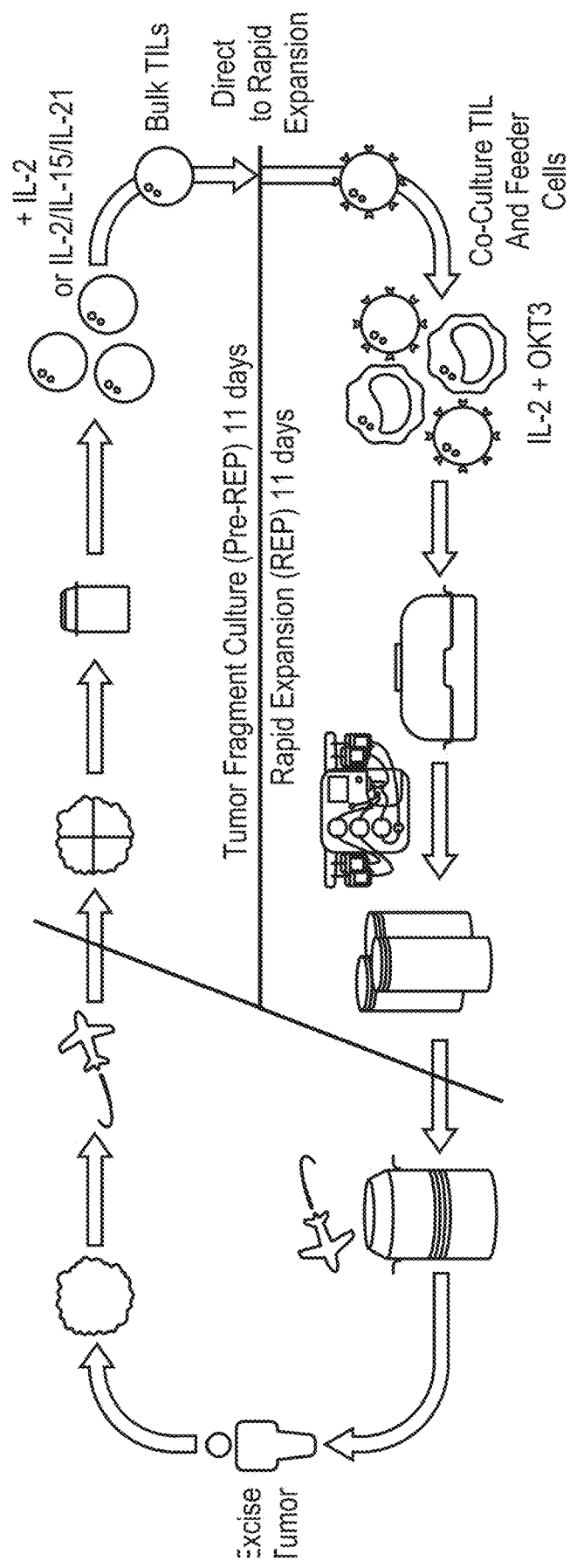
FIG. 68: Scheme of on exemplary embodiment of the Rapid Expansion Protocol (REP). Upon arrival the tumor is fragmented, placed into G-Rex flasks with IL-2 for TIL expansion (pre-REP expansion), for 11 days. For the triple cocktail studies, IL-2/IL-15/IL-21 is added at the initiation of the pre-REP. For the Rapid Expansion Protocol (REP), TIL are cultured with feeders and OKT3 for REP expansion for an additional 11 days.
Figure 69A:
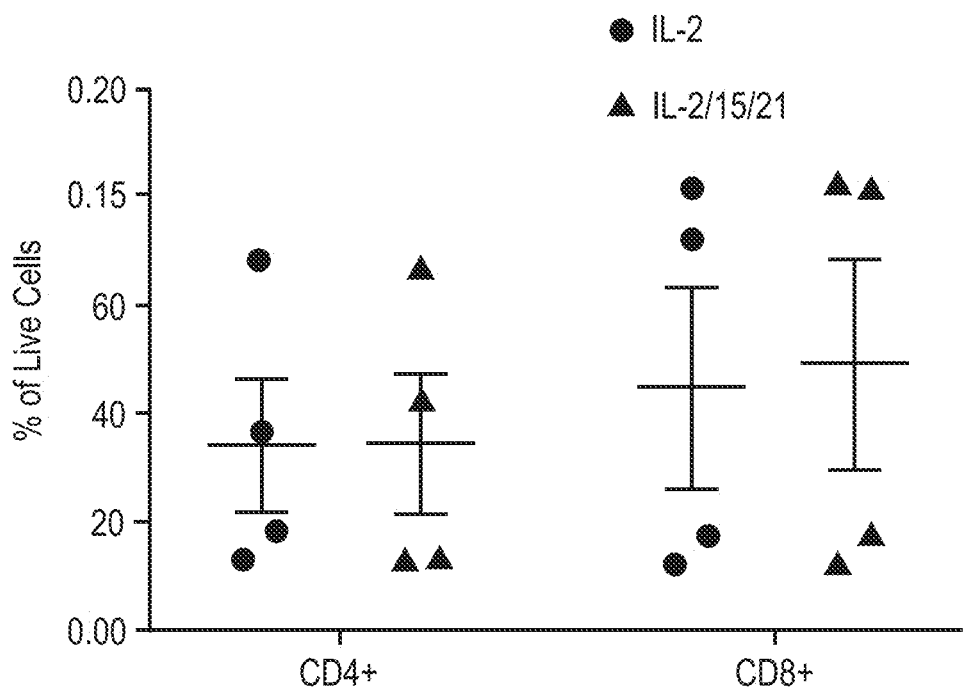
FIG. 69A-69B: TIL derived from melanoma (n=4), and lung (n=7) were assessed phenotypically for CD4+ and CD8+ cells using flow cytometry post pre-REP. *P-values represent the difference between the IL-2 and IL-12/IL-15/IL-21 in the CD8+ cells using student's unpaired t test.
Figure 69B:
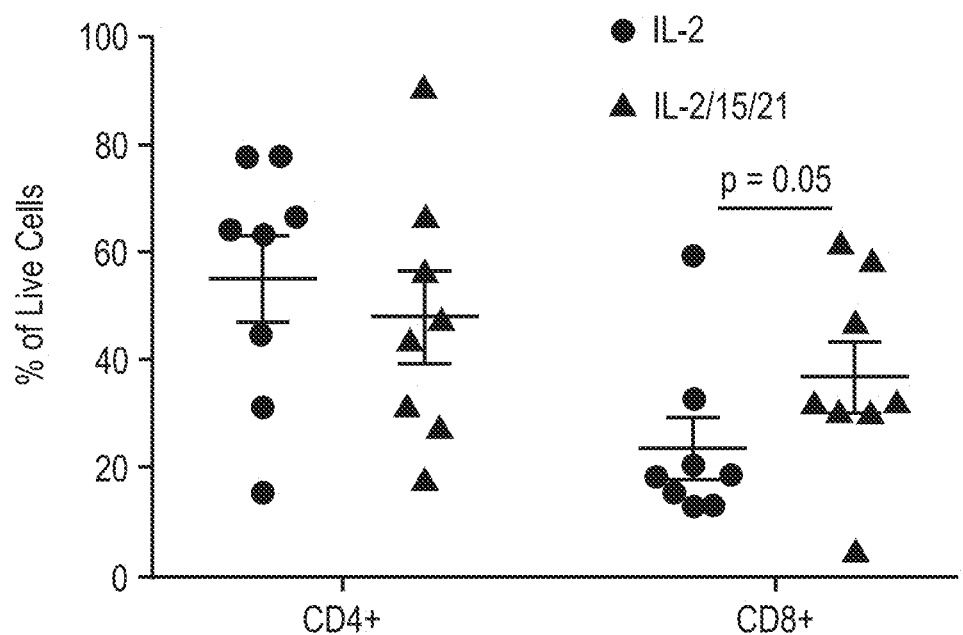
Figure 70A:
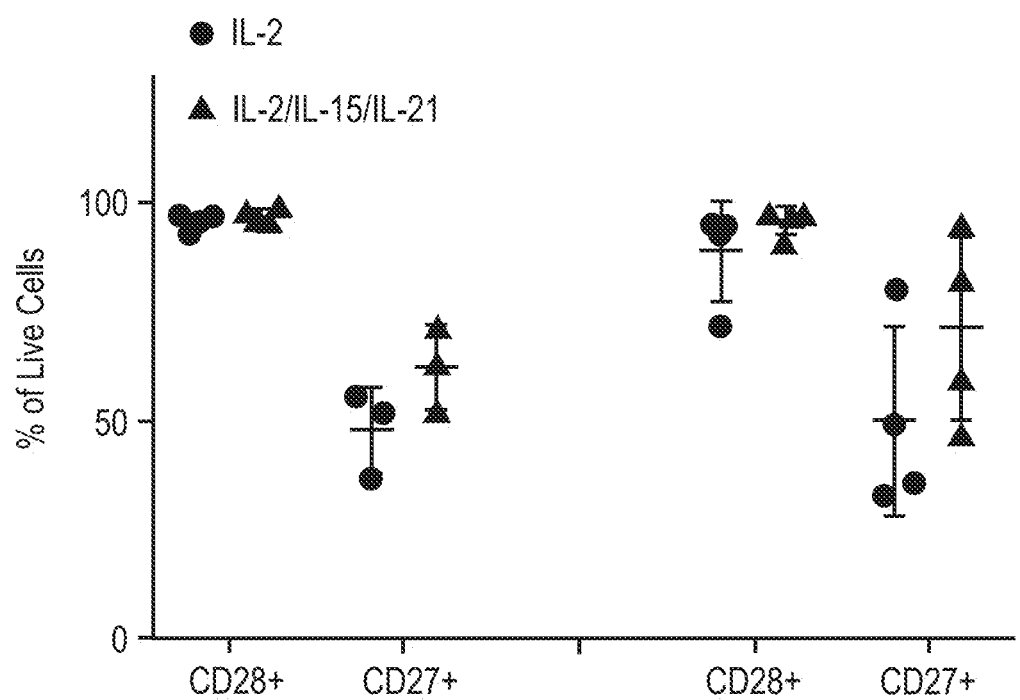
FIG. 70A-70B: TIL derived from melanoma (n=4), and lung (n=7) were assessed phenotypically for CD27+ and CD28+ in the CD4+ and CD8+ cells using flow cytometry post pre-REP.
Figure 70B:
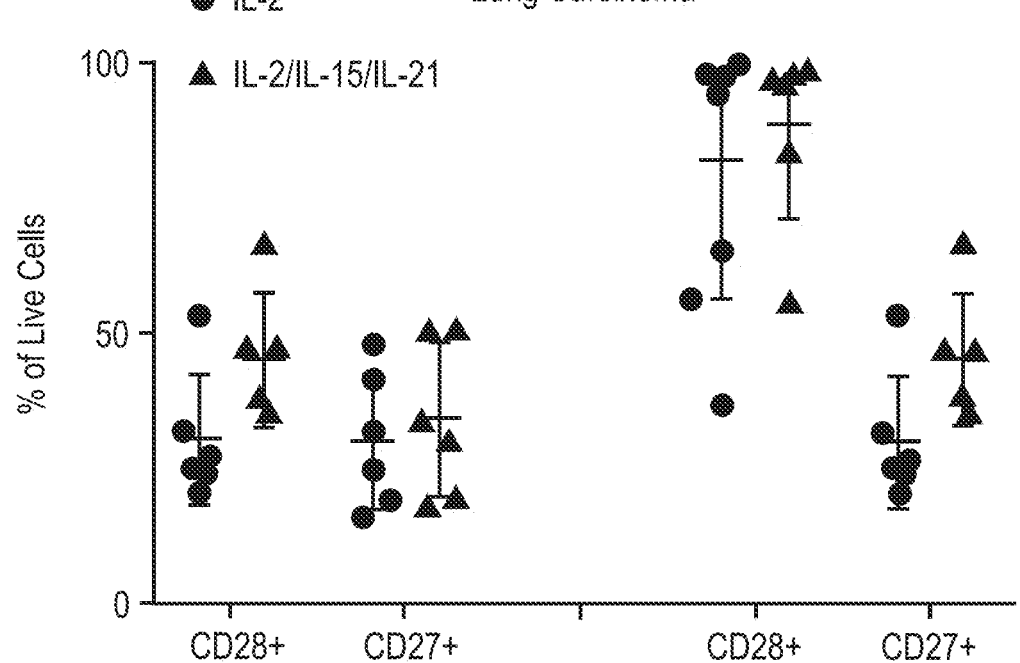
Figure 71A:
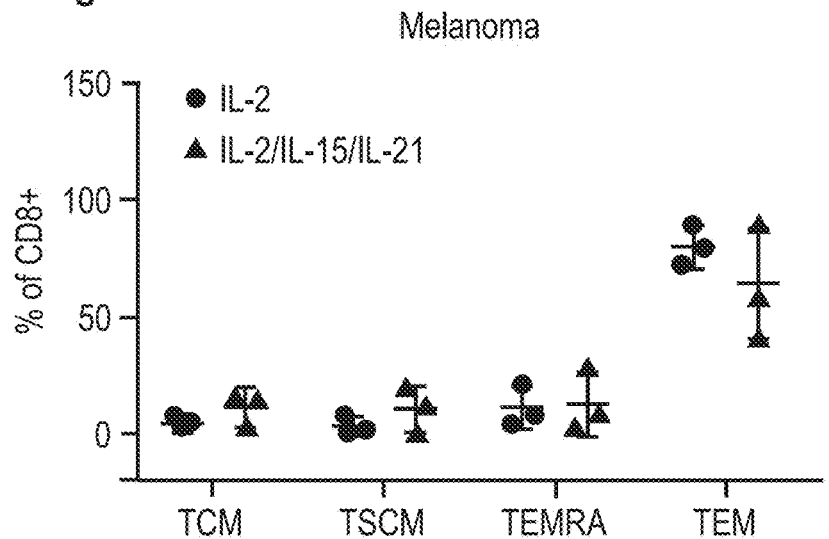
FIG. 71A-71C: TIL were assessed phenotypically for effector/memory subsets (CD45RA and CCR7) in the CD8+ cells and CD4+(data not shown) in melanoma (n=4) (A) and lung (n=8) (B). CXCR3 expression was assessed in melanoma and lung. All phenotypic expression was assessed using flow cytometry post pre-REP. TCM=central memory, TSCM=stem cell memory, TEMRA (effector T cells), TEM=effector memory.
Figure 71B:
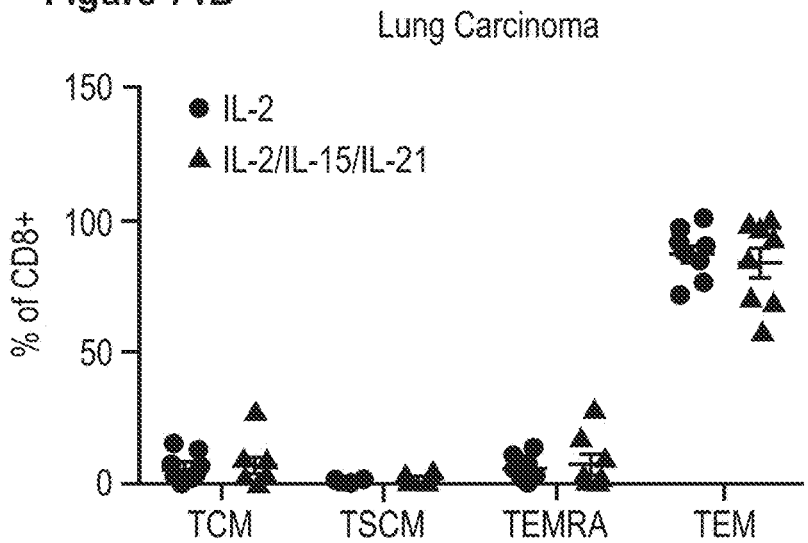
Figure 71C:
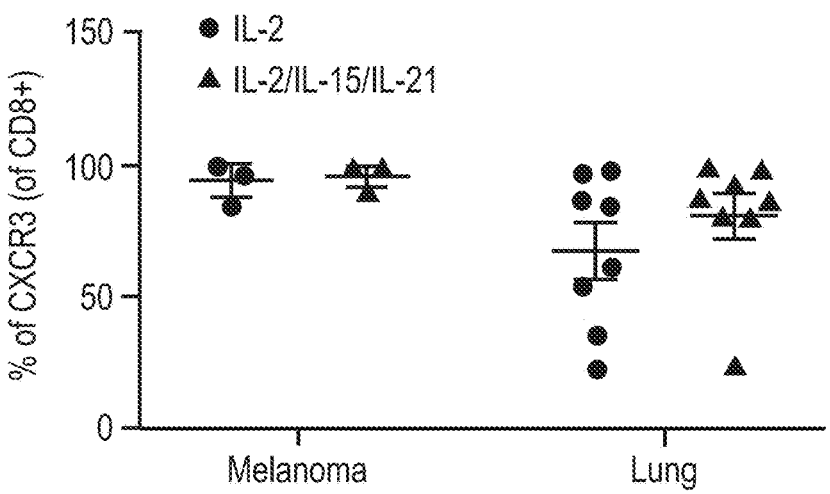
Figure 72A:
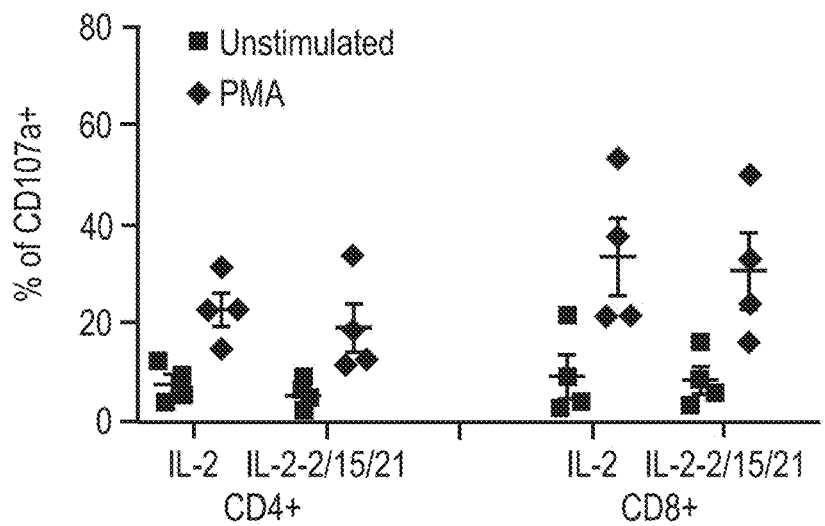
FIG. 72A-72C: TIL derived from (A) melanoma (n=4) and (B) lung (n=5) were assessed for CD107a+ expression in response to PMA stimulation for 4 hours in the CD4+ and CD8+ cells, by flow cytometry. (C) pre-REP TIL (n=5) were stimulated for 24 hours with soluble OKT3 (30 ng/ml) and the supernatants assessed for IFNγ by ELISA.
Figure 72B:
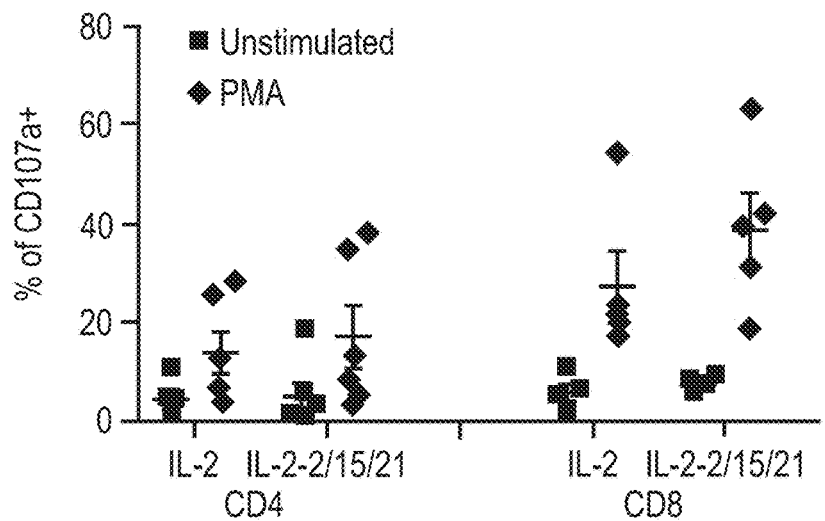
Figure 72C:
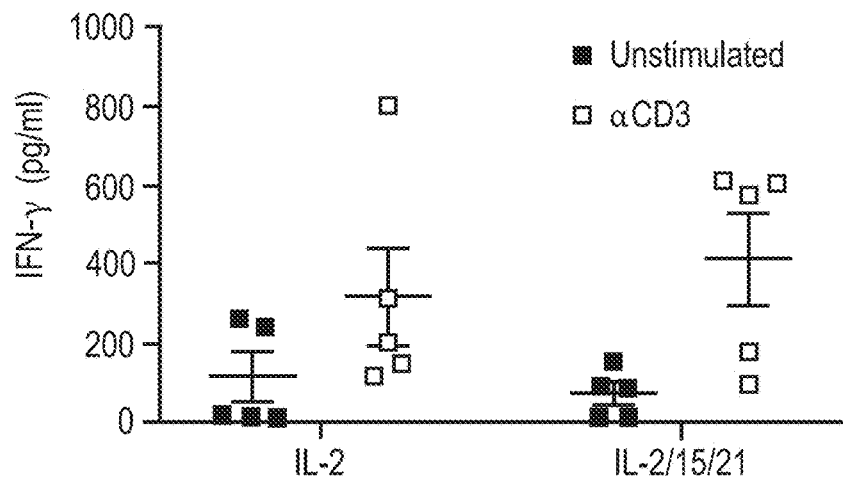
Figure 73A:
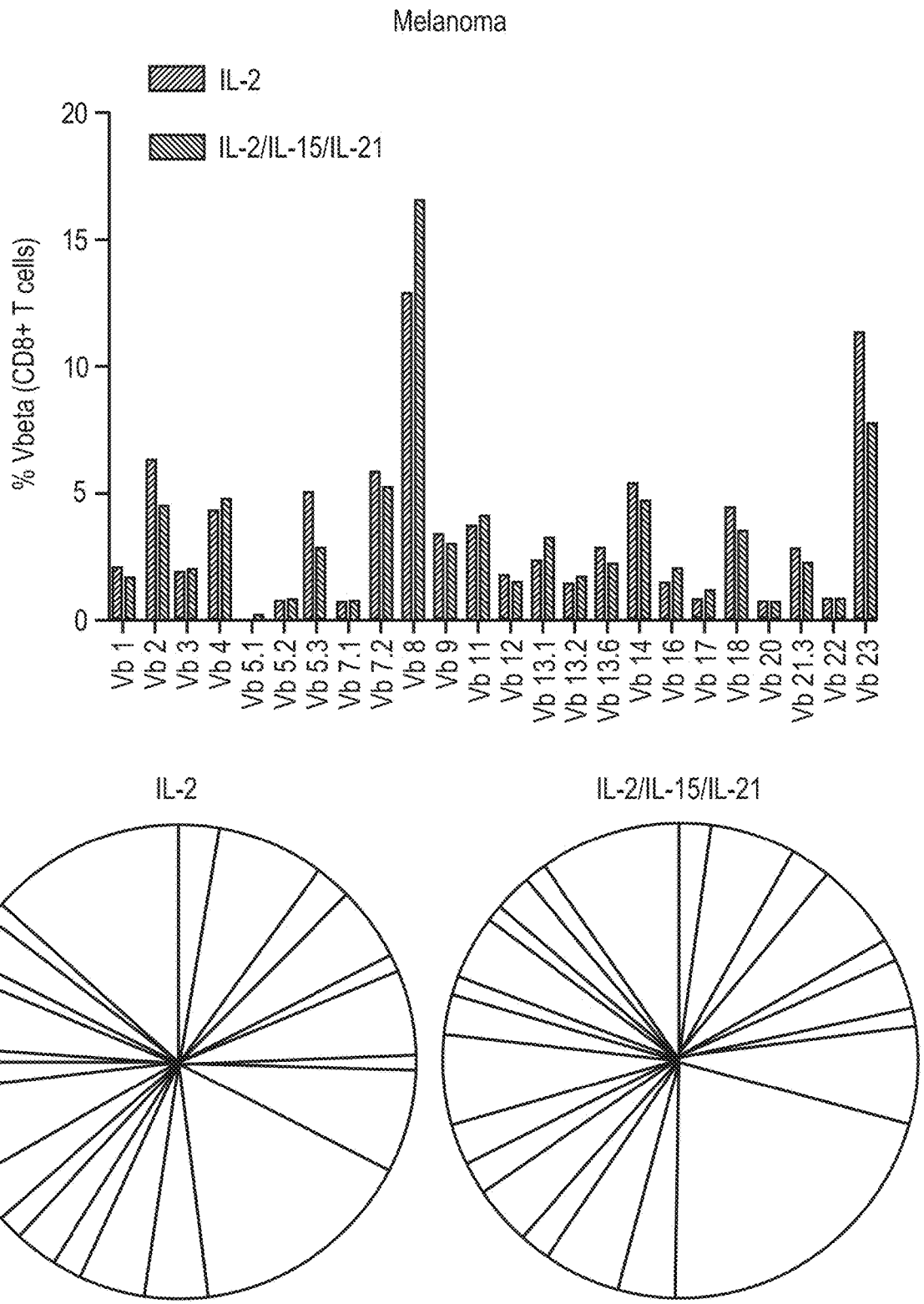
FIG. 73A-73B: The TCRvβ repertoire (24 specificities) were assessed in the TIL derived from melanoma (A) and lung (B) using the Beckman Coulter kit for flow cytometry.
Figure 73B:
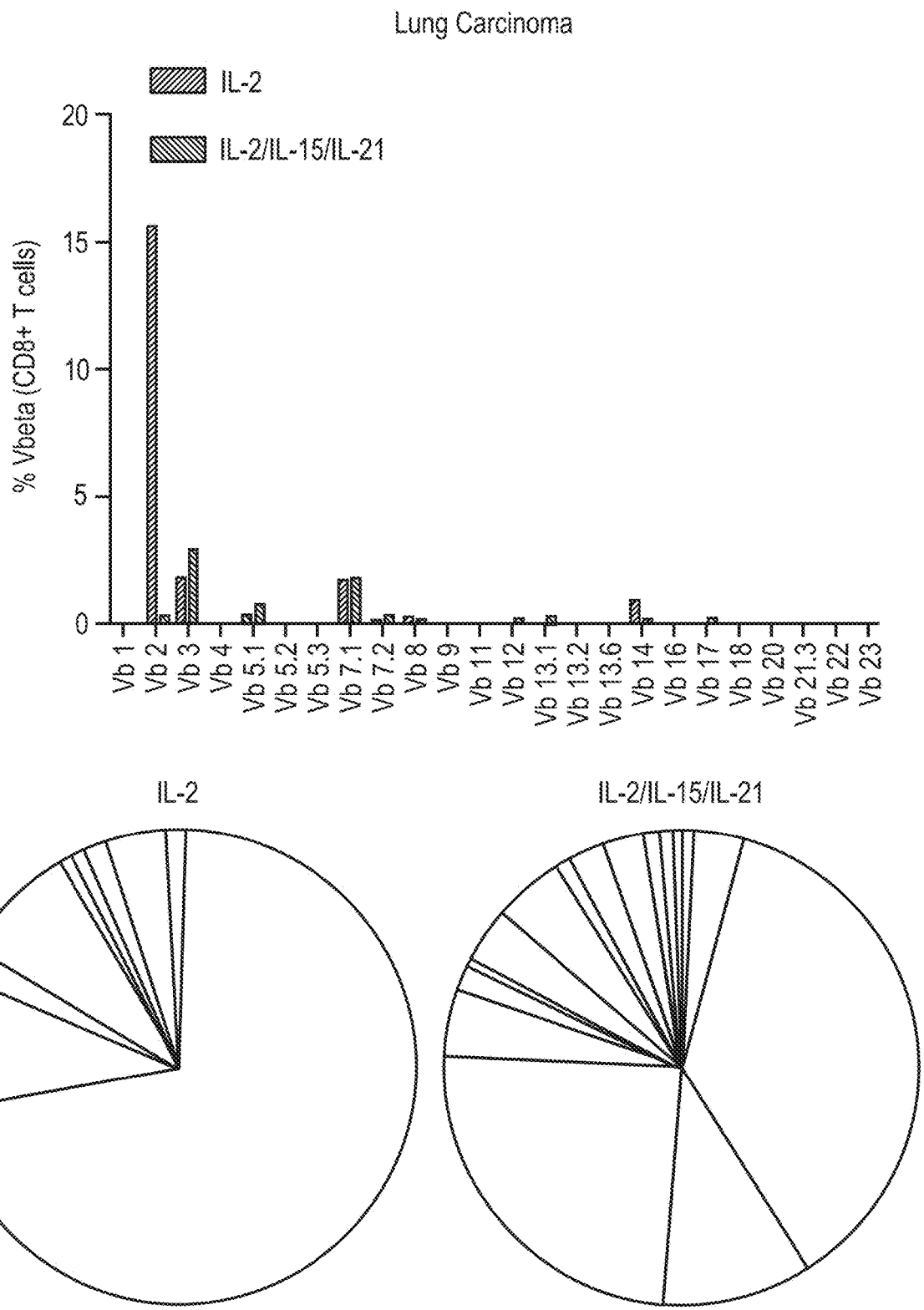
Figure 74:
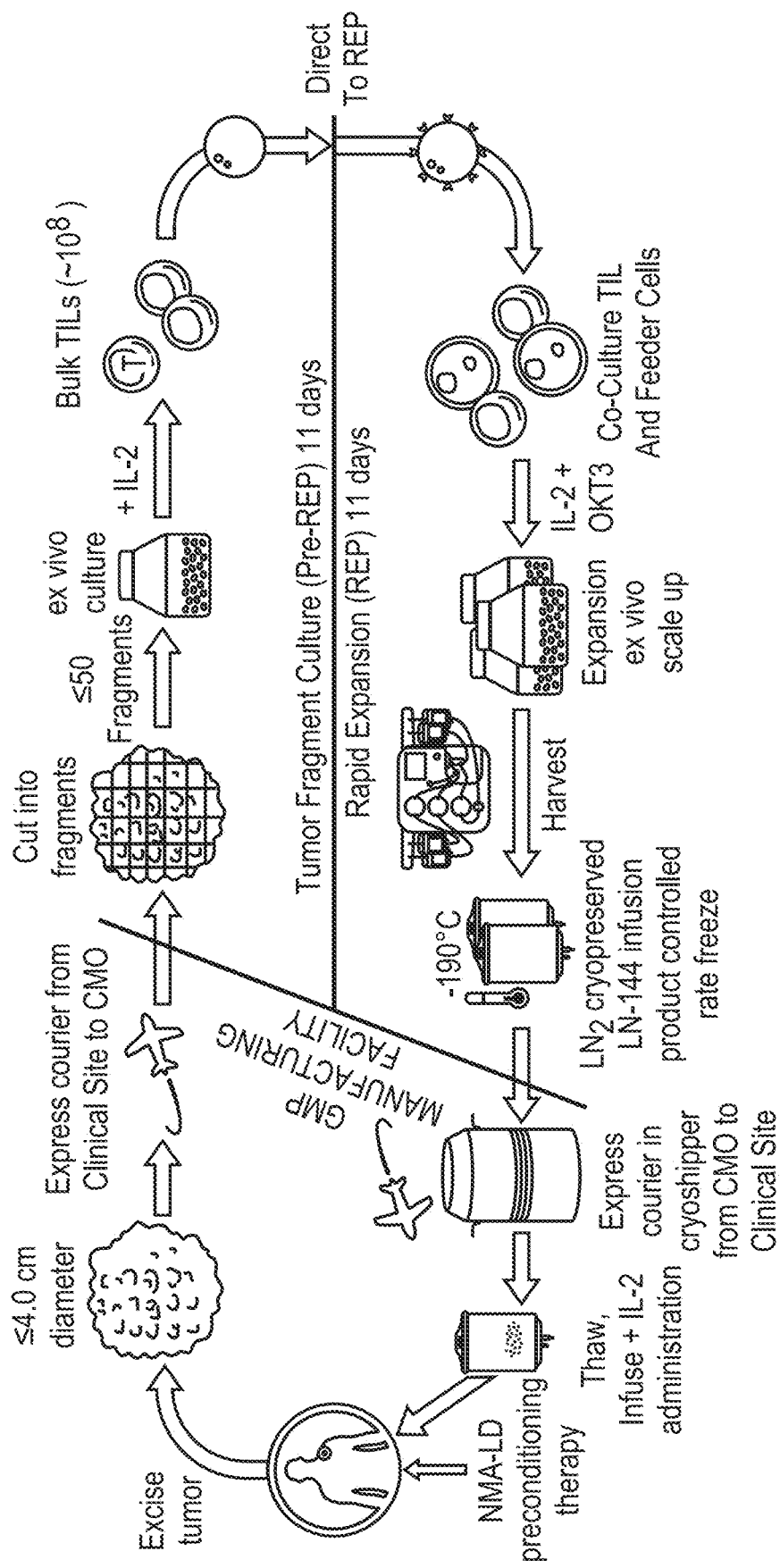
FIG. 74: Cryopreserved TIL exemplary manufacturing process (~22 days).
Figure 75A:
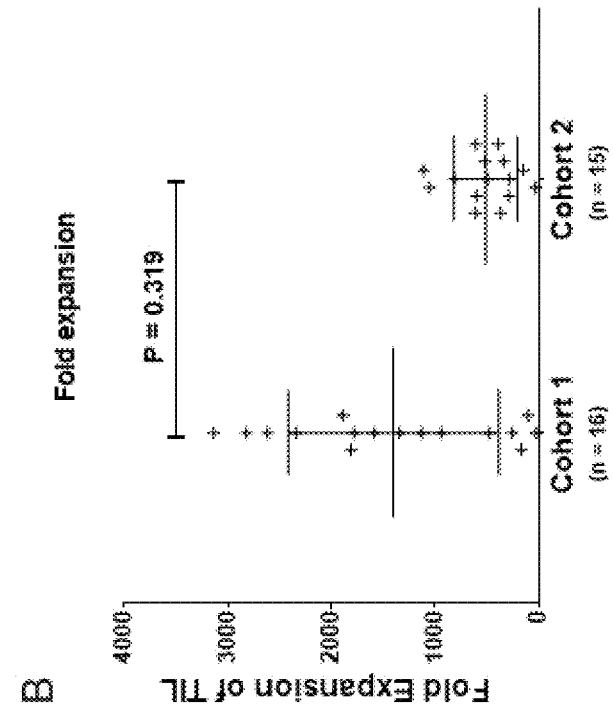
FIG. 75A-75B: On Day 22 the volume reduced cell product is pooled and sampled to determine culture performance prior to wash and formulation. Samples are analyzed on the NC-200 automated cell counter as previously described. Total viable cell density is determined by the grand mean of duplicate counts from 4 independent samples. The Generation 2 (Gen 2) process yields a TIL product of similar dose to Generation 1 (Gen 1; the Gen 1 mean=4.10× $10^{10}$ 2.92×$10^{10}$, Gen 2 mean=3.12×$10^{10}$ 2.19×$10^{10}$). B) Fold expansion is calculated for the REP phase as the dividend of the final viable cell density over the initial viable TIL seeding density. Gen 2 TIL products have a lower fold expansion relative to Gen 1 (Gen 1 mean=1.40×$10^3$±9.86× $10^2$, Gen 2 mean=5.11×$10^2$ s 2.95×$10^2$).
Figure 75B:
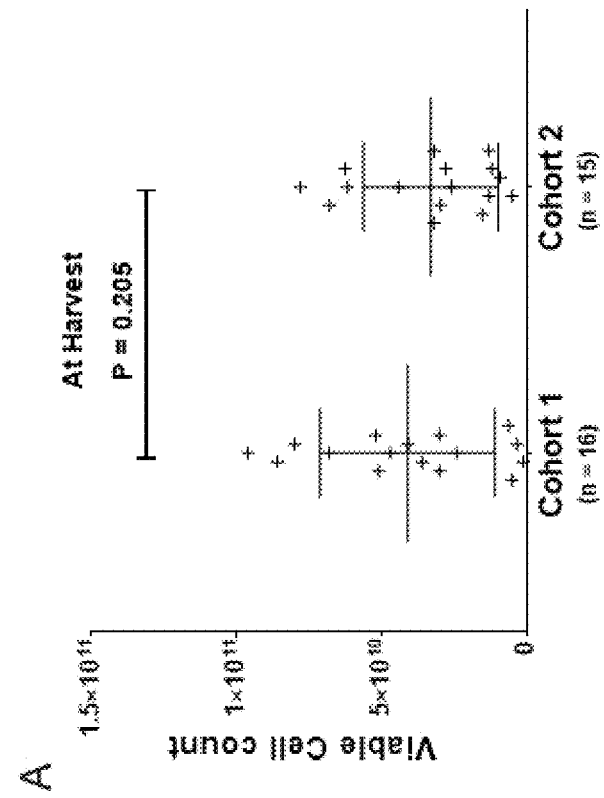
Figure 76:
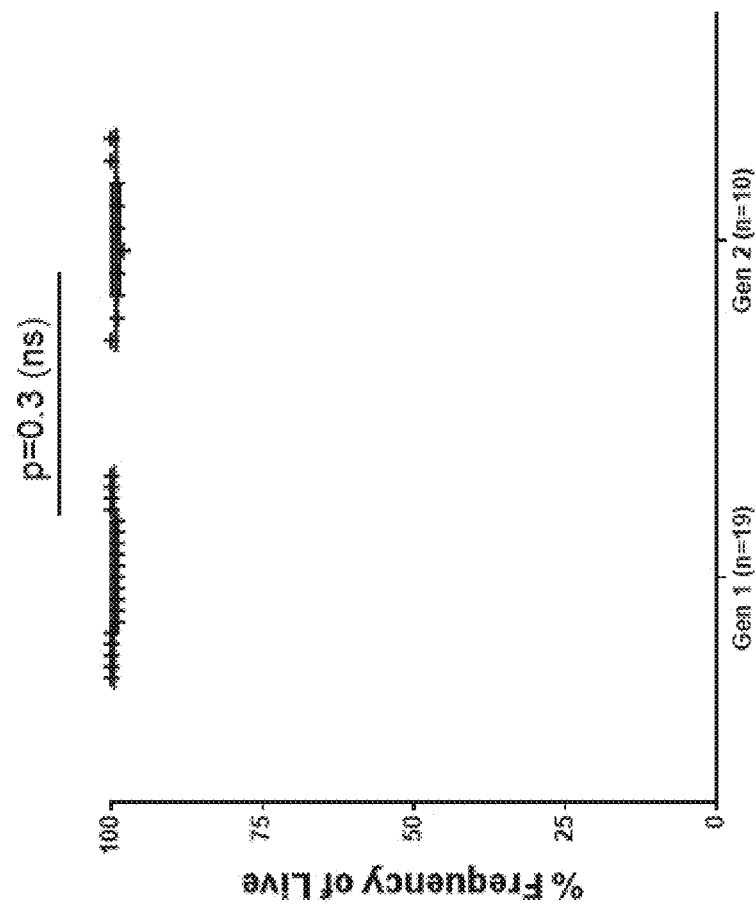
FIG. 76: Fresh formulated drug products were assayed for identity by flow cytometry for release. Gen 1 and Gen 2 processes produce highly purity T-cell cultures as defined by CD45, CD3 double positive phenotype (Gen1 #SD, Gen 2 #±SD). P-value was calculated using Mann-Whitney 't' test.
Figure 77B:
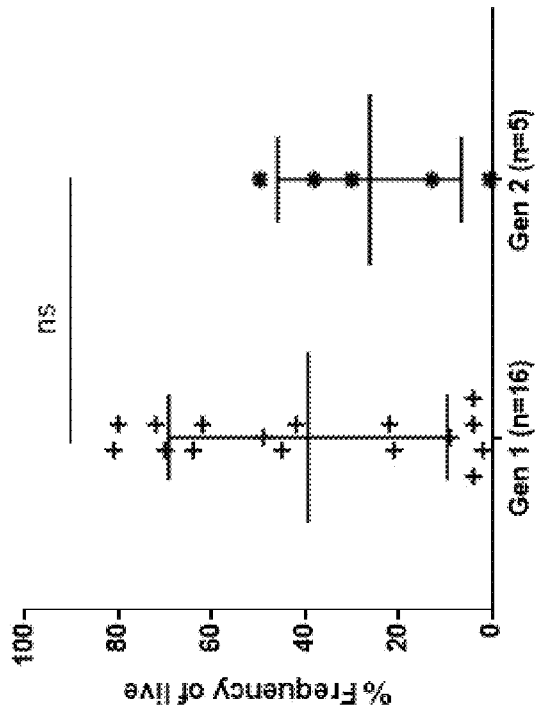
FIG. 77A-77B: Cryo preserved satellite vials of formulated drug product were thawed and assayed for extended phenotype by flow cytometry as previously described. Gen 1 and Gen 2 products express similar ratios of CD8 to CD4 T-cell subtypes. P-value was calculated using Mann-Whitney 't' test.
Figure 77A:
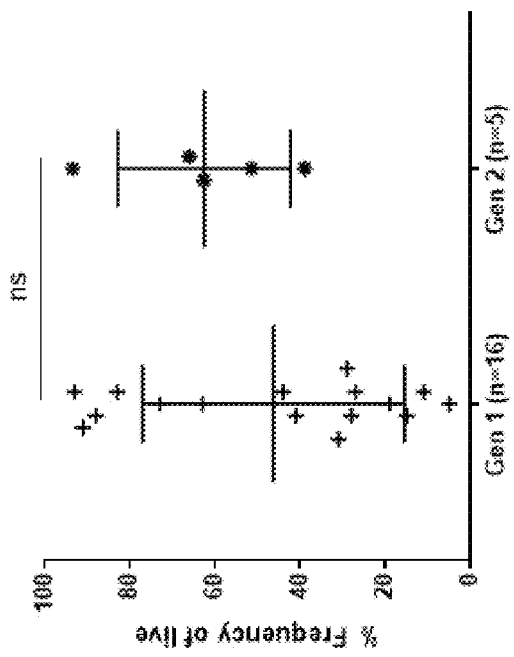
Figure 78B:
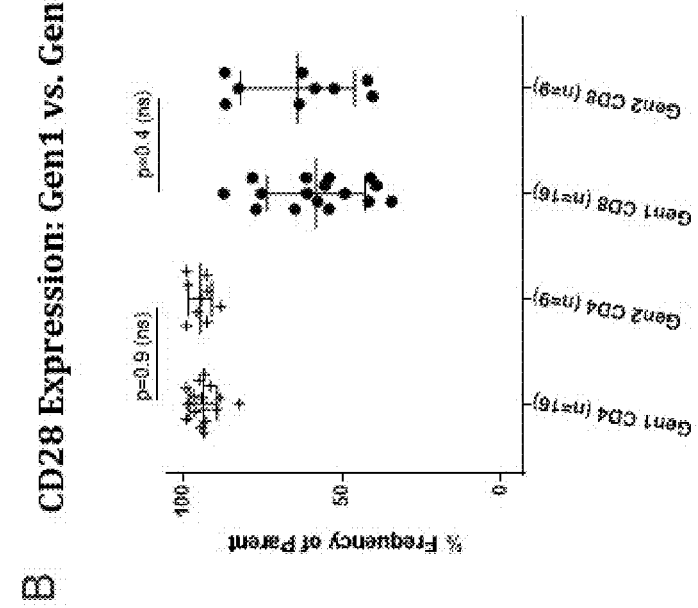
FIG. 78A-78B: Cryo preserved satellite vials of formulated drug product were thawed and assayed for extended phenotype by flow cytometry as previously described. Gen 1 and Gen 2 products express similar levels of costimulatory molecules CD27 and CD28 on T-cell subsets. P value was calculated using Mann-Whitney 't'test. Costimulatory molecules such as CD27 and CD28 are required to supply secondary and tertiary signaling necessary for effector cell proliferation upon T-cell receptor engagement.
Figure 78A:
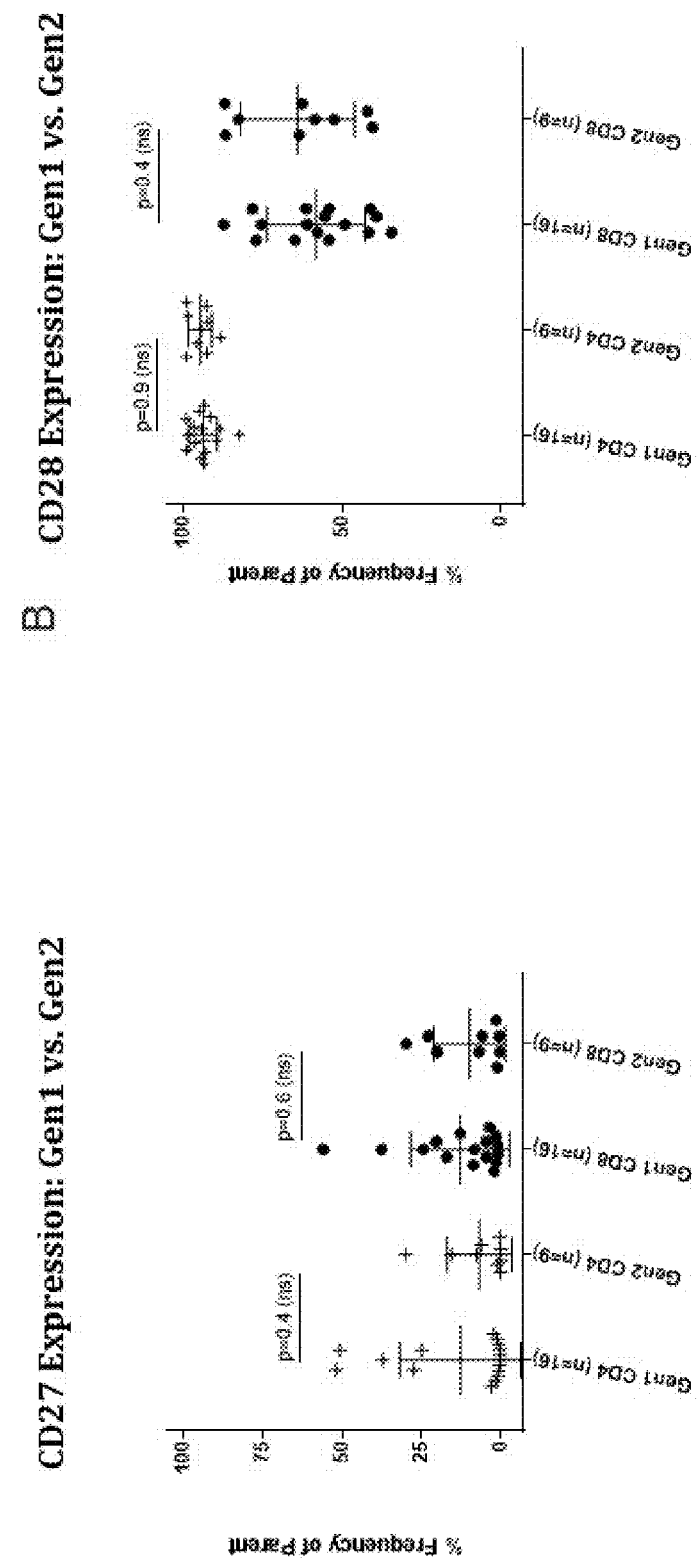
Figure 79:
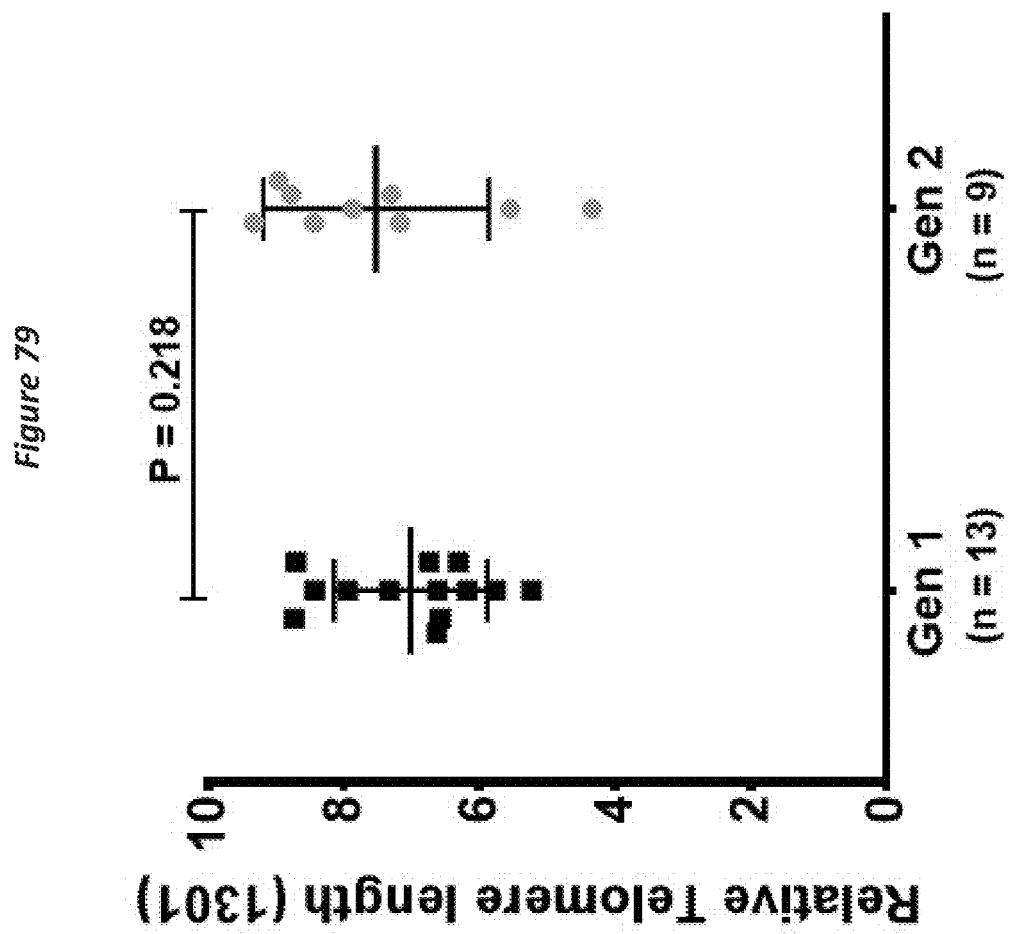
FIG. 79: Flow-FISH technology was used to measure the average length of the Telomere repeat as previously described. The above RTL value indicates that the average telomere fluorescence per chromosome/genome in Gen 1 (an embodiment of process 1C) is #%±SD %, and Gen 2 is #%±SD % of the telomere fluorescence per chromosome/genome in the control cells line (1301 Leukemia cell line). Data indicate that Gen 2 products on average have at least comparable telomere lengths to Gen 1 products. Telomere length is a surrogate measure of the length of ex vivo cell culture.
Figure 80:
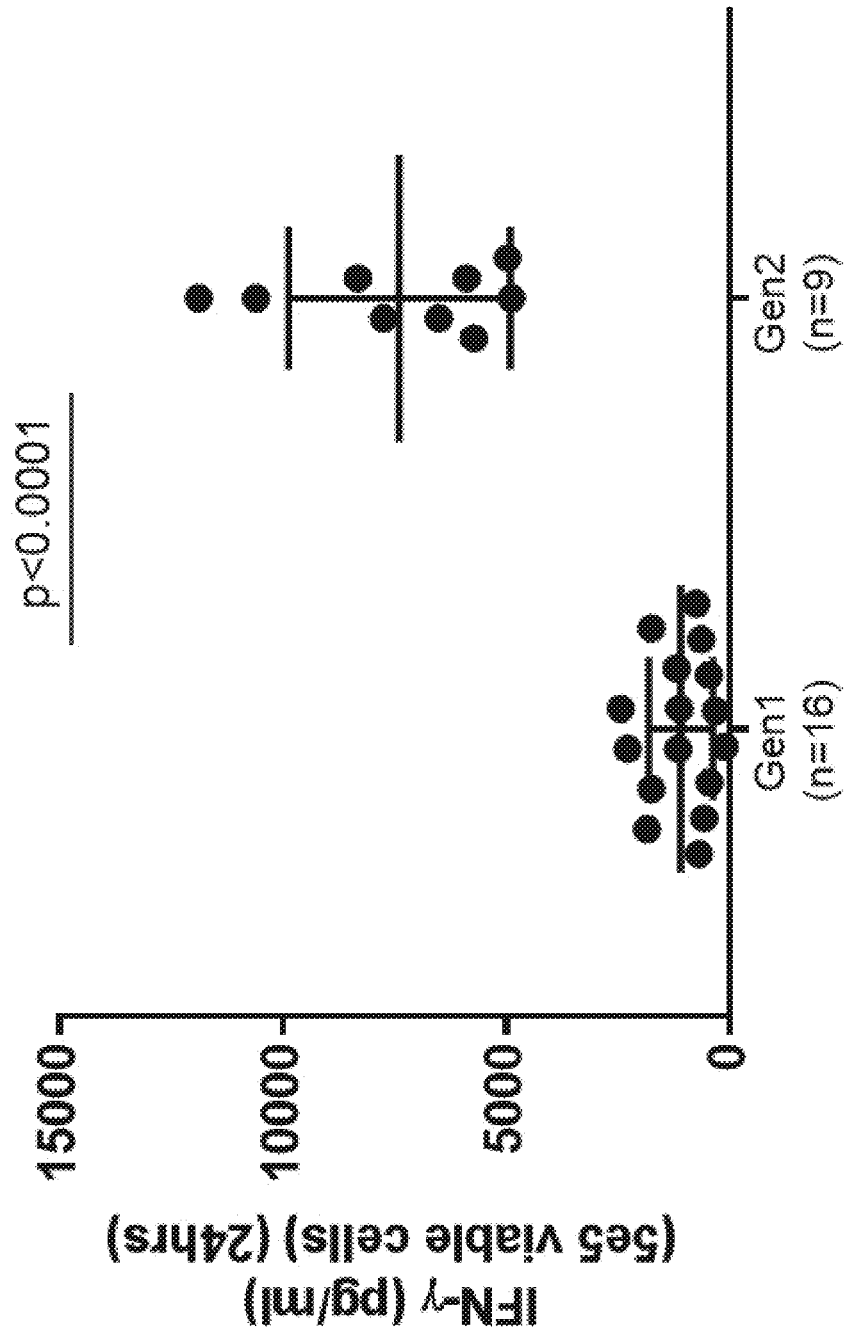
FIG. 80: Gen 2 (an embodiment of the process 2A) drug products exhibit and increased capability of producing IFN-γ relative to Gen 1 drug products. The ability of the drug product to be reactivated and secrete cytokine is a surrogate measure of in-vivo function upon TCR binding to cognate antigen in the context of HLA.
Figure 81A:
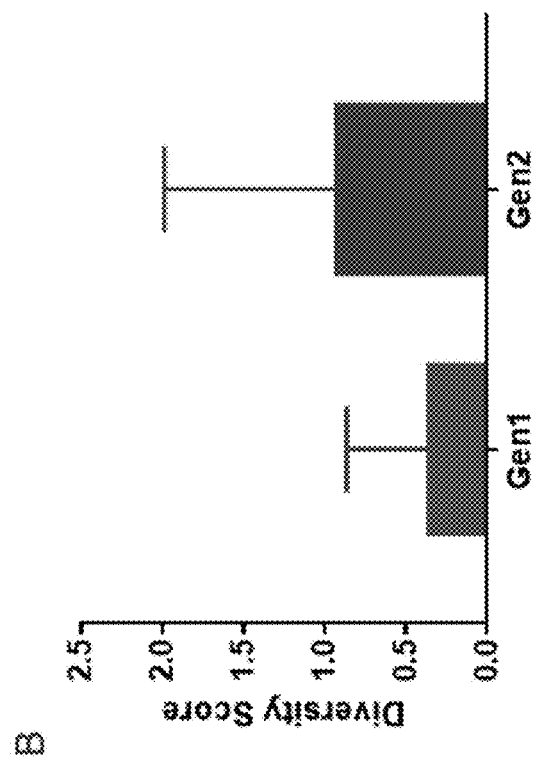
FIG. 81A-81B: T-cell receptor diversity: RNA from $10 \times 10^6$ TIL from Gen 1 (an embodiment of the process IC) and Gen 2 (an embodiment of the process 2A) drug products were assayed to determine the total number and frequency of unique CDR3 sequences present in each product. A) The total number of unique CDR3 sequences present in each product (Gen 1 n=#, mean±SD, Gen 2 n=#, mean±SD). B) Unique CDR3 sequences were indexed relative to frequency in each product to yield a score representative of the relative diversity of T-cell receptors in the product. TIL products from both processes are composed of polyclonal populations of T-cells with different antigen specificities and avidities. The breadth of the total T-cell repertoire may be indicative of the number of actionable epitopes on tumor cells.
Figure 81B:
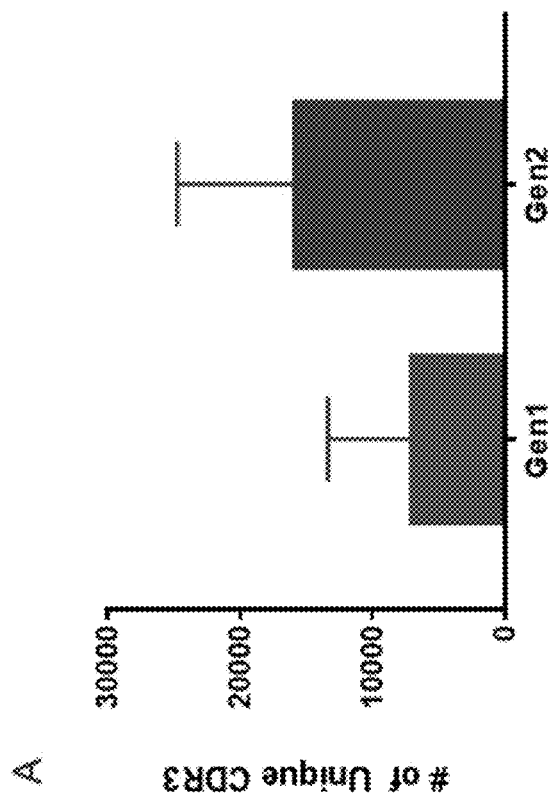
Figure 82:
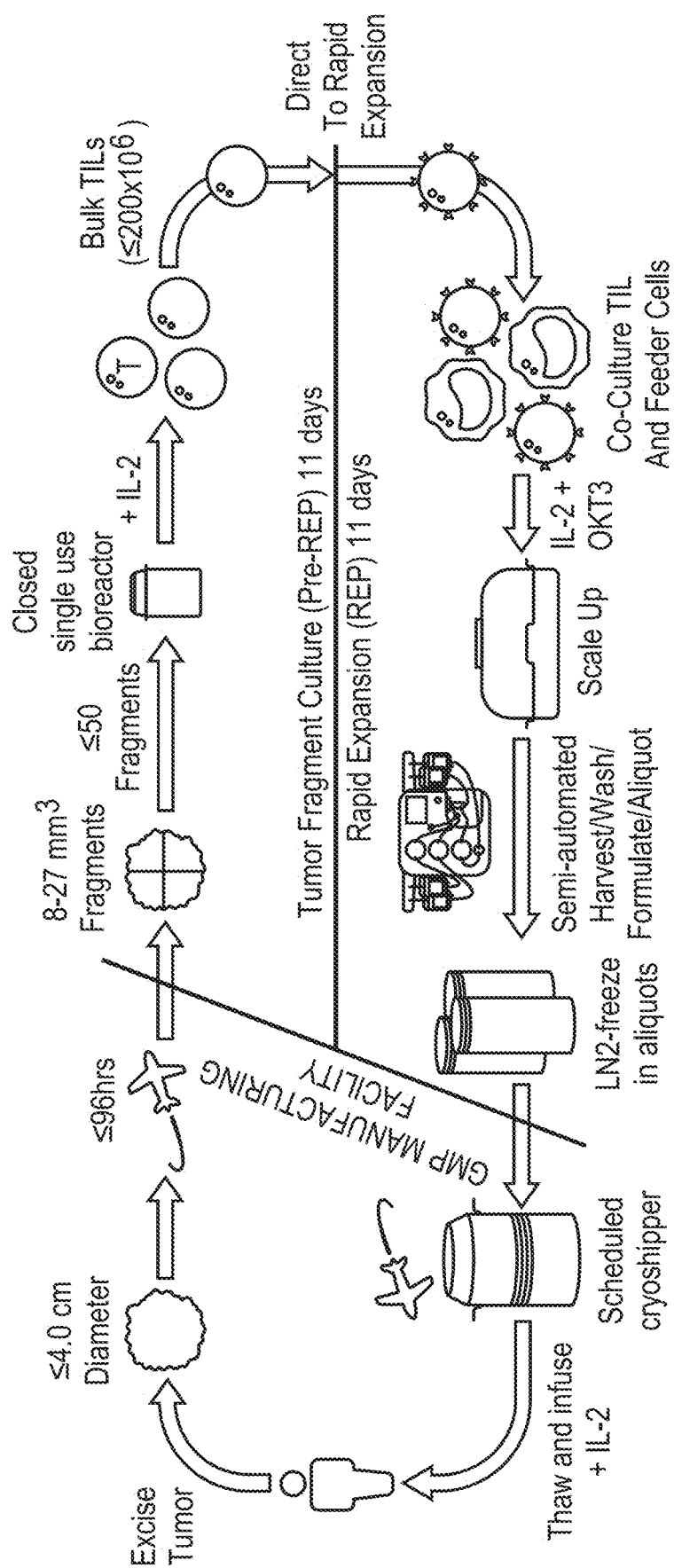
FIG. 82: Shows a diagram of an embodiment of process 2A, a 22-day process for TIL manufacturing.
Figure 85:
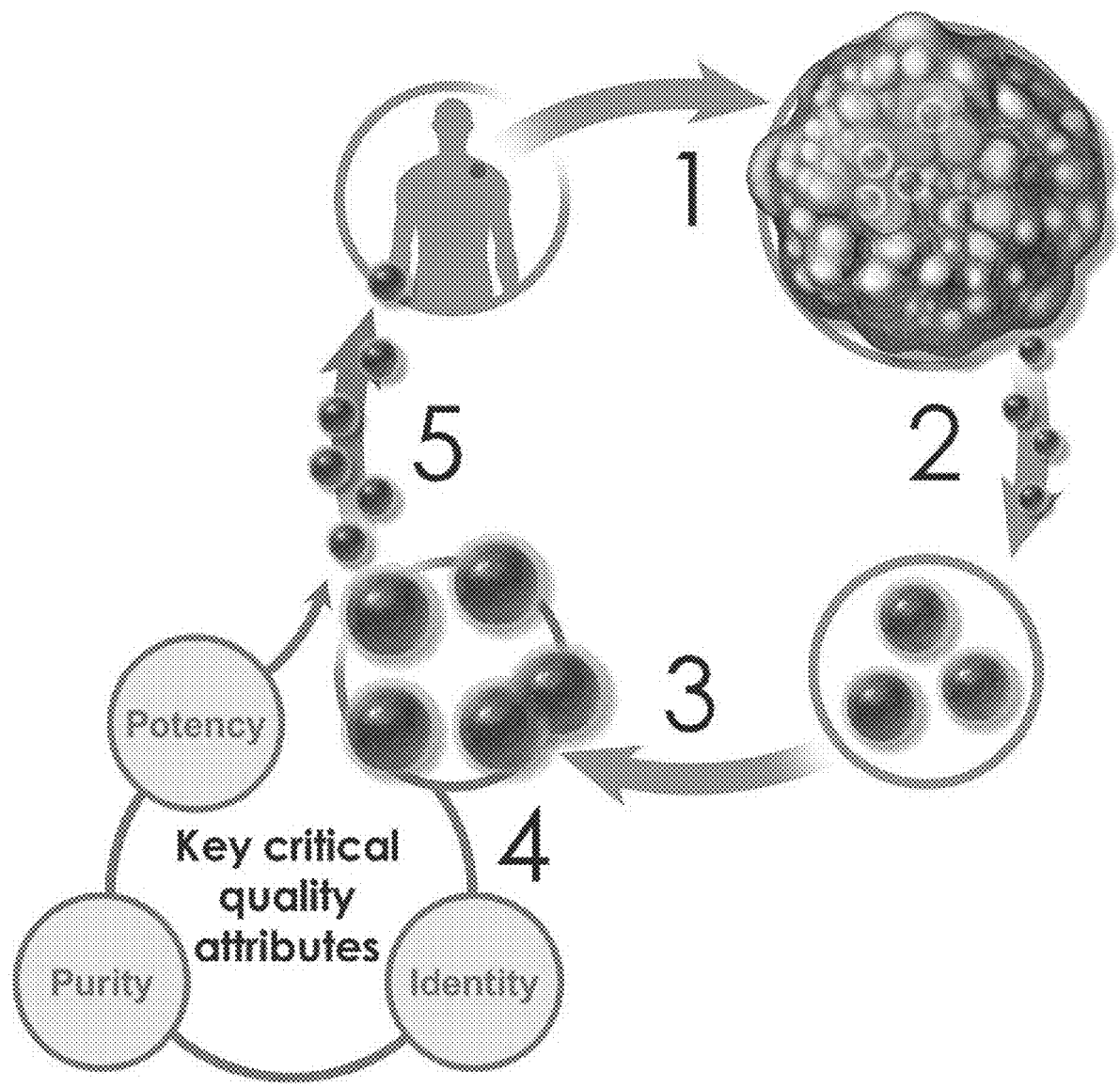
FIG. 85: Detailed scheme of an embodiment of a TIL therapy process.

Interferon-gamma ELISA (Quantikine). Production of IFN-γ was measured using Quantikine ELISA kit by R&D systems. CTS+SR produced comparable amounts of IFN-γ when compared to our standard condition. See, FIG. 67.

Example 22: T-Cell Growth Factor Cocktail IL-2/IL-15/IL-21 Enhances Expansion and Effector Function of Tumor-Infiltrating T Cells Adoptive T cell therapy with autologous tumor infiltrating lymphocytes (TIL) has demonstrated clinical efficacy in patients with metastatic melanoma and cervical carcinoma. In some studies, better clinical outcomes have positively correlated with the total number of cells infused and/or percentage of CD8+ T cells. Most current production regimens solely utilize IL-2 to promote TIL growth. Enhanced lymphocyte expansion has been reported using IL-15 and IL-21-containing regimens. This study describes the positive effects of adding IL-15 and IL-21 to the second generation IL-2-TIL protocol recently implemented in the clinic.

Materials and Methods

The process of generating TIL includes a pre-Rapid Expansion Protocol (pre-REP), in which tumor fragments of 1-3 mm$^3$ size are placed in media containing IL-2. During the pre-REP, TIL emigrate out of the tumor fragments and expand in response to IL-2 stimulation.

To further stimulate TIL growth, TIL are expanded through a secondary culture period termed the Rapid Expansion Protocol (REP) that includes irradiated PBMC feeders, IL-2 and anti-CD3. In this study, a shortened pre-REP and REP expansion protocol was developed to expand TIL while maintaining the phenotypic and functional attributes of the final TIL product.

This shortened TIL production protocol was used to assess the impact of IL-2 alone versus a combination of IL2/IL-15/IL-21. These two culture regimens were compared for the production of TIL grown from colorectal, melanoma, cervical, triple negative breast, lung and renal tumors. At the completion of the pre-REP, cultured TIL were assessed for expansion, phenotype, function (CD107a+ and IFNγ) and TCR VO repertoire.

pre-REP cultures were initiated using the standard IL-2 (600 IU/ml) protocol, or with IL-15 (180 IU/ml) and IL-21 (IU/ml) in addition to IL-2. Cells were assessed for expansion at the completion of the pre-REP. A culture was classified as having an increase expansion over the IL-2 if the overall growth was enhanced by at least 20%. The melanoma and lung phenotypic and functional studies are presented herein. See, Table 57 below.

TABLE 57

Enhancement in expansion during the pre-REP with IL-2/IL-15/IL-21 in multiple indications

| Tumor Histology | # of IL-2 versus IL-2/IL-15/IL-21 studies | # of studies demonstrating >20% enhancement of growth using IL-2/IL-15/IL-21 (compared to IL-2) |
|---|---|---|
| Melanoma | 5 | 1/5 (20%) |
| Lung | 8 | 3/8 (38%) |
| Colorectal | 11 | 7/11 (63%) |
| Cervical | 1 | 1/1 (100%) |
| Pancreatic | 2 | 2/2 (100%) |
| Glioblastoma | 1 | 1/1 (100%) |
| Triple Negative Breast | 1 | 1/2 (50%) |

These data demonstrate an increased TIL product yield when TIL were cultured with IL-2/IL15/IL-21 as compared to IL-2 alone, in addition to phenotypic and functional differences in lung.

The effect of the triple cocktail on TIL expansion was indication-specific and benefited most the low yield tumors.

The CD8+/CD4+ T cell ratio was increased by the treatment in NSCLC TIL product.

T cell activity appeared enhanced by the addition of IL-15 and IL-21 to IL-2, as assessed by CD107a expression levels in both melanoma and NSCLC.

The data provided here shows that TIL expansion using a shorter, more robust process, such as the 2A process described herein in the application and other examples, can be adapted to encompassing the IL-2/IL-15/IL-21 cytokine cocktail, thereby providing a means to further promote TIL expansion in particularly in specific indications.

Ongoing experiments are further evaluating the effects of IL-2/IL-15/IL-21 on TIL function.

Additional experiments will evaluate the effect of the triple cocktail during the REP (first expansion).

These observations are especially relevant to the optimization and standardization of TIL culture regimens necessary for large-scare manufacture of TIL with the broad applicability and availability required of a main-stream anti-cancer therapy.

Example 23: A Cryopreserved TIL Generated with an Abbreviated Method

Background

This example provides data related to a cryopreserved tumor infiltrating lymphocyte (TIL) product for LN-144, generated with an abbreviated method suitable for high throughput commercial manufacturing exhibits favorable quality attributes for adoptive cell transfer (ACT).

Existing methods for generating clinical TIL products involve open operator interventions followed by extended incubation periods to generate a therapeutic product. The Generation 1 process takes approximately 6 weeks and yields a fresh product. To bring TIL therapy to all patients that may benefit from its potential, an abbreviated 22 day culture method, Generation 2, suitable for centralized manufacturing with a cryopreserved drug product capable of shipment to distant clinical sites was developed. Generation 2 represents a flexible, robust, closed, and semi-automated cell production process that is amenable to high throughput manufacturing on a commercial scale. Drug products generated by this method have comparable quality attributes to those generated by the Generation 1 process.

Study Objectives:

Drug products generated by Generation 1 (a process 1C embodiment) and Generation 2 (a process 2A embodiment) processes were assayed to determine comparability in terms of the following quality attributes:

Dose and fold expansion.

T-cell purity and proportions of T-cell subsets.

Phenotypic expression of co-stimulatory molecules on T-cell subsets.

Average relative length of telomere repeats.

Ability to secrete cytokine in response to TCR reactivation.

T-cell receptor diversity.

Overview of TIL Therapy Process:

EXTRACTION: Patient's TIL are removed from suppressive tumor microenvironment (via surgical resection of a lesion)

EXPANSION: TIL expanded exponentially in culture with IL-2 to yield $10^9$-$10^{11}$ TIL, before infusing them into the patient PREPARATION: Patient receives NMA-LD (non-myeloablative lymphodepletion, cyclophosphamide: 60 mg/kg, IV×2 doses and fludarabine: 25 mg/m$^2$×5 doses) to eliminate potentially suppressive tumor microenvironment and maximize engraftment and potency of TIL therapy INFUSION: Patient is infused with their expanded TIL (LN-144) and a short duration of high-dose of IL-2 (600,000 IU/kg for up to 6 doses) to promote activation, proliferation, and anti-tumor cytolytic activity of TIL Flow cytometry: Formulated drug products were sampled and assayed for identity by FACS. Percent T-cells was determined as the CD45, CD3 double positive population of viable cells. Frozen satellite or sentinel vials for each process were thawed and assayed for extended phenotypic markers including CD3, CD4, CD8, CD27, and CD28.

Average relative length of telomere repeats: Flow-FISH technology was used to measure average length of telomere repeat. This assay was completed as described in the DAKO® Telomere PNA Kit/FITC for Flow Cytometry protocol. Briefly, 2×10$^6$ TIL cells were combined with 2×10$^6$ 1301 leukemia cells. The DNA was denatured at 82° C. for 10 minutes and the PNA-FITC probe was hybridized in the dark overnight at room temperature. Propidium Iodide was used to identify the cells in G0/1 phase.

Immunoassays: The ability of the drug product to secrete cytokine upon reactivation was measured following co-culture with mAb-coated beads (Life Technologies, anti-CD3, anti-CD28 & anti-CD137). After 24 hrs culture supernatants were harvested frozen, thawed, and assayed by ELISA using Quantikine IFNγ ELISA kit (R&D systems) according to manufacturer's instructions.

T-cell receptor diversity: RNA from final formulated products was isolated and subjected to a multiplex PCR with VDJ specific primers. CDR3 sequences expressed within the TIL product were semi-quantitatively amplified to determine the frequency and prevalence of unique TIL clones. Sequencing was performed on the Illumina MiSeq benchtop sequencer. Values were indexed to yield a score representative of the relative diversity of T-cell receptors in the product.

TABLE 58

Summary of Process Improvements in Generation 2 Manufacturing

| Process Step | Gen 1 | Gen 2 | Impact |
|---|---|---|---|
| Fragment Culture | ≤21 days, multiple bioreactors, multiple operator interventions | ≤11 days, single closed bioreactor, no intervention | Shortens culture, reduces interventions, amenable to automation. |
| TIL selection | IL-2 expanded TIL cryopreserved, tested, selection based on phenotype, thaw, ≤30 × 10$^6$ TIL to co-culture | ≤200 ×10$^6$ Bulk TIL direct to co-culture | Shorten process by allowing increased seeding of co-culture, reduces steps, eliminates testing |
| Rapid Expansion | ≤36 Bioreactors, 14 days | ≤5 Bioreactors, 11 days | Reduces operator interventions, closed system, shortens process, amenable to automation. |
| Harvest/Wash | Manual open volume reduction and harvest. Manual wash and concentration by centrifugation. | Closed semi-automated volume reduction and harvest. Automated wash and concentration. | Reduces operator interventions, automated, maintains closed system. |
| Formulation | Fresh hypothermic product (2-8° C.) | Cryopreserved product (≤−150° C.) | Shipping flexibility, patient scheduling, easier release testing, global trials |
| Manufacturing Time | 38 day process time | 22 day process time | Turnaround to patient, clean room throughput, COGs |

Analytical Methods and Instrumentation:

Dose and Viability: Final formulated products were sampled and assayed for total nucleated cells, total viable cells, and viability determined by acridine orange/DAPI counterstain using the NC-200 automated cell counter.

Results and Conclusions:

Results are provided in FIGS. 75 through 81.

The Generation 2 process produces a TIL product with comparable quality attributes to Generation 1.

Generation 2 produces similar quantities of highly pure TIL products that are composed similar proportions of T-cell subsets expressing comparable levels of co-stimulatory molecules relative to Gen 1.

Generation 2 TIL display increased diversity of TCR receptors which, when engaged, initiate robust secretion of cytokine.

The cryopreserved drug product introduces critical logistical efficiencies allowing flexibility in distribution.

Unlike prior processes, the Generation 2 abbreviated 22-day expansion platform presents a scalable and logistically feasible TIL manufacturing platform that allows for the rapid generation of clinical scale doses for patients in urgent need of therapy.

The Generation 2 TIL manufacturing protocol addresses many of the barriers that have thus far hindered the wider application of TIL therapy.

Example 24: Evaluating a Range of Allogeneic Feeder Cell:TIL Ratios from 100:1 to 25:1

This study tested the proliferation of TIL at 25:1 and 50:1 against the control of 100:1 allogeneic feeder cells to TIL currently utilized in Process 1C.

Studies published by the Surgery Branch at the National Cancer Institute have shown the threshold for optimal activation of TIL in the G-Rex 100 flask at $5\times10^6$ allogeneic feeder cells per cm$^2$ at the initiation of the REP[1]. This has been verified through mathematical modeling, and, with the same model, predicted that with a feeder layer optimized for cell:cell contact per unit area the proportion of allogeneic feeder cells relative to TIL may be decreased to 25:1 with minimal effect on TIL activation and expansion.

This study established an optimal density of feeder cells per unit area at REP onset, and validated the effective range of allogeneic feeder ratios at REP initiation needed to decrease and normalize the amount of feeder cells used per clinical lot. The study also validated the initiation of the REP with less than $200\times10^6$ TIL co-cultured with a fixed number of feeder cells.

A. Volume of a T-cell (10 μm diameter): $V=(4/3)\pi r^3=523.6$ μm$^3$

B. Columne of G-Rex 100 (M) with a 40 μm (4 cells) height: $V=(4/3)\pi r^3=4\times10^{12}$ m$^3$ C. Number cell required to fill column B: $4\times10^{12}$ μm$^3$/ 523.6 μm$^3=7.6\times10^8$ μm$^3$*0.64=4.86\times10^8$ D. Number cells that can be optimally activated in 4D space: $4.86\times10^8/24-20.25\times10^6$ E. Number of feeders and TIL extrapolated to G-Rex 500: TIL: $100\times10^6$ and Feeder: $2.5\times10^9$ Equation 1. Approximation of the number of mononuclear cells required to provide an icosahedral geometry for activation of TIL in a cylinder with a 100 cm$^2$ base. The calculation derives the experimental result of $5\times10^8$ for threshold activation of T-cells which closely mirrors NCI experimental data.[1] (C) The multiplier (0.64) is the random packing density for equivalent spheres as calculated by Jaeger and Nagel in 1992[2]. (D) The divisor 24 is the number of equivalent spheres that could contact a similar object in 4 dimensional space "the Newton number."[3]

REFERENCES

[1] Jin, Jianjian, et. al., Simplified Method of the Growth of Human Tumor Infiltrating Lymphocytes (TIL) in Gas-Permeable Flasks to Numbers Needed for Patient Treatment. J Immunother. 2012 April; 35(3): 283-292.

[2] Jaeger HM, Nagel SR. Physics of the granular state. Science. 1992 Mar. 20; 255(5051):1523-31.

[3] O. R. Musin (2003). "The problem of the twenty-five spheres". Russ. Math. Surv. 58 (4): 794-795.

Example 25: Studies of Key Quality Attributes for TIL Product

Background

Adoptive T-cell therapy with autologous tumor infiltrating lymphocytes (TIL) has demonstrated clinical efficacy in patients with metastatic melanoma and other tumors[1-3].

Most reports from clinical studies have included exploratory analyses of the infused TIL products with the intention of identifying quality attributes such as sterility, identity, purity, and potency that could relate to product efficacy and/or safety.[4,5]

Here we present the evaluation of three key product parameters from the TIL product that may contribute to a future quality control platform for use in the commercial manufacture of TIL.

Overview of TIL Therapy Process

1. The tumor was excised from the patient and transported to the GMP Manufacturing facility.

2. Upon arrival the tumor is fragmented and placed in flasks with IL-2 for a pre-Rapid Expansion Protocol (REP).

3. pre-REP TIL were further propagated in a REP protocol in the presence of irradiated PBMCs, anti-CD3 antibody (30 ng/mL), and IL-2 (3000 IU/mL).

4. TIL products were assessed for critical quality attributes including: (1) Identity (2) Purity, and (3) Potency.

5. Prior to infusion of expanded TIL (LN-144), patient received a non-myeloablative lymphodepletion regimen consisting of cyclophosphamide and fludarabine. Following infusion of TIL, patients received a short duration (up to 6 doses) of high-dose IL-2 (600,000 IU/kg) to support growth and engraftment of transferred TIL.

Study Objectives

Goal: To fully characterize TIL products for identity, purity, and potency, and thereby (a) guide the definition of critical quality attributes and (b) support the establishment of formal release criteria to be implemented in commercial production of TIL products.

Strategy: To develop the following analytical methodologies to support TIL product characterization. In particular, the following methods were performed: phenotypic analysis by flow cytometry for an identity and purity assessment, residual tumor cell detection assay for a measure of purity, and interferon-gamma release assay for assessment of potency.

Materials & Methods

Identity and Purity

Phenotypic characterization: TIL products were stained with anti-CD45, anti-CD3, anti-CD8, anti-CD4, anti-CD45RA, anti CCR7, anti CD62L, anti-CD19, anti-CD16, and anti-CD56 antibodies and analyzed by flow cytometry for the quantification of T and non-T cell subsets.

Purity

Residual tumor detection assay: TIL products were stained with anti-MCSP (melanoma-associated chondroitin sulfate proteoglycan) and anti-CD45 antibodies, as well as a Live/Dead fixable Aqua dye, then analyzed by flow cytometry for the detection of melanoma cells. Spiked controls were used to assess accuracy of tumor detection and to establish gating criteria for data analysis.

Potency

IFNγ release assay: TIL products were re-stimulated with anti-CD3/CD28/CD137 coated beads for 18 to 24 hours after which supernatants were harvested for assessment of IFNγ secretion using an ELISA assay.

Results

Figure 86A:
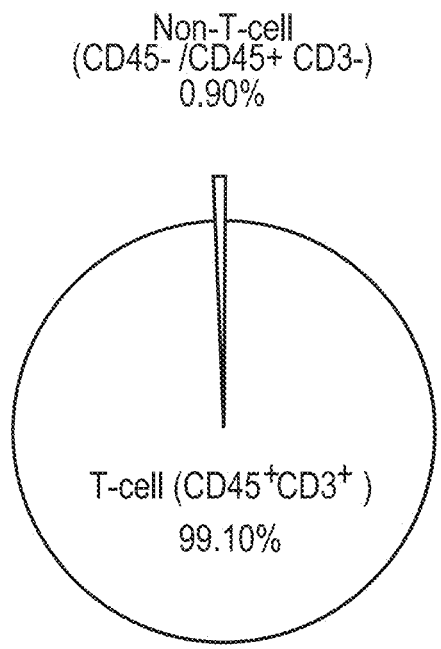
FIGS. 86A-86C: Phenotypic characterization of TIL products using 10-color flow cytometry assay. (A) Percentage of T-cell and non-T-cell subsets is defined by $CD45^+CD3^+$ and CD45-(non-lymphocyte)/$CD45^+CD3^-$ (non-T-cell lymphocyte), respectively. Overall, >99% of the TIL products tested consisted of T-cell ($CD45^+CD3^+$). Shown is an average of TIL products (n=10). (B) Percentage of two T-cell subsets including $CD45^+CD3^+CD8^+$ (blue open circle) and $CD45^+CD3^+CD4^+$ (pink open circle). No statistical difference in percentage of both subsets is observed using student's unpaired T test (P=0.68). (C) Non-T-cell population was characterized for four different subsets including: 1) Non-lymphocyte ($CD45^-$), 2) NK cell ($CD45^+CD3^-CD16^+/56^+$), 3) B-cell ($CD45^+CD19^+$), and 4) Non-NK/B-cell ($CD45^+CD3^-CD16^-CD56^-CD19^-$).
Figure 86B:
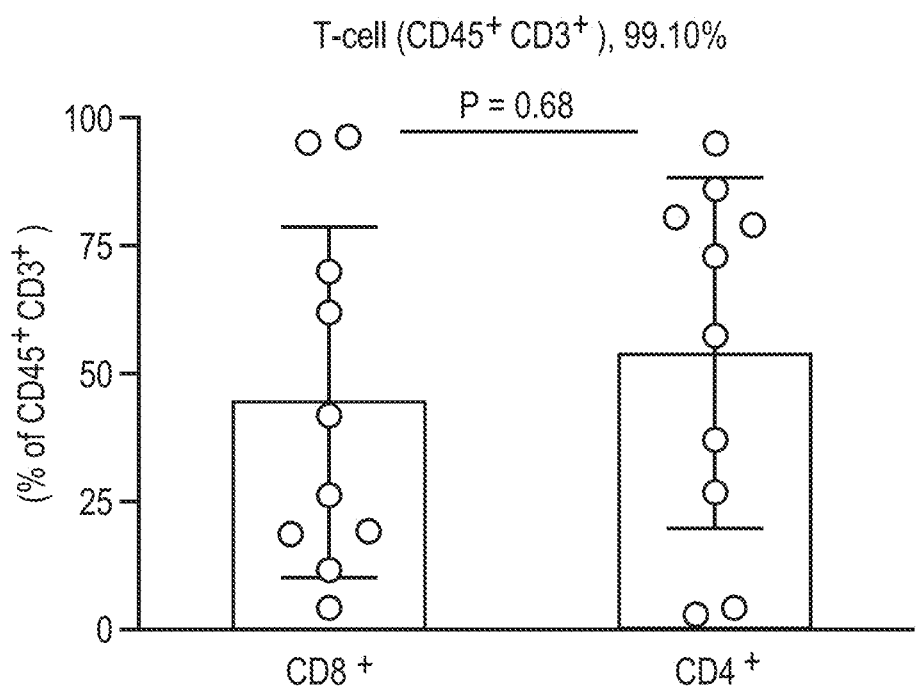
Figure 86C:
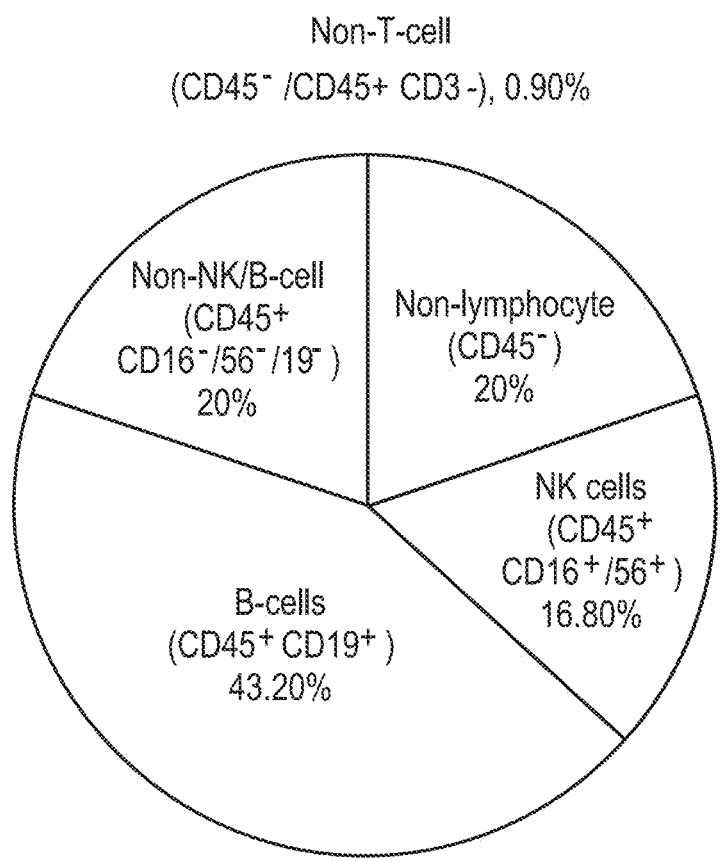

Identity: The majority (>99%) of melanoma TIL product was composed of CD45$^+$CD3$^+$ cells FIGS. 86A-86C provides phenotypic characterization of TIL products using 10-color flow cytometry assay. (A) Percentage of T-cell and non-T-cell subsets was defined by CD45$^+$CD3$^+$ and CD45$^-$ (non-lymphocyte)/CD45$^+$CD3$^-$ (non-T-cell lymphocyte), respectively. Overall, >99% of the TIL products tested consisted of T-cell (CD45$^+$CD3$^+$). Shown is an average of TIL products (n=10). (B) Percentage of two T-cell subsets including CD45$^+$CD3$^+$CD8$^+$ (blue open circle) and CD45$^+$CD3$^+$CD4$^+$ (pink open circle). No statistical difference in percentage of both subsets was observed using student's unpaired T test (P=0.68). (C) Non-T-cell population was characterized for four different subsets including: 1) Non-lymphocyte (CD45$^-$), 2) NK cell (CD45$^+$CD3$^-$CD16$^+$/56$^+$), 3) B-cell (CD45$^+$CD19$^+$), and 4) Non-NK/B-cell (CD45$^+$CD3$^-$CD16$^-$CD56$^-$CD19$^-$).

Identity: The majority of melanoma TIL product exhibited effector or memory T-cell phenotype, associated with T-cell cytotoxic function.

Figure 87A:
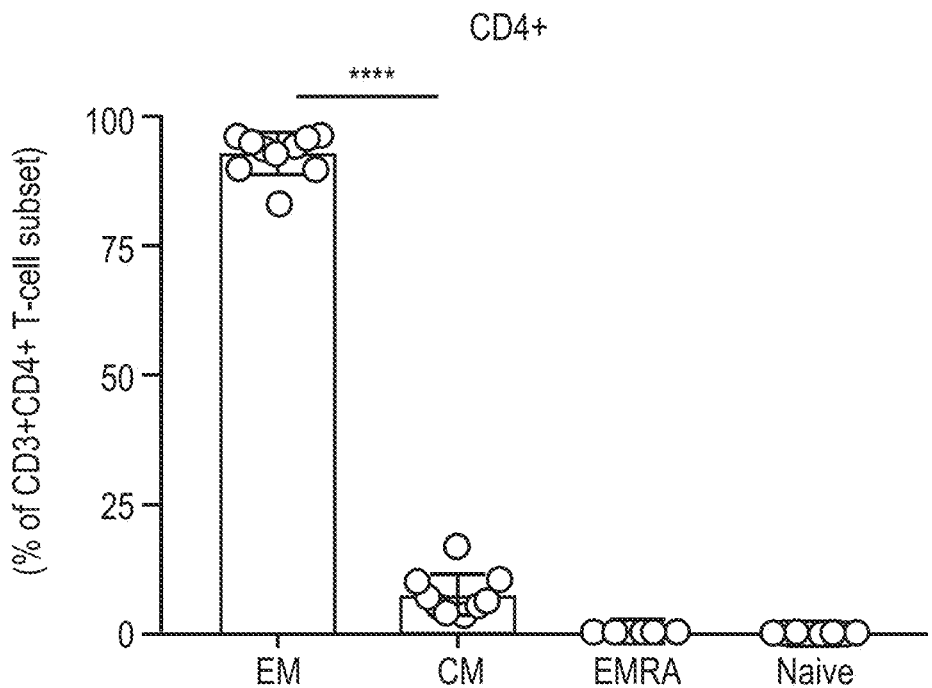
FIGS. 87A-87B: Characterization of T-cell subsets in CD45+CD3+CD4+ and CD45+CD3+CD8+ cell populations. Naïve, central memory (TCM), effector memory (TEF), and effector memory RA+(EMRA) T-cell subsets were defined using CD45RA and CCR7. Figures show representative T-cell subsets from 10 final TIL products in both CD4+(A), and CD8+(B) cell populations. Effector memory T-cell subset (blue open circle) is a major population (>93%) in both CD4+ and CD8+ subsets of TIL final product. Less than 7% of the TIL products cells is central memory subset (pink open circle). EMRA (gray open circle) and naïve (black open circle) subsets are barely detected in TIL product (<0.02%). p values represent the difference between EM and CM using student's unpaired T test
Figure 87B:
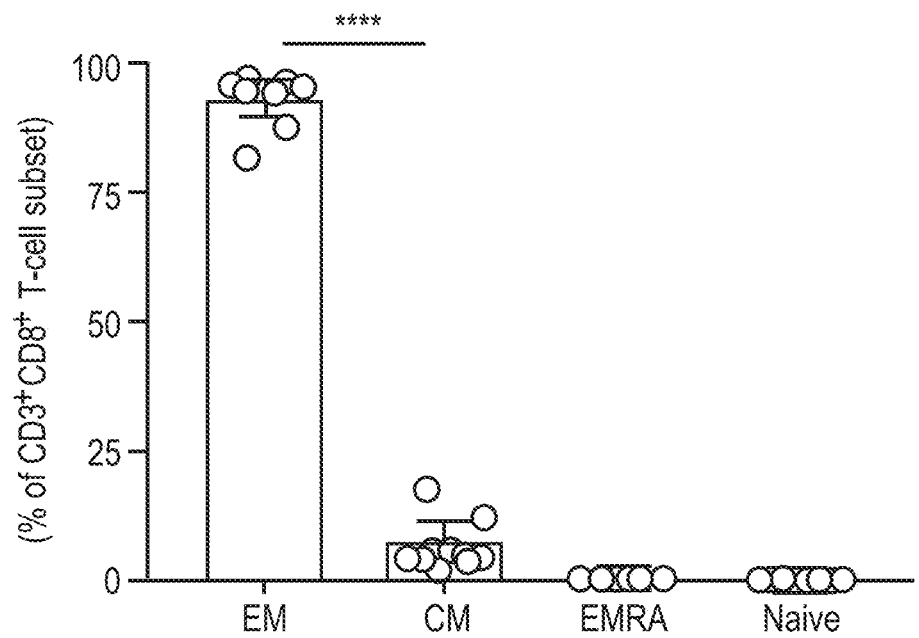

FIGS. 87A and 87B show the characterization of T-cell subsets in CD45$^+$CD3$^+$CD4$^+$ and CD45$^+$CD3$^+$CD8$^+$ cell populations. Naïve, central memory (TCM), effector memory (TEF), and effector memory RA$^+$ (EMRA) T-cell subsets were defined using CD45RA and CCR7. FIGS. 87A and 87B show representative T-cell subsets from 10 final TIL products in both CD4$^+$ (A), and CD8$^+$ (B) cell populations. Effector memory T-cell subset (blue open circle) were a major population (>93%) in both CD4$^+$ and CD8$^+$ subsets of TIL final product. Less than 7% of the TIL products cells were central memory subset (pink open circle). EMRA (gray open circle) and naïve (black open circle) subsets were barely detected in TIL product (<0.02%). p values represent the difference between EM and CM using student's unpaired T test.

Purity: MCSP represents an appropriate melanoma tumor marker for purity assay.

Figure 88A:
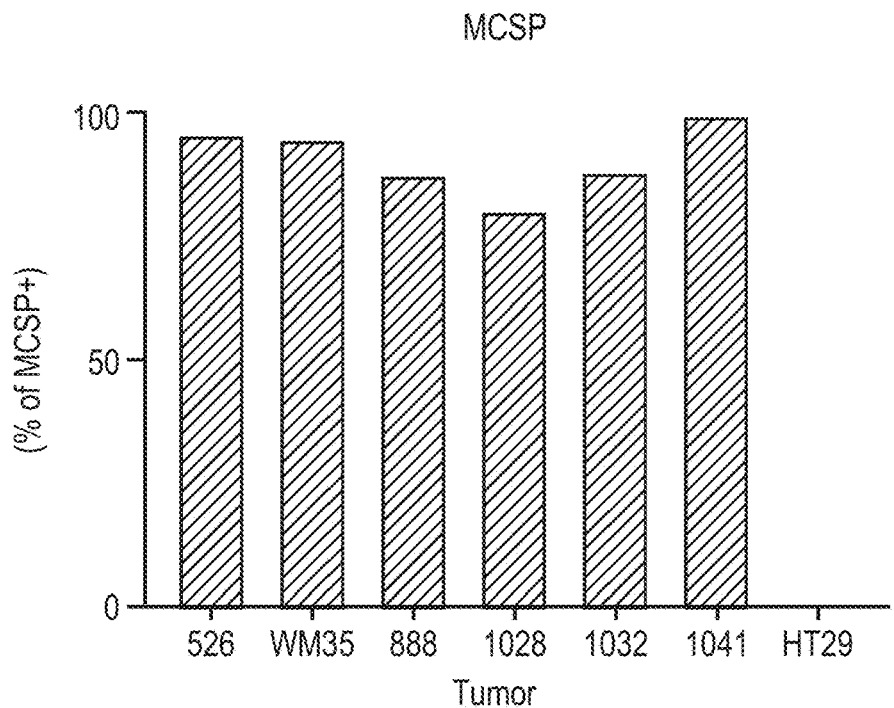
FIGS. 88A-88B: Detection of MCSP and EpCAM expression in melanoma tumor cells. Melanoma tumor cell lines (WM35, 526, and 888), patient-derived melanoma cell lines (1028, 1032, and 1041), and a colorectal adenoma carcinoma cell line (HT29 as a negative control) were characterized by staining for MCSP (melanoma-associated chondroitin sulfate proteoglycan) and EpCAM (epithelial cell adhesion molecule) markers. (A) Average of 90% of melanoma tumor cells express MCSP. (B) EpCAM expression was not detected in melanoma tumor cell lines as compared positive control HT29, an EpCAM+ tumor cell line.
Figure 88B:
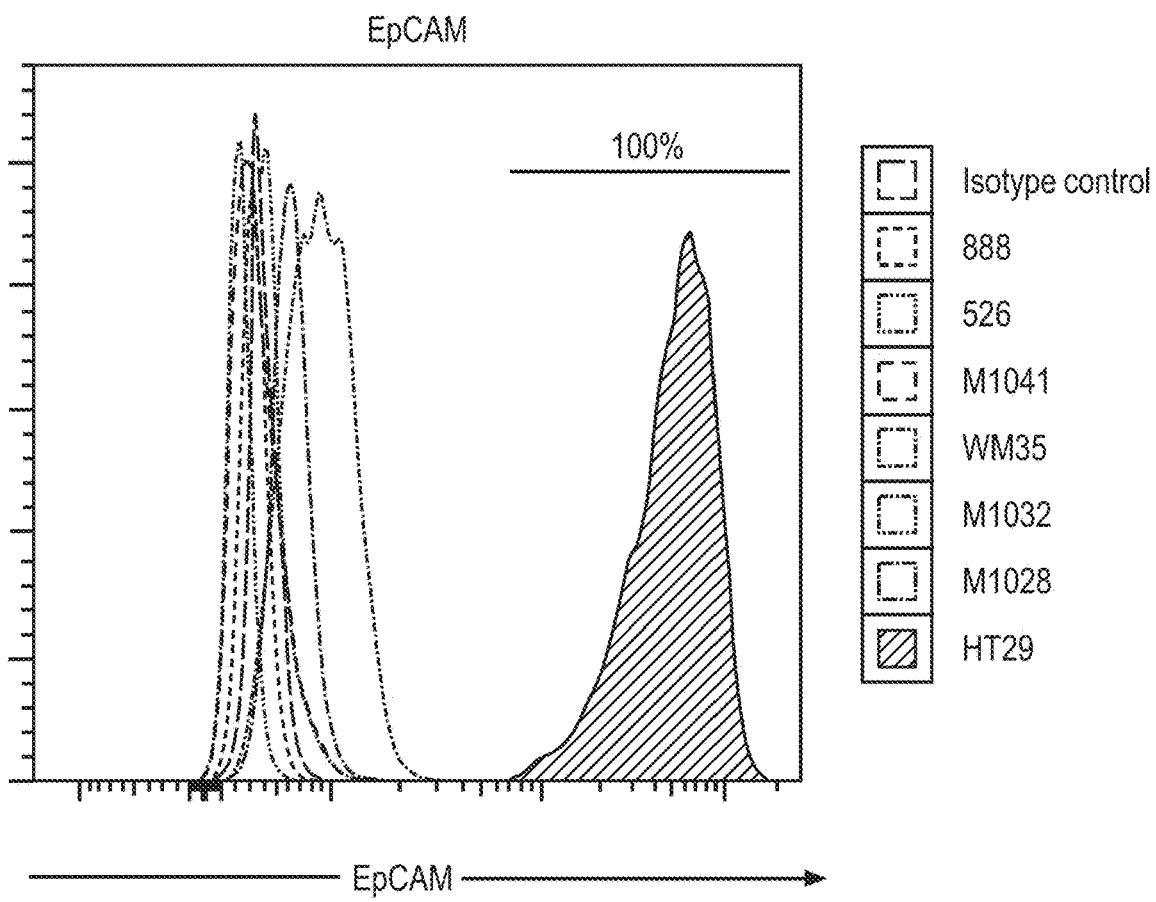

FIGS. 88A and 88B show the detection of MCSP and EpCAM expression in melanoma tumor cells. Melanoma tumor cell lines (WM35, 526, and 888), patient-derived melanoma cell lines were generated according to the methods described herein (1028, 1032, and 1041), and a colorectal adenoma carcinoma cell line (HT29 as a negative control) were characterized by staining for MCSP (melanoma-associated chondroitin sulfate proteoglycan) and EpCAM (epithelial cell adhesion molecule) markers. (A) Average of 90% of melanoma tumor cells expressed MCSP. (B) EpCAM expression was not detected in melanoma tumor cell lines as compared positive control HT29, an EpCAM+ tumor cell line.

Purity: Development of a flow cytometry-based assay for detection of residual tumor cells in TIL products.

Figures 89A, 89B:
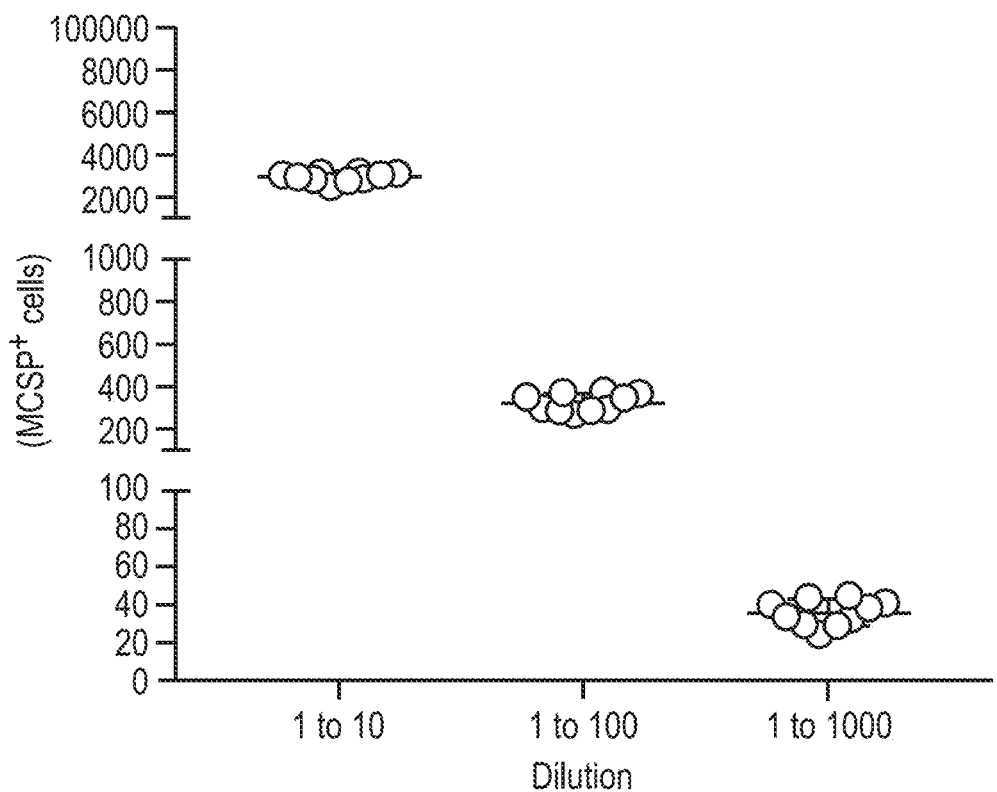
FIGS. 89A-89B: Detection of spiked controls for the determination of tumor detection accuracy. The assay was performed by spiking known amounts of tumor cells into PBMC suspensions (n=10). MCSP+526 melanoma tumor cells were diluted at ratios of 1:10, 1:100, and 1:1,000, then mixed with PBMC and stained with anti-MCSP and anti-CD45 antibodies and live/dead dye and analyzed by flow cytometry. (A) Approximately 3000, 300, and 30 cells were detected in the dilution of 1:10, 1:100, and 1:1000, respectively. (B) An average (AV) and standard deviation (SD) of cells acquired in each condition was used to define the upper and lower reference limits.

FIGS. 89A and 89B illustrate the detection of spiked controls for the determination of tumor detection accuracy. The assay was performed by spiking known amounts of tumor cells into PBMC suspensions (n=10). MCSP+526 melanoma tumor cells were diluted at ratios of 1:10, 1:100, and 1:1,000, then mixed with PBMC and stained with anti-MCSP and anti-CD45 antibodies and live/dead dye and analyzed by flow cytometry. (A) Approximately 3000, 300, and 30 cells were detected in the dilution of 1:10, 1:100, and 1:1000, respectively. (B) An average (AV) and standard deviation (SD) of cells acquired in each condition was used to define the upper and lower reference limits.

Purity: Qualification of residual tumor detection assay using spiked controls

Figures 90A, 90B:
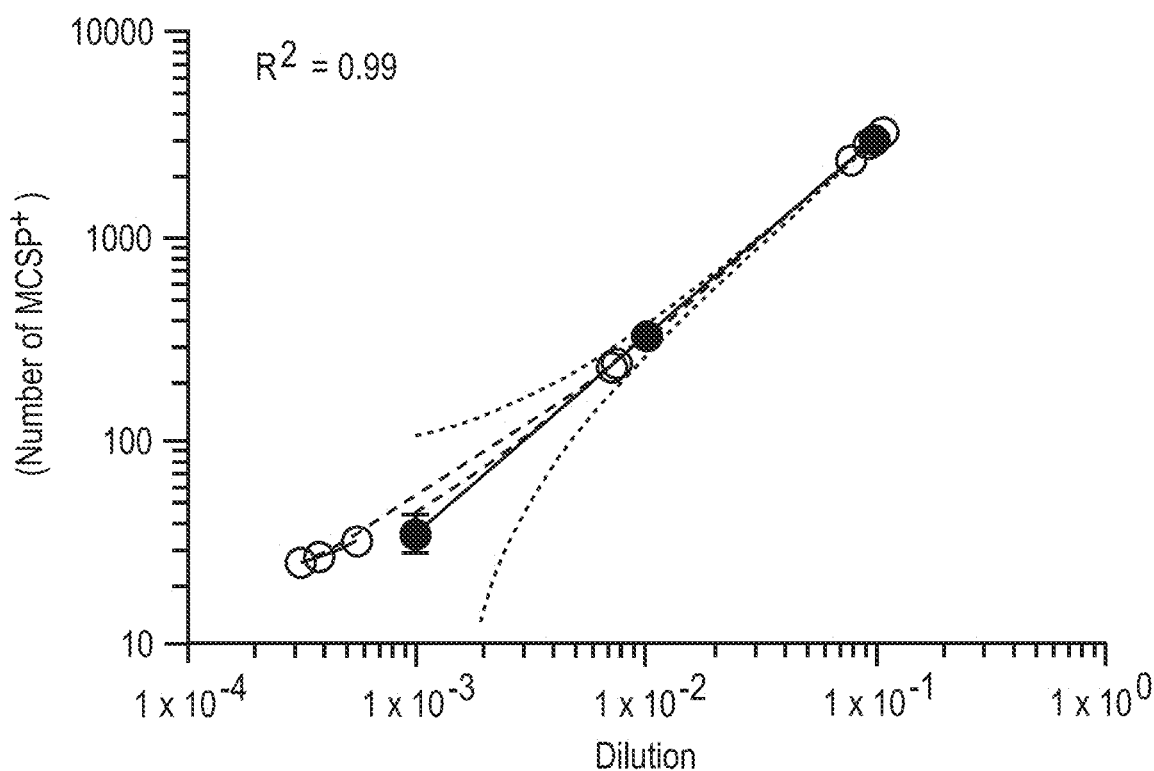
FIGS. 90A-90B: Repeatability study of upper and lower limits in spiked controls. Three independent experiments were performed in triplicate to determine the repeatability of spiking assay. (A) The number of $MCSP^+$ detected tumor cells were consistently within the range of upper and lower reference limits. (B) Linear regression plot demonstrates the correlation between $MCSP^+$ cells and spiking dilutions ($R^2$=0.99) with the black solid line showing the best fit. The green and gray broken lines represent the 95% prediction limits in standard curve and samples (Exp #1 to 3), respectively.

FIGS. 90A and 90B show the repeatability study of upper and lower limits in spiked controls. Three independent experiments were performed in triplicate to determine the repeatability of spiking assay. (A) The number of MCSP$^+$ detected tumor cells were consistently within the range of upper and lower reference limits. (B) Linear regression plot demonstrates the correlation between MCSP$^+$ cells and spiking dilutions ($R^2$=0.99) with the black solid line showing the best fit. The green and gray broken lines represent the 95% prediction limits in standard curve and samples (Exp #1 to 3), respectively.

Purity: Melanoma tumor cell contaminants were below the limits of assay detection in final TIL product.

Figures 91A, 91B:
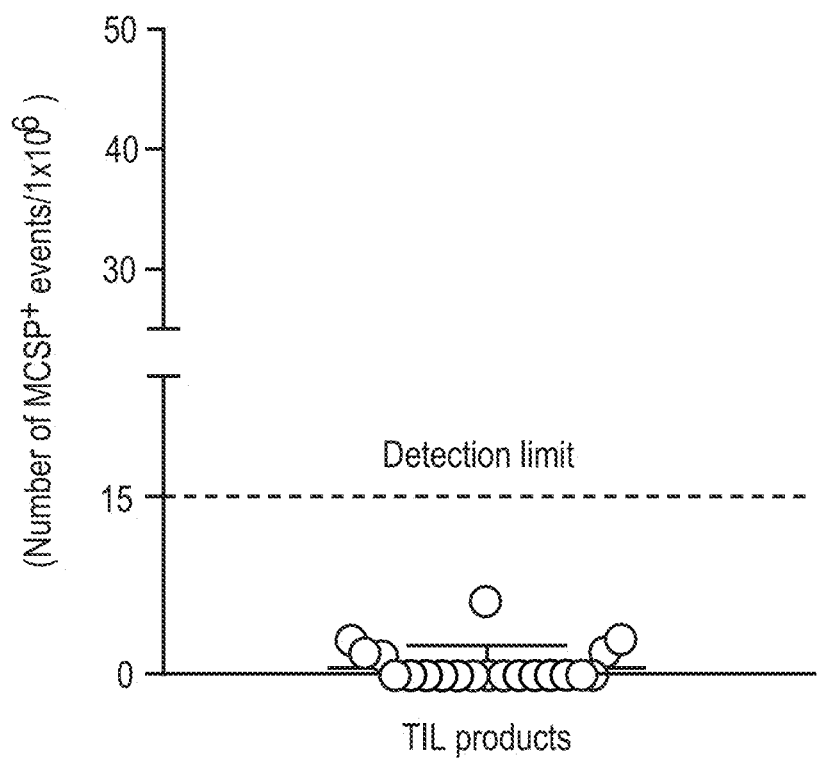
FIGS. 91A-91B: Detection of residual melanoma tumor in TIL products. TIL products were assessed for residual tumor contamination using the developed assay (n=15). (A and B) The median number and percentage of detectable MCSP+ events was 2 and 0.0002%, respectively.

FIGS. 91A and 91B show the detection of residual melanoma tumor in TIL products. TIL products were assessed for residual tumor contamination using the developed assay (n=15). The median number and percentage of detectable MCSP+ events was 2 and 0.0002%, respectively.

Potency: IFNγ secretion by TIL (consistently >1000 pg/ml) demonstrated effector function of TIL product.

Figure 92:
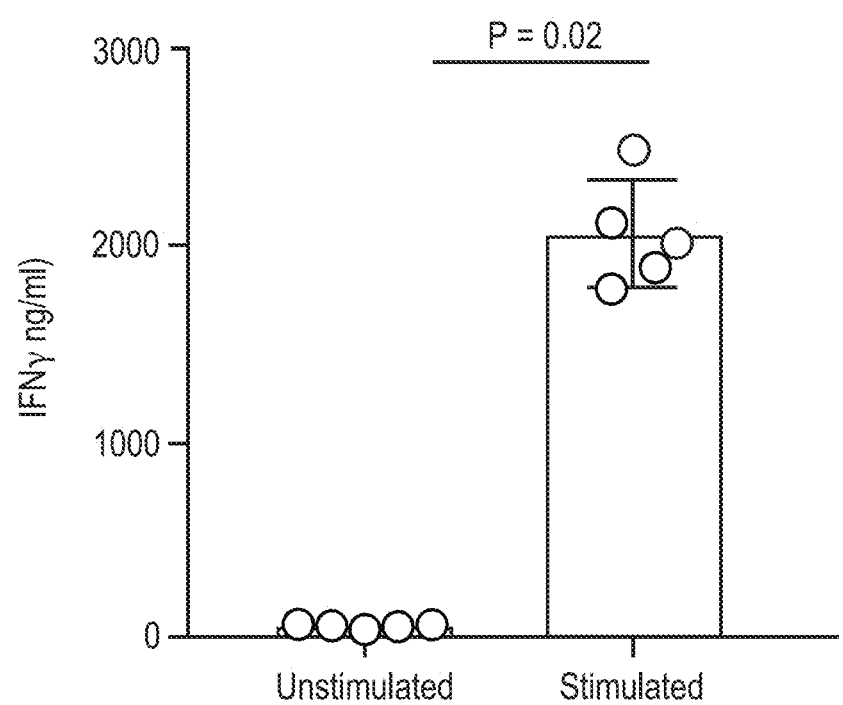
FIG. 92: Potency assessment of TIL products following T-cell activation. IFNγ secretion after re-stimulation with anti-CD3/CD28/CD137 in TIL products assessed by ELISA in duplicate (n=5). IFNγ secretion by the TIL products was significantly greater than unstimulated controls using Wilcoxon signed rank test (P=0.02), and consistently >1000 pg/ml. IFNγ secretion >200 pg/ml is considered to be potent. p value <0.05 is considered statistically significant.

FIG. 92 shows the potency assessment of TIL products following T-cell activation. IFNγ secretion after re-stimulation with anti-CD3/CD28/CD137 in TIL products assessed by ELISA in duplicate (n=5). IFNγ secretion by the TIL products was significantly greater than unstimulated controls using Wilcoxon signed rank test (P=0.02), and consistently >1000 pg/ml. IFNγ secretion >200 pg/ml was considered to be potent. p value <0.05 is considered statistically significant.

Conclusion

Key product parameters of identity, purity, and potency of TIL products were evaluated. TIL products manufactured according to the methods described herein consisted of greater than 99% CD45+CD3+ T cells. The majority of CD4+ and CD8+ TIL subsets exhibited an effector-memory phenotype, associated with T-cell cytotoxic function. A flow cytometry-based assay to detect contaminant melanoma tumor cells in final TIL product was successfully developed and qualified. Applying this assay, contaminant melanoma tumor cells in final TIL product were shown to be below the limits of assay detection. IFNγ secretion by final TIL product following anti-CD3/CD28/CD137 re-stimulation may serve as a potency assay for commercially manufactured TIL. These data provide the foundation of a quality control platform that will support further development of critical quality attributes for commercial production of TIL products.

Example 26: A Cryopreserved TIL Product Generated with an Abbreviated Method Suitable for High Throughput Commercial Manufacturing Exhibits Favorable Quality Attributes for Adoptive Cell Transfer Background Classical methods of generating tumor infiltrating lymphocytes (TIL) for adoptive cell transfer (ACT) involve multiple ex vivo incubation steps to yield a fresh (non-cryopreserved) infusion product.

Figure 93:
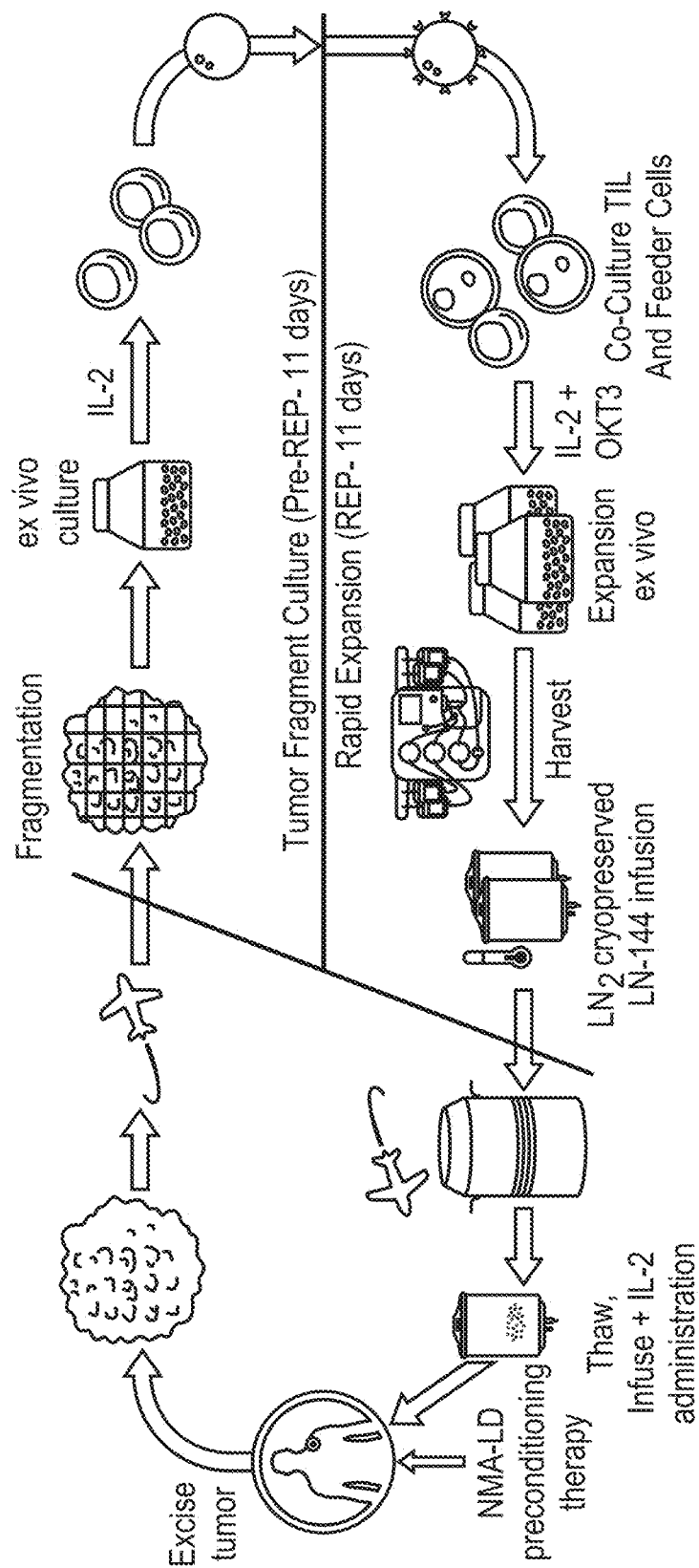
FIG. 93: Depiction of an embodiment of a cryopreserved TIL manufacturing process (22 days).

The first generation (Gen 1) process produced a dose of fresh TIL in approximately 6 weeks. A second generation (Gen 2) TIL manufacturing process which abbreviates the ex vivo culture duration to 22 days was developed (FIG. 93).

The Gen 2 process is suitable for centralized manufacturing and yields a cryopreserved TIL infusion product that brings convenience in scheduling, logistics, and delivery to the clinical sites. The cryopreserved TIL infusion product for LN-144 produced by the Gen 2 process has comparable quality attributes to the non-cryopreserved TIL infusion product for TILs generated by the Gen 1 method. The Gen 2 TIL manufacturing method represents a flexible, robust, closed, and semi-automated cell production process that is amenable to high throughput TIL manufacturing on a commercial scale.

Study Objective

TIL infusion products generated by Gen 1 and Gen 2 manufacturing processes were assessed to determine comparability in terms of the following quality attributes: (1) Cell count (dose), viability, growth rate of REP phase, (2) T-cell purity and phenotypic expression of co-stimulatory molecules on T-cell subsets, (3) Average relative length of telomere repeats, (4) Ability to secrete IFNγ in response to CD3, CD28, CD137 engagement, and (5) Diversity of T-cell receptors present in the final infusion product (FIG. 94).

Analytical Methods & Instrumentation

Cell Count and Viability: Final formulated infusion products were sampled and assayed for total nucleated cells, total viable cells, and viability determined by acridine orange/DAPI counterstain using the NC-200 automated cell counter. Process Development lots were assayed on the Nexcellom Cellometer K2 Cell Viability Counter using acridine orange/propidium iodine dual florescent staining.

Phenotypic markers: Formulated infusion products were sampled and assayed for identity by immunofluorescent staining. Percent T-cells was determined as the CD45+, CD3+(double positive) population of viable cells. Frozen satellite or sentinel vials for each process were thawed and assayed for extended phenotypic markers including CD3, CD4, CD8, CD27, and CD28. Fresh infusion products were acquired on the BD FACS Canto II, and extended phenotypic markers on thawed infusion products were acquired on the Bio-Rad ZE5 Cell Analyzer.

Average relative length of telomere repeats: Flow-FISH technology was used to measure average length of telomere repeat. This assay was completed as described in the DAKO® Telomere PNA Kit/FITC for Flow Cytometry protocol. Briefly, $2.0 \times 10^6$ TIL cells were combined with $2.0 \times 10^6$ human cell line (1301) leukemia T-cells. The DNA was denatured at 82° C. for 10 minutes and the PNA-FITC probe was hybridized in the dark overnight at room temperature. Propidium Iodide was used to identify the cells in G0/1 phase.

Immune function: The ability of the infusion product to secrete IFNγ upon reactivation was measured following co-culture with antibody coated beads (Life Technologies, anti-CD3, anti-CD28 & anti-CD137). After 24 hours culture supernatants were harvested, frozen, thawed, and assayed by ELISA using the Quantikine IFNγ ELISA kit (R&D systems) according to manufacturer's instructions.

T-cell receptor diversity: RNA from infusion products was isolated and subjected to a multiplex PCR with VDJ specific primers. CDR3 sequences expressed within the TIL product were semi-quantitatively amplified and deep sequenced to determine the frequency and prevalence of unique TIL clones. Sequencing was performed on the Illumina MiSeq benchtop sequencer. Values were indexed to yield a score representative of the relative diversity of T-cell receptors in the product.

Results

Figure 95A:
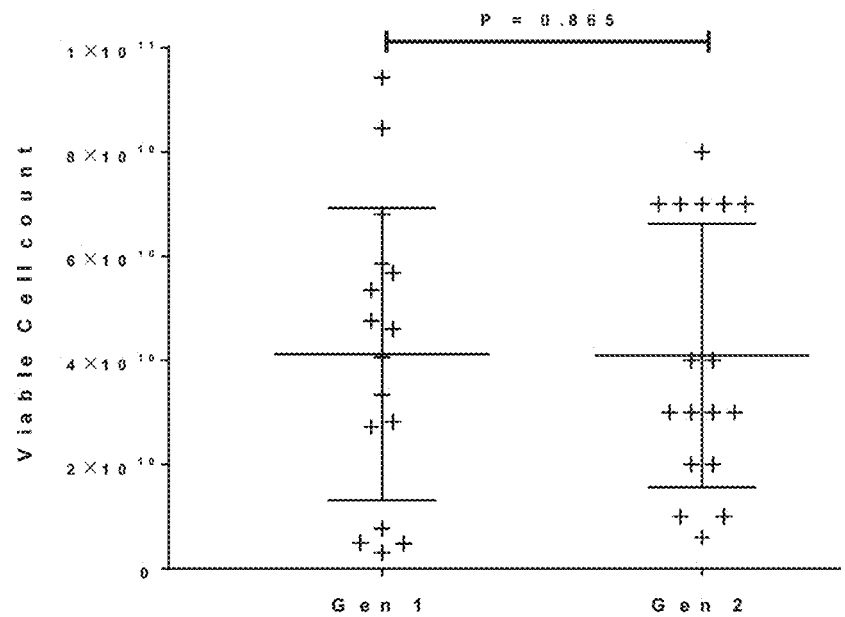
FIGS. 95A-95C: Total viable cells, growth rate, and viability. On Day 22 the volume reduced cell product is pooled and sampled to determine culture performance prior to wash and formulation. (A) Samples are analyzed on the NC-200 automated cell counter as previously described. Total viable cell density is determined by the grand mean of duplicate counts from 4 independent samples. The Gen 2 process yields a TIL product of similar dose to Gen 1 (Gen 1 mean=$4.10 \times 10^{10} \pm 2.8 \times 10^{10}$, Gen 2 mean=$4.12 \times 10^{10} \pm 2.5 \times 10^{10}$). (B) The growth rate is calculated for the REP phase as gr=ln(N(t)/N(0))/t. (C) Cell viability was assessed from 9 process development lots using the Cellometer K2 as previously described. No significant decrease in cell viability was observed following a single freeze-thaw cycle of the formulated product. Average reduction in viability upon thaw and sampling is 2.19%.
Figure 95B:
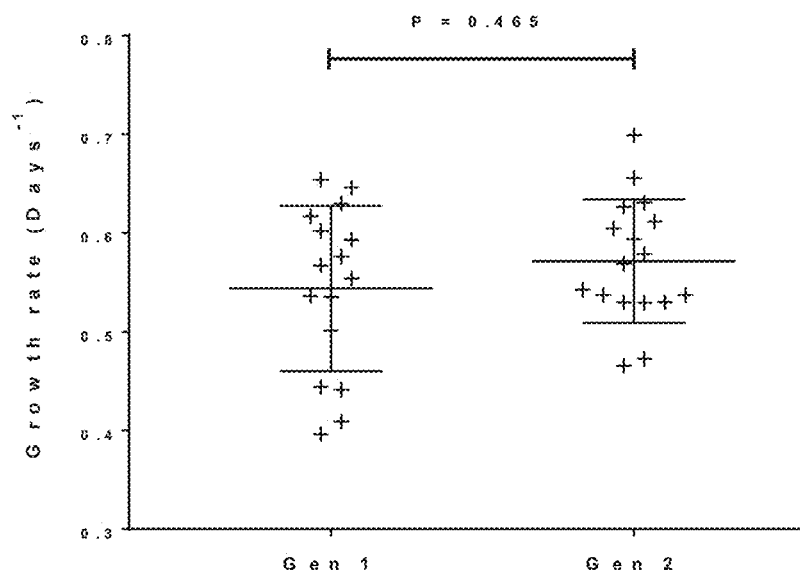
Figure 95C:
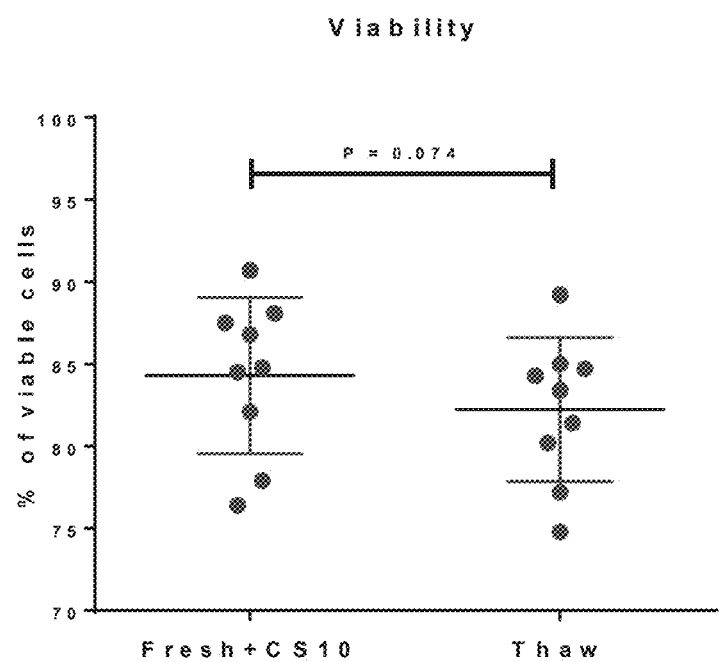

On Day 22 the volume reduced cell product was pooled and sampled to determine culture performance prior to wash and formulation. FIGS. 95A-95C shows total viable cells, growth rate, and viability. (A) Samples were analyzed on the NC-200 automated cell counter as previously described. Total viable cell density is determined by the grand mean of duplicate counts from 4 independent samples. The Gen 2 process yielded a TIL product of similar dose to Gen 1 (Gen 1 mean=$4.10 \times 10^{10} \pm 2.8 \times 10^{10}$, Gen 2 mean=$4.12 \times 10^{10} \pm 2.5 \times 10^{10}$). (B) The growth rate was calculated for the REP phase as. (C) Cell viability was assessed from 9 process development lots using the Cellometer K2 as previously described. No significant decrease in cell viability was observed following a single freeze-thaw cycle of the formulated product. Average reduction in viability upon thaw and sampling was 2.19%.

Figure 96A:
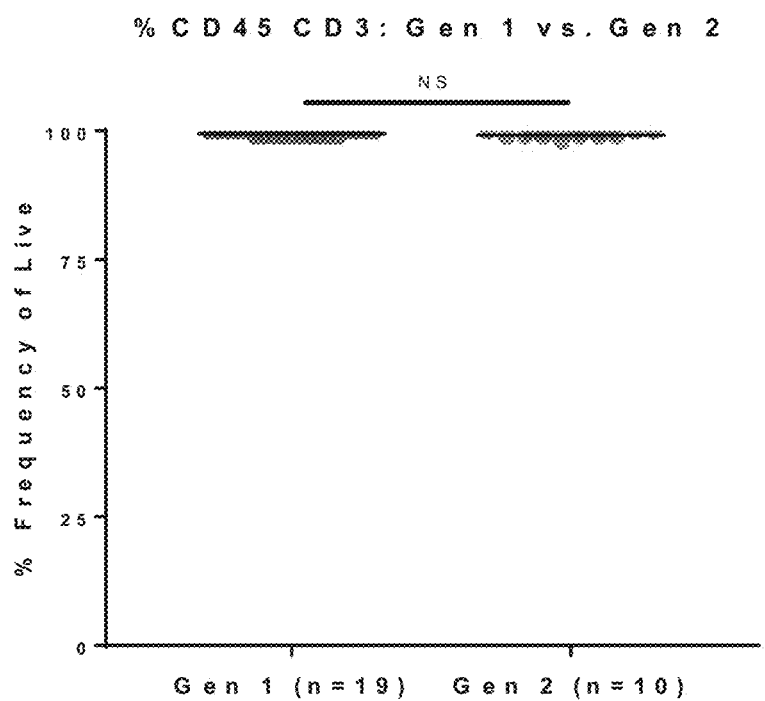
FIGS. 96A-96C: Gen 2 products are highly pure T-cell cultures which express costimulatory molecules at levels comparable to Gen 1. (A) Fresh formulated drug products were assayed for identity by flow cytometry for release. Gen 1 and Gen 2 processes produce high purity T-cell cultures as defined by CD45+, CD3+(double positive) phenotype. (B & C) Cryopreserved satellite vials of formulated drug product were thawed and assayed for extended phenotype by flow cytometry as previously described. Gen 1 and Gen 2 products express similar levels of costimulatory molecules CD27 and CD28 on T-cell subsets. Costimulatory molecules such as CD27 and CD28 are required to supply secondary and tertiary signaling necessary for effector cell proliferation upon T-cell receptor engagement. P-value was calculated using Mann-Whitney 't' test.
Figure 96B:
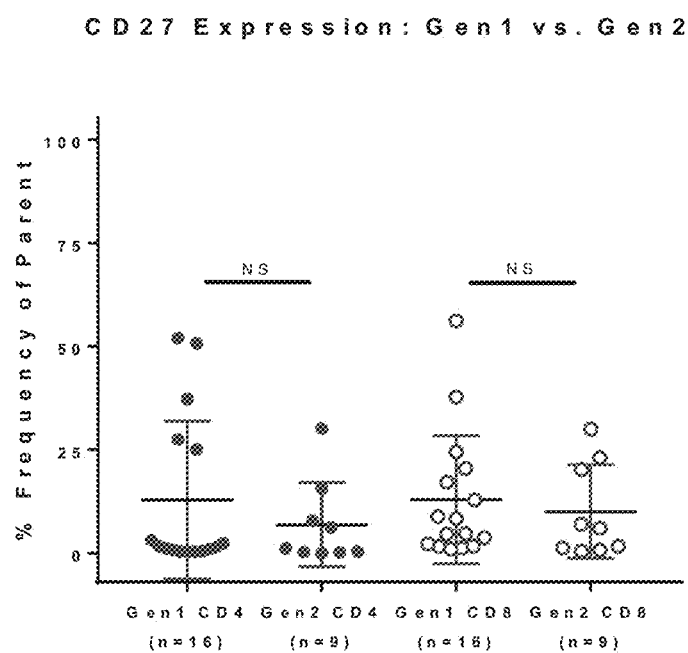
Figure 96C:
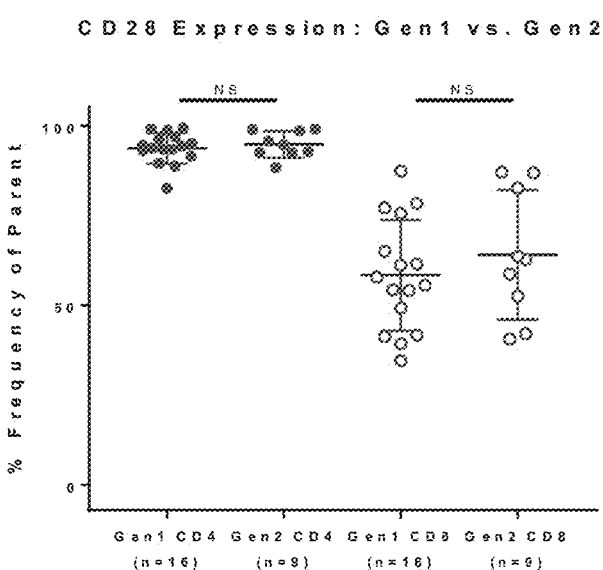

FIGS. 96A-96C show that Gen 2 products are highly pure T-cell cultures which express costimulatory molecules at levels comparable to Gen 1. (FIG. 96A) Fresh formulated drug products were assayed for identity by flow cytometry for release. Gen 1 and Gen 2 processes produce high purity T-cell cultures as defined by CD45+, CD3+(double positive) phenotype. (FIGS. 96B and 96C) Cryopreserved satellite vials of formulated drug product were thawed and assayed for extended phenotype by flow cytometry as previously described. Gen 1 and Gen 2 products expressed similar levels of costimulatory molecules CD27 and CD28 on T-cell subsets. Costimulatory molecules such as CD27 and CD28 may be required to supply secondary and tertiary signaling necessary for effector cell proliferation upon T-cell receptor engagement. P-value was calculated using Mann-Whitney 't' test.

Figure 97:
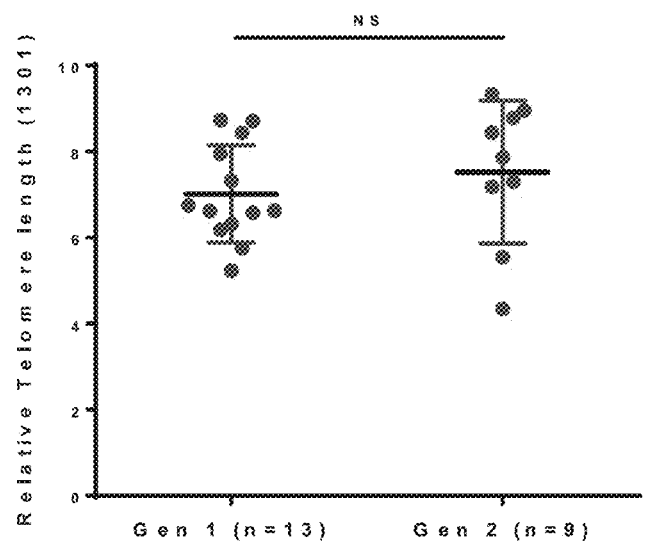
FIG. 97: Gen 2 products exhibit similar telomere lengths. However, some TIL populations may trend toward longer relative telomere.

FIG. 97 shows that Gen 2 products trend toward longer relative telomere. Lengths. Flow-FISH technology was used to measure the average length of the telomere repeat as previously described. The RTL value indicated that the average telomere fluorescence per chromosome/genome in Gen 1 was 7.5%±2.1%, and Gen 2 was 8.4% 1.8% of the telomere fluorescence per chromosome/genome in the control cells line (1301 Leukemia cell line). Data indicate Gen 2 products on average have comparable telomere lengths to Gen 1 products. Telomere length is a surrogate measure of the length of ex vivo cell culture.

Figure 98:
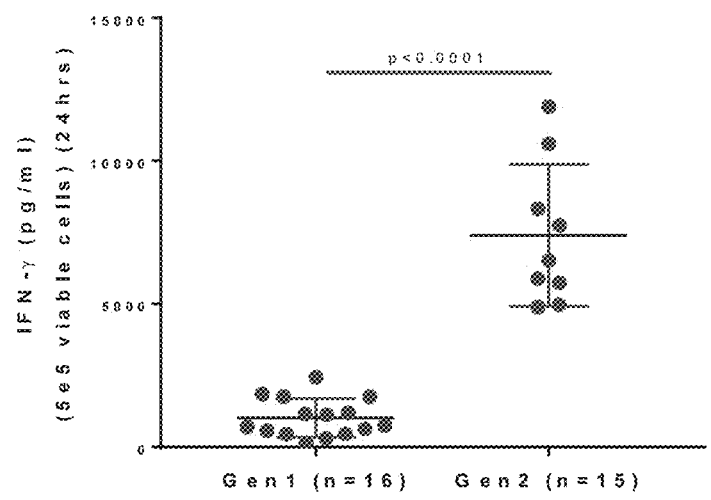
FIG. 98: Gen 2 drug products secrete IFNγ in response to CD3, CD28, and CD137 engagement.

FIG. 98 shows that Gen 2 drug products secrete IFNγ in response to CD3, CD28, and CD137 engagement. Cryopreserved drug products were thawed and incubated with antibody-coated beaded as previously described. Data is expressed as the amount of IFNγ produced by 5×105 viable cells in 24 hrs. Gen 2 drug products exhibited an increased ability to produce IFNγ upon reactivation relative to Gen 1 drug products. The ability of the drug product to be reactivated and secrete cytokine is a surrogate measure of in-vivo function upon TCR binding to cognate antigen in the context of HLA.

Figure 99A:
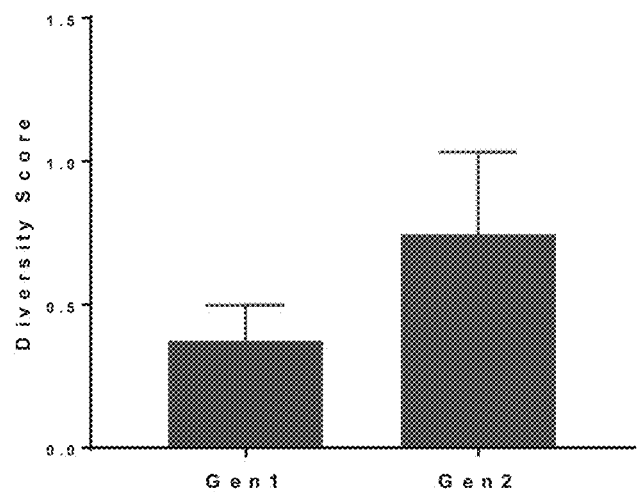
FIGS. 99A-99B: T-cell receptor diversity. (A) Unique CDR3 sequences were indexed relative to frequency in each product to yield a score representative of the overall diversity of T-cell receptors in the product. (B) The average total number of unique CDR3 sequences present in each infusion product.
Figure 99B:
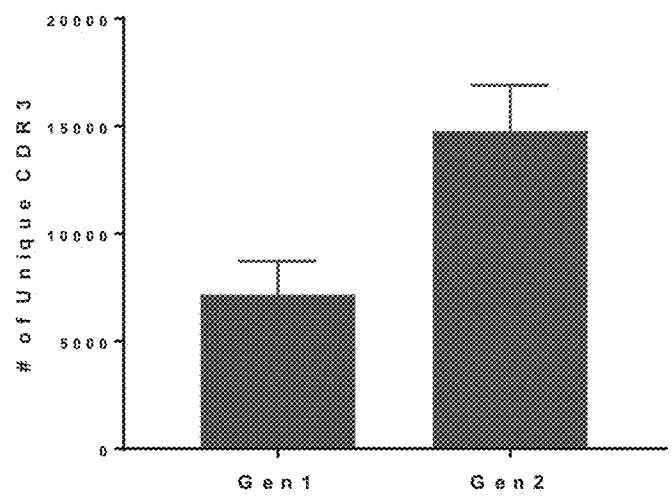

FIGS. 99A and 99B shows that Gen 2 drug products have an increased diversity of unique T-cell receptors. T-cell receptor diversity was assessed as follows. RNA from $10 \times 10^6$ TIL from Gen 1 and Gen 2 infusion products was assayed to determine the total number and frequency of unique CDR3 sequences present in each product. (FIG. 99A) Unique CDR3 sequences were indexed relative to frequency in each product to yield a score representative of the overall diversity of T-cell receptors in the product. (FIG. 99B) The average total number of unique CDR3 sequences present in each infusion product. TIL products from both processes were composed of polyclonal populations of T-cells with different antigen specificities and avidities. The breadth of the total T-cell repertoire may be indicative of the number of actionable epitopes presented on tumor cells.

Conclusions

The Gen 2 manufacturing process produced a TIL infusion product (LN-144) with comparable quality attributes to Gen 1. Gen 2 produced similar doses of highly pure TIL. T-cell subsets were in similar proportions and expressed costimulatory molecules at comparable levels of relative to Gen 1. Gen 2 TIL trended toward longer relative telomere length commensurate with reduced ex vivo culture period. Gen 2 TIL displayed an increased diversity of TCR receptors which, when engaged, initiated robust secretion of IFN-γ, a measure of cytolytic effector function. Thus, the Gen 2 abbreviated 22-day closed expansion process with cryopreserved infusion product presents a scalable and logistically feasible TIL manufacturing platform that allows for the rapid generation of clinical scale doses for cancer patients in immediate need of a novel therapy option.

REFERENCES

[1] Dudley, M. E. et al. Adoptive cell transfer therapy following non-myeloablative but lymphodepleting chemotherapy for the treatment of patients with refractory metastatic melanoma. *J. Clin Oncol* 23, 2346-2357, doi:10.1200/JCO.2005.00.240 (2005).
[2] Chandran, S. S. et al. Treatment of metastatic uveal melanoma with adoptive transfer of tumour-infiltrating lymphocytes: a single-centre, two-stage, single-arm, phase 2 study. *Lancet Oncol*, doi:10.1016/SI470-2045(17)30251-6 (2017).
[3] Stevanovic, S. et al. Complete regression of metastatic cervical cancer after treatment with human papillomavirus-targeted tumor-infiltrating T cells. *J Clin Oncol* 33, doi:10.1200/jco.2014.58.9093 (2015).
[4] FDA Reviewers and Sponsors: Content and Review of Chemistry, Manufacturing, and Control (CMC) Information for Human Gene Therapy Investigational New Drug Applications (INDs), 21 CFR 610.3(r), 2008.
[5] Richards J O, Treisman J, Garlie N, Hanson J P, Oaks M K. Flow cytometry assessment of residual melanoma cells in tumor-infiltrating lymphocyte cultures. Cytometry A 2012; 81:374-81.

Example 27: The T-Cell Growth Factor Cocktail IL-2/IL-15/IL-21 Enhanced Expansion and Effector Function of Tumor-Infiltrating T Cells in a Novel Process Described Herein Background Adoptive T cell therapy with autologous TILs has demonstrated clinical efficacy in patients with metastatic melanoma and cervical carcinoma. In some studies, better clinical outcomes have positively correlated with the total number of cells infused and/or percentage of CD8+ T cells. Most current production regimens solely utilize IL-2 to promote TIL growth. Enhanced lymphocyte expansion has been reported using IL-15 and IL-21-containing regimens. This study describes the positive effects and synergies of adding IL-15 and IL-21 to embodiments of process 2A and Generation 2 TIL manufacturing processes.

Generation of TIL Using a Novel Process Described Herein

Figures 100, 101:
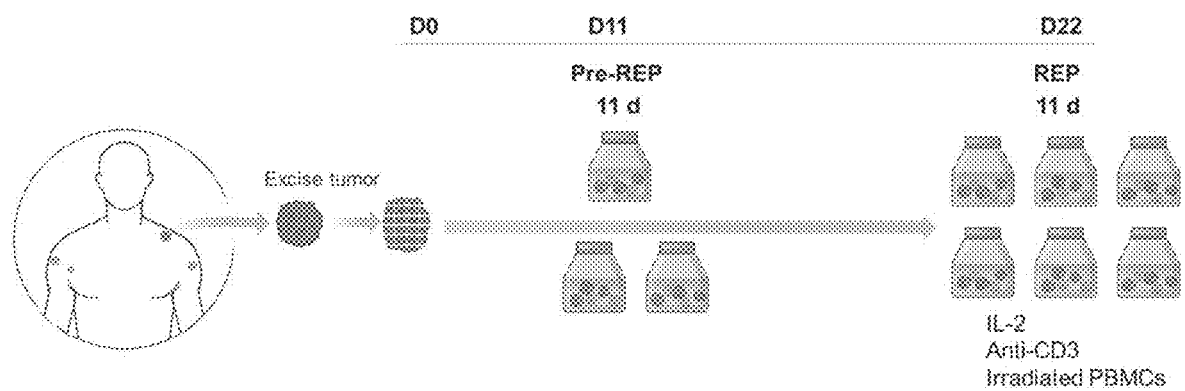
FIG. 100: An embodiment of a TIL manufacturing process of the present invention.
FIG. 101: Enhancement in expansion during the pre-REP with IL-2/IL-15/IL-21 in multiple tumor histologies.

The tumor is excised from the patient and transported to the GMP manufacturing facility or a laboratory for research purposes. Upon arrival the tumor was fragmented, and placed into flasks with IL-2 for pre-Rapid Expansion Protocol (pre-REP) for 11 days. For the triple cocktail studies, IL-2, IL-15, and IL-21 (IL-2/IL-15/IL-21) was added at the initiation of the pre-REP. For the Rapid Expansion Protocol (REP), TIL were cultured with feeders and anti-CD3 antibody for an additional 11 days (FIG. 100).

Materials and Methods

The process of generating TIL included a pre-Rapid Expansion Protocol (pre-REP), in which tumor fragments of 1-3 mm3 size were placed in media containing IL-2. During the pre-REP, TIL emigrated out of the tumor fragments and expand in response to IL-2 stimulation.

To further stimulate TIL growth, TIL were expanded through a secondary culture period termed the Rapid Expansion Protocol (REP) that included irradiated PBMC feeders, IL-2 and anti-CD3 antibody. A shortened pre-REP and REP expansion protocol was developed to expand TIL while maintaining the phenotypic and functional attributes of the final TIL product. This shortened TIL-generation protocol was used to assess the impact of IL-2 alone versus a combination of IL2/IL-15/IL-21 added to the pre-REP step. These two culture regimens were compared for the generation of TIL grown from colorectal, melanoma, cervical, triple negative breast, lung and renal tumors. At the completion of the pre-REP, cultured TIL were assessed for expansion, phenotype, function (CD107a+ and IFNγ) and TCR Vβ repertoire.

The study shows enhancement in expansion during the pre-REP with IL-2/IL-15/IL-21 in multiple tumor histologies. Pre-REP cultures were initiated using the standard IL-2 (6000 IU/mL) protocol, or with IL-15 (180 IU/mL) and IL-21 (1 IU/mL) in addition to IL-2 (FIG. 101). Cells were assessed for expansion at the completion of the pre-REP. A culture was classified as having increased expansion over the IL-2 if the overall growth was enhanced by at least 20%. Melanoma and lung phenotypic and functional studies are discussed further in the following paragraphs (bolded text in FIG. 101).

Figure 102A:
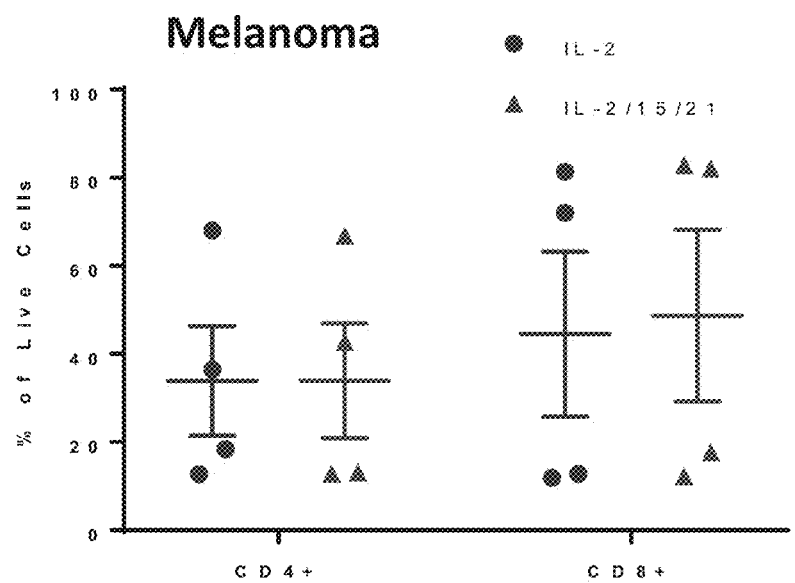
FIGS. 102A-102B: IL-2/IL-15/IL-21 enhanced the percentage of CD8+ cells in lung carcinoma, but not in melanoma. TIL derived from (A) melanoma (n=4), and (B) lung (n=7) were assessed phenotypically for CD4+ and CD8+ cells using flow cytometry post pre-REP.
Figure 102B:
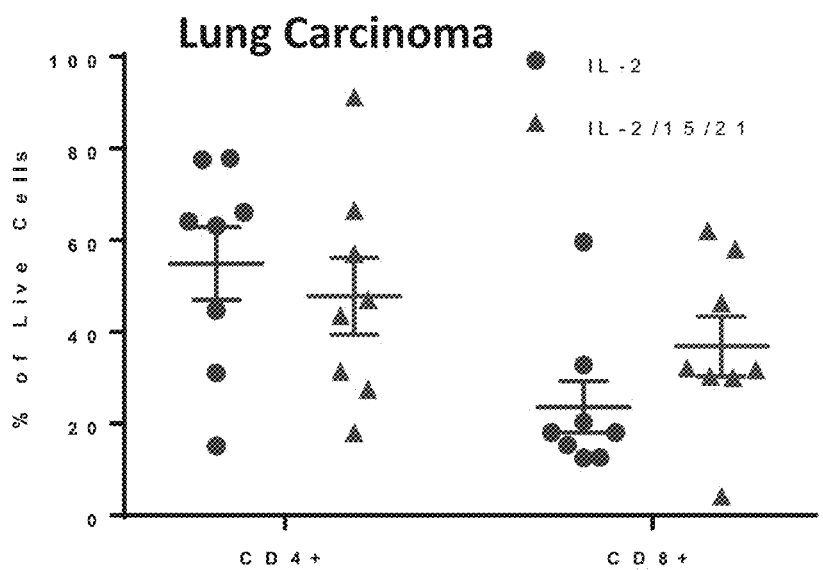

IL-2/IL-15/IL-21 enhanced the percentage of CD8+ cells in lung carcinoma, but not in melanoma. In FIGS. 102A and 102B, TIL derived from (A) melanoma (n=4), and (B) lung (n=7) were assessed phenotypically for CD4+ and CD8+ cells using flow cytometry post pre-REP. p value represents the difference between the IL-2 and IL-12/IL-15/IL-21 conditions using the student's unpaired t-test.

Figure 103A:
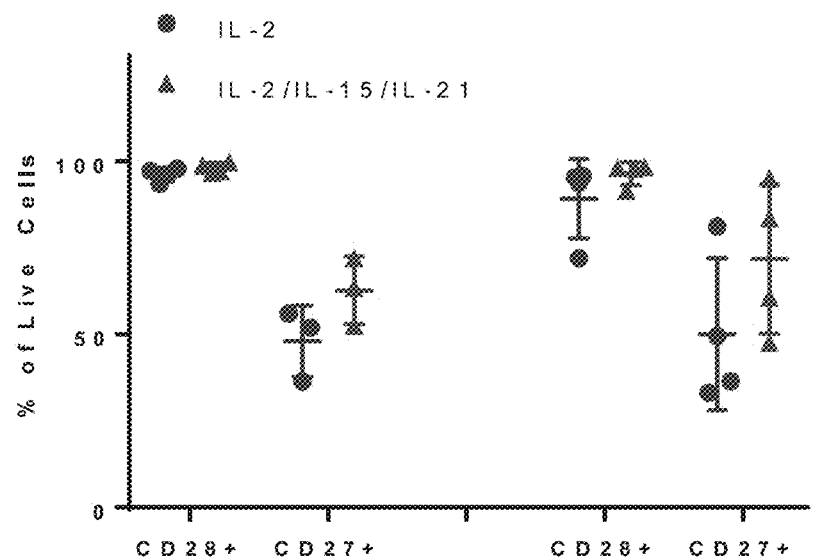
FIGS. 103A-103B: Expression of CD27 was slightly enhanced in CD8+ cells in cultures treated with IL-2/IL-15/IL-21. TIL derived from (A) melanoma (n=4), and (B) lung (n=7) were assessed phenotypically for CD27+ and CD28+ in the CD4+ and CD8+ cells using flow cytometry post pre-REP.
Figure 103B:
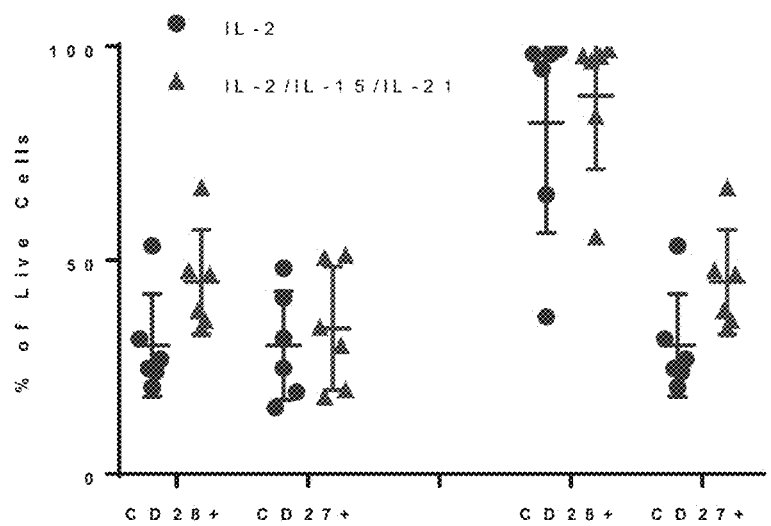

Expression of CD27 was slightly enhanced in CD8+ cells in cultures treated with IL-2/IL-15/IL-21. In FIGS. 103A and 103B, TIL derived from (A) melanoma (n=4), and (B) lung (n=7) were assessed phenotypically for CD27+ and CD28+ in the CD4+ and CD8+ cells using flow cytometry post pre-REP. Expression of CD27, a cellular marker associated with a younger phenotype that has correlated with outcomes to adoptive T cell therapy, was slightly enhanced in CD8+ TIL derived from culture with IL-2/IL-15/IL-21 vs IL-2 alone.

Figure 104A:
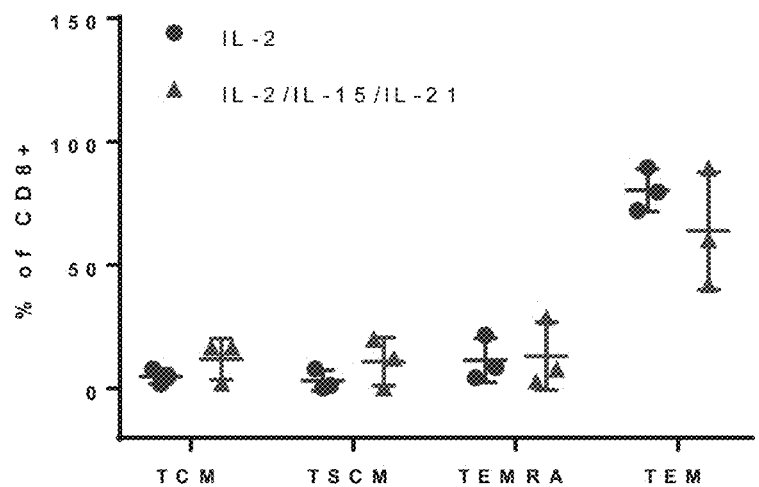
FIGS. 104A-104B: T cell subsets were unaltered with the addition of IL-15/IL-21. TIL were assessed phenotypically for effector/memory subsets (CD45RA and CCR7) in the CD8+ and CD4+(data not shown) cells from (A) melanoma (n=4), and (B) lung (n=8) via flow cytometry post pre-REP.
Figure 104B:
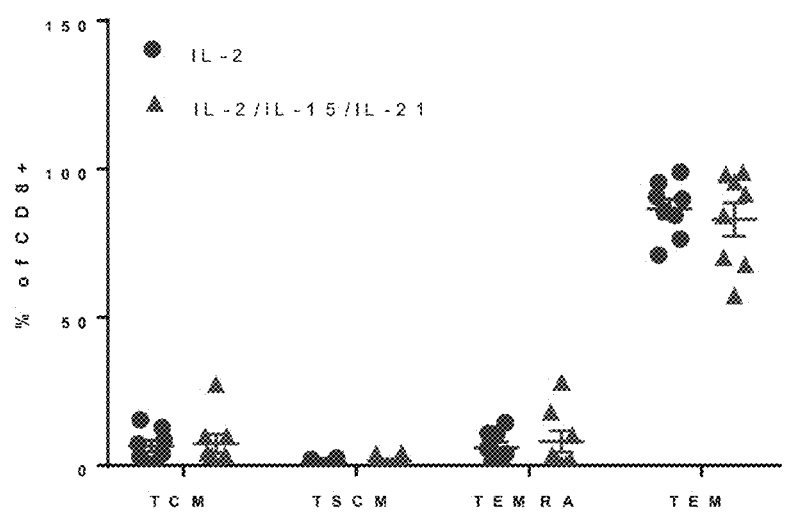

T cell subsets were unaltered with the addition of IL-15/IL-21. In FIGS. 104A and 104B, TIL were assessed phenotypically for effector/memory subsets (CD45RA and CCR7) in the CD8+ and CD4+(data not shown) cells from (A) melanoma (n=4), and (B) lung (n=8) via flow cytometry post pre-REP. TEM=effector memory (CD45RA−, CCR7−), TCM=central memory (CD45RA−, CCR7+), TSCM=stem cell memory (CD45RA+, CCR7+), TEMRA=effector T cells (CD45RA+CCR7−).

Figure 105A:
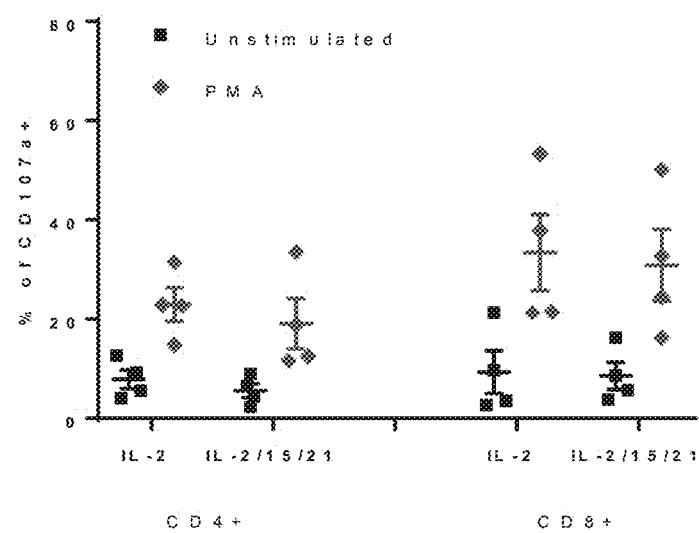
FIGS. 105A-105C: Functional capacity of TIL was differentially enhanced with IL-2/IL-15/IL-21. TIL derived from (A) melanoma (n=4) and (B) lung (n=5) were assessed for CD107a+ expression in response to PMA stimulation for 4 hours in the CD4+ and CD8+ cells, by flow cytometry. (C) pre-REP TIL derived from melanoma and lung were stimulated for 24 hours with soluble anti-CD3 antibody and the supernatants assessed for IFNγ by ELISA.
Figure 105B:
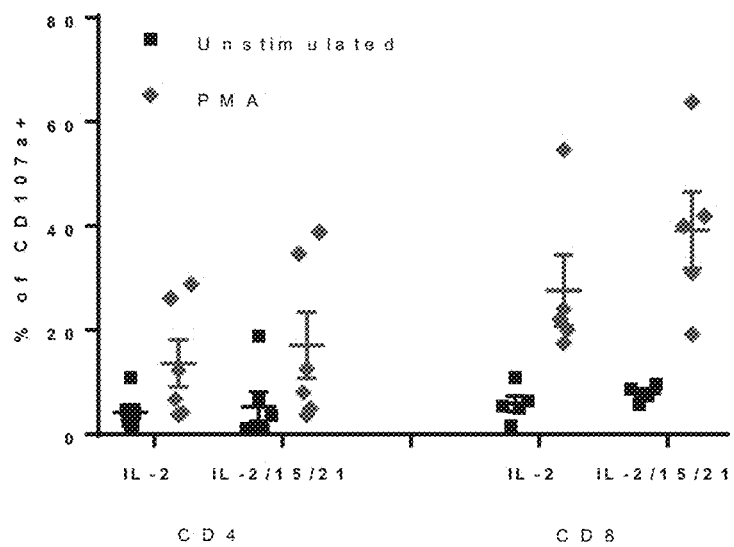
Figure 105C:
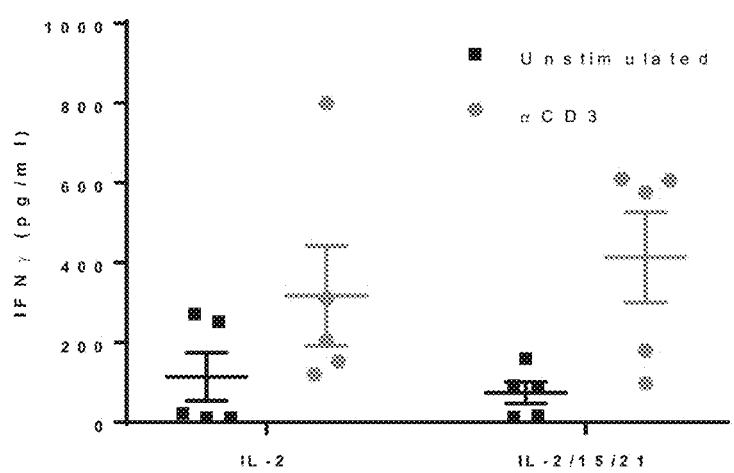

The functional capacity of TIL was differentially enhanced with IL-2/IL-15/IL-21. In FIGS. 105A and 105B, TIL derived from (A) melanoma (n=4) and (B) lung (n=5) were assessed for CD107a+ expression in response to PMA stimulation for 4 hours in the CD4+ and CD8+ cells, by flow cytometry. (C) pre-REP TIL derived from melanoma and lung were stimulated for 24 hours with soluble anti-CD3 antibody and the supernatants assessed for IFNγ by ELISA.

The relative frequency of the TCRvβ repertoire was altered in response to IL-2/IL-15/IL-21 in lung, but not in melanoma. In FIGS. 106A and 106B, the TCRvβ repertoire (24 specificities) were assessed in the TIL derived from a (A) melanoma and (B) lung tumor using the Beckman Coulter kit for flow cytometry.

Summary

This work demonstrates the ability of the IL-2/IL-15/IL-21 cocktail to enhance TIL numbers compared to IL-2 alone (>20%) in the Generation 2 process, in addition to impacting phenotypic and functional characteristics.

The effect of the triple cocktail on TIL expansion was histology dependent. The CD8+/CD4+ T cell ratio was increased with the addition of IL-2/IL-15/IL-21 in lung tumors. Addition of IL-15 and IL-21 enhanced CD107a expression and IFNγ production in TIL derived from lung tumors. The addition of IL-2/IL-15/IL-21 altered the TCRvβ repertoire in the lung. The Generation 2 TIL expansion process was used to encompass the IL-2/IL-15/IL-21 cytokine cocktail, thereby providing a means to further promote TIL expansion in specific tumor histologies, such as lung and colorectal tumors. These observations are especially relevant to the optimization and standardization of TIL culture regimens necessary for large-scare manufacture of TIL with the broad applicability and availability required of a main-stream anti-cancer therapy.

Example 28: Novel Cryopreserved Tumor Infiltrating Lymphocytes (LN-144) Administered to Patients with Metastatic Melanoma Demonstrated Efficacy and Tolerability in a Multicenter Phase 2 Clinical Trial Background The safety and efficacy of adoptive cell therapy (ACT) utilizing tumor infiltrating lymphocytes (TIL) has been studied in hundreds of patients with metastatic melanoma, and has demonstrated meaningful and durable objective response rates (ORR).[1] In an ongoing Phase 2 trial, C-144-01 utilizing centralized GMP manufacturing of TIL, both non-cryopreserved Generation 1 (Gen 1) and cryopreserved Generation 2 (Gen 2) TIL manufacturing processes were assessed.

Figure 107:
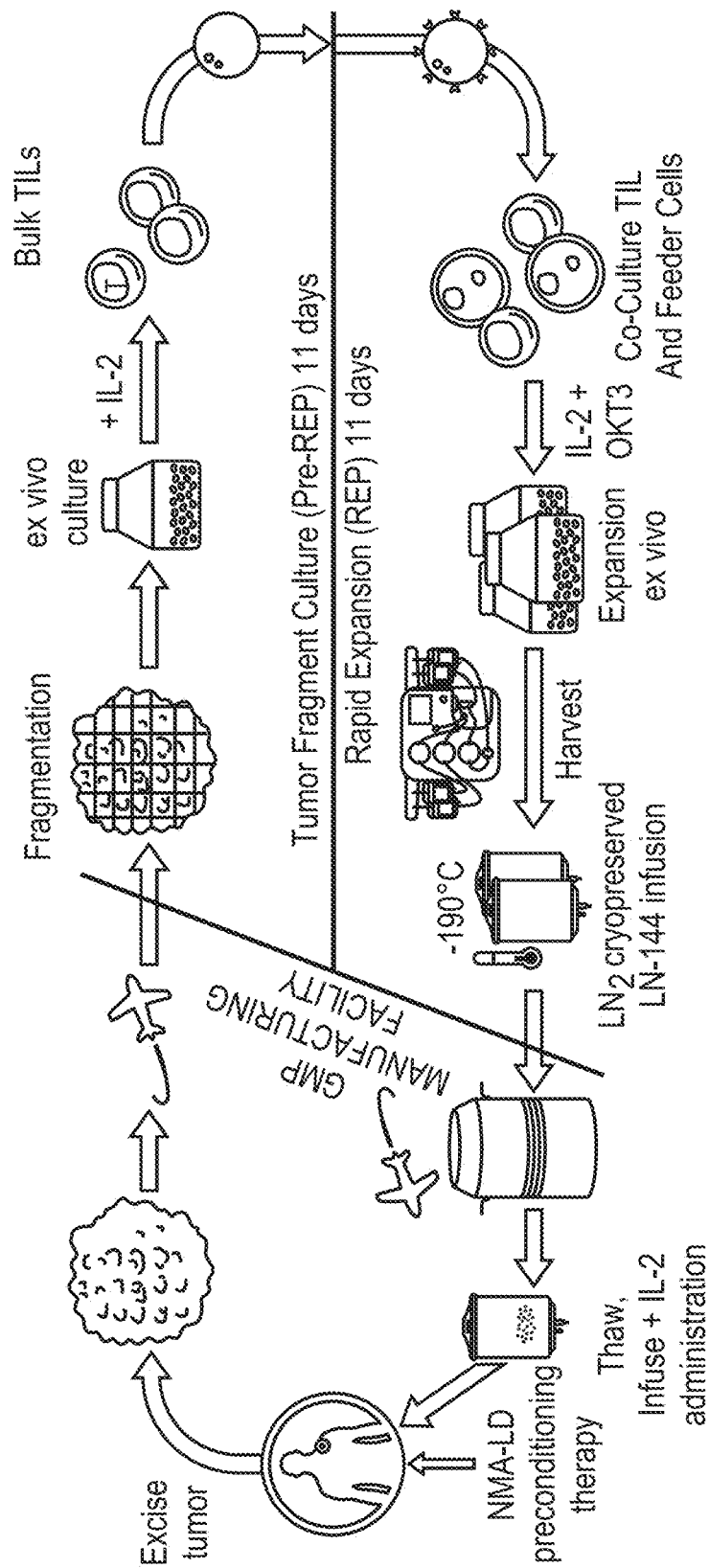
FIG. 107: Scheme of Gen 2 cryopreserved LN-144 manufacturing process.

Gen 1 is approximately 5-6 weeks in duration of manufacturing (administered in Cohort 1 of C-144-01 study), while Gen 2 is 22 days in duration of manufacturing (process 2A, administered in Cohort 2 of C-144-01 study). Preliminary data from Cohort 1 patients infused with the Gen 1 LN-144 manufactured product, was encouraging in treating post-PD-1 metastatic melanoma patients as the TIL therapy produced responses.[2] Benefits of Gen 2 included: (A) reduction in the time patients and physicians wait to infuse TIL to patient; (B) cryopreservation permits flexibility in scheduling, distribution, and delivery; and (C) reduction of manufacturing costs. Preliminary data from Cohort 2 is presented herein. FIG. 107 shows an embodiment of the Gen 2 cryopreserved LN-144 manufacturing process (process 2A).

Study Design: C-144-01 Phase 2 Trial in Metastatic Melanoma

Phase 2, Multicenter, 3-Cohort Study to Assess the Efficacy and Safety of Autologous Tumor Infiltrating Lymphocytes (LN-144) for Treatment of Patients with Metastatic Melanoma.

Key Inclusion Criteria: (1) Measurable metastatic melanoma and >1 lesion resectable for TIL generation; (2) Progression on at least one prior line of systemic therapy; (3) Age≥18; and (4) ECOG PS 0-1.

Figure 108:
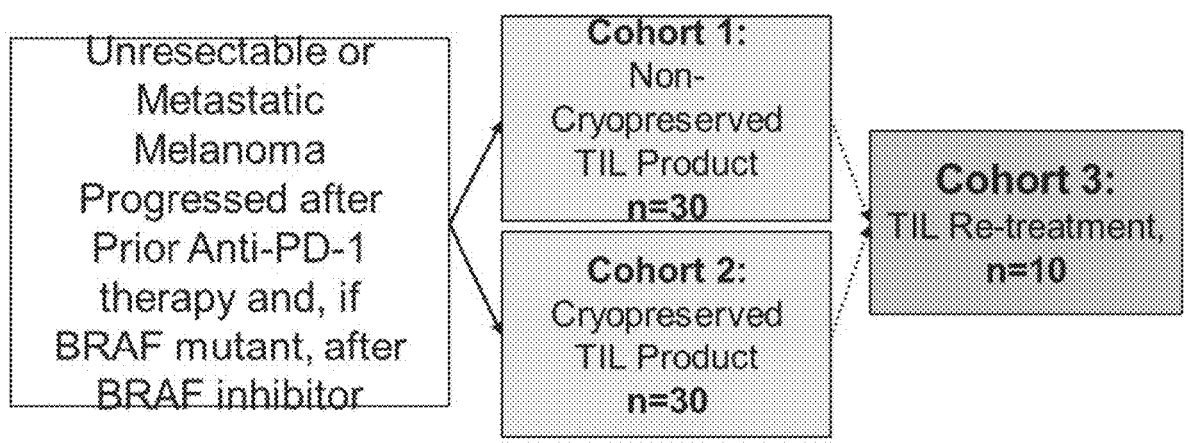
FIG. 108: Scheme of study design of multicenter phase 2 clinical trial of novel cryopreserved TILs administered to patients with metastatic melanoma.

Treatment Cohorts: (1) Non-Cryopreserved LN-144 product; (2) Cryopreserved LN-144 product; and (3) Retreatment with LN-144 for patients without response or who progress after initial response. FIG. 108 shows the study design.

Endpoints: (1) Primary: Efficacy defined as ORR and (2) Secondary: Safety and Efficacy.

Methods

Cohort 2 Safety Set: 13 patients who underwent resection for the purpose of TIL generation and received any component of the study treatment.

Cohort 2 Efficacy Set: 9 patients who received the NMA-LD preconditioning, LN-144 infusion and at least one dose of IL-2, and had at least one efficacy assessment. 4 patients did not have an efficacy assessment at the time of the data cut.

Biomarker data has been shown for all available data read by the date of the data cut.

Results

FIG. 109 provides a table illustrating the Comparison Patient Characteristics from Cohort 1 (ASCO 2017) vs Cohort 2. Cohort 2 has: 4 median prior therapies; all patients have received prior anti-PD-1 and anti-CTLA-4; and had higher tumor burden reflected by greater sum of diameters (SOD) for target lesions and higher mean LDH at Baseline. FIG. 110 provides a table showing treatment emergent adverse events (≥30%).

Figure 111:
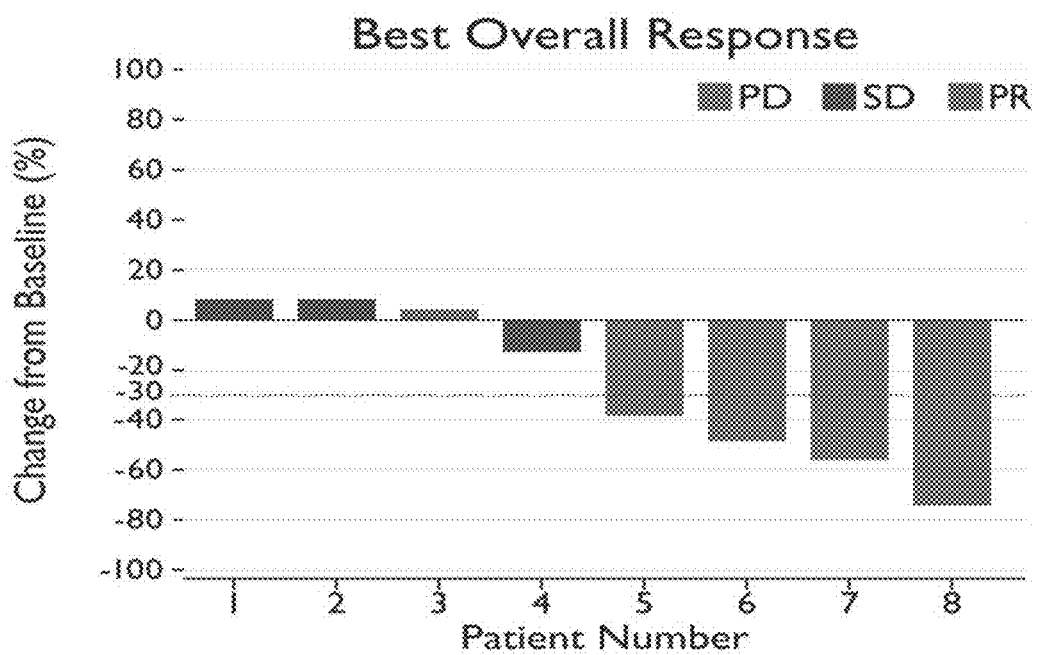
FIG. 111: Efficacy of the infusion product and TIL therapy.

For Cohort 2 (cryopreserved LN-144), the infusion product and TIL therapy characteristics were (1) mean number of TIL cells infused: 37×10$^9$, and (2) median number of IL-2 doses administrations was 4.5. FIG. 111 shows the efficacy of the infusion product and TIL therapy for Patients #1 to #8.

Figure 112:
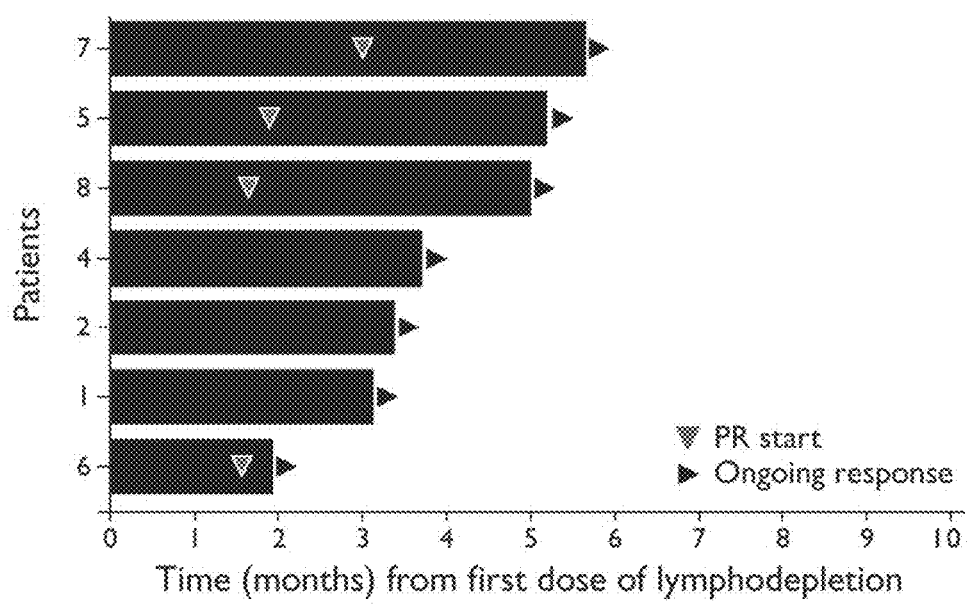
FIG. 112: Clinical status of response evaluable patients with SD or a better response.

FIG. 112 shows the clinical status of response evaluable patients with stable disease (SD) or a better response. A partial response (PR) for Patient 6 was unconfirmed as the patient did not reached the second efficacy assessment yet. One patient (Patient 9) passed away prior to the first assessment (still considered in the efficacy set).

Of the 9 patients in the efficacy set, one patient (Patient 9) was not evaluable (NE) due to melanoma-related death prior to first tumor assessment not represented on FIG. 112. Responses were seen in patients treated with Gen 2. The disease control rate (DCR) was 78%. Time to response was similar to Cohort 1. One patient (Patient 3) with progressive disease (PD) as best response was not included in the swim lane plot.

Figure 113:
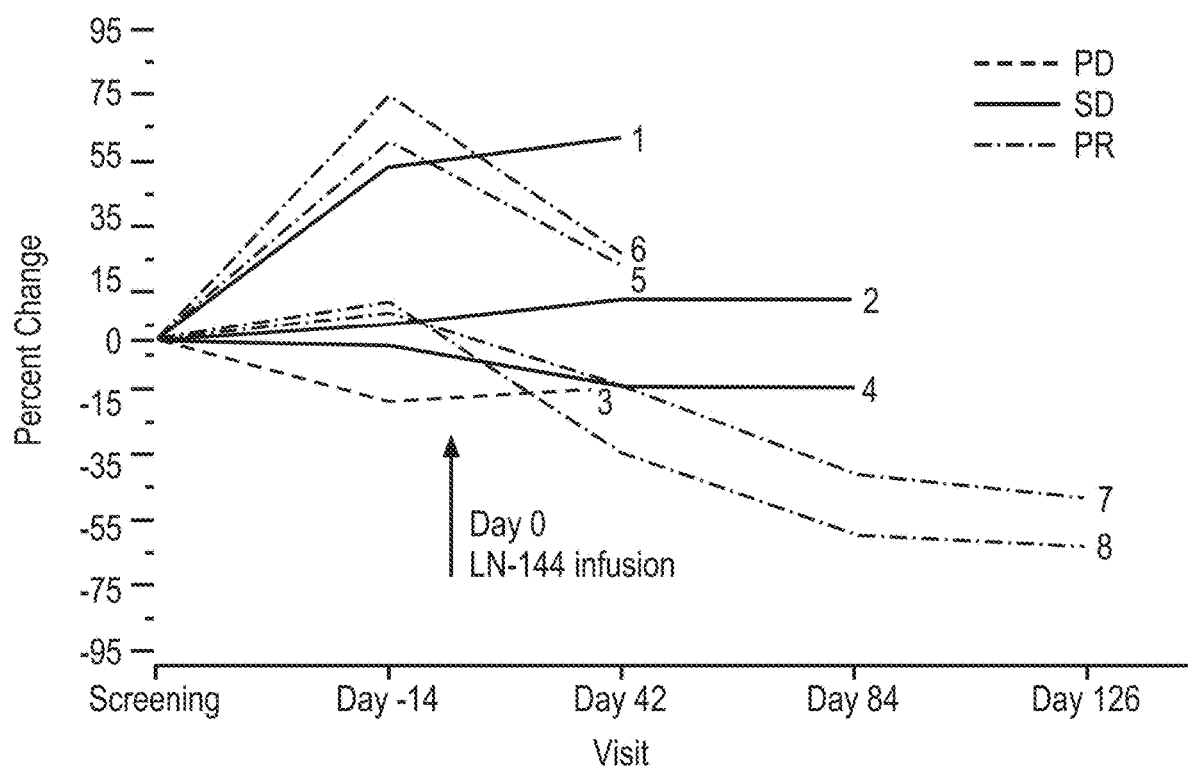
FIG. 113: Percent change in sum of diameters.

FIG. 113 shows the percent change in sum of diameters. Patient 9 had no post-LN-144 disease assessment due to melanoma-related death prior to Day 42. Day −14: % change of Sum of Diameters from Screening to Baseline (Day −14). Day −14 to Day 126: % change of SOD from Baseline. Day −14=Baseline. Day 0=LN-144 infusion.

Figure 114:
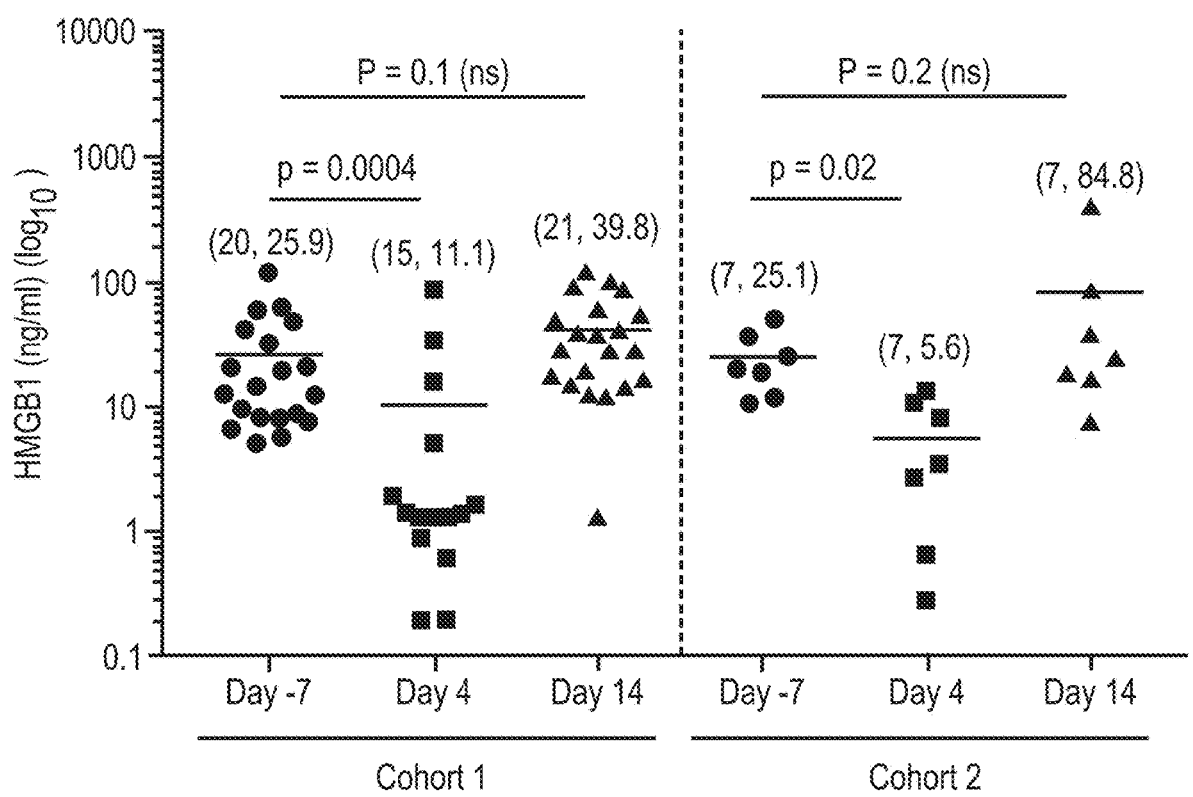
FIG. 114: An increase of HMGB1 level was observed upon TIL treatment.

Upon TIL treatment, an increase of HMGB1 was observed (FIG. 114). Plasma HMGB1 levels were measured using HMGB1 ELISA kit (Tecan US, Inc). Data shown represents fold change in HMGB1 levels pre (Day −7) and post (Day 4 and Day 14) LN-144 infusion in Cohort 1 and Cohort 2 patients (p values were calculated using two-tailed paired t-test based on log-transformed data). Sample size (bold and italicized) and mean (italicized) values are shown in parentheses for each time point. HMGB1 is secreted by activated immune cells and released by damaged tumor cells. The increased HMGB1 levels observed after treatment with LN-144 are therefore suggestive of an immune-mediated mechanism of anti-tumor activity.

Figure 115:
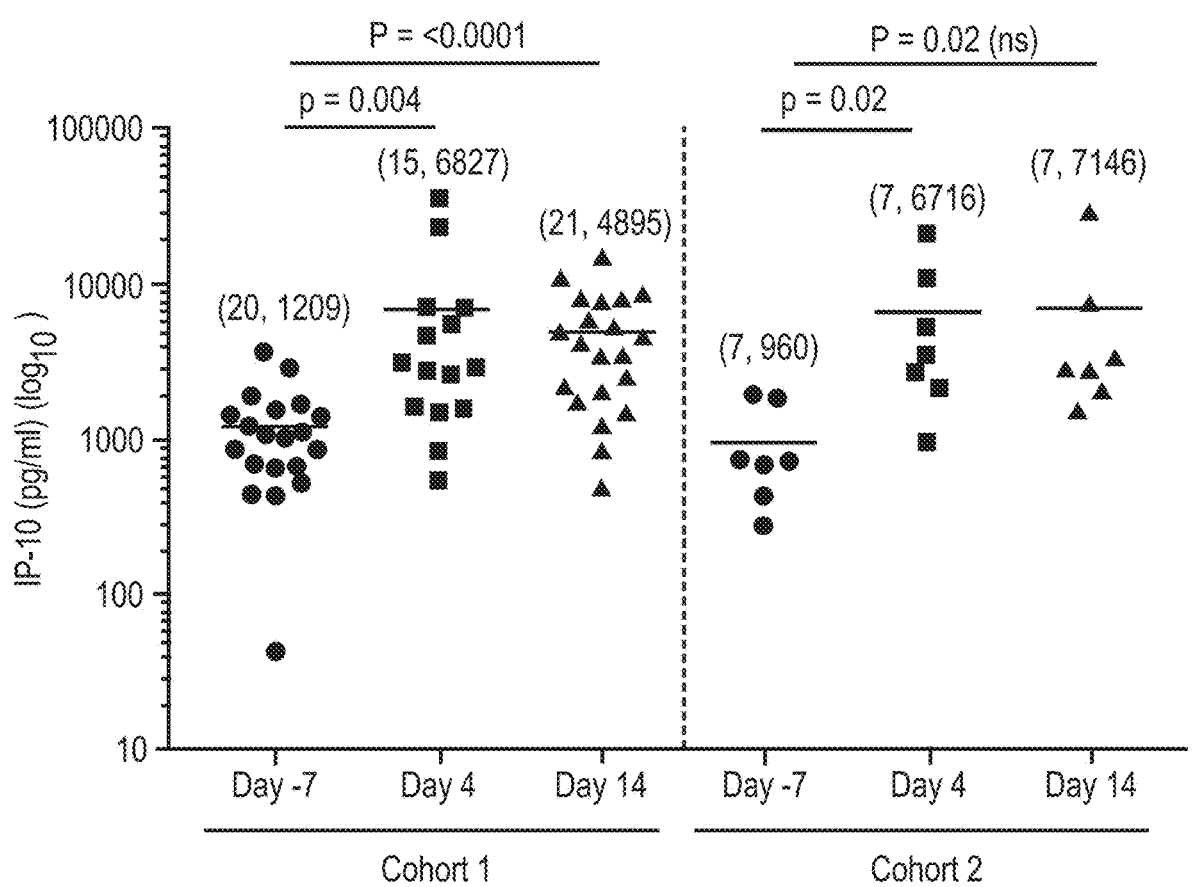
FIG. 115: An increase in the biomarker IL-10 was observed post-LN-144 infusion.
Figure 118:
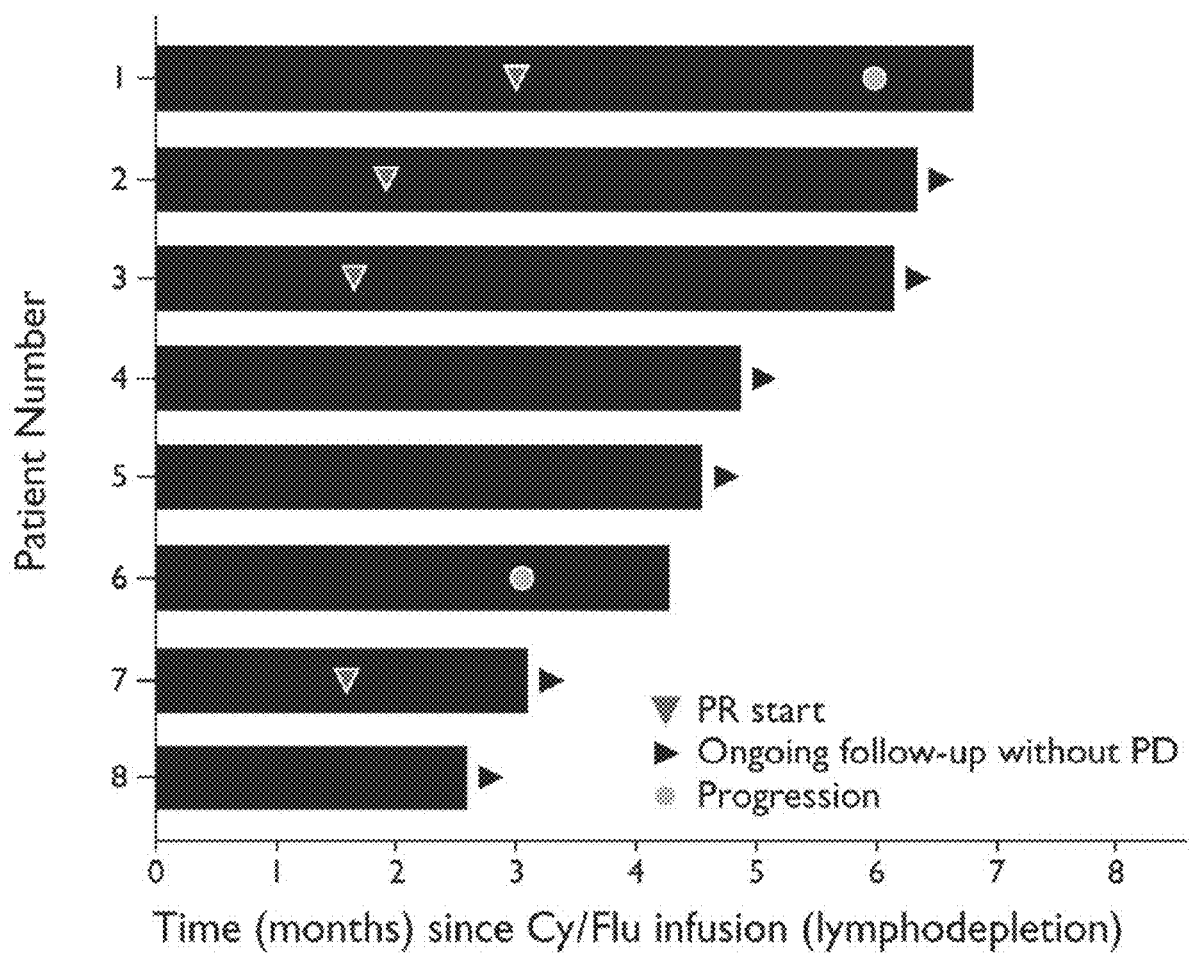
FIG. 118: Time to response for evaluable patients (stable disease or better) in Cohort 2 from the second data cut (N=17 patients). Of the 10 patients in the efficacy set, one patient (Patient 10) was not evaluable due to a melanoma-related death prior to the first tumor assessment not represented on the figure.
Figure 119:
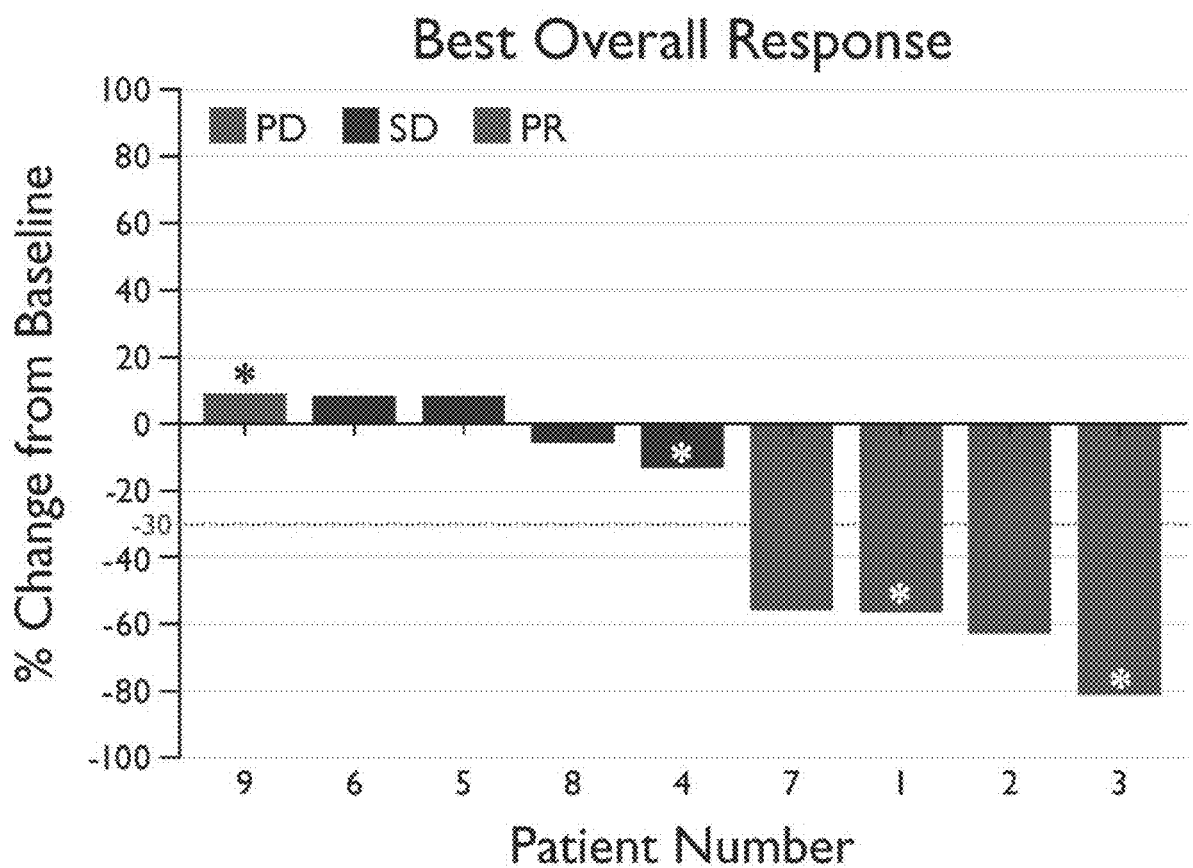
FIG. 119: Updated efficacy data for Cohort 2 from the second data cut (N=17 patients). The mean number of TILs infused is $34 \times 10^9$. The median number of prior therapies was 4.5. Patients with a BRAF mutation responded as well as patients with wild-type BRAF (a * refers to patients with a BRAF mutation). One patient (Patient 10) was not evaluable due to a melanoma-related death prior to the first tumor assessment but was still considered in the efficacy set. Abbreviations: PR, partial response; SD, stable disease; PD, progressive disease.

Plasma IP-10 levels were measured using Luminex assay. Data shown in FIG. 115 represents fold change in IP-10 levels pre (Day −7) and post (Day 4 and Day 14) LN-144 infusion in Cohort 1 and Cohort 2 patients (p values were calculated using two-tailed paired t-test based on log-transformed data). Sample size (bold and italicized) and mean (italicized) values are shown in parentheses for each time point. The post-LN-144 infusion increase in IP-10 is being monitored to understand possible correlation with TIL persistence.

Updated data from Cohort 2 (n=17 patients) is reported in FIG. 116 to FIG. 121. In comparison to Cohort 1 and an embodiment of the Gen 1 process, which showed a DCR of 64% and an overall response rate (ORR) of 29% (N=14), Cohort 2 and an embodiment of the Gen 2 process showed a DCR of 80% and an ORR of 40% (N=10).

Conclusions

Preliminary results from the existing data demonstrate comparable safety between Gen 1 and Gen 2 LN-144 TIL products. Administration of TILs manufactured with the Gen 2 process (process 2A, as described herein) leads to surprisingly increased clinical responses seen in advanced disease metastatic melanoma patients, all had progressed on anti-PD-1 and anti-CTLA-4 prior therapies. The DCR for cohort 2 was 78%.

Preliminary biomarker data is supportive of the cytolytic mechanism of action proposed for TIL therapy.

The embodiment of the Gen 2 manufacturing process described herein takes 22 days. This process significantly shortens the duration of time a patient has to wait to receive their TIL, offers flexibility in the timing of dosing the patients, and leads to a reduction of cost of manufacturing, while providing other advantages over prior approaches that allow for commercialization and registration with health regulatory agencies. Preliminary clinical data in metastatic melanoma using an embodiment of the Gen 2 manufacturing process also indicates a surprising improvement in clinical efficacy of the TILs, as measured by DCR, ORR, and other clinical responses, with a similar time to response and safety profile compared to TILs manufactured using the Gen 1 process. The unexpectedly improved efficacy of Gen 2 TIL product is also demonstrated by a more than five-fold increase in IFN-γ production (FIG. 98), which is correlated with improved efficacy in general (FIG. 122), significantly improved polyclonality (FIG. 99A and FIG. 99B), and higher average IP-10 and MCP-1 production (FIG. 123 to FIG. 126). Surprisingly, despite the much shorter process of Gen 2, many other critical characteristics of the TIL product are similar to those observed using more traditional manufacturing processes, including relative telomere length (FIG. 97) and CD27 and CD28 expression (FIG. 96B and FIG. 96C).

REFERENCES

[1]Goff, et al. Randomized, Prospective Evaluation Comparing Intensity of Lymphodepletion Before Adoptive Transfer of Tumor-Infiltrating Lymphocytes for Patients With Metastatic Melanoma. *J. Clin Oncol.* 2016 Jul. 10; 34(20):2389-97.

[2]Sarnaik A, Kluger H, Chesney J, et al. Efficacy of single administration of tumor-infiltrating lymphocytes (TIL) in heavily pretreated patients with metastatic melanoma following checkpoint therapy. *J Clin Oncol.* 2017; 35 [suppl; abstr 3045].

Example 29: HNSCC and Cervical Carcinoma Phase 2 Studies

Enrollment for the HNSCC (head and neck squamous cell carcinoma; C-145-03) phase 2 study. 13 patients consented to the study, TILs were harvested from 10 patients and ultimately 7 patients were infused with 1 more in progress.

Enrollment in the cervical carcinoma phase 2 study (C-145-04). 8 patients consented to the study, TILs were harvested from 4 patients and ultimately 2 patients were infused and 2 more in process.

The initial data from the ongoing study is provided in FIG. 127. Stable disease (SD) and or progressive response was observed in both HCNSCC and cervical cancer patients treated with the TIL therapy at up to 84 days.

Example 30: Production of a Cryopreserved TIL Cell Therapy

This examples describes the the cGMP manufacture of ovance Biotherapeutics, Inc. TIL Cell Therapy Process in G-Rex Flasks according to current Good Tissue Practices and current Good Manufacturing Practices.

This material will be manufactured under US FDA Good Manufacturing Practices Regulations (21 CFR Part 210, 211, 1270, and 1271), and applicable ICH Q7 standards for Phase I through Commercial Material.

4.0 Process Reference Expansion Plan

| Estimated Day (post-seed) | Activity | Target Criteria | Anticipated Vessels | Esti Vo |
|---|---|---|---|---|
| 0 | Tumor Dissection | ≤50 desirable tumor fragments per G-Rex100MCS | G-Rex100MCS 1 flask | |
| 11 | REP Seed | 5-200 × $10^6$ viable cells per G-Rex500MCS | G-Rex500MCS 1 flasks | |
| 16 | REP Split | 1 × $10^9$ viable cells per G-Rex500MCS | G-Rex500MCS <5 flasks | |
| 22 | Harvest | Total available cells | 3-4 CS-750 bags | |

4.2 Flask Volumes:

| Flask Type | Working Volume/Flask (mL) |
|---|---|
| G-Rex100MCS | 1000 |
| G-Rex500MCS | 5000 |

4.3 Inspection Procedure
4.3.1 Manufacturing personnel will perform 100% inspection of the final product bags during the fill process.
4.3.2 Prepare a container labeled "Failing Final Product Inspection".
4.3.3 Inspect for the following rejectable attributes:
  4.3.3.1 Gross visible particulates (fibers, particles not the same color as the suspension, etc.) (NOTE: Cellular/Tissue Agglomerations are not to be considered particulate rejects).
  4.3.3.2 Defects in the bag integrity, such as leaky seams/ports.
  4.3.3.3 Incomplete overwrap bag seal.
  4.3.3.4 Leaky seal.
  4.3.3.5 Sign of clumps.
4.3.4 Inspect for the following acceptable appearance attributes:
  4.3.4.1 Intact Bag
  4.3.4.2 No signs of clumps
4.3.5 If no rejectable attributes are observed, return the final product bag to the lot.
4.3.6 If any rejectable attributes are observed, label the bag with a "Rejected Product" label, place bag in the "Rejected" storage container.
4.4 Process Flow Diagram (see, FIG. 128)
5.0 Process Notes
5.1 Printouts containing final reported data results are to be attached to this Batch Record in the designated area. Each printout must be labeled with the Lot Number, Step Number (if applicable), and Initials and Date. If printouts are unavailable, readings must be recorded manually in place of printout and with reference to comment in comment section. A second associate must verify data.
5.2 Process steps may be performed concurrently when obtaining materials, during setup, post-process activities or as otherwise noted in step description.
5.3 Throughout this Batch Record, assume 1.0 mL/L=1.0 g/kg, unless otherwise specified.
5.4 If a critical material/consumable must be substituted in section 7.1, a comment will be made in section 10.0 and appropriate individuals contacted.
5.5 Round all data to the nearest tenth of a decimal point (xx.x) or within the tolerance of the equipment used (excludes printout data) unless otherwise noted throughout the batch record.
5.6 If equipment requires calibration for more than one parameter, and those calibration due dates are different, the earliest due date will be recorded.
5.7 All CO2 measurements recorded in this batch record will be read from a Vaisala CO2 analyzer at League Island 1. All CO2 measurements recorded in this batch record will be read from the LED Display at Commerce Center 3.
5.8 All incubators for League Island 1 will be humidified. All incubators for Commerce Center 3 will not be humidified.
5.9 Once opened, the following expiries apply at 2-8° C.: Human Serum, type AB (HI) Gemini, 1 month; 2-mercaptoethanol, 1 month. Gentamicin Sulfate, 50 mg/ml stock may be kept at room temperature for 1 month. Bags containing 10 L of AIM-V media may be warmed at room temperature once only for up to 24 hours prior to use.
5.10 The Receipt Number and Lot Number in Great Plains will be recorded in Section 7.1 Critical Materials/Consumables in the event that the WuXi AppTec Lot Number is not assigned to the material(s). The combination of the Receipt Number and Lot Number will replace the WuXi AppTec Lot number for new materials procured moving forward, as part of the implementation and validation of the Great Plains system.
5.11 When using the TSCD welder for connections, follow the instructions printed on the front of the machine. Ensure tubing is inserted properly as indicated on the machine. When loading tubing, ensure tubing is inserted so that a previous weld is not placed under the clamps of the welder (where possible). Also, ensure enough tubing remains for Steps following the welding. A hemostat should be placed on either side of the tubing before beginning welding process. After welding is complete, inspect the weld to ensure it is sealed and uniform around the tubing. Pinch or roll fingers along the connection to pop open the weld, then remove hemostats.
5.12 Prior to using the SEBRA® Hand-Held Tube Sealer each day, clean and inspect sealing head to ensure proper function. When using the SEBRA® Hand-Held Tube Sealer to separate tubing, create three seals in close proximity to each other. Ensure exterior of tubing is dry to prevent electrical arcing. Separate or detach the tubing by breaking the middle seal, unless instructed otherwise. Do not apply opposing forces on the tubing to prevent premature separation of the tubing during sealing events. Do not attempt to reseal a seal if first attempt is unsuccessful. If needed, perform "test welds" using the hand-held sealer and assess the hand-held sealer as necessary.
5.13 Thoroughly inspect all clamps and hemostats for flaws or damage that may result in a compromised ability to adequately stop flow or a potential to damage tubing.
5.14 If the Nucelocounter notification shows that counts 1 and/or 2 are above the optimal counting range ($5 \times 10^4$-$5 \times 10^6$ before accounting for dilution), N/A the rest of the cell count page. Prepare another cell solution sample, diluted with an appropriate dilution factor ([new dilution factor]=[previous dilution factor]×[reported cell count]÷[$5 \times 10^5$]) to get the VCD or "Live Cells" inside of the optimal range. If cell counts 1 and/or 2 are below the optimal range (too dilute), contacted area management, recorded "live cell" counts, and proceeded with calculations. Ensure to document cell counts out of optimal range in a footnote in either situation.
5.15 When recording tumor receipt information ensure that the Time of Tumor Removal from the patient is converted to Eastern Standard Time (EST) if not already, recorded as such on the Tumor Shipping Batch record. The elapsed time from Tumor Removal from Patient to Tumor Receipt in the lab should be calculated in EST.
5.16 During the Day 22 harvest two Gatherex™ may be used to harvest the TIL from the G-Rex500MCS flasks.

Both units may be used to remove supernatant and one of the two unit used to collect the TIL.

5.17 During all processing steps the minimum number of personnel allowed within the Grade B processing suite is two and the maximum number is ten (including environmental processing personnel).

5.18 When aliquotting media reagents at volumes ≤1.0 mL, rinse the pipet after dispensing.

5.19 Flasks will be re-incubated during media warming and in any other instance when not being actively processed. Incubation steps will only be recorded at the beginning and end of each section, when applicable. On non-scheduled processing days, flasks may be observed for information only, as per area management or client, without sanitizing the room or monitoring the equipment.

5.20 After the completion of processing Day 0, Tumor Dissection, seeding and flask incubation, all remaining fragments and pieces of the tumor are to be discarded appropriately.

6.0 Equipment

Equipment List: Day 0 CM1 Media Preparation/Tumor Wash Preparation/Tumor Dissection:
Magnehelic Gauge
Biological Safety Cabinet (BSC)
Incubator
CO2 Analyzer
Micropipetter (100-1000 μL)
Pipet-Aid
Baxa Repeater Pump
Sebra Tube Sealer
2-8° C. Refrigerator
−80° C. Freezer
−20° C. Freezer
Timer Equipment List: CM2 Preparation/Day 11 REP Seed
Magnehelic Gauge
Biological Safety Cabinet (BSC)
Incubator
Incubator
CO2 Analyzer
Dry Bath
Water Bath
CytoTherm
Welder
Gatherex
NC200 NucleoCounter
Baxa Repeater Pump
Sebra Tube Sealer Balance Equipment List: CM2 Preparation/Day 11 REP Seed
Centrifuge
Micropipetter (100-1000 μL)
Pipet-Aid
Timer
2-8° C. Refrigerator
−80° C. Freezer
Controlled Rate Freezer
LN2 Storage Freezer (Quarantine)
−20° C. Freezer Equipment List: CM4 Preparation/Day 16
Magnehelic Gauge
Biological Safety Cabinet (BSC)
Incubator
Incubator
CO2 Analyzer
Welder
Welder
Gatherex
NC200 NucleoCounter
Baxa Repeater Pump
Sebra Tube Sealer Balance
Micropipetter (100-1000 μL)
Pipet-Aid
2-8° C. Refrigerator
−80° C. Freezer Equipment List: Day 22 Formulation, Fill, Cryopreservation
Magnehelic Gauge
Biological Safety Cabinet (BSC)
Incubator
Incubator
CO2 Analyzer
Welder
Gatherex
NC200 NucleoCounter
Baxa Repeater Pump
Sebra Tube Sealer Balance
Micropipetter (20-200 μL) Pipet-Aid Equipment List: Day 22 Formulation, Fill, Cryopreservation
Pipet-Aid
2-8° C. Refrigerator
−80° C. Freezer
Controlled Rate Freezer
LN2 Storage Freezer
LN2 Storage Freezer (Quarantine)
LOVO Cell Processing System 7.0 Bill of Materials Materials: Day 0 CM1 Media Preparation/Tumor Wash Preparation/Tumor Dissection
Disposable Scalpels, Sterile
50 mL Serological Pipets, Sterile
1 mL Serological Plastic Pipet, Sterile
10 mL Serological Pipet, Sterile
Centrifuge Tube, 50 mL, 28×114 mm, Conical Base, Screw Cap, PP, Sterile
25 mL Serological Pipet, Sterile
5 mL Serological Pipet, Sterile
MF75 Series, Disposable Tissue Culture Filter, 1000 mL, aPES Filter, 0.2 μm, Sterile
Pipets, Serological 100 mL
2-mercaptoethanol 1000×, liquid, 55 mM in D-PBS
Hank's Balanced Sodium Salt Solution (1×), Liquid, w/o Calcium Chloride, Magnesium Chloride, Magnesium Sulfate
GlutaMAX 1-200 mM (100×), liquid
ART Barrier Pipet Tips, 1000 μL, Individually Wrapped, Sterile
150 mm Petri Dish, Extra-Depth, Sterile
6-well, Ultra-Low Attachment Plates, 9.5 cm2 Well Growth Area, PS, Sterile
Thermo Scientific Samco General-Purpose Transfer Pipettes. 7.7 mL, Sterile
Repeater Pump Fluid Transfer Set Male Luer Lock End
Long Forceps 8", Sterile
Gentamicin Sulfate, 50 mg/mL stock
Scientific Disposable Forceps, 4.5", Stainless Steel, Sterile
100 mm petri dish, Sterile Extra Depth
Pumpmatic Liquid-Dispensing System
Gentamicin Sulfate, 50 mg/mL stock
Syringe Cap Dual Function, Red
RPMI-1640, 1 L Bottle G-Rex 100M Flask Closed System
Sterile rulers
Reconstituted IL-2
Human Tumor Sample, Head and Neck Q N/A
Human Tumor Sample, Cervical Q N/A
GemCell Human Serum AB, Heat Inactivated Q N/A
Human Tumor Sample, Melanoma
GemCell Human Serum AB, Heat Inactivated
Materials: CM2 Preparation/Day 11 REP Seed
Luer-Lok Syringe, 60 mL Sterile Needle 16G×1.5" Sterile
50 mL Serological Pipets, Sterile
1 mL Serological Plastic, Pipet, Sterile
Nunc Internally Threaded Cryotube Vials, Sterile
10 mL Serological Pipet, Sterile
Centrifuge Tube, 15 mL
Centrifuge Tube, 50 mL
Pipets, Serological 100 mL
Syringe, 1 cc Sterile Luer-Lok
3 mL Syringe, Luer-Lok Tip, Sterile
5 mL Serological Pipet, Sterile
Nalgene *MF75* Series Filter Unit Receiver, 250 mL, Sterile
Nalgene MF75 Series Filter Unit Receiver, 500 mL, Sterile
1000 mL Nalgene Rapid-Flow Sterile Dispoasable Filter Unit, 0.22 µm PES
CryoStor CS-10
2-mercaptoethanol 1000× Liquid, 55 mM in D-PBS
GlutaMAX 1-200 mM (100×), liquid
1,000 µL ART Barrier Sterile Pipet Tips, Individual Wrap
VIA1 Cassettes
Transfer Pack Container, 1000 mL w/Coupler, Sterile
Transfer Pack 300 mL w/Coupler
Sterile Alcohol Pads
Repeater Pump Fluid Transfer Set Male Luer Lock Ends
CTS AIM V 1 L Bottle
MACS GMP CD3 pure (OKT-3)
Gentamicin Sulfate, 50 mg/mL stock
4" Tubing w/Piercing Pin and Syringe Adapter
Syringe Only Luer-Lok 10 mL
Tubing, Four Spike Male Luer Manifold
Gravity Blood Administration Set Y-type with No injection site, 170 µm blood filter
Pumpmatic Liquid-Dispensing System
10 L Labtainer 3 Port Bag
Gentamicin Sulfate, 50 mg/mL stock
100 mL Syringe
3000 mL Culture Bag
Origen Cell Connect CC2
Syringe Cap Dual Function Red
RPMI-1640, 1 L Bottle
G-Rex 500M Flask Closed System
Reconstituted IL-2
Allogeneic Irradiated Feeder Cells
Allogeneic Irradiated Feeder Cells
Human Serum, type AB(HI) Gemini
Human Serum, type AB(HI) Gemini
Materials: CM4 Preparation/Day 16
Luer-Lok Syringe, 60 mL Sterile
1 mL Serological Plastic Pipet, Sterile
Nunc Internally Threaded Cyrotube Vials, Sterile
10 mL Serological Pipets, Sterile
Centrifuge Tube, 15 mL
Centrifuge Tube, 50 mL
Pipets, Serological 100 mL
Syringe with Luer-Lock, sterile, 3 mL
5 mL Serological Pipet, Sterile
Syringe only Luer-Lok 10 mL
Nalgene *MF75* Series
Filter Unit Receiver, 250 mL, Sterile
GlutaMAX1-200 mM (100×), liquid
ART Barrier Pipet Tips, 1000 µL, Individually Wrapped, Sterile
VIA1 Cassettes
Materials: CM4 Preparation/Day 16
Transfer Pack Container, 1000 mL with Coupler, Sterile
Sterile Alcohol Pads
Repeater Pump Fluid Transfer Set Male Luer Lock Ends
CTS AIM-V 1000 mL □N/A
Plasma Transfer Set 4" Tubing with Female Luer Adapter
30 mL Luer-Lok Sterile Syringe
CTS AIM V 10 L bag
Pumpmatic Liquid-Dispensing System
10 L Labtainer 3 Port Bag
Syringe Cap Dual Function Red
G-Rex500M Flask Closed System
Reconstituted IL-2
Materials: Day 22 Formulation, Fill, Cryopreservation
Luer-Lok Syringe, 60 mL Sterile
Needle 16G×1.5" Sterile
50 mL Serological Pipets, Sterile
Nunc Internally Threaded Cryotubes Vials, Sterile
10 mL Serological Pipet, Sterile
Centrifuge Tube, 15 mL
Centrifuge Tube, 50 mL
Syringe, 1 cc Sterile Luer-Lok
3 mL Syringe, Luer-Lok Tip, Sterile
25 mL Serological Pipet, Sterile
5 mL Serological Pipet, Sterile
Syringe only Luer-Lok 10 mL
Pipets, Serological 100 mL
ART Barrier Sterile Pipet Tips, 200 µL Individual Wrap
VIA1-Cassettes
Plasma-Lyte A Injection 1L
LOVO Cell Washing Disposable Set
LOVO Ancillary Bag Kit
Sterile Alcohol Pads
Repeater Pump Fluid Transfer Set Male Luer Lock Ends
CTS AIM V 1 L Bottle
Human Albumin 25%
Plasma Transfer Set 4" Tubing with Female Luer Adapter
Tubing, Four Male Luer Manifold
Gravity Blood Administration
Set Y-type with No injection site, 170 µm blood filter
Pumpmatic Liquid-Dispensing System
10 L Labtainer 3 Port Bag
100 mL Syringe
Cryo bag CS750
3 L Culture Bag
Origen Cell Connect CC2
Syringe Cap Dual Function Red
Cryostor CS10, 100 mL Bag
Dispensing Spike, Vented
Reconstituted IL-2
8.0 Process
Step Description Process Information Primary
8.1 Day 0 CM1 Media Preparation
8.1.1 Checked room sanitization, line clearance, and materials. Confirmed room sanitization,
8.1.2 Ensured completion of pre-processing table.
8.1.3 Environmental Monitoring. Prior to processing, ensured pre-process environmental monitoring had been initiated.

8.1.4 Prepared RPMI 1640 Media In the BSC, using an appropriately sized pipette, removed 100.0 mL from 1000 mL RPMI 1640 Media and placed into an appropriately sized container labeled "Waste".

8.1.5 In the BSC added reagents to RPMI 1640 Media bottle. Added the following reagents to the RPMI 1640 Media bottle as shown in in table. Recorded volumes added.

Amount Added per bottle: Heat Inactivated Human AB Serum (100.0 mL); GlutaMax (10.0 mL); Gentamicin sulfate, 50 mg/mL (1.0 mL); 2-mercaptoethanol (1.0 mL)

8.1.6 Mixed Media. Capped RPMI 1640 Media bottle from Step 8.1.5 and swirled bottle to ensure reagents were mixed thoroughly.

8.1.7 Filtered RPMI media. Filtered RPMI 1640 Media from Step 8.1.6 through 1 L 0.22-micron filter unit.

8.1.8 Labeled filtered media. Aseptically capped the filtered media and labeled with the following information.

8.1.9 Removed unnecessary materials from BSC. Passed out media reagents from BSC, left Gentamicin Sulfate and HBSS in BSC for Formulated Wash Media preparation in Section 8.2.

8.1.10 Stored unused consumables. Transferred any remaining opened/thawed media reagents to appropriate storage conditions or disposed into waste.

NOTE: Assigned the appropriate open expiry to media reagents per Process Note 5.9 and labeled with batch record lot number 8.1.11 Thawed IL-2 aliquot. Thawed one 1.1 mL IL-2 aliquot (6×106 IU/mL) (BR71424) until all ice had melted. Recorded IL-2: Lot # and Expiry (NOTE: Ensured IL-2 label was attached).

8.1.12 Transferred IL-2 stock solution to media. In the BSC, transferred 1.0 mL of IL-2 stock solution to the CM1 Day 0 Media Bottle prepared in Step 8.1.8. Added CM1 Day 0 Media 1 bottle and IL-2 ($6 \times 10^6$ IU/mL) 1.0 mL.

8.1.13 Mixed and Relabeled. Capped and swirled the bottle to mix media containing IL-2. Relabeled as "Complete CM1 Day 0 Media" and assigned new lot number.

8.1.14 Sample Media per Sample Plan. Removed 20.0 mL of media using an appropriately sized pipette and dispensed into a 50 mL conical tube.

8.1.15 Labeled and stored. Sample labeled with sample plan inventory label and stored "Media Retain" sample at 2-8° C. until submitted to Login for testing per Sample Plan.

8.1.16 Signed for Sampling. Ensured that LIMS sample plan sheet was completed for removal of the sample.

8.1.17 Prepared "Tissue Pieces" conical tube. In BSC, transferred 25.0 mL of "Complete CM1 Day 0 Media" (prepared in Step 8.1.13) to a 50 mL conical tube. Labeled the tube as "Tissue Pieces" and batch record lot number.

8.1.18 Passed G-Rex100MCS into BSC. Aseptically passed G-Rex100MCS (W3013130) into the BSC.

8.1.19 Prepared G-Rex100MCS. In the BSC, closed all clamps on the G-Rex100MCS, leaving vent filter clamp open.

8.1.20 Prepared G-Rex100MCS. Connected the red line of G-Rex100MCS flask to the larger diameter end of the repeater pump fluid transfer set (W3009497) via luer connection.

8.1.21 Prepared Baxa Pump. Staged Baxa pump next to BSC. Removed pump tubing section of repeater pump fluid transfer set from BSC and installed in repeater pump.

8.1.22 Prepared to pump media. Within the BSC, removed the syringe from Pumpmatic Liquid-Dispensing System (PLDS) (W3012720) and discarded. NOTE: Ensured to not compromise the sterility of the PLDS pipette.

8.1.23 Prepared to pump media. Connected PLDS pipette to the smaller diameter end of repeater pump fluid transfer set via luer connection and placed pipette tip in "Complete CM1 Day 0 Media" (prepared in Step 8.1.13) for aspiration.

Opened all clamps between media and G-Rex100MCS.

8.1.24 Pumped Complete CM1 media into G-Rex100MCS flask. Set the pump speed to "High" and "9" and pumped all Complete CM1 Day 0 Media into G-Rex100MCS flask. Once all media was transferred, cleared the line and stopped pump.

8.1.25 Disconnected pump from flask. Ensured all clamps were closed on the flask, except vent filter. Removed the repeater pump fluid transfer set from the red media line, and placed a red cap (W3012845) on the red media line.

8.1.26 Heated seal. Removed G-Rex100MCS flask from BSC, heated seal (per Process Note 5.12) off the red cap from the red line near the terminal luer.

8.1.27 Labeled G-Rex100MCS. Labeled G-Rex100MCS flask with QA provided in-process "Day 0" label. Attached sample "Day 0" label below.

8.1.28 Monitored Incubator. Incubator parameters: Temperature LED Display: 37.0±2.0° C.; CO2 Percentage: 5.0±1.5% CO2

8.1.29 Warmed Media. Placed the 50 mL conical tube labeled "Tissue Fragments" prepared in Step 8.1.17 and the G-Rex100MCS prepared in Step 8.1.27 in incubator for ≥30 minutes of warming. Recorded warming times below. Recorded if Warm Time was ≥30 minutes (Yes/No).

[Tissue Fragments Conical or GRex100MCS]

8.1.30 Reviewed Section 8.1.

8.2 Day 0 Tumor Wash Media Preparation 8.2.1 Added Gentamicin to HBSS. In the BSC, added 5.0 mL Gentamicin (W3009832 or W3012735) to 1×500 mL HBSS Media (W3013128) bottle. Recorded volumes. Added per bottle: HBSS (500.0 mL); Gentamicin sulfate, 50 mg/ml (5.0 mL)

8.2.2 Capped HBSS bottle and swirled. Capped HBSS containing gentamicin prepared in Step 8.2.1 and swirled bottle to ensure reagents are mixed thoroughly.

8.2.3 Filtered Solution. Filtered HBSS containing gentamicin prepared in Step 8.2.1 through a 1 L 0.22-micron filter unit (W1218810).

8.2.4 Aseptically capped the filtered media and label. Aseptically capped the filtered media and labeled with the following information. Proceeded to SECTION 8.3.

8.2.5 Reviewed Section 8.2.

8.3 Day 0 Tumor Processing 8.3.1 Obtained Tumor. Obtained tumor specimen from QAR and transferred into suite at 2-8° C. immediately for processing. Ensured all necessary information is recorded on the Tumor Shipping Batch Record.

8.3.2 Recorded Tumor Information.

8.3.3 Affixed Tumor Label. Affixed tumor Attachment. QAR release sticker below. Attached Tumor Shipping Batch Record as #5.

8.3.4 Passed in necessary materials for tumor dissection into the BSC.

8.3.5 Opened Materials. Opened all materials inside the BSC, ensuring not to compromise the sterility of the items.

8.3.6 Labeled Materials. Labeled three 50 ml conical tubes: the first as "Forceps," the second as "Scalpel," and the third as "Fresh Tumor Wash Media". Labeled 5×100 mm petri dishes as "Wash 1," "Wash 2," "Wash 3," "Holding," and "Unfavorable." Labeled one 6 well plate as "Favorable Intermediate Fragments."

8.3.7 Aliquoted Tumor Wash Media. Using an appropriately sized pipette, transferred 5.0 mL of "Tumor Wash Media" prepared in Step 8.2.4 into each well of one 6-well plate for favorable intermediate tumor fragments (30.0 mL total). NOTE: The forceps and scalpels were stored in their respective tumor wash media conicals as needed during the tumor washing and dissection processes.

8.3.8 Aliquoted Tumor Wash Media. Using an appropriately sized pipette, transferred 50.0 mL of "Tumor Wash Media" prepared in Step 8.2.4 into each 100 mm petri dish for "Wash 1," "Wash 2," "Wash 3," and "Holding" (200.0 mL total).

8.3.9 Aliquoted Tumor Wash Media. Using an appropriately sized pipette, transfer 20.0 mL of "Tumor Wash Media" prepared in Step 8.2.4 into each 50 mL conical (60.0 mL total).

8.3.10 Prepared Lids for Tumor Pieces. Aseptically removed lids from two 6-well plates. The lids were utilized for selected tumor pieces. NOTE: Throughout tumor processing, DID NOT cross over open tissue culture plates and lids.

8.3.11 Passed the tumor into the BSC. Aseptically passed the tumor into the BSC. Recorded processing start time.

8.3.12 Tumor Wash 1 Using 8" forceps (W3009771), removed the tumor from the specimen bottle and transferred to the "Wash 1" dish prepared in Step 8.3.8.
NOTE: Retained the solution in specimen bottle.

8.3.13 Tumor Wash 1 Using forceps, gently washed tumor time from timer below: specimen and allowed it to sit for ≥3 minutes. Recorded wash time (MM:SS).

8.3.14 Prepared Bioburden Sample per Sample Plan. Transferred 20.0 mL (or available volume) of solution from the tumor specimen bottle into a 50 mL conical per sample plan.

8.3.15 Labeled and stored sample. Labeled with sample plan inventory label and stored bioburden sample collected in Step 8.3.14 at 2-8° C. until submitted for testing.

8.3.16 Signed for sampling. Ensured that LIMS sample plan sheet was completed for removal of the sample.

8.3.17 Tumor Wash 2. Using a new set of forceps removed the tumor from the "Wash 1" dish and transferred to the "Wash 2" dish prepared in Step 8.3.8.

8.3.18 Tumor Wash 2. Using forceps, washed tumor specimen by gently agitating for ≥3 minutes and allowed it to sit. Recorded time.

8.3.19 Prepared drops of Tumor Wash Media for desired tumor pieces. Using a transfer pipette, placed 4 individual drops of Tumor Wash Media from the conical prepared in Step 8.3.9 into each of the 6 circles on the upturned lids of the 6-well plates (2 lids). Placed an extra drop on two circles for a total of 50 drops.

8.3.20 Tumor Wash 3. Using forceps, removed the tumor from the "Wash 2" dish and transferred to the "Wash 3" dish prepared in Step 8.3.8.

8.3.21 Tumor Wash 3. Using forceps, washed tumor specimen by gently agitating and allowed it to sit for ≥3 minutes. Recorded time.

8.3.22 Prepared tumor dissection dish. Placed a ruler under 150 mm dish lid.

8.3.23 Transferred Tumor to Dissection Dish. Using forceps, aseptically transferred tumor specimen to the 150 mm dissection dish lid.

8.3.24 Measured Tumor. Arranged all pieces of tumor specimen end to end and recorded the approximate overall length and number of fragments. Took a clear picture of each tumor specimen.

8.3.25 Assessed Tumor. Assessed the tumor for necrotic/fatty tissue. Assessed whether ≥30% of entire tumor area observed to be necrotic and/or fatty tissue; if yes, contacted area management to ensure tumor was of appropriate size, then proceeded to Step 8.3.26. Assessed whether <30% of entire tumor area were observed to be necrotic or fatty tissue; if yes, proceeded to Step 8.3.27 and clean-up dissection was NOT performed.

8.3.26 If applicable: Clean-Up Dissection. If tumor was large and >30% of tissue exterior was observed to be necrotic/fatty, performed "clean up dissection" by removing necrotic/fatty tissue while preserving tumor inner structure using a combination of scalpel and/or forceps. NOTE: To maintain tumor internal structure, used only vertical cutting pressure. Did not cut in a sawing motion with scalpel. NOTE: Fat, necrotic, and extraneous tissue were placed in unfavorable dish.

8.3.27 Dissect TumorUsing a combination of scalpel and/or forceps, cut the tumor specimen into even, appropriately sized fragments (up to 6 intermediate fragments). NOTE: To maintain tumor internal structure, use only vertical cutting pressure. Did not cut in a sawing motion with scalpel. NOTE: Ensured to keep non-dissected intermediate fragments completely submerged in "Tumor Wash Media" (prepared in Step 8.2.4).

8.3.28 Transferred intermediate tumor fragments. Transferred each intermediate fragment to the "holding" dish from Step 8.3.8.

8.3.29 Dissected Tumor Fragments. Manipulated one intermediate fragment at a time, dissected the tumor intermediate fragment in the dissection dish into pieces approximately 3×3×3 mm in size, minimizing the amount of hemorrhagic, necrotic, and/or fatty tissues on each piece. NOTE: To maintain tumor internal structure, used only vertical cutting pressure. Did not cut in a sawing motion with scalpel.

8.3.30 Selected Tumor Pieces. Selected up to eight (8) tumor pieces without hemorrhagic, necrotic, and/or fatty tissue. Used the ruler for reference. Continued dissection until 8 favorable pieces have been obtained, or the entire intermediate fragment has been dissected. Transferred each selected piece to one of the drops of "Tumor Wash Media" prepared in Step 8.3.19.

8.3.31 Stored Intermediate Fragments to Prevent Drying. After selecting up to eight (8) pieces from the intermediate fragment, placed remnants of intermediate fragment into a new single well of "Favorable Intermediate Fragments" 6-well plate prepared in Step 8.3.7. NOTE: Fatty or necrotic tissue was placed in the "Unfavorable" dish (prepared in step 8.3.6).

8.3.32 Repeated Intermediate Fragment Dissection. Proceeded to the next intermediate fragment, repeated Steps 8.3.29-8.3.31 until all intermediate fragments had been processed, obtained fresh scalpels and forceps as needed.

8.3.33 Determined number of pieces collected. If desirable tissue remains, selected additional Favorable Tumor Pieces from the "favorable intermediate fragments" 6-well plate to fill the drops for a maximum of 50 pieces. Recorded the total number of dissected pieces created. NOTE: Ensuring to keep the tumor intermediate fragments hydrated with Wash Medium as necessary throughout dissection. Recorded Total quantity of dissected pieces collected.

8.3.34 Removed Conical Tube from Incubator. Removed the "Tissue Pieces" 50 mL conical tube from the incubator. Recorded time in Step 8.1.29. Ensured conical tube was warmed for ≥30 min.

8.3.35 Prepared Conical Tube. Passed "Tissue Pieces" 50 mL conical into the BSC, ensuring not to compromise the sterility of open processing surfaces.

8.3.36 Transferred Tumor Pieces to 50 mL Conical Tube. Using a transfer pipette, scapel, forceps or combination, transferred the selected 50 best tumor fragments from favorable dish lids to the "Tissue Pieces" 50 mL conical tube. NOTE: If a tumor piece was dropped during transfer and desirable tissue remains, additional pieces from the favorable tumor intermediate fragment wells were added. Recorded numbers of pieces.

8.3.37 Prepared BSC for G-REX100MCS. Removed all unnecessary items from BSC for vessel seed, retaining the favorable tissue plates if they contained extra fragments.

8.3.38 Removed G-REX100MCS from Incubator. Removed G-Rex100MCS containing media from incubator. Completed Step 8.1.29.

8.3.39 Passed flask into BSC. Aseptically passed G-Rex100MCS flask into the BSC. NOTE: When transferring the flask, did not hold from the lid or the bottom of the vessel. Transferred the vessel by handling the sides. NOTE: Only utilized IPA WIPES when handling G-Rex flasks.

8.3.40 Added tumor fragments to G-Rex100MCS flask. In the BSC, lifted G-Rex100MCS flask cap, ensuring that sterility of internal tubing was maintained.

Swirled conical tube with tumor pieces to suspend and quickly poured the contents into the G-Rex100MCS flask.

8.3.41 Evenly distributed pieces. Ensured that the tumor pieces were evenly distributed across the membrane of the flask. Gently tilted the flask back and forth if necessary to evenly distribute the tumor pieces.

8.3.42 Recorded total number of tumor fragments in vessel. Recorded number of tumor fragments on bottom membrane of vessel and number of observed to be floating in vessel. NOTE: If the number of fragments seeded were NOT equivalent to number of collected in Step 8.3.36H, contacted Area Management, and document in Section 10.0.

8.3.43 Incubate G-Rex flask Incubated G-Rex100MCS at the following parameters: Incubated G-Rex flask: Temperature LED Display: 37.0±2.0° C.; CO2 Percentage: 5.0±1.5% CO2

8.3.44 Calculated incubation window. Performed calculations to determine the proper time to remove G-Rex100MCS incubator on Day 11. Calculations: Time of incubation; lower limite=time of incubation+252 hours; upper limit=time of incubation+276 hours 8.3.45 Environmental Monitoring. After processing, verified BSC and personnel monitoring were performed.

8.3.46 Discarded materials. Storeed remaining unwarmed media at 2-8° C. and labeled. After process was complete, discarded any remaining warmed media and thawed aliquots of IL-2.

8.3.47 Sample submission. Ensured all Day 0 samples were submitted to Login and transferred in LIMS.

8.3.48 Review Section 8.3.

8.4 Day 11—Media Preparation 8.4.1 Checked room, sanitization, line clearance, and materials. Confirmed room sanitization, line clearance, and that materials are within expiry.

8.4.2 Pre-processing table. Equipment list: BSC; Balance; Sebra Tube Sealer; Gatherex™ Media Removal and Cell Recovery Device; Ensure QA provided placard is placed on the appropriate BSC; Ensure QA provided placard lot number and patient ID display matches the lot number and patient ID in this Batch Record.

8.4.3 Monitored Incubator. Monitored Incubator. Incubator parameters: Temperature LED Display: 37.0±2.0° C.; CO2 Percentage: 5.0±1.5% CO2. NOTE: Section 8.4 may be run concurrently with section 8.5.

8.4.4 Warmed media. Warmed 3×1000 mL RPMI 1640 Media (W3013112) bottles and 3×1000 mL AIM-V (W3009501) bottles in an incubator for ≥30 minutes. Recorded time. Media: RPMI 1640 and AIM-V. NOTE: Placed an additional 1×1000 ml bottle of AIM-V Media (W3009501) at room temperature for use in Step 8.5.34. Labeled the bottle "For Cell Count Dilutions Only" and the batch record lot number.

8.4.5 Environmental monitoring. Prior to processing, ensured pre-process environmental monitoring was performed as per SOP-00344.

8.4.6 Removed RPMI 1640 Media from incubator. Removed the RPMI 1640 Media when time was reached. Record end incubation time in Step 8.4.4. Ensure media was warmed for ≥30 min.

8.4.7 Prepared RPMI 1640 Media. In the BSC, removed 100.0 mL from each of the three pre-warmed 1000 mL RPMI 1640 Media bottles and placed into an appropriately sized container labeled "Waste".

8.4.8 In BSC add reagents to RPMI 1640 Media bottle. In the BSC added the following reagents to each of the three RPMI 1640 Media bottles. Recorded volumes added to each bottle. GemCell Human serum, Heat Inactivated Type AB (100.0 mL), GlutaMax (10.0 mL), Gentamicin sulfate, 50 mg/ml (1.0 mL), 2-mercaptoethanol (1.0 mL)

8.4.9 Filter Media. Caped bottles from Step 8.4.8 and swirled to ensure reagents were mixed thoroughly. Filtered each bottle of media through a separate 1 L 0.22-micron filter unit.

8.4.10 Labeled filtered media. Aseptically capped the filtered media and labeled each bottle with CM1 Day 11 Media.

8.4.11 Thawed IL-2 aliquot. Thawed 3×1.1 mL aliquots of IL-2 (6×106 IU/mL) (BR71424) until all ice had melted Recorded IL 2 lot # and Expiry. NOTE: EnsureIL-2 label is attached.

8.4.12 Removed AIM-V Media from the incubator. Removed the three bottles of AIM-V Media from the incubator. Recorded end incubation time in Step 8.4.4. Ensured media had been warmed for ≥30 minutes.

8.4.13 Add IL-2 to AIM-V. In the BSC, using a micropipette, added 3.0 mL of thawed IL-2 into one 1 L bottle of pre-warmed AIM-V media. Rinse micropipette tip with media after dispensing IL-2. Use a new sterile micropipette tip for each aliquot. Recorded the total volume added. Labeled bottle as "AIM-V Containing IL-2".
8.4.14 Transferred materials. Aseptically transferred a 10 L Labtainer Bag and a repeater pump transferr set into the BSC.
8.4.15 Prepared 10 L Labtainer media bag. Closed all lines on a 10 L Labtainer bag. Attached the larger diameter tubing end of a repeater pump transfer set to the middle female port of the 10 L Labtainer Bag via luer lock connection.
8.4.16 Prepare Baxa pump. Staged the Baxa pump next to the BSC. Fed the transfer set tubing through the Baxa pump situated outside of the BSC. Set the Baxa Pump to "High" and "9".
8.4.17 Prepared 10 L Labtainer media bag. In BSC, removed syringe from Pumpmatic Liquid-Dispensing System (PLDS) and discarded. NOTE: Ensured to not compromise the sterility of the PLDS pipette.
8.4.18 Prepared 10 L Labtainer media bag. Connected PLDS pipette to smaller diameter end of repeater pump fluid transfer set via luer connection and placed pipette tip in AIM-V media containing IL-2 bottle (prepared in Step 8.4.13) for aspiration. Opened all clamps between media bottle and 10 L Labtainer.
8.4.19 Pumped media into 10 L Labtainer. In the BSC, using the PLDS, transfer pre-warmed AIM-V media containing IL-2 prepared in Step 8.4.13, as well as two additional AIM-V bottles into the 10 L Labtainer bag. Added the three bottles of filtered CM1 Day 11 Media fomr Step 8.4.10. After addition of final bottle, cleared the line to the bag. NOTE: Stopped the pump between addition of each bottle of media.
8.4.20 Removed pumpmatic from Labtainer bag. Removed PLDS from the transfer set and placed a red cap on the luer of the line in the BSC.
8.4.21 Mixed media. Gently massaged the bag to mix.
8.4.22 Labeled media. In the BSC, labeled the media bag with the following information. Expiration date was 24 hours from the preparation date.
8.4.23 Sample media per sample plan. In the BSC, attached a 60 mL syringe to the available female port of the "Complete CM2 Day 11 Media" bag prepared in step 8.4.22. Removed 20.0 mL of media and place in a 50 mL conical tube. Placed a red cap on the female port of the "Complete CM2 Day 11 Media" Bag.
8.4.24 Labeled and stored sample. Labeled with sample plan inventory label and stored Media Retain Sample at 2-8° C. until submitted to Login for testing.
8.4.25 Sign for Sampling. Ensured that LIMS sample plan sheet was completed for removal of the sample.
8.4.26 Sealed the transfer set line. Outside the BSC, heat sealed off (per Process Note 5.12) the red cap on the transfer set line, close to red cap. Kept the transfer set on the bag.
8.4.27 Prepared Cell Count Dilution Tubes In the BSC, added 4.5 mL of AIM-V Media that had been labelled with "For Cell Count Dilutions" and lot number to four 15 mL conical tubes. Labeled the tubes with the lot number and tube number (1-4). Labeled 4 cryovials "Feeder" and vial number (1-4). Kept vials under BSC to be used in Step 8.5.30.
8.4.28 Transferred reagents from the BSC to 2-8° C. Transferred any remaining 2-mercaptoethanol, GlutaMax, and human serum from the BSC to 2-8° C. Ensured all reagents were labeled with the batch record lot number, and the appropriate open expiry per Process Note 5.9.
8.4.29 Prepared 1 L Transfer Pack. Outside of the BSC weld (per Process Note 5.11) a 1 L Transfer Pack to the transfer set attached to the "Complete CM2 Day 11 Media" bag prepared in step 8.4.22. Labeled transfer pack as "Feeder Cell CM2 Media" and lot number.
8.4.30 Prepared 1 L Transfer Pack. Made a mark on the tubing of the 1L Transfer Pack tubing a few inches away from the bag. Placed the empty Transfer Pack onto the scale so that the tubing was on the scale to the point of the mark.
8.4.31 Tared scale. Tared the scale and left the empty Transfer Pack on the scale.
8.4.32 Prepared feeder cell transfer pack. Set the Baxa pump to "Medium" and "4." Pumped 500.0±5.0 mL of "Complete CM2 Day 11" media prepared in Step 8.4.22 into Cell CM2 Media" transfer pack. Measured by weight and recorded the volume of Complete CM2 media added to the Transfer Pack.
8.4.33 Heated seal line. Once filled, heated seal the line per Process Note 5.12. Separated CM2 Day 11 media bag with transfer set from feeder cell media transfer pack, kept weld toward 1 L transfer pack.
8.4.34 If applicable: Incubated feeder cell media transfer pack. When applicable, placed the "Feeder Cell CM2 Media" transfer pack in incubator until used in Step 8.6.6.
8.4.35 Incubated Complete CM2 Day 11 Media. Placed "Complete CM2 Day 11 Media" prepared in Step 8.4.22 in incubator untiluse in Step 8.7.2.
8.4.36 Reviewed Section 8.4.
8.5 Day 11—TIL Harvest
8.5.1 Preprocessing table. Monitored incubator. Incubator parameters: Temperature LED Display: 37.0±2.0° C.; CO2 Percentage: 5.0±1.5% CO2. NOTE: Section 8.5 may be run concurrently with Sections 8.4 and 8.6.
8.5.2 Removed G-Rex100MCS from incubator. Performed check below to ensure incubation parameters are met before removing G-Rex100MCS from incubator. Lower limited from Step 8.3.44 B. Upper limit from Step 8.3.44 C. Recored Time of Removal from incubator. Determined: Is 8.3.44 B≤Time of Removal from incubator <Step 8.3.44 C? *IF NO CONTACT AREA MANAGEMENT. Carefully removed G-Rex100MCS from incubator and ensured all clamps were closed except large filter line. Recorded processing start time.
8.5.3 Prepared 300 mL Transfer Pack. Labeled a 300 mL Transfer pack as "TIL Suspension".
8.5.4 Prepared 300 mL Transfer Pack. Sterile welded (per Process Note 5.11) the TIL Suspension transfer (single line) of a Gravity Blood Filter. See, for example, FIG. 129.
8.5.5 Prepared 300 mL Transfer Pack. Placed the 300 mL Transfer Pack on a scale and record dry weight.
8.5.6 Prepared 1 L Transfer Pack. Labeled 1 L Transfer Pack as "Supernatant" and Lot number.
8.5.7 Welded transfer packs to G-Rex100MCS. Sterile welded (per Process Note 5.11) the red media removal line from the G-Rex100MCS to the "Supernatant" transfer pack. Sterile welded the clear cell removal line from the G-Rex100MCS to one of the two spike lines on the top of the blood filter connected to the "TIL Suspension" transfer pack prepared in Step 8.5.4. See, for example, FIG. 130.

8.5.8 GatheRex Setup. Placed G-Rex100MCS on the left side of the GatheRex and the "Supernatant" and "TIL Suspension" transfer packs to the right side.

8.5.9 GatheRex Setup. Install the red media removal line from the G Rex100MCS to the top clamp (marked with a red line) and tubing guides on the GatheRex. Installed the clear harvest line from the G-Rex100MCS to the bottom clamp (marked with a blue line) and tubing guides on the GatheRex.

8.5.10 GatheRex Setup. Attached the gas line from the GatheRex to the sterile filter of the G-Rex100MCS flask. NOTE: Before removing the supernatant from the G-Rex100MCS flask, ensured all clamps on the cell removal lines were closed.

8.5.11 Volume Reduction of G-Rex100MCS. Transferred ~900 mL of culture supernatant from the G-Rex100MCS to the 1 L Transfer Pack. Visually inspect G-Rex100MCS flask to ensure flask is level and media has been reduced to the end of the aspirating dip tube. NOTE: If the Gatherex stops prematurely, it was restarted by pressing the button with the arrow pointing to the right again.

8.5.12 Prepare flask for TIL Harvest. After removal of the supernatant, closed all clamps to the red line.

8.5.13 Initiation of TIL Harvest. Recorded the start time of the TIL harvest.

8.5.14 Initiation of TIL Harvest. Vigorously tapped flask and swirled media to release cells. Performed an inspection of the flask to ensure all cells have detached. NOTE: Contacted area management if cells did not detach.

8.5.15 Initiation of TIL Harvest. Tilt flask away from collection tubing and allowed tumor pieces to settle along edge. Slowly tipped flask toward collection tubing so pieces remained on the opposite side of the flask. NOTE: If the cell collection straw is not at the junction of the wall and bottom membrane, rapping the flask while tilted at a 450 angle is usually sufficient to properly position the straw.

8.5.16 TIL Harvested. Released all clamps leading to the TIL Suspension transfer pack.

8.5.17 TIL Harvested. Using the GatheRex, transferred the cell suspension through the blood filter into the 300 mL transfer pack. NOTE: Be sure to maintain the tilted edge until all cells and media are collected.

8.5.18 TIL Harvested. Inspect membrane for adherent cells.

8.5.19 Rinsed flask membrane. Rinsed the bottom of the G-Rex100MCS. Cover ~¼ of gas exchange membrane with rinse media. NOTE: If tumor pieces obstruct the harvest line, pause collection by pressing the "X" on the cell collection line. Press the "Release Clamps" button on the Gatherex and pick the transfer pack up and gently squeeze with increasing pressure until the fragment is removed. Do not squeeze the bag too hard, as this may cause the line or bag to rupture. Resume collection once obstruction has been removed.

8.5.20 Closed clamps on G-Rex100MCS. Ensured all clamps are closed.

8.5.21 Heat sealed. Heat sealed (per Process Note 5.12) the TIL suspension transfer pack as close to the weld as possible so that the overall tubing length remains approximately the same.

8.5.22 Heat sealed. Heat sealed the "Supernatant" transfer pack per Process Note 5.12. Maintained enough line to weld.

8.5.23 Calculated volume of TIL suspension. Recorded weight of TIL Suspension transfer pack and calculated the volume of cell suspension.

8.5.24 Prepared Supernatant Transfer Pack for Sampling. Welded (per Process Note 5.11) a 4" plasma transfer set to "supernatant" transfer pack, retaining the luer connection on the 4" plasma transfer set, and transferred into the BSC.

8.5.25 Prepared TIL Suspension Transfer Pack for Sampling. Welded (per Process Note 5.11) a 4" plasma transfer set to 300 mL "TIL Suspension" transfer pack, retained the luer connection on the 4" plasma transfer set, and transferred into the BSC.

8.5.26 Pulled Bac-T Sample. In the BSC, using an appropriately sized syringe, draw up approximately 20.0 mL of supernatant from the 1L "Supernatant" transfer pack and dispense into a sterile 50 mL conical tube labeled "Bac-T." Keep in BSC for use in Step 8.5.27.

8.5.27 Inoculated BacT per Sample Plan. Removed a 1.0 mL sample from the 50 mL conical labeled BacT prepared in Step 8.5.26 using an appropriately sized syringe and inoculated the anaerobic bottle. Recorded the time the bottle was inoculated using the space provided on the bottle label. Repeated the above for the aerobic bottle. NOTE: This step may be performed out of sequence.

8.5.28 Labeled and stored sample. Labeled with sample plan inventory label and stored Bac-T sample at room temperature, protected from light, until submitted to Login for testing per Sample Plan. NOTE: Did not cover barcode on bottle with label.

8.5.29 Signed for Sampling. Ensured that LIMS sample plan sheet was completed for removal of the sample.

8.5.30 TIL Cell Count Samples. Labeled 4 cryovials with vial number (1-4). Using separate 3 mL syringes, pulled 4×1.0 mL cell count samples from TIL Suspension Transfer Pack using the luer connection, and placed in respective cryovials.

8.5.31 Closed the luer connection. Placed a red cap (W3012845) on the line.

8.5.32 Incubated TIL. Placed TIL Transfer Pack in incubator until needed.

8.5.33 Perform Cell Counts Perform cell counts and calculations utilizing NC-200 and Process Note 5.14. Perform initial cell counts undiluted.

8.5.34 Recorded Cell Count sample volumes. NOTE: If no dilution needed, "Sample [µL]"=200, "Dilution [µL]"=0.

8.5.35 Determined Multiplication Factor. Total cell count sample Volume: 8.5.34A+8.5.34B. Multiplication Factor C÷8.5.34A.

8.5.36 Selected protocols and entered multiplication factors. Ensured the "Viable Cell Count Assay" protocol had been selected, all multiplication factors, and sample and diluent volumes had been entered. NOTE: If no dilution needed, enter "Sample [µL]"=200, "Dilution [µL]"=0

8.5.37 Recorded File Name, Viability and Cell Counts from Nucleoview 8.5.38 Determined the Average of Viable Cell Concentration and Viability of the cell counts performed. Viability (8.5.37A+8.5.37B)÷2. Viable Cell Concentration (8.5.37C+8.5.37D)÷2

8.5.39 Determined Upper and Lower Limit for counts. Lower Limit: 8.5.38F×0.9. Upper Limit: 8.5.38F×1.1.

8.5.40 Were both counts within acceptable limits? Lower Limit: 8.5.37 C and D≥8.5.39G. Upper Limit: 8.5.37 C and D≤8.5.39H. *If either result was "No" performed second set of counts in steps 8.5.41-8.5.48*.

8.5.41 If Applicable: Performed cell counts. Performed cell counts and calculations in utilizing NC-200 and Process Note 5.14. NOTE: Dilution was adjusted according based off the expected concentration of cells. Performed 8.5.42 If Applicable: Recorded Cell Count sample volumes.

8.5.43 If Applicable: Determined Multiplication Factor. Total cell count sample Volume: 8.5.42A+8.5.42B. Multiplication Factor C+8.5.42A D 8.5.44 If Applicable: Selected protocols and entered multiplication factors. Ensureed the "Viable Cell Count Assay" protocol was selected, all multiplication factors, and sample and diluent volumes were entered. NOTE: If no dilution needed, enter "Sample [µL]"=200, "Dilution [µL]"=0.

8.5.45 If Applicable: Recorded Cell Counts from Nucleoview 8.5.46 If Applicable: Determined the Average of Viable Cell Concentration and Viability of the cell counts performed. Determined averaged viable cell concentration.

8.5.47 If Applicable: Determined Upper and Lower Limit for counts. Lower Limit: 8.5.46F×0.9. Upper Limit: 8.5.46F×1.1.

8.5.48 If Applicable: Were counts within acceptable limits? Lower Limit: 8.5.45 C and D≥8.5.47G. Upper Limit: 8.5.45 C and D≤8.5.47H. NOTE: If either result is "No" continue to Step 8.5.49 to determine an average.

8.5.49 If Applicable: Determined an average Viable Cell Concentration from all four counts performed. Average Viable Cell Concentration (A+B+C+D)÷4=AVERAGE 8.5.50 Adjusted Volume of TIL Suspension Calculate the adjusted volume of TIL suspension after removal of cell count samples. Total TIL Cell Volume from Step 8.5.23C (A). Volume of Cell Count Sample Removed (4.0 ml) (B) Adjusted Total TIL Cell Volume C=A−B.

8.5.51 Calculated Total Viable TIL Cells. Average Viable Cell Concentraion*: 8.5.38 F* or 8.5.46 F* or *8.5.49E*; Total Volume: 8.5.50; Total Viable Cells: C=A×B. *Circle step reference used to determine Viable Cell Concentration. NOTE: If Total Viable TIL Cells is <5×106 cells contact Area Management and proceed to Step 8.7.1. If Total Viable TIL Cells is >5×10⁶, proceed to Step 8.5.52.

8.5.52 Calculation for flow cytometry. If the Total Viable TIL Cell count from Step 8.5.51C was ≥4.0×10⁷, calculated the volume to obtain 1.0×107 cells for the flow cytometry sample. *If there are <4.0×10⁷ cells, N/A the remaining fields in the table. Proceed to Step 8.7.1. Toal viable cells required for flow cytometry: 1.0×10⁷ cells. Volume of cells required for flow cytometry: Viable cell concentration from 8.5.51 divided by 1.0×10⁷ cells A.

8.5.53 If Applicable: Removed TIL from incubator. Removed TIL Suspension from incubator and recorded end incubation time in Step 8.5.32.

8.5.54 If Applicable: Removed flow cytometry sample as per Sample Plan. Using an appropriately sized syringe, removed the calculated volume (8.5.52 C) for the phenotyping sample from the TIL Suspension transfer pack and place in a 50 mL conical tube.

8.5.55 If Applicable: Labeled and stored flow cytometry sample. Labeled with sample plan inventory label and store Flow Cytometry sample at 2-8° C. until submitted to Login for testing per Sampling Plan.

8.5.56 Signed for Sampling. Ensure that LIMS sample plan sheet was completed for removal of the sample.

8.5.57 If Applicable: Recalculated Total Viable Cells and Volume flow. Calculated the remaining Total Viable Cells and remaining volume after the removal of cytometry sample below.

| Parameter | Formula | Result |
|---|---|---|
| Total Viable TIL | Step 8.5.51 C | A. cells |
| TIL removed for Flow Cytometry | 1 × 10⁷ cells | B. 1 × 10⁷ cells |
| Remaining Total Viable TIL | C = A − B | C. cells |
| Volume of TIL | Step 8.5.50C | D. mL |
| Volume of TIL removed | Step 8.5.52 C | E. mL |
| Remaining Volume of TIL | F = D − E | F. mL |

8.5.58 If Applicable: Calculated TIL volume. Calculated the volume of TIL suspension equal to 2.0×10⁸ viable cells.

| Total Viable Cells Required | Viable Cell Concentration from Step 8.5.51 A | Volume of TIL Suspension containing 2.0 × 10⁸ viable cells C = A ÷ B |
|---|---|---|
| A. 2.0 × 10⁸ cells | B. cells/mL | C. mL |

8.5.59 If Applicable: Calculated TIL volume to remove Calculate the excess volume of TIL cells to remove.

| Total Volume of TIL Suspension from Step 8.5.57F | Volume of suspension containing 2.0 × 10⁸ TIL from Step 8.5.58C | Volume of excess TIL to Remove C = A − B |
|---|---|---|
| A. | mL | B. |

8.5.60 If Applicable: Removed excess TIL. In the BSC, using an appropriately sized syringe, remove the calculated volume (Step 8.5.59C) from the TIL Suspension transfer pack. NOTE: Do not use a syringe more than once. Use multiple syringes if applicable. Placed in appropriately sized sterile container and label as date, and lot number. Placed a red cap on the "TIL Suspension" transfer pack line.

8.5.61 If Applicable: Placed TIL in Incubator. Placed TIL Suspension Transfer Pack in incubator until needed. Recorded time.

8.5.62 If Applicable: Calculations. Calculated total excess TIL removed. Step 8.5.51A Volume of TIL to Remove from Step 8.5.59C. Calcualted Total Excess TIL removed.

| Viable Cell Concentration from Step 8.5.51A | Volume of TIL to Remove from Step 8.5.59C | Total Excess TIL C = A × B removed |
|---|---|---|
| A. cells/mL | B. mL | C. cells |

8.5.63 If Applicable: Calculations. Calculated amount of CS-10 media to add to excess TIL cells from Step 8.5.62C. Target cell concentration for freezing is $1.0 \times 10^8$ cells/ml.

| Total Excess TIL Removed Step 8.5.62C | Target Concentration to Freeze | Volume of CS-10 to Add (mL) C = A ÷ B |
|---|---|---|
| A. cells | B. $1.0 \times 10^8$ cells/mL | C. mL |

8.5.64 If Applicable: Centrifuged excess TIL. Centrifuged the excess TIL cell suspension. Speed: 350×g. Time: 10:00 minutes. Temperature: Ambient Brake: Full (9). Acceleration: Full (9).

8.5.65 If Applicable: Observed conical tube. Recorded observations: Pellet observed? Supernatant was clear? *NOTE: If either answer was no, contact Area Management.

8.5.66 If Applicable: Added CS-10. In BSC, aseptically aspirate supernatant. Gently tap bottom of tube to resuspend cells in remaining fluid.

8.5.67 If Applicable: Added CS10. Slowly add the volume of CS10 calculated in Step 8.5.63C 8.5.68 If Applicable: Labeled vials. Labeled vials with QA provided labels. Attached a sample label.

8.5.69 If Applicable: Filled Vials. Aliquoted 1.0 mL cell suspension, into appropriately sized cryovials. NOTE: Did not fill more than 10 vials of Excess TIL.

8.5.70 If Applicable: Filled Vials. Aliquoted residual volume into appropriately sized cryovial per SOP-00242. If volume is ≤0.5 mL, add CS10 to vial until volume is 0.5 mL.

8.5.71 If Applicable: Filled Vials. Filled one vial with 1.0 mL of CS10 and label as "Blank".

8.5.72 If Applicable: Recorded number of vials filled. Recorded number of vials filled below, not including blank.

8.5.73 If Applicable: Environmental Monitoring. After processing, verified BSC and personnel monitoring had been performed TIL Cryopreservation of Sample 8.5.74 If Applicable: Calcualted Colume for Cryopreservation. Calculated the volume of cells required to obtain $1 \times 10^7$ cells for cryopreservation.

| Total Viable TIL required for cryopreservation | Viable Cell Concentration From Step 8.5.51A | Volume of Cells required for cryopreservation C = A ÷ B |
|---|---|---|
| A. $1 \times 10^7$ cells | B. cells/mL | C. mL |

8.5.75 If Applicable: Removed sample for Cryopreservation. In the BSC, using the appropriately sized syringe, removed the calculated volume (Step 8.5.74C) from the TIL Suspension transfer pack. Placed in appropriately sized conical tube and label as "Cryopreservation Sample $1 \times 10^7$ cells," dated, and lot number. Placed a red cap (W3012845) on the TIL Suspension transfer pack.

8.5.76 If Applicable: Placed TIL in Incubator. Placed TIL SuspensionTransfer Pack in incubator until needed.

8.5.77 If Applicable: Cryopreservation sample. Centrifuged the "Cryopreservation Sample $1 \times 10^7$ cells" according to the following parameters: Speed: 350×g, Time: 10:00 minutes, Temperature: Ambient, Brake: Full (9) Acceleration: Full (9). NOTE: Ensure proper units are set for speed and time on the centrifuge.

8.5.78 If Applicable: Observed conical tube. Recorded observations: Pellet observed? Supernatant is clear? *NOTE: If either answer is no, contact Area Management.

8.5.79 If Applicable: Added CS-10. In BSC, aseptically aspirate supernatant. Gently tap bottom of tube to resuspend cells in remaining fluid.

8.5.80 If Applicable: Added CS-10. Slowly added. 0.5 mL of CS10. Record edvolume added.

8.5.81 If Applicable: Labeled vial. Labeled vial with QA issued label.

8.5.82 If Applicable: Filled Vials. Aliquoted resuspended volume into labeled cryovial.

8.5.83 If Applicable: Filled blank. Filled another vial with 0.5 mL of CS10 and label as "Blank".

8.5.84 If Applicable: Recorded number of vials filled, not including "blank". Cryopreservation Sample Vials Filled at ~0.5 mL 8.5.85 If Applicable: Environmental Monitoring. After processing, verify BSC and personnel monitoring have been performed.

8.5.86 Review Section 8.5

8.6 Day 11—Feeder Cells 8.6.1 Obtained feeder cells. Obtained 3 bags of feeder cells with at least two different lot numbers from LN2 freezer. Kept cells on dry ice until ready to thaw. NOTE: Section 8.6 could be performed concurrently with Section 8.5.

8.6.2 Obtained feeder cells. Recorded feeder cell information. Confirmed that at least two different lots of feeder cells were obtained.

8.6.3 Prepared waterbath or Cryotherm. Prepared water bath or Cytotherm for Feeder Cell thaw.

8.6.4 Thawed Feeder Cells. Placed the Feeder Cell bags into individual zip top bags, based on Lot number, and thawed 37.0±2.0° C. water bath or cytotherm for ~3-5 minutes or until ice has just disappeared. Recorded thaw times below from timer.

8.6.5 Feeder cell harness preparation. Welded (per Process Note 5.11) 4S-4M60 to a CC2 Cell Connect (W3012820), replacing a single spike of the Cell Connect apparatus (B) with the 4-spike end of the 4S-4M60 manifold at (G). Welded H to G (see, for example, FIG. 131).

8.6.6 If applicable: Removed media from incubator. Removed the Feeder Cell CM2 Media transfer pack prepared in Step 8.4.34 from the incubator.

8.6.7 Attached media transfer pack Weld (per Process Note 5.11) the "Feeder Cell CM2 Media" transfer pack to a CC2 luer. NOTE: The bag will be attached to the side of the harness with the needless injection port.

8.6.8 Transfer harness. Transferred the assembly containing the Complete CM2 Day 11 Media into the BSC.

8.6.9 Pool thawed feeder cells. Within the BSC, pulled 10 mL of air into a 100 mL syringe. Used this to replace the 60 mL syringe on the CC2.

8.6.10 Pool thawed feeder cells. Wiped each port on the feeder cell bags with an alcohol pad prior to removing the cover. Spike the three feeder bags using three of the spikes of the CC2. NOTE: Maintained constant pressure while turning the spike in one direction. Ensure to not puncture the side of the port.

8.6.11 Pool Thawed Feeder Cells. Opened the stopcock so that the line from the feeder cell bags is open and the line to the needless injection port is closed.

8.6.12 Pool Thawed Feeder Cells. Drew up the contents of the feeder cell bags into the syringe. All three bags drained at once. Once feeder cell bags had been drained, while maintaining pressure on the syringe, clamped off the line to the feeder cell bags.

8.6.13 Recorded volume of feeder cells. Did not detach syringe below. the syringe from the harness. Recorded the total volume of feeder cells in the syringe.

8.6.14 Added feeder cells to transfer pack. Turned the stopcock so the line to the feeder cell bag ias closed and the line to the media Transfer Pack was open. Ensured the line to media transfer pack is unclamped.

8.6.15 Added feeder cells to transfer pack Dispensed the feeder cells from the syringe into the "Feeder Cell CM2 Media" transfer pack. Clamped off the line to the transfer pack containing the feeder cells and leave the syringe attached to the harness.

8.6.16 Mixed pooled feeder cells. Massaged bag to mix the pooled feeder cells in the transfer pack.

8.6.17 Labeled transfer pack. Labeled bag as "Feeder Cell Suspension" and Lot number.

8.6.18 Calculated total volume in Transfer Pack Calculated the total volume of feeder cell suspension.

8.6.19 Removed cell count samples. Using a separate 3 mL syringe for each sample, pulled 4×1.0 mL cell count samples from Feeder Cell Suspension Transfer Pack using the needless injection port. Aliquoted each sample into the cryovials labeled in Step 8.4.27. NOTE: Wiped the needless injection port with a sterile alcohol pad (W3009488) and mixed Feeder Cell Suspension between each sampling for cell counts.

8.6.20 Performed Cell Counts. Performed cell counts and calculations utilizing NC-200 and Process Note 5.14. Diluted cell count samples by adding 0.5 mL of cell suspension into 4.5 mL of AIM-V media labelled with the lot number and "For Cell Count Dilutions". This will give a 1:10 dilution. Adjusted if necessary.

8.6.21 Recorded Cell Count. Sample volumes 8.6.22 Determine Multiplication Factor

| Parameter | Formula | Result |
|---|---|---|
| Total cell count sample Volume | 8.6.21 A + 8.6.21 B | C. μL |
| Multiplication Factor | C ÷ 8.6.21A | D. |

8.6.23 Selected protocols and entered multiplication factors. Ensured the "Viable Cell Count Assay" protocol had been selected, all multiplication factors, and sample and diluent volumes had been entered.

8.6.24 Recorded File Name, Viability and Cell Counts from Nucleoview.

8.6.25 Determined the Average of Viable Cell Concentration and Viability of the cell counts performed.

| Parameter | Formula | Result |
|---|---|---|
| Viability | (8.6.24A + 8.6.24B) ÷ 2 | E. % |
| Viable Cell Concentration | (8.6.24C + 8.6.24D) ÷ 2 | F. cells/mL |

8.6.26 Determined Upper and Lower Limit for counts.

| Parameter | Formula | Result |
|---|---|---|
| Lower Limit | 8.6.25F × 0.9 | G. cells/mL |
| Upper Limit | 8.6.25F × 1.1 | H. cells/mL |

8.6.27 Were both counts within acceptable limits?

| Parameter | Formula | Result (Yes/No) |
|---|---|---|
| Lower Limit | 8.6.24 C and D ≥ 8.6.26G | |
| Upper Limit | 8.6.24 C and D ≤ 8.6.26H | |

NOTE: If either result was "No" performed second set of counts in steps 8.6.28-8.6.35.

8.6.28 If Applicable: Performed cell counts Perform cell counts and calculations in utilizing NC-200 per SOP-00314 and Process Note 5.14

NOTE: Dilution could be adjusted according based off the expected concentration of cells.

8.6.29 If Applicable: Recorded Cell Count, sample volumes. NOTE: If no dilution needed, enter "Sample [μL]"=200, "Dilution [μL]"=0.

8.6.30 If Applicable: Determined Multiplication Factor.

| Parameter | Formula | Result |
|---|---|---|
| Total cell count sample Volume | 8.6.29A + 8.6.29B | C. mL |
| Multiplication Factor | C ÷ 8.6.29A | D. |

8.6.31 Select protocols and enter multiplication factors. Ensure the "Viable Cell Count Assay" protocol was selected, all multiplication factors, and sample and diluent volumes were entered. NOTE: If no dilution needed, enter "Sample [μL]"=200, "Dilution [μL]"=0.

8.6.32 If Applicable: Recorded Cell Counts from Nucleoview 8.6.33 If Applicable: Determined the Average of Viable Cell Concentration and Viability of the cell counts performed.

| Parameter | Formula | Result |
|---|---|---|
| Viability | (8.6.32A + 8.6.32B) ÷ 2 | E. % |
| Viable Cell Concentration | (8.6.32C + 8.6.32D) ÷ 2 | F. cells/mL |

8.6.34 If Applicable: Determined Upper and Lower Limit for counts.

| Parameter | Formula | Result |
|---|---|---|
| Lower Limit | 8.6.33F × 0.9 | G. cells/mL |
| Upper Limit | 8.6.33F × 1.1 | H. cells/mL |

8.6.35 If Applicable: Were counts within acceptable limits?

| Parameter | Formula | Result (Yes/No) |
|---|---|---|
| Lower Limit | 8.6.32 C and D ≥ 8.6.34G | |
| Upper Limit | 8.6.32 C and D ≤ 8.6.34H | |

NOTE: If either result was "No," continued to step 8.6.36 to find a total Average Viable Cell Concentration and proceed with calculations.

8.6.36 If Applicable: Determined an average Viable Cell Concentration from all four counts performed.

8.6.37 Adjusted Volume of Feeder Cell Suspension. Calculated the adjusted volume of Feeder Cell suspension after removal of cell count samples. Total Feeder Cell Volume from Step 8.6.18C minutes 4.0 ml removed.

8.6.38 Calculate dTotal Viable Feeder Cells.

| Parameter | Formula | Result |
|---|---|---|
| Average Viable Cell Concentraion* | 8.6.25 F* -or- 8.6.33 F* -or- 8.6.36 E* | A. cells/mL |
| Total Volume | 8.6.37 C | B. mL |
| Total Viable Cells | A × B | C. cells |

If Total Viable Cells are $<5 \times 10^9$, proceed to Step 8.6.39. If Total Viable Cells are $\geq 5 \times 10^9$, proceed to Step 8.5.70.

8.6.39 If Applicable: Obtained additional Feeder Cells. Obtained an additional bag of feeder cells from LN2 freezer. Kept cells on dry ice until ready to thaw.

8.6.40 If Applicable: Obtained additional Feeder Cells. Recorded feeder cell information.

8.6.41 If Applicable: Thawed Additional Feeder Cells. Placed the 4th Feeder Cell bag into a zip top bag and thaw in a 37.0±2.0° C. water bath or cytotherm for ~3-5 minutes or until ice has just disappeared. Recorded thaw time.

8.6.42 If applicable: Pooled additional feeder cells. In the BSC, pulled 10 mL of air into a new 100 mL syringe. Used this to replace the syringe on the harness.

8.6.43 If applicable: Pooled additional feeder cells Wiped the port of the feeder cell bag with an alcohol pad prior to removing the cover. Spiked the feeder cell bag using one of the remaining spikes of the harness prepared in Step 8.6.7 NOTE: Maintained constant pressure while turning the spike in one direction. Ensured to not puncture the side of the port.

8.6.44 If applicable: Pooled additional feeder cells. Opened the stopcock so that the line from the feeder cell bag was open and the line to the needless injection port was closed.

8.6.45 If applicable: Pooled additional feeder cells. Drew up the contents of the feeder cell bag into the syringe. Recorded volume.

8.6.46 If Applicable: Measured Volume. Measured the volume of the feeder cells in the syringe and recorded below (B). Calculated the new total volume of feeder cells.

| Feeder Cell Volume from Step 8.6.37C | Feeder Cell Volume from Step 8.6.45 | Total Feeder Cell C = A + B Volume |
|---|---|---|
| A. mL | B. mL | C. mL |

8.6.47 If Applicable: Added Feeder Cells to Transfer Pack. Turned the stopcock so the line to the feeder cell bag was closed and the line to the "Feeder Cell Suspension" transfer pack was open. Ensured the line to the transfer pack was unclamped. Dispensed the feeder cells from the syringe into the "Feeder Cell Suspension" transfer pack. Clamped the line to the transfer pack and left the syringe attached to the harness.

8.6.48 If Applicable: Added Feeder Cells to Transfer Pack. Massaged bag to mix the pooled feeder cells in the Feeder Cell Suspension transfer pack.

8.6.49 If Applicable: Prepared dilutions. In the BSC, add 4.5 mL of AIM-V Media that has been labelled with "For Cell Count Dilutions" and lot number to four 15 mL conical tubes. Label the tubes with the lot number and tube number (1-4). Labeled 4 cryovials "Additional Feeder" and vial number (1-4).

8.6.50 If Applicable: Prepared cell counts. Using a separate 3 mL syringe for each sample, removed 4×1.0 mL cell count samples from Feeder Cell Suspension transfer pack, using the needless injection port. Aliquoted each sample into cryovials labeled in Step 8.6.49. NOTE: Wiped the needless injection port with a sterile alcohol pad and mix Feeder Cell Suspension between each sampling for cell counts.

8.6.51 If Applicable: Performed Cell Counts. Performed cell counts and calculations utilizing NC-200 and Process Note 5.14. Diluted cell count samples by adding 0.5 mL of cell suspension into 4.5 mL of AIM-V media labelled with the lot number and "For Cell Count Dilutions". This will give a 1:10 dilution. Adjusted if necessary.

8.6.52 If Applicable: Recorded Cell Count sample volumes.

8.6.53 If Applicable: Determined Multiplication Factor

| Parameter | Formula | Result |
|---|---|---|
| Total cell count sample Volume | 8.6.52A + 8.6.52B | C. μL |
| Multiplication | C ÷ 8.6.52A | D. |

8.6.54 If Applicable: Selected protocols and entered multiplication factors. Ensured the "Viable Cell Count Assay" protocol had been selected, all multiplication factors, and sample and diluent volumes had been entered.

8.6.55 If Applicable: Recorded File Name, Viability and Cell Counts from Nucleoview.

8.6.56 If Applicable: Determine the Average of Viable Cell Concentration and Viability of the cell counts performed.

| Parameter | Formula | Result |
|---|---|---|
| Viability | (8.6.55A + 8.6.55B) ÷ 2 | E. % |
| Viable Cell Concentration | (8.6.55C + 8.6.55D) ÷ 2 | F. cells/mL |

8.6.57 If Applicable: Determine Upper and Lower Limit for counts.

| Parameter | Formula | Result |
| --- | --- | --- |
| Lower Limit | 8.6.56F × 0.9 | G. cells/mL |
| Upper Limit | 8.6.56F × 1.1 | H. cells/mL |

Are both counts within acceptable limits? NOTE: If either result is "No" perform second set of counts in Steps 8.5.59-8.5.65

8.6.59 If Applicable: Performed cell counts. Performed cell counts and calculations in utilizing NC-200 and Process Note 5.14. NOTE: Dilution could be adjusted according based off the expected concentration of cells.

8.6.60 If Applicable: Recorded Cell Count sample volumes. NOTE: If no dilution was needed, entered "Sample [μL]"=200, "Dilution [μL]"=0

8.6.61 If Applicable: Determined Multiplication Factor.

| Parameter | Formula | Result |
| --- | --- | --- |
| Total cell count sample Volume | 8.6.60A + 8.6.60B | C. μL |
| Multiplication Factor | C ÷ 8.6.60A | D. |

8.6.62 If Applicable: Select protocols and enter multiplication factors. Ensured the "Viable Cell Count Assay" protocol has been selected, all multiplication factors, and sample and diluent volumes had been entered.
NOTE: If no dilution was needed, entered "Sample [μL]"=200, "Dilution [μL]"=0

8.6.63 If Applicable: Recorded Cell Counts from Nucleoview.

8.6.64 If Applicable: Determined the Average of Viable Cell Concentration and Viability of the cell counts performed.

| Parameter | Formula | Result |
| --- | --- | --- |
| Viability | (8.6.63A + 8.6.63B) ÷ 2 | E. % |
| Viable Cell Concentration | (8.6.63C + 8.6.63D) ÷ 2 | F. cells/mL |

8.6.65 If Applicable: Determined Upper and Lower Limit for counts

| Parameter | Formula | Result |
| --- | --- | --- |
| Lower Limit | 8.6.64F × 0.9 | G. cells/mL |
| Upper Limit | 8.6.64F × 1.1 | H. cells/mL |

8.6.66 If Applicable: Were counts within acceptable limits?

| Parameter | Formula | Result (Yes/No) |
| --- | --- | --- |
| Lower Limit | 8.6.63 C and D ≥ 8.6.65G | |
| Upper Limit | 8.6.63 C and D ≤ 8.6.65H | |

NOTE: If either result was "No," continue to Step 8.6.67 to find a total Average Viable Cell Concentration and proceeded with calculations.

8.6.67 If Applicable: Determined an average Viable Cell Concentration from all four counts performed.

8.6.68 If Applicable: Adjusted Volume of Feeder Cell Suspension. Calculated the adjusted volume of Feeder Cell suspension after removal of cell count samples. Total Feeder Cell Volume from Step 8.6.46C minutes 4.0 mL removed.

8.6.69 If Applicable: Calculated Total Viable Feeder Cells.

| Parameter | Formula | Result |
| --- | --- | --- |
| Average Viable Cell Concentraion* | 8.6.56 F* -or- 8.6.64 F* -or- 8.6.67 E* | A. cells/mL |
| Total Volume | 8.6.68 C | B. mL |
| Total Viable Cells | A × B | C. cells |

*Circled step reference used to determine Viable Cell Concentration.

8.6.70 Calculated Volume of Feeder Cells. Calculated the volume of Feeder Cell Suspension that was required to obtain 5×10$^9$ viable feeder cells.

| Number of Feeder Cells Required | Viable Cell Concentration from Step 8.6.38A* or Step 8.6.69A* | Volume of Feeder Cells = 5 × 10$^9$ viable cells C = A ÷ B |
| --- | --- | --- |
| A. 5 × 10$^9$ Viable Cells | B. cells/mL | C. mL |

*Circle applicable step 8.6.71 Calculated excess feeder cell volume. Calculated the volume of excess feeder cells to remove. Round down to nearest whole number.

| Total Volume of Feeder Cells in Transfer Pack from Step 8.6.46C* or Step 8.6.68C* | Volume of Feeder Cells = 5 × 10$^9$ viable cells from Step 8.6.70C | Volume of Excess Feeder Cells to remove, viable cells C = A − B |
| --- | --- | --- |
| A. mL | B. mL | C. mL |

*Circle applicable step 8.6.72 Removed excess feeder cells. In a new 100 mL syringe, pulled up 10 mL of air and attached the syringe to the harness.

8.6.73 Removed excess feeder cells. Opened the line to the "Feeder Cell Suspension" transfer pack. Using the syringe drew up the volume of feeder cells calculated in Step 8.6.71C plus an additional 10.0 mL from the Transfer Pack into a 100 mL syringe. Closed the line to the Feeder Cell Suspension transfer pack once the volume of feeder cells is removed. Did not remove final syringe. NOTE: Once a syringe has been filled, replaced it with a new syringe. Multiple syringes could be used to remove total volume. With each new syringe, pulled in 10 mL of air.

8.6.74 Recorded volume. Recorded the total volume (including the additional 10 mL) of feeder cells removed.

8.6.75 Added OKT3. In the BSC, using a 1.0 mL syringe and 16G needle, drew up 0.15 mL of OKT3.

8.6.76 Added OKT3. Aseptically removed the needle from the syringe and attach the syringe to the needless injection port. Injected the OKT3.
8.6.77 Added OKT3. Opened the stopcock to the "Feeder Cell Suspension" transfer pack and added 10 mL of feeder cells removed in Step 8.6.73 to flush OKT3 through the line.
8.6.78 Added OKT3. Turned the syringe upside down and push air through to clear the line to the Feeder Cell Suspension transfer pack.
8.6.79 Added OKT3. Left the remaining feeder cell suspension in the syringe. Closed all clamps and remove the harness from the BSC.
8.6.80 Heat Sealed. Heat sealed (per Process Note 5.12) the Feeder Cell Suspension transfer pack, leaving enough tubing to weld. Discarded the harness.
8.6.81 Review Section 8.6

8.7 Day 11 G-Rex Fill and Seed
8.7.1 Set up G-Rex500MCS. Outside the BSC, removed a G-Rex500MCS from packaging and inspected the flask for any cracks or kinks in the tubing. Ensured all luer connections and closures were tight. Closed all clamps on the G-Rex500MCS lines except for the vent filter line. Using a marker drew a line at the 4.5 L gradation.
8.7.2 Removed media from incubator. Removed the "Complete CM2 Day 11 Media", prepared in Step 8.4.35, from the incubator.
8.7.3 Prepared to pump media. Welded (per Process Note 5.11) the red line of the G-Rex500MCS to the repeater pump transfer set attached to the complete CM2 Day 11 Media.
8.7.4 Prepare to pump media. Hung the "Complete CM2 Day 11 Media" bag on an IV pole. Fed the pump tubing through the Baxa pump.
8.7.5 Pumped media into G-Rex500MCS. Set the Baxa pump to "High" and "9". Pumped 4.5 L of media into the G-Rex500MCS, filling to the line marked on the flask in Step 8.7.1.
8.7.6 Heat sealed. Heat sealed the red line (per Process Note 5.12) of the G-Rex500MCS near the weld created in Step 8.7.3.
8.7.7 Labeled Flask. Labeled the flask with the Attach a sample "Day 11 QA provided in-process "Day 11" label.
8.7.8 If applicable: Incubated flask. Held flask in incubator while waiting to seed with TIL.
8.7.9 Welded the Feeder Cell: Suspension transfer pack to the flask Sterile welded (per Process Note 5.11) the red line of the G-Rex500MCS to the "Feeder Cell Suspension" transfer pack.
8.7.10 Added Feeder Cells to G-Rex500MCS. Opened all clamps between Feeder Cell Suspension and G-Rex500MCS and added Feeder Cell Suspension to flask by gravity feed. Ensured the line has been completely cleared.
8.7.11 Heat sealed. Heat sealed (per Process Note 5.12) the red line near the weld created in Step 8.7.9.
8.7.12 Welded the TIL Suspension transfer pack to the flask. Sterile weld (per Process Note 5.11) the red line of the G-Rex500MCS to the "TIL Suspension" transfer pack.
8.7.13 Added TIL to G-Rex500MCS. Opened all clamps between TIL Suspension and G-Rex500MCS and added TIL Suspension to flask by gravity feed. Ensured the line has been completely cleared.
8.7.14 Heat sealed. Heat sealed (per process note 5.12) the red line near the weld created in Step 8.7.12 to remove the TIL suspension bag.
8.7.15 Incubated G-Rex500MCS. Checked that all clamps on the G-Rex500MCS were closed except the large filter line and place in the incubator. Incubator parameters: Temperature LED Display: 37.0±2.0° C., CO2 Percentage: 5.0±1.5% CO2.
8.7.16 Calculated incubation window. Performed calculations to determine the proper time to remove G-Rex500MCS from incubator on Day 16. Time of incubation (Step 8.7.15). Lower limit: Time of incubation+108 hours. Upper limit: Time of incubation+132 hours.
8.7.17 Environmental Monitoring. After processing, verified BSC and personnel monitoring had been performed.
8.7.18 Submit Samples. Submit samples to Login.
8.7.19 Review Section 8.7

8.8 Day 11 Excess TIL Cryopreservation
8.8.1 If Applicable: Froze Excess TIL Vials. Verified the CRF has been set up prior to freeze. Perform Cryopreservation.
8.8.2 If Applicable: Started CRF. Recorded the total number of vials placed into the CRF (not including blank). Verify number of vials transferred into the CRF matches total number of vials prepared in Step 8.5.72 or Step 8.5.84 Step 8.5.72C or Step 8.5.84
8.8.3 If applicable: Initiated automated portion of the freezing profile. Recorded START TIME for the initiation of the automated portion of the freezing profile.
8.8.4 If Applicable: Transferred vials from Controlled Rate Freezer to the appropriate storage. Upon completion of freeze, transfer vials from CRF to the appropriate storage container.
8.8.5 If applicable: Transferred vials to appropriate storage. Recorded storage location in LN2.
8.8.6 Review Section 8.8

8.9 Day 16 Media Preparation
8.9.1 Pre-warmed AIM-V Media. Removed three CTS AIM V 10 L media bags from 2-8° C. at least 12 hours prior to use and place at room temperature protected from light. Verify each bag is within expiry. Labeled each bag with Bag Number (1-3), lot number, date, and "warming start time HHMM". Record warming start time and date.
8.9.2 Calculated time Media from step 8.9.1 was warmed. Calculated the warming time of media bags 1, 2, and 3 from step 8.9.1. Ensured all bags have been warmed for a duration between 12 and 24 hours.
8.9.3 Checked room sanitization, line clearance, and materials. Confirmed room sanitization, line clearance, and materials.
8.9.4 Ensured completion of pre-processing table.
8.9.5 Environmental Monitoring. Prior to processing, ensured pre-process environmental monitoring had been initiated.
8.9.6 Setup 10 L Labtainer for Supernatant. In the BSC attached the larger diameter end of a fluid pump transfer set to one of the female ports of a 10 L Labtainer bag using the Luer connectors.
8.9.7 Setup 10 L Labtainer for Supernatant Label as "Supernatant" and Lot number.
8.9.8 Setup 10 L Labtainer for Supernatant Ensure all clamps were closed prior to removing from the BSC.

NOTE: Supernatant bag was used during TIL Harvest (Section 8.10), which may be performed concurrently with media preparation.

8.9.9 Thawed IL-2. Thawed 5×1.1 mL aliquots of IL-2 ($6 \times 10^6$ IU/mL) (BR71424) per bag of CTS AIM V media until all ice had melted. Recorded IL-2 Lot number and Expiry. Attahed IL-2 labels.

8.9.10 Aliquoted GlutaMax. In BSC, aliquoted 100.0 mL of Glutamax into an appropriately sized receiver. Recorded the volume added to each reciever NOTE: Initially prepared one bag of AIM-V media following Step 8.9.10-Step 8.9.28. Additional bags required were determined in Step 8.10.59.

8.9.11 Labeled receivers. Labeled each receiver as "GlutaMax."

8.9.12 Added IL-2 to GlutaMax. Using a micropipette, added 5.0 mL of IL-2 to each GlutaMax receiver. Ensured to rinse the tip per process note 5.18 and used a new pipette tip for each mL added. Recorded volume added to each Glutamax receiver below.

8.9.13 Labeled receivers. Labeled each receiver as "GlutaMax+IL-2" and receiver number.

8.9.14 Prepared CTS AIM V media bag for formulation. Ensured CTS AIM V 10 L media bag (W3012717) was warmed at room temperature and protected from light for 12-24 hours prior to use. Recorded end incubation time in Step 8.9.2.

8.9.15 Prepared CTS AIM V media bag for formulation. In the BSC, closed clamp on a 4" plasma transfer set, then connected to the bag using the spike ports. NOTE: Maintained constant pressure while turning the spike in one direction. Ensured to not puncture the side of the port.

8.9.16 Prepared CTS AIM V media bag for formulation. Connected the larger diameter end of a repeater pump fluid transfer set to the 4" plasma transfer set via luer.

8.9.17 Stage Baxa Pump. Stage Baxa pump next to BSC. Removed pump tubing section of repeater pump fluid transfer set from BSC and installed in repeater pump.

8.9.18 Prepared to formulate media. In BSC, removed syringe from Pumpmatic Liquid-Dispensing System (PLDS) and discarded. NOTE: Ensured to not compromise the sterility of the PLDS pipette.

8.9.19 Prepared to formulate media. Connected PLDS pipette to smaller diameter end of repeater pump fluid transfer set via luer connection and placed pipette tip in "GlutaMax+IL-2" prepared in Step 8.9.13 for aspiration Open all clamps between receiver and 10 L bag.

8.9.20 Pumped GlutaMax+IL-2 into bag. Set the pump speed to "Medium" and "3" and pump all "GlutaMax+IL-2" into 10 L CTS AIM V media bag. Once no solution remains, clear line and stop pump. Recorded the volume of GlutaMax containing IL-2 added to each Aim V bag below. Recorded/

8.9.21 Removed PLDS. Ensured all clamps were closed, and removed the PLDS pipette from the repeater pump fluid transfer set. Removed repeater pump fluid transfer set and red cap the 4" plasma transfer set.

8.9.22 Labeled Bags. Labeled each bag of "Complete CM4 Day 16 media" prepared.

8.9.23 Removee Media Retain per Sample Plan. Using a 30 mL syringe, removed 20.0 mL of "Complete CM4 Day 16 media" by attaching syringe to the 4" plasma transfer set and dispensed sample into a 50 mL conical tube. NOTE: Only removed the Media Retain Sample from the first bag of media prepared. NOTE: Ensure 4" plasma transfer set was either clamped or red capped after removal of syringe.

8.9.24 Attached new repeater pump fluid transfer set. Attached the larger diameter end of a new fluid pump transfer set onto the 4" plasma transfer set that was connected to the "Complete CM4 Day 16 media" bag.

8.9.25 Labeled and stored sample. Labeled with sample plan inventory label and stored media retain sample at 2-8° C. until submitted to Login for testing per Sample Plan.

8.9.26 Signed for Sampling. Ensured that LIMS sample plan sheet was completed for removal of the sample.

8.9.27 Monitor Incubator. Monitored Incubator. If applicable, per Step 8.9.10, monitor for additional bags prepared. Incubator parameters: Temperature LED Display: 37.0±2.0° C., CO2 Percentage: 5.0±1.5% CO2.

8.9.28 Warmed Complete CM4 Day 16 Media. Warmed the first bag of Complete CM4 Day 16 Media in incubator for ≥30 minutes until ready for use. If applicable, per Step 8.10.59, warmed additional bags.

8.9.29 Prepared Dilutions. In the BSC, added 4.5 mL of AIM-V Media that had been labelled with Batch record Lot Number and "For Cell Count Dilutions" to each 4×15 mL conical tube. Labeled the conical tubes with the lot number and tube number (1-4). Labeled 4 cryovials with vial number (1-4). Kept vials under BSC to be used in Step 8.10.31.

8.9.30 Reviewed Section 8.9

8.10 Day 16 REP Spilt 8.10.1 Pre-processing table.

8.10.2 Monitored Incubator. Monitored Incubator. Incubator parameters: Temperature LED Display: 37.0±2.0° C., CO2 Percentage: 5.0±1.5% CO2

8.10.3 Removed G-Rex500MCS from Incubator. Performed check below to ensure incubation parameters are met before removing G-Rex500MCS from incubator.

| Lower limit from Step 8.7.16B (DDMMYY HHMM) | Upper limit from Step 8.7.16C (DDMMYY HHMM) | Time of Removal from incubator (DDMMYY HHMM) | is 8.7.16B < Time of Removal from incubator < Step 8.7.16C Yes/No* |
|---|---|---|---|

Removed G-Rex500MCS from the incubator.

8.10.4 Setup 1 L Transfer Pack. Heat sealed a 1 L transfer pack (W3006645) per Processed Note 5.12, leaving ~12" of line.

8.10.5 Prepared 1 L Transfer Pack. Labeled 1 L transfer pack as TIL Suspension.

8.10.6 Weighed 1 L Transfer Pack Place 1 L transfer pack, including the entire line, on a scale and record dry weight.

8.10.7 GatheRex Setup. Sterile welded (per Process Note 5.11) the red media removal line from the G-Rex500MCS to the repeater pump transfer set on the 10 L labtainer bag "Supernatant" prepared in Step 8.9.8. Sterile welded the clear cell removal line from the G-Rex500MCS to the TIL Suspension transfer pack prepared in Step 8.10.5.

8.10.8 GatheRex Setup. Placed G-Rex500MCS flask on the left side of the GatheRex. Placed the supernatant labtainer bag and TIL suspension transfer pack to the right side.

8.10.9 GatheRex Setup. Installed the red media removal line from the G-Rex500MCS to the top clamp (marked with a red line) and tubing guides on the GatheRex. Installed the clear harvest line from the G-Rex500MCS to the bottom clamp (marked with a blue line) and tubing guids on the GatheRex.

8.10.10 GatheRex Setup. Attached the gas line from the GatheRex to the sterile filter of the G-Rex500 MCS. NOTE: Before removing the supernatant from the G-Rex500MCS, ensured all clamps on the cell removal lines were closed.

8.10.11 Volume Reduction of G-Rex500MCS. Transferred ~4.5 L of culture supernatant from the G-Rex500MCS to the 10 L Labtainer per SOP-01777. Visually inspect G-Rex500MCS to ensure flask as level and media had been reduced to the end of the aspirating dip tube. NOTE: If the GatheRex stops prematurely, it could be restarted by pressing the button with the arrow pointing to the right again.

8.10.12 Prepared flask for TIL Harvest. After removal of the supernatant, closed all clamps to the red line.

8.10.13 Initiation of TIL Harvest. Recorded the start time of the TIL harvest.

8.10.14 Initiation of TIL Harvest. Vigorously tap flask and swirl media to release cells. Performed an inspection of the flask to ensure all cells have detached. NOTE: Contact area management if cells did not detach.

8.10.15 Initiation of TIL Harvest. Tilted the flask to ensure hose is at the edge of the flask. Note: If the cell collection straw is not at the junction of the wall and bottom membrane, rapping the flask while tilted at a 450 angle is usually sufficient to properly position the straw.

8.10.16 TIL Harvest. Released all clamps leading to the TIL suspension transfer pack.

8.10.17 TIL Harvest. Using the GatheRex transferred the cell suspension into the TIL Suspension transfer pack. NOTE: Be sure to maintain the tilted edge until all cells and media are collected.

8.10.18 TIL Harvest. Inspected membrane for adherent cells.

8.10.19 Rinsee flask membrane. Rinsee the bottom of the G-Rex500MCS. Cover ~¼ of gas exchange membrane with rinse media.

8.10.20 Closed clamps on G-Rex500MCS. Ensured all clam ps are closed on the G-Rex500MCS.

8.10.21 Heat sealed. Heat sealed (per Process Note 5.12) the Transfer Pack containing the TIL as close to the weld as possible so that the overall tubing length remained approximately the same.

8.10.22 Heat sealed. Heat sealed the 10 L Labtainer containing the supernatant (per Process Note 5.12) and passed into the BSC for sample collection in Step 8.10.25.

8.10.23 Calculated volume of TIL suspension. Recorded weight of Transfer Pack with cell suspension and calculate the volume suspension.

8.10.24 Prepared transfer pack for sample removal. Welded (per Process Note 5.11) a 4" Plasma Transfer Set, to the TIL Suspension transfer pack from Step 8.10.21, leaving the female luer end attached as close to the bag as possible.

8.10.25 Removed testing samples from cell supernatant. In the BSC, remove 10.0 mL of supernatant from 10 L labtainer using female luer port and appropriately sized syringe. Placed into a 15 mL conical tube and label as "BacT" Retain the tube for BacT sample in Step 8.10.28.

8.10.26 Removed testing samples from cell supernatant. Using a separate syringe, removed 10.0 mL of supernatant and placed into a 15 mL conical tube. Retained the tube for *mycoplasma* sample for use in Step 8.10.32. Labeled tube as "*Mycoplasma* diluent"

8.10.27 Closed supernatant bag. Placed a red cap on the luer port to close the bag, and pass out of BSC.

8.10.28 Sterility & BacT Testing Sampling. In the BSC, removed a 1.0 mL sample from the 15 mL conical labeled BacT prepared in Step 8.10.25 using an appropriately sized syringe and inoculate the anaerobic bottle. Repeat the above for the aerobic bottle. NOTE: This step may be performed out of sequence.

8.10.29 Labeled and store samples. Labeled with sample plan inventory label and store BacT sample at room temperature, protected from light, until submitted to Login for testing per Sample Plan. NOTE: Did not cover barcode on bottle with label.

8.10.30 Signed for Sampling. Ensured that LIMS sample plan sheet is completed for removal of the sample.

8.10.31 Removed Cell Count Samples. In the BSC, using separate 3 mL syringes for each sample, removed 4×1.0 mL cell count samples from "TIL Suspension" transfer pack using the luer connection. Placed samples in cryovials prepared in Step 8.9.29.

8.10.32 Removed *Mycoplasma* Samples. Using a 3 mL syringe, removed 1.0 mL from TIL Suspension transfer pack and place into 15 mL conical labeled "*Mycoplasma* diluent" prepared in Step 8.10.26.

8.10.33 Label and store sample. Labeled with sample plan inventory label and stored *Mycoplasma* sample at 2-8° C. until submitted to Login for testing per Sample Plan.

8.10.34 Signed for Sampling. Ensured that LIMS sample plan sheet was completed for removal of the sample.

8.10.35 Prepared Transfer Pack for Seeding. In the BSC, attached the large diameter tubing end of a Repeater Pump Fluid Transfer Set set to the Luer adapter on the transfer pack containing the TIL. Clamped the line close to the transfer pack using a hemostat. Placed a red cap onto the end of the transfer set.

8.10.36 Placed TIL in Incubator. Removed cell suspension from the BSC and place in incubator until needed. Recorded time.

8.10.37 Performed Cell Counts. Performed cell counts and calculations utilizing NC-200 and Process Note 5.14. Diluted cell count samples initially by adding 0.5 mL of cell suspension into 4.5 mL of AIM-V media prepared in Step 8.9.29. This gave a 1:10 dilution.

8.10.38 Recorded Cell Count sample volumes 8.10.39 Determined Multiplication Factor.

| Parameter | Formula | Result |
|---|---|---|
| Total cell count sample Volume | 8.10.38A + 8.10.38B | C. μL |
| Multiplication Factor | C ÷ 8.10.38A | D. |

8.10.40 Selected protocols and enter multiplication factors. Ensured the "Viable Cell Count Assay" protocol had been selected, all multiplication factors, and sample and diluent volumes had been entered.

8.10.41 Recorded File Name, Viability and Cell Counts from Nucleoview.

8.10.42 Determined the Average of Viable Cell Concentration and Viability of the cell counts performed.

| Parameter | Formula | Result |
| --- | --- | --- |
| Viability | (8.10.41A + 8.10.41B) 2 | E. % |
| Viable Cell Concentration | (8.10.41C + 8.10.41D) 2 | F. cells/mL |

8.10.43 Determined Upper and Lower Limit for counts.

| Parameter | Formula | Result |
| --- | --- | --- |
| Lower Limit | 8.10.42F × 0.9 | G. cells/mL |
| Upper Limit | 8.10.42F × 1.1 | H. cells/mL |

8.10.44 Were both counts within acceptable limits?

| Parameter | Formula | Result (Yes/No) |
| --- | --- | --- |
| Lower Limit | 8.10.41C and D ≥ 8.10.43G | |
| Upper Limit | 8.10.41 C and D ≤ 8.10.43H | |

8.10.45 If Applicable: Performed cell counts. Performed cell counts and calculations in utilizing NC-200 and Process Note 5.14. NOTE: Dilution may be adjusted according based off the expected concentration of cells.

8.10.46 If Applicable: Recorded Cell Count sample volumes. NOTE: If no dilution was needed, enter "Sample [μL]"=200, "Dilution [μL]"=0

8.10.47 If Applicable: Determined Multiplication Factor.

| Parameter | Formula | Result |
| --- | --- | --- |
| Total cell count sample Volume | 8.10.46A + 8.10.46B | C.mL |
| Multiplication Factor | C ÷ 8.10.46A | D. |

8.10.48 If Applicable: Select protocols and enter multiplication factors.

Ensure the "Viable Cell Count Assay" protocol has been selected, all multiplication factors, and sample and diluent volumes have been entered. NOTE: If no dilution needed, enter "Sample [μL]"=200, "Dilution [μL]"=0

8.10.49 If Applicable: Recorded Cell Counts from Nucleoview 8.10.50 If Applicable: Determined the Average of Viable Cell Concentration and Viability of the cell counts performed.

| Parameter | Formula | Result |
| --- | --- | --- |
| Viability | (8.10.49A ÷ 8.10.49B) ÷ 2 | E. % |
| Viable Cell Concentration | (8.10.49C ÷ 8.10.49D) ÷ 2 | F. cells/mL |

8.10.51 If Applicable: Determined Upper and Lower Limit for counts.

| Parameter | Formula | Result |
| --- | --- | --- |
| Lower Limit | 8.10.50F × 0.9 | G. cells/mL |
| Upper Limit | 8.10.50F × 1.1 | H. cells/mL |

8.10.52 If Applicable: Were counts within acceptable limits?

| Parameter | Formula | Result (Yes/No) |
| --- | --- | --- |
| Lower Limit | 8.10.49 C and D ≥ 8.10.51G | |
| Upper Limit | 8.10.49 C and D ≤ 8.10.51H | |

NOTE: If either result is "No" continue to Step 8.10.53 to determine an average of all cell counts collected.

8.10.53 If Applicable: Determined an average Viable Cell Concentration from all four counts performed.

8.10.54 Adjusted Volume of TIL Suspension. Calculated the adjusted volume of TIL suspension after removal of cell count samples. Total TIL Cell Volume from Step 8.10.23C minus 5.0 mL removed for testing.

8.10.55 Calculated Total Viable TIL Cells.

| Parameter | Formula | Result |
| --- | --- | --- |
| Average Viable Cell Concentraion* | 8.10.42 F* -or- 8.10.50 F* -or- 8.10.53E* | A. cells/mL |
| Total Volume | 8.10.54 C | B. |
| Total Viable Cells | A × B | C. cells |

8.10.56 Calculated flasks for subculture. Calculated the total number of flasks to seed. NOTE: Rounded the number of G-Rex500MCS flasks to see up to the neared whole number.

| Total Viable Cell Count from Step 8.10.55C | Target Cells Required per Flask | Number of G-Rex500MCS Flasks to Seed |
| --- | --- | --- |
| A | B | C = A ÷ B |
| cells | 1.0 × 10$^9$ cells/flask | flasks |

NOTE: The maximum number of G-Rex500MCS flasks to seed was five. If the calculated number of flasks to seed exceeded five, only five were seeded USING THE ENTIRE VOLUME OF CELL SUSPENSION AVAILABLE 8.10.57 Calculate number of flasks for subculture

| Criteria | Yes/No |
| --- | --- |
| Number of G-Rex500MCS Flasks to Seed Step 8.10.56C ≤ 5 If yes, seed number of flasks calculated in Step 8.10.58. | |
| Number of G-Rex500MCS Flasks to Seed Step 8.10.56C > 5 If yes, seed 5 flasks with ALL available cells. | |

8.10.58 QA Review of Cell Count calculations performed in steps 8.10.38-8.10.57.

8.10.59 Determined number of additional media bags needed. Calculated the number of media bags required in addition to the bag prepared in Step 8.9.28.

| Number of G-Rex500MCS Flasks to Seed (Step 8.10.56C) A | Number of Media Bag Required B = A ÷ 2* | Number of Bags Prepared in Step 8.9.22 C | Number of Additional Bags to Prepare D = B − C |
|---|---|---|---|
| | | 1 | |

*Round the number of media bags required up to the next whole number.

8.10.60 If Applicable: Prepared additional media. Prepared one 10 L bag of "CM4 Day 16 Media" for every two G-Rex-500M flask needed calculated in Step 8.10.59D. Proceeded to Step 8.10.62 and seeded the first GREX-500M flask(s) while additional media is prepared and warmed.

8.10.61 If Applicable: Prepared additional media bags. Prepared and warmed the calculated number of additional media bags determined in Step 8.10.59D, repeating Step 8.9.10—Step 8.9.28.

8.10.62 Filled G-Rex500MCS. Opened a G-Rex500MCS on the benchtop and inspected for cracks in the vessel or kinks in the tubing. Ensured all luer connections and closures were tight. Made a mark at the 4500 mL line on the outside of the flask with a marker. Closed all clamps on the G-Rex500MCS except the large filter line.

8.10.63 Filled G-Rex500MCS. Sterile welded (per Process Note 5.11) the red media line of a G-Rex500MCS to the fluid transfer set on the media bag prepared in Step 8.9.28.

8.10.64 Prepared to pump media. Hung "CM4 Day 16 Media" on an IV pole. Fed the pump tubing through the Baxa pump.

8.10.65 Pump media into G-Rex500MCS. Set the Baxa pump on "High" and "9" and pump 4500 mL of media into the flask. Pumped 4.5 L of "CM4 Day 16 Media" into the G-Rex500MCS, filling to the line marked on the flask in Step 8.10.62. Once 4.5 L of media had been transferred, stopped the pump.

8.10.66 Heat Sealed. Heat sealed (per Process Note 5.12) the red media line of G-Rex500MCS, near the weld created in Step 8.10.63, removing the media bag.

8.10.67 Repeated Fill. Repeat Steps 8.10.62-8.10.66 for each flask calculated in Step 8.10.56C as media is warmed and prepared for use. NOTE: Multiple flasks may be filled at the same time using gravity fill or multiple pumps. NOTE: Fill only two flasks per bag of media.

8.10.68 Recorded and labelled flask(s) filled. Labeled each flask alphabetically as it is filled and with QA provided in-process "Day 16" labels.

8.10.69 Sample Labeled. Attached a sample "Day 16" label below.

8.10.70 If applicable: Incubated flask. Held flask in incubator while waiting to seed with TIL.

8.10.71 Verified Number of Flasks Filled. Recorded the total number of flasks filled.

8.10.72 Calculated volume of cell suspension to add. Calculated the target volume of TIL suspension to add to the new G-Rex500MCS flasks.

| Total Volume of TIL suspension from Step 8.10.54C A | Number of flask(s) filled from Step 8.10.71 | Target Volume of cell suspension to transfer to each flask C = A ÷ B |
|---|---|---|
| mL | | mL |

8.10.56C exceeds five only five will be seeded, USING THE ENTIRE VOLUME OF CELL SUSPENSION.

8.10.73 Prepared Flasks for Seeding. Removed G-Rex500MCS from Step 8.10.70 from the incubator.

8.10.74 Prepared for pumping. Closed all clamps on G-Rex500MCS except large filter line. Fed the pump tubing through the Baxa pump.

8.10.75 Removed TIL from incubator. Removed "TIL Suspension" transfer pack from the incubator and record incubation end time in Step 8.10.36.

8.10.76 Prepared cell suspension for seeding. Sterile welded (per Process Note 5.11) "TIL Suspension" transfer pack from Step 8.10.75 to pump inlet line.

8.10.77 Tared scale. Placed TIL suspension bag on a scale. Primed the line from the TIL suspension bag to the weld using the Baxa pump set to "Low" and "2". Tared the scale.

8.10.78 Seeded flask with TIL Suspension. Set Baxa pump to "Medium" and "5". Pump the volume of TIL suspension calculated in Step 8.10.72C into flask. Record the volume of TIL Suspention added to each flask.

8.10.79 Heat sealed. Heat sealed (per Process Note 5.12) the "TIL Suspension" transfer pack, leaving enough tubing to weld on the next flask. Used the line stripper to clear the residual TIL suspension in the G-Rex flask line into the vessel.

8.10.80 Filled remaining flasks. Between each flask seeded, ensured to mix "TIL Suspension" transfer pack and repeat Steps 8.10.76-8.10.79 to seed all remaining flaks. Filled flask(s) in alphabetical order.

8.10.81 Monitored Incubator. NOTE: If flasks must be split among two incubators, ensure to monitor both. Incubator parameters: Temperature LED Display: 37.0±2.0° C., CO2 Percentage: 5.0±1.5% CO2.

8.10.82 Incubated Flasks. Recorded the time each flask is placed in the incubator.

8.10.83 Calculated incubation window. Performed calculations below to determine the time range to remove G-Rex500MCS from incubator on Day 22.

| Flask | 8.10.83A Time of incubation (Step 8.10.82) (DDMMMYY HHMM) | 8.10.83B Lower limit: Time of incubation + 132 hours (DDMMMYY HHMM) | 8.10.83C Upper limit: Time of incubation + 156 hours (DDMMMYY HHMM) |
|---|---|---|---|

8.10.84 Environmental Monitoring. After processing, verified BSC and personnel monitoring had been performed.

8.10.85 Sample Submission. Ensured all Day 16 Samples were submitted to Login.

8.10.86 Reviewed Section 8.10.

8.11 Day 22 Wash Buffer Preparation 8.11.1 Checked room sanitization, line clearance, and materials.

8.11.2 Ensured completion of pre-processing checklist.

8.11.3 Environmental monitoring. Prior to processing, ensured pre-process environmental monitoring had been performed.

8.11.4 Prepared 10 L Labtainer Bag In BSC, attach a 4" plasma transfer set to a 10 L Labtainer Bag via luer connection.

8.11.5 Prepared 10 L Labtainer Bag Label as "Supernatant", lot number, and initial/date.

8.11.6 Prepared 10 L Labtainer Bag. Closed all clamps before transferring out of the BSC. NOTE: Prepared one 10 L Labtainer Bag for every two G-Rex500MCS flasks to be harvested. NOTE: Supernatant bag(s) were used in Section 8.12, which could be run concurrently with Section 8.11.

8.11.7 Welded fluid transfer set. Outside the BSC, closed all clamps on 4S-4M60. Welded (per Process Note 5.11) repeater fluid transfer set to one of the male luer ends of 4S-4M60. (See, for example, FIG. 132.)

8.11.8 Passed materials into the BSC. Passed Plasmalyte-A and Human Albumin 25% into the BSC. Pass the 4S-4M60 and repeater fluid transfer set assembly into the BSC.

| Component Description | Amount Needed |
| --- | --- |
| Plasmalyte-A | 3000.0 mL |
| Human Albumin 25% | 120.0 mL |
| 4S-4M60 with Repeater | 1 Apparatus |
| Fluid Transfer Set | Step 8.11.7 |

8.11.9 Pumped Plasmalyte into 3000 mL bag. Spiked three bags of Plasmalyte-A to the 4S-4M60 Connector set. NOTE: Wipe the port cover with an alcohol swab (W3009488) prior to removing. NOTE: Maintain constant pressure while turning the spike in one direction. Ensure to not puncture the side of the port.

8.11.10 Pumped Plasmalyte into 3000 mL bag. Connected an Origen 3000 mL collection bag via luer connection to the larger diameter end of the repeater pump transfer set.

8.11.11 Pumped Plasmalyte into 3000 mL bag. Closed clamps on the unused lines of the 3000 mL Origen Bag.

8.11.12 Pumped Plasmalyte into 3000 mL bag. Staged the Baxa pump next to the BSC. Fed the transfer set tubing through the Baxa pump situated outside of the BSC. Set pump to "High" and "9".

8.11.13 Pumped Plasmalyte into 3000 mL bag. Opened all clamps from the Plasmalyte-A to the 3000 mL Origen Bag.

8.11.14 Pump Plasmalyte into 3000 mL bag. Pumped all of the Plasmalyte-A into the 3000 mL Origen bag. Once all the Plasmalyte-A had been transferred, stopped the pump.

8.11.15 Pumped Plasmalyte into 3000 mL bag. If necessary, removed air from 3000 mL Origen bag by reversing the pump and manipulating the position of the bag.

8.11.16 Pumped Plasmalyte into 3000 mL bag. Closed all clamps. Remove the 3000 mL bag from the repeater pump fluid transfer set via luer connection and placed a red cap (W3012845) on the line to the bag.

8.11.17 Added Human Albumin 25% to 3000 mL Bag. Opened vented mini spike. Without compromising sterility of spike, ensured blue cap is securely fastened.

8.11.18 Added Human Albumin 25% to 3000 mL Bag. Spiked the septum of a Human Albumin 25% bottle with the vented mini spike. NOTE: Ensured to not compromise the sterility of the spike.

8.11.19 Added Human Albumin 25% to 3000 mL Bag. Repeated Step 8.11.17—Step 8.11.18 two times for a total of three (3) spiked Human Albumin 25% bottles.

8.11.20 Added Human Albumin 25% to 3000 mL Bag. Removed the blue cap from one vented mini spike and attach a 60 mL syringe to the Human Serum Albumin 25% bottle.

8.11.21 Added Human Albumin 25% to 3000 mL Bag. Draw up 60 mL of Human Serum Albumin 25%. NOTE: It may be necessary to use more than one bottle of Human Serum Albumin 25%. If necessary, disconnect the syringe from the vented mini spike and connect it to the next vented mini spike in a Human Serum Albumin 25% bottle. Do not remove vented mini spike from the Human Serum Albumin 25% bottle.

8.11.22 Added Human Albumin 25% to 3000 mL Bag. Once 60 mL has been obtained, remove the syringe from the vented mini spike.

8.11.23 Added Human Albumin 25% to 3000 mL Bag. Attach syringe to needleless injection port on 3000 mL Origen bag filled with Plasmalyte-A in Step 8.11.16. Dispensed all of the Human Albumin 25%. NOTE: Wiped needless injection port with an alcohol pad before each use.

8.11.24 Added Human Albumin 25% to 3000 mL Bag. Repeated Step 8.11.20-Step 8.11.23 to obtain a final volumeof 120.0 mL of Human Albumin 25%.

8.11.25 Mixed Bag. Gently mixed the bag after all of the Human Albumin 25% had been added.

8.11.26 Labeled Bag. Labeled as "LOVOWash Buffer" and lot number, and assign a 24 hour expiry.

8.11.27 Prepared IL-2 Diluent. Using a 10 mL syringe, removed 5.0 mL of LOVO Wash Buffer using the needleless injection port on the LOVO Wash Buffer bag. Dispensed LOVO wash buffer into a 50 mL conical tube and label as "IL-2 Diluent" and the lot number. NOTE: Wiped the needleless injection port with an alcohol pad before each use.

8.11.28 CRF Blank Bag LOVO Wash Buffer Aliquotted. Using a 100 mL syringe, drew up 70.0 mL of LOVO Wash Buffer from the needleless injection port. NOTE: Wiped the needleless injection port with an alcohol pad before each use.

8.11.29 CRF Blank Bag LOVO Wash Buffer Aliquotted. Placed a red cap on the syringe and label as "blank cryo bag" and lot number. NOTE: Held the syringe at room temp until needed in Step 8.14.3

8.11.30 Completed Wash Buffer Prep. Closed all clamps on the LOVO Wash Buffer bag.

8.11.31 Thawed IL-2. Thawed one 1.1 mL of IL-2 ($6 \times 10^6$ IU/mL)), until all ice has melted. Record IL-2 Lot number and Expiry. NOTE: Ensured IL-2 label is attached.

8.11.32 IL-2 Preparation. Added 50 µL IL-2 stock ($6 \times 10^6$ IU/mL) to the 50 mL conical tube labeled "IL-2 Diluent."

8.11.33 IL-2 Preparation. Relabeled conical as "IL-2 $6 \times 10^4$", the date, lot number, and 24 hour expiry. Cap and store at 2-8° C.

8.11.34 Cryopreservation Prep. Placed 5 cryo-cassettes at 2-8° C. to precondition them for final product cryopreservation.

8.11.35 Prepared Cell Count Dilutions. In the BSC, added 4.5 mL of AIM-V Media that has been labelled with lot number and "For Cell Count Dilutions" to 4 separate 15 mL conical tubes. Labeled the tubes with the batch record lot number and tube number (1-4). Set aside for use in Step 8.12.34

8.11.36 Prepared Cell Counts. Labeled 4 cryovials with vial number (1-4). Kept vials under BSC to be used in Step 8.12.33.

8.11.37 Reviewed Section 8.11

8.12 Day 22 TIL Harvest 8.12.1 Monitor Incubator. Monitored the incubator. Incubator Parameters Temperature LED display: 37±2.0° C., CO2 Percentage: 5%+1.5%. NOTE: Section 8.12 could be run concurrently with Section 8.11.

8.12.2 Removed G-Rex500MCS Flasks from Incubator. Performed check below to ensure incubation parameters were met before removing G-Rex500MCS from incubator.

| Flask | Shelf | Lower limit from Step 8.10.83 B (DDMMMYY HHMM) | Upper limit from Step 8.10.83 C (DDMMMYY HHMM) | Time of Removal from Incubator (DDMMMYY HHMM) | Is 8.10.83 B < Time of Removal from Incubator < Step 8.10.83 C Yes/No* |
|---|---|---|---|---|---|

NOTE:
This step must was performed as each flask is removed from the incubator.

8.12.3 Prepared TIL collection bag Labeled a 3000 mL collection bag as "TIL Suspension", lot number, and initial/date.

8.12.4 Sealed off extra connections. Heat sealed off two leur connections on the collection bag near the end of each connection per Process Note 5.12.

8.12.5 GatheRex Setup. Sterile welded (per Process Note 5.11) the red media removal line from the G-Rex500MCS to the 10 L labtainer bag prepared in Step 8.11.5. NOTE: Referenced Process Note 5.16 for use of multiple GatheRex devices.

8.12.6 GatheRex Setup. Sterile welded (per Process Note 5.11) the clear cell removal line from the G-Rex500MCS to the TIL Suspension collection bag prepared in Step 8.12.3. NOTE: Reference Process Note 5.16 for use of multiple GatheRex devices.

8.12.7 GatheRex Setup. Placed the G-Rex500MCS flask on the left side of the GatheRex. Placed the supernatant Labtainer bag and pooled TIL suspension collection bag to the right side.

8.12.8 GatheRex Setup. Installed the red media removal line from the G-Rex500MCS to the top clamp (marked with a red line) and tubing guides on the GatheRex. Installed the clear harvest line from the G-Rex500MCS to the bottom clamp (marked with a blue line) and tubing guides on the GatheRex.

8.12.9 GatheRex Setup. Attached the gas line from the GatheRex to the sterile filter of the G-Rex500MCS. NOTE: Before removing the supernatant from the G-Rex500MCS, ensured all clamps on the cell removal lines were closed.

8.12.10 Volume Reduction. Transferred ~4.5 L of supernatant from the G-Rex500MCS to the Supernatant bag. Visually inspected G-Rex500MCS to ensure flask is level and media had been reduced to the end of the aspirating dip tube. Repeat step if needed. NOTE: If the GatheRex stopped prematurely, it may be restarted by pressing the button with the arrow pointing to the right again.

8.12.11 Prepared flask for TIL Harvest. After removal of the supernatant, closed all clamps to the red line.

8.12.12 Initiated collection of TIL. Recorded the start time of the TIL harvest.

8.12.13 Initiated collection of TIL. Vigorously tap flask and swirl media to release cells. Performed an inspection of the flask to ensure all cells have detached. Placed "TIL Suspension" 3000 mL collection bag on dry wipes on a flat surface. NOTE: Contacted area management if cells did not detach.

8.12.14 Initiated collection of TIL. Tilted the flask to ensure hose is at the edge of the flask. NOTE: If the cell collection hose was not at the junction of the wall and bottom membrane, rapping the flask while tilted at a 450 angle is usually sufficient to properly position the hose.

8.12.15 TIL Harvest. Released all clamps leading to the TIL suspension collection bag.

8.12.16 TIL Harvest. Using the GatheRex, transferred the TIL suspension into the 3000 mL collection bag. NOTE: Maintained the tilted edge until all cells and media were collected.

8.12.17 TIL Harvest. Inspect membrane for adherent cells.

8.12.18 Rinsed flask membrane. Rinsed the bottom of the G-Rex500MCS. Covered ~¼ of gas exchange membrane with rinse media.

8.12.19 Close dclamps on G-Rex500MCS. Ensure all clamps are closed.

8.12.20 Heat sealed. Heat seal (per Process Note 5.12) the collection bag containing the TIL as close to the weld as possible so that the overall tubing length remained approximately the same.

8.12.21 Heat Sealed. Heat sealed (per Process Note 5.12) the Supernatant bag.

8.12.22 Completed harvest of remaining G-Rex 500 MCS flasks. Repeat Steps 8.12.2 and 8.12.5-8.12.21, pooling all TIL into the same collection bag.
NOTE: IT WAS NECESSARY TO REPLACE THE 10 L UPERNATANT BAG AFTER EVERY 2ND FLASK.
NOTE: Reference Process Note 5.16 for use of multiple GatheRex devices.

8.12.23 Prepared LOVO source bag. Obtained a new 3000 mL collection bag. Labeled as "LOVO Source Bag", lot number, and Initial/Date.

8.12.24 Prepared LOVO source bag. Heat sealed (per Process Note 5.12) the tubing on the "LOVO Source bag", removing the female luers, leaving enough line to weld.

8.12.25 Weighed LOVO Source Bag. Placed an appropriately sized plastic bin on the scale and tare. Place the LOVO Source Bag, including ports and lines, in the bin and record the dry weight 8.12.26 Transferred cell suspension into LOVO source bag. Closed all clamps of a 170 µm gravity blood filter.

8.12.27 Transferred cell suspension into LOVO source bag. Sterile welded (per Process Note 5.11) the long terminal end of the gravity blood filter to the LOVO source bag.

8.12.28 Transferred cell suspension into LOVO source bag. Sterile welded (per Process Note 5.11) one of the two source lines of the filter to "pooled TIL suspension" collection bag.

8.12.29 Transferred cell suspension into LOVO source bag. Once weld was complete, heat sealed (per Process Note 5.12) the unused line on the filter to remove it.

8.12.30 Transferred cell suspension into LOVO source bag. Opened all necessary clamps and elevate the TIL suspension by hanging the collection bag on an IV pole to initiate gravity-flow transfer of TIL through the blood filter and into the LOVO source bag. Gently rotated or knead the TIL Suspension bag while draining in order to keep the TIL in even suspension. Note: Did not allow the LOVO source bag to hang from the filtration apparatus. Laid LOVO source bag on dry wipes on a flat surface.

8.12.31 Closed all clamps. Once all TIL were transferred to the LOVO source bag, closed all clamps.

8.12.32 Heat Sealed. Heat sealed (per Process Note 5.12) as close to weld as possible to remove gravity blood filter.

8.12.33 Removed Cell Counts Samples. In the BSC, using separate 3 mL syringes for each sample, removed 4×1.0 mL cell count samples from the LOVO source bag using the needless injection port. Placed samples in the cryovials prepared in Step 8.11.36. NOTE: Wiped needless injection port with an alcohol pad and mix LOVO source bag between each sample.

8.12.34 Performed Cell Counts. Performed cell counts and calculations utilizing NC-200 and Process Note 5.14. Diluted cell count samples initially by adding 0.5 mL of cell suspension into 4.5 mL of AIM-V media prepared in Step 8.11.35. This gave a 1:10 dilution.

8.12.35 Recorded Cell Count sample volumes.

8.12.36 Determined Multiplication Factor

| Parameter | Formula | Result |
|---|---|---|
| Total cell count sample Volume | 8.12.35A + 8.12.35B | C. µL |
| Multiplication Factor | C ÷ 8.12.35A | D. |

8.12.37 Selected protocols and enter multiplication actors. Ensure the "Viable Cell Count Assay" protocol had been selected, all multiplication factors, and sample and diluent volumes had been entered. NOTE: If no dilution needed, enter "Sample [µL]"=200, "Dilution [µL]"=0

8.12.38 Record Cell Counts from Nucleoview 8.12.39 Determined the Average Viability, Viable Cell Concentration, and Total Nucleated Cell concentration of the cell counts performed.

| Parameter | Formula | Result |
|---|---|---|
| Viability | (8.12.38A + 8.12.38B) ÷ 2 | G. |
| Viable Cell Concentration | (8.12.38C + 8.12.38D) ÷ 2 | H. cells/mL |
| Total Nucleated Cell Concentration | (8.12.38E + 8.12.38F) ÷ 2 | I. cells/mL |

8.12.40 Determined Upper and Lower Limit for counts

| Parameter | Formula | Result |
|---|---|---|
| Lower Limit | 8.12.39H × 0.9 | J. cells/mL |
| Upper Limit | 8.12.39I × 1.1 | K. cells/mL |

8.12.41 Were both counts within acceptable limits?

| Parameter | Formula | Result (Yes/No) |
|---|---|---|
| Lower Limit | 8.12.38 C and D ≥ 8.12.40J | |
| Upper Limit | 8.12.38 C and D ≤ 8.12.40K | |

NOTE:
If either result was "No" performed second set of counts in steps 8.12.42-8.12.49.

NOTE: If either result was "No" performed second set of counts in steps 8.12.42-8.12.49.

8.12.42 If Applicable: Performed cell counts. Performed cell counts and calculations in utilizing NC-200 and Process Note 5.14. NOTE: Dilution may be adjusted according based off the expected concentration of cells.

8.12.43 If Applicable: Recorded Cell Count sample volumes 8.12.44 If Applicable: Determined Multiplication Factor

| Parameter | Formula | Result |
|---|---|---|
| Total cell count sample Volume | 8.12.43A + 8.12.43B | C. µL |
| Multiplication Factor | C ÷ 8.12.43A | D. |

8.12.45 If Applicable: Selected protocols and enter multiplication factors. Ensure the "Viable Cell Count Assay" protocol had been selected, all multiplication factors, and sample and diluent volumes had been entered. NOTE: If no dilution needed, enter "Sample [µL]"=200, "Dilution [µL]"=0

8.12.46 If Applicable: Record Cell Counts from Nucleoview 8.12.47 If Applicable: Determine the Average Viability, Viable Cell Concentration, and Total Nucleated Cell concentration of the cell counts performed.

| Parameter | Formula | Result |
|---|---|---|
| Viability | (8.12.46A + 8.12.46B) ÷ 2 | G. |
| Viable Cell Concentration | (8.12.46C + 8.12.46D) ÷ 2 | H. cells/mL |
| Total Nucleated Cell Concentration | (8.12.46E + 8.12.46F) ÷ 2 | I. cells/mL |

8.12.48 If Applicable: Determined Upper and Lower Limit for counts

| Parameter | Formula | Result |
| --- | --- | --- |
| Lower Limit | 8.12.47 H × 0.9 | J. cells/mL |
| Upper Limit | 8.12.47 H × 1.1 | K. cells/mL |

8.12.49 If Applicable: Were counts within acceptable limits?

| Parameter | Formula | Result (Yes/No) |
| --- | --- | --- |
| Lower Limit | 8.12.46 C and D ≥ 8.12.48J | |
| Upper Limit | 8.12.46 C and D ≤ 8.12.48K | |

NOTE:
If either result was "No" continue to Step 8.12.50 to determine an average 8.12.50 If Applicable: Determined an average Viable Cell Concentration and average Total Nucleated Cell Concentration from all four counts performed.

8.12.51 QA Review of Cell Counts. QA personnel review calculations performed in steps 8.12.38-8.12.50.

8.12.52 Weighed LOVO Source Bag. Placed an appropriately sized plastic bin on the scale and tare. Placed the full LOVO source bag in the bin and record the weight. Calculated the volume of cell suspension.

8.12.53 Calculate Total Viable TIL Cells.

| Parameter | Formula | Result |
| --- | --- | --- |
| Average Viable Cell Concentraion* | 8.12.39 H* -or- 8.12.47 H* -or- 8.12.50 E* | A. cells/mL |
| Total Volume | 8.12.52 C | B. mL |
| Total Viable Cells | A × B | C. cells |
| Is C ≥ 1.5 × 10$^9$? | Yes/No** | |

*Circled step reference used to determine Viable Cell Concentration.
**If "Yes," proceeded. If "No," contacted Area Management.

8.12.54 Calculate Total Nucleated Cells.

| Parameter | Formula | Result |
| --- | --- | --- |
| Average Total Nucleated Cell Concentraion* | 8.12.39 I* -or- 8.12.47 I* -or- 8.12.50 J* | A. cells/mL |
| Total Volume | 8.5.52 C | B. mL |
| Total Nucleated Cells | A × B | C. cells |

*Circled step reference used to determine Total Nucleated Cell Concentration.

8.12.55 Prepared Mycoplasma Diluent. In the BSC, removed 10.0 mL from one supernatant bag via luer sample port and placed in a 15 mL conical. Label 15 mL conical "Mycoplasma Diluent" and keep in the BSC for use in Step 8.14.69.

8.12.56 Review Section 8.12

8.13 LOVO 8.13.1 Turned on the LOVO using the switch on the back left of the instrument. NOTE: Steps 8.13.1-8.13.13 may be performed concurrently with Sections 8.11-8.12.

8.13.2 Checked weigh scales and pressure sensor.

8.13.3 Made sure there was nothing hanging on any of the weigh scales and reviewed the reading for each scale. Recorded values in Step 8.13.5. Note: If any of the scales read outside of a range of 0+/-2 g, performed weigh scale calibration 8.13.4 If all scales were in tolerance with no weight hanging, proceeded to hang a 1-kg weight on each scale (#1-4) and reviewed the reading. Recorded Values in Step 8.13.5.

8.13.5 Scale Checked. Recorded the displayed values for each scale. If values were in range, continue processing. If values were not in range, perform Calibration.

8.13.6 Reviewed the pressure sensor reading on the Instrument Operation Profile Screen and recorded. The acceptable range for the pressure reading was 0+/-10 mmHg. If displayed value was out of this range, stored a new atmospheric pressure setting, per the machine instructions.

8.13.7 Repeated steps. If a new weigh scale calibration had been performed or a new atmospheric pressure setting had been stored, repeated Steps 8.13.3-8.13.6.

8.13.8 Started the "TIL G-Rex Harvest" protocol from the drop-down menu.

8.13.9 The Solution 1 Screen displayed: Buffer type read PlasmaLyte 8.13.10-8.13.16 Followed the LOVO touch screen prompts.

8.13.17 Determined the final product target volume.

NOTE: Using the total nucleated cells (TNC) value from Step 8.12.54 C and the chart below, determined the final product target volume. Recorded the Final Product Volume (mL)

| Cell Range | Final Product (Retentate) Volume to Target (mL) |
| --- | --- |
| 0 < Total (Viable + Dead) Cells ≤ 7.1 × 10$^{10}$ | 165 |
| 7.1 × 10$^{10}$ < Total (Viable + Dead) Cells ≤ 1.1 × 10$^{11}$ | 215 |
| 1.1 × 10$^{11}$ < Total (Viable + Dead) Cells ≤ 1.5 × 10$^{11}$ | 265 |

Note:
If TVC from Step 8.12.53 C was >1.5 × 10$^{11}$ contacted Area Management.

8.13.18-8.13.22 Followed the LOVO touch screen prompts.

8.13.23 Loaded disposable kit. Prior to loading the disposable kit, wipe pressure sensor port with an alcohol wipe followed followed by a lint-free wipe. Load the disposable kit. Follow screen directions on loading the disposable kit.

8.13.24 Removed filtrate bag. When the standard LOVO disposable kit had been loaded, touched the Next button. The Container Information and Location Screen displayed. Removed filtrate bag from scale 8.13.25 Ensured Filtrate container was New and Off-Scale 8.13.26 Entered Filtrate capacity. Sterile welded a LOVO Ancillary Bag onto the male luer line of the existing Filtrate Bag. Ensured all clamps are open and fluid path is clear. Touch the Filtrate Container Capacity entry field. A numeric keypad displatys. Enter the total new Filtrate capacity (5,000 mL). Touch the button to accept the entry. NOTE: Estimated Filtrate Volume should not exceed 5000 mL.

8.13.27 Placed Filtrate container on benchtop. NOTE: If tubing was removed from the F clamp during welding, placed the tubing back into the clamp. Placed the new Filtrate container on the benchtop. DID NOT hang the Filtrate bag on weigh scale #3. Weigh scale #3 will be empty during the procedure.

8.13.28 Followed the LOVO touch screen prompts after changes to the filtrate container.

8.13.29 Ensured kit was loaded properly. The Disposable Kit Dry Checks overlay displays. Checked that the kit was loaded properly and all clamps were open. Checked all tubing for kinks or other obstructions and correct if possible. Ensured kit was properly installed and check all Robert's clamps. Pressed the Yes button. All LOVO mechanical clamps closed automatically and the Checking Disposable Kit Installation screen displays. The LOVO went through a series of pressurizing steps to check the kit.

8.13.30 Kit Check Results. If the Kit check passed, proceeded to the next step. *If No, a second Kit Check could be performed after checks have been complete. *If No, Checked all tubing for kinks or other obstructions and correct *If No, Ensured kit was properly installed and check all Robert's clamps. If the 2nd kit check failed: Contact area management and prepare to installation of new kit in Section 10.0. Repeat Step 8.13.23-Step 8.13.30 needed.

8.13.31 Attached PlasmaLyte. The Connect Solutions screen displayed. The wash value would always be 3000 mL. Entered this value on screen. Sterile welded the 3000 mL bag of PlasmaLyte to the tubing passing through Clamp 1 per Process Note 5.11. Hung the PlasmaLyte bag on an IV pole placing both corner bag loops on the hook.

8.13.32 Verified that the PlasmaLyte was attached. Opened any plastic clamps. Verified that the Solution Volume entry was 3000 mL. Touched the "Next" button. The Disposable Kit Prime overlay displayed. Verified that the PlasmaLyte was attached and any welds and plastic clamps on the tubing leading to the PlasmaLyte bag were open, then touched the Yes button 8.13.33 Observed that the PlasmaLyte is moving. Disposable kit prime starts and the Priming Disposable Kit Screen displays. Visually observed that PlasmaLyte moving through the tubing connected to the bag of PlasmaLyte. If no fluid was moving, pressed the Pause Button on the screen and determined if a clamp or weld was still closed. Once the problem had been solved, pressed the Resume button on the screen to resume the Disposable Kit Prime. When disposable kit prime finished successfully, the Connect Source Screen displayed.

8.13.34-8.13.35 Followed the LOVO touch screen prompts.

8.13.36 Attached Source container to tubing. Sterile weld the LOVO Source Bag prepared in Step 8.12.31 to the tubing passing through Clamp S per Process Note 5.11. It could be necessary to remove the tubing from the clamp. Note: Made sure to replace source tubing into the S clamp if removed.

8.13.37 Hung Source container. Hung the Source container on the IV pole placing both corner bag loops on the hook. DID NOT hang the Source on weigh scale #1. Opened all clamps to the source bag.

8.13.38 Verified Source container was attached. Touched the Next button. The Source Prime overlay displayed. Verified that the Source wasattached to the disposable kit, and that any welds and plastic clamps on the tubing leading to the Source were open. Touched the Yes button.

8.13.39 Confirm PlasmaLyte was moving. Source prime started and the Priming Source Screen displayed. Visually observed that PlasmaLyte is moving through the tubing attached to the Source bag. If no fluid is moving, press the Pause Button on the screen and determine if a clamp or weld is still closed. Once the problem was solved, pressed the Resume button on the screen to resume the Source Prime.

8.13.40 Started Procedure Screen. When the Source prime finishes successfully, the Start Procedure Screen displays. Pressed Start, the "Pre-Wash Cycle 1" pause screen appears immediately after pressing start.

8.13.41 Inverted In Process Bag. Removed the In Process Bag from weigh scale #2 (can also remove tubing from the In Process top port tubing guide) and manually invert it to allow the wash buffer added during the disposable kit prime step to coat all interior surfaces of the bag. Re-hang the In Process Bag on weigh scale #2 (label on the bag was facing to the left). Replace the top port tubing in the tubing guide, if it was removed.

8.13.42 Inverted Source bag. Before pressing the Start button, mixed the Source bag without removing it from the IV pole by massaging the bag corners and gently agitating the cells to create a homogeneous cell suspension. Pressed the Resume button. The LOVO started processing fluid from the Source bag and the Wash Cycle 1 Screen displays.

8.13.43 Source Rinse Pause. The Rinse Source Pause screen displayed once the source container is drained and the LOVO had added wash buffer to the Source bag. Without removing the Source bag from IV pole, massaged the corners and mixed well. Pressed Resume.

8.13.44 Mix In Process Bag Pause. To prepare cells for another pass through the spinner, the In Process Bag was diluted with wash buffer. After adding the wash buffer to the In Process Bag, the LOVO pauses automatically and displays the "Mix In Process Bag" Pause Screen. Without removing the bag from the weigh scale, mixed the product well by gently squeezing the bag. Press Resume.

8.13.45 Massage In Process Corners Pause. When the In Process Bag was empty, wash buffer was added to the bottom port of the In Process Bag to rinse the bag. After adding the rinse fluid, the LOVO paused automatically and displayed the "Massage IP corners" Pause Screen. When the "Massage IP corners" Pause Screen displayed, DO NOT remove the bag from weigh scale #2. With the In Process Bag still hanging on weigh scale #2, massage the corners of the bag to bring any residual cells into suspension. Ensured the bag was not swinging on the weigh scale and pressed the Resume button.

8.13.46 Wait for Remove Products Screen. At the end of the LOVO procedure, the Remove Products Screen screen displayed. When this Screen displays, all bags on the LOVO kit could be manipulated. Note: Did not touch any bags until the Remove Products displayed.

8.13.47 Removed retentate bag. Placed a hemostat on the tubing very close to the port on the Retentate bag to keep the cell suspension from settling into the tubing. Heat sealed (per Process Note 5.12) below the hemostat, making sure to maintain enough line to weld in Step 8.13.48. Removed the retentate bag.

8.13.48 Prepared retentate bag for formulation. Welded (per Process Note 5.11) the female luer lock end of a 4" Plasma Transfer Set to the retentate bag. Transfered the retentate bag to the BSC for use in Step 8.14.11.

8.13.49 Removed Products. Followed the instructions on the Remove Products Screen. Closed all clamps on the LOVO kit to prevent fluid movement.

8.13.50 Removed Products. Touched the Next button. All LOVO mechanical clamps opened and the Remove Kit Screen displayed.

8.13.51 Recorded Data. Followed the instructions on the Remove Kit screen. Touched the "Next" button. All LOVO mechanical clamps close and the Results Summary Screen displays. Recorded the data from the results summary screen in table exactly as they are displayed. Closed all pumps and filter support. Removed the kit when prompted to do so by the LOVO.

NOTE: All Times recorded were recorded directly from the LOVO Results Summary Screen in HH:MM:SS format and (HH:MM:SS) format when applicable 8.13.52-8.13.54 Protocol Selection through LOVO shutdown. Follow the LOVO screen prompts.

8.13.55 Review Section 8.13

8.14 Final Formulation and Fill 8.14.1 Target volume/bag calculation. From the table below, selected the number of CS750 bags to be filled, target fill volume per bag, volume removed for retain per bag, and final target volume per bag that corresponded to the Volume of LOVO Retentate from Step 8.13.22.

| Volume of LOVO product | Volume of CS10 to add to product | Final Predicted Volume of formulated product | Number of bags to be filled | Target Fill Volume per bag | Volume removed for retain per bag | Final Target Volume per bag |
|---|---|---|---|---|---|---|
| 165 mL | 165 mL | 330 mL | 3 | 107 mL | 7 mL | 100 mL |
| 215 mL | 215 mL | 430 mL | 4 | 105 mL | 5 mL | 100 mL |
| 265 mL | 265 mL | 530 mL | 4 | 130 mL | 5 mL | 125 mL |

8.14.2 Prepared CRF Blank. CalculateD volume of CS-10 and LOVO wash buffer to formulate blank bag.

| Final Target Volume per Bag 8.14.1E<br>A | Blank LOVO Wash Buffer Volume<br>B = A/2 | Blank CS-10 Volume (mL)<br>C = B |
|---|---|---|
| mL | mL | mL |

8.14.3 Prepared CRF Blank. Outside of the BSC, using the syringe of LOVO Wash Buffer prepared in Step 8.11.29, added volume calculated in Step 8.14.2 B to an empty CS750 bag via luer connection. Note: Blank CS750 bag formulation does not need to be done aseptically.

8.14.4 Prepared CRF Blank Using an appropriately sized syringe, added the volume of CS-10 calculated in Step 8.14.2 to the same CS750 bag prepared in Step 8.14.3. Placed a red cap on the CS750 bag.

8.14.5 Prepared CRF Blank. Removed as much air as possible from the CS-750 bag as possible. Heat sealed (per Process Note 5.12) the CS750 bag as close to the bag as possible, removing the tubing.

8.14.6 Prepared CRF Blank.Label CS750 bag with "CRF Blank", lot number, and initial/date. Placed the CRF Blank on cold packs until it was placed in the CRF.

8.14.7 Calculated required volume of IL-2. Calculated the volume of IL-2 to add to the Final Product

| Parameter | Formula | Result |
|---|---|---|
| Final Retentate Volume | Step 8.13.51 | A. mL |
| Final Formulated Volume | B = A × 2 | B. mL |
| Final IL-2 Concentration desired (IU/mL) | 300 IU/mL | C. 300 IU/mL |
| IU of IL-2 Required | D = B × C | D. IU |
| IL-2 Working Stock from Step 8.11.33 | $6 \times 10^4$ IU/mL | E. $6 \times 10^4$ IU/mL |
| Volume of IL-2 to Add to Final Product | F = D ÷ E | F. mL |

8.14.8 Assembled Connect apparatus. Sterile welded (per Process Note 5.11) a 4S-4M60 to a CC2 Cell Connect replacing a single spike of the Cell Connect apparatus (B) with the 4-spike end of the 4S-4M60 manifold at (G). (See, for example, FIG. 135.)

8.14.9 Assembled Connected apparatus. Sterile welded (per Process Note 5.11) the CS750 Cryobags to the harness prepared in Step 8.14.8, replacing one of the four male luer ends (E) with each bag. Reference Step 8.14.1 to determine the number of bags needed. (See, for example, FIG. 136.)

8.14.10 Assembled Connected apparatus. Welded (per Process Note 5.11) CS-10 bags to spikes of the 4S-4M60. Kept CS-10 cold by placing the bags between two cold packs conditioned at 2-8° C. (See, for example, FIG. 137.)

8.14.11 Passed materials into the BSC.

| Item | Item # or Step Reference | Quantity |
|---|---|---|
| 4" plasma transfer set | | 1 |
| IL-2 (6.0 × 10$^4$) aliquot | 8.11.33 | 1 |
| Appropriate size syringe to add IL2 | 8.14.7F | 1 |
| LOVO retentate bag | 8.13.48 | 1 |
| Red Caps | | 5 |

8.14.12 Prepared TIL with IL-2. Using an appropriately sized syringe, removed amount of IL-2 determined in Step 8.14.7 from the "IL-2 6×10$^4$" aliquot.

8.14.13 Prepared TIL with IL-2. Connect the syringe to the retentate bag prepared in Step 8.13.48 via the Luer connection and inject IL-2.

8.14.14 Prepare TIL with IL-2Clear the line by pushing air from the syringe through the line.

8.14.15 Labeled Formulated TIL Bag. Closed the clamp on the transfer set and label bag as "Formulated TIL" and passed the bag out of the BSC.

8.14.16 If applicable: Sample per sample plan. If there was remaining "IL-2 6×10$^4$" aliquot prepared in step 8.11.33, remove a ~5 mL sample retain according to the sample plan using an appropriately sized syringe and dispense into a 50 mL conical tube.

8.14.17 If applicable: Sampled per sample plan. Labeled with sample plan inventory label and stored at 2-8° C. until submitted to Login for testing per Sample Plan.

8.14.18 If applicable: Sampled per sample plan. Ensured that LIMS sample plan sheet was filled out for removal of the sample.

8.14.19 Added the Formulated TIL bag to the apparatus. Once IL-2 had been added, welded (per Process Note 5.11) the "Formulated TIL" bag to the remaining spike (A) on the apparatus prepared in Step 8.14.10. (See, for example, FIG. 138.)

8.14.20 Added CS10. Passed the assembled apparatus with attached Formulated TIL, CS-750 bags, and CS-10 into the BSC. NOTE: The CS-10 bag and all CS-750 bags were placed between two cold packs preconditioned at 2-8° C. Did not place Forumulated TIL bag on cold packs.

8.14.21 Added CS10. Ensured all clamps were closed on the apparatus. Turn the stopcock so the syringe was closed.

8.14.22 Switched Syringes. Drew ~10 mL of air into a 100 mL syringe and replaced the 60 mL syringe on the apparatus.

8.14.23 Added CS10. Turned stopcock so that the line to the CS750 bags is closed. Open clamps to the CS-10 bags and pull volume calculated in Step 8.14.1B into syringe. NOTE: Multiple syringes will be used to add appropriate volume of CS-10. NOTE: Record volume from each syringe in Step 8.14.26

8.14.24 Added CS10. Closed clamps to CS-10 and open clamps to the Formulated TIL bag and add the CS-10. Note: Add first 10.0 mL of CS10 at approximately 10.0 mL/minute. Add remaining CS-10 at approximate rate of 1.0 mL/sec. Note: Multiple syringes were used to add appropriate volume of CS-10. Did not reuse a syringe once it had been dispensed.

8.14.25 Added CS10. Recorded time. NOTE: The target time from first addition of CS-10 to beginning of freeze is 30

8.14.26 Added CS10. Recorded the volume of each CS10 addition and the total volume added. Total volume match calculated volume from Step 8.14.1B 8.14.27 Added CS10. Closed all clamps to the CS10 bags.

8.14.28 Prepared CS-750 bags. Turned the stopcock so that the syringe was open. Opened clamps to the Formulated TIL bag and drew up suspension stopping just before the suspension reaches the stopcock.

8.14.29 Prepared CS-750 bags. Closed clamps to the formulated TIL bag. Turned stopcock so that it was open to the empty CS750 final product bags.

8.14.30 Prepared CS-750 bags. Using a new syringe, removed as much air as possible from the CS750 final product bags by drawing the air out. While maintaining pressure on the syringe plunger, clamped the bags shut.

8.14.31 Prepared CS-750 bags. Draw ~20 mL air into a new 100 mL syringe and connect to the apparatus. NOTE: Each CS-750 final product bag should be between two cold packs to keep formulated TIL suspension cold.

8.14.32 Dispensed cells. Turned the stopcock so the line to the final product bags was closed. Pulled the volume calculated in Step 8.14.1 from the Formulated TIL bag into the syringe. NOTE: Multiple syringes could be used to obtain correct volume.

8.14.33 Dispensed cells. Turned the stopcock so the line to the formulated TIL bag is closed. Working with one final product bag at a time, dispense cells into a final product bag. Recorded volume of cells added to each CS750 bag in Step 8.14.35

8.14.34 Dispensed cells. Cleared the line with air from the syringe so that the cells are even with the top of the spike port. Closed the clamp on the filled bag. Repeated Step 8.14.29-Step 8.14.34 for each final product bag, gently mixing formulated TIL bag between each.

8.14.35 Dispensed cells. Record volume of TIL placed in each final product bag below.

8.14.36 Removed air from final product bags and take retain. Once the last final product bag was filled, closed all clamps.

8.14.37 Removed air from final product bags and take retain. Drew 10 mL of air into anew 100 mL syringe and replace the syringe on the apparatus.

8.14.38 Removed air from final product bags and take retain. Manipulating a single bag at a time, drew all of the air from each product bag plus the volume of product for retain determined in Step 8.14.1 D. NOTE: Upon removal of sample volume, inverted the syringe and used air to clear the line to the top port of the product bag. Clamped the line to the bag once the retain volume and air was removed.

8.14.39 Recorded Volume Removed. Recorded volume of retain removed from each bag.

8.14.40 Dispensed Retain. Dispensed retain into a 50 mL conical tube and label tube as "Retain" and lot number. Repeat Step 8.14.37-Step 8.14.39 for each bag.

8.14.41 Prepared final product for cryopreservation. With a hemostat, clamped the lines close to the bags. Removed syringe and red cap luer connection on the apparatus that the syringe was on. Passed apparatus out of the BSC.

8.14.42 Prepared final product for cryopreservation. Heat sealed (per Process Note 5.12) at F, removing the empty retentate bag and the CS-10 bags. NOTE: Retained luer connection for syringe on the apparatus. Disposed of empty retentate and CS-10 Bags. (See, for example, FIG. 139.)

8.14.43 Performed visual inspection. NOTE: Step 8.14.43-Step 8.14.46 may be performed concurrently with Step 8.14.47-Step 8.14.68.

8.14.44 Final Product Label Sample. Labeled final product bags. Attached sample final product label below.

8.14.45 Prepared final product for cryopreservation. Held the cryobags on cold pack or at 2-8° C. until cryopreservation.

8.14.46 Prepared external labels. Ensured the QA issued external labels that will be attached to the cassettes labels match corresponding final product label. Attached QA issued external labels to cassettes. Attached a sample external label below:

8.14.47 Removed Cell Count Sample. Using an appropriately sized pipette, remove 2.0 mL of retain removed in Step 8.14.38 and place in a 15 mL conical tube to be used for cell counts.

8.14.48 Performed Cell Counts. Performed cell counts and calculations utilizing the NC-200 per SOP-00314 and Process Note 5.14. NOTE: Diluted only one sample to appropriate dilution to verify dilution is sufficient. Diluted additional samples to appropriate dilution factor and proceed with counts.

8.14.49 Recorded Cell Count sample volumes. NOTE: If no dilution needed, "Sample [μL]"=200, "Dilution [μL]"=0

8.14.50 Determined Multiplication Factor

| Parameter | Formula | Result |
|---|---|---|
| Total cell count sample Volume | 8.14.49A + 8.14.49B | C. μL |
| Multiplication Factor | C ÷ 8.14.49A | D. |

8.14.51 Select protocols and enter multiplication actors. Ensure the "Viable Cell Count Assay" protocol has been selected, all multiplication factors, and sample and diluent volumes have been entered per SOP—00314 NOTE: If no dilution needed, enter "Sample [µL]"=200, "Dilution [µL]"=0

8.14.52 Recorded File Name, Viability and Cell Counts from Nucleoview.

8.14.53 Determined the Average of Viable Cell Concentration and Viability of the cell counts performed.

| Parameter | Formula | Result |
| --- | --- | --- |
| Viability | (8.14.52A + 8.14.52B) ÷ 2 | E. % |
| Viable Cell Concentration | (8.14.52C + 8.14.52D) ÷ 2 | F. cells/mL |

8.14.54 Determined Upper and Lower Limit for counts.

| Parameter | Formula | Result |
| --- | --- | --- |
| Lower Limit | 8.14.53F × 0.9 | G. cells/mL |
| Upper Limit | 8.14.53F × 1.1 | H. cells/mL |

8.14.55 Were both counts within acceptable limits?

| Parameter | Formula | Result (Yes/No) |
| --- | --- | --- |
| Lower Limit | 8.14.52 C and D ≥ 8.14.54G | |
| Upper Limit | 8.14.52 C and D ≤ 8.14.54H | |

NOTE: If either result is "No" perform second set of counts in steps 8.14.56-8.14.63

8.14.56 If Applicable: Performed cell counts. Performed cell counts and calculations in utilizing NC-200 per SOP-00314 and Process Note 5.14. NOTE: Dilution may be adjusted according based off the expected concentration of cells.

8.14.57 If Applicable: Recorded Cell Count sample volumes.

8.14.58 If Applicable: Determined Multiplication Factor

| Parameter | Formula | Result |
| --- | --- | --- |
| Total cell count sample Volume | 8.14.57A + 8.14.57B | C. mL |
| Multiplication Factor | C ÷ 8.14.57A | D. |

8.14.59 If Applicable: Selected protocols and entered multiplication factors. Ensured the "Viable Cell Count Assay" protocol had been selected, all multiplication factors, and sample and diluent volumes had been entered. NOTE: If no dilution needed, enter "Sample [µL]"=200, "Dilution [µL]"=0

8.14.60 If Applicable: Recorded Cell Counts from Nucleoview 8.14.61 If Applicable: Determined the Average of Viable Cell Concentration and Viability of the cell counts performed.

| Parameter | Formula | Result |
| --- | --- | --- |
| Viability | (8.14.60A + 8.14.60B) ÷ 2 | E. % |
| Viable Cell Concentration | (8.14.60C + 8.14.60D) ÷ 2 | F. cells/mL |

8.14.62 If Applicable: Determined Upper and Lower Limit for counts.

| Parameter | Formula | Result |
| --- | --- | --- |
| Lower Limit | 8.14.61F × 0.9 | G. cells/mL |
| Upper Limit | 8.14.61F × 1.1 | H. cells/mL |

8.14.63 If Applicable: Were counts within acceptable limits?

| Parameter | Formula | Result (Yes/No) |
| --- | --- | --- |
| Lower Limit | 8.14.60 C and D ≥ 8.14.62G | |
| Upper Limit | 8.14.60 C and D ≤ 8.14.62H | |

NOTE: If either result is "No" continue to Step 8.14.64 to determine an average.

8.14.64 If Applicable: Determined an average Viable Cell Concentration from all four counts performed.

8.14.65 Calculated Flow. Cytometry Sample. Performed calculation to ensure sufficient cell concentration for flow cytometry sampling.

| Viable Cell Concentration From Step 8.14.53 F* Or Step 8.14.61 F* Or Step 8.14.64 E* A | Target Volume Required for $6 \times 10^7$ TVC B = $6 \times 10^7$ cells/A | Is B ≤ 1.0 mL? (Yes/No**) |
| --- | --- | --- |
| cells/mL | mL | |

*Circle step reference used to determine Viable Cell Concentration
**NOTE: If "No", contact area management.

8.14.66 Calculated IFN-γ. Sample Performed calculation to ensure sufficient cell concentration for IFN-γ sampling.

| Viable Cell Concentration From Step 8.14.53 F* Or Step 8.14.61 F* Or Step 8.14.64 E* A | Volume Required for Minimum $1.5 \times 10^7$ TVC B = $1.5 \times 10^7$ cells/A | Is B ≤ 1.0 mL? (Yes/No**) |
| --- | --- | --- |
| cells/mL | mL | |

*Circle step reference used to determine Viable Cell Concentration
**NOTE: If "No", contact area management.

8.14.67 Reported Results. Completed forms for submission with samples.

8.14.68 Heat Sealed. Once sample volumes had been determined, heat sealed (per Process Note 5.12) Final Product Bags as close to the bags as possible to remove from the apparatus.

8.14.69 Labeled and Collected Samples per Sample Plan.

| Sample | Number of Containers | Sample Volume to Add to Each | Container Type | Destination |
|---|---|---|---|---|
| *Mycoplasma | 1 | 1.0 mL | 15 mL Conical | Login |
| Endotoxin | 2 | 1.0 mL | 2 mL Cryovial | Login |
| Gram Stain | 1 | 1.0 mL | 2 mL Cryovial | Login |
| IFN-g | 1 | 1.0 mL | 2 mL Cryovial | Login |
| Flow Cytometry | 1 | 1.0 mL | 2 mL Cryovial | Login |
| **Bac-T Sterility | 2 | 1.0 mL | Bac-T Bottle | Login |
| QC Retain | 4 | 1.0 mL | 2 mL Cryovial | CRF |
| Satellite Vials | 10 | 0.5 mL | 2 mL Cryovial | CRF |

*NOTE: For the Mycoplasma sample, add formulated cell suspension volume to the 15 mL conical labelled "Mycoplasm a Diluent" from Step 8.12.55.
**NOTE: Proceed to Step 8.14.70 for Bac -T inoculation.

8.14.70 Sterility & BacT. Testing Sampling. In the BSC, remove a 1.0 mL sample from the retained cell suspension collected in Step 8.14.38 using an appropriately sized syringe and inoculate the anaerobic bottle. Repeat the above for the aerobic bottle. NOTE: Store Bac-T bottles are room temperature and protect from light.

8.14.71 Labeled and stored samples. Labeled all samples with sample plan inventory labels and store appropriately until transfer to Login. NOTE: Proceeded to Section 8.15 for cryopreservation of final product and samples.

8.14.72 Signed for sampling. Ensured that LIMS sample plan sheet is completed for removal of the samples.

8.14.73 Sample Submission. Submitted all Day 22 testing samples to Login.

8.14.74 Environmental Monitoring. After processing, verified BSC and personnel monitoring had been performed.

8.14.75 Review Section 8.14

8.15 Final Product Cryopreservation 8.15.1 Prepared Controlled Rate Freezer. Verified the CRF had been set up prior to freeze. Record CRF Equipment. Cryopreservation is performed.

8.15.2 Set up CRF probes. Punctured the septum on the CRF blank bag. Inserted the 6 mL vial temperature probe.

8.15.3 Placed final product and samples in CRF. Placed blank bag into preconditioned cassette and transferred into the approximate middle of the CRF rack. Transferred final product cassettes into CRF rack and vials into CRF vial rack.

8.15.4 Placed final product and samples in CRF. Transferred product racks and vial racks into the CRF. Recorded the time that the product is transferred into the CRF and the chamber temperature in Step 8.15.5. NOTE: Evenly distributed the cassettes and vial rack in the CRF, allowed as much space as possible between each shelf.

8.15.5 Determined the time needed to reach 4° C.±1.5° C. and proceed with the CRF run. Once the chamber temperature reached 4° C.±1.5° C., started the run. Recorded time.

| Parameter | Formula | Value |
|---|---|---|
| Time Final Product is transferred to CRF | (HHMM) | |
| Temperature Final Product is transferred into CRF | From monitor | ° C. |
| B. CRF Start Time | (HHMM) | |
| Elapsed Time from Formulation to CRF Start | C = B − Step 8.14.25A | min |

8.15.6 CRF Completed and Stored. Stopped the CRF after the completion of the run. Remove cassettes and vials from CRF. Transferred cassettes and vials to vapor phase LN2 for storage. Recorded storage location Post Processing Summary
  Post-Processing: Final Drug Product
    (Day 22) Determination of CD3+ Cells on Day 22 REP by Flow Cytometry
    (Day 22) Gram Staining Method (GMP)
    (Day 22) Bacterial Endotoxin Test by Gel Clot LAL Assay (GMP)
    (Day 16) BacT Sterility Assay (GMP)
    (Day 16) Mycoplasma DNA Detection by TD-PCR (GMP)
    Acceptable Appearance Attributes (Step 8.14.43)
    (Day 22) BacT Sterility Assay (GMP)
    (Day 22) IFN-gamma Assay The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

SEQUENCES

SEQ ID NO:1 is the amino acid sequence of the heavy chain of muromonab.
SEQ ID NO:2 is the amino acid sequence of the light chain of muromonab.
SEQ ID NO:3 is the amino acid sequence of a recombinant human IL-2 protein.

SEQ ID NO:4 is the amino acid sequence of aldesleukin.
SEQ ID NO:5 is the amino acid sequence of a recombinant human IL-4 protein.
SEQ ID NO:6 is the amino acid sequence of a recombinant human IL-7 protein.
SEQ ID NO:7 is the amino acid sequence of a recombinant human IL-15 protein.
SEQ ID NO:8 is the amino acid sequence of a recombinant human IL-21 protein.

Amino Acid Sequences of Muromonab.

| Identifier | Sequence (One-Letter Amino Acid Symbols) | |
|---|---|---|
| SEQ ID NO: 1 Muromonab heavy chain | QVQLQQSGAE LARPGASVKM SCKASGYTFT RYTMHWVKQR PGQGLEWIGY INPSRGYTNY | 60 |
| | NQKFKDKATL TTDKSSSTAY MQLSSLTSED SAVYYCARYY DDHYCLDYWG QGTTLTVSSA | 120 |
| | KTTAPSVYPL APVCGGTTGS SVTLGCLVKG YFPEPVTLTW NSGSLSSGVH TFPAVLQSDL | 180 |
| | YTLSSSVTVT SSTWPSQSIT CNVAHPASST KVDKKIEPRP KSCDKTHTCP PCPAPELLGG | 240 |
| | PSVFLFPPKP KDTLMISRTP EVTCVVVDVS HEDPEVKFNW YVDGVEVHNA KTKPREEQYN | 300 |
| | STYRVVSVLT VLHQDWLNGK EYKCKVSNKA LPAPIEKTIS KAKGQPREPQ VYTLPPSRDE | 360 |
| | LTKNQVSLTC LVKGFYPSDI AVEWESNGQP ENNYKTTPPV LDSDGSFFLY SKLTVDKSRW | 420 |
| | QQGNVFSCSV MHEALHNHYT QKSLSLSPGK | 450 |
| SEQ ID NO: 2 Muromonab light chain | QIVLTQSPAI MSASPGEKVT MTCSASSSVS YMNWYQQKSG TSPKRWIYDT SKLASGVPAH | 60 |
| | FRGSGSGTSY SLTISGMEAE DAATYYCQOW SSNPFTFGSG TKLEINRADT APTVSIFPPS | 120 |
| | SEQLTSGGAS VVCFLNNFYP KDINVKWKID GSERQNGVLN SWTDQDSKDS TYSMSSTLTL | 180 |
| | TKDEYERHNS YTCEATHKTS TSPIVKSFNR NEC | 213 |

Amino Acid Sequences of Interleukins.

| Identifier | Sequence (One-Letter Amino Acid Symbols) | |
|---|---|---|
| SEQ ID NO: 3 recombinant human IL-2 (rhIL-2) | MAPTSSSTKK TQLQLEHLLL DLQMILNGIN NYKNPKLTRM LTFKFYMPKK ATELKHLQCL | 60 |
| | EEELKPLEEV LNLAQSKNFH LRPRDLISNI NVIVLELKGS ETTFMCEYAD ETATIVEFLN | 120 |
| | RWITFCQSII STLT | 134 |
| SEQ ID NO: 4 Aldesleukin | PTSSSTKKTQ LQLEHLLLDL QMILNGINNY KNPKLTRMLT FKFYMPKKAT ELKHLQCLEE | 60 |
| | ELKPLEEVLN LAQSKNFHLR PRDLISNINV IVLELKGSET TFMCEYADET ATIVEFLNRW | 120 |
| | ITFSQSIIST LT | 132 |
| SEQ ID NO: 5 recombinant human IL-4 (rhIL-4) | MHKCDITLQE IIKTLNSLTE QKTLCTELTV TDIFAASKNT TEKETFCRAA TVLRQFYSHH | 60 |
| | EKDTRCLGAT AQQFHRHKQL IRFLKRLDRN LWGLAGLNSC PVKEANQSTL ENFLERLKTI | 120 |
| | MREKYSKCSS | 130 |
| SEQ ID NO: 6 recombinant human IL- 7 (rhIL-7) | MDCDIEGKDG KQYESVLMVS IDQLLDSMKE IGSNCLNNEF NFFKRHICDA NKEGMFLFRA | 60 |
| | ARKLRQFLKM NSTGDFDLHL LKVSEGTTIL LNCTGQVKGR KPAALGEAQP TKSLEENKSL | 120 |
| | KEQKKLNDLC FLKRLLQEIK TCWNKILMGT KEH | 153 |
| SEQ ID NO: 7 recombinant human IL-15 (rhIL-15) | MNWVNVISDL KKIEDLIQSM HIDATLYTES DVHPSCKVTA MKCFLLELQV ISLESGDASI | 60 |
| | HDTVENLIIL ANNSLSSNGN VTESGCKECE ELEEKNIKEF LQSFVHIVQM FINTS | 115 |

What is claimed is:

1. A method for expanding tumor infiltrating lymphocytes (TILs) into a therapeutic population of TILs, the method comprising:
   (a) performing a first expansion by (i) thawing cryopreserved dissociated tumor materials comprising a first population of TILs from a tumor that was resected from a subject with cancer, dissociated after the resection, and cryopreserved after the dissociation, and (ii) culturing the first population of TILs in a cell culture medium comprising IL-2, and optionally OKT-3, to produce a second population of TILs, wherein the first expansion is performed in a closed system providing a first gas-permeable surface area, wherein the first expansion is performed for about 3-14 days to obtain the second population of TILs;
   (b) performing a second expansion by supplementing the cell culture medium of the second population of TILs with additional IL-2, optionally OKT-3, and antigen presenting cells (APCs), to produce a third population of TILs, wherein the second expansion is performed for about 7-14 days to obtain the third population of TILs, wherein the second expansion is performed in the closed system providing a second gas-permeable surface area, and wherein the transition from step (a) to step (b) occurs without opening the closed system; and
   (c) harvesting the third population of TILs, wherein the harvested third population of TILs is a therapeutic population of TILs, and wherein the transition from step (b) to step (c) occurs without opening the closed system.

2. The method of claim 1, wherein the dissociated tumor materials comprise a tumor digest.

3. The method of claim 1, wherein the dissociated tumor materials comprise one or more tumor fragments.

4. The method of claim 1, wherein obtaining the dissociated tumor materials comprises mechanically disrupting the tumor resected from the subject.

5. The method of claim 4, wherein obtaining the dissociated tumor materials further comprises purifying the disassociated tumor materials using a density gradient separation.

6. The method of claim 1, wherein obtaining the dissociated tumor materials comprises enzymatically disrupting the tumor resected from the subject.

7. The method of claim 6, wherein the enzymatic disruption is performed in an enzymatic media.

8. The method of claim 7, wherein the enzymatic media comprises a mixture of enzymes.

9. The method of claim 8, wherein the mixture of enzymes comprises a collagenase.

10. The method of claim 8, wherein the mixture of enzymes comprises a DNase.

11. The method of claim 8, wherein the mixture of enzymes comprised a collagenase and a DNase.

12. The method of claim 1, wherein the method further comprises performing the step of:
   (d) transferring the therapeutic population of TILs obtained from step (c) to an infusion bag, wherein the transition from step (c) to step (d) occurs without opening the closed system.

13. The method of claim 12, wherein the method further comprises performing the step of: (e) cryopreserving the infusion bag.

14. The method of claim 13, wherein the method further comprises performing the step of: (f) administering a therapeutically effective dosage of the therapeutic population of TILs from the cryopreserved infusion bag in step (e) to the subject.

15. The method of claim 14, wherein the third population of TILs harvested in step (c) comprises sufficient TILs for administering the therapeutically effective dosage of the TILs in step (f).

16. The method of claim 14, wherein the therapeutically effective dosage of the TILs in step (f) comprises from about $1 \times 10^9$ to about $9 \times 10^{10}$ TILs.

17. The method of claim 14, wherein the therapeutically effective dosage in step (f) comprises from about $1\times10^9$ to about $5\times10^9$ TILs.

18. The method of claim 14, wherein the therapeutically effective dosage in step (f) comprises from about $5\times10^9$ to about $1\times10^{10}$ TILs.

19. The method of claim 14, wherein the therapeutically effective dosage in step (f) comprises from about $1\times10^{10}$ to about $5\times10^{10}$ TILs.

20. The method of claim 1, wherein the first expansion is performed within a period of about 7 days.

21. The method of claim 1, wherein the second expansion is performed within a period of about 14 days.

22. The method of claim 1, wherein the first expansion is performed within a first period of about 7 days and the second expansion is performed within a second period of about 14 days.

23. The method of claim 1, wherein step (a) through step (b) are performed within a period of about 21 days.

24. The method of claim 1, wherein the first expansion is performed within a period of about 12 days.

25. The method of claim 1, wherein the second expansion is performed within a period of about 12 days.

26. The method of claim 1, wherein the first expansion is performed within a period of about 12 days and the second expansion is performed within a period of about 12 days.

27. The method of claim 1, wherein step (a) through step (b) are performed within a period of about 24 days.

28. The method of claim 1, wherein step (a) through step (b) are performed in a period of about 24 days.

29. The method of claim 1, wherein the cancer is selected from the group consisting of melanoma, ovarian cancer, cervical cancer, non-small-cell lung cancer (NSCLC), lung cancer, bladder cancer, breast cancer, cancer caused by human papilloma virus, head and neck cancer (including head and neck squamous cell carcinoma (HNSCC)), renal cancer, and renal cell carcinoma.

30. The method of claim 1, wherein the cancer is a melanoma.

* * * * *

```
                  SEQUENCE LISTING

Sequence total quantity: 53
SEQ ID NO: 1            moltype = AA  length = 450
FEATURE                 Location/Qualifiers
REGION                  1..450
                        note = Muromonab heavy chain
source                  1..450
                        mol_type = protein
                        organism = synthetic construct
SEQUENCE: 1
QVQLQQSGAE LARPGASVKM SCKASGYTFT RYTMHWVKQR PGQGLEWIGY INPSRGYTNY   60
NQKFKDKATL TTDKSSSTAY MQLSSLTSED SAVYYCARYY DDHYCLDYWG QGTTLTVSSA  120
KTTAPSVYPL APVCGGTTGS SVTLGCLVKG YFPEPVTLTW NSGSLSSGVH TFPAVLQSDL  180
YTLSSSVTVT SSTWPSQSIT CNVAHPASST KVDKKIEPRP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 2            moltype = AA  length = 213
FEATURE                 Location/Qualifiers
```

```
REGION                   1..213
                         note = Muromonab light chain
source                   1..213
                         mol_type = protein
                         organism = synthetic construct
SEQUENCE: 2
QIVLTQSPAI MSASPGEKVT MTCSASSSVS YMNWYQQKSG TSPKRWIYDT SKLASGVPAH    60
FRGSGSGTSY SLTISGMEAE DAATYYCQQW SSNPFTFGSG TKLEINRADT APTVSIFPPS   120
SEQLTSGGAS VVCFLNNFYP KDINVKWKID GSERQNGVLN SWTDQDSKDS TYSMSSTLTL   180
TKDEYERHNS YTCEATHKTS TSPIVKSFNR NEC                                213

SEQ ID NO: 3             moltype = AA   length = 134
FEATURE                  Location/Qualifiers
REGION                   1..134
                         note = recombinant human IL-2 (rhIL-2)
source                   1..134
                         mol_type = protein
                         organism = synthetic construct
SEQUENCE: 3
MAPTSSSTKK TQLQLEHLLL DLQMILNGIN NYKNPKLTRM LTFKFYMPKK ATELKHLQCL    60
EEELKPLEEV LNLAQSKNFH LRPRDLISNI NVIVLELKGS ETTFMCEYAD ETATIVEFLN   120
RWITFCQSII STLT                                                     134

SEQ ID NO: 4             moltype = AA   length = 132
FEATURE                  Location/Qualifiers
REGION                   1..132
                         note = Aldesleukin
source                   1..132
                         mol_type = protein
                         organism = synthetic construct
SEQUENCE: 4
PTSSSTKKTQ LQLEHLLLDL QMILNGINNY KNPKLTRMLT FKFYMPKKAT ELKHLQCLEE    60
ELKPLEEVLN LAQSKNFHLR PRDLISNINV IVLELKGSET TFMCEYADET ATIVEFLNRW   120
ITFSQSIIST LT                                                       132

SEQ ID NO: 5             moltype = AA   length = 130
FEATURE                  Location/Qualifiers
REGION                   1..130
                         note = recombinant human IL-4 (rhIL-4)
source                   1..130
                         mol_type = protein
                         organism = synthetic construct
SEQUENCE: 5
MHKCDITLQE IIKTLNSLTE QKTLCTELTV TDIFAASKNT TEKETFCRAA TVLRQFYSHH    60
EKDTRCLGAT AQQFHRHKQL IRFLKRLDRN LWGLAGLNSC PVKEANQSTL ENFLERLKTI   120
MREKYSKCSS                                                          130

SEQ ID NO: 6             moltype = AA   length = 153
FEATURE                  Location/Qualifiers
REGION                   1..153
                         note = recombinant human IL-7 (rhIL-7)
source                   1..153
                         mol_type = protein
                         organism = synthetic construct
SEQUENCE: 6
MDCDIEGKDG KQYESVLMVS IDQLLDSMKE IGSNCLNNEF NFFKRHICDA NKEGMFLFRA    60
ARKLRQFLKM NSTGDFDLHL LKVSEGTTIL LNCTGQVKGR KPAALGEAQP TKSLEENKSL   120
KEQKKLNDLC FLKRLLQEIK TCWNKILMGT KEH                                153

SEQ ID NO: 7             moltype = AA   length = 115
FEATURE                  Location/Qualifiers
REGION                   1..115
                         note = recombinant human IL-15 (rhIL-15)
source                   1..115
                         mol_type = protein
                         organism = synthetic construct
SEQUENCE: 7
MNWVNVISDL KKIEDLIQSM HIDATLYTES DVHPSCKVTA MKCFLLELQV ISLESGDASI    60
HDTVENLIIL ANNSLSSNGN VTESGCKECE ELEEKNIKEF LQSFVHIVQM FINTS        115

SEQ ID NO: 8             moltype = AA   length = 132
FEATURE                  Location/Qualifiers
REGION                   1..132
                         note = recombinant human IL-21 (rhIL-21)
source                   1..132
                         mol_type = protein
                         organism = synthetic construct
SEQUENCE: 8
MQDRHMIRMR QLIDIVDQLK NYVNDLVPEF LPAPEDVETN CEWSAFSCFQ KAQLKSANTG    60
```

```
NNERIINVSI KKLKRKPPST NAGRRQKHRL TCPSCDSYEK KPPKEFLERF KSLLQKMIHQ    120
HLSSRTHGSE DS                                                        132

SEQ ID NO: 9            moltype = AA  length = 255
FEATURE                 Location/Qualifiers
REGION                  1..255
                        note = human 4-1BB, Tumor necrosis factor receptor
                          superfamily, member 9(Homo sapiens)
source                  1..255
                        mol_type = protein
                        organism = synthetic construct
SEQUENCE: 9
MGNSCYNIVA TLLLVLNFER TRSLQDPCSN CPAGTFCDNN RNQICSPCPP NSFSSAGGQR     60
TCDICRQCKG VFRTRKECSS TSNAECDCTP GFHCLGAGCS MCEQDCKQGQ ELTKKGCKDC    120
CFGTFNDQKR GICRPWTNCS LDGKSVLVNG TKERDVVCGP SPADLSPGAS SVTPPAPARE    180
PGHSPQIISF FLALTSTALL FLLFFLTLRF SVVKRGRKKL LYIFKQPFMR PVQTTQEEDG    240
CSCRFPEEEE GGCEL                                                     255

SEQ ID NO: 10           moltype = AA  length = 256
FEATURE                 Location/Qualifiers
REGION                  1..256
                        note = murine 4-1BB, Tumor necrosis factor receptor
                          superfamily, member9 (Mus musculus)
source                  1..256
                        mol_type = protein
                        organism = synthetic construct
SEQUENCE: 10
MGNNCYNVVV IVLLLVGCEK VGAVQNSCDN CQPGTFCRKY NPVCKSCPPS TFSSIGGQPN     60
CNICRVCAGY FRFKKFCSST HNAECECIEG FHCLGPQCTR CEKDCRPGQE LTKQGCKTCS    120
LGTFNDQNGT GVCRPWTNCS LDGRSVLKTG TTEKDVVCGP PVVSFSPSTT ISVTPEGGPG    180
GHSLQVLTLF LALTSALLLA LIFITLLLFSV LKWIRKKFPH IFKQPFKKTT GAAQEEDACS    240
CRCPQEEEGG GGGYEL                                                    256

SEQ ID NO: 11           moltype = AA  length = 441
FEATURE                 Location/Qualifiers
REGION                  1..441
                        note = heavy chain for utomilumab
source                  1..441
                        mol_type = protein
                        organism = synthetic construct
SEQUENCE: 11
EVQLVQSGAE VKKPGESLRI SCKGSGYSFS TYWISWVRQM PGKGLEWMGK IYPGDSYTNY     60
SPSFQGQVTI SADKSISTAY LQWSSLKASD TAMYYCARGY GIFDYWGQGT LVTVSSASTK    120
GPSVFPLAPC SRSTSESTAA LGCLVKDYFP EPVTVSWNSG ALTSGVHTFP AVLQSSGLYS    180
LSSVVTVPSS NFGTQTYTCN VDHKPSNTKV DKTVERKCCV ECPPCPAPPV AGPSVFLFPP    240
KPKDTLMISR TPEVTCVVVD VSHEDPEVQF NWYVDGVEVH NAKTKPREEQ FNSTFRVVSV    300
LTVVHQDWLN GKEYKCKVSN KGLPAPIEKT ISKTKGQPRE PQVYTLPPSR EEMTKNQVSL    360
TCLVKGFYPS DIAVEWESNG QPENNYKTTP PMLDSDGSFF LYSKLTVDKS RWQQGNVFSC    420
SVMHEALHNH YTQKSLSLSP G                                              441

SEQ ID NO: 12           moltype = AA  length = 214
FEATURE                 Location/Qualifiers
REGION                  1..214
                        note = light chain for utomilumab
source                  1..214
                        mol_type = protein
                        organism = synthetic construct
SEQUENCE: 12
SYELTQPPSV SVSPGQTASI TCSGDNIGDQ YAHWYQQKPG QSPVLVIYQD KNRPSGIPER     60
FSGSNSGNTA TLTISGTQAM DEADYYCATY TGFGSLAVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                                214

SEQ ID NO: 13           moltype = AA  length = 116
FEATURE                 Location/Qualifiers
REGION                  1..116
                        note = heavy chain variable region for utomilumab
source                  1..116
                        mol_type = protein
                        organism = synthetic construct
SEQUENCE: 13
EVQLVQSGAE VKKPGESLRI SCKGSGYSFS TYWISWVRQM PGKGLEWMGK IYPGDSYTNY     60
SPSFQGQVTI SADKSISTAY LQWSSLKASD TAMYYCARGY GIFDYWGQGT LVTVSS        116

SEQ ID NO: 14           moltype = AA  length = 108
FEATURE                 Location/Qualifiers
REGION                  1..108
                        note = light chain variable region for utomilumab
source                  1..108
```

```
                            mol_type = protein
                            organism = synthetic construct
SEQUENCE: 14
SYELTQPPSV SVSPGQTASI TCSGDNIGDQ YAHWYQQKPG QSPVLVIYQD KNRPSGIPER    60
FSGSNSGNTA TLTISGTQAM DEADYYCATY TGFGSLAVFG GGTKLTVL                108

SEQ ID NO: 15               moltype = AA  length = 6
FEATURE                     Location/Qualifiers
REGION                      1..6
                            note = heavy chain CDR1 for utomilumab
source                      1..6
                            mol_type = protein
                            organism = synthetic construct
SEQUENCE: 15
STYWIS                                                                6

SEQ ID NO: 16               moltype = AA  length = 17
FEATURE                     Location/Qualifiers
REGION                      1..17
                            note = heavy chain CDR2 for utomilumab
source                      1..17
                            mol_type = protein
                            organism = synthetic construct
SEQUENCE: 16
KIYPGDSYTN YSPSFQG                                                   17

SEQ ID NO: 17               moltype = AA  length = 8
FEATURE                     Location/Qualifiers
REGION                      1..8
                            note = heavy chain CDR3 for utomilumab
source                      1..8
                            mol_type = protein
                            organism = synthetic construct
SEQUENCE: 17
RGYGIFDY                                                              8

SEQ ID NO: 18               moltype = AA  length = 11
FEATURE                     Location/Qualifiers
REGION                      1..11
                            note = light chain CDR1 for utomilumab
source                      1..11
                            mol_type = protein
                            organism = synthetic construct
SEQUENCE: 18
SGDNIGDQYA H                                                         11

SEQ ID NO: 19               moltype = AA  length = 7
FEATURE                     Location/Qualifiers
REGION                      1..7
                            note = light chain CDR2 for utomilumab
source                      1..7
                            mol_type = protein
                            organism = synthetic construct
SEQUENCE: 19
QDKNRPS                                                               7

SEQ ID NO: 20               moltype = AA  length = 11
FEATURE                     Location/Qualifiers
REGION                      1..11
                            note = light chain CDR3 for utomilumab
source                      1..11
                            mol_type = protein
                            organism = synthetic construct
SEQUENCE: 20
ATYTGFGSLA V                                                         11

SEQ ID NO: 21               moltype = AA  length = 448
FEATURE                     Location/Qualifiers
REGION                      1..448
                            note = heavy chain for urelumab
source                      1..448
                            mol_type = protein
                            organism = synthetic construct
SEQUENCE: 21
QVQLQQWGAG LLKPSETLSL TCAVYGGSFS GYYWSWIRQS PEKGLEWIGE INHGGYVTYN    60
PSLESRVTIS VDTSKNQFSL KLSSVTAADT AVYYCARDYG PGNYDWYFDL WGRGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
```

```
YRVVSVLTVL HQDWLNGKEY KCKVSNKGLP SSIEKTISKA KGQPREPQVY TLPPSQEEMT    360
KNQVSLTCLV KGFYPSDIAV EWESNGQPEN NYKTTPPVLD SDGSFFLYSR LTVDKSRWQE    420
GNVFSCSVMH EALHNHYTQK SLSLSLGK                                       448

SEQ ID NO: 22          moltype = AA  length = 216
FEATURE                Location/Qualifiers
REGION                 1..216
                       note = light chain for urelumab
source                 1..216
                       mol_type = protein
                       organism = synthetic construct
SEQUENCE: 22
EIVLTQSPAT LSLSPGERAT LSCRASQSVS SYLAWYQQKP GQAPRLLIYD ASNRATGIPA     60
RFSGSGSGTD FTLTISSLEP EDFAVYYCQQ RSNWPPALTF CGGTKVEIKR TVAAPSVFIF    120
PPSDEQLKSG TASVVCLLNN FYPREAKVQW KVDNALQSGN SQESVTEQDS KDSTYSLSST    180
LTLSKADYEK HKVYACEVTH QGLSSPVTKS FNRGEC                              216

SEQ ID NO: 23          moltype = AA  length = 120
FEATURE                Location/Qualifiers
REGION                 1..120
                       note = variable heavy chain for urelumab
source                 1..120
                       mol_type = protein
                       organism = synthetic construct
SEQUENCE: 23
MKHLWFFLLL VAAPRWVLSQ VQLQQWGAGL LKPSETLSLT CAVYGGSFSG YYWSWIRQSP     60
EKGLEWIGEI NHGGYVTYNP SLESRVTISV DTSKNQFSLK LSSVTAADTA VYYCARDYGP    120

SEQ ID NO: 24          moltype = AA  length = 110
FEATURE                Location/Qualifiers
REGION                 1..110
                       note = variable light chain for urelumab
source                 1..110
                       mol_type = protein
                       organism = synthetic construct
SEQUENCE: 24
MEAPAQLLFL LLLWLPDTTG EIVLTQSPAT LSLSPGERAT LSCRASQSVS SYLAWYQQKP     60
GQAPRLLIYD ASNRATGIPA RFSGSGSGTD FTLTISSLEP EDFAVYYCQQ               110

SEQ ID NO: 25          moltype = AA  length = 5
FEATURE                Location/Qualifiers
REGION                 1..5
                       note = heavy chain CDR1 for urelumab
source                 1..5
                       mol_type = protein
                       organism = synthetic construct
SEQUENCE: 25
GYYWS                                                                  5

SEQ ID NO: 26          moltype = AA  length = 16
FEATURE                Location/Qualifiers
REGION                 1..16
                       note = heavy chain CDR2 for urelumab
source                 1..16
                       mol_type = protein
                       organism = synthetic construct
SEQUENCE: 26
EINHGGYVTY NPSLES                                                     16

SEQ ID NO: 27          moltype = AA  length = 13
FEATURE                Location/Qualifiers
REGION                 1..13
                       note = heavy chain CDR3 for urelumab
source                 1..13
                       mol_type = protein
                       organism = synthetic construct
SEQUENCE: 27
DYGPGNYDWY FDL                                                        13

SEQ ID NO: 28          moltype = AA  length = 11
FEATURE                Location/Qualifiers
REGION                 1..11
                       note = light chain CDR1 for urelumab
source                 1..11
                       mol_type = protein
                       organism = synthetic construct
SEQUENCE: 28
RASQSVSSYL A                                                          11
```

```
SEQ ID NO: 29            moltype = AA   length = 7
FEATURE                  Location/Qualifiers
REGION                   1..7
                         note = light chain CDR2 for urelumab
source                   1..7
                         mol_type = protein
                         organism = synthetic construct
SEQUENCE: 29
DASNRAT                                                                    7

SEQ ID NO: 30            moltype = AA   length = 11
FEATURE                  Location/Qualifiers
REGION                   1..11
                         note = light chain CDR3 for urelumab
source                   1..11
                         mol_type = protein
                         organism = synthetic construct
SEQUENCE: 30
QQRSDWPPAL T                                                              11

SEQ ID NO: 31            moltype = AA   length = 230
FEATURE                  Location/Qualifiers
REGION                   1..230
                         note = Fc domain
source                   1..230
                         mol_type = protein
                         organism = synthetic construct
SEQUENCE: 31
KSCDKTHTCP PCPAPELLGG PSVFLFPPKP KDTLMISRTP EVTCVVVDVS HEDPEVKFNW          60
YVDGVEVHNA KTKPREEQYN STYRVVSVLT VLHQDWLNGK EYKCKVSNKA LPAPIEKTIS         120
KAKGQPREPQ VYTLPPSREE MTKNQVSLTC LVKGFYPSDI AVEWESNGQP ENNYKTTPPV         180
LDSDGSFFLY SKLTVDKSRW QQGNVFSCSV MHEALHNHYT QKSLSLSPGK                    230

SEQ ID NO: 32            moltype = AA   length = 22
FEATURE                  Location/Qualifiers
REGION                   1..22
                         note = linker
source                   1..22
                         mol_type = protein
                         organism = synthetic construct
SEQUENCE: 32
GGPGSSKSCD KTHTCPPCPA PE                                                   22

SEQ ID NO: 33            moltype = AA   length = 22
FEATURE                  Location/Qualifiers
REGION                   1..22
                         note = linker
source                   1..22
                         mol_type = protein
                         organism = synthetic construct
SEQUENCE: 33
GGSGSSKSCD KTHTCPPCPA PE                                                   22

SEQ ID NO: 34            moltype = AA   length = 27
FEATURE                  Location/Qualifiers
REGION                   1..27
                         note = linker
source                   1..27
                         mol_type = protein
                         organism = synthetic construct
SEQUENCE: 34
GGPGSSSSSS SKSCDKTHTC PPCPAPE                                              27

SEQ ID NO: 35            moltype = AA   length = 27
FEATURE                  Location/Qualifiers
REGION                   1..27
                         note = linker
source                   1..27
                         mol_type = protein
                         organism = synthetic construct
SEQUENCE: 35
GGSGSSSSSS SKSCDKTHTC PPCPAPE                                              27

SEQ ID NO: 36            moltype = AA   length = 29
FEATURE                  Location/Qualifiers
REGION                   1..29
                         note = linker
source                   1..29
                         mol_type = protein
```

```
                        organism = synthetic construct
SEQUENCE: 36
GGPGSSSSSS SSSKSCDKTH TCPPCPAPE                               29

SEQ ID NO: 37           moltype = AA   length = 29
FEATURE                 Location/Qualifiers
REGION                  1..29
                        note = linker
source                  1..29
                        mol_type = protein
                        organism = synthetic construct
SEQUENCE: 37
GGSGSSSSSS SSSKSCDKTH TCPPCPAPE                               29

SEQ ID NO: 38           moltype = AA   length = 24
FEATURE                 Location/Qualifiers
REGION                  1..24
                        note = linker
source                  1..24
                        mol_type = protein
                        organism = synthetic construct
SEQUENCE: 38
GGPGSSGSGS SDKTHTCPPC PAPE                                    24

SEQ ID NO: 39           moltype = AA   length = 23
FEATURE                 Location/Qualifiers
REGION                  1..23
                        note = linker
source                  1..23
                        mol_type = protein
                        organism = synthetic construct
SEQUENCE: 39
GGPGSSGSGS DKTHTCPPCP APE                                     23

SEQ ID NO: 40           moltype = AA   length = 21
FEATURE                 Location/Qualifiers
REGION                  1..21
                        note = linker
source                  1..21
                        mol_type = protein
                        organism = synthetic construct
SEQUENCE: 40
GGPSSSGSDK THTCPPCPAP E                                       21

SEQ ID NO: 41           moltype = AA   length = 25
FEATURE                 Location/Qualifiers
REGION                  1..25
                        note = linker
source                  1..25
                        mol_type = protein
                        organism = synthetic construct
SEQUENCE: 41
GGSSSSSSSS GSDKTHTCPP CPAPE                                   25

SEQ ID NO: 42           moltype = AA   length = 246
FEATURE                 Location/Qualifiers
REGION                  1..246
                        note = Fc domain
source                  1..246
                        mol_type = protein
                        organism = synthetic construct
SEQUENCE: 42
METDTLLLWV LLLWVPAGNG DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK 120
CKVSNKALPA PIEKTISKAK GQPREPQVYT LPPSREEMTK NQVSLTCLVK GFYPSDIAVE 180
WESNGQPENN YKTTPPVLDS DGSFFLYSKL TVDKSRWQQG NVFSCSVMHE ALHNHYTQKS 240
LSLSPG                                                           246

SEQ ID NO: 43           moltype = AA   length = 11
FEATURE                 Location/Qualifiers
REGION                  1..11
                        note = linker
source                  1..11
                        mol_type = protein
                        organism = synthetic construct
SEQUENCE: 43
SGSGSGSGSG S                                                  11

SEQ ID NO: 44           moltype = AA   length = 12
```

```
FEATURE                 Location/Qualifiers
REGION                  1..12
                        note = linker
source                  1..12
                        mol_type = protein
                        organism = synthetic construct
SEQUENCE: 44
SSSSSSGSGS GS                                                          12

SEQ ID NO: 45           moltype = AA  length = 16
FEATURE                 Location/Qualifiers
REGION                  1..16
                        note = linker
source                  1..16
                        mol_type = protein
                        organism = synthetic construct
SEQUENCE: 45
SSSSSSGSGS GSGSGS                                                      16

SEQ ID NO: 46           moltype = AA  length = 254
FEATURE                 Location/Qualifiers
REGION                  1..254
                        note = 4-1BBL
source                  1..254
                        mol_type = protein
                        organism = synthetic construct
SEQUENCE: 46
MEYASDASLD PEAPWPPAPR ARACRVLPWA LVAGLLLLLL LAAACAVFLA CPWAVSGARA       60
SPGSAASPRL REGPELSPDD PAGLLDLRQG MFAQLVAQNV LLIDGPLSWY SDPGLAGVSL      120
TGGLSYKEDT KELVVAKAGV YYVFFQLELR RVVAGEGSGS VSLALHLQPL RSAAGAAALA      180
LTVDLPPASS EARNSAFGFQ GRLLHLSAGQ RLGVHLHTEA RARHAWQLTQ GATVLGLFRV      240
TPEIPAGLPS PRSE                                                       254

SEQ ID NO: 47           moltype = AA  length = 168
FEATURE                 Location/Qualifiers
REGION                  1..168
                        note = 4-1BBL soluble domain
source                  1..168
                        mol_type = protein
                        organism = synthetic construct
SEQUENCE: 47
LRQGMFAQLV AQNVLLIDGP LSWYSDPGLA GVSLTGGLSY KEDTKELVVA KAGVYYVFFQ       60
LELRRVVAGE GSGSVSLALH LQPLRSAAGA AALALTVDLP PASSEARNSA FGFQGRLLHL      120
SAGQRLGVHL HTEARARHAW QLTQGATVLG LFRVTPEIPA GLPSPRSE                   168

SEQ ID NO: 48           moltype = AA  length = 118
FEATURE                 Location/Qualifiers
REGION                  1..118
                        note = variable heavy chain for 4B4-1-1 version 1
source                  1..118
                        mol_type = protein
                        organism = synthetic construct
SEQUENCE: 48
QVQLQQPGAE LVKPGASVKL SCKASGYTFS SYWMHWVKQR PGQVLEWIGE INPGNGHTNY       60
NEKFKSKATL TVDKSSSTAY MQLSSLTSED SAVYYCARSF TTARGFAYWG QGTLVTVS       118

SEQ ID NO: 49           moltype = AA  length = 107
FEATURE                 Location/Qualifiers
REGION                  1..107
                        note = variable light chain for 4B4-1-1 version 1
source                  1..107
                        mol_type = protein
                        organism = synthetic construct
SEQUENCE: 49
DIVMTQSPAT QSVTPGDRVS LSCRASQTIS DYLHWYQQKS HESPRLLIKY ASQSISGIPS       60
RFSGSGSGSD FTLSINSVEP EDVGVYYCQD GHSFPPTFGG GTKLEIK                   107

SEQ ID NO: 50           moltype = AA  length = 119
FEATURE                 Location/Qualifiers
REGION                  1..119
                        note = variable heavy chain for 4B4-1-1 version 2
source                  1..119
                        mol_type = protein
                        organism = synthetic construct
SEQUENCE: 50
QVQLQQPGAE LVKPGASVKL SCKASGYTFS SYWMHWVKQR PGQVLEWIGE INPGNGHTNY       60
NEKFKSKATL TVDKSSSTAY MQLSSLTSED SAVYYCARSF TTARGFAYWG QGTLVTVSA      119

SEQ ID NO: 51           moltype = AA  length = 108
```

```
FEATURE             Location/Qualifiers
REGION              1..108
                    note = variable light chain for 4B4-1-1 version 2
source              1..108
                    mol_type = protein
                    organism = synthetic construct
SEQUENCE: 51
DIVMTQSPAT QSVTPGDRVS LSCRASQTIS DYLHWYQQKS HESPRLLIKY ASQSISGIPS    60
RFSGSGSGSD FTLSINSVEP EDVGVYYCQD GHSFPPTFGG GTKLEIKR                108

SEQ ID NO: 52       moltype = AA  length = 120
FEATURE             Location/Qualifiers
REGION              1..120
                    note = variable heavy chain for H39E3-2
source              1..120
                    mol_type = protein
                    organism = synthetic construct
SEQUENCE: 52
MDWTWRILFL VAAATGAHSE VQLVESGGGL VQPGGSLRLS CAASGFTFSD YWMSWVRQAP    60
GKGLEWVADI KNDGSYTNYA PSLTNRFTIS RDNAKNSLYL QMNSLRAEDT AVYYCARELT   120

SEQ ID NO: 53       moltype = AA  length = 109
FEATURE             Location/Qualifiers
REGION              1..109
                    note = variable light chain for H39E3-2
source              1..109
                    mol_type = protein
                    organism = synthetic construct
SEQUENCE: 53
MEAPAQLLFL LLLWLPDTTG DIVMTQSPDS LAVSLGERAT INCKSSQSLL SSGNQKNYLW    60
YQQKPGQPPK LLIYYASTRQ SGVPDRFSGS GSGTDFTLTI SSLQAEDVA               109
```